US012528790B2

(12) United States Patent
Okano et al.

(10) Patent No.: US 12,528,790 B2
(45) Date of Patent: Jan. 20, 2026

(54) AMIDE DERIVATIVE HAVING ANTIVIRAL ACTIVITY

(71) Applicants: Shionogi & Co., Ltd., Osaka (JP); UBE Corporation, Yamaguchi (JP)

(72) Inventors: Azusa Okano, Osaka (JP); Yusuke Tateno, Osaka (JP); Kouhei Nodu, Osaka (JP); Shinji Suzuki, Osaka (JP); Toshiyuki Akiyama, Osaka (JP); Masaaki Matoyama, Yamaguchi (JP); Hiroto Akaza, Yamaguchi (JP); Takashi Fukuda, Yamaguchi (JP)

(73) Assignees: SHIONOGI & CO., LTD., Osaka (JP); UBE CORPORATION, Yamaguchi (JP)

( * ) Notice: Subject to any disclaimer, the term of this patent is extended or adjusted under 35 U.S.C. 154(b) by 361 days.

(21) Appl. No.: 18/034,318

(22) PCT Filed: Oct. 27, 2021

(86) PCT No.: PCT/JP2021/039623
§ 371 (c)(1),
(2) Date: Apr. 27, 2023

(87) PCT Pub. No.: WO2022/092141
PCT Pub. Date: May 5, 2022

(65) Prior Publication Data

US 2023/0382893 A1 Nov. 30, 2023

(30) Foreign Application Priority Data

Oct. 28, 2020 (JP) ................................ 2020-180856

(51) Int. Cl.
*C07D 403/04* (2006.01)
*A61P 31/14* (2006.01)
(Continued)

(52) U.S. Cl.
CPC ............ *C07D 403/04* (2013.01); *A61P 31/14* (2018.01); *C07D 401/14* (2013.01);
(Continued)

(58) Field of Classification Search
CPC ................ C07D 403/04; C07D 401/14; C07D 405/14; C07D 413/14; C07D 417/14;
(Continued)

(56) References Cited

FOREIGN PATENT DOCUMENTS

| | | |
|---|---|---|
| JP | 2009-532417 | 9/2009 |
| JP | 2014-509625 | 4/2014 |
| JP | 2015-516976 | 6/2015 |
| WO | 2007/115933 | 10/2007 |
| WO | 2012/080447 | 6/2012 |
| WO | 2012/130905 | 10/2012 |

(Continued)

OTHER PUBLICATIONS

Extended European Search Report issued Sep. 23, 2024 in European Patent Application No. 21886259.7.
English language translation of International Search Report issued Nov. 30, 2021 in corresponding International (PCT) Patent Application No. PCT/JP2021/039623.
English language translation of International Preliminary Report on Patentability issued May 2, 2023 in corresponding International (PCT) Patent Application No. PCT/JP2021/039623.
C. Efstathiou et al., "Revisiting respiratory syncytial virus's interaction with host immunity, towards novel therapeutics", Cellular and Molecular Life Sciences, vol. 77, pp. 5045-5058, 2020.
Harrison C. Bergeron et al., "Emerging small and large molecule therapeutics for respiratory syncytial virus", Expert Opinion on Investigational Drugs, vol. 29, No. 3, pp. 285-294, 2020.
Sandra Piras et al., "Dichloro-Phenyl-Benzotriazoles: A New Selective Class of Human Respiratory Syncytial Virus Entry Inhibitors", Frontiers in Chemistry, vol. 7, Article 247, Apr. 2019.
CAS Registry No. 2649634-02-4, SciFinder$^n$®, 1 page, 2023.
G. Stuart Cockerill et al., "State of the Art in Respiratory Syncytial Virus Drug Discovery and Development", Journal of Medicinal Chemistry, vol. 62, pp. 3206-3227, 2019.

*Primary Examiner* — Rebecca L Anderson
(74) *Attorney, Agent, or Firm* — Wenderoth, Lind & Ponack, L.L.P.

(57) ABSTRACT

The present invention provides a compound represented by formula (I):

(I)

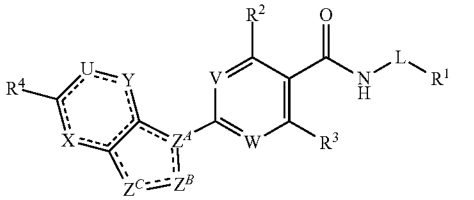

wherein the dashed line indicates the presence or absence of a bond; $R^1$ is carboxy or the like; L is substituted or unsubstituted non-aromatic carbocyclyldiyl or the like; $R^2$ is substituted or unsubstituted alkyl; $R^3$ is a hydrogen atom or the like; X is $=CR^X-$ or $=N-$; Y is $=CR^Y-$ or $=N-$; U is $-CR^U=$ or $-N=$; V is $-CR^V=$ or $-N=$; W is $=CR^W-$ or $=N-$; $Z^A$ is $-C=$ or $-N-$; $Z^B$ is $-CR^5R^6-$ or the like; $Z^C$ is $-CR^7R^8-$ or the like; $R^X$, $R^Y$, $R^V$ and $R^W$ are each independently a hydrogen atom or the like; $R^U$ is a hydrogen atom or the like; $R^5$ and $R^6$ are each independently a hydrogen atom or the like; $R^7$ and $R^8$ are each independently a hydrogen atom or the like; $R^4$ is substituted or unsubstituted alkyloxy or the like, or a pharmaceutically acceptable salt thereof, having an antiviral activity; and a pharmaceutical composition comprising the same.

32 Claims, No Drawings

(51) Int. Cl.

| | |
|---|---|
| ***C07D 401/14*** | (2006.01) |
| ***C07D 405/14*** | (2006.01) |
| ***C07D 413/14*** | (2006.01) |
| ***C07D 417/14*** | (2006.01) |
| ***C07D 471/10*** | (2006.01) |
| ***C07D 491/107*** | (2006.01) |
| ***C07D 491/20*** | (2006.01) |
| ***C07D 495/10*** | (2006.01) |
| ***C07D 519/00*** | (2006.01) |

(52) U.S. Cl.
CPC ......... *C07D 405/14* (2013.01); *C07D 413/14* (2013.01); *C07D 417/14* (2013.01); *C07D 471/10* (2013.01); *C07D 491/107* (2013.01); *C07D 491/20* (2013.01); *C07D 495/10* (2013.01); *C07D 519/00* (2013.01)

(58) Field of Classification Search
CPC .............. C07D 471/10; C07D 491/107; C07D 491/20; C07D 495/10; C07D 519/00; A61P 31/14
See application file for complete search history.

(56) References Cited

FOREIGN PATENT DOCUMENTS

| | | |
|---|---|---|
| WO | 2013/158776 | 10/2013 |
| WO | 2014/031784 | 2/2014 |
| WO | 2014/070976 | 5/2014 |
| WO | 2015/026792 | 2/2015 |
| WO | 2016/138158 | 9/2016 |
| WO | 2016/148145 | 9/2016 |
| WO | 2016/174079 | 11/2016 |
| WO | 2017/196982 | 11/2017 |
| WO | 2019/106004 | 6/2019 |
| WO | 2019/110563 | 6/2019 |
| WO | 2019/149734 | 8/2019 |
| WO | 2019/206828 | 10/2019 |
| WO | 2020/109224 | 6/2020 |
| WO | 2020/234333 | 11/2020 |
| WO | 2021/066922 | 4/2021 |
| WO | 2021/150806 | 7/2021 |
| WO | 2021/198981 | 10/2021 |
| WO | 2021/214136 | 10/2021 |
| WO | 2022/086840 | 4/2022 |
| WO | 2022/182861 | 9/2022 |
| WO | 2022/211812 | 10/2022 |

AMIDE DERIVATIVE HAVING ANTIVIRAL ACTIVITY

TECHNICAL FIELD

The present invention relates to compounds useful for the treatment and/or prevention of respiratory syncytial virus (hereinafter referred to as "RSV") infection and related diseases caused by the infection and also to pharmaceutical compositions containing the same. In particular, the present invention relates to amide derivatives having RSV inhibitory activity.

BACKGROUND ART

Human respiratory syncytial virus (RSV) is a negative-sense single-stranded RNA virus, which belongs to the genus Pneumovirus of the Paramyxoviridae family, and is the most common cause of bronchiolitis and pneumonia in infants under 1 year of age. Most children become infected with RSV before their second birthday, and about 1-3% of those infected require hospitalization. The elderly and adults with heart, lung or immune system disorders are particularly susceptible and at high risk for severe illness and complications (Non-Patent Document 1).

There are two antigenic subtypes A and B of RSV. These two types co-circulate generally in RSV outbreaks. However, the ratio of these types varies geographically and seasonally, and this is considered as one of the reasons for different clinical impact in each outbreak. Therefore, in view of the treatment for RSV, agents effective against both subtypes A and B are desirable (Non-Patent Document 1).

To date, there has been no vaccine that can prevent RSV infection. Palivizumab is a monoclonal antibody used prophylactically to prevent RSV infection in high-risk infants, e.g., preterm infants, and infants with heart or lung disease. The high cost of treatment with palivizumab has limited the use of this drug. A nucleic acid analog, ribavirin, was approved in the United States as the only antiviral agent to treat RSV infection, but its efficacy is limited and there is a concern of side effect profile. Therefore, there is a need for a safe and effective RSV treatment that can be widely used for all types of RSV and age groups from infants to the elderly (Non-Patent Document 1).

Inhibitors targeting on the F protein involved in RSV membrane fusion, such as Ziresovir, JNJ-53718678 and RV-521, inhibitors targeting on the N protein involved in genome stabilization, such as EDP-938, and inhibitors targeting on polymerase of L protein, such as PC786, are in clinical development for RSV therapy (Non-Patent Document 2).

To date, no amide derivative having RSV inhibitory activity, such as those described in this application, are known.

PRIOR ART DOCUMENT

Non-Patent Document

Non-Patent Document 1: Cellular and Molecular Life Sciences, 2020, Jun. 16, 1-14

Non-Patent Document 2: Expert Opinion on Investigational Drugs, 2020, Mar. 29, 3, 285-294

SUMMARY OF THE INVENTION

Problem to be Solved by the Invention

The purpose of the present invention is to provide novel compounds having RSV inhibitory activity. More preferably, the present invention provides compounds useful for the treatment and/or prevention of RSV infection and related diseases caused by the infection, and medicaments containing the same.

Means for Solving the Problem

The present invention relates to the following items (1) to (17).

(1) A compound of the formula (I):

(I)

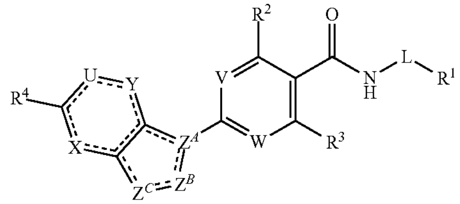

wherein:

the dashed line indicates the presence or absence of a bond;

$R^1$ is carboxy, cyano, substituted or unsubstituted aromatic heterocyclyl, $—C(═O)—NR^{1B}R^{1C}$ or $—CH═CHC(═O)—OH$;

$R^{1B}$ and $R^{1C}$ are each independently a hydrogen atom, substituted or unsubstituted alkyl, substituted or unsubstituted aminosulfonyl or substituted or unsubstituted non-aromatic heterocyclylsulfonyl;

L is substituted or unsubstituted non-aromatic carbocyclyldiyl, substituted or unsubstituted non-aromatic heterocyclyldiyl or substituted or unsubstituted alkylene;

$R^2$ is substituted or unsubstituted alkyl;

$R^3$ is a hydrogen atom, substituted or unsubstituted alkyl, substituted or unsubstituted alkyloxy, substituted or unsubstituted amino or substituted or unsubstituted carbamoyl;

X is $═CR^X—$ or $═N—$;

Y is $═CR^Y—$ or $═N—$;

U is $—CR^U═$ or $—N═$;

V is $—CR^V═$ or $—N═$;

W is $═CR^W—$ or $═N—$;

$Z^A$ is $—C═$ or $—N—$;

$Z^B$ is $—CR^5R^6—$, $—CR^5═$, $—NR^5—$ or $—N═$;

$Z^C$ is $—CR^7R^8—$, $—CR^7═$, $—NR^7—$ or $═N—$;

$R^X$, $R^Y$, $R^V$ and $R^W$ are each independently a hydrogen atom, cyano, halogen, substituted or unsubstituted alkyl or substituted or unsubstituted carbamoyl;

$R^U$ is a hydrogen atom, substituted or unsubstituted alkyloxy, substituted or unsubstituted non-aromatic heterocyclyloxy, substituted or unsubstituted non-aromatic carbocyclyloxy, substituted or unsubstituted alkyl, substituted or unsubstituted alkenyl, substituted or unsubstituted amino, hydroxy, halogen, substituted or unsubstituted aromatic carbocyclyl, substituted or unsubstituted aromatic heterocyclyl, substituted or unsubstituted non-aromatic heterocyclyl or substituted or unsubstituted non-aromatic carbocyclyl;

$R^5$ and $R^6$ are each independently a hydrogen atom, substituted or unsubstituted non-aromatic heterocyclyl, hydroxy or substituted or unsubstituted alkyl, or $R^5$ and $R^6$ are taken together to form oxo;

$R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, substituted or unsubstituted alkylsulfonyl, or $R^7$ and $R^8$ are taken together with the carbon atom to which they are attached to form a substituted or unsubstituted non-aromatic carbon ring or a substituted or unsubstituted non-aromatic heterocyclic ring; or $R^5$ and $R^7$ are taken together with the carbon atoms to which they are attached to form a substituted or unsubstituted non-aromatic carbon ring or a substituted or unsubstituted aromatic carbon ring; or $R^4$ is a hydrogen atom, substituted or unsubstituted alkyloxy, substituted or unsubstituted non-aromatic heterocyclyloxy, substituted or unsubstituted non-aromatic carbocyclyloxy, substituted or unsubstituted aromatic carbocyclyloxy, substituted or unsubstituted aromatic heterocyclyloxy, substituted or unsubstituted alkyl, substituted or unsubstituted alkenyl, substituted or unsubstituted amino, substituted or unsubstituted carbamoyl, hydroxy, halogen, substituted or unsubstituted aromatic carbocyclyl, substituted or unsubstituted aromatic heterocyclyl, substituted or unsubstituted non-aromatic carbocyclyl or substituted or unsubstituted non-aromatic heterocyclylcarbonyl, or $R^4$ and $R^U$ are taken together with the carbon atom to which they are attached to form a substituted or unsubstituted non-aromatic heterocyclic ring, or a pharmaceutically acceptable salt thereof.

(2) The compound of item (1), wherein $R^1$ is carboxy, or a pharmaceutically acceptable salt thereof.

(3) The compound of item (1) or (2), wherein L is substituted or unsubstituted non-aromatic carbocyclyldiyl, or a pharmaceutically acceptable salt thereof.

(4) The compound of any one of items (1) to (3), wherein $R^3$ is a hydrogen atom, or a pharmaceutically acceptable salt thereof.

(5) The compound of any one of items (1) to (4), wherein V is —N═ and W is ═N—, or a pharmaceutically acceptable salt thereof.

(6) The compound of any one of items (1) to (5), wherein the group of the formula:

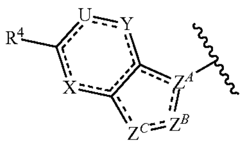

is

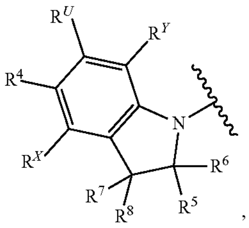

,

-continued

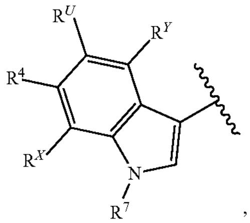

,

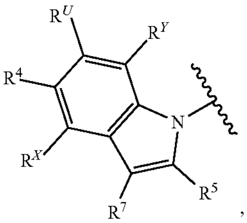

,

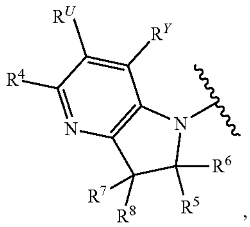

,

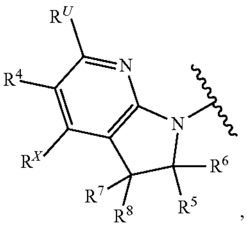

,

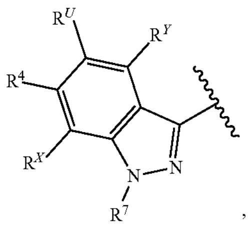

,

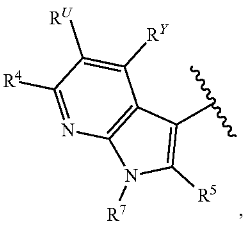

,

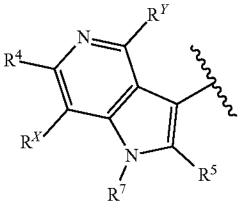

or

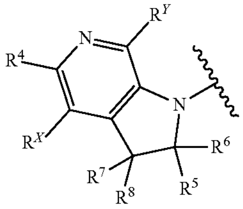

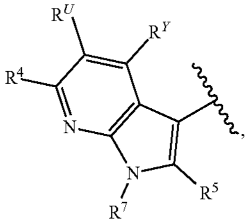

,

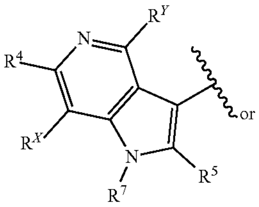

or

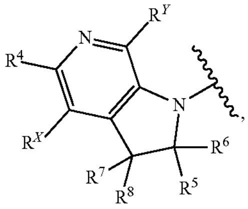

, wherein each symbol is as defined in item (1), or a pharmaceutically acceptable salt thereof.

(7) The compound of any one of items (1) to (6), wherein the group of the formula:

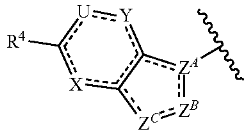

is

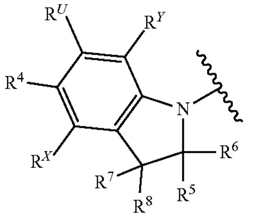

or

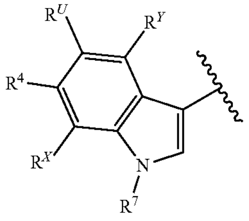

wherein each symbol is as defined in item (1), or a pharmaceutically acceptable salt thereof.

(8) The compound of any one of items (1) to (7), wherein the group of the formula:

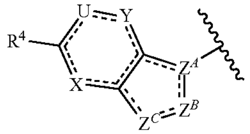

is

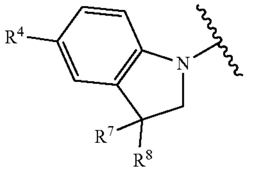

or

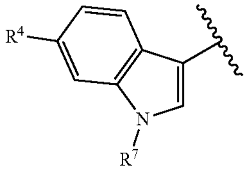

wherein each symbol is as defined in item (1), or a pharmaceutically acceptable salt thereof.

(9) The compound of any one of items (1) to (8), wherein the group of the formula:

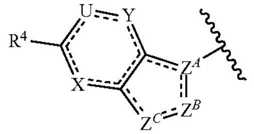

is

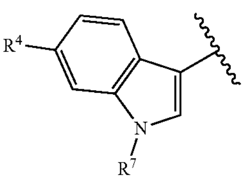

wherein $R^4$ is as defined in item (1); and $R^7$ is substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl or substituted or unsubstituted non-aromatic carbocyclylsulfonyl, or a pharmaceutically acceptable salt thereof.

(10) The compound of any one of items (1) to (8), wherein the group of the formula:

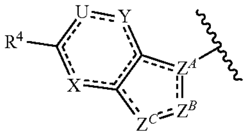

is

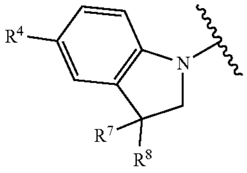

wherein $R^4$ is as defined in item (1); and $R^7$ and $R^8$ are each independently a hydrogen atom or substituted or unsubstituted alkyl, or $R^7$ and $R^8$ are taken together with the carbon atom to which they are attached to form a substituted or unsubstituted non-aromatic carbon ring or a substituted or unsubstituted non-aromatic heterocyclic ring, or a pharmaceutically acceptable salt thereof.

(11) The compound of any one of items (1) to (10), wherein $R^4$ is substituted or unsubstituted alkyloxy, substituted or unsubstituted non-aromatic heterocyclyloxy, substituted or unsubstituted non-aromatic carbocyclyloxy, substituted or unsubstituted aromatic carbocyclyloxy, substituted or unsubstituted alkyl, substituted or unsubstituted alkenyl, substituted or unsubstituted amino, hydroxy, halogen, substituted or unsubstituted aromatic carbocyclyl, substituted or unsubstituted non-aromatic heterocyclyl or substituted or unsubstituted non-aromatic carbocyclyl, or a pharmaceutically acceptable salt thereof.

(12) The compound of any one of items (1) to (11), wherein $R^4$ is substituted or unsubstituted non-aromatic heterocyclyloxy or substituted or unsubstituted non-aromatic carbocyclyloxy, or a pharmaceutically acceptable salt thereof.

(13) The compound of item (1) selected from the group consisting of compounds I-082, I-162, I-481, I-496, I-503, I-506, I-549, I-552, I-568, I-569, I-570, I-571, I-591, I-613, I-617 and I-618, or a pharmaceutically acceptable salt thereof.

(14) A pharmaceutical composition comprising the compound of any one of items (1) to (13) or a pharmaceutically acceptable salt thereof.

(15) The pharmaceutical composition of item (14) having an anti-RS virus activity.

(16) A method for the treatment and/or prevention of RSV infection, characterized in that the compound of any of the items (1) to (13) or a pharmaceutically acceptable salt thereof is administered.

(17) The compound of any one of items (1) to (13) or a pharmaceutically acceptable salt thereof for the treatment and/or prevention of RSV infection.

(18) Use of the compound of any one of items (1) to (13), or a pharmaceutically acceptable salt thereof for the manufacture of a medicament for the treatment and/or prevention of RSV infection.

Effect of the Invention

The compounds of the present invention have RSV inhibitory activity and are useful as therapeutic and/or prophylactic agents for RSV infection and related diseases caused by the infection.

MODE FOR CARRYING OUT THE INVENTION

Hereinafter, the meaning of each term used in the present specification will be described. Unless particularly stated otherwise, each term is used in the same sense, either alone or in combination with other terms.

The term "consist of" means having only the constituent elements.

The term "comprise" means that elements are not limited to the constituent elements, and elements that are not described are not excluded.

Hereinafter, the present invention will be described while showing exemplary embodiments. Throughout the present specification, it should be understood that, unless particularly stated otherwise, an expression of a singular form also includes the concept of a plural form thereof. Therefore, it should be understood that, unless particularly stated otherwise, an article for a singular form (for example, in the case of English, "a", "an", "the", or the like) also includes the concept of a plural form thereof.

Furthermore, it should be understood that, unless particularly stated otherwise, the terms used in the present specification are used in the meanings normally used in the above-described art.

Accordingly, unless otherwise defined, all terminologies and scientific and technical terms used in the present specification have the same meanings as commonly understood by those having ordinary skill in the art to which the present invention belongs.

In a case of contradiction, priority is given to the present specification (including definitions).

"Halogen" includes a fluorine atom, a chlorine atom, a bromine atom, and an iodine atom. Particularly, fluorine atom and chlorine atom are preferred.

"Alkyl" includes linear or branched hydrocarbon groups each having 1 to 15 carbon atoms, preferably 1 to 10 carbon atoms, more preferably 1 to 6 carbon atoms, and even more preferably 1 to 4 carbon atoms. Examples include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Preferred embodiments of "alkyl" include methyl, ethyl, n-propyl, isopropyl, n-butyl, isobutyl, sec-butyl, tert-butyl, and n-pentyl. More preferred embodiments include methyl, ethyl, n-propyl, isopropyl, and tert-butyl.

"Alkenyl" includes linear or branched hydrocarbon groups each having one or more double bond(s) at any position and having 2 to 15 carbon atoms, preferably 2 to 10 carbon atoms, more preferably 2 to 6 carbon atoms, and even more preferably 2 to 4 carbon atoms. Examples include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

Preferred embodiments of "alkenyl" include vinyl, allyl, propenyl, isopropenyl, and butenyl. More preferred embodiments include ethenyl and n-propenyl.

"Alkynyl" includes linear or branched hydrocarbon groups each having one or more triple bond(s) at any position and having 2 to 10 carbon atoms, preferably 2 to 8 carbon atoms, more preferably 2 to 6 carbon atoms, and even more preferably 2 to 4 carbon atoms. Alkynyl may further have a double bond at any position. Examples include ethynyl, propynyl, butynyl, pentynyl, hexynyl, heptynyl, octynyl, nonynyl, and decynyl.

Preferred embodiments of "alkynyl" include ethynyl, propynyl, butynyl, and pentynyl. More preferred embodiments include ethynyl and propynyl.

"Alkylene" includes liner or branched divalent hydrocarbon groups each having 1 to 15 carbon atoms, preferably 1 to 10 carbon atoms, more preferably 1 to 6 carbon atoms, and even more preferably 1 to 4 carbon atoms. Examples include methylene, ethylene, trimethylene, propylene, tetramethylene, pentamethylene, and hexamethylene.

"Aromatic carbocyclyl" means a cyclic aromatic hydrocarbon group having a single ring or two or more rings. Examples include phenyl, naphthyl, anthryl, and phenanthryl.

Preferred embodiments of "aromatic carbocyclyl" include phenyl.

"Aromatic carbon ring" means a ring derived from the above "aromatic carbocyclyl".

"$R^5$ and $R^7$ are taken together with the carbon atoms to which they are attached to form a substituted or unsubstituted aromatic carbon ring" includes, for example, the following rings.

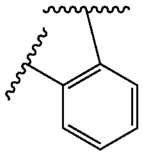 [SMILES: *c1ccccc1*]

"Non-aromatic carbocyclyl" means a cyclic saturated hydrocarbon group or a cyclic non-aromatic unsaturated hydrocarbon group, both having a single ring or two or more rings. The "non-aromatic carbocyclyl" having two or more rings also includes a non-aromatic carbocyclyl having a single ring or two or more rings, to which the ring in the above "aromatic carbocyclyl" is fused.

Furthermore, the "non-aromatic carbocyclyl" also includes a bridged group or a group forming a spiro ring, such as follows.

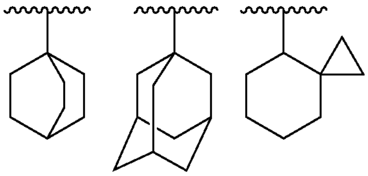

A non-aromatic carbocyclyl having a single ring preferably has 3 to 16 carbon atoms, more preferably 3 to 12 carbon atoms, and even more preferably 4 to 8 carbon atoms. Examples include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

A non-aromatic carbocyclyl having two or more rings preferably has 8 to 20 carbon atoms, and more preferably 8 to 16 carbon atoms. Examples include indanyl, indenyl, acenaphthyl, tetrahydronaphthyl, and fluorenyl.

"Non-aromatic carbon ring" means a ring derived from the above "non-aromatic carbocyclyl".

Examples of "$R^5$ and $R^7$ are taken together with the carbon atoms to which they are attached to form a substituted or unsubstituted non-aromatic carbon ring" include the following rings.

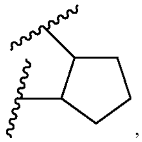, 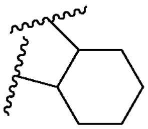, 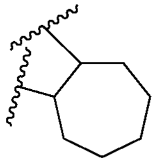,

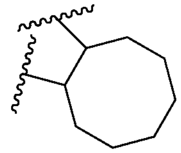

Examples of “$R^7$ and $R^8$ are taken together with the carbon atom to which they are attached to form a substituted or unsubstituted non-aromatic carbon ring” include the following rings.

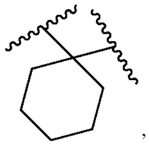, 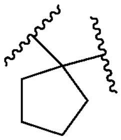, 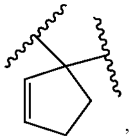, 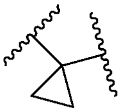

“Non-aromatic carbocyclyldiyl” means a divalent group derived from the above “non-aromatic carbon ring”. Examples include cyclopropanediyl, cyclobutanediyl, cyclopentanediyl, cyclohexanediyl, cycloheptanediyl, cyclooctanediyl, bicyclo[2.2.2]octanediyl, bicyclo[2.2.1]heptanediyl, adamantanediyl. One carbon atom may have two bonding hands. Examples include cyclohexane-1,1-diyl and adamantane-2,2-diyl.

“Aromatic heterocyclyl” means an aromatic cyclic group having a single ring or two or more rings, which has one or more identical or different heteroatom(s) optionally selected from O, S, and N in the ring(s).

An aromatic heterocyclyl having two or more rings also includes an aromatic heterocyclyl having a single ring or two or more rings, to which a ring in the above “aromatic carbocyclyl” is fused, and the bonding hand may be carried by any of the rings.

The aromatic heterocyclyl having a single ring is preferably a 5- to 8-membered ring, and more preferably a 5-membered or 6-membered ring. Examples of 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl. Examples of 6-membered aromatic heterocyclyl include pyridyl pyridazinyl, pyrimidinyl, pyrazinyl, and triazinyl.

The aromatic heterocyclyl having two rings is preferably a 8- to 10-membered ring, and more preferably a 9-membered or 10-membered ring. Examples include indolyl, isoindolyl, indazolyl, indolizinyl, quinolinyl, isoquinolinyl, cinolinyl, phthalazinyl, quinazolinyl, naphthyridinyl, quinoxalinyl, purinyl, pteridinyl, benzimidazolyl, benzisoxazolyl, benzoxazolyl benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

The aromatic heterocyclyl having three or more rings is preferably 13- to 15-membered ring. Examples include carbazolyl, acridinyl, xanthenyl, phenothiazinyl, phenoxathiinyl, phenoxazinyl, and dibenzofuryl.

“Aromatic heterocyclic ring” means a ring derived from the above “aromatic heterocyclyl”.

“Non-aromatic heterocyclyl” means a non-aromatic cyclic group having a single ring or two or more rings, which has one or more identical or different heteroatom(s) optionally selected from O, S, and N in the ring(s). A non-aromatic heterocyclyl having two or more rings also includes a non-aromatic heterocyclyl having a single ring or two or more rings, to which a ring in each of the above “aromatic carbocyclyl”, “non-aromatic carbocyclyl”, and/or “aromatic heterocyclyl” is fused, as well as a non-aromatic carbocyclyl having a single ring or two or more rings, to which a ring in the above “aromatic heterocyclyl” is fused, and the bonding hand may be carried by any of the rings.

Furthermore, the “non-aromatic heterocyclyl” also includes a bridged group or a group forming a spiro ring, such as follows.

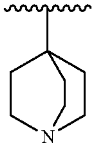 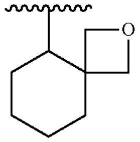

The non-aromatic heterocyclyl having a single ring is preferably a 3- to 8-membered ring, and more preferably a 5-membered or 6-membered ring.

Examples of 3-membered non-aromatic heterocyclyl include thiiranyl, oxiranyl, and aziridinyl. Examples of 4-membered non-aromatic heterocyclyl include oxetanyl and azetidinyl. Examples of 5-membered non-aromatic heterocyclyl include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl, and thiolanyl. Examples of 6-membered non-aromatic heterocyclyl include dioxanyl, thianyl, piperidyl, piperazinyl, morpholinyl, morpholino, thiomorpholinyl, thiomorpholino, dihydropyridyl, tetrahydropyridyl, tetrahydropyranyl, dihydroxazinyl, tetrahydropyridazinyl, hexahydropyrimidinyl, dioxazinyl, thiinyl, and thiazinyl. Examples of 7-membered non-aromatic heterocyclyl include hexahydroazepinyl, tetrahydrodiazepinyl, and oxepanyl.

The non-aromatic heterocyclyl having two or more rings is preferably an 8- to 20-membered ring, and more preferably an 8- to 10-membered ring. Examples include indolinyl, isoindolinyl, chromanyl, and isochromanyl.

“Non-aromatic heterocyclic ring” means a ring derived from the above “non-aromatic heterocyclyl”.

Examples of “$R^7$ and $R^8$ are taken together with the carbon atom to which they are attached to form a substituted or unsubstituted non-aromatic heterocyclic ring” include the following rings.

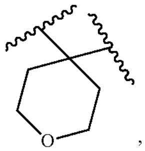, 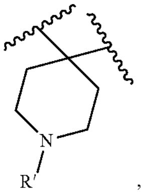, 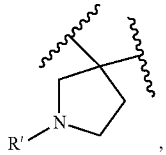,

-continued

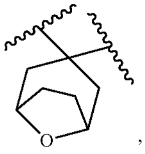,
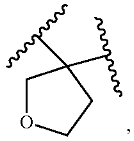,
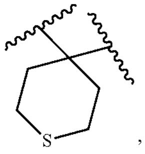,
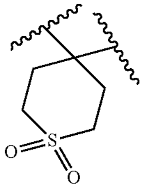

wherein

R' is a hydrogen atom, substituted or unsubstituted alkyl, substituted or unsubstituted alkyloxycarbonyl, substituted or unsubstituted aromatic heterocyclyl, substituted or unsubstituted non-aromatic carbocyclyl, substituted or unsubstituted carbamoyl, substituted or unsubstituted non-aromatic heterocyclyl, or substituted or unsubstituted alkylcarbonyl.

Examples of "$R^4$ and $R^U$ are taken together with the carbon atom to which they are attached to form a substituted non-aromatic heterocyclic ring" include the following rings.

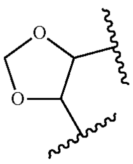,
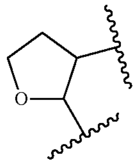,
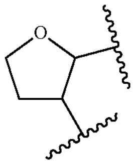

"Non-aromatic heterocyclyldiyl" means a divalent group derived from the above "non-aromatic heterocyclic ring". "Non-aromatic heterocyclyldiyl" include non-aromatic ring diyl of 1 to 9 carbons containing 1 to 4 nitrogen, oxygen and/or sulfur atoms. Examples include pyrrolindiyl, pyrrolidinediyl, imidazolinediyl, imidazolidinediyl, pyrazolinediyl, pyrazolidinediyl, piperidinediyl, piperazinediyl, morpholindiyl, tetrahydropyranediyl. One carbon atom may have two bonding hands. Examples include tetrahydropyran-4,4-diyl, and piperidine-4,4-diyl.

"Trialkylsilyl" means a group having three of the above "alkyls" bonded to a silicon atom. The three alkyl groups may be the same or different. Examples include trimethylsilyl, triethylsilyl, and tert-butyldimethylsilyl.

In the present specification, the phrase "may be substituted with Substituent Group α" means that "may be substituted with one or more group(s) selected from Substituent Group α". The same also applies to substituent groups β, γ, and γ'.

Examples of substituents for "substituted alkyl", "substituted alkenyl", "substituted alkynyl", "substituted alkyloxy", "substituted alkenyloxy", "substituted alkynyloxy", "substituted alkylcarbonyloxy", "substituted alkenylcarbonyloxy", "substituted alkynylcarbonyloxy", "substituted alkylcarbonyl", "substituted alkenylcarbonyl", "substituted alkynylcarbonyl", "substituted alkyloxycarbonyl", "substituted alkenyloxycarbonyl", "substituted alkynyloxycarbonyl", "substituted alkylsulfanyl", "substituted alkenylsulfanyl", "substituted alkynylsulfanyl", "substituted alkylsulfinyl", "substituted alkenylsulfinyl", "substituted alkynylsulfinyl", "substituted alkylsulfonyl", "substituted alkenylsulfonyl", and "substituted alkynylsulfonyl" include the following Substituent Group A. One or more group(s) selected from the following Substituent Group A may be attached to a cabon atom at any position.

Substituent Group A: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azido, hydrazino, ureido, amidino, guanidino, pentafluorothio, trialkylsilyl, alkyloxy which may be substituted with Substituent Group α, alkenyloxy which may be substituted with Substituent Group α, alkynyloxy which may be substituted with Substituent Group α, alkylcarbonyloxy which may be substituted with Substituent Group α, alkenylcarbonyloxy which may be substituted with Substituent Group α, alkynylcarbonyloxy which may be substituted with Substituent Group α, alkylcarbonyl which may be substituted with Substituent Group α, alkenylcarbonyl which may be substituted with Substituent Group α, alkynylcarbonyl which may be substituted with Substituent Group α, alkyloxycarbonyl which may be substituted with Substituent Group α, alkenyloxycarbonyl which may be substituted with Substituent Group α, alkynyloxycarbonyl which may be substituted with Substituent Group α, alkylsulfanyl which may be substituted with Substituent Group α, alkenylsulfanyl which may be substituted with Substituent Group α, alkynylsulfanyl which may be substituted with Substituent Group α, alkylsulfinyl which may be substituted with Substituent Group α, alkenylsulfinyl which may be substituted with Substituent Group α, alkynylsulfinyl which may be substituted with Substituent Group α, alkylsulfonyl which may be substituted with Substituent Group α, alkenylsulfonyl which may be substituted with Substituent Group α, alkynylsulfonyl which may be substituted with Substituent Group α, amino which may be substituted with Substituent Group β, imino which may be substituted with Substituent Group β, carbamoyl which may be substituted with Substituent Group β, sulfamoyl which may be substituted with Substituent Group β, aromatic carbocyclyl which may be substituted with Substituent Group γ, non-aromatic carbocyclyl which may be substituted with Substituent Group γ', aromatic heterocyclyl which may be substituted with Substituent Group γ, non-aromatic heterocyclyl which may be substituted with Substituent Group γ', aromatic carbocyclyloxy which may be substituted with Substituent Group γ, non-aromatic carbocyclyloxy which may be substituted with Substituent Group γ', aromatic heterocyclyloxy which may be substituted with Substituent Group γ, non-aromatic heterocyclyloxy which may be substituted with Substituent Group γ', aromatic carbocyclylcarbonyloxy which may be substituted with Substituent Group γ, non-aromatic carbocyclylcarbonyloxy which may be substituted with Substituent Group γ', aromatic heterocyclylcarbonyloxy which may be substituted with Substituent Group γ, non-aromatic heterocyclylcarbonyloxy which may be substituted with Substituent Group γ', aromatic carbocyclylcarbonyl which may be substituted with Substituent Group γ, non-aromatic carbocyclylcarbonyl which may be substituted with Substituent Group γ', aromatic heterocyclylcarbonyl which may be substituted with Substituent Group γ, non-aromatic heterocyclylcarbonyl which may be substituted with Substituent Group γ', aromatic carbocyclyloxycarbonyl which may be substituted with Substituent Group γ, non-aromatic carbocyclyloxycarbonyl which may be substituted with Substituent Group γ', aromatic heterocyclyloxycarbonyl which may be substituted with Substituent Group γ, non-aromatic heterocyclyloxycarbonyl which may be substituted with Substituent Group γ', aromatic carbocyclylalkyloxy which may be substituted with Substituent Group γ, non-aromatic carbocyclylalkyloxy which may be substituted with Substituent Group γ', aromatic heterocyclylalkyloxy which may be substituted with Substituent Group γ, non-aromatic heterocyclylalkyloxy which may be substituted with Substituent Group γ', aromatic carbocyclylalkyloxycarbonyl which may be substituted with Substituent Group γ, non-aromatic carbocyclylalkyloxycarbonyl which may be substituted with Substituent Group γ', aromatic heterocyclylalkyloxycarbonyl which may be substituted with Substituent Group γ, non-aromatic heterocyclylalkyloxycarbonyl which may be substituted with Substituent Group γ', aromatic carbocyclylsulfanyl which may be substituted with Substituent Group γ, non-aromatic carbocyclylsulfanyl which may be substituted with Substituent Group γ', aromatic heterocyclylsulfanyl which may be substituted with Substituent Group γ, non-aromatic heterocyclylsulfanyl which may be substituted with Substituent Group γ', aromatic carbocyclylsulfinyl which may be substituted with Substituent Group γ, non-aromatic carbocyclylsulfinyl which may be substituted with Substituent Group γ', aromatic heterocyclylsulfinyl which may be substituted with Substituent Group γ, non-aromatic heterocyclylsulfinyl which may be substituted with Substituent Group γ', aromatic carbocyclylsulfonyl which may be substituted with Substituent Group γ, non-aromatic carbocyclylsulfonyl which may be substituted with Substituent Group γ', aromatic heterocyclylsulfonyl which may be substituted with Substituent Group γ, and non-aromatic heterocyclylsulfonyl which may be substituted with Substituent Group γ'.

Substituent Group α: halogen, hydroxy, carboxy, alkyloxy, haloalkyloxy, alkenyloxy, alkynyloxy, sulfanyl, and cyano.

Substituent Group β: halogen, hydroxy, carboxy, cyano, alkyl which may be substituted with Substituent Group α, alkenyl which may be substituted with Substituent Group α, alkynyl which may be substituted with Substituent Group α, alkylcarbonyl which may be substituted with Substituent Group α, and alkenylcarbonyl which may be substituted with group α, alkynylcarbonyl which may be substituted with group α, alkylsulfanyl which may be substituted with group α, alkenylsulfanyl which may be substituted with group α, alkynylsulfanyl which may be substituted with group α alkylsulfinyl which may be substituted with Substituent Group α, alkenylsulfinyl which may be substituted with Substituent Group α, alkynylsulfinyl which may be substituted with Substituent Group α, alkylsulfonyl which may be substituted with Substituent Group α alkenylsulfonyl which may be substituted with Substituent Group α, alkynylsulfonyl which may be substituted with Substituent Group α, aromatic carbocyclyl which may be substituted with Substituent Group γ, non-aromatic carbocyclyl which may be substituted with Substituent Group γ', aromatic heterocyclyl which may be substituted with Substituent Group γ, non-aromatic heterocyclyl which may be substituted with Substituent Group γ', aromatic carbocyclylalkyl which may be substituted with Substituent Group γ, non-aromatic carbocyclylalkyl which may be substituted with Substituent Group γ', aromatic heterocyclylalkyl which may be substituted with Substituent Group γ, non-aromatic heterocyclylalkyl which may be substituted with Substituent Group γ', aromatic carbocyclylcarbonyl which may be substituted with Substituent Group γ, non-aromatic carbocyclylcarbonyl which may be substituted with Substituent Group γ', aromatic heterocyclylcarbonyl which may be substituted with Substituent Group γ, non-aromatic heterocyclylcarbonyl which may be substituted with group γ', aromatic carbocyclyloxycarbonyl which may be substituted with group γ, non-aromatic carbocyclyloxycarbonyl which may be substituted with group γ', aromatic heterocyclyloxycarbonyl which may be substituted with group γ, non-aromatic heterocyclyloxycarbonyl which may be substituted with group γ', aromatic carbocyclylsulfanyl which may be substituted with group γ, non-aromatic carbocyclylsulfanyl which may be substituted with Substituent Group γ', aromatic heterocyclylsulfanyl which may be substituted with group γ, non-aromatic heterocyclylsulfanyl which may be substituted with Substituent Group γ', aromatic carbocyclylsulfinyl which may be substituted with Substituent Group γ, non-aromatic carbocyclylsulfinyl which may be substituted with Substituent Group γ', aromatic heterocyclylsulfinyl which may be substituted with Substituent Group γ, non-aromatic heterocyclylsulfinyl which may be substituted with group γ', aromatic carbocyclylsulfonyl which may be substituted with group γ, non-aromatic carbocyclylsulfonyl which may be substituted with group γ', aromatic heterocyclylsulfonyl which may be substituted with Substituent Group γ, and non-aromatic heterocyclylsulfonyl which may be substituted with Substituent Group γ'.

Substituent Group γ: Substituent Group α, alkyl, haloalkyl, hydroxyalkyl, alkenyl, alkynyl, alkylcarbonyl, haloalkylcarbonyl, alkenylcarbonyl, and alkynylcarbonyl.

Substituent Group γ': Substituent Group γ and oxo.

Examples of substituents on the ring of "substituted aromatic carbon ring" and "aromatic heterocyclic ring" for "substituted aromatic carbocyclyl", "substituted aromatic heterocyclyl", "substituted aromatic carbocyclyloxy", "substituted aromatic heterocyclyloxy", "substituted aromatic carbocyclylcarbonyloxy", "substituted aromatic heterocyclylcarbonyloxy", "substituted aromatic carbocyclylcarbonyl", "substituted aromatic heterocyclylcarbonyl", "substituted aromatic carbocyclyloxycarbonyl", "substituted aromatic heterocyclyloxycarbonyl", "substituted aromatic carbocyclylsulfanyl", "substituted aromatic heterocyclylsulfanyl", "substituted aromatic carbocyclylsulfinyl", "substituted aromatic heterocyclylsulfinyl", "substituted aromatic carbocyclylsulfonyl", "substituted aromatic heterocyclylsulfonyl", "substituted aromatic carbon ring formed by $R^5$ and $R^7$ together with the carbon atom to which they are attached" include the following Substituent Group B. One or more group(s) selected from the following Substituent Group B may be attached to an atom at any position on the ring.

Substituent Group B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azido, hydrazino, ureido, amidino guanidino, pentafluorothio, trialkylsilyl, alkyl substituted with Substituent Group α, alkenyl substituted with Substituent Group α, alkynyl substituted with Substituent Group α, alkyloxy substituted with Substituent Group α, alkenyloxy substituted with Substituent Group α, alkynyloxy substituted with Substituent Group α, alkylcarbonyloxy which may be substituted with Substituent Group α, alkenylcarbonyloxy which may be substituted with Substituent Group α, alkynylcarbonyloxy which may be substituted with Substituent Group α, alkylcarbonyl which may be substituted with group α, alkenylcarbonyl which may be substituted with group α, alkynylcarbonyl which may be substituted with group α, alkyloxycarbonyl which may be substituted with group α, alkenyloxycarbonyl which may be substituted with group α, alkynyloxycarbonyl which may be substituted with group α, alkylsulfanyl which may be substituted with Substituent Group α, alkenylsulfanyl which may be substituted with Substituent Group α, alkynylsulfanyl which may be substituted with Substituent Group α, alkylsulfinyl which may be substituted with Substituent Group α, alkenylsulfinyl which may be substituted with group α, alkynylsulfinyl which may be substituted with group α, alkylsulfonyl which may be substituted with group ca, alkenylsulfonyl which may be substituted with group α, alkynylsulfonyl which may be substituted with group α, amino which may be substituted with Substituent Group β, imino which may be substituted with Substituent Group β, carbamoyl which may be substituted with Substituent Group β, sulfamoyl which may be substituted with Substituent Group β, aromatic carbocyclyl which may be substituted with Substituent Group γ, non-aromatic carbocyclyl which may be substituted with Substituent Group γ', aromatic heterocyclyl which may be substituted with Substituent Group γ, non-aromatic heterocyclyl which may be substituted with Substituent Group γ', aromatic carbocyclyloxy which may be substituted with Substituent Group γ, non-aromatic carbocyclyloxy which may be substituted with Substituent Group γ', aromatic heterocyclyloxy which may be substituted with Substituent Group γ, non-aromatic heterocyclyloxy which may be substituted with Substituent Group γ', aromatic carbocyclylcarbonyloxy which may be substituted with Substituent Group γ, non-aromatic carbocyclylcarbonyloxy which may be substituted with Substituent Group γ', aromatic heterocyclylcarbonyloxy which may be substituted with Substituent Group γ, non-aromatic heterocyclylcarbonyloxy which may be substituted with Substituent Group γ', aromatic carbocyclylcarbonyl which may be substituted with group γ, non-aromatic carbocyclylcarbonyl which may be substituted with group γ', aromatic heterocyclylcarbonyl which may be substituted with group γ, non-aromatic heterocyclylcarbonyl which may be substituted with Substituent Group γ', aromatic carbocyclyloxycarbonyl which may be substituted with Substituent Group γ, non-aromatic carbocyclyloxycarbonyl which may be substituted with Substituent Group γ', aromatic heterocyclyloxycarbonyl which may be substituted with Substituent Group γ, non-aromatic heterocyclyloxycarbonyl which may be substituted with Substituent Group γ', aromatic carbocyclylalkyl which may be substituted with Substituent Group γ, non-aromatic carbocyclylalkyl which may be substituted with Substituent Group γ', aromatic heterocyclylalkyl which may be substituted with Substituent Group γ, non-aromatic heterocyclylalkyl which may be substituted with Substituent Group γ', aromatic carbocyclylalkyloxy which may be substituted with Substituent Group γ, non-aromatic carbocyclylalkyloxy which may be substituted with Substituent Group γ', aromatic heterocyclylalkyloxy which may be substituted with Substituent Group γ, non-aromatic heterocyclylalkyloxy which may be substituted with Substituent Group γ', aromatic carbocyclylalkyloxycarbonyl which may be substituted with Substituent Group γ, non-aromatic carbocyclylalkyloxycarbonyl which may be substituted with group γ', aromatic heterocyclylalkyloxycarbonyl which may be substituted with Substituent Group γ, non-aromatic heterocyclylalkyloxycarbonyl which may be substituted with Substituent Group γ', aromatic carbocyclylalkyloxyalkyl, which may be substituted with Substituent Group γ, non-aromatic carbocyclylalkyloxyalkyl which may be substituted with Substituent Group γ', aromatic heterocyclylalkyloxyalkyl which may be substituted with Substituent Group γ, non-aromatic heterocyclylalkyloxyalkyl which may be substituted with Substituent Group γ', aromatic carbocyclylsulfanyl which may be substituted with Substituent Group γ, non-aromatic carbocyclylsulfanyl which may be substituted with Substituent Group γ', aromatic heterocyclylsulfanyl which may be substituted with Substituent Group γ, non-aromatic heterocyclylsulfanyl which may be substituted with group γ', aromatic carbocyclylsulfinyl which may be substituted with group γ, non-aromatic carbocyclylsulfinyl which may be substituted with group γ', aromatic heterocyclylsulfinyl which may be substituted with Substituent Group γ, non-aromatic heterocyclylsulfinyl which may be substituted with Substituent Group γ', aromatic carbocyclylsulfonyl which may be substituted with Substituent Group γ, non-aromatic carbocyclylsulfonyl which may be substituted with Substituent Group γ', aromatic heterocyclylsulfonyl which may be substituted with Substituent Group γ, and non-aromatic heterocyclylsulfonyl which may be substituted with Substituent Group γ'.

Examples of substituents on the ring of "non-aromatic carbon ring" or "non-aromatic heterocyclic ring" for "substituted non-aromatic carbocyclyl", "substituted non-aromatic heterocyclyl", "substituted non-aromatic carbocyclyloxy", "substituted non-aromatic heterocyclyloxy", "substituted non-aromatic carbocyclylcarbonyloxy", "substituted non-aromatic heterocyclylcarbonyloxy", "substituted non-aromatic carbocyclylcarbonyl", "subustituted non-aromatic heterocyclylcarbonyl", "substituted non-aromatic carbocyclyloxycarbonyl", "substituted non-aromatic heterocyclyloxycarbonyl", "substituted non-aromatic carbocyclylsulfanyl", "substituted non-aromatic heterocyclylsulfanyl", "substituted non-aromatic carbocyclylsulfinyl", "substituted non-aromatic heterocyclylsulfinyl", "substituted non-aromatic carbocyclylsulfonyl", "substituted non-aromatic heterocyclylsulfonyl", "substituted non-aromatic carbocyclyldiyl", "substituted non-aromatic heterocyclyldiyl", "substituted non-aromatic carbocyclyloxyimino", "substituted non-aromatic carbocyclyliminooxy", "substituted non-aromatic carbon ring formed by $R^5$ and $R^7$ together with the carbon atom to which they are attached", "substituted non-aromatic carbon ring formed by $R^7$ and $R^8$ together with the carbon atom to which they are attached", "substituted non-aromatic heterocyclic ring formed by $R^7$ and $R^8$ together with the carbon atom to which they are attached" and "substituted non-aromatic heterocyclic ring formed by $R^4$ and $R^U$ together with the carbon atom to which they are attached" include the following Substituent Group C. One or more group(s) selected from the following Substituent Group C may be attached to an atom at any position of the ring.

Substituent Group C: Substituent Group B and oxo.

When "non-aromatic carbon ring" or "non-aromatic heterocyclic ring" is substituted with "oxo", it means a ring in which two hydrogen atoms on a carbon atom are substituted, as follows.

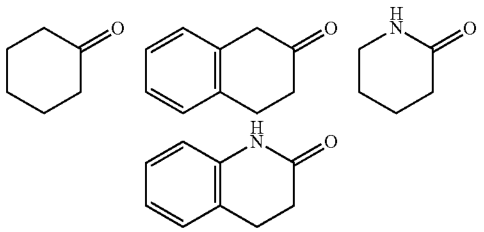

Examples of the substituent group for "substituted amino", "substituted imino", "substituted carbamoyl" and "substituted sulfamoyl" are as listed in Substituent Group D, as follows, and may be one or two groups selected from Substituent Group D.

Substituent Group D: halogen, hydroxy, carboxy, cyano, alkyl which may be substituted with Substituent Group α, alkenyl which may be substituted with Substituent Group α, alkynyl which may be substituted with Substituent Group α, alkylcarbonyl which may be substituted with Substituent Group α, and alkenylcarbonyl which may be substituted with Substituent Group α, alkynylcarbonyl which may be substituted with Substituent Group α, alkylsulfanyl which may be substituted with Substituent Group α, alkenylsulfanyl which may be substituted with Substituent Group α alkynylsulfanyl, alkylsulfinyl which may be substituted with Substituent Group α, alkenylsulfinyl which may be substituted with Substituent Group α, alkynylsulfinyl which may be substituted with Substituent Group α, alkylsulfonyl which may be substituted with Substituent Group α, alkenylsulfonyl which may be substituted with Substituent Group α, alkynylsulfonyl which may be substituted with Substituent Group α, amino which may be substituted with Substituent Group β, imino which may be substituted with Substituent Group β, carbamoyl which may be substituted with Substituent Group β, sulfamoyl which may be substituted with Substituent Group β, sulfamoyl which may be substituted with substituent group, aromatic carbocyclyl which may be substituted with Substituent Group γ, non-aromatic carbocyclyl which may be substituted with Substituent Group γ', aromatic heterocyclyl which may be substituted with Substituent Group γ, non-aromatic heterocyclyl which may be substituted with Substituent Group γ', aromatic carbocyclylalkyl which may be substituted with Substituent Group γ, non-aromatic carbocyclylalkyl which may be substituted with Substituent Group γ', aromatic heterocyclylalkyl which may be substituted with Substituent Group γ, non-aromatic heterocyclylalkyl which may be substituted with Substituent Group γ', aromatic carbocyclylcarbonyl which may be substituted with Substituent Group γ, non-aromatic carbocyclylcarbonyl which may be substituted with Substituent Group γ', aromatic heterocyclylcarbonyl which may be substituted with Substituent Group γ, non-aromatic heterocyclylcarbonyl which may be substituted with Substituent Group γ', aromatic carbocyclyloxycarbonyl which may be substituted with Substituent Group γ, non-aromatic carbocyclyloxycarbonyl which may be substituted with Substituent Group γ', aromatic heterocyclyloxycarbonyl which may be substituted with Substituent Group γ, non-aromatic heterocyclyloxycarbonyl which may be substituted with Substituent Group γ', aromatic carbocyclylsulfanyl which may be substituted with Substituent Group γ, non-aromatic carbocyclylsulfanyl which may be substituted with Substituent Group γ', aromatic heterocyclylsulfanyl which may be substituted with Substituent Group γ, non-aromatic heterocyclylsulfanyl which may be substituted with Substituent Group γ', aromatic carbocyclylsulfinyl which may be substituted with Substituent Group γ, non-aromatic carbocyclylsulfinyl which may be substituted with Substituent Group γ', aromatic heterocyclylsulfinyl which may be substituted with Substituent Group γ, non-aromatic heterocyclylsulfinyl which may be substituted with Substituent Group γ', aromatic carbocyclylsulfonyl which may be substituted with Substituent Group γ, non-aromatic carbocyclylsulfonyl which may be substituted with Substituent Group γ', aromatic heterocyclylsulfonyl which may be substituted with Substituent Group γ, and non-aromatic heterocyclylsulfonyl which may be substituted with Substituent Group γ'.

In the compound of the formula (I), prefferred embodiments for $R^1$, $R^{1B}$, $R^{1C}$, L, $R^2$, $R^3$, X, Y, U, V, W, $Z^A$, $Z^B$, $Z^C$, $R^5$, $R^6$, $R^7$, $R^8$, $R^X$, $R^Y$, $R^V$, $R^W$, $R^U$ and $R^4$ are shown below. Embodiments of the compound of the formula (I) include any combination of the following specific examples.

$R^1$ is carboxy, cyano, substituted or unsubstituted aromatic heterocyclyl, —C(=O)—$NR^{1B}R^{1C}$ or —CH=CHC(=O)—OH; wherein $R^{1B}$ and $R^{1C}$ are each independently a hydrogen atom, substituted or unsubstituted alkyl, substituted or unsubstituted aminosulfonyl or substituted or unsubstituted non-aromatic heterocyclylsulfonyl (hereinafter referred to as a-1).

$R^1$ is carboxy or —C(=O)—$NR^{1B}R^{1C}$; wherein $R^{1B}$ and $R^{1C}$ are each independently a hydrogen atom, substituted or unsubstituted alkyl, substituted or unsubstituted aminosulfonyl, or substituted or unsubstituted non-aromatic heterocyclylsulfonyl (hereinafter referred to as a-2).

$R^1$ is carboxy (hereinafter referred to as a-3).

L is substituted or unsubstituted non-aromatic carbocyclyldiyl, substituted or unsubstituted non-aromatic heterocyclyldiyl or substituted or unsubstituted alkylene (hereinafter referred to as b-1).

L is substituted or unsubstituted non-aromatic carbocyclyldiyl or substituted or unsubstituted non-aromatic heterocyclyldiyl (hereinafter referred to as b-2).

L is substituted or unsubstituted non-aromatic carbocyclyldiyl (hereinafter referred to as b-3).

L is substituted or unsubstituted adamantanediyl or substituted or unsubstituted cyclohexanediyl (hereinafter referred to as b-4).

L is substituted or unsubstituted adamantane-2,2-diyl or substituted or unsubstituted cyclohexane-1,1-diyl (hereinafter referred to as b-5).

L is non-aromatic carbocyclyldiyl substituted with one or more substituent(s) selected from Substituent Group a (Substituent Group a: cyano, alkyloxy, hydroxy and halogen) or unsubstituted non-aromatic carbocyclyldiyl (hereinafter referred to as b-6).

L is adamantanediyl substituted with one or more substituent(s) selected from Substituent Group a, or unsubstituted adamantanediyl (hereinafter referred to as b-7).

L is adamantane-2,2-diyl substituted with one or more substituent(s) selected from Substituent Group a, or unsubstituted adamantane-2,2-diyl (hereinafter referred to as b-8).

L is cyclohexanediyl substituted with halogen or unsubstituted cyclohexanediyl (hereinafter referred to as b-9).

L is cyclohexane-1,1-diyl substituted with halogen or unsubstituted cyclohexane-1,1-diyl (hereinafter referred to as b-10).

L is adamantanediyl substituted with one or more substituent(s) selected from Substituent Group a, unsubstituted adamantanediyl, cyclohexanediyl substituted with halogen or unsubstituted cyclohexanediyl (hereinafter referred to as b-11).

L is adamantane-2,2-diyl substituted with one or more substituent(s) selected from Substituent Group a, unsubstituted adamantane-2,2-diyl, cyclohexane-1,1-diyl substituted with halogen or unsubstituted cyclohexane-1,1-diyl (hereinafter referred to as b-12).

L is adamantane-2,2-diyl substituted with one or more substituent(s) selected from Substituent Group a (hereinafter referred to as b-13).

L is unsubstituted adamantane-2,2-diyl (hereinafter referred to as b-14).

L is cyclohexane-1,1-diyl substituted with halogen (hereinafter referred to as b-15).

L is unsubstituted cyclohexane-1,1-diyl (hereinafter referred to as b-16).

$R^2$ is substituted or unsubstituted alkyl (hereinafter referred to as c-1).

$R^2$ is alkyl substituted with halogen or unsubstituted alkyl (hereinafter referred to as c-2).

$R^2$ is alkyl substituted with halogen (hereinafter referred to as c-3).

$R^3$ is a hydrogen atom, substituted or unsubstituted alkyl, substituted or unsubstituted alkyloxy, substituted or unsubstituted amino, or substituted or unsubstituted carbamoyl (hereinafter referred to as d-1).

$R^3$ is a hydrogen atom, substituted or unsubstituted alkyl, substituted or unsubstituted alkyloxy or substituted or unsubstituted amino (hereinafter referred to as d-2).

$R^3$ is a hydrogen atom or substituted or unsubstituted alkyl (hereinafter referred to as d-3).

$R^3$ is a hydrogen atom or alkyl substituted with one or more substituent(s) selected from Substituent Group b (Substituent Group b: dialkylamino, amino and hydroxy) or unsubstituted alkyl (hereinafter referred to as d-4).

$R^3$ is a hydrogen atom (hereinafter referred to as d-5).

X is $=CR^X-$ or $=N-$, wherein $R^X$ is a hydrogen atom, cyano, halogen, substituted or unsubstituted alkyl or substituted or unsubstituted carbamoyl (hereinafter referred to as e-1).

X is $=CR^X-$ or $=N-$, wherein $R^X$ is a hydrogen atom, halogen or substituted or unsubstituted alkyl (hereinafter referred to as e-2).

X is $=CR^X-$ or $=N-$, wherein $R^X$ is a hydrogen atom, halogen or unsubstituted alkyl (hereinafter referred to as e-3).

X is $=CH-$ or $=N-$ (hereinafter referred to as e-4).

X is $=CH-$ (hereinafter referred to as e-5).

X is $=N-$ (hereinafter referred to as e-6).

Y is $=CR^Y-$ or $=N-$, wherein $R^Y$ is a hydrogen atom, cyano, halogen, substituted or unsubstituted alkyl or substituted or unsubstituted carbamoyl (hereinafter referred to as f-1).

Y is $=CR^Y-$ or $=N-$, wherein $R^Y$ is a hydrogen atom or halogen (hereinafter referred to as f-2).

Y is $=CH-$ or $=N-$ (hereinafter referred to as f-3).

Y is $=CH-$ (hereinafter referred to as f-4).

Y is $=N-$ (hereinafter referred to as f-5).

U is $-CR^U=$ or $-N=$, wherein $R^U$ is a hydrogen atom, substituted or unsubstituted alkyloxy, substituted or unsubstituted non-aromatic heterocyclyloxy, substituted or unsubstituted non-aromatic carbocyclyloxy, substituted or unsubstituted alkyl, substituted or unsubstituted alkenyl, substituted or unsubstituted amino, hydroxy, halogen, substituted or unsubstituted aromatic carbocyclyl, substituted or unsubstituted aromatic heterocyclyl, substituted or unsubstituted non-aromatic heterocyclyl or substituted or unsubstituted non-aromatic carbocyclyl (hereinafter referred to as g-1).

U is $-CR^U=$ or $-N=$, wherein $R^U$ is a hydrogen atom, halogen, substituted or unsubstituted non-aromatic carbocyclyloxy, substituted or unsubstituted non-aromatic heterocyclyloxy or substituted or unsubstituted alkyloxy (hereinafter referred to as g-2).

U is $-CR^U=$ or $-N=$, wherein $R^U$ is a hydrogen atom, halogen, non-aromatic carbocyclyloxy substituted with pyrazolyl or unsubstituted non-aromatic carbocyclyloxy, non-aromatic heterocyclyloxy substituted with oxetanyl or unsubstituted non-aromatic heterocyclyloxy, or unsubstituted alkyloxy (hereinafter referred to as g-3).

U is $-CH=$ or $-N=$(hereinafter referred to as g-4).

U is $-CH=$(hereinafter referred to as g-5).

U is $-N=$(hereinafter referred to as g-6).

V is $-CR^V=$ or $-N=$, wherein $R^V$ is a hydrogen atom, cyano, halogen, substituted or unsubstituted alkyl or substituted or unsubstituted carbamoyl (hereinafter referred to as h-1) V is $-CR^V=$ or $-N=$, wherein $R^V$ is a hydrogen atom, cyano or substituted or unsubstituted carbamoyl (hereinafter referred to as h-2).

V is $-CR^V=$ or $-N=$, wherein $R^V$ is a hydrogen atom, cyano or unsubstituted carbamoyl (hereinafter referred to as h-3).

V is $-CH=$ or $-N=$(hereinafter referred to as h-4).

V is $-CH=$(hereinafter referred to as h-5).

V is $-N=$(hereinafter referred to as h-6).

W is $=CR^W-$ or $=N-$, wherein $R^W$ is a hydrogen atom, cyano, halogen, substituted or unsubstituted alkyl or substituted or unsubstituted carbamoyl (hereinafter referred to as i-1).

W is $=CH-$ or $=N-$ (hereinafter referred to as i-2).

W is $=CH-$ (hereinafter referred to as i-3).

W is $=N-$ (hereinafter referred to as i-4).

$Z^A$ is $-C=$ or $-N-$ (hereinafter referred to as j-1).

$Z^A$ is $-C=$(hereinafter referred to as j-2).

$Z^A$ is $-N-$ (hereinafter referred to as j-3).

$Z^B$ is $-CR^5R^6-$, $-CR^5=$, $-NR^5-$ or $-N=$, wherein $R^5$ and $R^6$ are each independently a hydrogen atom, substituted or unsubstituted non-aromatic heterocyclyl, hydroxy or substituted or unsubstituted alkyl, or $R^5$ and $R^6$ are taken together to form oxo (hereinafter referred to as k-1).

$Z^B$ is $-CR^5R^6-$, $-CR^5=$ or $-NR^5-$, wherein $R^5$ and $R^6$ are each independently a hydrogen atom, substituted or unsubstituted non-aromatic heterocyclyl, hydroxy or substituted or unsubstituted alkyl, or $R^5$ and $R^6$ are taken together to form oxo (hereinafter referred to as k-2).

$Z^B$ is $-CR^5R^6-$ or $-CR^5=$, wherein $R^5$ and $R^6$ are each independently a hydrogen atom, substituted or unsubstituted non-aromatic heterocyclyl, hydroxy or substituted or unsubstituted alkyl, or $R^5$ and $R^6$ are taken together to form oxo (hereinafter referred to as k-3).

$Z^B$ is $-CR^5R^6-$, wherein $R^5$ and $R^6$ are each independently a hydrogen atom, substituted or unsubstituted non-aromatic heterocyclyl, hydroxy or substituted or unsubstituted alkyl, or $R^5$ and $R^6$ are taken together to form oxo (hereinafter referred to as k-4).

$Z^B$ is —$CR^5$═, wherein $R^5$ is a hydrogen atom, substituted or unsubstituted non-aromatic heterocyclyl, hydroxy or substituted or unsubstituted alkyl (hereinafter referred to as k-5).

$Z^B$ is —$CR^5R^6$— or —$CR^5$═, wherein $R^5$ and $R^6$ are each independently a hydrogen atom, substituted or unsubstituted non-aromatic heterocyclyl, or $R^5$ and $R^6$ are taken together to form oxo (hereinafter referred to as k-6).

$Z^B$ is —$CR^5R^6$—, wherein $R^5$ and $R^6$ are each independently a hydrogen atom, substituted or unsubstituted non-aromatic heterocyclyl, or $R^5$ and $R^6$ are taken together to form oxo (hereinafter referred to as k-7).

$Z^B$ is —$CR^5$═, wherein $R^5$ is a hydrogen atom or substituted or unsubstituted non-aromatic heterocyclyl (hereinafter referred to as k-8).

$Z^B$ is —$CR^5R^6$— or —$CR^5$═, wherein $R^5$ and $R^6$ are each independently a hydrogen atom (hereinafter referred to as k-9).

$Z^B$ is —$CR^5R^6$—, wherein $R^5$ and $R^6$ are each independently a hydrogen atom (hereinafter referred to as k-10).

$Z^B$ is —$CR^5$═, wherein $R^5$ is a hydrogen atom (hereinafter referred to as k-11).

$Z^B$ is —$CR^5R^6$— or —$CR^5$═, wherein $R^5$ and $R^6$ are each independently a hydrogen atom or unsubstituted non-aromatic heterocyclyl, or $R^5$ and $R^6$ are taken together to form oxo (hereinafter referred to as k-12).

$Z^B$ is —$CR^5R^6$—, wherein $R^5$ and $R^6$ are each independently a hydrogen atom or unsubstituted non-aromatic heterocyclyl, or $R^5$ and $R^6$ are taken together to form oxo (hereinafter referred to as referred to as k-13).

$Z^B$ is —$CR^5$═, wherein $R^5$ is a hydrogen atom or unsubstituted non-aromatic heterocyclic (hereinafter referred to as k-14).

$Z^B$ is —$CH_2$— (hereafter referred to as k-15).

$Z^B$ is —CH═(hereafter referred to as k-16).

$Z^C$ is —$CR^7R^8$—, —$CR^7$═, —$NR^7$— or ═N—, wherein $R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, substituted or unsubstituted alkylsulfonyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as 1-1).

$Z^C$ is —$CR^7R^8$—, —$CR^7$═ or —$NR^7$—, wherein $R^7$ and $R^a$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, substituted or unsubstituted alkylsulfonyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as 1-2).

$Z^C$ is —$CR^7R^8$— or —$NR^7$—, wherein $R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, substituted or unsubstituted alkylsulfonyl, or $R^7$ and $R^8$ are taken together with the carbon atom to which they are attached to form a substituted or unsubstituted non-aromatic carbon ring or a substituted or unsubstituted non-aromatic heterocyclic ring. (hereinafter referred to as 1-3).

$Z^C$ is —$CR^7R^8$—, wherein $R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, substituted or unsubstituted alkylsulfonyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as 1-4).

$Z^C$ is —$NR^7$—, wherein $R^7$ is a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl or substituted or unsubstituted alkylsulfonyl (hereinafter referred to as 1-5).

$Z^C$ is —$CR^7R^8$— or —$NR^7$—, wherein $R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as 1-6).

$Z^C$ is —$CR^7R^8$—, wherein $R^7$ and $R^8$ are each independently a hydrogen atom, substituted or unsubstituted alkyl, substituted or unsubstituted non-aromatic carbocyclyl, substituted or unsubstituted non-aromatic heterocyclyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as 1-7).

$Z^C$ is —$NR^7$—, wherein $R^7$ is a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, or substituted or unsubstituted non-aromatic carbocyclylsulfonyl (hereinafter referred to as 1-8).

$Z^C$ is —$CR^2R^8$— or —$NR^7$—, wherein $R^7$ and $R^8$ are each independently a hydrogen atom, alkyl substituted with one or more substituent(s) selected from Substituent Group c (Substituent Group c: halogen, hydroxy, alkyloxy, non-aromatic carbocyclyl, non-aromatic carbocyclyl substituted with halogen, non-aromatic heterocyclyl, non-aromatic heterocyclylcarbonyl and aromatic carbocyclyl) or unsubstituted alkyl, non-aromatic carbocyclyl substituted with one or more substituent(s) selected from Substituent Group d (Substituent Group d: halogen, alkyloxy, cyano, hydroxy, haloalkyl and alkyloxy substituted with phenyl) or unsubstituted non-aromatic carbocyclyl, non-aromatic heterocyclyl substituted with haloalkyl or unsubstituted non-aromatic heterocyclyl, aromatic carbocyclyl substituted with one or more substituent(s), selected from Substituent Group e (Substituent Group e: halogen, alkyl, haloalkyl, alkyloxy and cyano) or unsubstituted aromatic carbocyclyl, aromatic heterocyclyl substituted with one or more substituent(s) selected from Substituent Group f (Substituent Group group f: alkyl, halogen, haloalkyl, alkyloxy, hydroxy and cyano) or unsubstituted aromatic heterocyclyl, unsubstituted non-aromatic carbocyclyloxycarbonyl, unsubstituted non-aromatic heterocyclyloxycarbonyl, unsubstituted non-aromatic carbocyclylsulfonyl, or $R^7$ and $R^8$ are taken together with the carbon atom to which they are attached to form a non-aromatic carbon ring substituted with halogen or a unsubstituted non-aromatic carbon ring or to form a non-aromatic heterocyclic ring substituted with one or more substituent(s) selected from Substituent Group g (Substituent Group g: alkyl, haloalkyl, alkylcarbonyl, alkyloxycarbonyl substituted with phenyl, alkyloxycarbonyl, non-aromatic heterocyclyl, alkylcarbamoyl, non-aromatic carbocyclyl, aromatic heterocyclyl and aromatic heterocyclyl substituted with halogen) or a unsubstituted non-aromatic heterocyclic ring (hereinafter referred to as referred to as 1-9).

$Z^C$ is —$CR^7R^8$—, wherein $R^7$ and $R^8$ are each independently a hydrogen atom, unsubstituted alkyl, unsubstituted non-aromatic carbocyclyl, unsubstituted non-aromatic heterocyclyl, or $R^7$ and $R^8$ are taken together with the carbon atom to which they are attached to form a non-aromatic carbon ring substituted with halogen or a unsubstituted non-aromatic carbon ring or to form a non-aromatic heterocyclic ring subsitituted with one or more substituent(s) selected from Substituent Group g or a unsubstituted non-aromatic heterocyclic ring (hereinafter referred to as 1-10).

$Z^C$ is —$NR^7$—, wherein $R^7$ is a hydrogen atom, alkyl substituted with one or more substituent(s) selected from Substituent Group c or unsubstituted alkyl, non-aromatic carbocyclyl substituted with one or more substituent(s) selected from Substituent Group d or unsubstituted non-aromatic carbocyclyl, non-aromatic heterocyclyl substituted with haloalkyl or unsubstituted non-aromatic heterocyclyl, aromatic carbocyclyl substituted with one or more substituent(s) selected from Substituent Group e or unsubstituted aromatic carbocyclyl, aromatic heterocyclyl substituted with one or more substituent(s) selected from Substituent Group f or unsubstituted aromatic heterocyclyl, unsubstituted non-aromatic carbocyclyloxycarbonyl, unsubstituted non-aromatic heterocyclyloxycarbonyl, or unsubstituted non-aromatic carbocyclylsulfonyl (hereinafter referred to as referred to as 1-11).

$Z^C$ is —$CR^7R^8$—, wherein $R^7$ and $R^8$ are each independently unsubstituted alkyl (hereinafter referred to as 1-12).

$Z^C$ is —$NR^7$—, wherein $R^7$ is unsubstituted alkyl (hereinafter referred to as 1-13).

$R^4$ is a hydrogen atom, substituted or unsubstituted alkyloxy, substituted or unsubstituted non-aromatic heterocyclyloxy, substituted or unsubstituted non-aromatic carbocyclyloxy, substituted or unsubstituted aromatic carbocyclyloxy, substituted or unsubstituted aromatic heterocyclyloxy, substituted or unsubstituted alkyl, substituted or unsubstituted alkenyl, substituted or unsubstituted amino, substituted or unsubstituted carbamoyl, hydroxy, halogen, substituted or unsubstituted aromatic carbocyclyl, substituted or unsubstituted aromatic heterocyclyl, substituted or unsubstituted non-aromatic carbocyclyl or substituted or unsubstituted non-aromatic heterocyclylcarbonyl, or $R^4$ and $R^U$ are taken together with the carbon atom to which they are attached to form a substituted or unsubstituted non-aromatic heterocyclic ring (hereinafter referred to as m-1).

$R^4$ is substituted or unsubstituted alkyloxy, substituted or unsubstituted non-aromatic heterocyclyloxy, substituted or unsubstituted non-aromatic carbocyclyloxy, substituted or unsubstituted aromatic carbocyclyloxy, substituted or unsubstituted aromatic heterocyclyloxy, substituted or unsubstituted alkyl, substituted or unsubstituted alkenyl, substituted or unsubstituted amino, substituted or unsubstituted carbamoyl, hydroxy, halogen, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclylcarbonyl, or $R^4$ and $R^U$ are taken together with the carbon atom to which they are attached to form a substituted or unsubstituted non-aromatic heterocyclic ring (hereinafter referred to as referred to as m-2).

$R^4$ is substituted or unsubstituted alkyloxy, substituted or unsubstituted non-aromatic heterocyclyloxy, substituted or unsubstituted non-aromatic carbocyclyloxy, substituted or unsubstituted aromatic carbocyclyloxy, substituted or unsubstituted alkyl, substituted or unsubstituted alkenyl, substituted or unsubstituted amino, substituted or unsubstituted carbamoyl, hydroxy, halogen, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclylcarbonyl, or $R^4$ and $R^U$ are taken together with the carbon atom to which they are attached to form a substituted or unsubstituted non-aromatic heterocyclic ring (hereinafter referred to as m-3).

$R^4$ is alkyloxy substituted with one or more substituent(s) selected from Substituent Group h (Substituent Group h: halogen, hydroxy, alkyloxy, cyano, alkylcarbonyloxy, substituted aromatic heterocyclyl (substituents: alkyl or alkyloxy), non-aromatic heterocyclyl, substituted non-aromatic heterocyclyl (substituents: aromatic heterocyclyl, alkyl or halogen), aromatic heterocyclylamino, aromatic carboyclyl, and aromatic carbocyclyl substituted with alkyloxy) or unsubstituted alkyloxy; non-aromatic heterocyclyloxy substituted with one or more substituent(s) selected from Substituent Group j (Substituent Group j: alkyl, halogen, haloalkyl, cyanoalkyl, alkylcarbonyl, alkylcarbamoyl, alkyloxycarbonyl, alkyloxyalkyl, alkylsulfonylalkyl, non-aromatic heterocyclyl, substituted aromatic heterocyclyl (substituents: alkyl, alkyloxy, halogen, haloalkyl or cyano), aromatic heterocyclyl, non-aromatic carbocyclyl, non-aromatic carbocyclyl substituted with halogen, substituted non-aromatic heterocyclyl (substituents: halogen or alkylcarbonyl), non-aromatic heterocyclylalkyl, non-aromatic carbocyclylalkyl, non-aromatic carbocyclylalkyl substituted with halogen, aromatic heterocyclylalkyl substituted with alkyl, non-aromatic heterocyclylcarbonyl, non-aromatic carbocyclylcarbonyl, aromatic heterocyclylcarbonyl, aromatic carbocyclylalkyloxycarbonyl, and non-aromatic carbocyclylsulfonyl) or unsubstituted non-aromatic heterocyclyloxy;

non-aromatic carbocyclyloxy substituted with one or more substituent(s) selected from Substituent Group k (Substituent Group k: alkyl, halogen, haloalkyl, alkyloxy, alkylsulfonyl, haloalkylamino, alkylamino, aromatic heterocyclyl, non-aromatic heterocyclyl substituted with halogen, non-aromatic heterocyclyl, aromatic heterocyclyl substituted with halogen, aromatic heterocyclylamino substituted with halogen, non-aromatic heterocyclylalkyl substituted with halogen, non-aromatic carbocyclyloxy, and non-aromatic carbocyclyliminooxy substituted with halogen) or unsubstituted non-aromatic carbocyclyloxy;

aromatic carbocyclyloxy;

alkyl or substituted with one or more substituent(s) selected from Substituent Group 1 (Substituent Group 1: halogen, aromatic carbocyclyl, aromatic carbocyclyl substituted with alkyloxy, non-aromatic heterocyclyl, and substituted non-aromatic heterocyclyl (substituents: aromatic heterocyclyl, non-aromatic heterocyclyl subsittuted with alkyl or halogen), and non-aromatic carboyclyloxyimino substituted with halogen) or unsubstituted alkyl;

alkenyl substituted with one or more substituent(s) selected from Substituent Group m (Substituent Group m: aromatic carbocyclyl substituted with alkyloxy, non-aromatic heterocyclyl, and non-aromatic heterocyclyl substituted with aromatic carbocyclylalkyloxycarbonyl) or unsubstituted alkenyl;

amino substituted with one or more substituent(s) selected from Substituent Group n (Substituent Group n: aromatic carbocyclylalkyl substituted with alkyloxy, aromatic carbocyclylcarbonyl substituted with alkyloxy, non-aromatic heterocyclyl substituted with aromatic heterocyclyl, aromatic heterocyclyl, aromatic carbocyclylsulfonyl, aromatic carbocyclylcarbonyl, alkyl, and aromatic heterocyclyl substituted with haloalkyl) or unsubstituted amino;

carbamoyl substituted with haloalkyl or unsubstituted carbamoyl;

hydroxy;

halogen;

aromatic carbocyclyl substituted with alkyloxyalkyl or unsubstituted aromatic carbocyclyl;

unsubstituted aromatic hetrocyclyl;

non-romatic hetrocyclyl substituted with one or more substituent(s) selected from Substituent Group o (Substituent Group o: aromatic heterocyclyl, aromatic carbocyclylalkyl, aromatic heterocyclylalkyl, and haloalkyl) or unsubstituted non-aromatic hetrocyclyl;

non-aromatic carbocyclyl substituted with one or more substituent(s) selected from Substituent Group p (Substituent Group p: carbamoyl and dialkylcarbamoyl) or unsubstituted non-aromatic carbocyclyl;

non-aromatic heterocyclylcarbonyl substituted with one or more substituent(s) selected from Substituent Group q (Substituent Group q: aromatic heterocyclyl, haloalkyl, non-aromatic heterocyclyl substituted with halogen, aromatic heterocyclyl substituted with halogen, halogen, and alkyloxy) or unsubstituted non-aromatic heterocyclylcarbonyl;

non-aromatic carbocyclyloxyimino substituted with halogen; or $R^4$ and $R^U$ are taken together with the carbon atom to which they are attached to form a non-aromatic heterocyclic ring substituted with halogen or a unsubstituted non-aromatic heterocyclic ring (hereinafter referred to as m-4).

$R^4$ is substituted or unsubstituted alkyloxy, substituted or unsubstituted non-aromatic heterocyclyloxy, substituted or unsubstituted non-aromatic carbocyclyloxy, substituted or unsubstituted carbamoyl, or substituted or unsubstituted non-aromatic heterocyclylcarbonyl (hereinafter referred to as referred to as m-5).

$R^4$ is alkyloxy substituted with one or more substituent(s) selected from Substituent Group h or unsubstituted alkyloxy, non-aromatic heterocyclyloxy substituted with one or more substituent(s) selected from Substituent Group j or unsubstituted non-aromatic heterocyclyloxy, non-aromatic carbocyclyloxy substituted with one or more substituent(s) selected from Substituent Group k or unsubstituted non-aromatic carbocyclyloxy, carbamoyl substituted with haloalkyl or unsubisttuted carbamoyl, or non-aromatic heterocyclylcarbonyl substituted with one or more substituent(s) selected from Substituent Group q or unsubstituted non-aromatic heterocyclylcarbonyl (hereinafter referred to as m-6).

$R^4$ is substituted or unsubstituted alkyloxy, substituted or unsubstituted non-aromatic heterocyclyloxy, or substituted or unsubstituted non-aromatic carbocyclyloxy (hereinafter referred to as m-7).

$R^4$ is alkyloxy substituted with one or more substituent(s) selected from Substituent Group h or unsubstituted alkyloxy, non-aromatic heterocyclyloxy substituted with one or more substituent(s) selected from Substituent Group j or unsubstituted non-aromatic heterocyclyloxy, or non-aromatic carbocyclyloxy substituted with one or more substituent(s) selected from Substituent Group k or unsubstituted non-aromatic carbocyclyloxy (hereinafter referred to as m-8).

$R^4$ is substituted or unsubstituted alkyloxy (hereinafter referred to as m-9).

$R^4$ is alkyloxy substituted with one or more substituent(s) selected from Substituent Group h or unsubstituted alkyloxy (hereinafter referred to as m-10).

$R^4$ is substituted or unsubstituted non-aromatic heterocyclyloxy (hereinafter referred to as m-11).

$R^4$ is non-aromatic heterocyclyloxy substituted with one or more substituent(s) selected from Substituent Group j or unsubstituted non-aromatic heterocyclyloxy (hereinafter referred to as m-12).

$R^4$ is substituted or unsubstituted non-aromatic carbocyclyloxy (hereinafter referred to as m-13).

$R^4$ is non-aromatic carbocyclyloxy substituted with one or more substituent(s) selected from Substituent Group k or unsubstituted non-aromatic carbocyclyloxy (hereinafter referred to as m-14).

$R^4$ is non-aromatic carbocyclyloxy substituted with one or more substituent(s) selected from Substituent Group k (hereinafter referred to as m-15).

$R^4$ is substituted non-aromatic carbocyclyloxy (substituent: non-aromatic heterocyclyl substituted with halogen) (hereinafter referred to as m-16).

$R^4$ is substituted non-aromatic heterocyclyloxy (substituents: aromatic heterocyclyl) (hereinafter referred to as m-17).

$R^4$ is substituted non-aromatic heterocyclyloxy (substituents: aromatic heterocyclyl substituted with halogen) (hereinafter referred to as m-18).

$R^4$ is substituted non-aromatic heterocyclyloxy (substituents: haloalkyl) (hereinafter referred to as m-19).

$R^4$ is substituted non-aromatic carbocyclyloxy (substituent: haloalkylamino) (hereinafter referred to as m-20).

Furthermore, examples of the compound of formula (I) encompass all combination of the specific examples as shown below.

Preferred embodiments of the group of the formula:

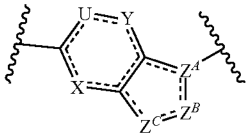

and $R^1$, $R^{1B}$, $R^{1C}$, L, $R^2$, $R^3$, V, W, $R^5$, $R^6$, $R^7$, $R^8$, $R^X$, $R^Y$, $R^Y$, $R^W$, $R^U$ and $R^4$ are shown below.

The group of the formula:

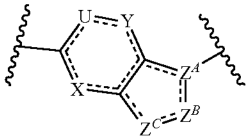

is one represented by the formula (I-a), (I-b), (I-c), (I-d), (I-e), (I-f), (I-g), (I-h) or (I-i) as follows.

(I-a)

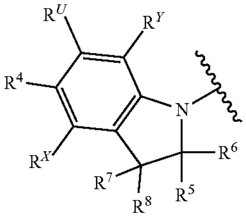

, (I-b)

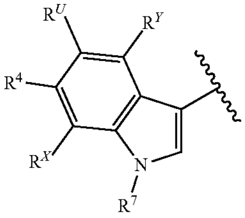

, (I-c)

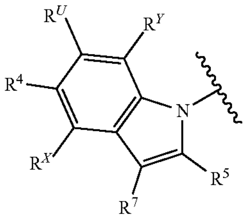

, (I-d)

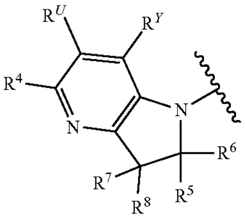

,

-continued (I-e)

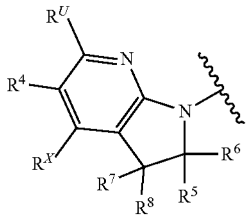

, (I-f)

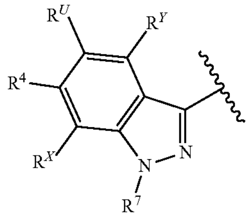

, (I-g)

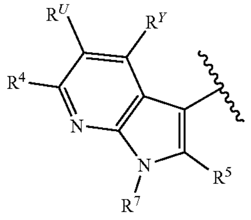

, (I-h)

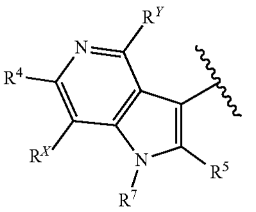

or (I-i)

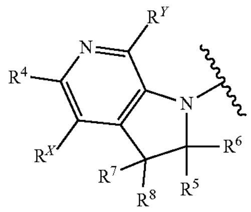

The group of the formula:

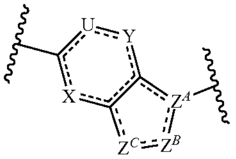

is one represented by the formula (I-a), (I-b), (I-h) or (I-i).

The group of the formula:

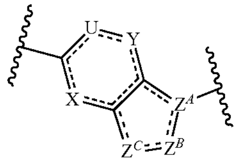

is one represented by the formula (I-a), (I-b) or (I-i).

The group of the formula:

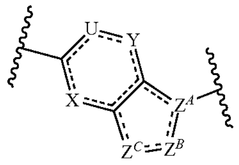

is one represented by the formula (I-a) or (I-b).

The group of the formula:

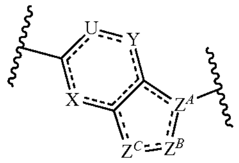

is one represented by the formula (I-a).

The group of the formula:

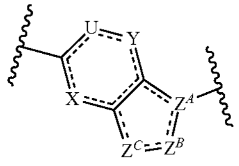

is one represented by the formula (I-b).

$R^X$ is a hydrogen atom, cyano, halogen, substituted or unsubstituted alkyl or substituted or unsubstituted carbamoyl (hereinafter referred to as ee-1).

$R^X$ is a hydrogen atom, halogen or substituted or unsubstituted alkyl (hereinafter referred to as ee-2).

$R^X$ is a hydrogen atom, halogen or unsubstituted alkyl (hereinafter referred to as ee-3)

$R^X$ is a hydrogen atom (hereinafter referred to as ee-4).

$R^Y$ is a hydrogen atom, cyano, halogen, substituted or unsubstituted alkyl or substituted or unsubstituted carbamoyl (hereinafter referred to as ff-1).

$R^Y$ is a hydrogen atom or halogen (hereinafter referred to as ff-2).

$R^Y$ is a hydrogen atom (hereinafter referred to as ff-3).

$R^U$ is a hydrogen atom, substituted or unsubstituted alkyloxy, substituted or unsubstituted non-aromatic heterocyclyloxy, substituted or unsubstituted non-aromatic carbocyclyloxy, substituted or unsubstituted alkyl, substituted or unsubstituted alkenyl, substituted or unsubstituted amino, hydroxy, halogen, substituted or unsubstituted aromatic carbocyclyl, substituted or unsubstituted aromatic heterocyclyl, substituted or unsubstituted non-aromatic heterocyclyl or substituted or unsubstituted non-aromatic carbocyclyl (hereinafter referred to as gg-1).

$R^U$ is a hydrogen atom, halogen, substituted or unsubstituted non-aromatic carbocyclyloxy, substituted or unsubstituted non-aromatic heterocyclyloxy or substituted or unsubstituted alkyloxy (hereinafter referred to as gg-2).

$R^U$ is a hydrogen atom, halogen, non-aromatic carbocyclyloxy substituted with pyrazolyl or unsubstituted non-aromatic carbocyclyloxy, non-aromatic heterocyclyloxy substituted with oxetanyl or unsubstituted non-aromatic heterocyclyloxy, or unsubstituted alkyloxy (hereinafter referred to as gg-3).

$R^U$ is a hydrogen atom (hereinafter referred to as gg-4).

$R^5$ and $R^6$ are each independently a hydrogen atom, substituted or unsubstituted non-aromatic heterocyclyl, hydroxy or substituted or unsubstituted alkyl, or $R^5$ and $R^6$ are taken together to form oxo (hereinafter referred to as kk-1).

$R^5$ is a hydrogen atom, substituted or unsubstituted non-aromatic heterocyclyl, hydroxy or substituted or unsubstituted alkyl (hereinafter referred to as kk-5).

$R^5$ and $R^6$ are each independently a hydrogen atom, substituted or unsubstituted non-aromatic heterocyclyl, or $R^5$ and $R^6$ are taken together to form oxo (hereinafter referred to as kk-6).

$R^5$ is a hydrogen atom, substituted or unsubstituted non-aromatic heterocyclyl (hereinafter referred to as kk-8).

$R^5$ and $R^6$ are each independently a hydrogen atom (hereinafter referred to as kk-9).

$R^5$ is a hydrogen atom (hereinafter referred to as kk-10).

$R^5$ and $R^6$ are each independently a hydrogen atom, unsubstituted non-aromatic heterocyclyl, or $R^5$ and $R^6$ are taken together to form oxo (hereinafter referred to as kk-12).

$R^5$ is a hydrogen atom or unsubstituted non-aromatic heterocyclyl (hereinafter referred to as kk-14).

$R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, substituted or unsubstituted alkylsulfonyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as ll-1).

$R^7$ is a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl or substituted or unsubstituted alkylsulfonyl (hereinafter referred to as ll-5).

$R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted, non-aromatic heterocyclyloxycarbonyl, substituted or unsubstituted non-aromatic carbocyclylsulfonyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as ll-6).

$R^7$ and $R^8$ are each independently a hydrogen atom, substituted or unsubstituted alkyl, substituted or unsubstituted non-aromatic carbocyclyl, substituted or unsubstituted non-aromatic heterocyclyl, or $R^7$ and $R^8$ are taken together with the carbon atom to which they are attached to form a substituted or unsubstituted non-aromatic carbon ring or a substituted or unsubstituted non-aromatic heterocyclic ring (hereinafter referred to as ll-7).

$R^7$ is a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, or substituted or unsubstituted non-aromatic carbocyclylsulfonyl (hereinafter referred to as ll-8).

$R^7$ and $R^8$ are each independently a hydrogen atom, alkyl substituted with one or more substituent(s) selected from Substituent Group c or unsubstituted alkyl, non-aromatic carbocyclyl substituted with one or more substituent(s) selected from Substituent Group d or unsubstituted non-aromatic carbocyclyl, non-aromatic heterocyclyl substituted with haloalkyl or unsubstituted non-aromatic heterocyclyl, aromatic carbocyclyl substituted with one or more substituent(s) selected from Substituent Group e or unsubstituted aromatic carbocyclyl, aromatic heterocyclyl substituted with one or more substituent(s) selected from Substituent Group f or unsubstituted aromatic heterocyclyl, unsubstituted non-aromatic carbocyclyloxycarbonyl, unsubstituted non-aromatic heterocyclyloxycarbonyl, unsubstituted non-aromatic carbocyclylsulfonyl, or $R^7$ and $R^8$ are taken together with the carbon atom to which they are attached to form a non-aromatic carbon ring substituted with halogen or a unsubstituted non-aromatic carbon ring or non-aromatic heterocyclic ring substituted with one or more substituent(s) selected from Substituent Group g or unsubstituted non-aromatic heterocyclic ring (hereinafter referred to as ll-9).

$R^7$ and $R^8$ are each independently a hydrogen atom, unsubstituted alkyl, unsubstituted non-aromatic, carbocyclyl, unsubstituted non-aromatic heterocyclyl, or $R^7$ and $R^8$ are taken together with the carbon atom to which they are attached to form a non-aromatic carbon ring substituted with halogen or a unsubstituted non-aromatic carbon ring or a non-aromatic heterocyclic ring substituted with one or more substituent(s) selected from Substituent Group g or a unsubstituted non-aromatic heterocyclic ring (hereinafter referred to as ll-10).

$R^7$ and $R^8$ are each independently unsubstituted alkyl (hereinafter referred to as ll-11).

$R^7$ is a hydrogen atom, alkyl substituted with one or more substituent(s) selected from Substituent Group c or unsubstituted alkyl, non-aromatic carbocyclyl substituted with one or more substituent(s) selected from Substituent Group d or unsubstituted non-aromatic carbocyclyl, non-aromatic heterocyclyl substituted with haloalkyl or unsubstituted non-aromatic heterocyclyl, aromatic carbocyclyl substituted with one or more substituent(s) selected from Substituent Group e or unsubstituted aromatic carbocyclyl, aromatic heterocyclyl substituted with one or more substituent(s) selected from Substituent Group f or unsubstituted aromatic heterocyclyl, unsubstituted non-aromatic carbocyclyloxycarbonyl, unsubstituted non-aromatic heterocyclyloxycarbonyl or unsubstituted non-aromatic carbocyclylsulfonyl (hereinafter referred to as ll-12).

$R^7$ is unsubstituted alkyl (hereinafter referred to as ll-13).

$R^7$ and $R^8$ are taken together with the carbon atom to which they are attached to form a unsubstituted non-aromatic heterocyclic ring (hereinafter referred to as ll-14).

$R^7$ and $R^B$ are taken together with the carbon atom to which they are attached to form a non-aromatic carbon ring substituted with halogen (hereinafter referred to as ll-15).

$R^7$ is substituted non-aromatic carbon ring (substituent: halogen) (hereinafter referred to as ll-16).

$R^7$ is substituted alkyl (substituent: alkyloxy) (hereinafter referred to as ll-17).

$R^1$ is as defined in the above (a-1), (a-2) or (a-3).

L is as defined in the above (b-1), (b-2), (b-3), (b-4), (b-5), (b-6), (b-7), (b-8), (b-9), (b-10), (b-11), (b-12), (b-13), (b-14), (b-15) or (b-16).

$R^2$ is as defined in the above (c-1), (c-2) or (c-3).

$R^3$ is as defined in the above (d-1), (d-2), (d-3), (d-4) or (d-5).

V is as defined in the above (h-1), (h-2), (h-3), (h-4), (h-5) or (h-6).

W is as defined in the above (i-1), (i-2), (i-3) or (i-4).

$R^4$ is as defined in the above (m-1), (m-2), (m-3), (m-4), (m-5), (m-6), (m-7), (m-8), (m-9), (m-10), (m-11), (m-12), (m-13), (m-14), (m-15), (m-16), (m-17), (m-18), (m-19) or (m-20)

(1-A)

In one embodiment, a compound of the formula (I) is a compound, wherein the group of the formula:

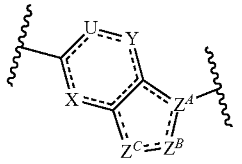

is as defined in (I-a), $R^X$ is as defined in (ee-4), $R^Y$ is as defined in (ff-3), $R^U$ is as defined in (gg-4), $R^5$ and $R^6$ are as defined in (kk-9), $R^7$ and $R^8$ are as defined in (ll-14), $R^1$ is as defined in (a-3), L is as defined in (b-14), $R^2$ is as defined in (c-3), $R^3$ is as defined in (d-5), V is as defined in (h-6), W is as defined in (i-4), and $R^4$ is as defined in (m-17).

(1-B)

In one embodiment, a compound of formula (I) is a compound, wherein the group of the formula:

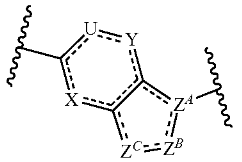

is as defined in (I-b), $R^X$ is as defined in (ee-4),
$R^Y$ is as defined in (ff-3),
$R^U$ is as defined in (gg-4),
$R^7$ is as defined in (ll-15),
$R^1$ is as defined in (a-3),
L is as defined in (b-14),
$R^2$ is as defined in (c-3),
$R^3$ is as defined in (d-5),
V is as defined in (h-6),
W is as defined in (i-3), and
$R^4$ is as defined in (m-17).

(1-C)

In one embodiment, a compound of formula (I) is a compound, wherein the group of the formula:

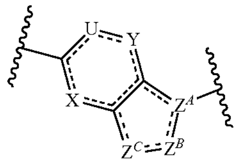

is as defined in (I-b), $R^X$ is as defined in (ee-4),
$R^Y$ is as defined in (ff-3),
$R^U$ is as defined in (gg-4),
$R^7$ is as defined in (ll-15),
$R^1$ is as defined in (a-3),
L is as defined in (b-14),
$R^2$ is as defined in (c-3),
$R^3$ is as defined in (d-5),
V is as defined in (h-6),
W is as defined in (i-4), and
$R^4$ is as defined in (m-16).

(1-D)

In one embodiment, a compound of formula (I) is a compound, wherein the group of the formula:

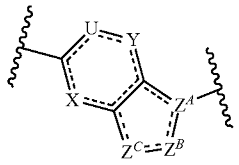

is as defined in (I-b), $R^X$ is as defined in (ee-4),
$R^Y$ is as defined in (ff-3),
$R^U$ is as defined in (gg-4),
$R^7$ is as defined in (ll-13),
$R^1$ is as defined in (a-3),
L is as defined in (b-14),
$R^2$ is as defined in (c-3),
$R^3$ is as defined in (d-5),
V is as defined in (h-6),
W is as defined in (i-4), and
$R^4$ is as defined in (m-16).

(1-E)

In one embodiment, a compound of formula (I) is a compound, wherein the group of the formula:

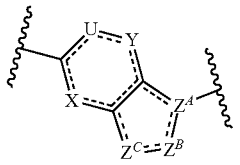

is as defined in (I-i), $R^X$ is as defined in (ee-4),
$R^Y$ is as defined in (ff-3),
$R^5$ and $R^6$ are as defined in (kk-9),
$R^7$ and $R^8$ are as defined in (ll-14),
$R^1$ is as defined in (a-3),
L is as defined in (b-14),
$R^2$ is as defined in (c-3),
$R^3$ is as defined in (d-5),
V is as defined in (h-6),
W is as defined in (i-4), and
$R^4$ is as defined in (m-18).

(1-F)

In one embodiment, a compound of formula (I) is a compound, wherein the group of the formula:

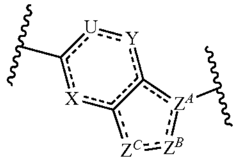

is as defined in (I-a), $R^X$ is as defined in (ee-4),
$R^Y$ is as defined in (ff-3),
$R^U$ is as defined in (gg-4),
$R^5$ and $R^6$ are as defined in (kk-9),
$R^7$ and $R^8$ are as defined in (ll-14),
$R^1$ is as defined in (a-3),
L is as defined in (b-14),
$R^2$ is as defined in (c-3),
$R^3$ is as defined in (d-5),
V is as defined in (h-6),
W is as defined in (i-4), and
$R^4$ is as defined in (m-16).

(1-G)

In one embodiment, a compound of formula (I) is a compound, wherein the group of the formula:

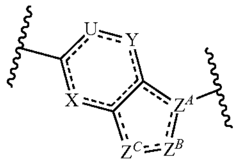

is as defined in (I-a), $R^X$ is as defined in (ee-4), $R^Y$ is as defined in (ff-3), $R^U$ is as defined in (gg-4), $R^5$ and $R^6$ are as defined in (kk-9), $R^7$ and $R^8$ are as defined in (ll-14), $R^1$ is as defined in (a-3), L is as defined in (b-14), $R^2$ is as defined in (c-3), $R^3$ is as defined in (d-5), V is as defined in (h-6), W is as defined in (i-4), and $R^4$ is as defined in (m-19).

(1-H)

In one embodiment, a compound of formula (I) is a compound, wherein the group of the formula:

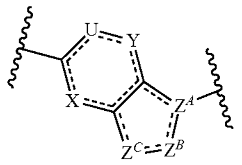

is as defined in (I-a), $R^X$ is as defined in (ee-4), $R^Y$ is as defined in (ff-3), $R^U$ is as defined in (gg-4), $R^5$ and $R^6$ are as defined in (kk-9), $R^7$ and $R^8$ are as defined in (ll-14), $R^1$ is as defined in (a-3), L is as defined in (b-14), $R^2$ is as defined in (c-3), $R^3$ is as defined in (d-5), V is as defined in (h-6), W is as defined in (i-4), and $R^4$ is as defined in (m-20).

(1-I)

In one embodiment, a compound of formula (I) is a compound, wherein the group of the formula:

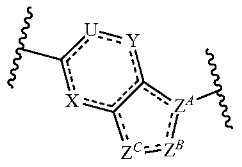

is as defined in (I-b), $R^X$ is as defined in (ee-4), $R^Y$ is as defined in (ff-3), $R^U$ is as defined in (gg-4), $R^7$ is as defined in (ll-17), $R^1$ is as defined in (a-3), L is as defined in (b-14), $R^2$ is as defined in (c-3), $R^3$ is as defined in (d-5), V is as defined in (h-6), W is as defined in (i-4), and $R^4$ is as defined in (m-16).

(1-J)

In one embodiment, a compound of formula (I) is a compound, wherein the group of the formula:

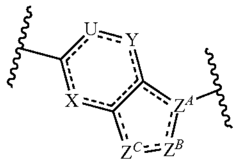

is as defined in (I-a), $R^X$ is as defined in (ee-4), $R^Y$ is as defined in (ff-3), $R^U$ is as defined in (gg-4), $R^5$ and $R^6$ are as defined in (kk-9), $R^7$ and $R^8$ are as defined in (ll-11), $R^1$ is as defined in (a-3), L is as defined in (b-14), $R^2$ is as defined in (c-3), $R^3$ is as defined in (d-5), V is as defined in (h-6), W is as defined in (i-4), and $R^4$ is as defined in (m-16).

Compounds of formula (I) are not limited limited to specific isomers, but include all possible isomers (e.g., keto-enol isomers, imine-enamin isomers, diastereoisomers, optical isomers, rotational isomers, etc.), racemates or mixtures thereof.

One or more hydrogen, carbon, and/or other atom(s) of the compounds of formula (I) may be substituted by isotope (s) of hydrogen, carbon, and/or other atom(s), respectively. Examples of such isotopes include hydrogen, carbon, nitrogen, oxygen, phosphorus, sulfur, fluorine, iodine, and chlorine, as in the cases of $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{123}I$, and $^{36}Cl$, respectively. The compounds of formula (I) also include compounds substituted with such isotopes. The compounds substituted with the isotopes are also useful as pharmaceutical products and include all radiolabeled forms of the compounds of formula (I). Furthermore, a "radiolabeling method" for producing the "radiolabeled forms" is also included in the present invention, and the "radiolabeled forms" are useful as tools for metabolic pharmacokinetics studies, studies on binding assay, and/or diagnostics.

Radiolabeled entities of the compound of formula (I) can be prepared by methods well known in the art. For example, tritium-labeled compounds of formula (I) can be prepared by introducing tritium into certain compounds of formula (I) by a catalytic dehalogenation reaction using tritium. This method involves reacting a compound indicated by formula (I) with an appropriately halogen-substituted precursor and tritium gas in the presence or absence of a base, in the presence of a suitable catalyst, e.g. Pd/C. The process includes other suitable methods for preparing tritium-labeled compounds described in "Isotopes in the Physical and Biomedical Sciences, Vol. 1, Labeled Compounds (Part A), Chapter 6 (1987). $^{14}C$-Labeled compounds can be prepared by using raw materials having $^{14}C$ carbons.

Examples of pharmaceutically acceptable salts of the compounds of formula (I) include salts of compounds of formula (I) with alkali metals (for example, lithium, sodium, and potassium), alkaline earth metals (for example, calcium and barium), magnesium, transition metals (for example, zinc and iron), ammonia, organic bases (for example, trimethylamine, triethylamine, dicyclohexylamine, ethanolamine, diethanolamine, triethanolamine, meglumine, ethylenediamine, pyridine, picoline, and quinoline), and amino acids, or salts with inorganic acids (for example, hydrochloric acid, sulfuric acid, nitric acid, carbonic acid, hydrobromic acid, phosphoric acid, and hydroiodic acid) and organic acids (for example, formic acid, acetic acid, propionic acid, trifluoroacetic acid, citric acid, lactic acid, tartaric acid, oxalic acid, maleic acid, fumaric acid, succinic acid, mandelic acid, glutaric acid, malic acid, benzoic acid, phthalic acid, ascorbic acid, benzenesulfonic acid, p-toluenesulfonic acid, methanesulfonic acid, ethanesulfonic acid, and trifluoroacetic acid). These salts can be formed according to methods that are conventionally carried out.

The compounds of formula (I) or pharmaceutically acceptable salts thereof may form solvates (e.g., hydrate and the like), co-crystals and/or crystal polymorphs. The present invention encompasses those various solvates co-crystals and crystal polymorphs. The "solvates" may be those wherein any numbers of solvent molecules (e.g. water melecules and the like) are coordinated with the compounds of formula (I). When the compounds of formula (I) or pharmaceutically acceptable salts thereof are allowed to stand in the atmosphere, the compounds may absorb water, resulting in attachement of adsorbed water or formation of hydrates. Recrystallization of the compounds of formula (I) or pharmaceutically acceptable salts thereof may produce crystal polymorphs. The "co-crystal" means that a compound of formula (I) or a salt thereof and a counter molecule exist in the same crystal lattice, which may contain any number of counter molecules.

The compounds of formula (I) of the present invention or pharmaceutically acceptable salts thereof may form prodrugs, and the present invention also includes such various prodrugs. A prodrug is a derivative of a compound of the present invention having a group that can be chemically or metabolically degraded, and is a compound which becomes a pharmaceutically active compound of the present invention in vivo as a result of solvolysis or under physiological conditions. Prodrugs include compounds that are subjected to enzymatic oxidation, reduction, hydrolysis, and the like under physiological conditions in the living body and are converted to the compounds of formula (I); compounds that are hydrolyzed by gastric acid or the like and are converted to the compounds of formula (I); and the like. Methods for selecting and producing an appropriate prodrug derivative are described in, for example, "Design of Prodrugs, Elsevier, Amsterdam, 1985". A prodrug may have activity per se.

When the compound of formula (I) or its pharmaceutically acceptable salt has hydroxyl group(s), the prodrugs may be acyloxy derivatives and sulfonyloxy derivatives that are prepared by, for example, reacting a compound having hydroxyl group(s) with suitable acyl halide, suitable acid anhydride, suitable sulfonyl chloride, suitable sulfonyl anhydride or mixed anhydride, or by reacting with a condensing agent. Examples include $CH_3COO$—, $C_2H_5COO$—, tert-BuCOO—, $C_{15}H_{31}COO$—, PhCOO—, (m-NaOOCPh)COO—, $NaOOCCH_2CH_2COO$—, $CH_3CH(NH_2)COO$—, $CH_2N(CH_3)_2COO$—, $CH_3SO_3$—, $CH_3CH_2SO_3$—, $CF_3SO_3$—, $CH_2FSO_3$—, $CF_3CH_2SO_3$—, p-$CH_3$—O-$PhSO_3$—, $PhSO_3$— and p-$CH_3PhSO_3$—.

The following examples of fromulations are only exemplified and not intended to limit the scope of the invention.

The compound of the present invention can be administered as a pharmaceutical composition by any conventional route, particularly enterally, for example, orally, for example, in the form of a tablet or a capsule; parenterally, for example, in the form of an injectable preparation or a suspension; and topically, for example, in the form of a lotion, a gel, an ointment or a cream, or as a pharmaceutical composition in a transnasal form or a suppository form. A pharmaceutical composition comprising the compound of the present invention in a free form or in the form of a pharmaceutically acceptable salt together with at least one pharmaceutically acceptable carrier or diluent can be produced by a mixing, granulating, or coating method in a conventional manner. For example, the oral composition can be a tablet, a granular preparation, or a capsule, each containing an excipient, a disintegrating agent, a binder, a lubricating agent, and the like, as well as an active ingredient and the like. Furthermore, the composition for injection can be prepared as a solution or a suspension, may be sterilized, and may contain a preservative, a stabilizer, a buffering agent, and the like.

The compounds of the invention are useful for the following symptoms caused by RSV, and suh symptoms caused by RSV vary from mild common cold-like symptoms to severe lower respiratory tract diseases such as bronchiolitis and pneumonia. In other words, it is useful for common cold symptoms such as cough, runny nose, and fever, as well as for symptoms such as wheezing and trapped breathing that occur in more severe cases, and for diseases such as bronchitis and pneumonia that occur as a result of worsening of these symptoms.

(Method for Producing the Compounds of the Invention)

The compounds of formula (I) according to the present invention can be produced by, for example, the general synthesis method described below. Regarding extraction, purification, and the like, the treatments carried out in ordinary experiments of organic chemistry may be carried out.

The compounds of the present invention can be produced with reference to techniques known in the art.

(Method A)

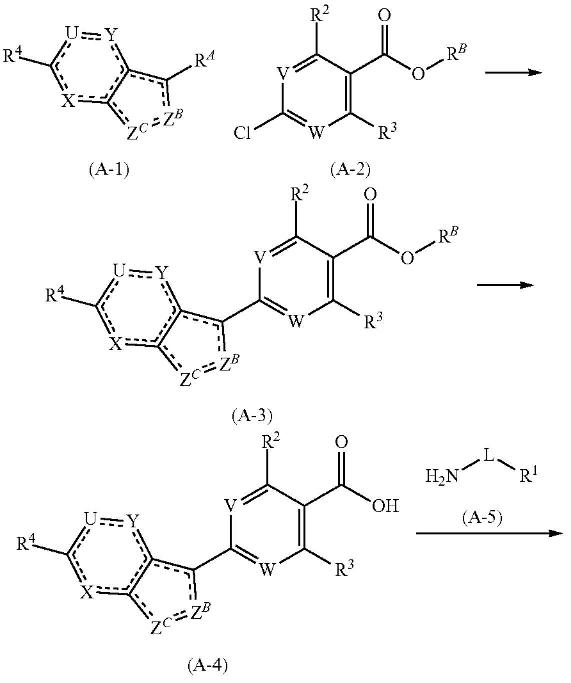

(A-1) (A-2)

(A-3)

(A-4)

-continued

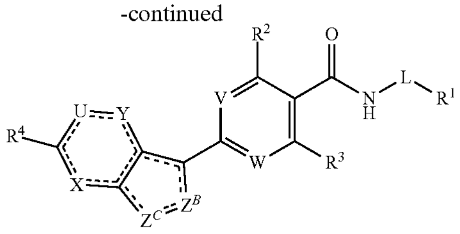

(I-A)

wherein each symbol is as defined above, and $R^A$ is —$B(OH)_2$, —Sn(C1-C6 alkyl)$_3$, etc., and $R^B$ is C1-C6 alkyl, etc.

Step 1

Compound (A-3) can be obtained by reacting Compound (A-1) with Compund (A-2) in a solvent (e.g., tetrahydrofuran, toluene, dimethylformamide, 1,4-dioxane, ethanol, water, etc.) or a mixed solvent thereof, in the presence of a metal catalyst (e.g., tetrakis(triphenylphosphine)palladium, bis(triphenylphosphine)palladium(II) dichloride, bis(tri-tert-butylphosphine)palladium, etc.) and a base (e.g., potassium carbonate, sodium hydrogen carbonate, sodium phosphate, sodium hydrogen phosphate, potassium phosphate, potassium hydrogen phosphate, lithium hydroxide, sodium hydroxide, potassium hydroxide, potassium tert-butoxide, etc.) at 20° C. to a reflux temperature of the solvent for 0.1 to 48 hours, preferably 0.5 to 12 hours.

Step 2

Deprotection reaction for the carboxyl protecting group of Compound (A-3) can be carried out by conventional method, for example, as described in Protective Groups in Organic Synthesis, Theodora W Green (John Wiley & Sons).

Step 3

Compound (I-A) can be obtained by reacting Compound (A-4) with compound (A-5) in a solvent (e.g., dimethylformamide, tetrahydrofuran, dichloromethane, acetonitrile, water, etc.) or a mixed solvent thereof, in the presence or absence of a base (e.g., triethylamine, pyridine, diisopropylamine, 1-methylimidazole, etc.) using a dehydration-condensation agent (e.g., dicyclohexylcarbodiimide, carbonyldiimidazole, EDC·HCl, HATU, etc.).

Alternativly, an acylating reagent (e.g., thionyl chloride, oxalyl chloride, etc.) is added to Compound (A-4) in a solvent (e.g., tetrahydrofuran, 1,4-dioxane, dichloromethane, dimethylformamide, etc.) in the presence or absence of a base (e.g., pyridine, triethylamine, diisopropylamine, 1-methylimidazole, etc.) to form acid chloride, which is then added with Compound (A-5) and the reaction is carried out at −20° C. to 60° C., preferably −10° C. to 30° C. for 0.1 hour to 24 hours, preferably 0.5 hours to 12 hours to afford Compound (I-A).

(Method B)

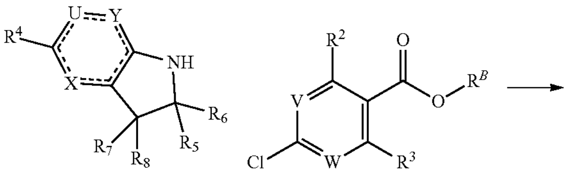

(B-1) (A-2)

-continued

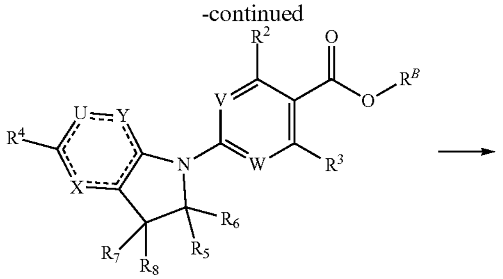

(B-2)

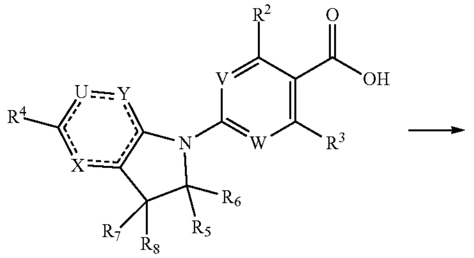

(B-3)

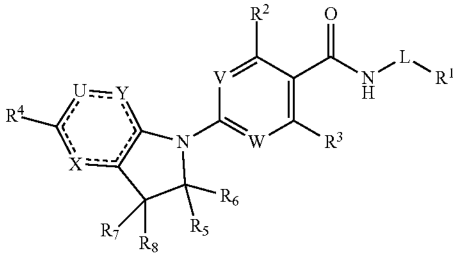

(I-B)

wherein each symbol is as defined above.

Step 1

Compound (B-2) can be obtained by reacting Compound (B-1) with Compound (A-2) in a solvent (e.g., 1,4-dioxane, toluene, tetrahydrofuran, dimethylformamide, N-methylpyrrolidone, etc.) in the presence or absence of a base (e.g., triethylamine, diisopropylamine, cesium carbonate, potassium carbonate, sodium hydride, etc.) or an acid (e.g., toluenesulfonic acid, acetic acid, hydrogen chloride, sulfuric acid, etc.) at 20° C. to a reflux temperature of the solvent, preferably 40° C. to 120° C., for 0.1 hour to 48 hours, preferably 0.5 hours to 12 hours.

Alternatively, Compound (B-2) can be obtained by reacting Compound (B-1) with Compound (A-2) in a solvent (e.g., 1,4-dioxane, toluene, tetrahydrofuran, dimethylformamide, N-methylpyrrolidone, butanol, water, etc.) or a mixed solvent thereof, in the presence or absence of a ligand (e.g., Xantphos, diphenylphosphinoferrocene, X-phos, etc.) and in the presence of a metal catalyst (e.g., palladium acetate, bis(dibenzylideneacetone)palladium, tetrakis (triphenylphosphine)palladium, bis(triphenylphosphine)palladium(II) dichloride, bis(tri-tert-butylphosphine, etc.), and a base (e.g., potassium tert-butoxide, sodium tert-butoxide, sodium carbonate, potassium carbonate, cesium carbonate, sodium phosphate, sodium hydrogen phosphate, lithium hydroxide, sodium hydroxide, etc.) for 0.1 to 48 hours, preferably 0.5 to 12 hours, at 20° C. to a reflux temperature of the solvent, or in some cases a temperature under microwave irradiation.

Step 2 and Step 3

Compound (I-B) can be obtained by carrying out Step 2 and Step 3 of Method A, using Compound (B-2).

(Method C)

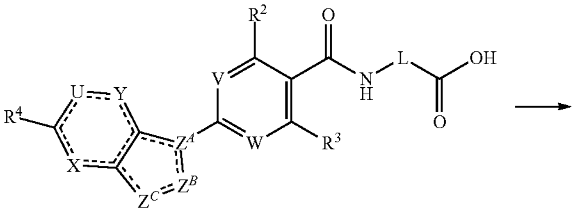

(C-1)

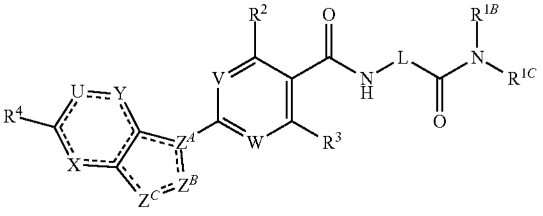

(I-C)

wherein each symbol is as defined above

Step 1

Compound (I-C) can be obtained by reacting Compound (C-1) with $NHR^{1B}R^{1C}$ in a solvent (e.g., dimethylformamide, tetrahydrofuran, dichloromethane, acetonitrile, water, etc.) or a mixed solvent thereof, in the presence of a dehydration-condensation agent (e.g., dicyclohexylcarbodiimide, carbonyldiimidazole, EDC HCl, HATU, etc.) and a base (e.g., triethylamine, pyridine, diisopropylamine, 1-methylimidazole, sodium hydride, etc.).

(Method D)

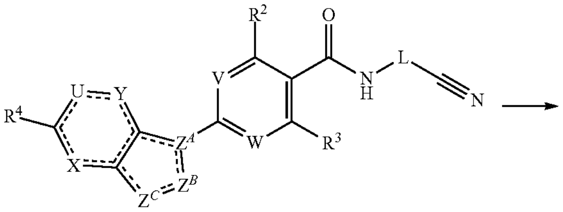

(D-1)

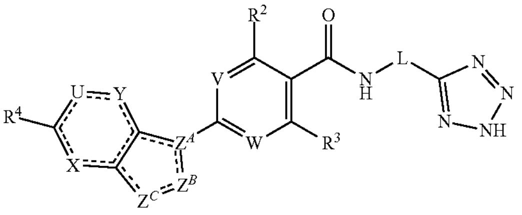

(I-D)

wherein each symbol is as defined above.

Step 1

Compound (I-D) can be obtained by reacting Compound (D-1) with an azide compound (e.g., azidotrimethylsilane, sodium azide, tributyltin azide, etc.) in a solvent (e.g., 1,4-dioxane, dimethylformamide, water, etc.) or a mixed solvent thereof, in the presence of an additive (e.g., dibutylstannane, zinc chloride, ammonium chloride, etc.) at 60° C. to a reflux temperature of the solvent, or in some cases a temperature under microwave irradiation, for 0.5 to 48 hours, preferably 1 to 4 hours.

(Method E)

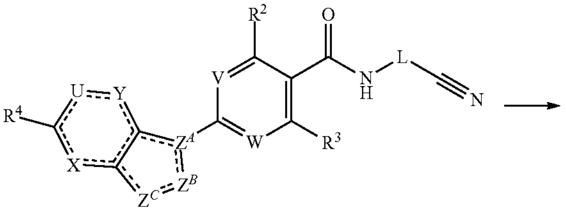

(D-1)

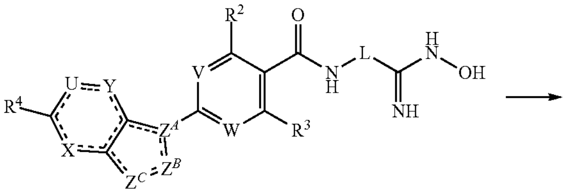

(E-2)

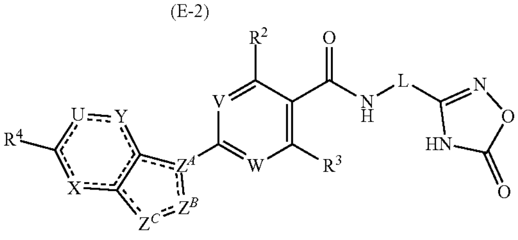

(I-E)

wherein each symbol is as defined above.

Step 1

Compound (E-2) can be obtaned by reacting Compound (D-1) with hydroxyamine, etc., in a solvent (e.g., methanol, ethanol, tetrahydrofuran, water, etc.) or a mixed solvent thereof, in the presence or absence of a base (e.g., potassium carbonate, triethylamine, etc.) at room temperature to a reflux temperature of the solvent or in some case a temperature under microwave irradiation.

Step 2

Compound (I-E) can be obtained by reacting Compound (E-2) with 1,1'-carbonyldiimidazole or ethyl chloroformate in a solvent (e.g., dimethylformamide, chloroform, dichloromethane, tetrahydrofuran, toluene, etc.) or a mixed solvent thereof, in the presence of a base (e.g., triethylamine, DBU, potassium carbonate, etc.) at room temperature to a reflux temperature of the solvent.

(Method F)

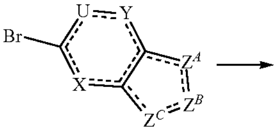

(F-1)

-continued

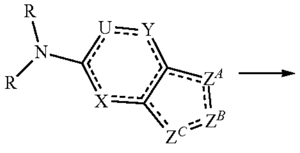

(F-2)

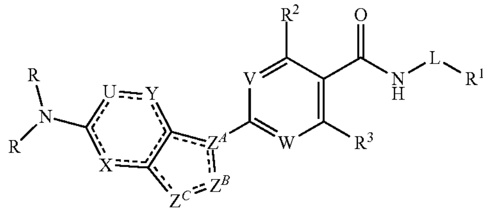

(I-F)

wherein R is a group independently selected from Substituent Group n, and the other symbols are as defined above.

Step 1

Compound (F-2) can be obtaned by reacting Compound (F-1) with amine in a solvent (e.g., 1,4-dioxane, toluene, tetrahydrofuran, dimethylformamide, N-methylpyrrolidone, butanol, water, etc.) or a mixed solvent thereof, in the presence or absence of a ligand (e.g., Xantphos, diphenylphosphinoferrocene, X-Phos, BINAP, etc.) and in the presence of a metal catalyst (e.g., palladium acetate, bis(dibenzylideneacetone)palladium, tetrakis(triphenylphosphine)palladium, bis(triphenylphosphine)palladium(II) dichloride, bis(tri-tert-butylphosphine), etc.) and a base (e.g., potassium tert-butoxide, sodium tert-butoxide, sodium carbonate, potassium carbonate, cesium carbonate, sodium phosphate, sodium hydrogen phosphate, lithium hydroxide, sodium hydroxide, etc.) at 20° C. to a reflux temperature of the solvent or in some cases a temperature under microwave irradiation for 0.1 to 48 hours, preferably for 0.5 to 12 hours.

Step 2

Compound (I-F) can be obtained by carrying out Step 1 of Method A or Step 1 of Method B, using Compound (F-2).

(Method G)

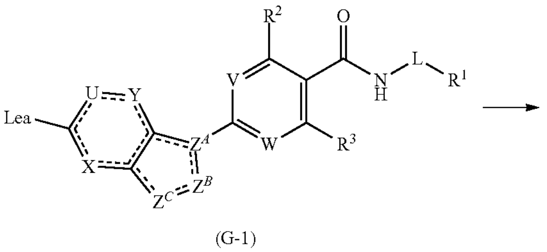

(G-1)

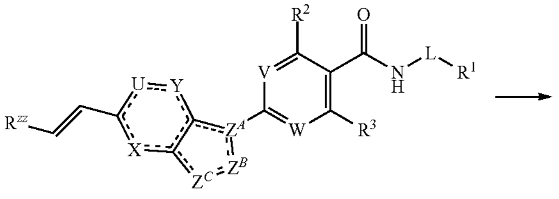

(G-2)

-continued

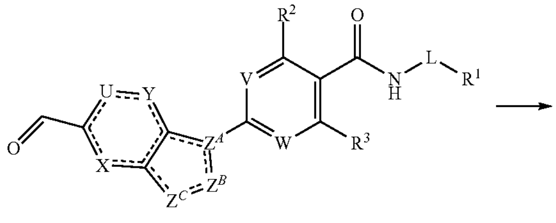

(G-3)

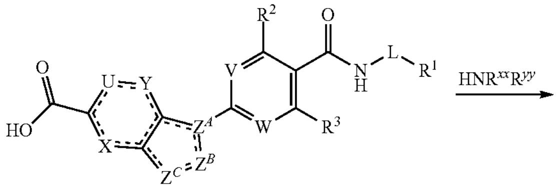

(G-4)

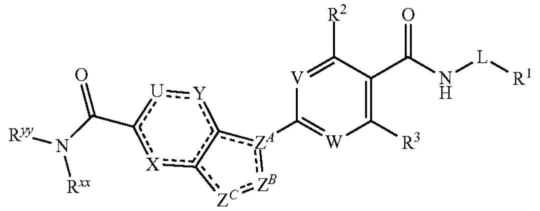

(I-G)

wherein each symbol is as defined above, Lea is a leaving group, $R^{zz}$ is a hydrogen atom, C1-C6 alkyl, etc., $R^{xx}$ and $R^{yy}$ are each independently a hydrogen atom, C1-C6 alkyl, etc., or $R^{xx}$ and $R^{yy}$ are taken together with the adjacent nitrogen atom to form a ring.

Step 1

Compound (G-2) can be obtained by carrying out Step 1 of Method A, using Compound (G-1).

Step 2

Compound (G-3) can be obtained by reacting Compound (G-2) in a solvent (e.g., 1,4-dioxane, tetrahydrofuran, or water, etc.) or a mixed solvent thereof, adding with sodium periodate or oxon and ruthenium chloride or potassium osmite. Alternatively, ozonide is obtained by ozone oxidation, followed by treatment with a reducing agent (e.g., zinc, dimethyl sulfide, triphenylphosphine, etc.) to obtain Compound (G-3).

Step 3

Compound (G-4) can be obtained by reacting Compound (G-3) in a solvent (e.g., tetrahydrofuran, tert-butanol, water, etc.) or a mixed solvent thereof, adding with sodium dihydrogen phosphate and sodium chlorite in the presence of 2-methyl-2-butene, sulfamic acid, etc.

Step 4

Compound (I-G) can be obtained by carrying out Step 1 of Method C, using Compound (G-4).

(Method H)

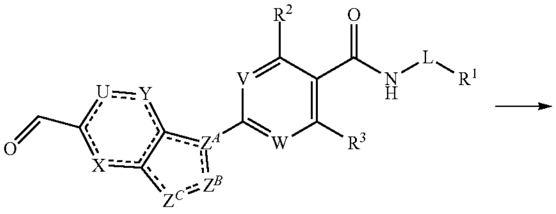

(G-3)

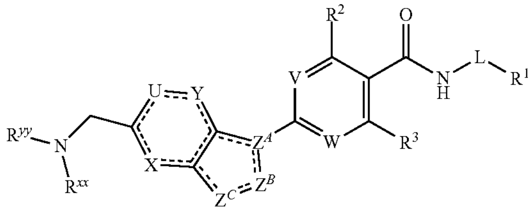

(I-H)

wherein each symbol is as defined above, and $R^{xx}$ and $R^{yy}$ are hydrogen atoms, C1-C6 alkyl, or $R^{xx}$ and $R^{yy}$ are taken together with the adjacent nitrogen atom to form a ring.

Step 1

Compound (I-H) can be obtained by reacting Compound (G-3) with $NHR^{yy}R^{xx}$ in a solvbent (e.g., chloroform, tetrahydrofuran, acetonitrile, acetic acid, etc.) or a mixed solvent thereof, in the presence of a reducing agent (e.g., sodium triacetoxyborohydride, 2-picoline borane, etc.) at room temperature to a reflux temperature of the solvent for 0.1 to 48 hours, preferably for 0.5 to 8 hours.

(Method J)

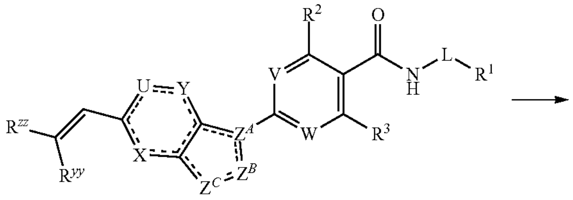

(J-1)

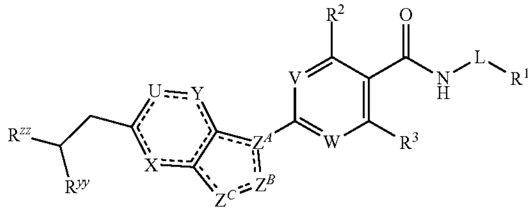

(I-J)

wherein each symbol is as defined above, and $R^{zz}$ and $R^{yy}$ are hydrogen atoms, C1-C6 alkyl, aromatic carbocyclyl, aromatic heterocyclyl, etc.

Step 1

Compound (I-J) can be obtained by catalytic hydrogenation of Compound (J-1) in a solvent (e.g., tetrahydrofuran, methanol, toluene, chloroform, etc.) or a mixedd solvent thereof, in the presence of a heterogeneous catalyst (e.g., palladium on carbon, palladium hydroxide, Raney nickel, platinum oxide, etc.).

Since the compound of the present invention has an anti-RSV action, i.e., CPE (CytoPathic Effect) inhibiting action, the compound is useful as a therapeutic and/or prophylactic agent for diseases such as such as bronchiolitis and pneumonia.

Furthermore, the compound of the present invention has utility as a medicine, and preferably, the compound of the present invention has any one or a plurality of the following excellent features.

a) Inhibitory activity against CYP enzymes (for example, CYP1A2, CYP2C9, CYP2C19, CYP2D6, and CYP3A4) is weak.
b) Satisfactory pharmacokinetics such as high bioavailability and adequate clearance are exhibited.
c) Metabolic stability is high.
d) Irreversible inhibitory activity is not exhibited against CYP enzymes (for example, CYP3A4) within the concentration range of the measurement conditions described in the present specification.
e) Mutagenicity is not exhibited.
f) The cardiovascular risk is low.
g) High solubility is exhibited.
h) High RSV type A, CPE inhibiting action and high RSV type B inhibiting action are exhibited.
i) The amount of virus in the lungs is reduced.

The pharmaceutical compositions of the present invention can be administered either orally or parenterally. Examples of a parenteral administration include transdermal, subcutaneous, intravenous, intra-arterial, intramuscular, intraperitoneal, transmucosal, inhalation, transnasal, ocular instillation, ear instillation, and intravaginal administration.

For oral administration, the pharmaceutical composition may be prepared into any dosage form that is commonly used, such as a solid preparation for internal use (for example, tablet, powder, granule, capsule, pill, or film), or a liquid preparation for internal use (for example, suspension, emulsion, elixir, syrup, limonade, spirit preparation, aromatic water preparation, extract, decoction, tincture, etc.) and administered. The tablet may be a dragee, a film-coated tablet, an enteric-coated tablet, a sustained release tablet, a troche, a sublingual tablet, a buccal tablet, a chewable tablet, or an orally disintegrating tablet; the powder preparation and granular preparation may be dry syrups; and the capsule may be a soft capsule, a microcapsule, or a sustained release capsule.

For parenteral administration, a pharmaceutical composition can be suitably administered in any dosage form that is commonly used, such as an injectable preparation, an infusion, or a preparation for external use (for example, an eye drop, a nasal drop, an ear drop, an aerosol, an inhalant, a lotion, an impregnating agent, a liniment, a gargling agent, an enema, an ointment, a plaster, a jelly, a cream, a patch, a poultice, a powder preparation for external use, or a suppository). The injectable preparation may be an O/W, W/O, O/W/O, or W/O/W type emulsion, or the like.

A pharmaceutical composition can be obtained by mixing an effective amount of the compound of the present invention with various pharmaceutical additives appropriate for the dosage form, such as an excipient, a binder, a disintegrating agent, and a lubricating agent, as necessary. Furthermore, the pharmaceutical composition can be prepared into a pharmaceutical composition for use for a child, an elderly, a patient with a serious case, or a surgical operation, by appropriately changing the effective amount of the compound of the present invention, the dosage form, and/or various pharmaceutical additives. For example, a pharmaceutical composition for use for a child may be administered to a neonate (less than 4 weeks after birth), an infant (from 4 weeks after birth to less than 1 year), a preschool child (from 1 year to less than 7 years), a child (from 7 years to less than 15 years), or a patient 15 year to 18 years of age. For example, a pharmaceutical composition for an elderly may be administered to a patient 65 years of age or older.

It is desirable to set the amount of administration of the pharmaceutical composition of the present invention after considering the age and body weight of the patient, the type and degree of the disease, the route of administration, and the like; however, in the case of oral administration, the amount of administration is usually 0.05 to 100 mg/kg/day and is preferably in the range of 0.1 to 10 mg/kg/day. In the case of parenteral administration, the amount of administration may vary greatly depending on the route of administration; however, the amount of administration is usually 0.005 to 10 mg/kg/day and is preferably in the range of 0.01 to 1 mg/kg/day. This may be administered once a day or several times a day.

The compound of the present invention may be used in combination with L-protein inhibitors, F-protein inhibitors, N-protein enzyme inhibitors, etc. (hereinafter referred to as concomitant drug), for the purpose of enhancing the action of the compound, reducing the amount of administration of the compound, or the like. At this time, the timing of administration for the compound of the present invention and the concomitant drug is not limited, and these may be administered simultaneously to the target of administration or may be administered with a time difference. Furthermore, the compound of the present invention and the concomitant drug may be administered as two or more kinds of preparations each including active ingredients, or may be administered as a single preparation including those active ingredients.

The amount of administration of the concomitant drug can be appropriately selected based on the clinically used dosage. Furthermore, the blending ratio of the compound of the present invention and the concomitant drug can be appropriately selected according to the target of administration, the route of administration, the target disease, symptoms, combination, and the like. For example, when the target of administration is a human being, 0.01 to 100 parts by weight of the concomitant drug may be used with respect to 1 part by weight of the compound of the present invention.

EXAMPLES

Hereinafter, the present invention will be described in more detail by way of Examples, Reference Examples, and Test Examples; however, the present invention is not intended to be limited by these.

Abbreviations as used herein have the following meanings.

$Boc_2O$: di-tert-butyl dicarbonate
DIAD: diisopropyl azodicarboxylate
DMEAD: bis(2-methoxyethyl) azodicarboxylate
DMAP: 4-dimethylaminopyridine
HATU: O-(7-azabenzotriazol-1-yl)-1,1,3,3-tetramethyluronium hexafluorophosphate
Me4tBuXphos: 2-di-tert-butylphosphino-3,4,5,6-tetramethyl-2',4',6'-triisopropyl-1,1'-biphenyl
TolBINAP: 2,2'-bis(di-p-tolylphosphino)-1,1'-binaphthyl
Ts: tosyl
$Pd_2(dba)_3$: tris(dibenzylideneacetone)bispalladium
$PdCl_2(dppf)$: 1,1'-bis(diphenylphosphino)ferrocene]palladium(II) dichloride dichloromethane adduct
$Pd(PPh_3)_4$: tetrakis(triphenylphosphine)palladium
Xantphos Pd G3: [(4,5-bis(diphenylphosphino)-9,9-dimethylxanthene)-2-(2'-amino-1,1'-biphenyl)]palladium (II) methanesulfonate
Xantphos Pd G2: chloro[(4,5-bis(diphenylphosphino)-9,9-dimethylxanthene)-2-(2'-amino-1,1'-biphenyl)]palladium(II)
X-Phos: 2,4,6-triisopropyl-2'-(dicyclohexylphosphino)biphenyl (Method for Identifying Compound)

The NMR analysis obtained in each Example was performed at 400 MHz, and measurement was made using DMSO-$d_6$ and $CDCl_3$. Furthermore, when NMR data are shown, there are occasions in which all the measured peaks are not described.

The term RT in the specification indicates retention time in a LC/MS: liquid chromatography/mass analysis, and the retention time was measured under the following conditions.

(Method 1)

Column: ACQUITY UPLC (registered trademark) BEH C18 (1.7 μm i.d. 2.1×50 mm) (Waters)
Flow rate: 0.8 mL/min UV detection wavelength: 254 nm (detection range 190-500 nm)
Mobile phase: [A] was 0.1% formic acid-containing aqueous solution, and [B] was 0.1% formic acid-containing acetonitrile solution.
Gradient: A linear gradient of 5% to 100% solvent [B] was carried out for 3.5 minutes, and then 100% solvent [B] was maintained for 0.5 minutes.

(Method 2)

Column: ACQUITY UPLC (registered trademark) BEH C18 (1.7 μm i.d. 2.1×50 mm) (Waters)
Flow rate: 0.8 mL/min
UV detection wavelength: 254 nm (detection range 190-400 nm)
Mobile phase: [A] was 0.1% formic acid-containing aqueous solution, and [B] was 0.1% formic acid-containing acetonitrile solution.
Gradient: A linear gradient of 5% to 100% solvent [B] was carried out for 3.5 minutes, and then 100% solvent [B] was maintained for 0.5 minutes.

(Method 3)

Column: Shim-pack XR-ODS (2.2 μm, i.d. 50×3.0 mm) (Shimadzu)
Flow rate: 1.6 mL/min
UV detection wavelength: 254 nm (detection range 190-800 nm)
Mobile phase: [A] was 0.1% formic acid-containing aqueous solution, and [B] was 0.1% formic acid-containing acetonitrile solution
Gradient: A linear gradient of 10% to 100% solvent [B] was carried out for 3 minutes, and then 100% solvent [B] was maintained for 0.5 minutes.

(Method 4)

Column: ACQUITY UPLC (registered trademark) BEH C18 (1.7 μm) i.d. 2.1×50 mm) (Waters)
Flow rate: 0.8 mL/min
UV detection wavelength: 254 nm (detection range 210-500 nm)
Mobile phase: [A] was 0.1% formic acid-containing aqueous solution, and [B] was 0.1% formic acid-containing acetonitrile solution
Gradient: A linear gradient of 5% to 100% solvent [B] was carried out for 3.5 minutes, and then 100% solvent [B] was maintained for 0.5 minutes.

(Method 5)

Column: ACQUITY UPLC (registered trademark) BEH C18 (1.7 μm), i.d. 2.1×50 mm) (Waters)

Flow rate: 0.8 mL/min

UV detection wavelength: 254 nm (detection range 190-500 nm)

Mobile phase: [A] was 10 mM ammonium carbonate-containing aqueous solution, and [B] was acetonitrile Gradient: A linear gradient of 5% to 100% solvent [B] was carried out for 3.5 minutes, and then 100% solvent [B] was maintained for 0.5 minutes.

(Method 6)

Column: ACQUITY UPLC (registered trademark) BEH C18 (1.7 μm) i.d. 2.1×50 mm) (Waters)

Flow rate: 0.8 mL/min

UV detection wavelength: 254 nm (detection range 190-400 nm)

Mobile phase: [A] was 10 mM ammonium carbonate-containing aqueous solution, and [B] was acetonitrile Gradient: A linear gradient of 5% to 100% solvent [B] was carried out for 3.5 minutes, and then 100% solvent [B] was maintained for 0.5 minutes.

(Method 7)

Column: ACQUITY UPLC (registered trademark) BEH C18 (1.7 μm) i.d. 2.1×50 mm) (Waters)

Flow rate: 0.8 mL/min

UV detection wavelength: 254 nm (detection range 190-500 nm)

Mobile phase: [A] was 0.1% formic acid-containing aqueous solution, and [B] was 0.1% formic acid-containing acetonitrile solution Gradient: A linear gradient of 70% to 100% solvent [B] was carried out for 3.5 minutes, and then 100% solvent [B] was maintained for 0.5 minutes.

(Method 8)

Column: ACQUITY UPLC (registered trademark) BEH C18 (1.7 μm) i.d. 2.1×50 mm) (Waters)

Flow rate: 0.8 mL/min

UV detection wavelength: 254 nm (detection range 190-500 nm)

Mobile phase: [A] was 10 mM ammonium carbonate-containing aqueous solution, and [B] was acetonitrile Gradient: A linear gradient of 50% to 100% solvent [B] was carried out for 3.5 minutes, and then 100% solvent [B] was maintained for 0.5 minutes.

(Method 9)

Column: ACQUITY UPLC (registered trademark) BEH C18 (1.7 μm) i.d. 2.1×50 mm) (Waters)

Flow rate: 0.6 mL/min

UV detection wavelength: 254 nm (detection range 190-500 nm)

Mobile phase: [A] was 0.1% formic acid-containing aqueous solution, and [B] was 0.1% formic acid-containing acetonitrile solution Gradient: A linear gradient of 25% to 95% solvent [B] was carried out for 1.5 minutes, and then 95% solvent [B] was maintained for 1.5 minutes.

(Method 10)

Column: ACQUITY UPLC (registered trademark) BEH C18 (1.7 μm) i.d. 2.1×50 mm) (Waters)

Flow rate: 0.6 mL/min

UV detection wavelength: 254 nm (detection range 190-500 nm)

Mobile phase: [A] was 0.1% formic acid-containing aqueous solution, and [B] was 0.1% formic acid-containing acetonitrile solution Gradient: A linear gradient of 25% to 95% solvent [B] was carried out for 1.5 minutes, and then. 95% solvent [B] was maintained for 1.5 minutes.

(Method 11)

Column: ACQUITY UPLC (registered trademark) CSH C18 (1.7 μm i.d. 2.1×50 mm) (Waters)

Flow rate: 0.6 mL/min

UV detection wavelength: 254 nm (detection range 190-500 nm)

Mobile phase: [A] was 0.1% formic acid-containing aqueous solution, and [B] was 0.1% formic acid-containing acetonitrile solution Gradient: A linear gradient of 25% to 95% solvent [B] was carried out for 1.5 minutes, and then 95% solvent [B] was maintained for 1.5 minutes.

In the specification, the mention of MS (m/z) indicates the value observed by mass spectrometry.

Example 1

Synthesis of Compound (I-023)

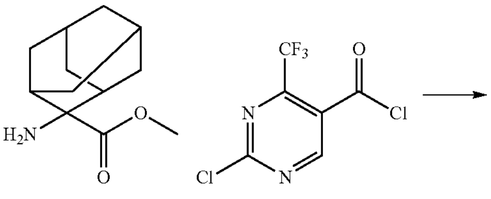

1 2

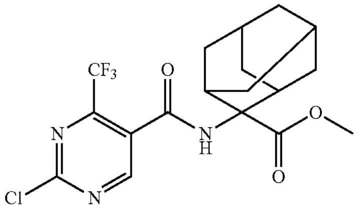

3

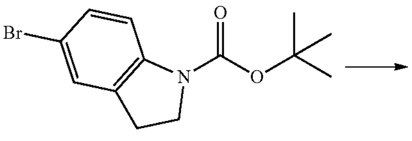

4

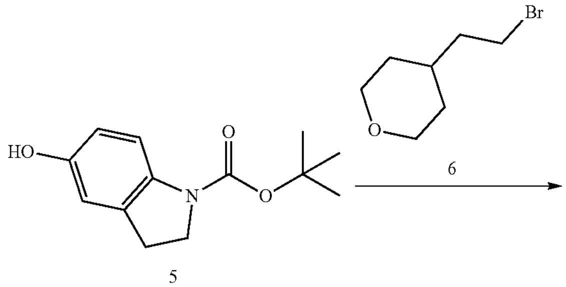

5

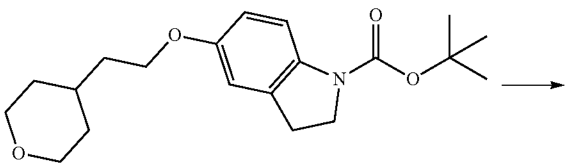

7

-continued

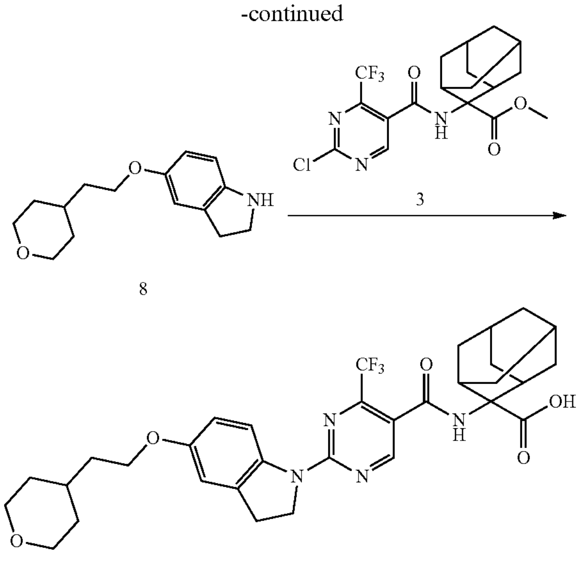

8

3

I-023

Step 1 Synthesis of Compound 3

To Compound 1 (910 mg, 3.62 mmol) were added chloroform (20 mL) and diisopropylethylamine (0.76 mL, 4.34 mmol), and then Compound 2 (887 mg, 3.62 mmol) udner ice-cooling. The mixture was warmed to room temperature and stirred for 2 hours, and then water was added. The mixture was extracted with chloroform, and the two layers were separated. The organic layer was washed with water and dried over anhydrous magnesium sulfate. The solvent was removed under reduced pressure, and the residue was added with ethyl acetate-hexane. The solid was filtered to obtain Compound 3 (1.34 g, yield 81%).

$^1$H-NMR ($CDCl_3$) δ: 1.75-1.82 (m, 6H), 1.87-1.97 (m, 4H), 2.15 (m, 2H), 2.60 (s, 2H), 3.78 (s, 3H), 6.00 (s, 1H), 8.98 (s, 1H).

Step 2 Synthesis of Compound 5

To Compound 4 (22.6 g, 76 mmol) were added 1,4-dioxane (158 mL), bis(pinacolato)diborone (25 g, 98 mmol), $PdCl_2$(dppf) (6.2 g, 7.6 mmol) and potassium acetate (11.1 g, 1 14 mmol), and the mixure was stirred at 100° C. After 3 hours, the mixture was cooled to room temperature and filtered through Celite (registered trademark). The filtrate was concentrated under reduced pressure, and the residue was added with diisopropyl ether to precipitate a solid. The precipitated solid was removed by filtration, and the filtrate was concentrated under reduced pressure.

The concentrated residue was dissolved in tetrahydrofuran (226 mL) and mixed with 1 mol/L aqueous sodium hydroxide solution (114 mL, 114 mmol), and 30% aqueous hydrogen peroxide solution (11.6 mL, 114 mmol) were added. After stirring at room temperature for 1 hour, the reaction was quenched by adding aqueous sodium thiosulfate. The two layers were separated by extraction with ethyl acetate, and the organic layer was washed with water and dried over anhydrous magnesium sulfate. The solvent was removed under reduced pressure, and the residue was purified by silica gel column chromatography (hexane-ethyl acetate) to afford Compound 5 (7.7 g, yield 43%).

$^1$H-NMR ($CDCl_3$) δ: 1.57 (s, 9H), 3.04 (t, J=8.8 Hz, 2H), 3.96 (m, 2H), 4.58 (s, 1H), 6.61 (d, J=8.8 Hz, 1H), 6.64 (s, 1H), 7.34 (brs, 0.4H), 7.73 (brs, 0.6H).

Step 3 Synthesis of Compound 7

To Compound 5 (2.5 g, 10.6 mmol) were added dimethylformamide (25 mL), Compound 6 (3.08 g, 15.9 mmol) and potassium carbonate (2.94 g, 21.3 mmol), and the mixure was stirred at 60° C. for 5 hours. The reaction solution was added with water and extracted with ethyl acetate. The two layers were separated, and the organic layer was washed with water and dried over anhydrous magnesium sulfate. The solvent was removed under reduced pressure, and the residue was purified by silica gel column chromatography (hexane-ethyl acetate) to afford Compound 7 (2.55 g, yeald 69%).

$^1$H-NMR ($CDCl_3$) δ: 1.35 (m, 2H), 1.57 (s, 9H), 1.60-1.82 (m, 5H), 3.05 (t, J=8.8 Hz, 2H), 3.40 (td, J=12.0, 1.6 Hz, 2H), 3.90-4.00 (m, 6H), 6.68 (d, J=8.8 Hz, 1H), 6.72 (s, 1H), 7.34 (brs, 0.4H), 7.73 (brs, 0.6H).

Step 4 Synthesis of Compound 8

To Compound 7 (2.55 g, 7.34 mmol) were added dichloromethane (20 mL) and trifluoroacetic acid (10 mL, 130 mmol). After stirring at room temperature for 1 hour, aqueous sodium bicarbonate solution was added to neutralize the mixture. The two layers were separated by extraction with chloroform, and the organic layer was washed with water and dried over anhydrous magnesium sulfate. The solvent was removed under reduced pressure to afford Compound 8 (1.95 g) as a crude product.

$^1$H-NMR ($CDCl_3$) δ: 1.35 (m, 2H), 1.61-1.84 (m, 5H), 2.78 (brs, 1H), 3.01 (t, J=8.4 Hz, 2H), 3.40 (td, J=12.0, 1.6 Hz, 2H), 3.54 (t, J=8.4 Hz, 2H), 3.91-4.00 (m, 4H), 6.57-6.61 (m, 2H), 6.76 (s, 1H).

Step 5 Synthesis of Compound (I-023)

To Compound 8 (107 mg, 0.43 mmol) were added 1,4-dioxane (3 m L), triethylamine (0.149 mL, 1.08 mmol) and Compound 3 (150 mg, 0.36 mmol), and the mixture was stirred at 50° C. for 2 hours. The mixture was added with water and extracted with chloroform. The organic layer was washed with water, dried over anhydrous magnesium sulfate, and the solvent was removed under reduced pressure.

To the residue were added tetrahydrofuran (2 mL), ethanol (2 mL) and 4 mol/L aqueous lithium hydroxide solution (0.90 mL, 3.6 mmol). The mixture was stirred at 90° C. for 8 hours and 10% aqueous citric acid solution was added. The mixture was extracted with chloroform, and the two layers were separated. The organic layer was washed with water and dried over anhydrous magnesium sulfate. The solvent was removed under reduced pressure, and the residue was purified by silica gel column chromatography (chloroform-methanol) to afford Compound (I-023) (90 mg, yield 41%).

$^1$H-NMR (DMSO-$d_6$) δ: 1.22 (m, 2H), 1.53-1.72 (m, 11H), 1.80 (brs, 2H), 2.03-2.16 (m, 4H), 2.54 (s, 2H), 3.19 (t, J=8.4 Hz, 2H), 3.28 (m, 2H), 3.83 (dd, J=11.2, 0.8 Hz, 2H), 4.00 (t, J=6.4 Hz, 2H), 4.21 (t, J=8.4 Hz, 2H), 6.82 (dd, J=8.8, 1.2 Hz, 1H), 6.94 (d, J=1.2 Hz, 1H), 8.16 (d, J=8.8 Hz, 1H), 8.46 (s, 1H), 8.67 (s, 1H), 12.3 (s, 1H).

Example 2

Synthesis of Compound (I-033)

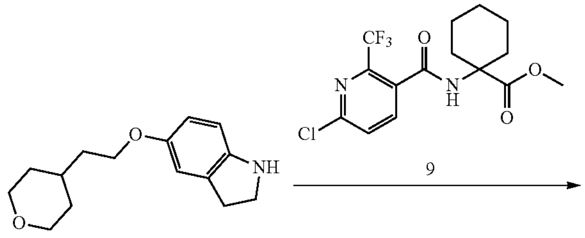

8

9

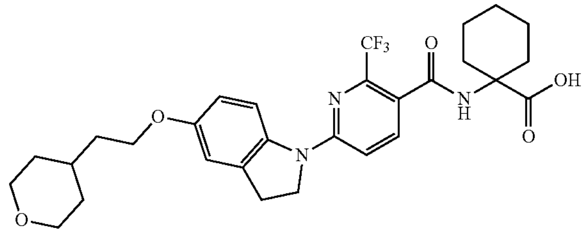

I-033

Step 1 Synthesis of Compound (I-033)

Compound 8 (41 mg, 0.16 mmol) and Compound 9 (40 mg, 0.11 mmol), which was synthesized in the same manner as Compound 3, were dissolved in 1,4-dioxane (0.5 mL), and Xantphos Pd G3 (10 mg, 0.01 mmol) and potassium carbonate (38 mg, 0.27 mmol) were added. After stirring at 100° C. for 3 hours, water was added. The mixture was extracted with chloroform, and the organic layer was washed with water and dried over anhydrous magnesium sulfate. The solvent was removed under reduced pressure.

To the residue were added ethanol (0.5 mL) and tetrahydrofuran (0.5 mL) to dissolve, and 4 mol/L aqueous lithium hydroxide solution (0.27 mL) was added. The mixture was stirred at 50° C. for 4 hours. Aqueous citric acid solution was added, and the mixture was extracted with chloroform. The organic layer was washed with water, dried over anhydrous magnesium sulfate, and the solvent was removed under reduced pressure. The residue was purified by silica gel column chromatography (chloroform-methanol) to afford Compound (I-033) (20 mg, yield 33%).

$^1$H-NMR (DMSO-$d_6$) δ: 1.15-1.30 (m, 3H), 1.50-1.78 (m, 12H), 2.03-2.10 (m, 2H), 3.22 (m, 2H), 3.29 (m, 2H), 3.83 (dd, J=10.8, 3.2 Hz, 2H), 3.98 (t, J=6.4 Hz, 2H), 4.06 (t, J=8.0 Hz, 2H), 6.77 (dd, J=8.8, 3.5 Hz, 1H), 6.89 (s, 1H), 7.06 (d, J=8.8 Hz, 1H), 7.72 (d, J=8.8 Hz, 1H), 8.24 (d, J=8.8 Hz, 1H), 8.44 (s, 1H), 12.2 (s, 1H).

Example 3

Synthesis of Compound (I-082)

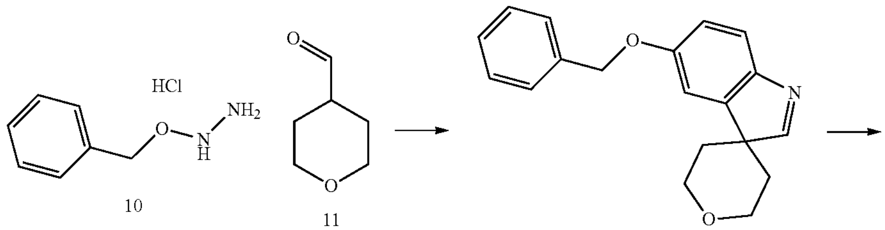

10 11 12

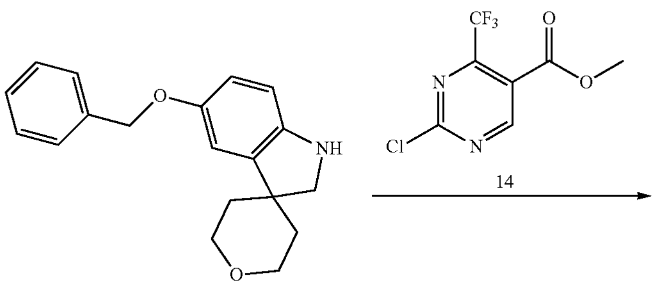

14

13

-continued
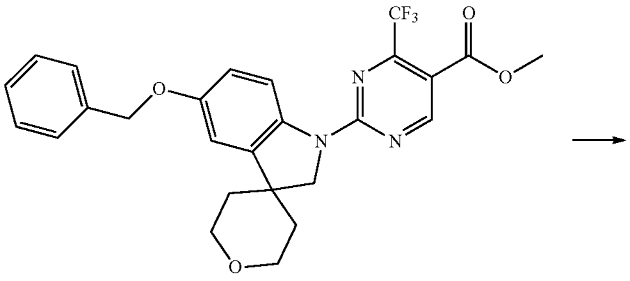
15
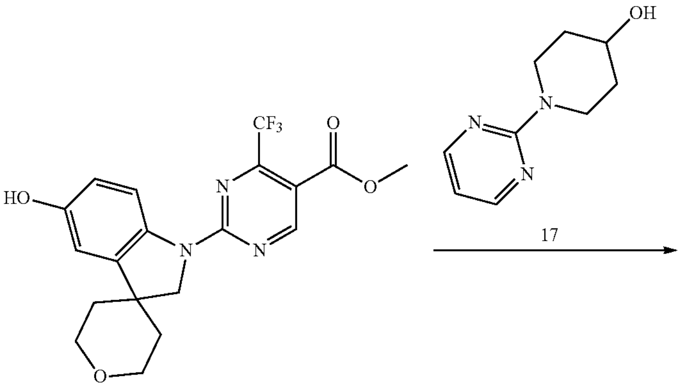
17
16
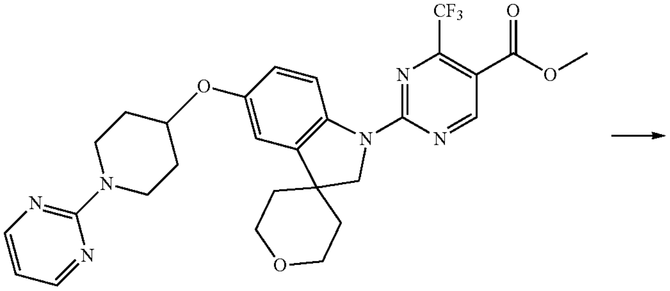
18
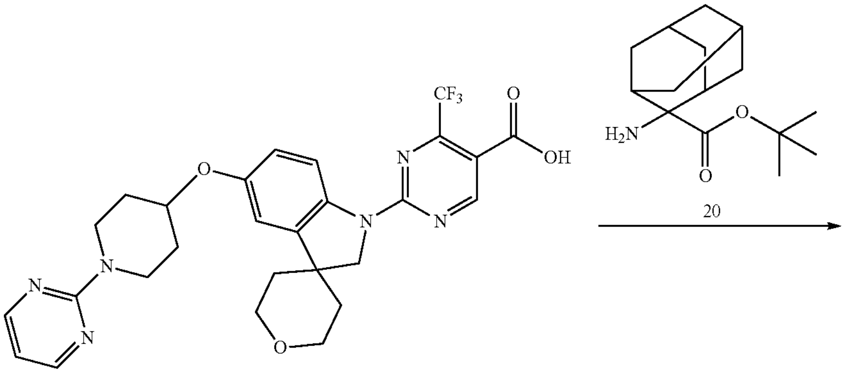
20
19

-continued

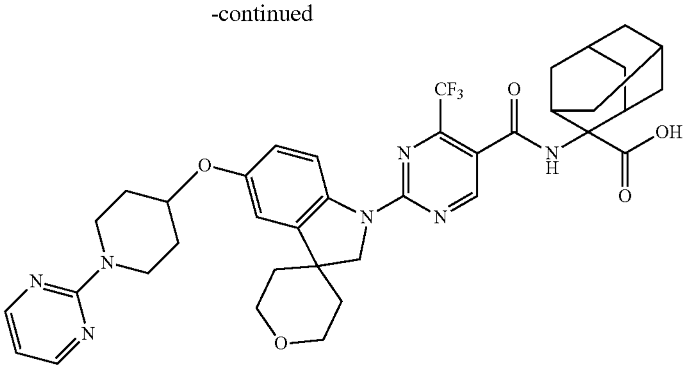

I-082

Step 1: Synthesis of Compound 12

Compound 10 (31 g, 124 mmol) and compound 11 (16.9 g, 148 mmol) were suspended in dichloromethane (600 mL) and cooled under ice bath. Trifluoroacetic acid (19 mL, 247 mmol) was added. After 30 minutes, the mixture was warmed to 45° C., and stirred for 3 hours. The mixture was added with aqueous sodium carbonate solution to neutralize under ice-cooling and filtered through Celite (registered trademark). The two layers of filtrate was separated, and the organic layer was washed with water and dried over anhydrous magnesium sulfate. The solvent was removed under reduced pressure, and diethyl ether was added to the residue. The solid was filtered to obtain Compound 12 (9.04 g, yield 25%).

$^1$H-NMR ($CDCl_3$) δ: 1.63 (m, 2H), 1.93 (ddd, J=13.6, 10.0, 4.0 Hz, 2H), 3.90 (m, 2H), 4.10 (m, 2H), 5.10 (s, 2H), 6.97 (dd, J=8.4, 2.4 Hz, 1H), 7.06 (d, J=2.4 Hz, 1H), 7.34 (m, 1H), 7.40 (m, 2H), 7.45 (m, 2H), 7.56 (d, J=8.4 Hz, 1H), 8.32 (s, 1H).

LC/MS(ESI):m/z=294 [M+H]+, RT=1.96 min, LC/MS Method 1

Step 2 Synthesis of Compound 13

Compound 12 (18 g, 61.4 mmol) was suspended in methanol (180 mL), and sodium borohydride (2.55 g, 67.5 mmol) was added under ice-cooling. After 10 minutes, the mixture was warmed to room temperature, and stirred for 2 hours. Aqueous ammonium chloride was added udner ice-cooling, and the mixute was extracted with chloroform. The organic layer was washed with water and dried over anhydrous magnesium sulfate. The residue was added with diisopropyl ether, and the solvent was removed under reduced pressure. The solid was filtered to obtain Compound 13 (16.1 g, yield 89%).

$^1$H-NMR ($CDCl_3$) δ: 1.65 (d, J=13.6 Hz, 2H), 1.94 (m, 2H), 3.52 (m, 2H), 3.55 (m, 2H), 3.96 (m, 2H), 4.99 (s, 2H), 6.59 (d, J=8.4 Hz, 1H), 6.70 (d, J=8.4, 2.4 Hz, 1H), 6.79 (d, J=2.4 Hz, 1H), 7.26 (s, 1H), 7.31 (m, 1H), 7.38 (m, 2H), 7.43 (m, 2H).

LC/MS(ESI):m/z=296 [M+H]+, RT=1.67 min, LC/MS Method 1

Step 3 Synthesis of Compound 15

Compound 13 (16.1 g, 54.5 mmol) was dissolved in 1,4-dioxane (242 mL), and triethylamine (17.4 mL, 125 mmol) and Compound 14 (14.4 g, 60 mmol) were added, and the mixture was stirred at 50° C. for −3 hours. After cooling, water was added and the mixture was extracted with chloroform. The organic layer was washed with water and dried over anhydrous magnesium sulfate. The solvent was removed under reduced pressure, and ethyl acetate-hexane was added to the residue. The solid was filtered to obtain Compound 15 (25.3 g, yield 93%).

$^1$H-NMR (DMSO-$d_6$) δ: 1.58 (m, 2H), 1.98 (m, 2H), 3.52 (m, 2H), 3.86 (s, 3H), 3.90 (m, 2H), 4.27 (m, 2H), 5.12 (s, 2H), 6.98 (m, 1H), 7.13 (d, J=2.4 Hz, 1H), 7.34 (m, 1H), 7.40 (m, 2H), 7.47 (m, 2H), 8.21 (m, 1H), 9.11 (s, 1H).

LC/MS(ESI):m/z=500 [M+H]+, RT=3.10 min, LC/MS Method 1

Step 4 Synthesis of Compound 16

To Compound 15 (25.3 g, 50.7 mmol) were added chloroform (253 mL) and tetrahydrofuran (127 mL) to dissolve, and 5 wt % Palladium hydroxide (5 g, 1.78 mmol) was added. The mixture was stirred for 2 hours at room temperature under hydrogen atmosphere. The mixture was filtered through Celite (registered trademark), and the filtrate was concentrated under reduced pressure. Ethyl acetate-hexane was added to the residue, and the solid was filtered to obtain Compound 16 (19.6 g, yield 95%).

$^1$H-NMR (DMSO-$d_6$) δ: 1.58 (m, 2H), 1.88 (m, 2H), 3.52 (m, 2H), 3.86 (s, 3H), 3.89 (m, 2H), 4.24 (m, 2H), 6.71 (dd, J=8.8, 2.4 Hz, 1H), 6.76 (d, J=2.4 Hz, 1H), 8.13 (m, 1H), 9.09 (s, 1H), 9.42 (s, 1H).

LC/MS(ESI):m/z=410 [M+H]+, RT=2.20 min, LC/MS Method 1

Step 5 Synthesis of Compound 18

Compound 16 (16.1 g, 39.3 mmol), Compound 17 (10.6 g, 59.0 mmol), triphenylphosphine (16.5 g, 62.9 mmol) were dissolved in tetrahydrofuran (217 mL) and cooled under ice bath, and DIAD (11.47 mL, 59.0 mmol) was added dropwise. After the addition, the mixture was warmed to 40° C., and stirred for 2 hours. The reaction mixture was allowed to room temperature and concentrated under reduced pressure. Ethyl acetate-diisopropyl ether was added, and the solid was filtered to obtain Compound 18 (20.3 g, yield 91%).

$^1$H-NMR (DMSO-$d_6$) δ: 1.52-1.63 (m, 4H), 1.97-2.05 (m, 4H), 3.46-3.58 (m, 4H), 3.87 (s, 3H), 3.90 (m, 2H), 4.20-4.28 (m, 4H), 4.69 (m, 1H), 6.61 (t, J=4.8 Hz, 1H), 6.96 (m, 1H), 7.11 (d, J=2.0 Hz, 1H), 8.22 (m, 1H), 8.36 (d, J=4.8 Hz, 2H), 9.12 (s, 1H).

LC/MS(ESI):m/z=571 [M+H]+, RT=2.95 min, LC/MS Method 1

Step 6 Synthesis of Compound 19

To Compound 18 (20.3 g, 35.6 mmol) were added tetrahydrofuran (203 mL), ethanol (203 mL) and 4 mol/L aqueous lithium hydroxide solution (44.5 mL, 178 mmol). After stirring at 50° C. for 4 hours, the mixture was allowed to room temperature, and 10% aqueous citric acid solution was added. Water was added, and the precipitated solid was filtered to obtain Compound 19 (19 g, yield 96%).

$^1$H-NMR (DMSO-$d_6$) δ: 1.52-1.61 (m, 4H), 1.97-2.05 (m, 4H), 3.46-3.57 (m, 4H), 3.90 (m, 2H), 4.24 (m, 2H), 4.26 (s, 2H), 4.69 (m, 1H), 6.61 (t, J=4.4 Hz, 1H), 6.96 (dd, J=8.8, 2.8 Hz, 1H), 7.10 (d, J=2.8 Hz, 1H), 8.22 (d, J=8.8 Hz, 1H), 8.36 (d, J=4.4 Hz, 2H), 9.11 (s, 1H), 13.54 (s, 1H).

LC/MS(ESI):m/z=557 [M+H]+, RT=2.44 min, LC/MS Method 1

Step 7 Synthesis of Compound (I-082)

To Compound 19 (795 mg, 1.43 mmol) were added dimethylformamide (8 mL), Compound 20 (431 mg, 1.71 mmol), HATU (706 mg, 1.86 mmol) and triethylamine (0.495 mL, 3.57 mmol) at room temperature. The mixture was stirred for 2 hours. Water was added to the reaction solution, and the precipitated solid was filtered. To the solid were added dichloromethane (5 mL) and trifluoroacetic acid (5 mL, 65 mmol), and the mixture was stirred at room temperature for 2 hours. Aqueous sodium bicarbonate was added to neutralize the mixture, and then 10% aqueous citric acid solution was added to acidify again, and the mixture was extracted with chloroform. The organic layer was washed with water and dried over anhydrous magnesium sulfate. The solvent was removed under reduced pressure, and the residue was purified by silica gel column chromatography (chloroform-methanol) to afford Compound (I-082) (820 mg, yield 78%).

$^1$H-NMR (DMSO-$d_6$) δ: 1.52-1.60 (m, 6H), 1.65-1.69 (m, 4H), 1.80 (m, 2H), 1.94-2.17 (m, 8H), 2.54 (brs, 2H), 3.46-3.58 (m, 4H), 3.90 (m, 2H), 4.22 (s, 2H), 4.26 (m, 2H), 4.67 (m, 1H), 6.61 (t, J=4.4 Hz, 1H), 6.93 (dd, J=8.8, 2.0 Hz, 1H), 7.08 (d, J=2.0 Hz, 1H), 8.17 (d, J=8.8 Hz, 1H), 8.36 (d, J=4.4 Hz, 2H), 8.46 (s 1H), 8.68 (s, 1H), 12.34 (s, 1H).

Example 4

Synthesis of Compound (I-148)

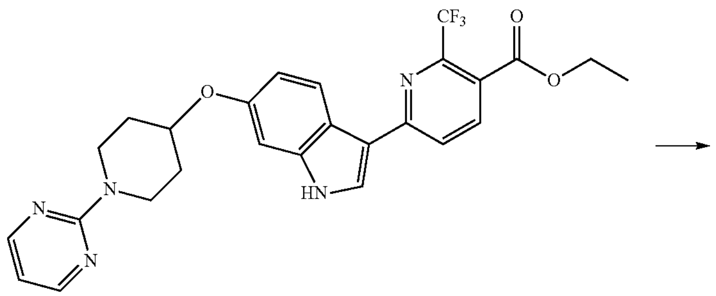

21

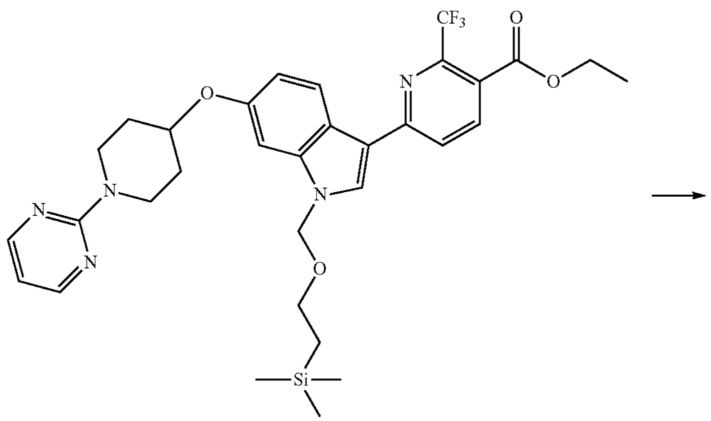

22

-continued
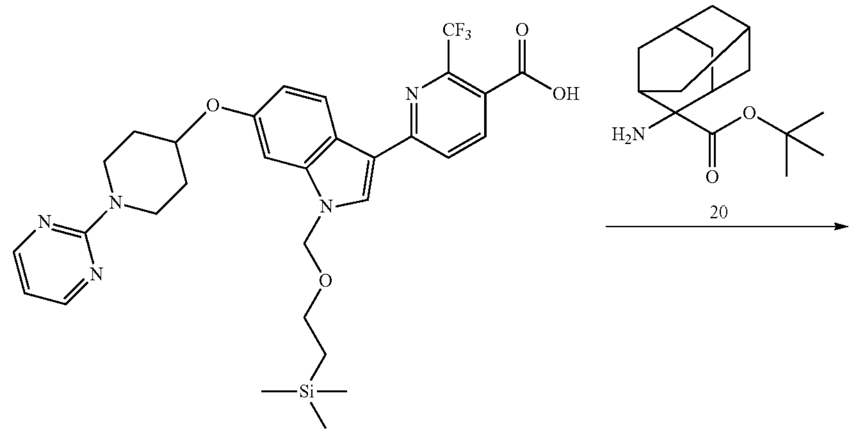
20
23
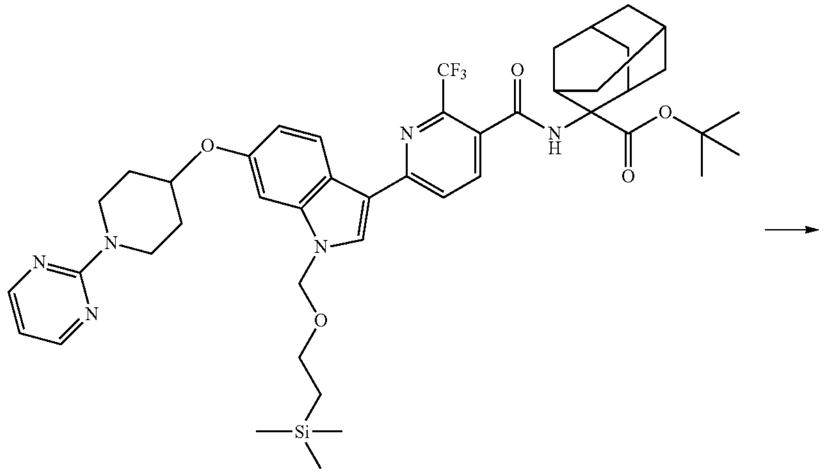
24
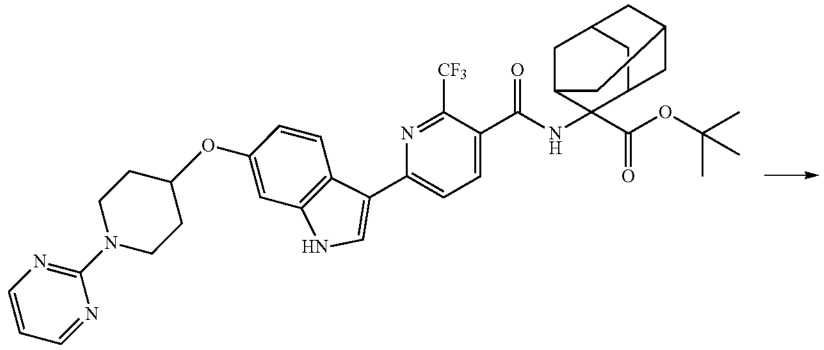
25

-continued

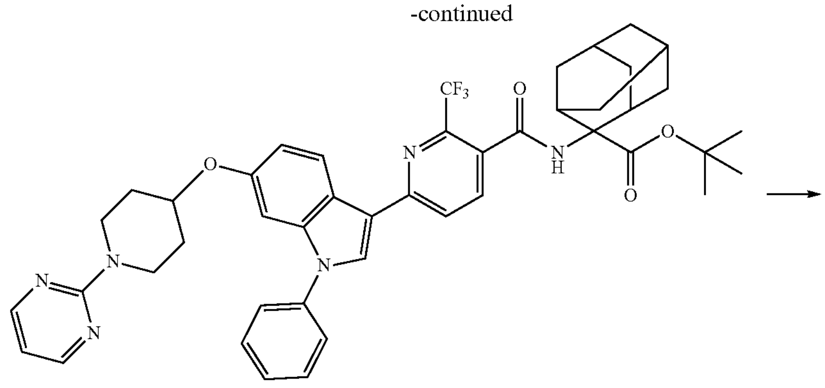

26

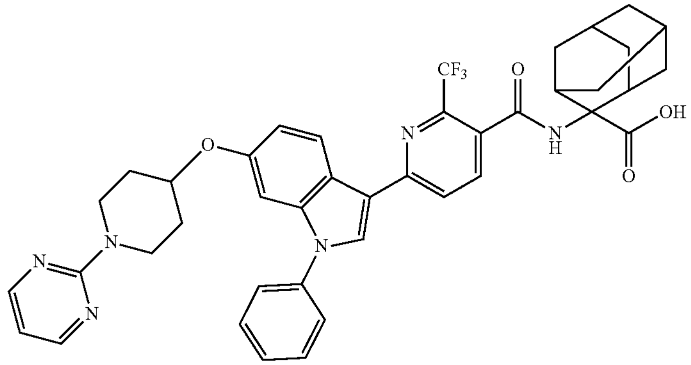

I-148

Step 1: Synthesis of Compound 22

To a solution of Compound 21 (100 mg, 0.20 mmol) (see Example 6 for the synthetic method) in dimethylformamide (1 mL) were added 60 wt % sodium hydride (11 mg, 0.29 mmol) and 2-(trimethylsilyl)ethoxymethyl chloride (49 mg, 0.29 mmol) under ice-cooling, and the mixture was stirred at room temperature for 1.5 hours. Saturated aqueous ammonium chloride solution was added, followed by extraction with ethyl acetate. The organic layer was washed with water, dried over anhydrous sodium sulfate, and the solvent was removed under reduced pressure. The residue was purified by silica gel column chromatography (hexane-ethyl acetate) to afford Compound 22 (74 mg, yield 59%).

LC/MS(ESI):m/z=642 [M+H]+, RT=1.182 min, LC/MS Method 7

Step 2 Synthesis of Compound 23

To a solution of Compound 22 (74 mg, 0.12 mmol) in ethanol (0.7 mL) was added 4 mol/L lithium hydroxide solution (0.28 mL, 1.16 mmol), and the mixture was stirred at 50° C. for 1 h 40 min. 10% aqueous citric acid solution was added, and the mixture was extracted with chloroform. After drying the organic layer with anhydrous sodium sulfate, the solvent was removed under reduced pressure to afford Compound 23 (73 mg) as a crude product.

LC/MS(ESI):m/z=614[M+H]+, RT=3.04 min, LC/MS Method 1

Step 3 Synthesis of Compound 24

Compound 23 (71 mg, 0.12 mmol) was dissolved in dimethylformamide (1.0 mL), and Compound 20 (30 mg, 0.12 mmol), HATU (52 mg, 0.14 mmol) and triethylamine (17 mg, 0.17 mmol) were added. After stirring at room temperature for 17 hours, water was added, and the precipitated solid was filtered to obtain Compound 24 (93 mg, yield 96%).

LC/MS(ESI):m/z=847[M+H]+, RT=2.80 min, LC/MS Method 7

Step 4: Synthesis of Compound 25

To a solution of Compound 24 (84 mg, 0.10 mmol) in tetrahydrofuran (0.3 mL) were added 1 mol/L tetrabutylammonium fluoride-tetrahydrofuran solution (0.50 mL, 0.50 mmol) and ethylenediamine (89 mg, 1.50 mmol), and the mixture was stirred with heating under reflux for 8 hours. 10% aqueous ammonium chloride solution was added, and the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 25 (70 mg, yield 99%).

LC/MS(ESI):m/z=717[M+H]+, RT=1.42 min, LC/MS Method 1

Step 5: Synthesis of Compound 26

To Compound 25 (460 mg, 0.64 mmol) were added 1,4-dioxane (6.9 mL), (1R,2R)-cyclohexane-1,2-diamine (22 mg, 0.19 mmol), tripotassium phosphate (272 mg, 1.28 mmol), iodobenzene (236 mg, 1.16 mmol) and copper(I) iodide (12 mg, 0.06 mmol), and the mixture was stirred with heating under reflux for 8 hours. Water was added, and the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 26 (500 mg, yield 98%).

LC/MS(ESI):m/z=793[M+H]+, RT=3.71 min, LC/MS Method 1

Step 6: Synthesis of Compound (I-148)

The compound was synthesized in the same manner as in Step 8 of Example 10.

$^1$H-NMR (DMSO-$d_6$) δ: 1.66-1.71 (m, 10H), 2.00-2.13 (m, 6H), 2.59 (s, 2H), 3.53-3.57 (m, 2H), 4.16 (dd, J=13.0, 6.4, 3.9 Hz, 2H), 4.66-4.72 (m, 1H), 6.60 (t J=4.8 Hz, 1H), 7.07-7.10 (m, 2H), 7.49 (t, J=7.3 Hz, 1H), 7.64-7.66 (m, 2H), 7.70-7.72 (m, 2H), 7.80 (d, J=8.3 Hz, 1H), 8.25 (d, J=8.3 Hz, 1H), 8.35 (d, J=4.8 Hz, 2H), 8.53-8.54 (m, 3H), 12.32 (s, 1H).

Example 5

Synthesis of Compound (I-159) and Compound (I-182)

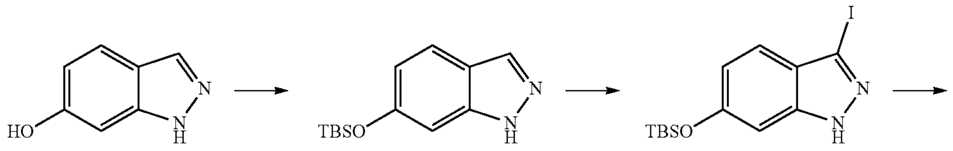

27 28 29

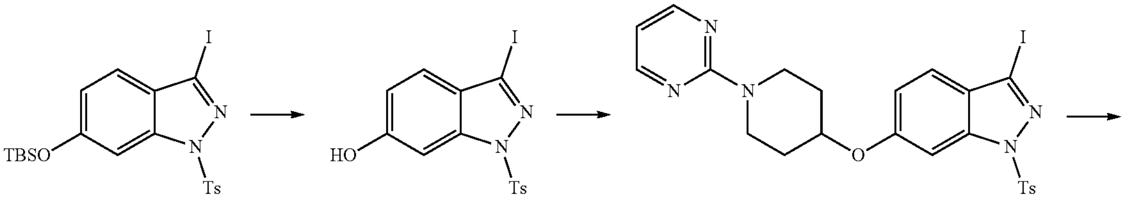

30 31 32

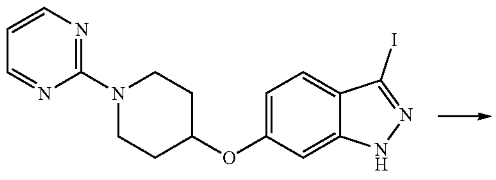

33

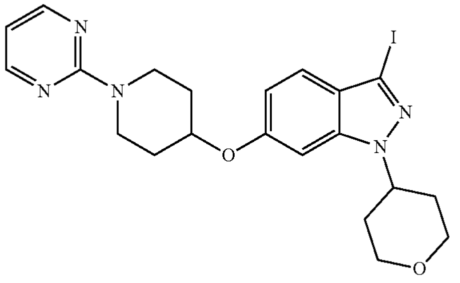

34

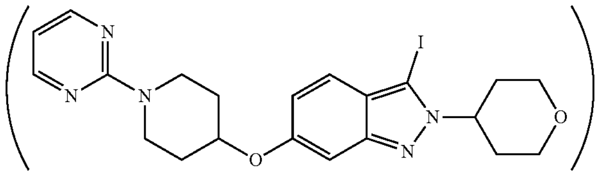

35

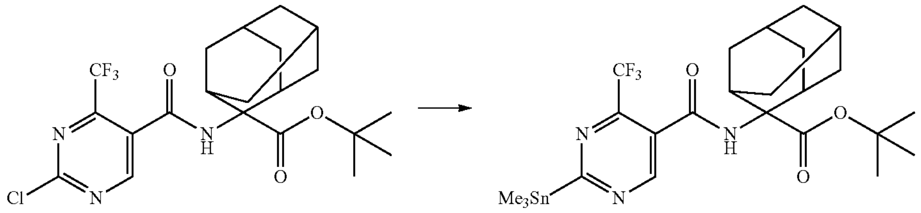

36 37

-continued

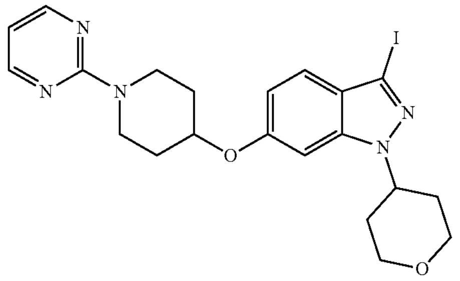

38

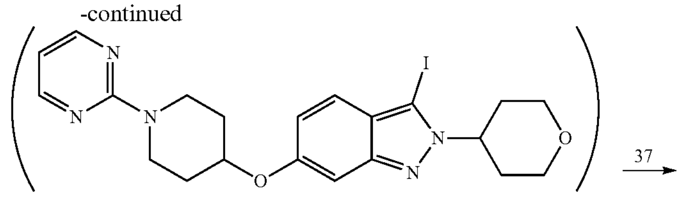

39

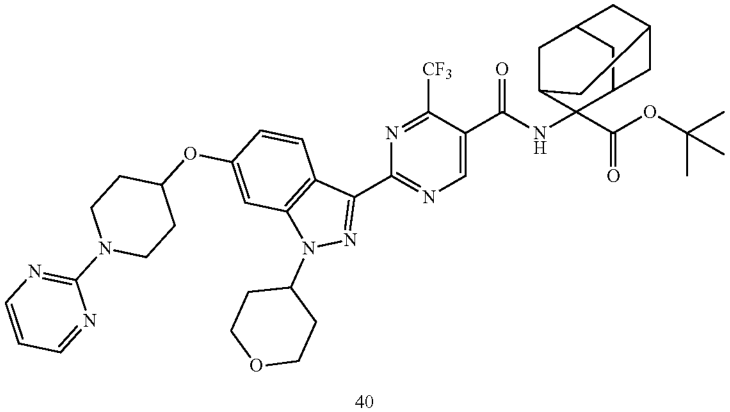

40

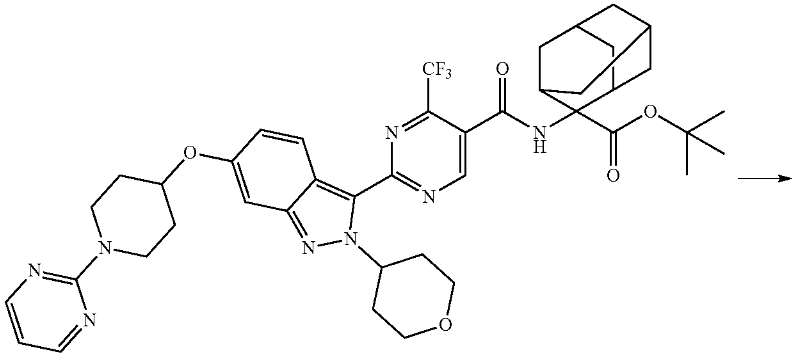

41

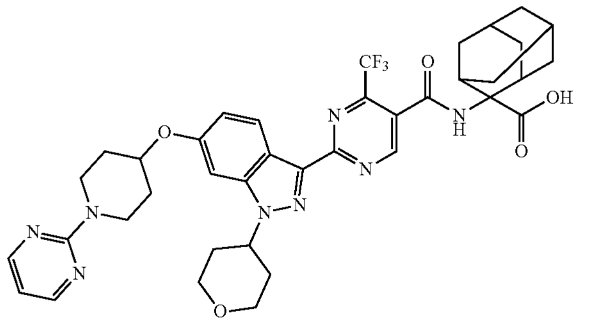

I-159

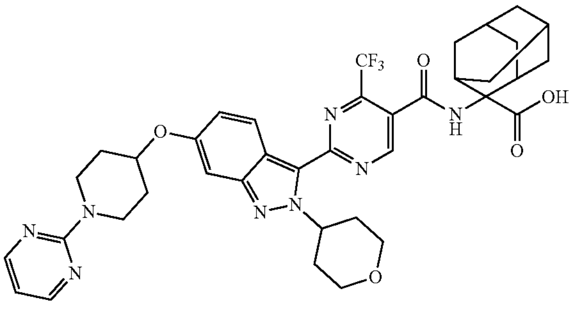

I-182

Step 1: Synthesis of Compound 28

To a solution of Compound 27 (2.01 g, 15.00 mmol) in dimethylformamide (20.1 mL) were added imidazole (1.53 g, 22.50 mmol) and tert-butyldimethylsilyl chloride (2.71 g, 18.00 mmol), and the mixture was stirred at room temperature for 40 minutes.

Water was added, followed by extraction with ethyl acetate. The organic layer was washed with water, dried over anhydrous sodium sulfate, and the solvent was removed under reduced pressure. The residue was purified by silica gel column chromatography (hexane-ethyl acetate) to afford Compound 28 (3.79 g, yield 100%).

LC/MS(ESI):m/z=249 [M+H]+, RT=2.66 min, LC/MS Method 1

Step 2: Synthesis of Compound 29

To a solution of Compound 28 (3.73 g, 15.00 mmol) in tetrahydrofuran (74.5 mL) were added potassium tert-butoxide (3.87 g, 34.50 mmol) and iodine (8.76 g, 34.50 mmol) udner ice-cooling, and the mixture was stirred for 1 hour udner ice-cooling. 20% aqueous sodium thiosulfate solution was added, the mixture was extracted with ethyl acetate. The organic layer was washed with water, dried over anhydrous sodium sulfate, and the solvent was removed under reduced pressure to afford Compound 29 (5.42 g) as a crude product.

LC/MS(ESI):m/z=375 [M+H]+, RT=3.09 min, LC/MS Method 1

Step 3: Synthesis of Compound 30

To a solution of Compound 29 (5.42 g, 14.48 mmol) in dichloromethane (54.2 mL) were added triethylamine (2.49 g, 24.61 mmol) and p-toluenesulfonyl chloride (2.49 g, 17.37 mmol) udner ice-cooling. The mixture was stirred at room temperature for 18 hours and filtered off the insoluble material. The filtrate was concentrated under reduced pressure, and the residue was purified by silica gel column chromatography (hexane-ethyl acetate) to afford Compound 30 (6.48 g, yield 82%).

LC/MS(ESI):m/z=529 [M+H]+, RT=3.67 min, LC/MS Method 1

Step 4: Synthesis of Compound 31

To a solution of Compound 30 (6.39 g, 12.09 mmol) in tetrahydrofuran (31.9 mL) was added 1 mol/L tetrabutylammonium fluoride-tetrahydrofuran solution (13.3 mL, 13.3 mmol) under ice-cooling, and the mixture was stirred at room temperature for 30 minutes. 0.4 mol/L hydrochloric acid was added, followed by extraction with ethyl acetate. The organic layer was washed with water, dried over anhydrous sodium sulfate, and the solvent was removed under reduced pressure. The residue was purified by silica gel column chromatography (hexane-ethyl acetate), and solidified with hexane-ethyl acetate to afford Compound 31 (2.87 g, yield 57%).

LC/MS(ESI):m/z=415 [M+H]+, RT=2.30 min, LC/MS Method 1

Step 5: Synthesis of Compound 32

The compound was synthesized in the same manner as in Step 3 of Example 6.

LC/MS(ESI):m/z=576 [M+H]+, RT=3.03 min, LC/MS Method 1

Step 6: Synthesis of Compound 33

To Compound 32 (6.09 g, 10.58 mmol) were added ethanol (122 mL), water (146 mL) and 8 mol/L aqueous sodium hydroxide solution (6.61 mL, 52.90 mL), and the mixture was stirred at 80° C. for 80 minutes. The organic solvent was removed under reduced pressure, followed by extraction with ethyl acetate. The organic layer was washed with water, dried over anhydrous sodium sulfate, and the solvent was removed under reduced pressure. The reide was suspended to chloroform, and solid was filetred to afford Compound 33 (2.93 g, yield 66%).

LC/MS(ESI):m/z=422 [M+H]+, RT=2.21 min, LC/MS Method 1

Step 7: Synthesis of Compound 34 and Compound 35

Compound 33 (3.45 g, 8.19 mmol) was dissolved in dimethylformamide (34.5 mL), and cesium carbonate (5.33 g, 16.36 mmol) and tetrahydro-2H-pyran-4-yl methanesulfonate (681 mg, 16.36 mmol) was added, and the mixture was stirred at 80° C. for 6 hours. Water was added, and the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 34 and Compound 35 as about 4:1 mixture (4.20 g, yield 100%).

Compound 34

LC/MS(ESI):m/z=506[M+H]+, RT=2.65 min, LC/MS Method 1

Compound 35

LC/MS(ESI):m/z=506[M+H]+, RT=2.39 min, LC/MS Method 1

Step 8: Synthesis of Compound 37

Compound 36 (2.00 g, 4.35 mmol), which was synthesized in the same manner as Compound 3, was suspended in toluene (40 mL), and 1,1,1,2,2,2-hexamethyldistannane (2.00 g, 4.35 mmol) and $Pd(PPh_3)_4$ (0.75 g, 0.65 mmol), and the mixture was stirred with heating under reflux for 1 hour. Water was added, and the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 37 (1.74 g, yield 68%).

LC/MS(ESI):m/z=590 [M+H]+, RT=3.34 min, LC/MS Method 1

Step 9: Synthesis of Compound 40 and Compound 41

The 4:1 mixture of Compound 38 and Compound 39 (1.01 g, 2.00 mmol) were dissolved in dimethylformamide (20 mL), and Compound 37 (1.74 g, 2.96 mmol) and $Pd(PPh_3)_4$ (0.35 g, 0.30 mmol), lithium chloride (0.17 g, 4.00 mmol) and copper(I) iodide (38 mg, 0.20 mmol) were added, and the mixture was stirred at 95° C. for 8.5 hours. Water was added, and the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 40 (505 mg, yield 31%) and Compound 41 (120 mg, yield 8%).

Compound 40

LC/MS(ESI):m/z=803[M+H]+, RT=3.43 min, LC/MS Method 1

Compound 41

LC/MS(ESI):m/z=803[M+H]+, RT=3.50 min, LC/MS Method 1

Step, 10: Synthesis of Compound (I-159) and Compound (I-182)

The compound was synthesized in the same manner as in Step 8 of Example 10.

Compound (I-159)

$^{1}$H-NMR ($CDCl_3$) δ: 1.78-1.83 (m, 6H), 1.92-1.95 (m, 4H), 2.03-2.12 (m, 6H), 2.23 (d, J=12.4 Hz, 2H), 2.56 (ddd, J=24.8, 12.4, 4.3 Hz, 2H), 2.67 (s, 2H), 3.64 (t, J=12.4 Hz, 2H), 3.79-3.85 (m, 2H), 4.14-4.21 (m, 4H), 4.70-4.76 (m, 2H), 6.38 (s, 1H), 6.51 (t, J=4.8 Hz, 1H), 6.97 (d, J=1.8 Hz, 1H), 7.06 (dd, J=9.0, 1.8 Hz, 1H), 8.34 (d, J=4.8 Hz, 2H), 8.49 (d, J=9.0 Hz, 1H), 9.16 (s, 1H), 12.12 (s, 1H).

Compound (I-182)

$^{1}$H-NMR ($CDCl_3$) δ: 1.79-2.26 (m, 18H), 2.50 (ddd, J=24.2, 11.5, 4.2 Hz, 2H), 2.68 (s, 2H), 3.60 (t, J 11.5 Hz, 2H), 3.68-3.74 (m, 2H), 4.15-4.26 (m, 4H), 4.64-4.69 (m, 1H), 5.95 (tt, J=11.5, 4.0 Hz, 1H), 6.30 (s, 1H), 6.49 (t, J=4.8 Hz, 1H), 7.01 (dd, J=9.2, 1.9 Hz, 1H), 7.17 (d, J=1.9 Hz, 1H), 8.32-8.33 (m, 3H) 9.15 (s, 1H), 12.12 (s, 1H).

Example 6

Synthesis of Compound (I-162)

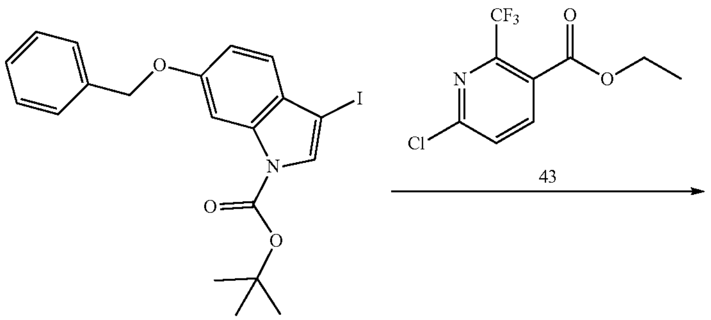

42

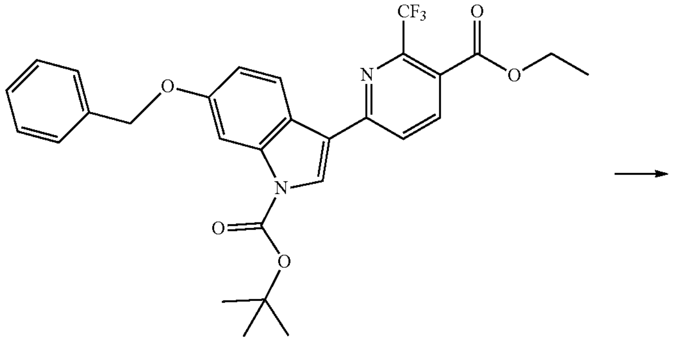

44

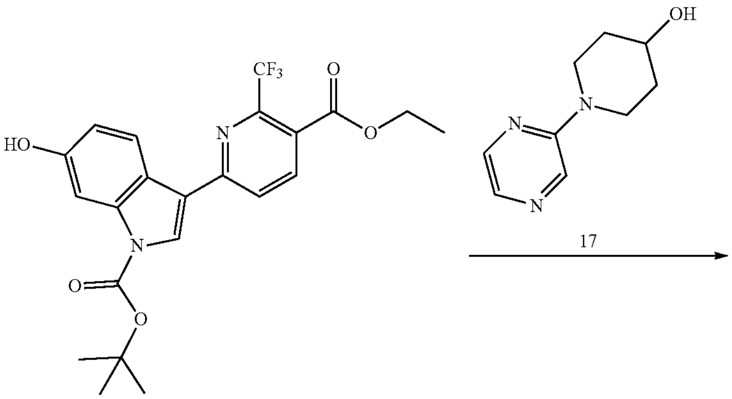

45

-continued
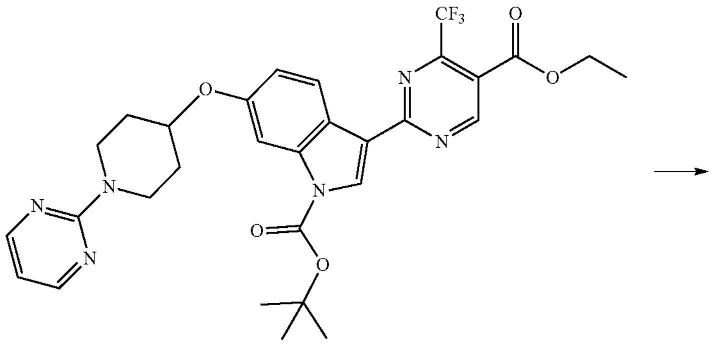
46
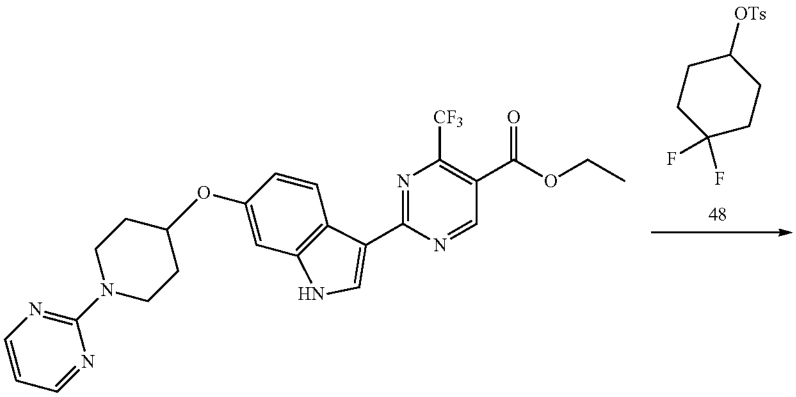
21
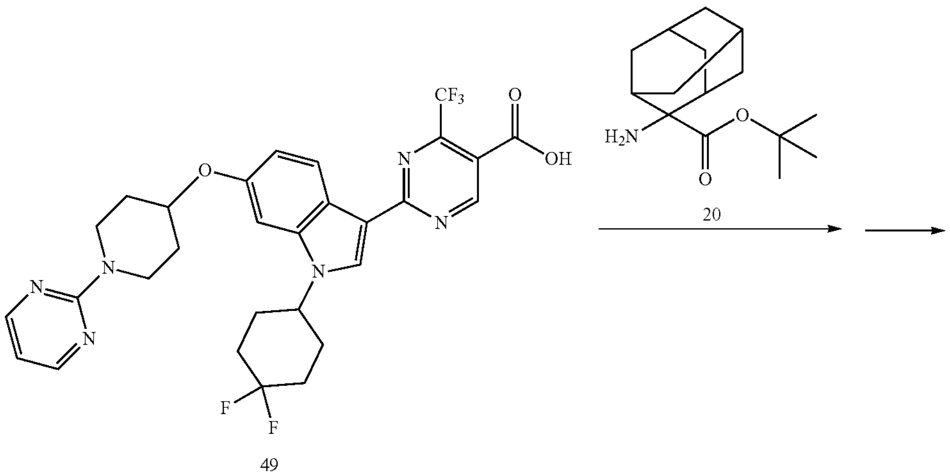
49

-continued

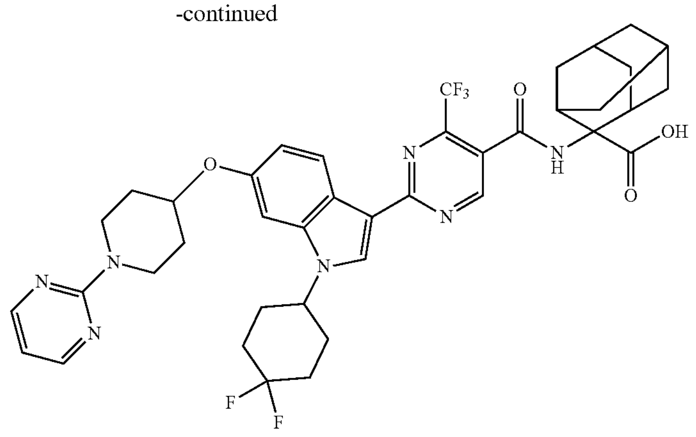

I-162

Step 1: Synthesis of Compound 44

To Compound 42 (10 g, 22.3 mmol) were added tetrahydrofuran (100 mL) and triisopropylborate (4.19 g, 22.3 mmol), and the mixture was cooled to −78° C. with dry ice-acetone. To the solution was added dropwise 1.59 mol/L n-butyl lithium-hexane solution (19.6 mL, 31.2 mmol). The solution was stirred at −78° C. for 20 minutes. The reaction was quenched by adding saturated aqueous ammonium chloride solution, warmed to room temperature, followed by extraction with ethyl acetate. The organic layer was washed with water, dried over anhydrous sodium sulfate, and the solvent was removed under reduced pressure. To the residue obtained were added 1,4-dioxane (102 mL), Compound 43 (6.2 g, 24.5 mmol), $PdCl_2$(dppf) (1.82 g, 2.23 mmol) and 2.2 mol/L aqueous potassium carbonate solution (20.4 mL, 44.5 mmol), and the mixture was stirred at 100° C. for 2 hours. After cooling, water was added, followed by extraction with ethyl acetate. The layers were separated, and the organic layer was washed with water and dried over anhydrous sodium sulfate. The solvent was removed under reduced pressure, and the residue was purified by silica gel column chromatography (hexane-ethyl acetate) to afford Compound 44 (7.1 g, yield 59%).

$^1$H-NMR ($CDCl_3$) δ: 1.42 (t, J=7.2 Hz, 3H), 1.70 (s, 9H), 4.44 (q, J=7.2 Hz, 2H), 5.17 (s, 2H), 7.10 (dd, J=8.8, 2.8 Hz, 1H), 7.34 (m, 1H), 7.40 (m, 2H), 7.48 (m 2H), 7.77-7.90 (m, 2H), 8.11-8.16 (m, 2H), 8.47 (d, J=8.8 Hz, 1H).

LC/MS(ESI):m/z=541[M+H]+, RT=3.21 min, LC/MS Method 1

Step 2: Synthesis of Compound 45

To Compound 44 (30.7 g, 56.8 mmol) were added tetrahydrofuran (307 mL) and 20 wt % palladium on activated carbon (6.34 g, 11.7 mmol). The mixture was stirred at room temperature under hydrogen atmosphere for 2 hours. The mixture was filtered with Celite (registered trademark), and the filtrate was concentrated under reduced pressure. Ethyl acetate-hexane was added to the residue, and the solid was filtered to obtain Compound 45 (22.0 g, yield 86%).

$^1$H-NMR ($CDCl_3$) δ: 1.42 (t, J=7.2 Hz, 3H), 1.71 (s, 9H), 4.44 (q, J=7.2 Hz, 2H), 4.94 (s, 1H), 6.93 (dd, J=8.8, 2.4 Hz, 1H), 7.71 (brs, 1H), 7.88 (d, J=8.4 Hz, 1H), 8.11 (s, 1H), 8.14 (d, J=8.4 Hz, 1H), 8.46 (d, J=8.8 Hz, 1H).

LC/MS(ESI):m/z=451 [M+H]+, RT=2.84 min, LC/MS Method 1

Step 3: Synthesis of Compound 46

To Compound 45 (3.27 g, 7.26 mmol) were added tetrahydrofuran (39.2 mL), Compound 17 (1.69 g, 9.44 mmol), triphenylphosphine (2.48 g, 9.44 mmol) and DMEAD (2.21 g, 9.44 mmol). The mixture was stirred at 50° C. for 1 hour, the reaction was quenched with water. The organic layer was extracted with ethyl acetate, washed with water, and dried over anhydrous sodium sulfate. The solvent was removed under reduced pressure, and the residue was purified by silica gel column chromatography (hexane-ethyl acetate) to afford Compound 46 (4.07 g, yield 92%).

$^1$H-NMR ($CDCl_3$) δ: 1.42 (t, J=7.2 Hz, 3H), 1.72 (s, 9H), 1.90 (m, 2H), 2.06 (m, 2H), 3.76 (m, 2H), 4.19 (m, 2H), 4.44 (q, J=7.2 Hz, 2H), 4.67 (m, 1H), 6.48 (t, J=4.4 Hz, 1H), 7.06 (dd, J=8.8, 2.0 Hz, 1H), 7.83 (brs, 1H), 7.89 (d, J=8.0 Hz, 1H), 8.13-8.16 (m, 2H), 8.32 (d, J=4.8 Hz, 2H), 8.49 (d, J=8.8 Hz, 1H).

LC/MS(ESI):m/z=612 [M+H]+, RT=3.59 min, LC/MS Method 1

Step 4: Synthesis of Compound 21

To Compound 46 (4.17 g, 6.82 mmol) were added dichloromethane (41.7 mL) and trifluoroacetic acid (41.7 mL, 541 mmol), and the mixture was stirred at room temperature for 1 hour 30 minutes. The reaction solution was concentrated under reduced pressure and neutralized with saturated aqueous sodium bicarbonate solution. The mixture was extracted with chloroform and dried over anhydrous sodium sulfate. The solvent was removed under reduced pressure, and chloroform was added to the residue. The solid was filtered to obtain Compound 21 (800 mg, yield 22%). The filtrate was again concentrated under reduced pressure. Tolene was added to solidify the residue, and the solid was filtered to obtain Compound 21 (1.73 g, yield 48%). The filtrate was further concentrated under reduced pressure, and the residue was purified by silica gel column chromatography (hexane-ethyl acetate) to afford Compound 21 (520 mg, yield 15%).

$^1$H-NMR ($CDCl_3$) δ: 1.42 (t, J=7.2 Hz, 3H), 1.88 (m, 2H), 2.06 (m, 2H), 3.71 (m, 2H), 4.21 (m, 2H), 4.43 (q, J=7.2 Hz, 2H), 4.61 (m, 1H), 6.48 (t, J=4.8 Hz, 1H), 6.98 (d, J=2.0 Hz,

1H), 7.02 (dd, J=8.8, 2.0 Hz, 1H), 7.78-7.84 (m, 2H), 8.11 (d, J=8.4 Hz, 1H), 8.32 (d, J=4.8 Hz, 2H), 8.42-8.48 (m, 2H).

LC/MS(ESI):m/z=512 [M+H]+, RT=2.80 min, LC/MS Method 1

Step 5: Synthesis of Compound 49

Compound 21 (800 mg, 1.56 mmol) was dissolved in dimethylformamide (12 mL), and 60 wt % sodium hydride (94 mg, 2.35 mmol) and Compound 48 (681 mg, 2.35 mmol) were added under ice-cooling. After stirring at 90° C. for 30 minutes, the mixture was again cooled under ice bath and 60 wt % sodium hydride (94 mg, 2.35 mmol) and Compound 48 (681 mg, 2.35 mmol) were added. After stirring at 90° C. for 30 minutes, the mixture was again cooled under ice bath and 60 wt % sodium hydride (94 mg, 2.35 mmol) and Compound 48 (681 mg, 2.35 mmol) were added. After stirring at 90° C. for 30 minutes, the mixture was again cooled under ice bath and 60 wt % sodium hydride (94 mg, 2.35 mmol) and Compound 48 (681 mg, 2.35 mmol) were added. After stirring at 90° C. for 30 minutes, the mixture was again cooled under ice bath and 60 wt % sodium hydride (94 mg, 2.35 mmol) and Compound 48 (681 mg, 2.35 mmol) were added, and the mixture was stirred at 90° C. for 30 minutes. The reaction solution was poured into 10% aqueous citric acid solution to quench the reaction, followed by extraction with ethyl acetate. The organic layer was washed with water and dried over anhydrous sodium sulfate. The solvent was removed under reduced pressure, and the residue was purified by silica gel column chromatography (chloroform-methanol) to afford Compound 49 (900 mg, yield 96%).

$^1$H-NMR ($CDCl_3$) δ: 1.71-2.24 (m, 10H), 2.35 (m, 2H), 3.77 (m, 2H), 4.20 (m, 2H), 4.32 (m, 1H), 4.67 (m, 1H), 6.54 (t, J=4.8 Hz, 1H), 6.96 (d, J=2.0 Hz, 1H), 7.05 (dd, J=8.8, 2.0 Hz, 1H), 7.80 (d, J=8.4 Hz, 1H), 7.82 (s, 1H), 8.23 (d, J=8.0 Hz, 1H), 8.39 (t, J=4.8 Hz, 2H), 8.50 (d, J=8.8 Hz, 1H).

LC/MS(ESI):m/z=602 [M+H]+, RT=2.71 min, LC/MS Method 1

Step 6: Synthesis of Compound (I-162)

The compound was synthesized in the same manner as in Step 7 of Example 3.

$^1$H-NMR (DMSO-$d_6$) δ: 1.55-1.71 (m, 8H), 1.81 (brs, 2H), 1.98-2.25 (m, 14H), 2.58 (s, 2H), 3.62 (m, 2H), 4.19 (m, 2H), 4.68-4.78 (m, 2H), 6.62 (t, J=4.8 Hz, 1H), 6.98 (dd, J=8.8, 2.0 Hz, 1H), 7.31 (d, J=2.0 Hz, 1H), 7.73 (d, J=8.4 Hz, 1H), 8.17 (d, J=8.4 Hz, 1H), 8.37 (d, J=4.4 Hz, 2H), 8.41-8.44 (m, 2H), 8.49 (s 1H), 12.32 (s, 1H).

LC/MS(ESI):m/z=779 [M+H]+, RT=3.06 min, LC/MS Method 1

Example 7

Synthesis of Compound (I-165)

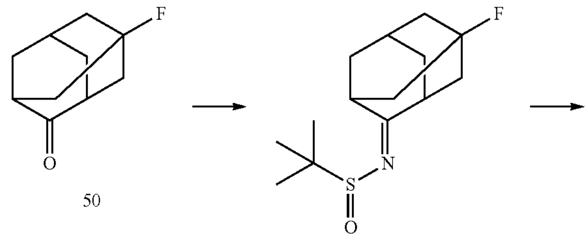

50 51

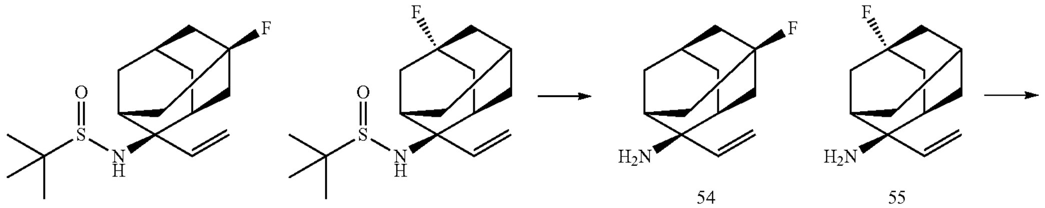

52 53 54 55

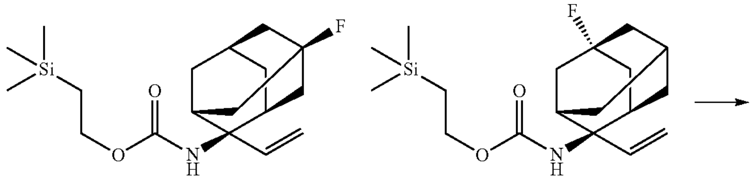

56 57

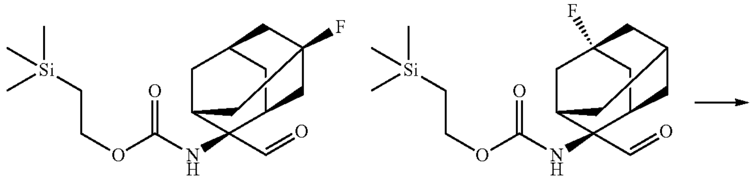

58 59

-continued
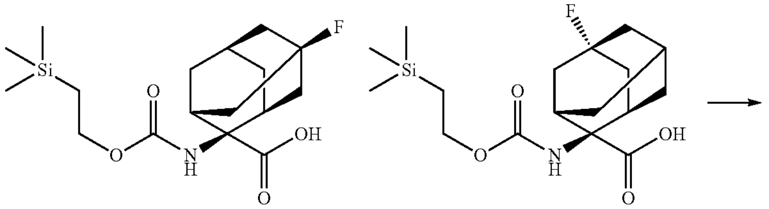
60 61
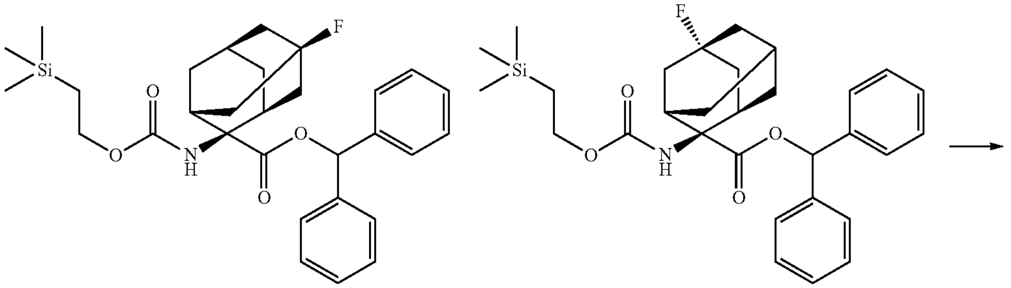
62 63
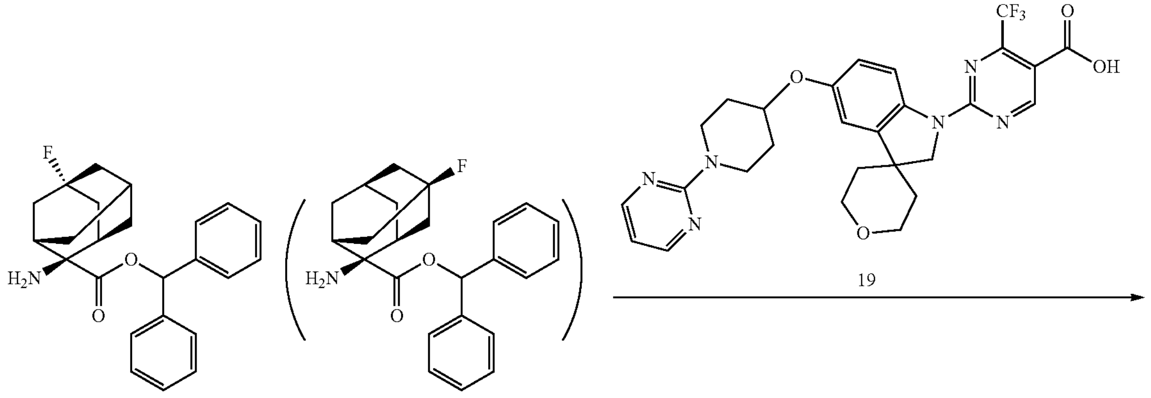
64 65 19
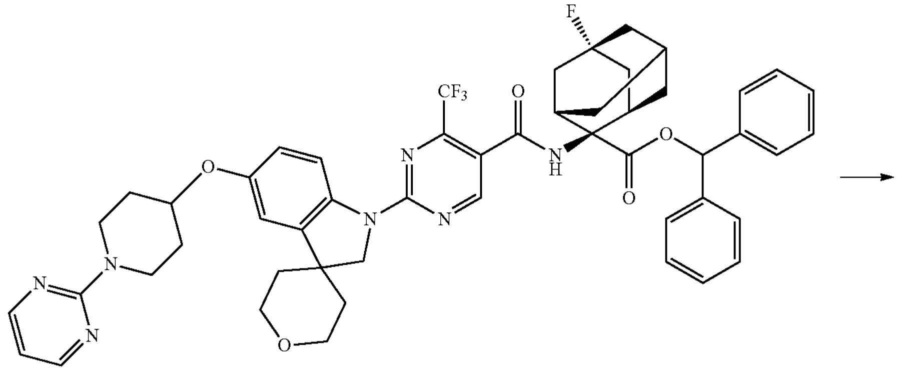
66

-continued

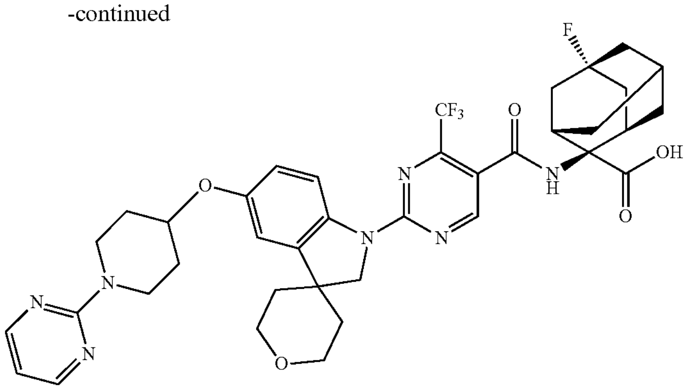

I-165

Step 1: Synthesis of Compound 51

Compound 50 (49.9 g, 297 mmol) and 2-methyl-2 propanesulfinamide (53.9 g, 445 mmol) were added to tetrahydrofuran (250 mL), and tetraethyl orthotitanate (137 mL, 653 mmol) was added at room temperature. The mixture was stirred at 80° C. for 1 hour and then poured into acetonitrile (1 L). Water (53.5 g) was added to quench the reaction. After stirring for 10 minutes, anhydrous magnesium sulfate was added, and the solid was filtered off. The filtrate was concentrated under reduced pressure, and the residue was purified by silica gel column chromatography (hexane-ethyl acetate) to afford Compound 51 (58.9 g, yield 70%).

LC/MS(ESI):m/z=272 [M+H]+, RT=1.81 min, LC/MS Method 2

Step 2: Synthesis of Mixture of Compound 52 and Compound 53

Compound 51 (70.3 g, 241 mmol) was dissolved in tetrahydrofuran (211 mL), and 1 mol/L vinylmagnesium bromide (361 mL, 361 mmol) was added dropwise under ice-cooling. The reaction was quenched with aqueous ammonium chloride solution, followed by extraction with ethyl acetate and washed with water, and the organic layer was concentrated under reduced pressure. The resulting solid was suspended with hexane, and the solid was filtered to obtain a mixture of Compound 52 and Compound 53 (46.1 g, yield 64%).

LC/MS(ESI):m/z=300 [M+H]+, RT=2.01 min, LC/MS Method 2

Step 3: Synthesis of Mixture of Compound 54 and Compound 55

To the mixture of Compound 52 and Compound 53 (70.7 g, 236 mmol) was added 2 mol/L hydrogen chloride methanol solution (354 mL, 708 mmol) and stirred at room temperature for 1 hour. Water and ethyl acetate were added for extraction. The aqueous layer was neutralized by adding aqueous sodium bicarbonate solution, followed by extraction with chloroform. The chloroform layer was dried over anhydrous magnesium sulfate, and the solvent was removed under reduced pressure to afford a mixture of Compound 54 and Compound 55 as crude product (55.2 g).

LC/MS(ESI):m/z=196 [M+H]+, RT=1.01 min, LC/MS Method 2

Step 4: Synthesis of Mixture of Compound 56 and Compound 57

The mixture of Compound 54 and Compound 55 (55.2 g, 223 mmol) was dissolved in tetrahydrofuran (497 mL), and 1-[2-(trimethylsilyl)ethoxycarbonyl]pyrrolidine-2,5-dione (100 g, 387 mmol) was added. After stirring at room temperature for 1 hour, 1-[2-(trimethylsilyl)ethoxycarbonyl]pyrrolidine-2,5-dione (12.5 g, 48.2 mmol) was added additionally. After stirring for 1 hour 40 minutes, aqueous citric acid solution was added. The mixture was extracted with ethyl acetate. The organic layer was washed with water and concentrated under reduced pressure. Hexane was added to the resulting solid, and the insoluble material was filtered off. The filtrate was concentrated under reduced pressure, and the residue was purified by silica gel column chromatography (hexane-ethyl acetate) to afford a mixture of Compound 56 and Compound 57 (65.0 g, yield 86%).

$^1$H-NMR ($CDCl_3$) δ: 0.03 (s, 9H), 0.92-0.98 (m, 2H), 1.49-1.56 (m, 2H), 1.73-1.80 (m, 2H), 1.87-2.01 (m, 4H), 2.13-2.28 (m, 3H), 2.56 (brs, 2H), 4.09 (m, 2H), 4.62 (s, 1H), 5.20-5.31 (m, 2H), 6.10 (dd, J=17.6, 2.8 Hz, 1H).

Step 5: Synthesis of Mixture of Compound 58 and Compound 59

The mixture of Compound 56 and Compound 57 (67.0 g, 197 mmol) was dissolved in acetonitrile (1179 mL), and water (395 mL), sodium periodate (127 g, 592 mmol), 2,6-lutidine (63.4 g, 592 mmol), potassium osmate dihydrate (7.27 g, 19.7 mmol) were added. The mixture was stirred at 60° C. for 1 hour, then sodium periodate (42.2 g, 197 mmol) was added. After 2 hours, the reaction was cooled under ice bath and quenched with aqueous sodium thiosulfate. The mixture was extracted with ethyl acetate, and the organic layer was washed with 10% aqueous citric acid solution, and washed with 3% aqueous sodium bicarbonate solution. The organic layer was dried over anhydrous magnesium sulfate, and the solvent was removed under reduced pressure. The residue was purified by silica gel column chromatography (hexane-ethyl acetate) to afford a mixture of Compound 58 and Compound 59 (32.5 g, yield 48%).

$^1$H-NMR ($CDCl_3$) δ: 0.03 (s, 9H), 0.92-1.00 (m, 2H), 1.56-1.98 (m, 8H), 2.09-2.28 (m, 3H), 2.63-2.69 (m, 2H), 4.12 (m, 2H), 4.81-4.89 (m, 1H), 9.60-9.74 (m, 2H).

Step 6: Synthesis of Mixture of Compound 60 and Compound 61

The mixture of Compound 58 and Compound 59 (36.1 g, 106 mmol) were dissolved in tert-butyl alcohol (361 mL)

and water (65 mL), and 2-methyl-2-butene (63.8 mL, 603 mmol) was added. Potassium dihydrogen phosphate (57.5 g, 423 mmol) and sodium chlorite (76 g, 846 mmol) were dissolved in water (300 mL) and added dropwise udner ice-cooling. After stirring under ice-cooling for 1 hour, the reaction was quenched with aqueous sodium thiosulfate. The mixture was extracted with ethyl acetate. The organic layer was washed with water and dried over anhydrous magnesium sulfate, and the solvent was removed under reduced pressure to afford a mixture of Compound 60 and Compound 61 as a crude product (45 g).

LC/MS(ESI):m/z=356 [M−H]−, RT=2.32 min and 2.41 min, LC/MS Method 2

Step 7: Synthesis of Mixture of Compound 62 and Compound 63

The crude product of mixture of Compound 60 and Compound 61 (45 g) was dissolved in tetrahydrofuran (227 mL) and methanol (227 mL), and diphenyldiazomethane (61.8 g, 318 mmol) was added. After stirring at room temperature for 2 hours, acetic acid (18.2 mL) was added. After stirring at room temperature for 1 hour, water was added, followed by extraction with ethyl acetate. The organic layer was washed with aqueous sodium carbonate solution and dried over magnesium sulfate. The solvent was removed under reduced pressure, and the residue was purified by silica gel column chromatography (hexane-ethyl acetate). The fraction was concentrated, and the residue was solidified by adding hexane, and the solid was filtered to obtain a mixture of Compound 62 and Compound 63 (21.5 g, yield 39%).

$^1$H-NMR ($CDCl_3$) δ: 0.03 (s, 9H), 0.73-0.94 (m, 2H), 1.50-1.56 (m, 2H), 1.75-1.96 (m, 6H), 2.10-2.20 (m, 3H), 2.84 (brs, 2H), 3.95 (m, 2H), 4.83 (brs, 1H), 6.90-6.93 (m, 1H), 7.25-7.31 (m, 10H).

Step 8: Synthesis of Compound 64

To the mixture of Compound 62 and Compound 63 (43.2 g, 82 mmol) were added 1 mol/L tetrabutylammonium fluoride-tetrahydrofuran solution (866 mL) and acetic acid (42.4 mL), and the mixture was stirred with heating under reflux for 15 hours. Aqueous sodium bicarbonate solution was added to neutralize, followed by extraction with ethyl acetate. The organic layer was washed three times with aqueous ammonium chloride solution, followed by sodium bicarbonate solution and brine. The organic layes was dried over anhydrous magnesium sulfate, and the solvent was removed under reduced pressure. The residue was purified by silica gel column chromatography (hexane-ethyl acetate) to separate the less polar Compound 65 from the high polar Compound 64 to afford Compound 64 (19.5 g, yield 56%).

$^1$H-NMR (DMSO-$d_6$) δ: 1.30-1.35 (m, 2H), 1.65-1.77 (m, 6H), 1.99-2.11 (m, 3H), 2.19-2.27 (m, 2H), 2.35 (brs, 2H), 6.82 (s, 1H), 7.27 (m, 2H), 7.35 (m, 4H), 7.45 (m, 4H).

Step 9: Synthesis of Compound 66

Compound 66 was synthesized in the same manner as in Step 3 of Example 4.

LC/MS(ESI):m/z=918 [M+H]+, RT=3.06 min, LCMS method 1

Step 10: Synthesis of Compound (I-165)

Compound 66 (66 mg, 0.07-2 mmol) was dissolved in dichloromethane (4 mL), and anisole (40 mg, 0.37 mmol) and trifluoroacetic acid (2 mL) were added udner ice-cooling. After stirring for 30 minutes udner ice-cooling, the reaction mixture was concentrated under reduced pressure. The residue was dissolved in dichloromethane and neutralized with aqueous sodium carbonate. Citric acid solution was added to the aqueous layer, followed by extraction with dichloromethane. The combined organic layers were dried over anhydrous sodium sulfate, and the solvent was removed under reduced pressure. The residue was purified by silica gel column chromatography (chloroform-methanol) to afford Compound (I-165) (33 mg, yield 61%).

$^1$H-NMR (DMSO-$d_6$) δ: 1.45-1.48 (m, 2H), 1.53-1.60 (m, 4H), 1.78-1.84 (m, 4H), 1.97-2.05 (m, 6H), 2.16-2.24 (m, 3H), 2.82 (s, 2H), 3.48-3.56 (m, 4H), 3.88-3.92 (m, 2H), 4.22-4.26 (m, 4H), 4.64-4.70 (m, 1H). 6.61 (t, J=4.8 Hz, 1H), 6.94 (d, J=8.0 Hz, 1H), 7.09 (d, J=2.4 Hz, 1H), 8.17 (d, J=4.4 Hz, 1H), 8.36 (d, J=4.8 Hz, 2H), 8.63 (brs, 1H), 8.71 (s, 1H), 12.67 (brs, 1H).

Example 8

Synthesis of Compound (I-228)

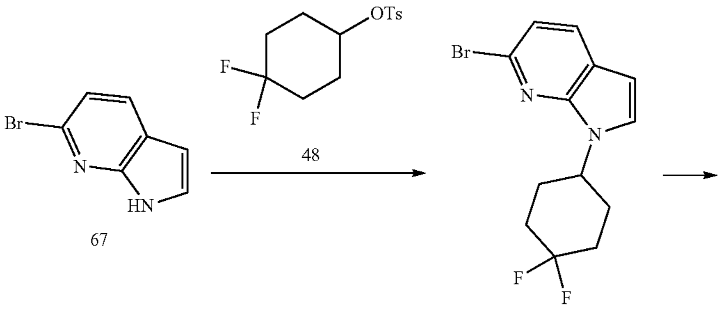

67

68

-continued
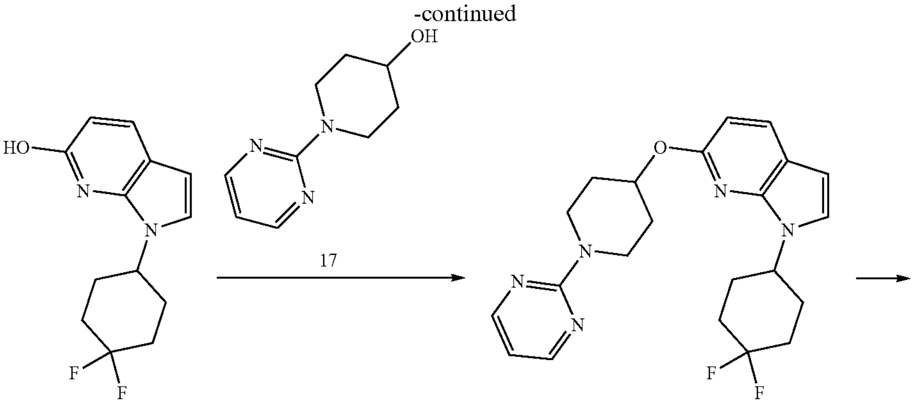
69 70
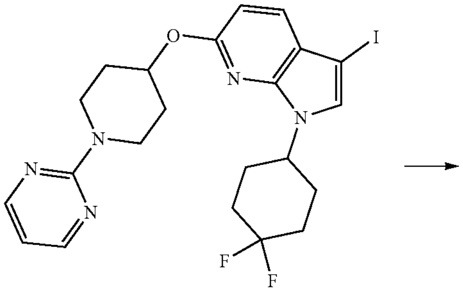
71
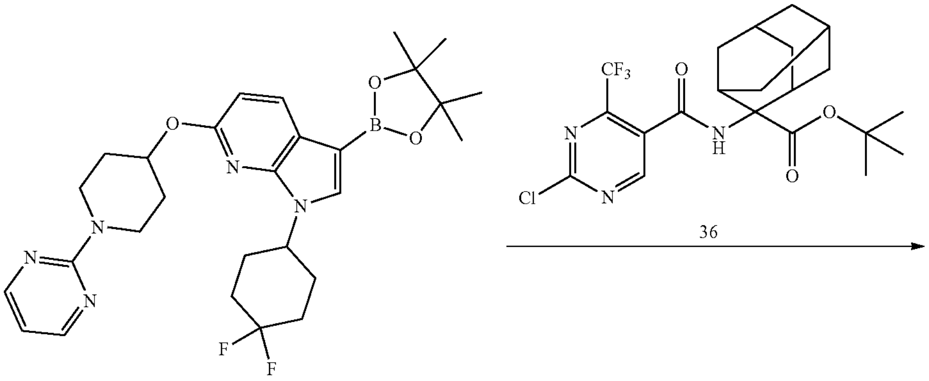
72
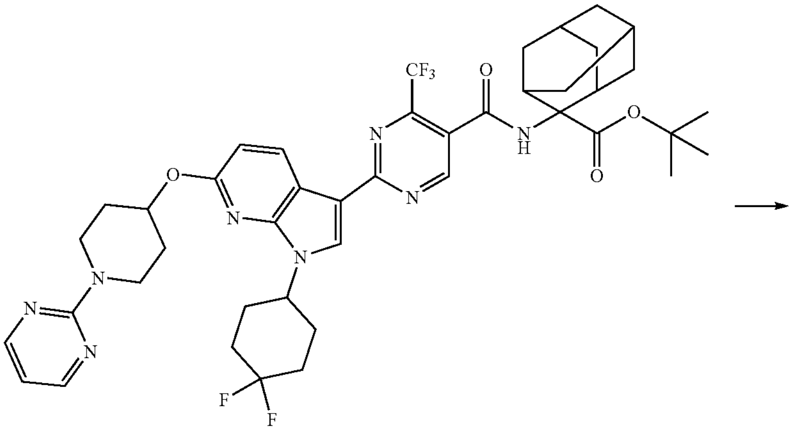
73

-continued

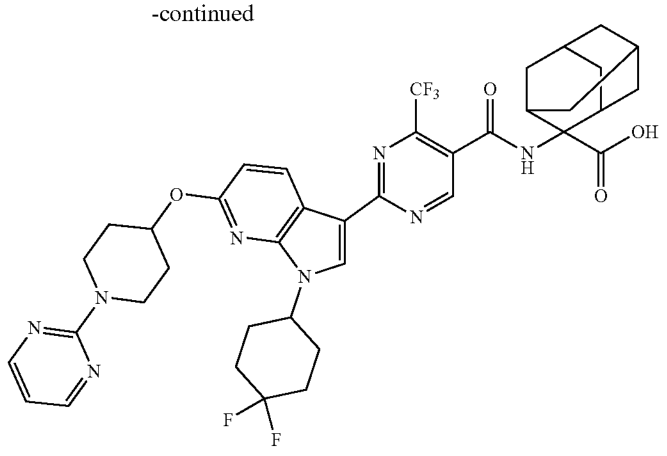

I-228

Step 1: Synthesis of Compound 68

To a solution of Compound 67 (300 mg, 1.52 mmol) in N-methylpyrrolidone (4.42 mL) was added 60 wt % sodium hydride (61 mg, 1.53 mmol) with stirring under argon flow at room temperature, and the mixture was stirred for 10 min at room temperature. Compound 48 (442 mg, 1.52 mmol) was then added at room temperature. After stirring at 100° C. for 3 hours, Compound 48 (442 mg, 1.52 mmol) and 60 wt % sodium hydride (61 mg, 1.53 mmol) were added, and the mixture was stirred at 80° C. for 5 hours. After completion of the reaction, saturated aqueous ammonium chloride solution was added to the reaction solution, followed by extraction with ethyl acetate. The organic layer was washed with brine and dried over anhydrous sodium sulfate. The solvent was concentrated under reduced pressure, and the residue was purified by silica gel column chromatography (hexane-ethyl acetate) to afford Compound 68 (252 mg, yield 53%).

LC/MS (DUIS):m/z=315 [M+H]+, RT=1.59 min, LC/MS Method 9

Step 2: Synthesis of Compound 69

Compound 68 (50 mg, 0.16 mmol) was dissolved in 1,4-dioxane (0.5 mL) and water (0.5 mL), and 8 mol/L potassium hydroxide solution (0.06 mL, 0.48 mmol), $Pd_2(dba)_3$ (15 mg, 0.02 mmol), 5-(Di-t-butylphosphino)-1',3',5'-triphenyl-1,4'-bi-1H-pyrazole (16 mg, 0.03 mmol) were added with stirring under argon flow at room temperature, and mixture was stirred at 75° C. After 2 hours, water was added, followed by extraction with ethyl acetate. The organic layer was washed with brine and dried over anhydrous sodium sulfate. The solvent was removed under reduced pressure, and the residue was purified by silica gel column chromatography (hexane-ethyl acetate) to afford Compound 69 as crude product (51 mg).

LC/MS (DUIS):m/z=253 [M+H]+, RT=1.04 min, LC/MS Method 9

Step 3: Synthesis of Compound 70

To the crude product of Compound 69 (49 mg, 0.19 mmol) in tetrahydrofuran (0.98 mL) were added Compound 17 (70 mg, 0.39 mmol), 1.9 mol/L DIAD-toluene solution (145 μL, 0.28 mmol), triphenylphosphine (74 mg, 0.28 mmol) under argon flow at room temperature, and the mixtue was stirred for 2 hours at room temperature. After completion of the reaction, aqueous sodium bicarbonate solution was added to the reaction solution, followed by extraction with ethyl acetate. The organic layer was washed with brine and dried over anhydrous sodium sulfate. The solvent was removed under reduced pressure, and the residue was purified by silica gel column chromatography (hexane-ethyl acetate) to afford Compound 70 (47 mg, 58%).

LC/MS (DUIS):m/z=414 [M+H]+, RT=1.77 min, LC/MS Method 9

Step 4: Synthesis of Compound 71

The compound was synthesized in the same manner as in Step 5 of Example 9.

LC/MS (DUIS):m/z=540 [M+H]+, RT=1.98 min, LC/MS Method 9

Step 5: Synthesis of Compound 72

The compound was synthesized in the same manner as in Step 6 of Example 9.

LC/MS (DUIS):m/z=540 [M+H]+, RT=2.00 min, LC/MS Method 9

Step 6: Synthesis of Compound 73

The compound was synthesized in the same manner as in Step 1 of Example 6.

LC/MS (DUIS):m/z=837 [M+H]+, RT=2.29 min, LC/MS Method 9

Step 7: Synthesis of Compound (I-228)

The compound was synthesized in the same manner as in Step 8 of Example 10.

$^1$H-NMR (DMSO-$d_6$) δ: 1.55-1.84 (m, 10H), 2.02-2.28 (m, 14H), 2.55-2.58 (m, 2H), 3.45-3.55 (m, 2H), 4.30-4.42 (m, 2H), 4.70-4.83 (m, 1H), 5.23-5.33 (m, 1H)—, 6.63 (t, J=4.8 Hz, 1H), 6.79 (d, J=8.5 Hz, 1H), 8.31 (s, 1H), 8.37 (d, J=4.6 Hz, 2H)), 8.61 (d, J=8.5 Hz, 1H), 8.65 (brs, 1H), 8.87 (s, 1H), 12.51 (brs, 1H).

LC/MS(ESI):m/z=781 [M+H]+, RT=1.86 min, LC/MS Method 10

Example 9
Synthesis of Compound (I-268)
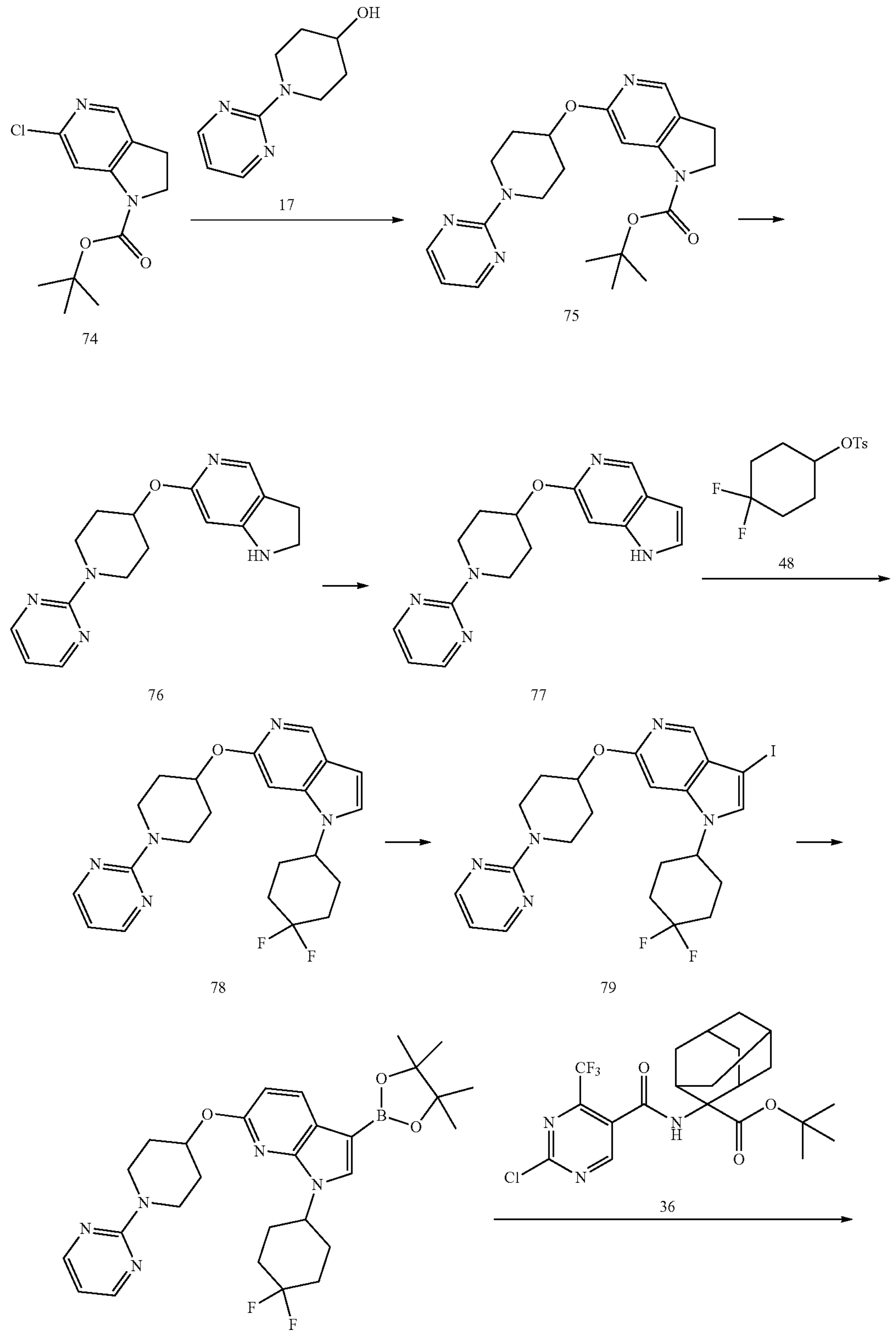
74
75
76
77
78
79
80

-continued

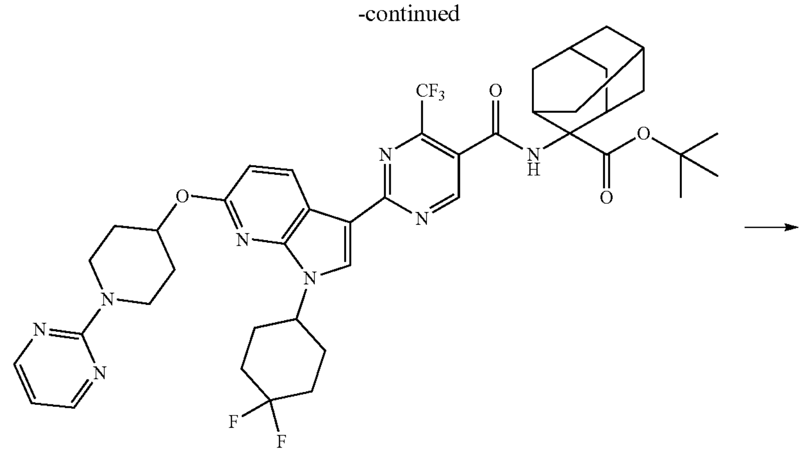

81

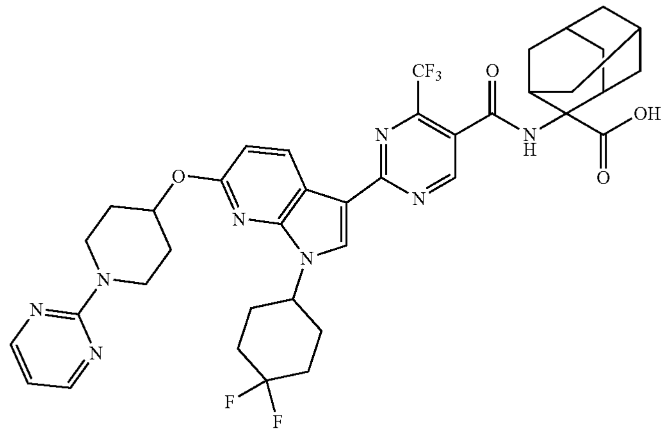

I-268

Step 1: Synthesis of Compound 75

To a solution of Compound 17 (760 mg, 4.24 mmol) in toluene (10 mL) was added 60 wt % sodium hydride (283 mg, 7.08 mmol) with stirring under argon flow at room temperature, and the mixture was stirred at 70° C. for 15 min. Compound 74 (910 mg, 3.57 mmol), $Pd_2(dba)_3$ (324 mg, 0.354 mmol), (R)-(+)-TolBINAP (240 mg, 0.354 mmol) were added at room temperature, and the mixture was stirred at 100° C. After 30 min, water was added, followed by extraction with ethyl acetate. The organic layer was washed with brine and dried over anhydrous magnesium sulfate. The solvent was removed under reduced pressure, and the residue was purified by silica gel column chromatography (hexane-ethyl acetate) to afford Compound 75 (899 mg, yield 63%).

LC/MS (DUIS):m/z=398 [M+H]+, RT=1.17 min, LC/MS Method 9

Step 2: Synthesis of Compound 76

To a solution of Compound 75 (899 mg, 2.26 mmol) in dichloromethane (2 mL) was added trifluoroacetic acid (2 mL, 26.1 mmol) with stirring under argon flow at room temperature, and the mixture was stirred for 6 hours. After completion of the reaction, aqueous sodium bicarbonate solution was added to the reaction solution, followed by extraction with ethyl acetate. The organic layer was washed with brine and dried over anhydrous magnesium sulfate. The solvent was removed under reduced pressure to obtain Compound 76 (695 mg, yield 100%).

LC/MS (DUIS):m/z=298 [M+H]+, RT=0.35 min, LC/MS Method 9

Step 3: Synthesis of Compound 77

To a solution of Compound 76 (530 mg, 1.78 mmol) in toluene (15.9 mL) was added manganese dioxide (775 mg, 8.91 mmol) at room temperature with stirring under argon flow, and the mixture was stirred at 120° C. for 6 hours. Then, after stirring at room temperature for 18 hours, manganese dioxide (775 mg, 8.91 mmol) was added at room temperature with stirring under argon flow, followed by stirring at 120° C. for 2 hours. After completion of the reaction, the solution was filtered through Celite (registered trademark), washed with ethyl acetate, and the filtrate was concentrated under reduced pressure to afford Compound 77 (342 mg, yield 65%) LC/MS (DUIS):m/z=296 [M+H]+, RT=0.36 min, LC/MS Method 9

Step 4: Synthesis of Compound 78

To a solution of Compound 77 (370 mg, 1.25 mmol) in N-methylpyrrolidone (7.4 mL) were added cesium carbonate (1.22 g, 3.74 mmol) and Compound 48 (1.09 g, 3.75 mmol) at room temperature with stirring under argon flow, and the mixture was stirred at 120° C. for 3 hours. Then, cesium carbonate (1.22 g, 3.74 mmol) and Compound 48 (1.09 g, 3.75 mmol) were added at room temperature, and the mixture was stirred at 120° C. for 2 hours. Additionally, cesium carbonate (1.22 g, 3.74 mmol) and Compound 48 (1.09 g, 3.75 mmol) were added at room temperature, and the mixture was stirred at 120° C. for 2 hours. After completion of the reaction, water was added to the reaction solution, followed by extraction with ethyl acetate. The organic layer was washed with brine and dried over anhydrous magnesium sulfate. The solvent was removed under reduced pressure, and the residue was purified by silica gel column chromatography (hexane-ethyl acetate) to afford Compound 78 (520 mg, yield 100%).

LC/MS (DUIS):m/z=414 [M+H]+, RT=0.91 min, LC/MS Method 9

Step 5: Synthesis of Compound 79

To a solution of Compound 78 (470 mg, 1.14 mmol) in dimethylformamide (4.7 mL) was added N-iodosuccinimide (280 mg, 1.25 mmol) at room temperature with stirring under argon flow, and the mixture was stirred at room temperature for 30 minutes. After completion of the reaction, aqueous sodium bicarbonate solution was added to the reaction solution, followed by extraction with ethyl acetate. The organic layer was washed with brine and dried over anhydrous sodium sulfate. The solvent was removed under reduced pressure, and the residue was purified by silica gel column chromatography (hexane-ethyl acetate) to afford Compound 79 (180 mg, yield 29%).

LC/MS(ESI):m/z=540 [M+H]+, RT=1.43 min, LC/MS Method 10

Step 6: Synthesis of Compound 80

To a solution of Compound 79 (180 mg, 0.33 mmol) in 1,4-dioxane (3.6 mL) were added triethylamine (185 μL, 1.33 mmol), 4,4,5,5-tetramethyl-1,3,2-dioxaborolane (195 μL, 1.34 mmol), X-Phos (32 mg, 0.07 mmol), $Pd_2$ (dba) 3 (31 mg, 0.03 mmol) at room temperature with stirring under argon flow, and the mixture was stirred at 95° C. for 1 hour. After completion of the reaction, water was added to the reaction solution, followed by extraction with ethyl acetate. The organic layer was washed with brine and dried over anhydrous sodium sulfate. The solvent was removed under reduced pressure, and the residue was purified by silica gel column chromatography (hexane-ethyl acetate) to afford Compound 80 (111 mg, yield 62%).

LC/MS(ESI):m/z=540 [M+H]+, RT=1.29 min, LC/MS Method 10

Step 7: Synthesis of Compound 81

The compound was synthesized in the same manner as in Step 1 of Example 6.

LC/MS(ESI):m/z=837 [M+H]+, RT=1.99 min, LC/MS Method 10

Step 8: Synthesis of Compound (I-268)

The compound was synthesized in the same manner as in Step 8 of Example 10.

$^1$H-NMR (DMSO-$d_6$) δ: 1.49-1.84 (m, 10H), 2.01-2.22 (m, 14H), 2.56-2.60 (m, 2H), 3.54-3.63 (m, 2H), 4.21-4.31 (m, 2H), 4.60-4.73 (m, 1H), 5.33-5.43 (m, 1H), 6.62 (t, J=4.8 Hz, 1H), 7.15 (s, 1H), 8.37 (d, J=4.8 Hz, 2H), 8.41 (brs, 1H), 8.51 (brs, 1H), 8.89 (s, 1H), 9.23 (s, 1H), 12.51 (brs, 1H).

LC/MS (DUIS):m/z=781 [M+H]+, RT=1.56 min, LC/MS Method 9

Example 10

Synthesis of Compound (I-269)

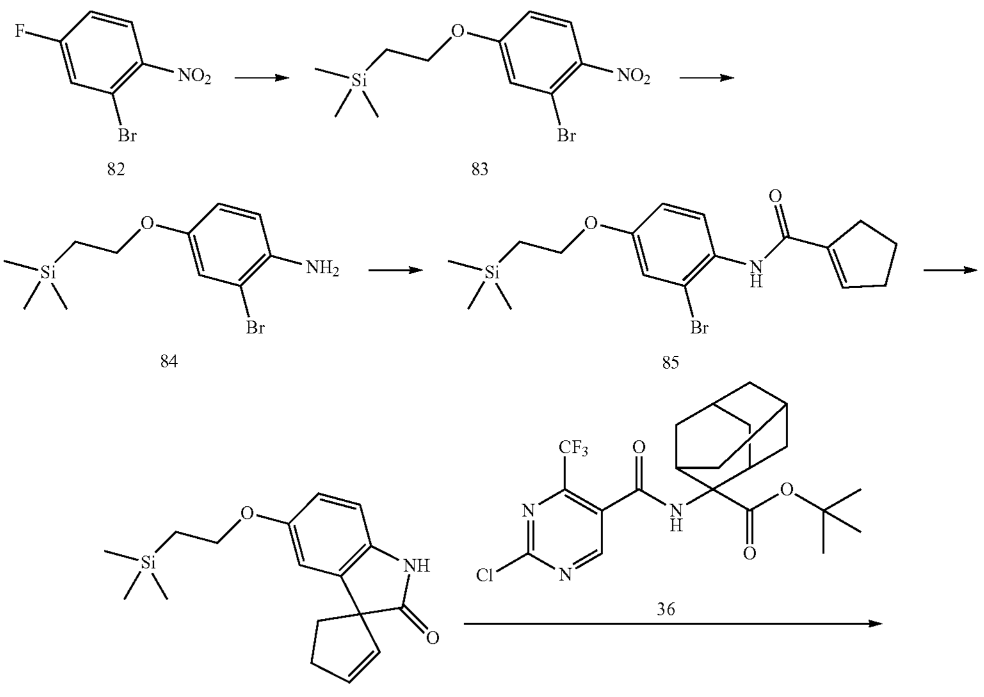

82 83 84 85 86

-continued

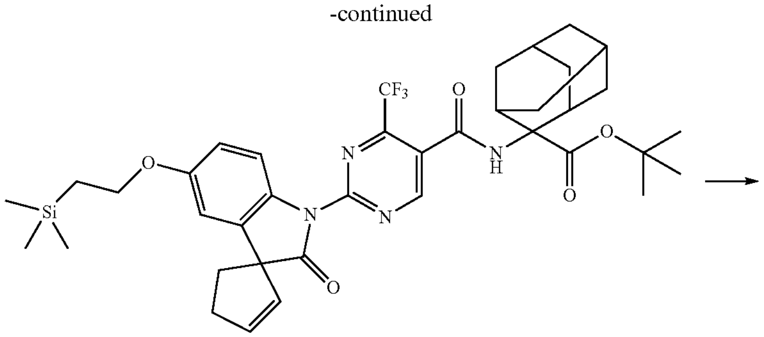

87

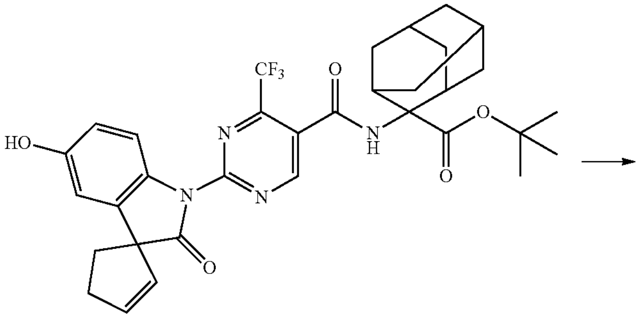

88

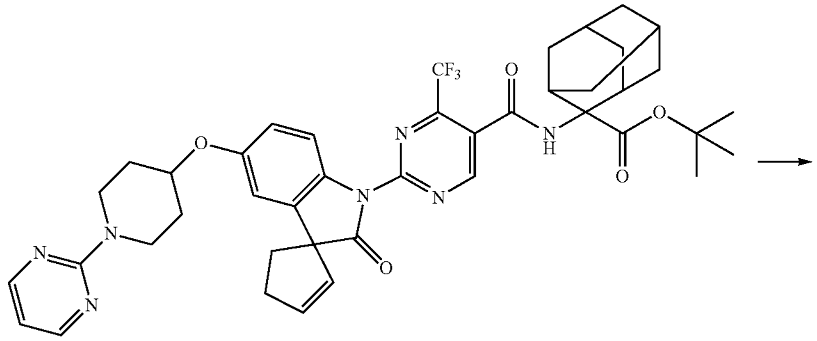

89

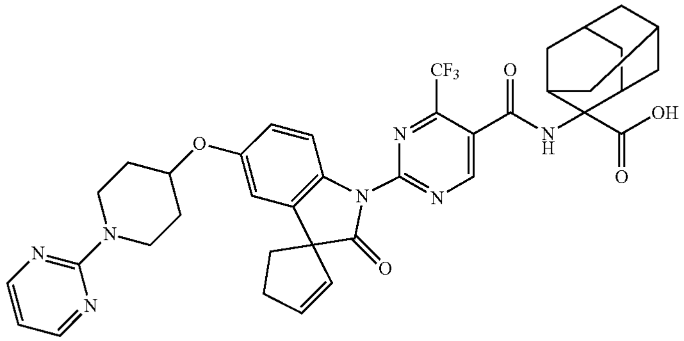

I-269

Step 1: Synthesis of Compound 83

2-(Trimethylsilyl)ethan-1-ol (1.08 g, 9.10 mmol) was dissolved in tetrahydrofuran (10 mL), and 60 wt % sodium hydride (218 mg, 5.46 mmol) was aded under ice-cooling. After 5 minutes, Compound 82 (1.00 g, 4.55 mmol) was added, and the mixture was, stirred at room temperature for 3 hours. The reaction was quenched with water, followed by extraction with ethyl acetate. The organic layer was washed with water and dried over anhydrous sodium sulfate. The solvent was removed under reduced pressure, and the residue was purified by silica gel column chromatography (hexane-ethyl acetate) to afford Compound 83 (1.45 g, yield 100%).

$^1$H-NMR ($CDCl_3$) δ: 1.10 (s, 9H), 1.16 (t, J=8.0 Hz, 2H), 4.14 (t, J=8.0 Hz, 2H), 6.88 (dd, J=9.2, 2.8 Hz, 1H), 7.18 (d, J=2.8 Hz, 1H), 7.98 (d, J=9.2 Hz, 1H).

Step 2: Synthesis of Compound 84

Compound 83 (500 mg, 1.57 mmol) was dissolved in ethanol (5 mL), and water (1 mL), ammonium chloride (336 mg, 6.28 mmol) and iron (438 mmol, 7.85 mmol) were added, and the mixture was stirred at 90° C. for 3 hours. The reaction solution was cooled and then diluted with ethyl acetate (30 mL), and the insoluble material was filtered off using Celite (registered trademark). Water was added to the filtrate, followed by extraction with ethyl acetate. The organic layer was washed with water and dried over anhydrous sodium sulfate. The solvent was removed under reduced pressure, and the residue was purified by silica gel column chromatography (hexane-ethyl acetate) to afford Compound 84 (303 mg, yield 67%). LC/MS(ESI):m/z=288 [M+H]+, RT=2.83 min, LC/MS Method 1

Step 3: Synthesis of Compound 85

Compound 84 (1.93 g, 6.70 mmol) was dissolved in dimethylformamide (10 mL), and cyclopent-1-ene-1-carboxylic acid (1.08 g, 1.44 mmol), triethylamine (3.39 g, 33.5 mmol) and HATU (3.80 g, 10.1 mmol) were added, and the mixture was stirred at room temperature for 6 hours. Water was added to the reaction solution, followed by extraction with ethyl acetate. The organic layer was washed with saturated aqueous sodium bicarbonate solution and washed with water. The organic layer was dried over anhydrous sodium sulfate, and the solvent was removed under reduced pressure. The residue was purified by silica gel column chromatography (hexane-ethyl acetate) to afford Compound 85 (816 mg, yield 32%).

LC/MS(ESI):m/z=382 [M+H]+, RT=3.08 min, LC/MS Method 1

Step 4: Synthesis of Compound 86

Compound 85 (816 mg, 2.13 mmol) was dissolved in dimethylformamide (6 mL), and triethylamine (1.08 g, 10.6 mmol) and $PdCl_2$(dppf) (156 mg, 0.213 mmol) were added, and the mixture was stirred at 80° C. for 2 hours. After the reaction solution was allowed to cool, water was added, followed by extraction with ethyl acetate. The organic layer was washed with water and dried over anhydrous sodium sulfate. The solvent was removed under reduced pressure, and the residue was purified by silica gel column chromatography (hexane-ethyl acetate) to afford Compound 86 (467 mg, yield 73%).

LC/MS(ESI):m/z=302 [M+H]+, RT=2.50 min, LC/MS Method 1

Step 5: Synthesis of Compound 87

Compound 86 (218 mg, 0.723 mmol) was dissolved in 1,4-dioxane (2 mL), and Compound 36 (399 mg, 0.868 mmol), cesium carbonate (707 mg, 2.17 mmol) and Xantphos Pd G2 (129 mg, 0.145 mmol) were added, and the mixture was stirred at 100° C. for 1 hour under nitrogen atmosphere. After cooling, the mixture was diluted with ethyl acetate (10 mL), and the insoluble material was filtered off. The solvent was removed under reduced pressure, and the residue was purified by silica gel column chromatography (hexane-ethyl acetate) to afford Compound 87 (404 mg, yield 77%).

LC/MS(ESI):m/z=725 [M+H]+, RT=3.54 min, LC/MS Method 1

Step 6: Synthesis of Compound 88

To Compound 87 (404 mg, 0.557 mmol) was added 1 mol/L tetrabutylammonium fluoride-tetrahydrofuran solution (10 mL, 10 mmol), and the mixture was stirred at 80° C. for 1 hour. After cooling, water was added, followed by extraction with ethyl acetate. The orgnic layer was washed with water, dried over anhydrous sodium sulfate, and the solvent was removed under reduced pressure. The residue was dissolved in, dimethylformamide (8 mL), and triethylamine (169 mg, 1.67 mmol) and HATU (318 mg, 0.835 mmol) were added, and the mixture was stirred at room temperature for 30 minutes. Methanol (20 mL) and potassium carbonate (231 mg, 1.67 mmol) were added, and the mixture was stirred at room temperature for 30 minutes, water was added to the reaction solution, followed by extracted with ethyl acetate. The organic layer was washed with water and dried over anhydrous sodium sulfate. The solvent was removed under reduced pressure, and the residue was purified by silica gel column chromatography (hexane-ethyl acetate) to afford Compound 88 (203 mg, yield 58%). LC/MS(ESI):m/z=625 [M+H]+, RT=2.77 min, LC/MS Method 1

Step 7: Synthesis of Compound 89

The compound was synthesized in the same manner as in Step 5 of Example 3.

LC/MS(ESI):m/z=786 [M+H]+, RT=3.11 min, LC/MS Method 1

Step 8: Synthesis of Compound (I-269)

Compound 89 (50 mg, 0.064 mmol) was dissolved in trifluoroacetic acid (4 mL), and the mixture was stirred at room temperature for 1 hour. The reaction solution was concentrated, dissolved in dichloromethane, and neutralized with saturated aqueous sodium bicarbonate solution. Aqueous citric acid solution was added to the reaction solution to acidify again, followed by extraction with dichloromethane. The organic layer was dried over anhydrous sodium sulfate, and the solvent was removed in vacuo. The residue was purified by silica gel column chromatography (chloroform-methanol) to afford Compound (I-269) (30 mg, yield 65%).

$^1$H-NMR ($CDCl_3$) δ: 1.77-2.05 (m, 15H), 2.19-2.27 (m, 3H), 2.61-2.67 (m, 3H), 2.70-2.76 (m, 0.1H), 2.78-2.87 (m, 1H), 3.69-3.75 (m, 2H), 4.11-4.19 (m, 2H), 4.51-4.57 (m, 1H), 5.53-5.56 (m, 1H), 6.24-6.27 (m, 1H), 6.49 (t, J=5.2 Hz, 1H), 6.55 (brs, 1H), 6.81 (d, J=2.8 Hz, 1H), 6.90 (dd, J=8.8, 2.4 Hz, 1H), 7.88 (d, J=9.2 Hz, 1H), 8.32 (d, J=4.8 Hz, 2H), 9.12 (s, 1H).

Example 11
Synthesis of Compound (I-270)
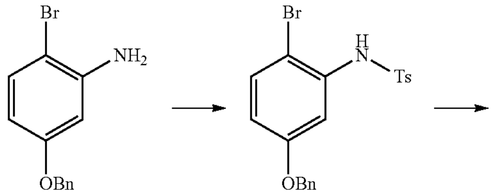
90 91
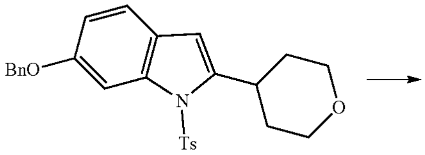
92
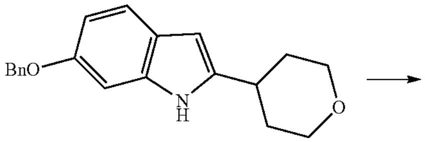
93
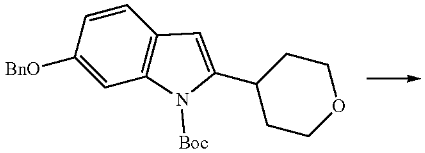
94
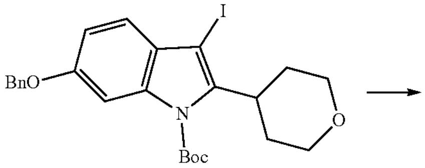
95
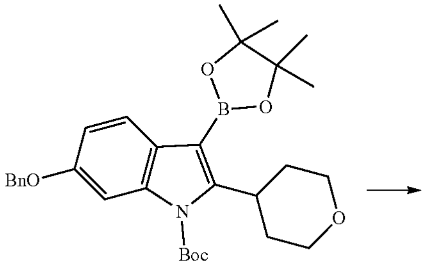
96
-continued
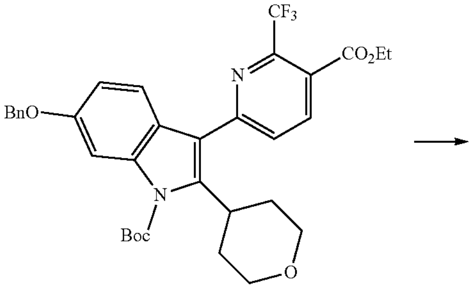
97
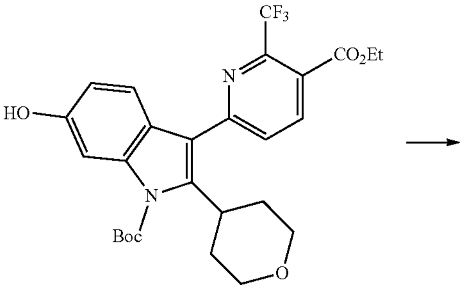
98
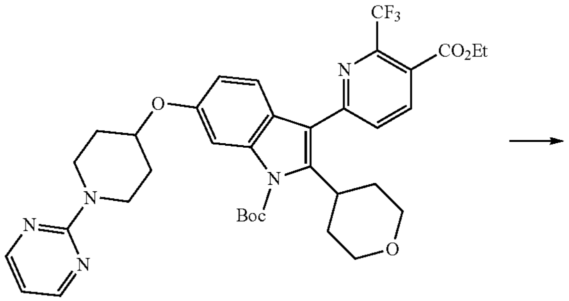
99
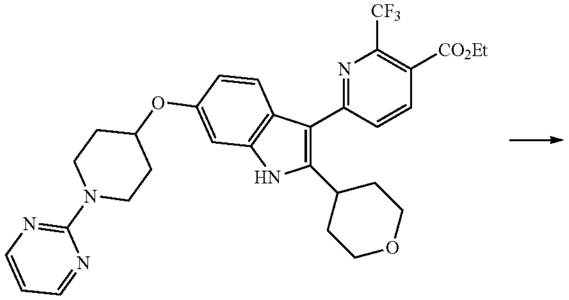
100
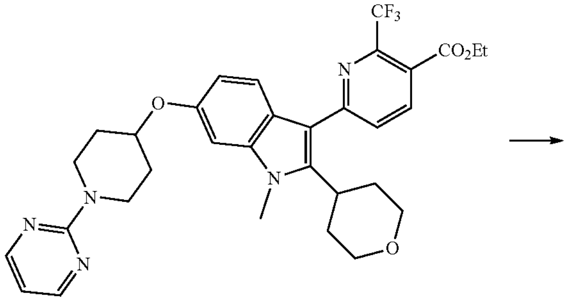
101

-continued

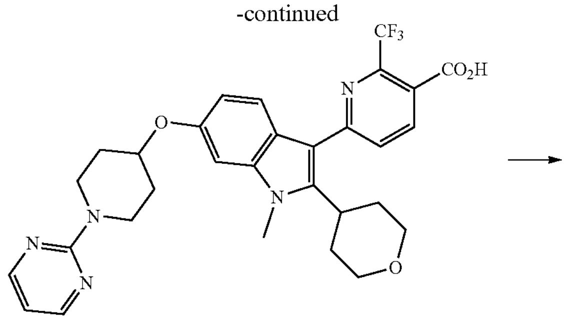

102

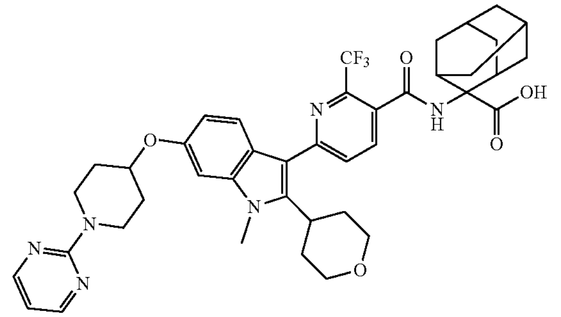

I-270

Step 1: Synthesis of Compound 91

Compound 90 (1.64 g, 5.60 mmol) was dissolved in dichloromethane (16.4 mL), and pyridine (1.33 g, 16.80 mmol) and paratoluenesulfonyl chloride (2.14 g, 11.20 mmol) were added udner ice-cooling. After stirring at room temperature for 1.5 hours, triethylamine (1.70 g, 16.80 mmol) and 1-methylpiperazine (1.12 g, 11.20 mmol) were added, and the mixture was stirred for 30 minutes. Concentrated hydrochloric acid was added udner ice-cooling, and the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 91 (2.08 g, yield 86%).

LC/MS(ESI):m/z=432 [M+H]+, RT=2.76 min, LC/MS Method 1

Step 2: Synthesis of Compound 92

Compound 91 (0.45 g, 1.04 mmol) was dissolved in dimethylformamide (2.89 mL), and 4-ethynyltetrahydro-2H-pyran (0.17 g, 1.56 mmol), copper(I) iodide (39 mg, 0.21 mmol), triethylamine (2.11 g, 20.82 mmol) and $PdCl_2$(dppf) (76 mg, 0.10 mmol) were added, and the mixture was stirred at 100° C. for 8 hours. After adding water, the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 92 (0.35 g, yield 73%). LC/MS(ESI):m/z=462 [M+H]+, RT=2.99 min, LC/MS Method 1

Step 3: Synthesis of Compound 93

To a solution of Compound 92 (200 mg, 0.43 mmol) in tetrahydrofuran (0.4 mL) was added 1 mol/L tetrabutylammonium fluoride-tetrahydrofuran solution (8.67 mL, 8.67 mmol), and the mixture was stirred with heating under reflux for 17 hours. After addition of 1 mol/L hydrochloric acid, the mixture was extracted with ethyl acetate. The organic layer was washed with water, dried over anhydrous sodium sulfate, and the solvent was removed under reduced pressure. The residue was purified by silica gel column chromatography (chloroform-methanol) to afford Compound 93 (130 mg, yield 98%).

LC/MS(ESI):m/z=308 [M+H]+, RT=2.35 min, LC/MS Method 1

Step 4: Synthesis of Compound 94

To a solution of Compound 93 (130 mg, 0.42 mmol) in tetrahydrofuran (1.3 mL) were added $Boc_2O$ (220 mg, 1.01 mmol) and DMAP (5.2 mg, 0.04 mmol), and the mixture was stirred at room temperature for 21 hours. The reaction solution was concentrated under reduced pressure, and the residue was purified by silica gel column chromatography (hexane-ethyl acetate) to afford Compound 94 (160 mg, yield 93%).

LC/MS(ESI):m/z=408[M+H]+, RT=3.18 min, LC/MS Method 1

Step 5: Synthesis of Compound 95

Iodine (62 mg, 0.25 mmol) was dissolved in dichloromethane (0.5 mL), and pyridine (39 mg, 0.49 mmol) and iodobenzene bis(trifluoroacetate (106 mg, 0.25 mmol) were added, and the mixture was stirred at room temperature for 15 min. To this solution was added the solution of Compound 94 (100 mg, 0.25 mmol) in dichloromethane (2 mL) udner ice-cooling, and the mixture was stirred at room temperature for 30 minutes. After addition of 10% aqueous sodium thiosulfate solution, the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 95 (115 mg, yield 88%).

$^1$H-NMR ($CDCl_3$) δ: 1.63-1.65 (m, 2H), 1.67 (s, 9H), 2.70 (ddd, J=25.3, 11.8, 4.1 Hz, 2H), 3.53 (td, J=11.8, 1.7 Hz, 2H), 3.76-3.82 (m, 1H), 4.11 (dd, J=11.8, 4.1 Hz, 2H), 5.13 (s, 2H), 6.99 (dd, J=8.6, 2.2 Hz, 1H), 7.29-7.33 (m, 2H), 7.38 (t, J=7.3 Hz, 2H), 7.45 (d, J=7.3 Hz, 2H), 7.60 (d, J=2.2 Hz, 1H).

Step 6: Synthesis of Compound 96

Compound 95 (113 mg, 0.21 mmol) was dissolved in 1,4-dioxane (2.3 mL), and 2-isopropoxy-4,4,5,5-tetramethyl-1,3,2-dioxaborolane (163 mg, 1.27 mmol), X-Phos (30 mg, 0.06 mmol), $Pd_2(dba)_3$ (39 mg, 0.04 mmol) and triethylamine (129 mg, 1.27 mmol) were added, and the mixture was stirred at 95° C. for 2.5 hours. Water was added, followed by extraction with ethyl acetate. The organic layer was washed with water, dried over anhydrous sodium sulfate, and the solvent was removed under reduced pressure. The residue was purified by silica gel column chromatography (hexane-ethyl acetate) to afford Compound 96 (110 mg, yield 97%).

$^1$H-NMR ($CDCl_3$) δ: 1.40 (s, 12H), 1.67 (s, 9H), 1.73 (d, J=12.0 Hz, 2H), 2.42 (ddd, J=24.8, 12.0, 4.1 Hz, 2H), 3.50 (t, J=10.9 Hz, 2H), 3.72-3.77 (m, 1H), 4.07 (dd, J=10.9, 4.1

Hz, 2H), 5.11 (s, 2H), 6.92 (dd, J=8.5, 2.3 Hz, 1H), 7.29-7.39 (m, 3H), 7.45 (d, J=7.2 Hz, 2H), 7.59 (d, J=2.3 Hz, 1H), 7.77 (d, J=8.5 Hz, 1H).

Step 7: Synthesis of Compound 97

Compound 96 (108 mg, 0.20 mmol) was dissolved in 1,4-dioxane (1.4 mL), and Compound 43 (57 mg, 0.22 mmol), $PdCl_2$(dppf) (17 mg, 0.02 mmol), water (0.3 mL) and cesium carbonate (132 mg, 0.41 mmol) were added, and the mixture was stirred with heating under reflux for 1 hour. After cooling, water was added, followed by extraction with ethyl acetate. The organic layer was washed with water, dried over anhydrous sodium sulfate, and the solvent was removed under reduced pressure. The residue was purified by silica gel column chromatography (hexane-ethyl acetate) to afford Compound 97 (92 mg, yield 73%).

LC/MS(ESI):m/z=625[M+H]+, RT=3.45 min, LC/MS Method 1

Step 8: Synthesis of Compound 98

To Compound 97 (90 mg, 0.14 mmol) were added tetrahydrofuran (0.63 mL), ethanol (0.63 mL) and 20 wt % palladium carbon (18 mg, 0.17 mmol). The mixture was stirred for 2.5 hours at room temperature under hydrogen atmosphere. The reaction mixture was filtered through Celite (registered trademark), the filtrate was concentrated under reduced pressure to afford Compound 98 (100 mg) as a crude product.

LC/MS(ESI):m/z=535[M+H]+, RT=2.72 min, LC/MS Method 1

Step 9: Synthesis of Compound 99

The compound was synthesized in the same manner as in Step 3 of Example 6.

LC/MS(ESI):m/z=696[M+H]+, RT=3.08 min, LC/MS Method 1

Step 10: Synthesis of Compound 100

The compound was synthesized in the same manner as in Step 4 of Example 6.

LC/MS(ESI):m/z=596[M+H]+, RT=2.61 min, LC/MS Method 1

Step 11: Synthesis of Compound 101

To a solution of Compound 100 (34 mg, 0.06 mmol) in dimethylformamide (0.5 mL) were added 60 wt % sodium hydride (3.4 mg, 0.09 mmol) and methyl iodide (16 mg, 0.11 mmol) udner ice-cooling, and the mixture was stirred at room temperature for 1 hour. After adding ice water, the mixture was extracted with ethyl acetate. The organic layer was washed with water, dried over anhydrous sodium sulfate, and the solvent was removed under reduced pressure. The residue was purified by silica gel column chromatography (hexane-ethyl acetate) to afford Compound 101 (26 mg, yield 75%).

LC/MS(ESI):m/z=610[M+H]+, RT=3.04 min, LC/MS Method 1

Step 12: Synthesis of Compound 102

The compound was synthesized in the same manner as in Step 2 of Example 4.

LC/MS(ESI):m/z=582[M+H]+, RT=2.25 min, LC/MS Method 1

Step 13: Synthesis of Compound (I-270)

The compound was synthesized in the same manner as in Step 6 of Example 6.

$^1$H-NMR ($CDCl_3$) δ: 1.78-2.32 (m, 20H), 2.70 (s, 2H), 3.48 (t, J=11.0 Hz, 2H), 3.73 (ddd, J=13.2, 8.3, 4.1 Hz, 2H), 3.91-3.94 (m, 4H), 4.08-4.15 (m, 2H), 4.19 (dq, J=13.2, 4.1 Hz, 2H), 4.59-4.65 (m, 1H), 6.14 (s, 1H), 6.49 (t, J=4.7 Hz, 1H), 6.90-6.91 (m, 2H), 7.60 (d, J=8.2 Hz, 1H), 7.81 (d, J=8.2 Hz, 1H), 7.98 (d, J=8.2 Hz, 1H), 8.33 (d, J=4.7 Hz, 2H), 12.12 (s, 1H).

Example 12

Synthesis of Compound (I-486)

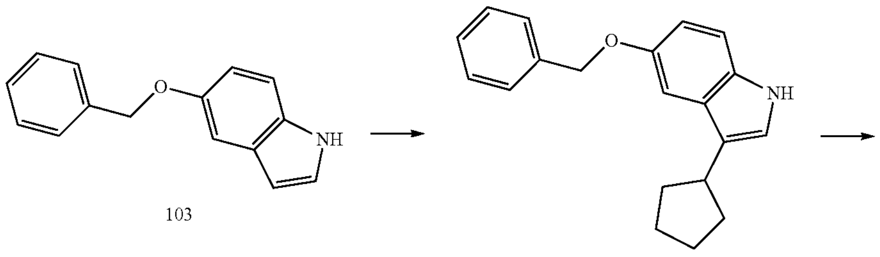

103

104

-continued
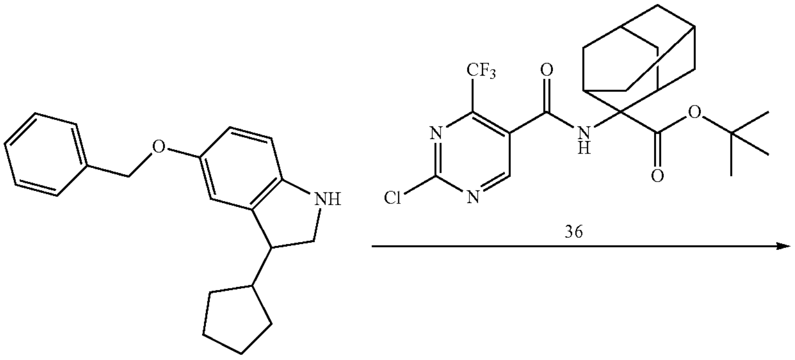
105
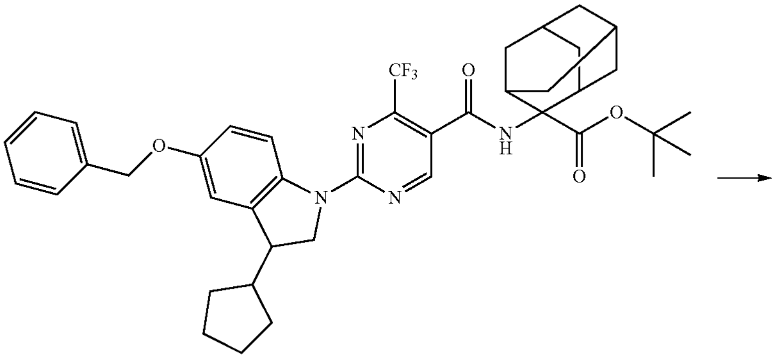
106
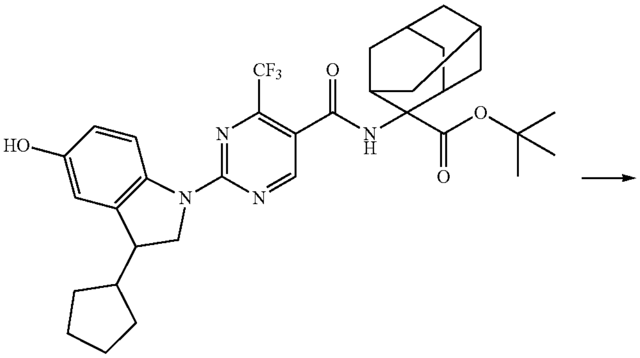
107
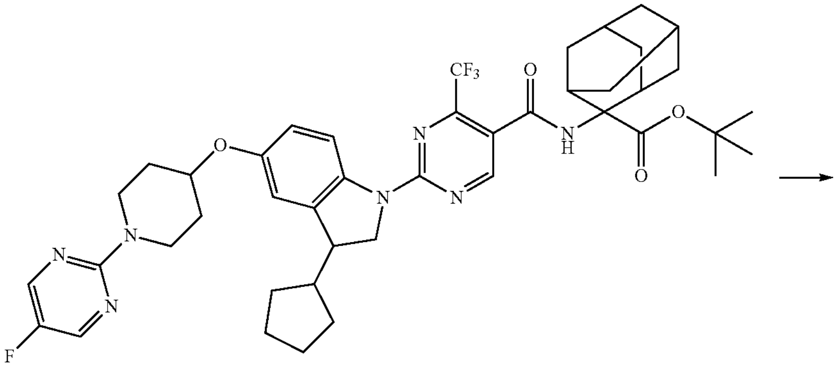
108

-continued

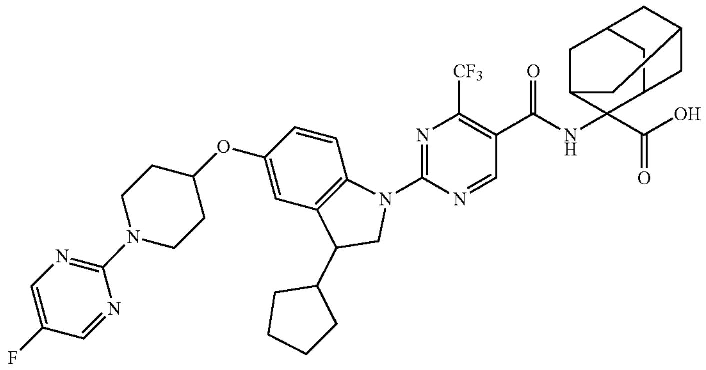

I-486

Step 1: Synthesis of Compound 104

A solution of triethylsilane (1.7 mL, 10.75 mmol) and trichloroacetic acid (1.1 g, 6.72 mmol) in toluene (5 mL) was stirred at 70° C., and a solution of Compound 103 (1 g, 4.48 mmol) and cyclopentanone (414 mg, 4.93 mmol) in toluene (10 mL) was added dropwise. The mixture was stirred at 70° C. for 40 min. The mixture was cooled to room temperature, and 10% aqueous sodium carbonate solution was added. The mixture was extracted with ethyl acetate. The organic layer was washed with water and dried over anhydrous sodium sulfate. The solvent was removed under reduced pressure, and the residue was purified by silica gel column chromatography (hexane-ethyl acetate) to afford Compound 104 (600 mg, yield 46%).

LC/MS(ESI):m/z=292 [M+H]+, RT=2.98 min, LC/MS Method 1

Step 2: Synthesis of Compound 105

Compound 104 (570 mg, 1.96 mmol) was dissolved in acetic acid (2 mL), and sodium cyanoborohydride (246 mg, 3.91 mmol) was added udner ice-cooling. After stirring at room temperature for 50 minutes, aqueous potassium carbonate solution was added to neutralize the mixture. The mixture was extracted with ethyl acetate. The organic layer was washed with water and dried over anhydrous sodium sulfate. The solvent was removed under reduced pressure, and the residue was purified by silica gel column chromatography (hexane-ethyl acetate) to afford Compound 105 (340 mg, yield 59%).

LC/MS(ESI):m/z=294 [M+H]+, RT=1.74 min, LC/MS Method 1

Step 3: Synthesis of Compound 106

Compound 36 (266 mg, 0.58 mmol), diisopropylamine (0.2 mL, 1.16 mmol) and Compound 105 (170 mg, 0.58 mmol) were dissolved in 1,4-dioxane (2.55 mL) and stirred at 90° C. for 1 hour. Water was added, followed by extraction with ethyl acetate. The organic layer was washed with water and dried over anhydrous sodium sulfate. The solvent was removed under reduced pressure, and the residue was purified by amino column chromatography (hexane-ethyl acetate) to afford Compound 106 (330 mg, yield 80%).

LC/MS(ESI):m/z=717 [M+H]+, RT=2.96 min, LC/MS Method 7

Step 4: Synthesis of Compound 107

The compound was synthesized in the same manner as in Step 4 of Example 3.

LC/MS(ESI):m/z=627 [M+H]+, RT=3.42 min, LC/MS Method 1

Step 5: Synthesis of Compound 108

The compound was synthesized in the same manner as in Step 5 of Example 3.

LC/MS(ESI):m/z=806 [M+H]+, RT=3.12 min, LC/MS Method 7

Step 6: Synthesis of Compound (I-486)

The compound was synthesized in the same manner as in Step 8 of Example 10.

$^1$H-NMR ($CDCl_3$) δ: 1.23-1.72 (m, 5H), 1.81 (dd, J=14.9, 7.5 Hz, 9H), 1.95-1.99 (m, 8H), 2.15-2.21 (m, 3H), 2.68 (s, 2H), 3.38-3.41 (m, 1H), 3.66-3.68 (m 2H), 4.09-4.14 (m, 3H), 4.28 (t, J=10.5 Hz, 1H), 4.50-4.53 (m, 1H), 6.02 (s, 1H), 6.86-6.92 (m, 2H), 8.20 (s, 2H), 8.28 (d, J=8.3 Hz, 1H), 8.78 (s, 1H), 12.34 (s, 1H).

LC/MS(ESI):m/z=750 [M+H]+, RT=3.56 min, LC/MS Method 1

Example 13
Synthesis of Compound (I-591)
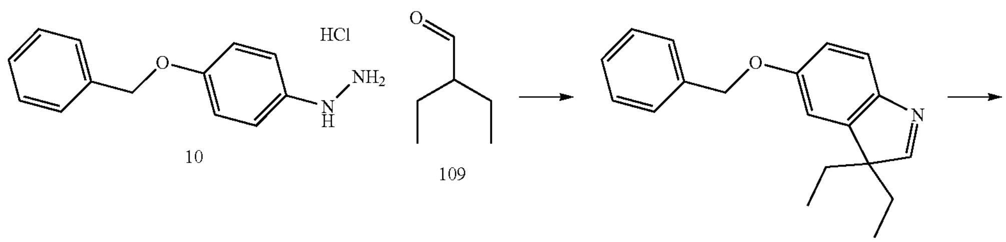
10 109 110
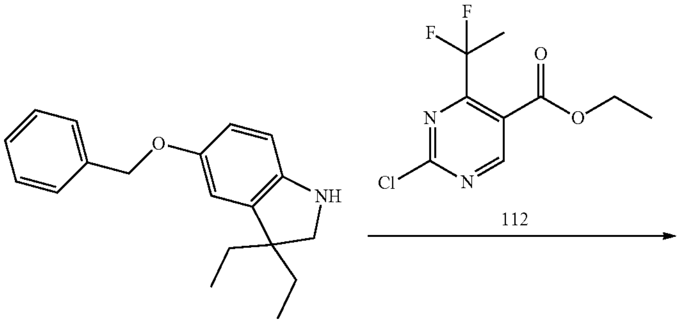
112
111
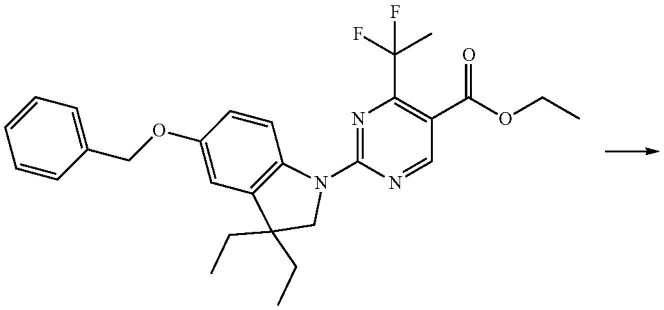
113
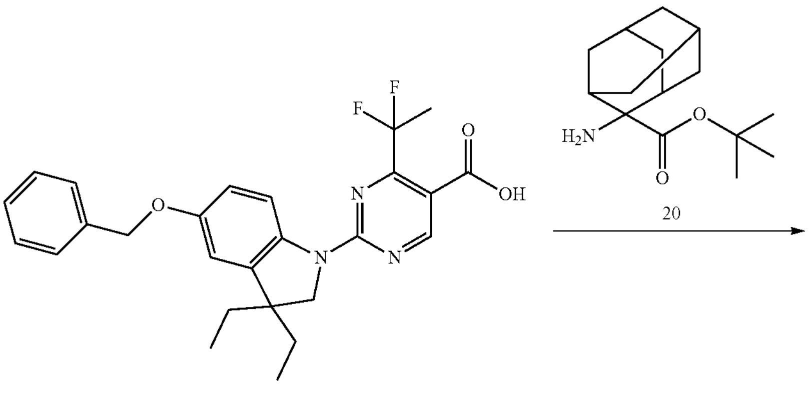
20
114

-continued
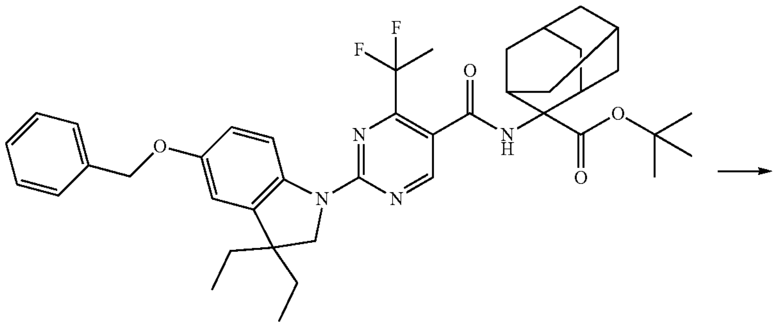
115
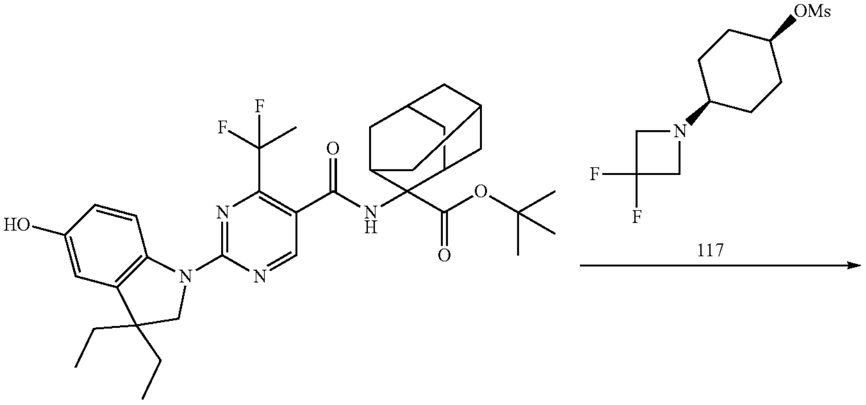
116
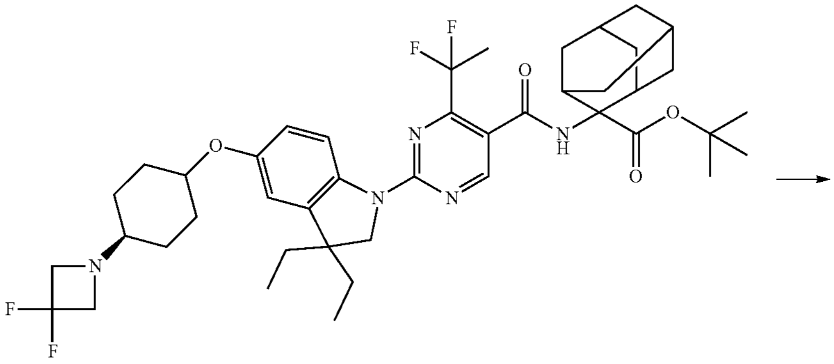
118
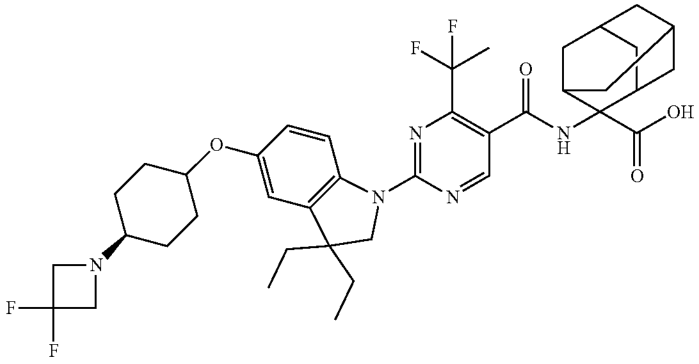
I-591

Step 1: Synthesis of Compound 110

Compound 10 (42 g, 166 mmol) and Compound 109 (16.6 g, 166 mmol) were suspended in dichloromethane (250 mL) and cooled under ice bath. Trifluoroacetic acid (25.6 mL, 332 mmol) was added, and the mixture was warmed to 45° C., and stirred for 5 hours. The mixture was cooled under ice bath, and neutralized by the addition of aqueous sodium carbonate solution, followed by extraction with chloroform. The organic layer was washed with water and dried over anhydrous sodium sulfate. The solvent was removed under reduced pressure, and the residue was purified by silica gel column chromatography (hexane-ethyl acetate) to afford Compound 110 (8.9 g, yield 19%).

LC/MS(ESI):m/z=280 [M+H]+, RT=2.59 min, LC/MS Method 1

Step 2: Synthesis of Compound 111

The Compound was synthesized in the same manner as in Step 2 of Example 3.

LC/MS(ESI):m/z=282 [M+H]+, RT=1.57 min, LC/MS Method 1

Step 3: Synthesis of Compound 113

The Compound was synthesized in the same manner as in Step 3 of Example 3.

LC/MS(ESI):m/z=496 [M+H]+, RT=3.60 min, LC/MS Method 1

Step 4: Synthesis of Compound 114

The compound was synthesized in the same manner as in Step 6 of Example 3.

LC/MS(ESI):m/z=468 [M+H]+, RT=3.14 min, LC/MS Method 1

Step 5: Synthesis of Compound 115

Compound 114 (570 mg, 1.22 mmol) and Compound 20 (429 mg, 1.71 mmol) were dissolved in dimethylformamide (8.6 mL), and HATU (788 mg, 2.07 mmol) and triethylamine (0.39 mL, 2.8 mmol) were added. After stirring at room temperature for 15 hours, water was added. The precipitated solid was filtered and purified by silica gel column chromatography (hexane-ethyl acetate) to afford Compound 115 (740 mg, yield 87%).

LC/MS(ESI):m/z=701 [M+H]+, RT=3.88 min, LC/MS Method 1

Step 6: Synthesis of Compound 116

The compound was synthesized in the same manner as in Step 4 of Example 3.

LC/MS(ESI):m/z=611 [M+H]+, RT=1.42 min, LC/MS Method 7

Step 7: Synthesis of Compound 118

Compound 116 (70 mg, 0.115 mmol) was dissolved in dimethylformamide (1.05 mL). Cesium carbonate (45 mg, 0.14 mmol) and Compound 117 (31 mg, 0.11 mmol) were added, and the mixture was stirred at 90° C. for 1 hour. The same amount of cesium carbonate and Compound 117 were added four times every 30 minutes. After confirming the consumption of starting material, water was added to quench the reaction. The mixture was extracted with ethyl acetate. The organic layer was washed with water and dried over anhydrous sodium sulfate. The solvent was removed under reduced pressure, and the residue was purified by amino column chromatography (hexane-ethyl acetate) to afford Compound 118 (63 mg, yield 70%).

LC/MS(ESI):m/z=784 [M+H]+, RT=3.17 min, LC/MS Method 1

Step 8: Synthesis of Compound (I-591)

The compound was synthesized in the same manner as in Step 8 of Example 10.

$^1$H-NMR (DMSO-$d_6$) δ: 0.70 (t, J=7.3 Hz, 6H), 1.12-1.24 (m, 2H), 1.29-1.39 (m, 2H), 1.53-1.78 (m, 14H), 1.98-2.24 (m, 10H), 2.50-2.55 (m, 2H), 3.54 (t, J=12.4 Hz, 4H), 3.95 (s, 2H), 4.26-4.29 (m, 1H), 6.81-6.83 (m, 2H), 8.16 (d, J=8.8 Hz, 1H), 8.29 (s, 1H), 8.47 (s, 1H), 12.27 (br s, 1H).

Example 14

Synthesis of Compound (I-594)

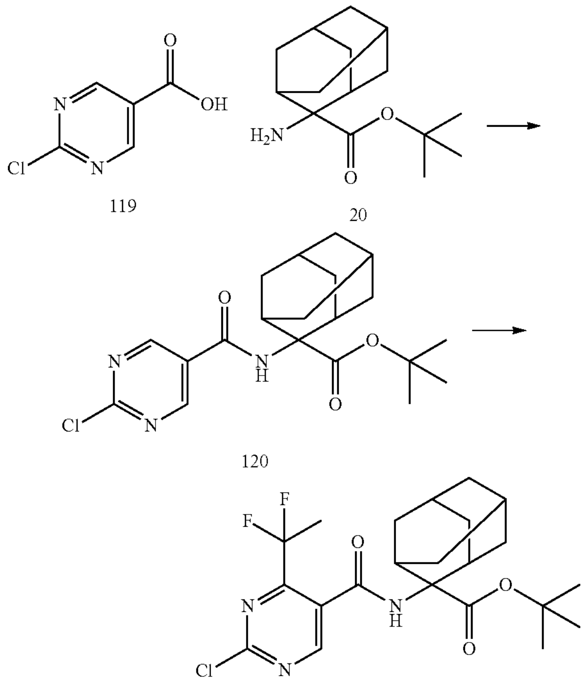

119

20

120

121

Step 1: Synthesis of Compound 120

Compound 119 (3 g, 18.9 mmol) was dissolved in dichloromethane (30 mL), and oxalyl chloride (1.8 mL, 20.8 mmol) and dimethylformamide (0.15 mL, 1.9 mmol) were added under ice-cooling. After stirring at room temperature for 1 hour, the reaction solution was concentrated under reduced pressure.

The residue was dissolved in dichloromethane (5 mL), and added dropwise to a solution of Compound 20 (4.76 g, 18.9 mmol) and triethylamine (5.3 mL, 37.8 mmol) in dichloromethane (30 mL) udner ice-cooling. After 1 hour, the reaction was quenched by adding water, followed by extraction with chloroform. The organic layer was washed with water and dried over anhydrous magnesium sulfate. The solvent was removed under reduced pressure, and the residue was suspended in ethyl acetate and diisopropyl ether. The solid was filtered to obtain Compound 120 (7.0 g, yield 94%).

$^1$H-NMR ($CDCl_3$) δ: 1.46 (s, 9H), 1.73-1.82 (m, 6H), 1.86-1.99 (m, 4H), 2.17 (m, 2H), 2.59 (s, 2H), 6.14 (s, 1H), 8.95 (s, 2H).

Step 2: Synthesis of Compound 121

Compound 120 (3.8 g, 9.7 mmol) was suspended in acetonitrile (30 mL) and water (15 mL), and 2,2-difluoropropionic acid (2.1 g, 19.4 mmol), silver nitrate (4.9 g, 29.1 mmol) and ammonium persulfate (8.8 g, 38.8 mmol) were added. The mixture was warmed to 80° C., and stirred for 1 hour. The reaction was cooled under ice bath, quenched with aqueous sodium thiosulfate solution, followed by filtration trhough Celite (registered trademark). The filtrate was extracted with ethyl acetate. The organic layer was washed with water and dried over anhydrous magnesium sulfate. The solvent was removed under reduced pressure, and the residue was purified by silica gel column chromatography (hexane-ethyl acetate) to afford Compound 121 (670 mg, yield 15%).

$^1$H-NMR (DMSO-$d_6$) δ: 1.42 (s, 9H), 1.56 (m, 2H), 1.65-1.79 (m, 4H), 1.99 (t, J=19.2 Hz, 3H), 2.05 (m, 4H), 2.53 (s, 2H), 8.54 (s, 1H), 8.74 (s, 1H).

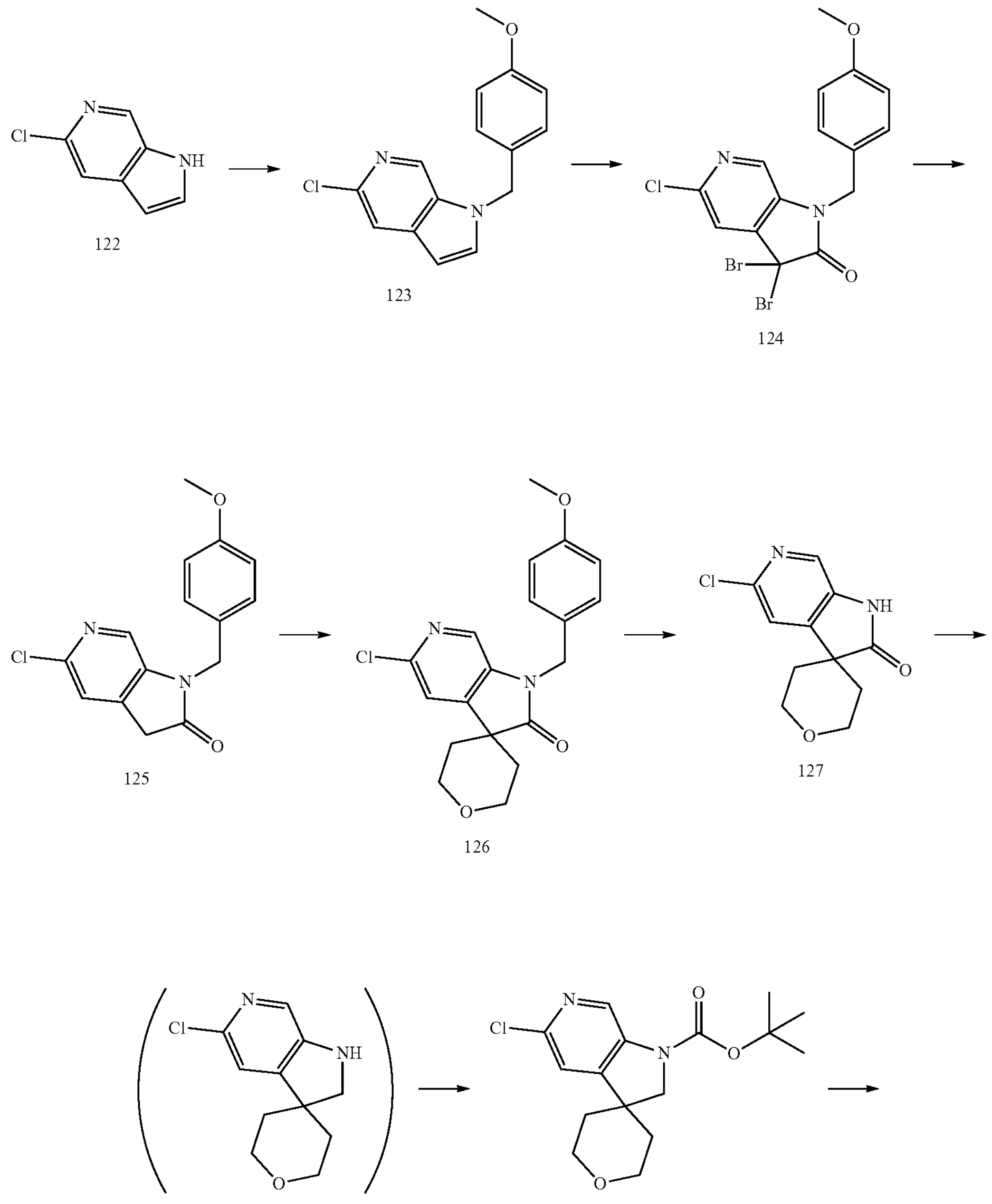

122 123 124

125 126 127

128 129

-continued
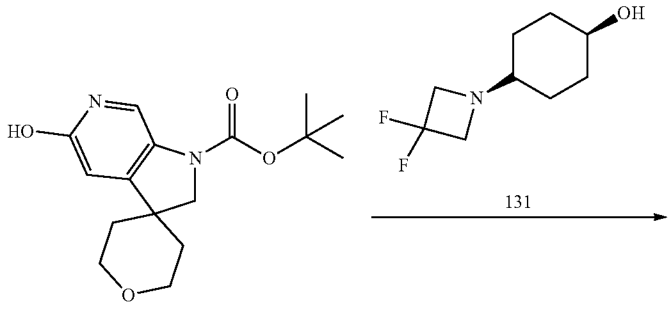
130
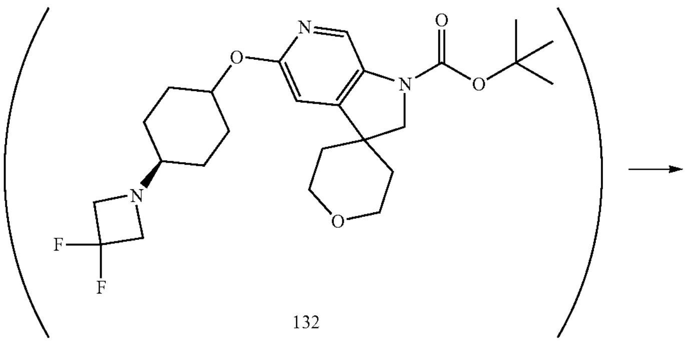
132
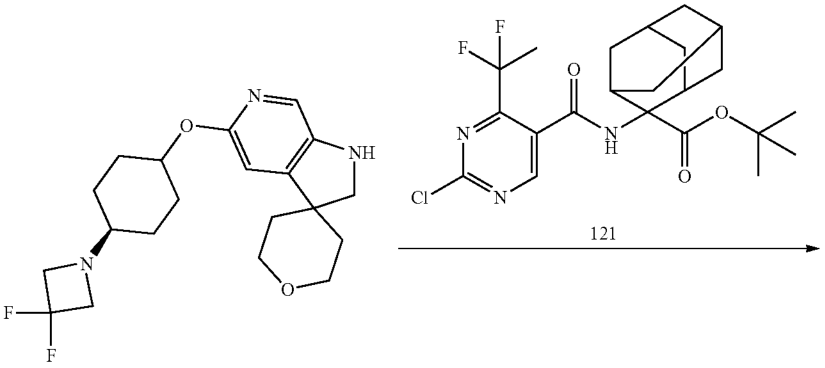
133
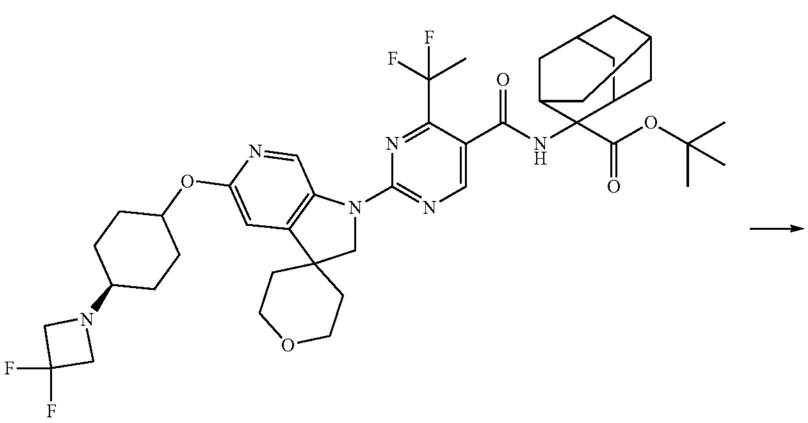
134

-continued

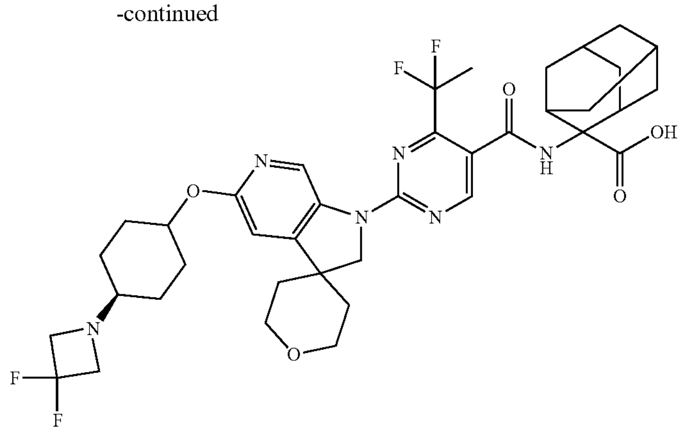

I-594

Step 1: Synthesis of Compound 123

Compound 122 (51.5 g, 337 mmol) was dissolved in dimethylformamide (386 mL), and cesium carbonate (165 g, 506 mmol), 4-methoxybenzyl chloride (53.4 g, 341 mmol) were added. After stirring at room temperature for 45 minutes, water was added. The mixture was extracted with ethyl acetate. The organic layer was washed with water and dried over anhydrous sodium sulfate, and the solvent was removed under reduced pressure. The residue was solidified by adding hexane and ethyl acetate, and filtered to obtain Compound 123 (90.9 g, yield 99%).

LC/MS(ESI):m/z=273 [M+H]+, RT=2.21 min, LC/MS Method 1

Step 2: Synthesis of Compound 124

Compound 123 (81.2 g, 298 mmol) was dissolved in 1,4-dioxane (812 mL), and pyridinium tribromide (349 g, 1.09 mol) was added. After stirring at room temperature for 45 minutes, water was added. The mixture was extracted with ethyl acetate. The organic layer was washed with water and dried over anhydrous sodium sulfate. The solvent was removed under reduced pressure to afford Compound 124 (154.6 g) as a crude product.

LC/MS(ESI):m/z=445 [M+H]+, RT=2.58 min, LC/MS Method 1

Step 3: Synthesis of Compound 125

The crude product of Compound 124 (154.6 g) was dissolved in tetrahydrofuran (1065 mL) and methanol (266 mL) and acetic acid (42.6 mL), and zinc (97 g, 1490 mmol) was added under ice-cooling. After stirring for 1 hour, the reaction solution was filtered through Celite (registered trademark) to remove insoluble material. The filtrate was concentrated under reduced pressure, and water was added to the resulting solid. The suspension was stirred at room temperature, and the solid was filtered to obtain Compound 125 (87 g, yield 100%).

LC/MS(ESI):m/z=289 [M+H]+, RT=2.58 min, LC/MS Method 1

Step 4: Synthesis of Compound 126

Compound 125 (220 mg, 0.76 mmol) was dissolved in dimethylformamide (3.3 mL), and cesium carbonate (745 mg, 2.29 mmol) and 2-iodoethyl ether (497 mg, 1.52 mmol) were added. After stirring at room temperature for 3 hours, water was added. The mixture was extracted with ethyl acetate. The organic layer was washed with water and dried over anhydrous magnesium sulfate. The solvent was removed under reduced pressure, and the residue was purified by silica gel column chromatography (hexane-ethyl acetate) to afford Compound 126 (245 mg, yield 90%).

LC/MS(ESI):m/z=359 [M+H]+, RT=2.05 min, LC/MS Method 1

Step 5: Synthesis of Compound 127

To Compound 126 (130 mg, 0.36 mmol) were added trifluoroacetic acid (0.52 mL) and trifluoromethanesulfonic acid (0.33 mL), and the mixture was stirred at 50° C. for 1 hour. The reaction solution was poured into aqueous sodium carbonate solution and neutralized, followed by extraction with ethyl acetate. The organic layer was washed with water, dried over anhydrous sodium sulfate, and the solvent was removed under reduced pressure. The residue was solidified by adding ethyl acetate and diisopropyl ether, and the solid was filtered to obtain Compound 127 (56 mg, yield 65%).

LC/MS(ESI):m/z=239 [M+H]+, RT=1.22 min, LC/MS Method 1

Step 6: Synthesis of Compound 129

To Compound 127 (640 mg, 2.68 mmol) was added 0.91 mol/L borane-tetrahydrofuran complex-tetrahydrofuran solution (20 mL, 18.2 mmol), and the mixture was stirred at 70° C. for 30 minutes. After ice cooling, methanol (10 mL) was added, and the mixture was stirred at 80° C. for 30 minutes. After cooling, the reaction solution was concentrated under reduced pressure, and the residue was dissolved in dichloromethane (10 mL). Triethylamine (1.36 g, 13.4 mmol), $Boc_2O$ (2.92 g, 13.4 mmol), dimethylaminopyridine (327 mg, 2.68 mmol) were added, and the mixture was stirred at room temperature for 16 hours. The reaction solution was concentrated, and the residue was purified by silica gel column chromatography (hexane-ethyl acetate) to afford Compound 129 (550 mg, yield 63%) LC/MS(ESI): m/z=325 [M+H]+, RT=2.27 min, LC/MS Method 1

Step 8: Synthesis of Compound 130

Compound 129 (200 mg, 0.616 mmol) was dissolved in 1,4-dioxane (3 mL), and Me4tBuXphos (30 mg, 0.062 mmol), $Pd_2(dba)_3$ (28 mg, 0.031 mmol), 6 mol/L aqueous potassium hydroxide solution (0.36 mL, 2.16 mmol) were added, and the mixture was stirred at 100° C. for 1 hour. After cooling, the mixture was neutralized with 2 mol/L hydrochloric acid solution and extracted with dichloromethane. The organic layer was washed with water and dried over anhydrous sodium sulfate. The solvent was removed under reduced pressure. Ethyl acetate-diisopropyl ether was added to the residue obtained, and the precipitated solid was filtered to obtain Compound 130 (171 mg, yield 91%).

LC/MS(ESI):m/z=307 [M+H]+, RT=1.42 min, LC/MS Method 1

Step 9: Synthesis of Compound 133

Compound 130 (171 mg, 0.558 mmol) was dissolved in tetrahydrofuran (2 mL), and triphenylphosphine (293 mg, 1.12 mmol), Compound 131 (213 mg, 1.12 mmol) and DIAD (226 mg, 1.12 mmol) were added, and the mixture was stirred at room temperature. After 30 minutes, triphenylphosphine (293 mg, 1.12 mmol), Compound 131 (213 mg, 1.12 mmol) and DIAD (226 mg, 1.12 mmol) were added. After stirring at room temperature for 1 hour, the solvent was removed under reduced pressure.

Trifluoroacetic acid (4 mL) was added to the residue and stirred at room temperature for 1 hour. The reaction solution was concentrated. Dichloromethane was added to the residue to dissolve. Aqueous sodium bicarbonate solution was added to neutralize, and the layers were separated. The aqueous layer was extracted with dichloromethane, and the organic layers were combined and dried over anhydrous sodium sulfate. The solvent was removed under reduced pressure, and the residue was purified by silica gel column chromatography (hexane-ethyl acetate) to afford Compound 133 (212 mg, yield 100%).

LC/MS(ESI):m/z=380 [M+H]+, RT=0.80 min, LC/MS Method 1

Step 10: Synthesis of Compound 134

Compound 133 (70 mg, 0.184 mmol) was dissolved in 1,4-dioxane (2 mL), and Compound 121 (101 mg, 0.221 mmol), potassium carbonate (76 mg, 0.552 mmol), Xanthos Pd G3 (26 mg, 0.028 mmol) were added. The mixture was' stirred at 80° C. for 90 minutes under a nitrogen atmosphere. Water was added and extracted with ethyl acetate. The organic layer was washed with water and dried over anhydrous sodium sulfate. The solvent was removed under reduced pressure, and the residue was purified by silica gel column chromatography (hexane-ethyl acetate) to afford Compound 134 (66 mg, yield 45%). LC/MS(ESI):m/z=799 [M+H]+, RT=2.49 min, LC/MS Method 8

Step 11: Synthesis of Compound (I-594)

Compound 134 (66 mg, 0.083 mmol) was dissolved in trifluoroacetic acid (4 mL) and stirred at room temperature for 1 hour. The reaction solution was concentrated, dissolved in dichloromethane, and neutralized with aqueous sodium bicarbonate solution. The reaction solution was made acidic again by adding aqueous citric acid solution, and extracted with dichloromethane.

The organic layer was dried over anhydrous sodium sulfate. The solvent was removed, and the residue was purified by silica gel column chromatography (chloroform-methanol) to afford compound (I-594) (37 mg, yield 60%). $^1$H-NMR (DMSO-$d_6$) δ: 1.12-1.24 (m, 2H), 1.35-1.43 (m, 2H), 1.53-1.79 (m, 12H), 1.90-2.14 (m, 11H), 2.20-2.26 (m, 1H), 2.56 (s, 2H), 3.50-3.58 (m, 6H), 3.87-3.90 (m, 2H), 4.21 (s, 2H), 4.88-4.95 (m, 1H), 6.85 (s, 1H), 8.37 (brs, 1H), 8.54 (s, 1H), 8.91 (s, 1H), 12.33 (brs, 1H).

Reference Example

Synthesis of Compound 117 and Compound 131

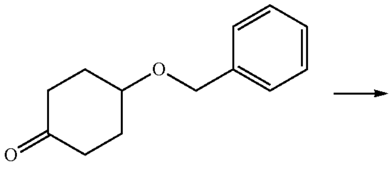

135

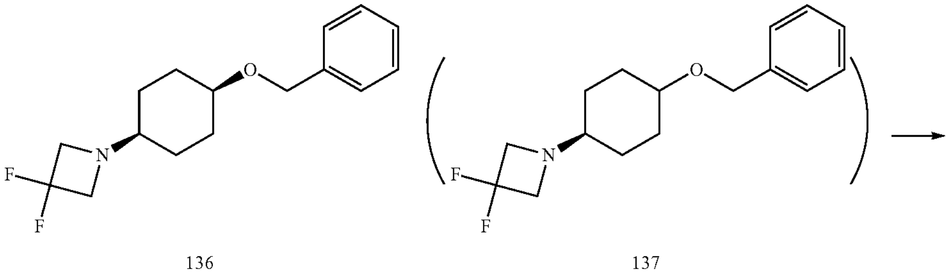

136

137

-continued

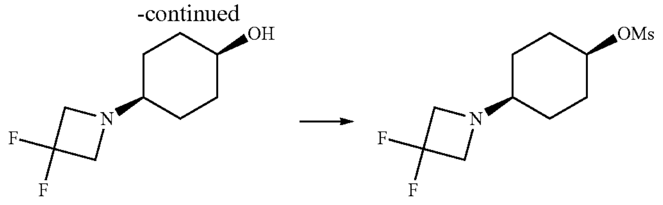

131 117

Step 1: Synthesis of Compound 136 and Compound 137

Compound 135 (1.0 g, 4.90 mmol) was dissolved in dichloromethane (10 mL), and 3,3-Difluoroazetidine hydrochloride (1.27 g, 9.79 mmol), triethylamine (1.26 mL, 9.79 mmol), acetic acid (0.28 mL, 4.90 mmol) and sodium triacetoxyborohydride (2.08 g, 9.79 mmol) were added and stirred for 3 hours. Water was added, followed by extraction with chloroform. The organic layer was washed with water and dried over anhydrous sodium sulfate. The residue was purified by silica gel column chromatography (hexane-ethyl acetate) to afford Compound 136 (846 mg, 61% yield) and Compound 137 (454 mg, yield 33%).

Compound 136

$^1$H-NMR ($CDCl_3$) δ: 1.44-1.60 (m, 6H), 1.90-1.96 (m, 2H), 2.14-2.19 (m, 1H), 3.53 (t, J=12.4 Hz, 4H), 3.55 (m, 1H), 4.50 (s, 2H), 7.23-7.28 (m, 1H), 7.30-7.36 (m, 4H).

LC/MS(ESI):m/z=282 [M+H]+, RT=1.24 min, LC/MS Method 1

Compound 137

$^1$H-NMR ($CDCl_3$) δ: 1.08-1.18 (m, 2H), 1.26-1.39 (m, 2H), 1.77-1.81 (m, 2H), 2.05-2.15 (m, 3H), 3.33-3.40 (m, 1H), 3.54 (t, J=11.6 Hz, 4H), 4.54 (s, 2H), 7.25-7.30 (m, 1H), 7.31-7.34 (m, 4H) LC/MS(ESI):m/z=282 [M+H]+, RT=1.20 min, LC/MS Method 1

Step 2: Synthesis of Compound 131

Compound 136 (0.72 g, 2.55 mmol) was dissolved in ethanol (10.7 mL), and 10 wt % palladium carbon (1.09 g, 0.51 mmol) was added. The mixture was stirred at 50° C. for 3 hours under hydrogen atmosphere. The reaction solution was filtered through Celite (registered trademark), and the filtrate was concentrated under reduced pressure to afford Compound 131 (0.42 g, yield 86%).

Compound 131

$^1$H-NMR ($CDCl_3$) δ: 1.30 (brs, 1H), 1.44-1.61 (m, 6H), 1.69-1.79 (m, 2H), 2.20 (m, 1H), 3.53 (t, J=12.0 Hz, 4H), 3.81 (m, 1H)).

Step 3: Synthesis of Compound 117

Compound 131 (300 mg, 1.57 mmol) was dissolved in dichloromethane (3 mL), and triethylamine (0.44 mL, 3.14 mmol) and methanesulfonyl chloide (0.18 mL, 2.35 mmol) were added under ice-cooling. After 1 hour 30 minutes, aqueous ammonium chloride solution was added, followed by extraction with ethyl acetate. The organic layer was washed with water and dried over anhydrous magnesium sulfate. The solvent was removed under reduced pressure to afford Compound 117 (419 mg, yield 99%).

$^1$H-NMR ($CDCl_3$) δ: 1.53-1.59 (m, 4H), 1.62-1.72 (m, 2H), 2.03-2.13 (m, 2H), 2.23 (m, 1H), 3.00 (s, 3H), 3.54 (t, J=12.0 Hz, 4H), 4.86 (m, 1H).

Example 15

Synthesis of Compound (I-570)

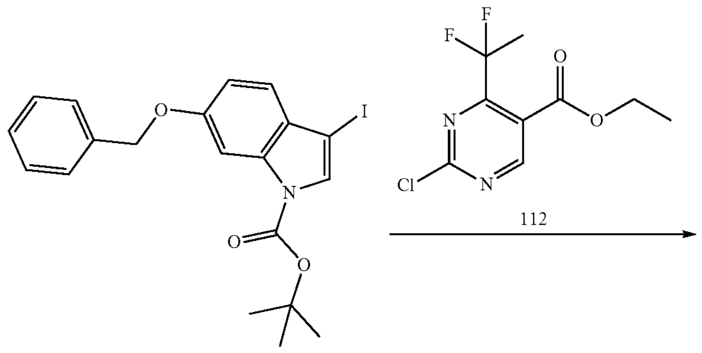

42

-continued
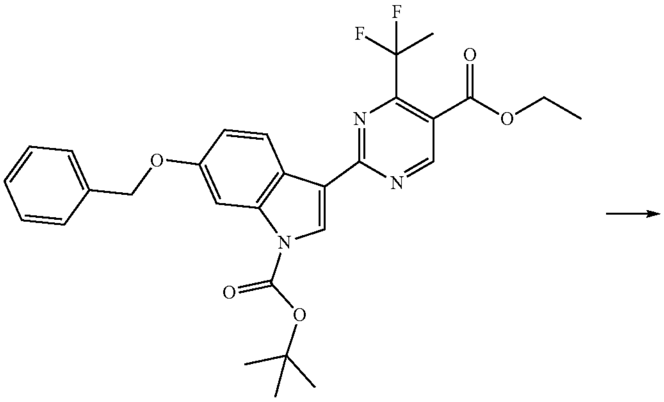
138
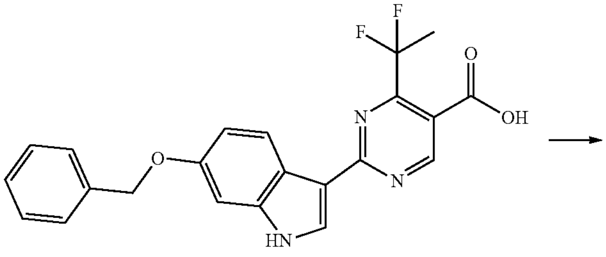
139
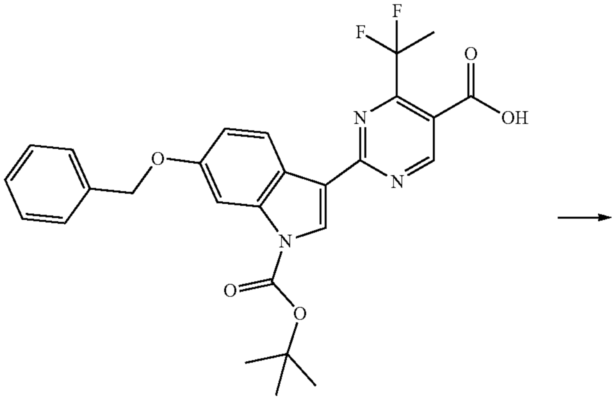
140
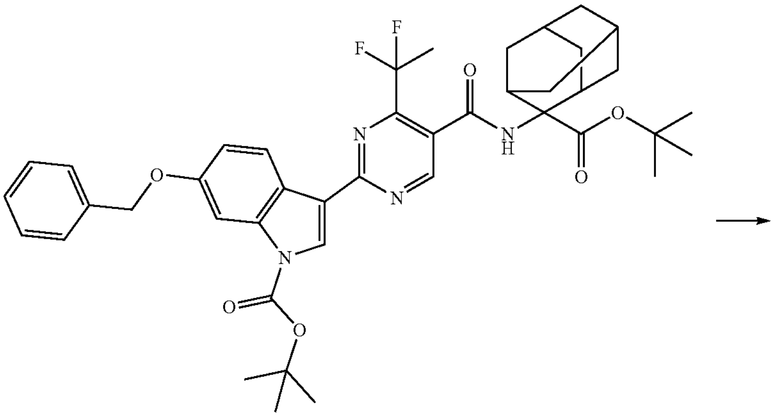
141

-continued
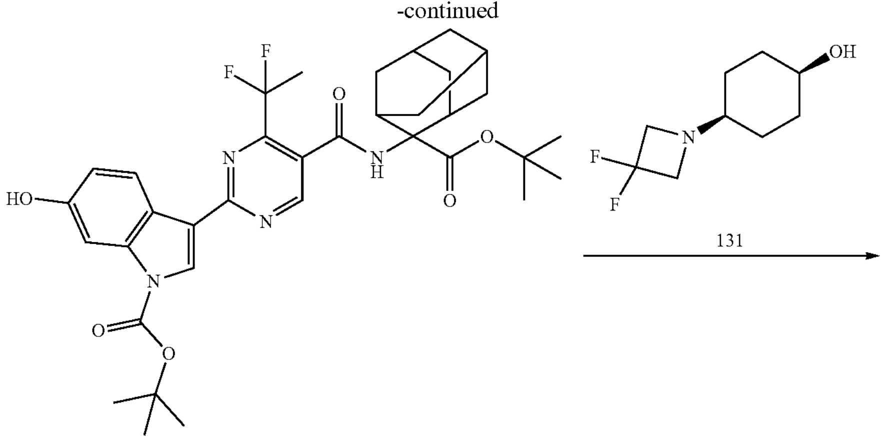
142
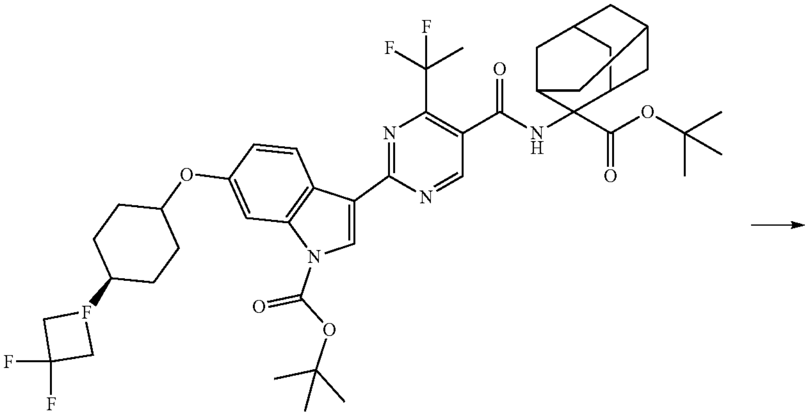
143
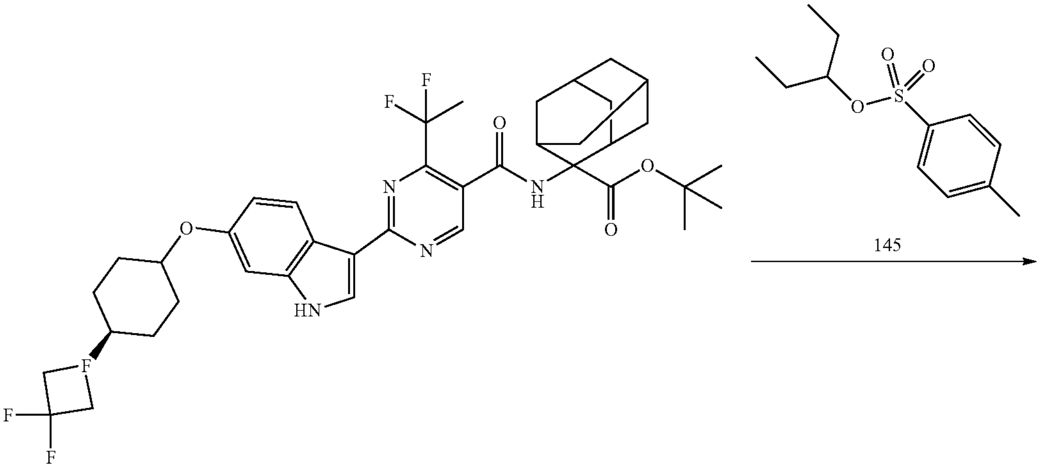
144

-continued

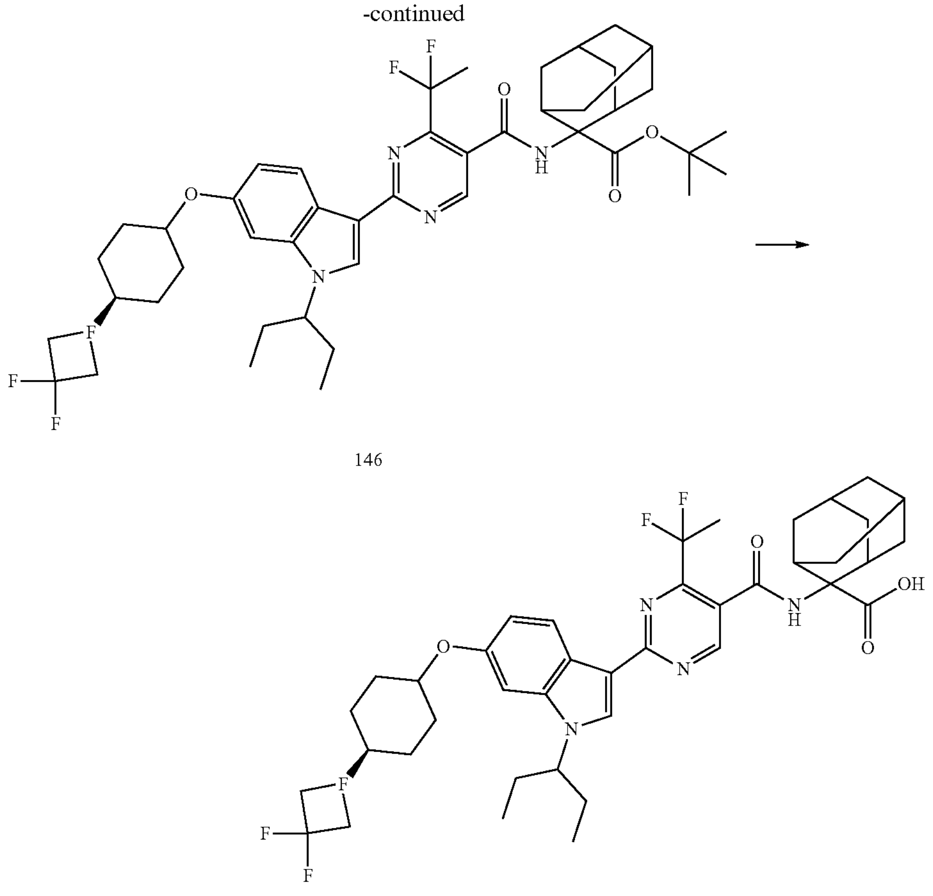

146

I-570

Step 1: Synthesis of Compound 138

The compound was synthesized in the same manner as in Step 1 of Example 6.

$^1$H-NMR (DMSO-$d_6$) δ: ppm 1.33, (t, J=7.15 Hz, 3H), 1.67 (s, 9H), 2.17 (t, J=19.32 Hz, 3H), 4.38 (q, J=7.15 Hz, 2H), 5.21 (s, 2H), 7.16 (dd, J=8.9, 2.3 Hz, 1H), 7.32-7.38 (m, 1H), 7.39-7.44 (m, 2H), 7.48-7.52 (m, 2H), 7.82 (d, J=2.1 Hz, 1H), 8.43 (s, 1H), 8.45 (d, J=8.9 Hz, 1H), 9.19 (s, 1H).

LC/MS (DUIS):m/z=538 [M+H]+, RT=2.08 min, LC/MS Method 9

Step 2: Synthesis of Compound 139

To a solution of Compound 138 (7.48 g, 13.9 mmol) in tetrahydrofuran (59.8 mol), methanol (29.9 mL) and water (15.0 mL) was added lithium hydroxide monohydrate (2.92 g, 69.6 mmol) at room temperature, and the mixture was stirred for 5 hours at room temperature. After completion of the reaction, the mixture was concentrated under reduced pressure, and the residue was diluted with water and neutralized with 2 mol/L hydrochloric acid (35 mL, 70.0 mmol), and the solution was extracted with ethyl acetate. The organic layer was washed with brine, dried over anhydrous sodium sulfate, and concentrated under reduced pressure to afford Compound 139 (4.81 g, yield 84%).

$^1$H-NMR (DMSO-$d_6$) δ: ppm 2.14 (t, J=19.1 Hz, 3H), 5.16 (s, 2H), 6.96 (dd, J=8.8, 2.3 Hz, 1H), 7.07 (d, J=2.3 Hz, 1H), 7.29-7.37 (m, 1H), 7.38-7.45 (m, 2H), 7.47-7.52 (m, 2H), 8.23 (d, J=2.9 Hz, 1H), 8.34 (d, J=8.7 Hz, 1H), 9.00 (s, 1H), 11.76 (d, J=2.4 Hz, 1H), 13.45 (br s, 1H).

LC/MS (DUIS):m/z=410 [M+H]+, RT=1.32 min, LC/MS Method 9

Step 3: Synthesis of Compound 140

To a solution of Compound 139 (4.8 g, 11.72 mmol) in dichloromethane (48.0 mL) and dimethylformamide (2.0 mL) were added triethylamine (2.45 mL, 17.58 mmol), $Boc_2O$ (3.23 mL, 14.06 mmol) and DMAP (72 mg, 0.59 mmol) at room temperature with stirring under argon flow, and the mixture was stirred at room temperature for 4 hours. After completion of the reaction, water was added, and the mixture was extracted with ethyl acetate. The organic layer was washed with 0.5 mol/L hydrochloric acid and brine, dried over anhydrous magnesium sulfate, and concentrated under reduced pressure. Then hexane-ethyl acetate mixture was added, and the mixture was sonicated and filtered. Washng with additional hexane-ethyl acetate mixture and drying to afford Compound 140 (2.46 g, yield 41%).

$^1$H-NMR (DMSO-$d_6$) δ: ppm 1.67 (s, 9H), 2.16 (t, J=19.3 Hz, 3H), 5.21 (s, 2H), 7.16 (dd, J=8.8, 2.4 Hz, 1H), 7.32-7.37 (m, 1H), 7.39-7.44 (m, 2H), 7.48-7.52 (m, 2H), 7.83 (d, J=2.3 Hz, 1H), 8.42 (s, 1H), 8.46 (d, J=8.8 Hz, 1H), 9.17 (s, 1H), 13.81 (br s, 1H).

LC/MS (DUIS):m/z=510 [M+H]+, RT=1.79 min, LC/MS Method 9

Step 4: Synthesis of Compound 141

The compound was synthesized in the same manner as in Step 3 of Example 4.

$^1$H-NMR (DMSO-$d_6$) δ: ppm 1.45 (s, 9H), 1.54-1.60 (m, 2H), 1.67 (s, 9H), 1.68-1.73 (m, 4H), 1.77-1.86 (m, 2H), 2.10 (t, J=19.2 Hz, 3H), 2.00-2.18 (m, 4H), 2.52-2.57 (m, 2H), 5.21 (s, 2H), 7.16 (dd, J=8.9, 2.3 Hz, 1H), 7.32-7.37 (m, 1H), 7.39-7.44 (m, 2H), 7.48-7.52 (m, 2H), 7.82 (d, J=2.4 Hz, 1H) 8.40 (s, 1H), 8.48 (d, J=8.8 Hz, 1H), 8.56 (br s, 1H), 8.79 (s, 1H).

LC/MS (DUIS):m/z=743 [M+H]+, RT=2.37 min, LC/MS Method 9

Step 5: Synthesis of Compound 142

The compound was synthesized in the same manner as in Step 2 of Example 6.

$^1$H-NMR (DMSO-$d_6$) δ: ppm 1.45 (s, 9H), 1.57 (m, 2H), 1.62-1.73 (m, 4H), 1.67 (s, 9H), 1.78-1.84 (m, 2H), 2.10 (t, J=19.1 Hz, 3H), 2.00-2.18 (m, 4H), 2.51-2.55 (m, 2H), 6.89 (dd, J=8.7, 2.3 Hz, 1H), 7.63 (d, J=2.1 Hz, 1H), 8.32 (s, 1H), 8.36 (d, J=8.7 Hz, 1H), 8.55 (br s, 1H), 8.77 (s, 1H), 9.68 (s, 1H).

LC/MS (DUIS):m/z=653 [M+H]+, RT=1.92 min, LC/MS Method 9

Step 6: Synthesis of Compound 143

The compound was synthesized in the same manner as in Step 5 of Example 3.

$^1$H-NMR (DMSO-$d_6$) δ: ppm 1.12-1.25 (m, 2H), 1.39-1.51 (m, 2H), 1.45 (s, 9H), 1.54-1.62 (m, 2H), 1.68 (s, 9H), 1.69-1.73 (m, 4H), 1.75-1.85 (m, 4H), 2.10 (t J=19.1 Hz, 3H), 2.01-2.18 (m, 6H), 2.21-2.30 (m, 1H), 2.52-2.55 (m, 2H), 3.55 (t, J=12.3 Hz, 4H), 4.32-4.42 (m, 1H), 7.06 (dd, J=8.8, 2.3 Hz, 1H), 7.69 (d J=2.1 Hz, 1H), 8.40 (s, 1H), 8.45 (d, J=8.8 Hz, 1H), 8.55 (br s, 1H), 8.78 (s, 1H).

LC/MS (DUIS):m/z=826 [M+H]+, RT=1.88 min, LC/MS Method 9

Step 7: Synthesis of Compound 144

The compound was synthesized in the same manner as in Step 2.

$^1$H-NMR (DMSO-$d_6$) 5 ppm 1.12-1.24 (m, 2H), 1.37-1.42 (m, 2H), 1.45 (s, 9H), 1.53-1.61 (m, 2H), 1.65-1.74 (m, 4H), 1.75-1.85 (m, 4H), 2.08 (t, J=19.0 Hz, 3H), 2.00-2.19 (m, 6H), 2.20-2.28 (m, 1H), 2.52-2.55 (m, 2H), 3.55 (t, J=12.4 Hz, 4H), 4.25-4.37 (m, 1H), 6.86 (dd, J=8.8, 2.3 Hz, 1H), 7.00 (d, J=2.3 Hz, 1H) 8.19 (d, J=2.8 Hz, 1H), 8.32 (d, J=8.8 Hz, 1H), 8.46 (s, 1H), 8.64 (s, 1H), 11.62 (d, J=2.6 Hz, 1H).

LC/MS (DUIS):m/z=726 [M+H]+, RT=1.47 min, LC/MS Method 9

Step 8: Synthesis of Compound 146

To a solution of Compound 144 (50 mg, 0.07 mmol) in N-methylpyrrolidone (1.0 mL) were added cesium carbonate (67 mg, 0.21 mmol) and Compound 145 (50 mg, 0.21 mmol) at room temperature with stirring under argon flow, and the mixture was stirred at 100° C. for 2 hours. Then, cesium carbonate (67 mg, 0.21 mmol) and Compound 145 (50 mg, 0.21 mmol) were added, and the mixture was stirred at 100° C. for 3 hours. Further, cesium carbonate (67 mg, 0.21 mmol) and Compound 145 (50 mg, 0.21 mmol) were added, and the mixture was stirred at 100° C. for 4 hours. After completion of the reaction, water was added to the reaction solution, and the mixture was extracted with ethyl acetate. The organic layer was washed with brine, dried over anhydrous magnesium sulfate, and concentrated under reduced pressure. The residue was purified by silica gel column chromatography (hexane-ethyl acetate). Further purification by amino column chromatography (hexane-ethyl acetate) afforded Compound 146 (42 mg, 77%).

$^1$H-NMR (DMSO-$d_6$) δ: ppm 0.72 (t, J=7.3 Hz, 6H), 1.19-1.28 (m, 2H), 1.35-1.43 (m, 2H), 1.45 (s, 9H), 1.53-1.62 (m, 2H), 1.65-1.72 (m, 4H), 1.74-1.83 (m, 4H), 1.91 (qd, J=7.2 Hz, 4H), 2.09 (t, J=19.0 Hz, 3H), 2.01-2.18 (m, 6H), 2.20-2.30 (m, 1H), 2.52-2.56 (m, 2H), 3.55 (t, J=12.4 Hz, 4H), 4.32-4.47 (m, 2H), 6.89 (dd, J=8.9, 2.1 Hz, 1H), 7.21 (d, J=1.9 Hz, 1H), 8.24 (s, 1H), 8.35 (d, J=8.8 Hz, 1H), 8.45 (br s, 1H), 8.63 (s, 1H).

LC/MS(ESI):m/z=796 [M+H]+, RT=1.82 min, LC/MS Method 10

Step 9: Synthesis of Compound (I-570)

The compound was synthesized in the same manner as in Step 8 of Example 10.

$^1$H-NMR (DMSO-$d_6$) δ: ppm 0.71 (t, J=7.3 Hz, 6H), 1.18-1.29 (m, 2H), 1.34-1.47 (m, 2H), 1.48-1.59 (m, 2H), 1.59-1.73 (m, 4H), 1.75-1.83 (m, 4H), 1.86-1.94 (m, 4H), 2.08 (t, J=19.0 Hz, 3H), 2.00-2.18 (m, 6H), 2.19-2.28 (m, 1H), 2.55-2.61 (m, 2H), 3.55 (t, J=12.4 Hz, 4H), 4.34-4.47 (m, 2H), 6.88 (dd, J=8.9, 2.1 Hz, 1H), 7.20 (d, J=1.9 Hz, 1H), 8.21 (s, 1H), 8.35 (d, J=8.8 Hz, 1H), 8.46 (br s, 1H), 8.64 (s, 1H), 12.45 (br s, 1H).

LC/MS (DUIS):m/z=740 [M+H]+, RT=1.36 min, LC/MS Method 9

The following compounds were synthesized according to the above general synthesis methods and the Examples as described above.

In the structural formula, "wedge-shaped" and "dashed line" indicate stereo configuration. In particular, for compounds where the stereo configuration is indicated, the column of "stereochemistry" is defined as follows.

blank: as indicated a: racemate b: single isomer, but its stereochemistry is unknown c: diastereomeric mixture, provided that I-273, I-371, I-376, I-403, I-414, I 451, I-11, I-12 and I-13 include their racemates.

d: the configuration of the substituent group of $Z^c$ ($R^7$) is as indicated, and the configuration of the substituent group of $R^4$ is unknown e: the configuration of the substituent group of $Z^c$($R^7$) is unknown, and the configuration of the substituent group of $R^4$ is as indicated f: racemate, and the relative configuration of cis/trans is single but unknown.

TABLE 1
| Compound No. | Chemical Structure | [M + H] | Retention Time (min) | LC/MS Condition | Stereo-Chemistry |
|---|---|---|---|---|---|
| I-1 | 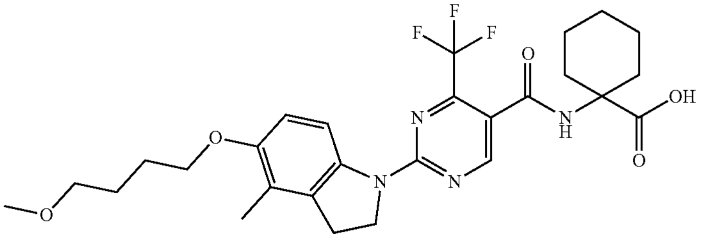 [SMILES: COCCCCOc1ccc2c(c1C)CCN2c1ncc(C(=O)NC2(C(=O)O)CCCCC2)c(C(F)(F)F)n1] | 551 | 2.76 | 1 | |
| I-2 | 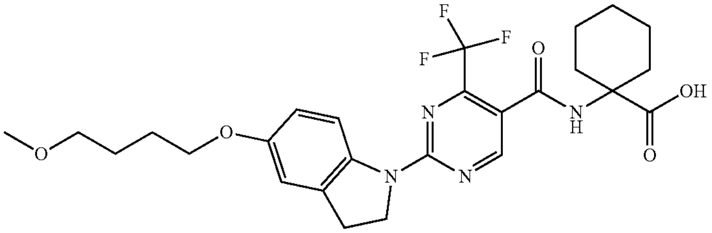 [SMILES: COCCCCOc1ccc2c(c1)CCN2c1ncc(C(=O)NC2(C(=O)O)CCCCC2)c(C(F)(F)F)n1] | 537 | 2.57 | 2 | |
| I-3 | 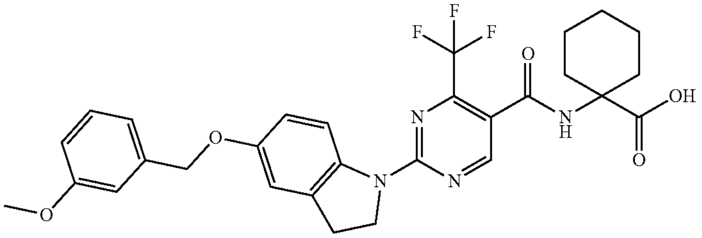 [SMILES: COc1cccc(COc2ccc3c(c2)CCN3c2ncc(C(=O)NC3(C(=O)O)CCCCC3)c(C(F)(F)F)n2)c1] | 571 | 2.72 | 3 | |
| I-4 | 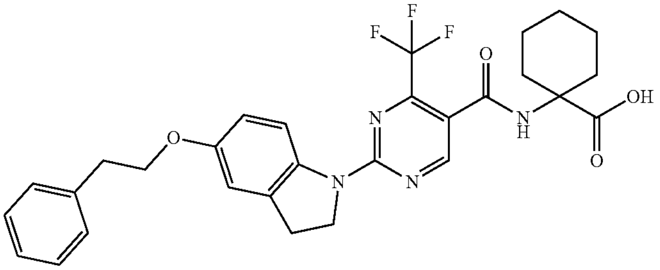 [SMILES: O=C(NC1(C(=O)O)CCCCC1)c1cnc(N2CCc3cc(OCCc4ccccc4)ccc32)nc1C(F)(F)F] | 555 | 2.87 | 3 | |
| I-5 | 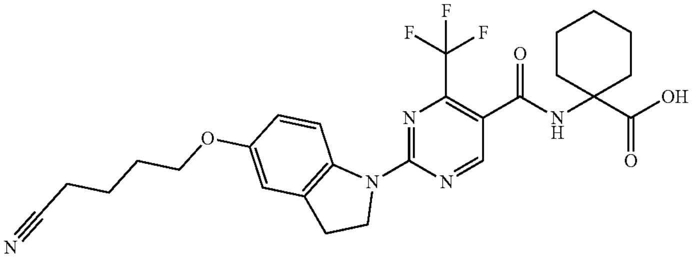 [SMILES: N#CCCCCOc1ccc2c(c1)CCN2c1ncc(C(=O)NC2(C(=O)O)CCCCC2)c(C(F)(F)F)n1] | 532 | 2.35 | 3 | |
| I-6 | 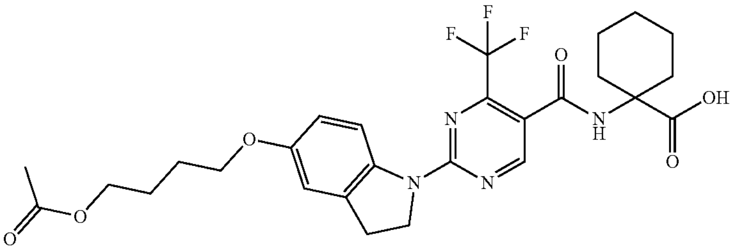 [SMILES: CC(=O)OCCCCOc1ccc2c(c1)CCN2c1ncc(C(=O)NC2(C(=O)O)CCCCC2)c(C(F)(F)F)n1] | 565 | 2.49 | 3 | |

TABLE 1-continued
| Compound No. | Chemical Structure | [M + H] | Retention Time (min) | LC/MS Condition | Stereo-Chemistry |
|---|---|---|---|---|---|
| I-7 | 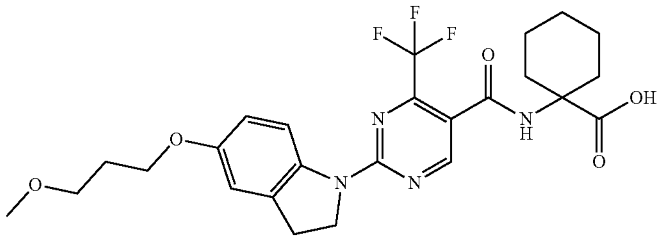 [SMILES: COCCCOc1ccc2c(c1)CCN2c1ncc(C(=O)NC2(C(=O)O)CCCCC2)c(C(F)(F)F)n1] | 523 | 2.42 | 3 | |
| I-8 | 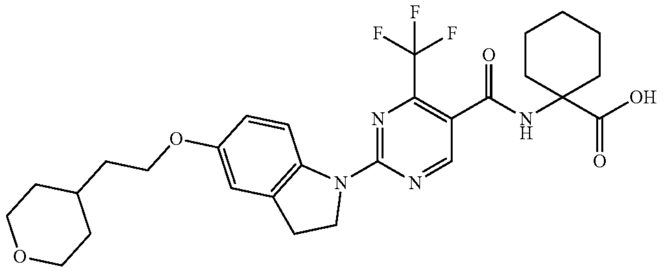 [SMILES: O=C(NC1(C(=O)O)CCCCC1)c1cnc(N2CCc3cc(OCCC4CCOCC4)ccc32)nc1C(F)(F)F] | 563 | 2.54 | 3 | |
TABLE 2
| Compound No. | Chemical Structure | [M + H] | Retention Time (min) | LC/MS Condition | Stereo-Chemistry |
|---|---|---|---|---|---|
| I-9 | 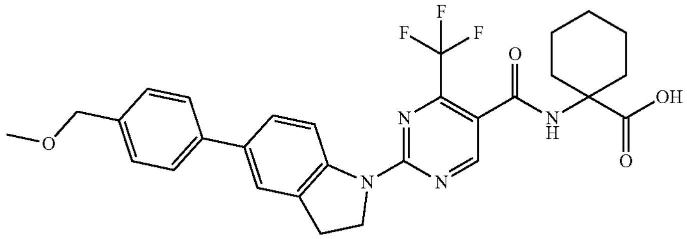 [SMILES: COCc1ccc(-c2ccc3c(c2)CCN3c2ncc(C(=O)NC3(C(=O)O)CCCCC3)c(C(F)(F)F)n2)cc1] | 555 | 2.75 | 3 | |
| I-10 | 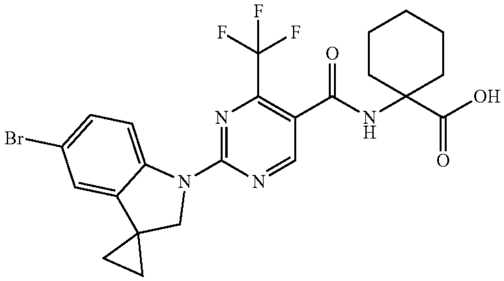 [SMILES: O=C(NC1(C(=O)O)CCCCC1)c1cnc(N2CC3(CC3)c3cc(Br)ccc32)nc1C(F)(F)F] | 539 | 2.88 | 3 | |
| I-11 | 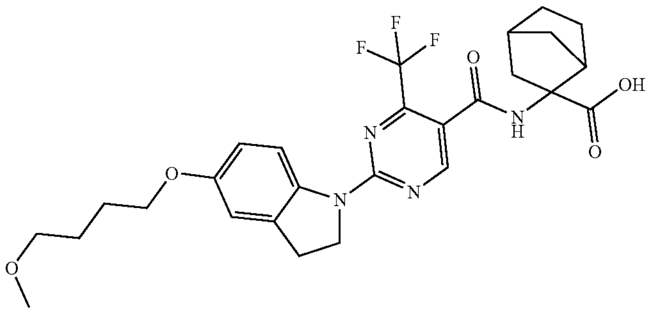 [SMILES: COCCCCOc1ccc2c(c1)CCN2c1ncc(C(=O)NC2(C(=O)O)CC3CCC2C3)c(C(F)(F)F)n1] | 549 | 2.59 | 3 | c |

TABLE 2-continued
| Compound No. | Chemical Structure | [M + H] | Retention Time (min) | LC/MS Condition | Stereo-Chemistry |
|---|---|---|---|---|---|
| I-12 | 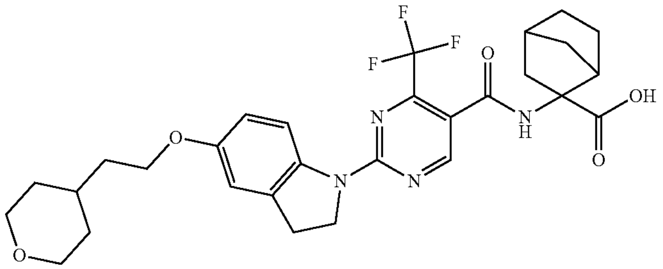 [SMILES: O=C(NC1(C(=O)O)CC2CCC1C2)c1cnc(N2CCc3cc(OCCC4CCOCC4)ccc32)nc1C(F)(F)F] | 575 | 2.55 | 4 | c |
| I-13 | 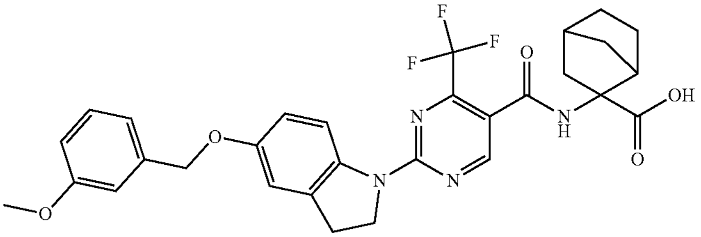 [SMILES: COc1cccc(COc2ccc3c(c2)CCN3c2ncc(C(=O)NC3(C(=O)O)CC4CCC3C4)c(C(F)(F)F)n2)c1] | 583 | 2.80 | 4 | c |
| I-14 | 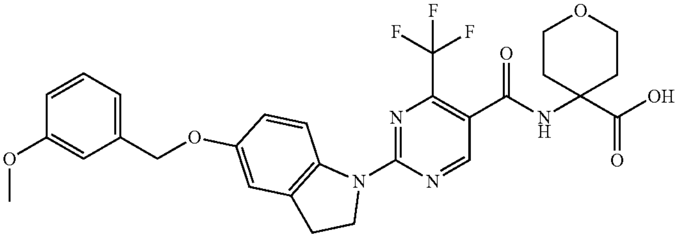 [SMILES: COc1cccc(COc2ccc3c(c2)CCN3c2ncc(C(=O)NC3(C(=O)O)CCOCC3)c(C(F)(F)F)n2)c1] | 573 | 2.46 | 1 | |
| I-15 | 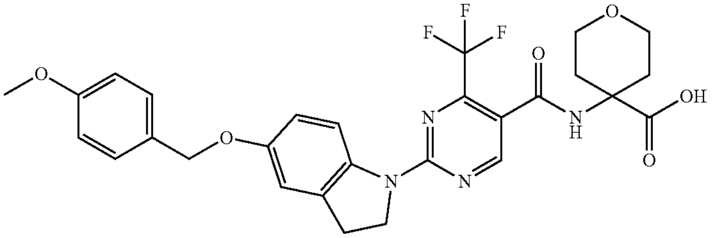 [SMILES: COc1ccc(COc2ccc3c(c2)CCN3c2ncc(C(=O)NC3(C(=O)O)CCOCC3)c(C(F)(F)F)n2)cc1] | 573 | 2.41 | 1 | |
| I-16 | 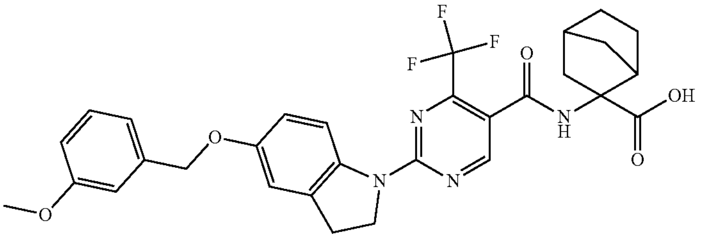 [SMILES: COc1cccc(COc2ccc3c(c2)CCN3c2ncc(C(=O)NC3(C(=O)O)CC4CCC3C4)c(C(F)(F)F)n2)c1] | 583 | 2.79 | 1 | b |

TABLE 3
| Compound No. | Chemical Structure | [M + H] | Retention Time (min) | LC/MS Condition | Stereo-Chemistry |
|---|---|---|---|---|---|
| I-17 | 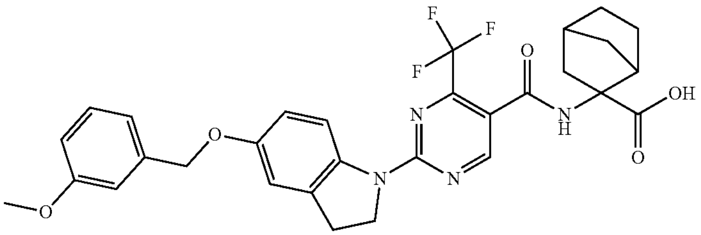 [SMILES: COc1cccc(COc2ccc3c(c2)CCN3c2ncc(C(=O)NC3(C(=O)O)CC4CCC3C4)c(C(F)(F)F)n2)c1] | 583 | 2.81 | 1 | b |
| I-18 | 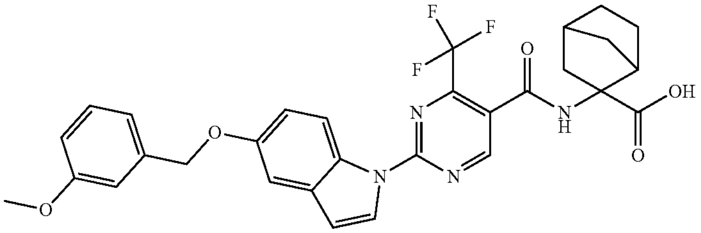 [SMILES: COc1cccc(COc2ccc3c(ccn3-c3ncc(C(=O)NC4(C(=O)O)CC5CCC4C5)c(C(F)(F)F)n3)c2)c1] | 581 | 2.87 | 1 | b |
| I-19 | 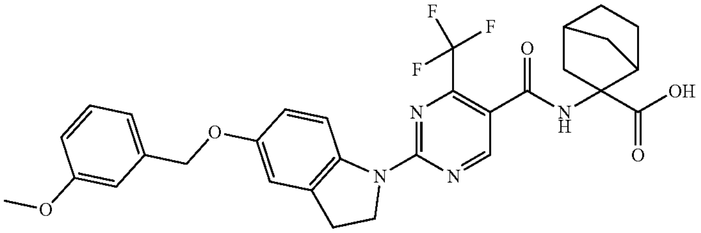 [SMILES: COc1cccc(COc2ccc3c(c2)CCN3c2ncc(C(=O)NC3(C(=O)O)CC4CCC3C4)c(C(F)(F)F)n2)c1] | 583 | 2.77 | 1 | b |
| I-20 | 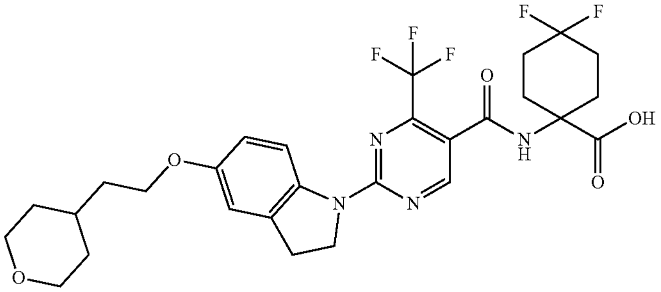 [SMILES: O=C(NC1(C(=O)O)CCC(F)(F)CC1)c1cnc(N2CCc3cc(OCCC4CCOCC4)ccc32)nc1C(F)(F)F] | 599 | 2.55 | 1 | |
| I-21 | 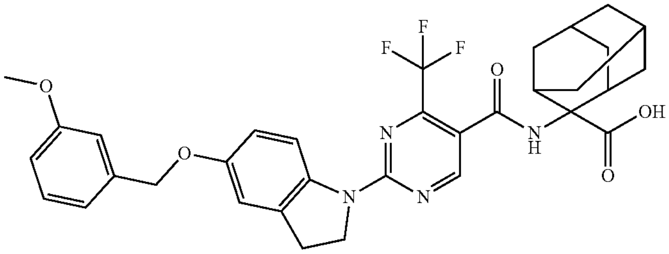 [SMILES: COc1cccc(COc2ccc3c(c2)CCN3c2ncc(C(=O)NC3(C(=O)O)C4CC5CC(C4)CC3C5)c(C(F)(F)F)n2)c1] | 623 | 3.04 | 1 | |
| I-22 | 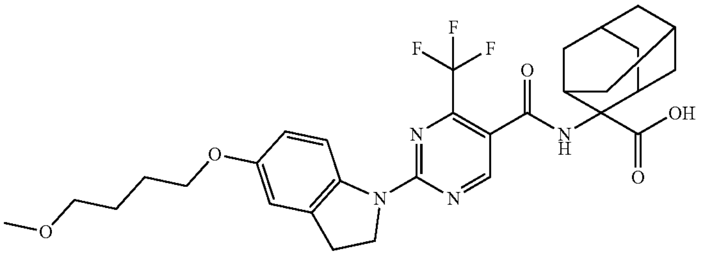 [SMILES: COCCCCOc1ccc2c(c1)CCN2c1ncc(C(=O)NC2(C(=O)O)C3CC4CC(C3)CC2C4)c(C(F)(F)F)n1] | 589 | 2.87 | 1 | |

TABLE 3-continued
| Compound No. | Chemical Structure | [M + H] | Retention Time (min) | LC/MS Condition | Stereo-Chemistry |
|---|---|---|---|---|---|
| I-23 | 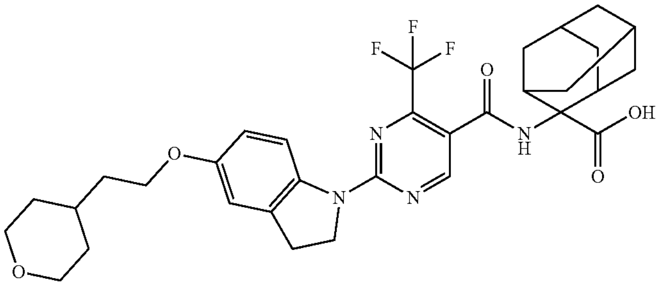 [SMILES: O=C(NC1(C(=O)O)C2CC3CC(C2)CC1C3)c1cnc(N2CCc3cc(OCCC4CCOCC4)ccc32)nc1C(F)(F)F] | 615 | 2.90 | 1 | |
| I-24 | 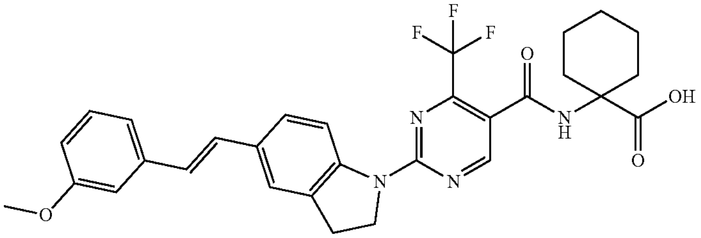 [SMILES: COc1cccc(/C=C/c2ccc3c(c2)CCN3c2ncc(C(=O)NC3(C(=O)O)CCCCC3)c(C(F)(F)F)n2)c1] | 567 | 2.92 | 1 | |
TABLE 4
| Compound No. | Chemical Structure | [M + H] | Retention Time (min) | LC/MS Condition | Stereo-Chemistry |
|---|---|---|---|---|---|
| I-25 | 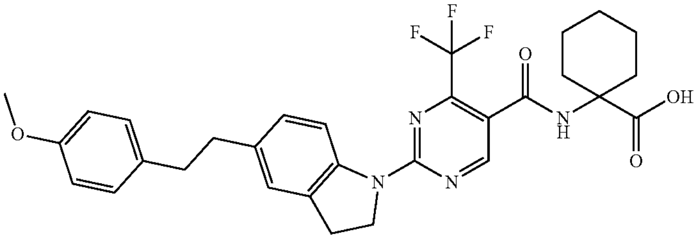 [SMILES: COc1ccc(CCc2ccc3c(c2)CCN3c2ncc(C(=O)NC3(C(=O)O)CCCCC3)c(C(F)(F)F)n2)cc1] | 569 | 2.97 | 1 | |
| I-26 | 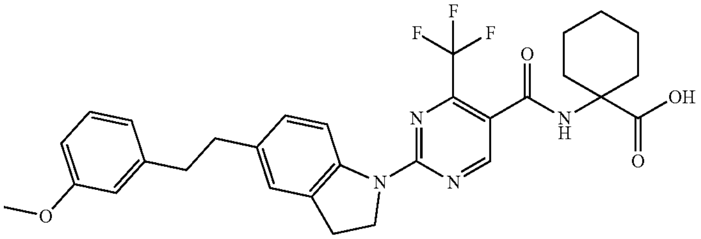 [SMILES: COc1cccc(CCc2ccc3c(c2)CCN3c2ncc(C(=O)NC3(C(=O)O)CCCCC3)c(C(F)(F)F)n2)c1] | 569 | 2.95 | 1 | |
| I-27 | 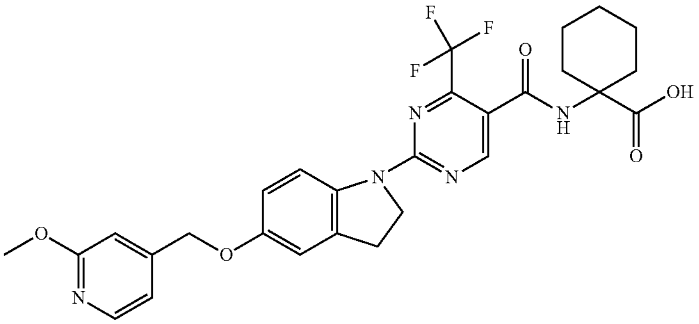 [SMILES: COc1cc(COc2ccc3c(c2)CCN3c2ncc(C(=O)NC3(C(=O)O)CCCCC3)c(C(F)(F)F)n2)ccn1] | 572 | 2.51 | 1 | |

TABLE 4-continued
| Compound No. | Chemical Structure | [M + H] | Retention Time (min) | LC/MS Condition | Stereo-Chemistry |
|---|---|---|---|---|---|
| I-28 | 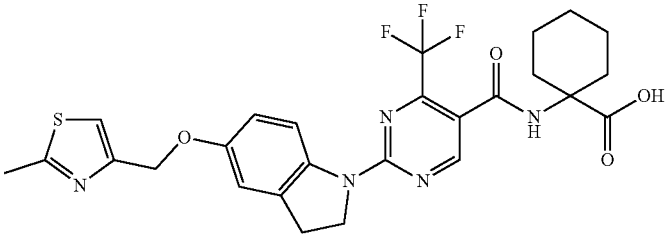 [SMILES: Cc1nc(COc2ccc3c(c2)CCN3c2ncc(C(=O)NC3(C(=O)O)CCCCC3)c(C(F)(F)F)n2)cs1] | 562 | 2.41 | 1 | |
| I-29 | 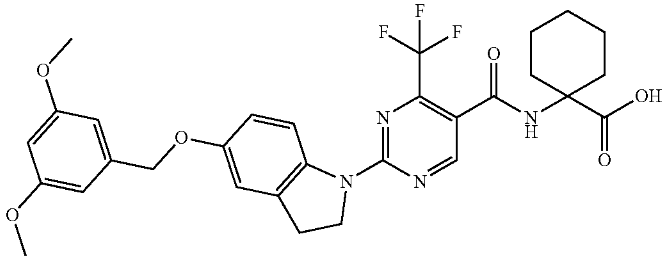 [SMILES: COc1cc(COc2ccc3c(c2)CCN3c2ncc(C(=O)NC3(C(=O)O)CCCCC3)c(C(F)(F)F)n2)cc(OC)c1] | 601 | 2.74 | 1 | |
| I-30 | 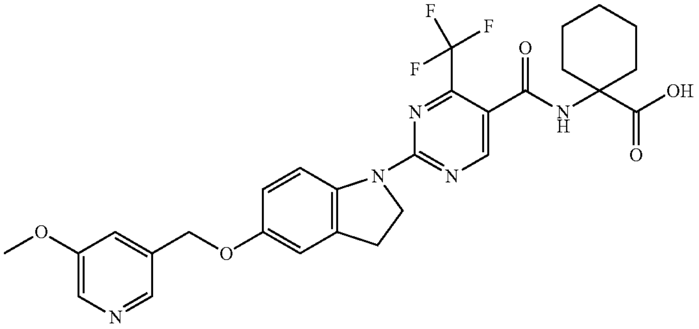 [SMILES: COc1cncc(COc2ccc3c(c2)CCN3c2ncc(C(=O)NC3(C(=O)O)CCCCC3)c(C(F)(F)F)n2)c1] | 572 | 2.12 | 1 | |
| I-31 | 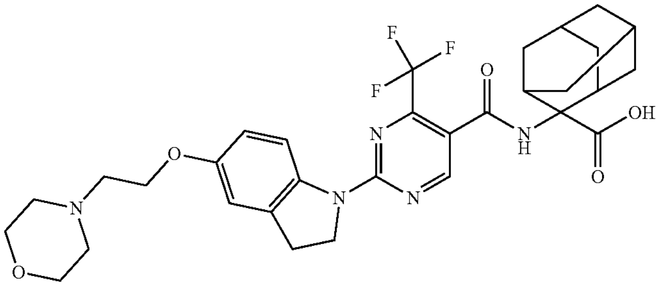 [SMILES: O=C(NC1(C(=O)O)C2CC3CC(C2)CC1C3)c1cnc(N2CCc3cc(OCCN4CCOCC4)ccc32)nc1C(F)(F)F] | 616 | 2.01 | 1 | |
TABLE 5
| Compound No. | Chemical Structure | [M + H] | Retention Time (min) | LC/MS Condition | Stereo-Chemistry |
|---|---|---|---|---|---|
| I-32 | 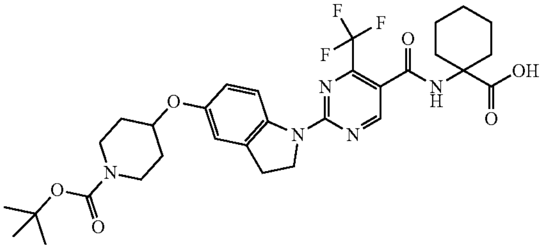 [SMILES: CC(C)(C)OC(=O)N1CCC(Oc2ccc3c(c2)CCN3c2ncc(C(=O)NC3(C(=O)O)CCCCC3)c(C(F)(F)F)n2)CC1] | 634 | 2.84 | 1 | |

TABLE 5-continued
| Compound No. | Chemical Structure | [M + H] | Retention Time (min) | LC/MS Condition | Stereo-Chemistry |
| --- | --- | --- | --- | --- | --- |
| I-33 | 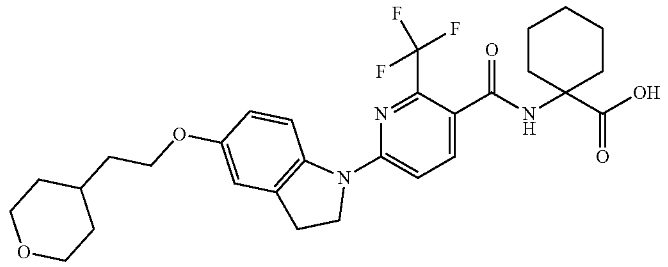 [SMILES: O=C(NC1(C(=O)O)CCCCC1)c1ccc(N2CCc3cc(OCCC4CCOCC4)ccc32)nc1C(F)(F)F] | 562 | 2.56 | 1 | |
| I-34 | 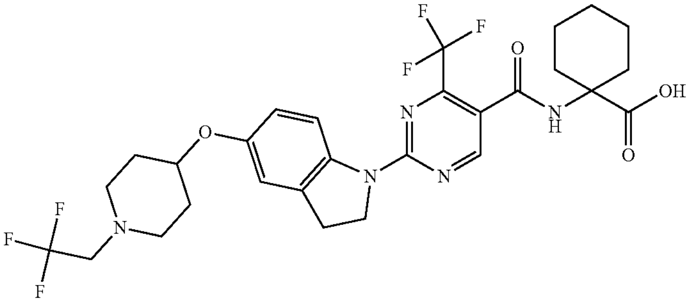 [SMILES: O=C(NC1(C(=O)O)CCCCC1)c1cnc(N2CCc3cc(OC4CCN(CC(F)(F)F)CC4)ccc32)nc1C(F)(F)F] | 616 | 2.54 | 1 | |
| I-35 | 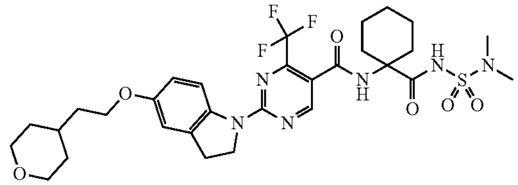 [SMILES: CN(C)S(=O)(=O)NC(=O)C1(NC(=O)c2cnc(N3CCc4cc(OCCC5CCOCC5)ccc43)nc2C(F)(F)F)CCCCC1] | 669 | 2.78 | 1 | |
| I-36 | 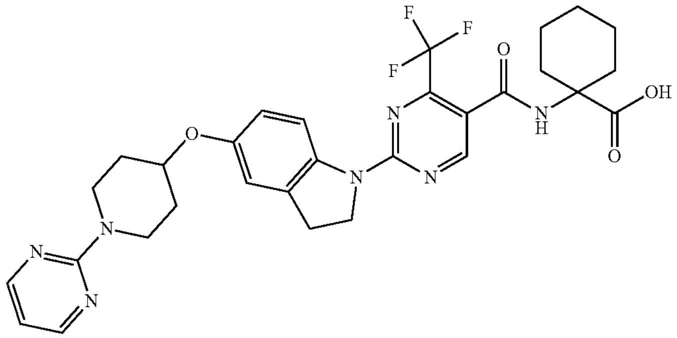 [SMILES: O=C(NC1(C(=O)O)CCCCC1)c1cnc(N2CCc3cc(OC4CCN(c5ncccn5)CC4)ccc32)nc1C(F)(F)F] | 612 | 2.61 | 1 | |
| I-37 | 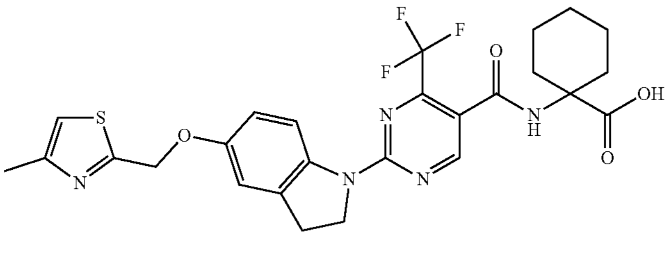 [SMILES: Cc1csc(COc2ccc3c(c2)CCN3c2ncc(C(=O)NC3(C(=O)O)CCCCC3)c(C(F)(F)F)n2)n1] | 562 | 2.48 | 1 | |

TABLE 5-continued
| Compound No. | Chemical Structure | [M + H] | Retention Time (min) | LC/MS Condition | Stereo-Chemistry |
|---|---|---|---|---|---|
| I-38 | 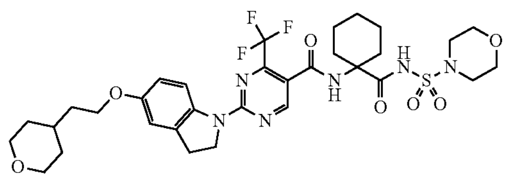 [SMILES: O=C(NC1(C(=O)NS(=O)(=O)N2CCOCC2)CCCCC1)c1cnc(N2CCc3cc(OCCC4CCOCC4)ccc32)nc1C(F)(F)F] | 711 | 2.71 | 1 | |
TABLE 6
| Compound No. | Chemical Structure | [M + H] | Retention Time (min) | LC/MS Condition | Stereo-Chemistry |
|---|---|---|---|---|---|
| I-39 | 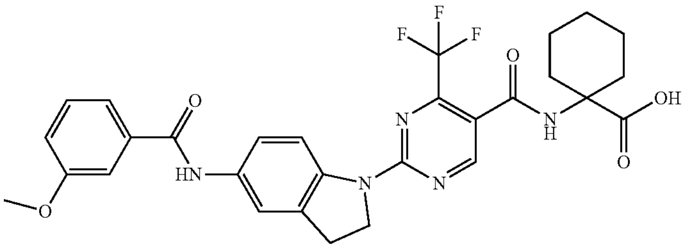 [SMILES: COc1cccc(C(=O)Nc2ccc3c(c2)CCN3c2ncc(C(=O)NC3(C(=O)O)CCCCC3)c(C(F)(F)F)n2)c1] | 584 | 2.40 | 1 | |
| I-40 | 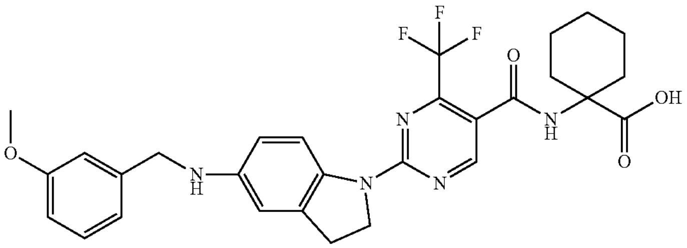 [SMILES: COc1cccc(CNc2ccc3c(c2)CCN3c2ncc(C(=O)NC3(C(=O)O)CCCCC3)c(C(F)(F)F)n2)c1] | 570 | 2.42 | 1 | |
| I-41 | 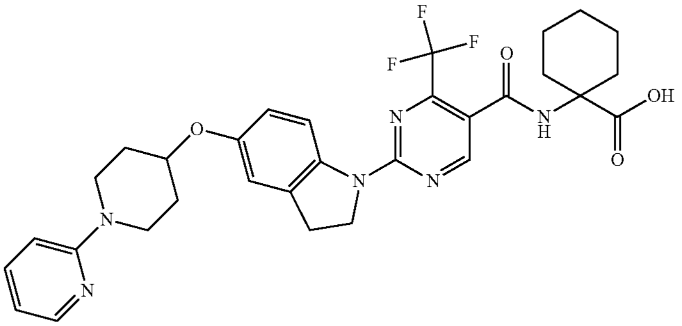 [SMILES: O=C(NC1(C(=O)O)CCCCC1)c1cnc(N2CCc3cc(OC4CCN(c5ccccn5)CC4)ccc32)nc1C(F)(F)F] | 611 | 2.42 | 1 | |
| I-42 | 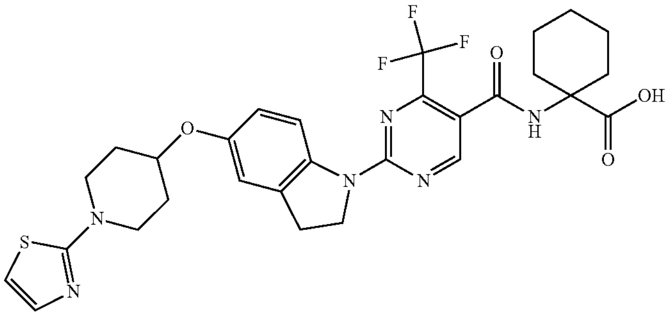 [SMILES: O=C(NC1(C(=O)O)CCCCC1)c1cnc(N2CCc3cc(OC4CCN(c5nccs5)CC4)ccc32)nc1C(F)(F)F] | 617 | 2.20 | 1 | |

TABLE 6-continued
| Compound No. | Chemical Structure | [M + H] | Retention Time (min) | LC/MS Condition | Stereo-Chemistry |
|---|---|---|---|---|---|
| I-43 | 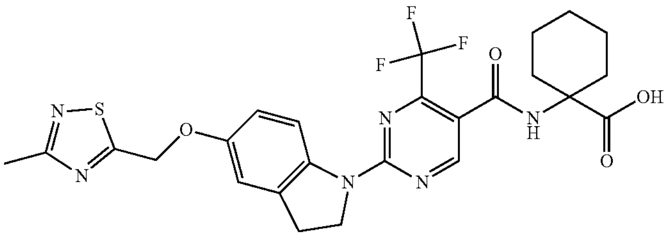 [SMILES: Cc1nsc(COc2ccc3c(c2)CCN3c2ncc(C(=O)NC3(C(=O)O)CCCCC3)c(C(F)(F)F)n2)n1] | 563 | 2.46 | 1 | |
| I-44 | 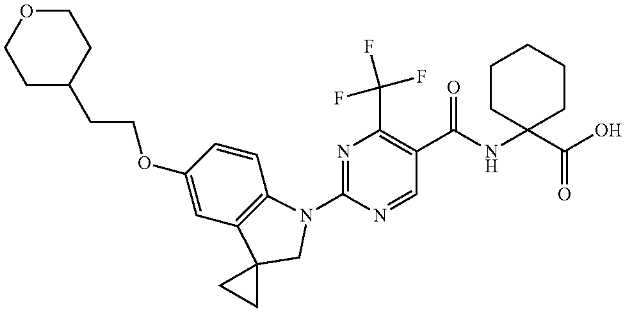 [SMILES: O=C(NC1(C(=O)O)CCCCC1)c1cnc(N2CC3(CC3)c3cc(OCCC4CCOCC4)ccc32)nc1C(F)(F)F] | 589 | 2.76 | 1 | |
| I-45 | 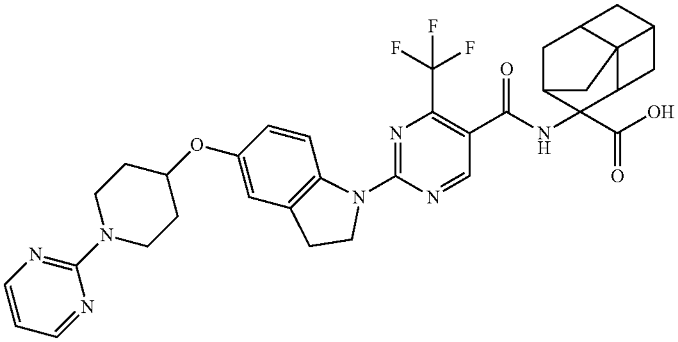 [SMILES: O=C(NC1(C(=O)O)C2CC3CC4CC1C34C2)c1cnc(N2CCc3cc(OC4CCN(c5ncccn5)CC4)ccc32)nc1C(F)(F)F] | 664 | 2.90 | 1 | |
TABLE 7
| Compound No. | Chemical Structure | [M + H] | Retention Time (min) | LC/MS Condition | Stereo-Chemistry |
|---|---|---|---|---|---|
| I-46 | 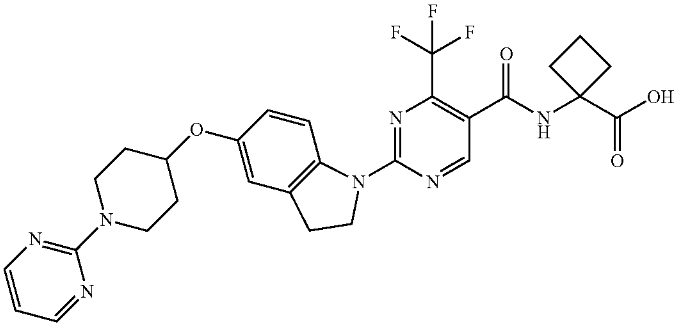 [SMILES: O=C(NC1(C(=O)O)CCC1)c1cnc(N2CCc3cc(OC4CCN(c5ncccn5)CC4)ccc32)nc1C(F)(F)F] | 584 | 2.33 | 1 | |

TABLE 7-continued
| Compound No. | Chemical Structure | [M + H] | Retention Time (min) | LC/MS Condition | Stereo-Chemistry |
|---|---|---|---|---|---|
| I-47 | 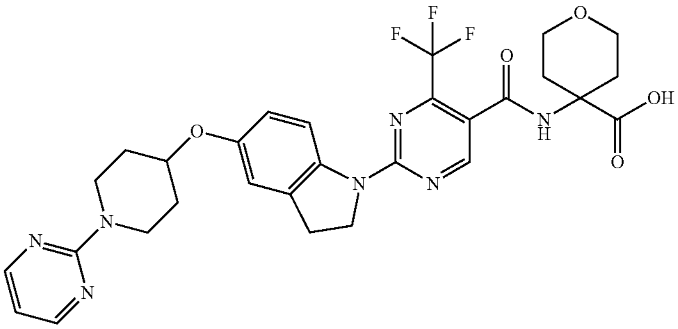 [SMILES: O=C(NC1(C(=O)O)CCOCC1)c1cnc(N2CCc3cc(OC4CCN(c5ncccn5)CC4)ccc32)nc1C(F)(F)F] | 614 | 2.16 | 1 | |
| I-48 | 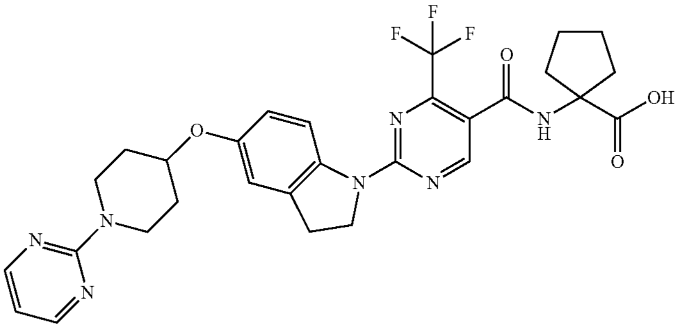 [SMILES: O=C(NC1(C(=O)O)CCCC1)c1cnc(N2CCc3cc(OC4CCN(c5ncccn5)CC4)ccc32)nc1C(F)(F)F] | 598 | 2.43 | 1 | |
| I-49 | 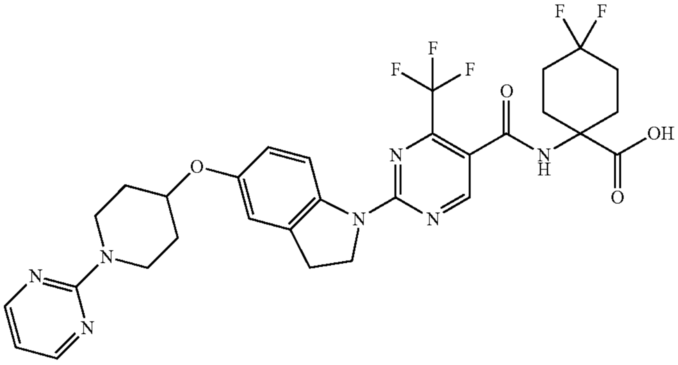 [SMILES: O=C(NC1(C(=O)O)CCC(F)(F)CC1)c1cnc(N2CCc3cc(OC4CCN(c5ncccn5)CC4)ccc32)nc1C(F)(F)F] | 648 | 2.51 | 1 | |
| I-50 | 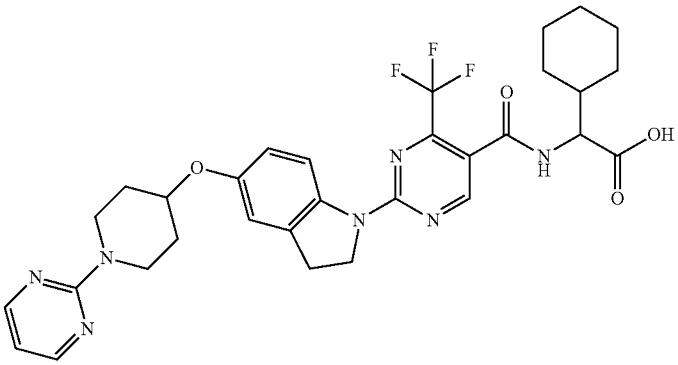 [SMILES: O=C(NC(C(=O)O)C1CCCCC1)c1cnc(N2CCc3cc(OC4CCN(c5ncccn5)CC4)ccc32)nc1C(F)(F)F] | 626 | 2.70 | 1 | a |

TABLE 7-continued
| Compound No. | Chemical Structure | [M + H] | Retention Time (min) | LC/MS Condition | Stereo-Chemistry |
|---|---|---|---|---|---|
| I-51 | 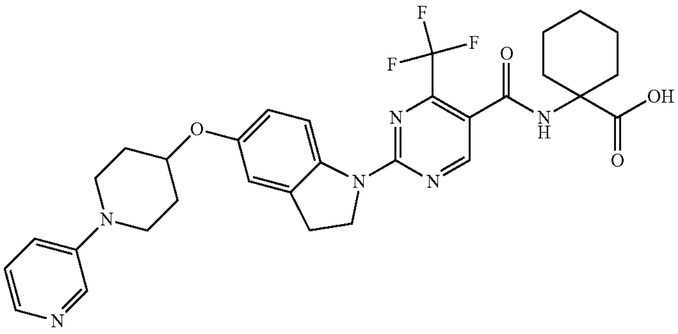 [SMILES: O=C(NC1(C(=O)O)CCCCC1)c1cnc(N2CCc3cc(OC4CCN(c5cccnc5)CC4)ccc32)nc1C(F)(F)F] | 611 | 2.01 | 1 | |
TABLE 8
| Compound No. | Chemical Structure | [M + H] | Retention Time (min) | LC/MS Condition | Stereo-Chemistry |
|---|---|---|---|---|---|
| I-52 | 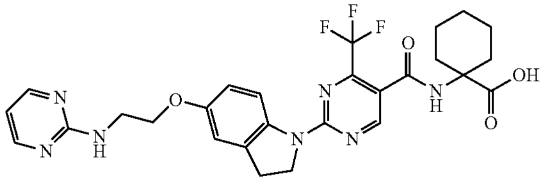 [SMILES: O=C(NC1(C(=O)O)CCCCC1)c1cnc(N2CCc3cc(OCCNc4ncccn4)ccc32)nc1C(F)(F)F] | 572 | 2.07 | 1 | |
| I-53 | 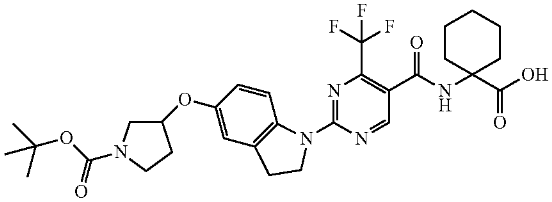 [SMILES: CC(C)(C)OC(=O)N1CCC(Oc2ccc3c(c2)CCN3c2ncc(C(=O)NC3(C(=O)O)CCCCC3)c(C(F)(F)F)n2)C1] | 618 | 2.69 | 1 | a |
| I-54 | 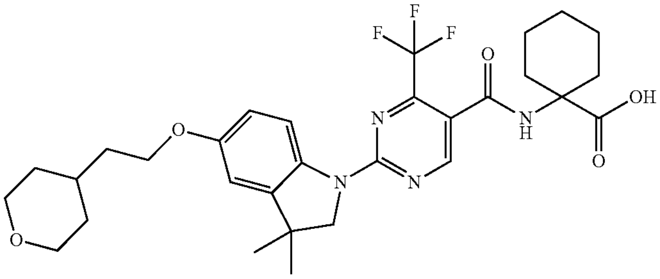 [SMILES: CC1(C)CN(c2ncc(C(=O)NC3(C(=O)O)CCCCC3)c(C(F)(F)F)n2)c2ccc(OCCC3CCOCC3)cc21] | 591 | 2.80 | 1 | |
| I-55 | 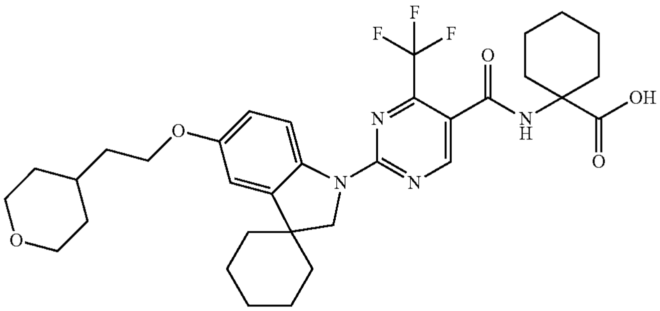 [SMILES: O=C(NC1(C(=O)O)CCCCC1)c1cnc(N2CC3(CCCCC3)c3cc(OCCC4CCOCC4)ccc32)nc1C(F)(F)F] | 631 | 3.09 | 1 | |

TABLE 8-continued
| Compound No. | Chemical Structure | [M + H] | Retention Time (min) | LC/MS Condition | Stereo-Chemistry |
|---|---|---|---|---|---|
| I-56 | 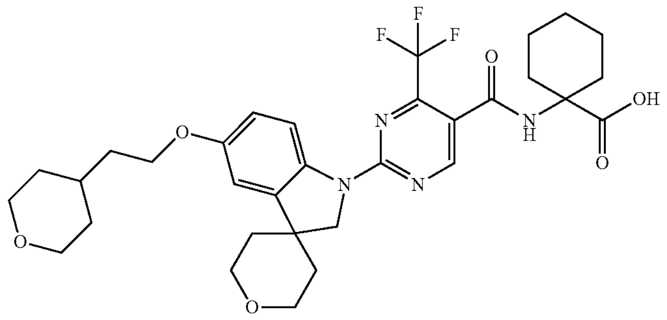 [SMILES: O=C(NC1(C(=O)O)CCCCC1)c1cnc(N2CC3(CCOCC3)c3cc(OCCC4CCOCC4)ccc32)nc1C(F)(F)F] | 633 | 2.54 | 1 | |
| I-57 | 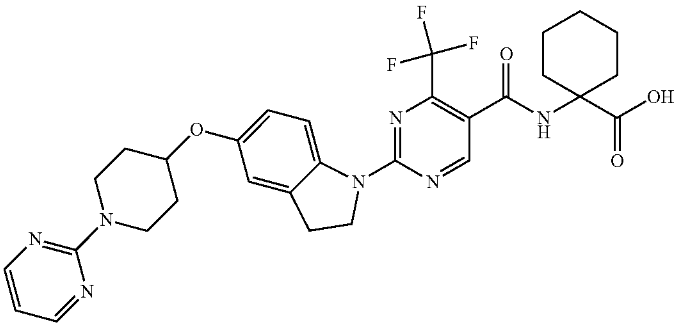 [SMILES: O=C(NC1(C(=O)O)CCCCC1)c1cnc(N2CCc3cc(OC4CCN(c5ncccn5)CC4)ccc32)nc1C(F)(F)F] | 612 | 2.48 | 1 | |
| I-58 | 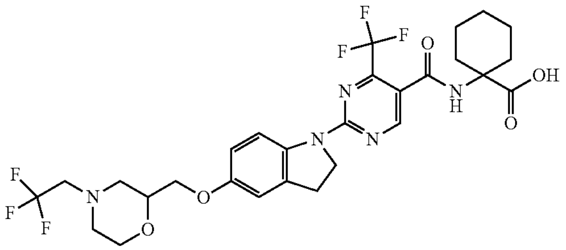 [SMILES: O=C(NC1(C(=O)O)CCCCC1)c1cnc(N2CCc3cc(OCC4CN(CC(F)(F)F)CCO4)ccc32)nc1C(F)(F)F] | 632 | 2.61 | 1 | a |
TABLE 9
| Compound No. | Chemical Structure | [M + H] | Retention Time (min) | LC/MS Condition | Stereo-Chemistry |
|---|---|---|---|---|---|
| I-59 | 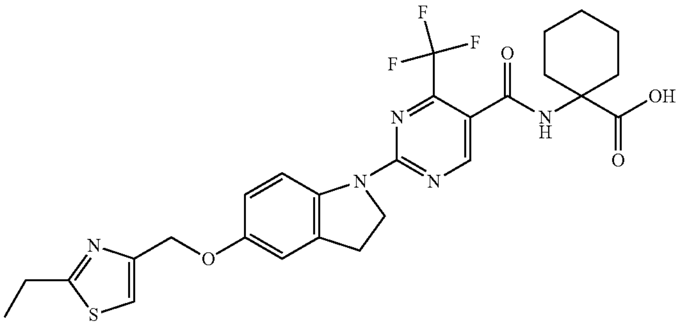 [SMILES: CCc1nc(COc2ccc3c(c2)CCN3c2ncc(C(=O)NC3(C(=O)O)CCCCC3)c(C(F)(F)F)n2)cs1] | 576 | 2.59 | 1 | |

TABLE 9-continued
| Compound No. | Chemical Structure | [M + H] | Retention Time (min) | LC/MS Condition | Stereo-Chemistry |
|---|---|---|---|---|---|
| I-60 | 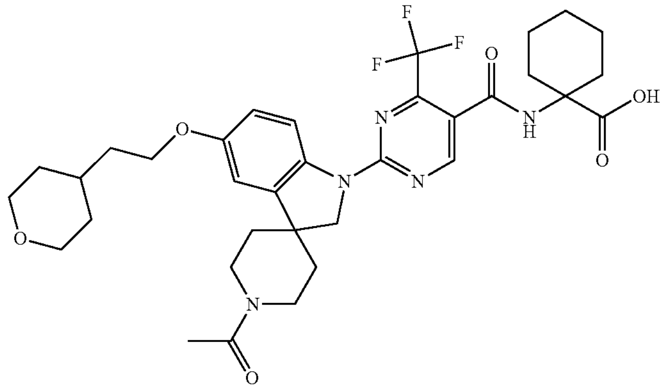 [SMILES: CC(=O)N1CCC2(CC1)CN(c1ncc(C(=O)NC3(C(=O)O)CCCCC3)c(C(F)(F)F)n1)c1ccc(OCCC3CCOCC3)cc12] | 574 | 2.32 | 1 | |
| I-61 | 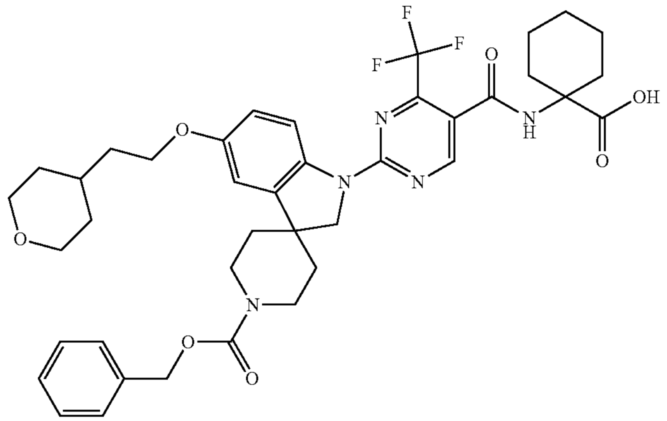 [SMILES: O=C(NC1(C(=O)O)CCCCC1)c1cnc(N2CC3(CCN(C(=O)OCc4ccccc4)CC3)c3cc(OCCC4CCOCC4)ccc32)nc1C(F)(F)F] | 766 | 2.92 | 1 | |
| I-62 | 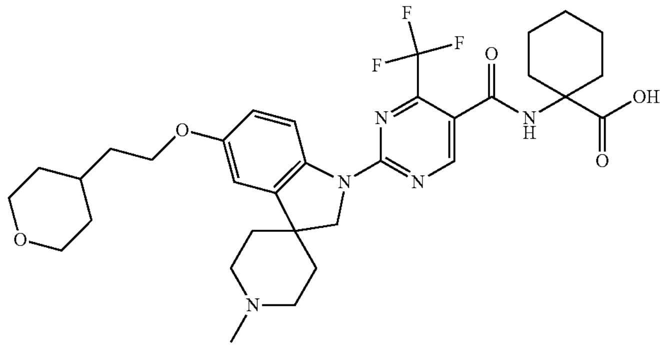 [SMILES: CN1CCC2(CC1)CN(c1ncc(C(=O)NC3(C(=O)O)CCCCC3)c(C(F)(F)F)n1)c1ccc(OCCC3CCOCC3)cc12] | 646 | 2.06 | 1 | |
| I-63 | 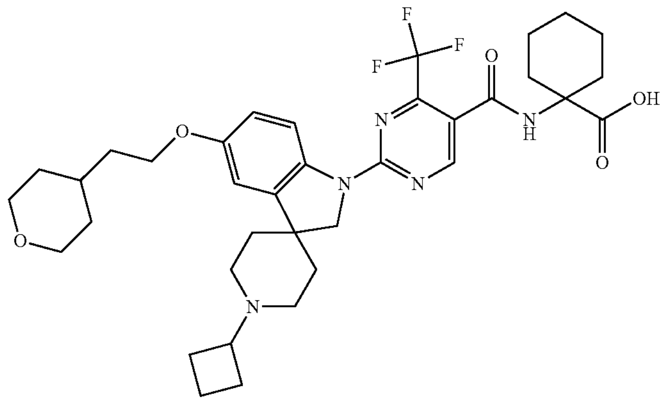 [SMILES: O=C(NC1(C(=O)O)CCCCC1)c1cnc(N2CC3(CCN(C4CCC4)CC3)c3cc(OCCC4CCOCC4)ccc32)nc1C(F)(F)F] | 686 | 2.32 | 1 | |

TABLE 9-continued
| Compound No. | Chemical Structure | [M + H] | Retention Time (min) | LC/MS Condition | Stereo-Chemistry |
| --- | --- | --- | --- | --- | --- |
| I-64 | 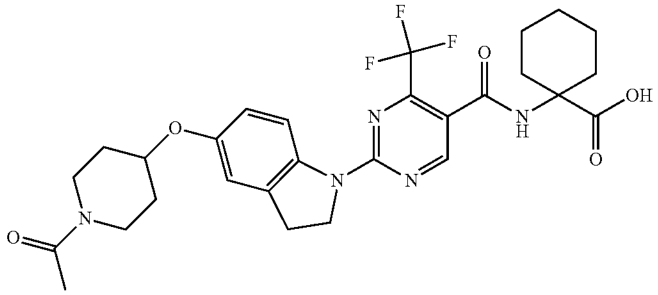 [SMILES: CC(=O)N1CCC(Oc2ccc3c(c2)CCN3c2ncc(C(=O)NC3(C(=O)O)CCCCC3)c(C(F)(F)F)n2)CC1] | 576 | 2.11 | 1 | |
TABLE 10
| Compound No. | Chemical Structure | [M + H] | Retention Time (min) | LC/MS Condition | Stereo-Chemistry |
| --- | --- | --- | --- | --- | --- |
| I-65 | 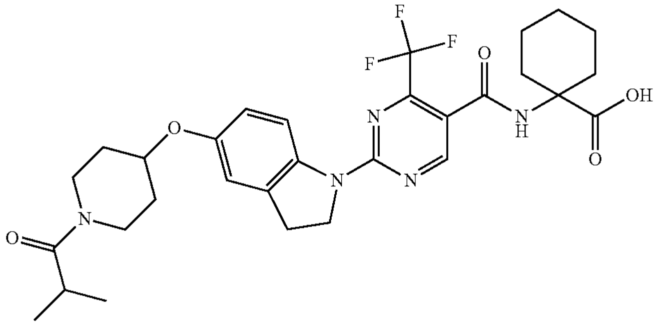 [SMILES: CC(C)C(=O)N1CCC(Oc2ccc3c(c2)CCN3c2ncc(C(=O)NC3(C(=O)O)CCCCC3)c(C(F)(F)F)n2)CC1] | 604 | 2.38 | 1 | |
| I-66 | 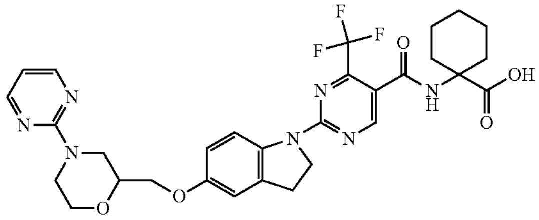 [SMILES: O=C(NC1(C(=O)O)CCCCC1)c1cnc(N2CCc3cc(OCC4CN(c5ncccn5)CCO4)ccc32)nc1C(F)(F)F] | 628 | 2.48 | 1 | a |
| I-67 | 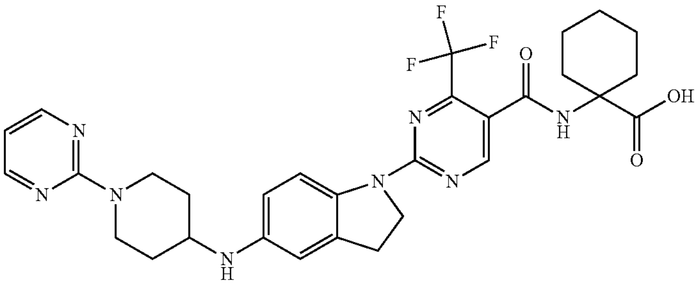 [SMILES: O=C(NC1(C(=O)O)CCCCC1)c1cnc(N2CCc3cc(NC4CCN(c5ncccn5)CC4)ccc32)nc1C(F)(F)F] | 611 | 2.01 | 1 | |

TABLE 10-continued
| Compound No. | Chemical Structure | [M + H] | Retention Time (min) | LC/MS Condition | Stereo-Chemistry |
|---|---|---|---|---|---|
| I-68 | 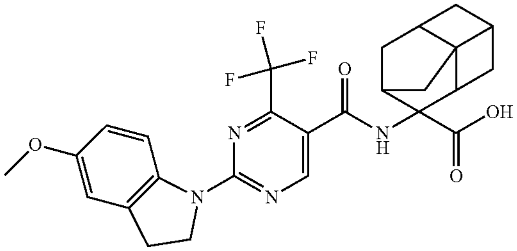 [SMILES: COc1ccc2c(c1)CCN2c1ncc(C(=O)NC2(C(=O)O)C3CC4CC5CC2C45C3)c(C(F)(F)F)n1] | 517 | 2.69 | 1 | |
| I-69 | 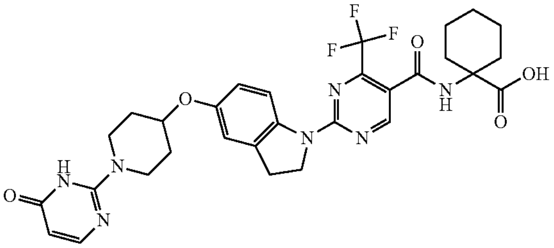 [SMILES: O=C(NC1(C(=O)O)CCCCC1)c1cnc(N2CCc3cc(OC4CCN(c5nccc(=O)[nH]5)CC4)ccc32)nc1C(F)(F)F] | 628 | 1.94 | 1 | |
| I-70 | 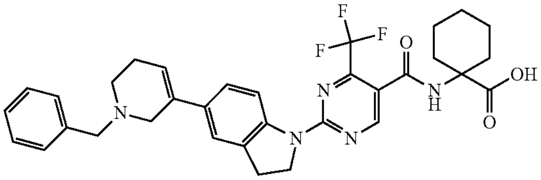 [SMILES: O=C(NC1(C(=O)O)CCCCC1)c1cnc(N2CCc3cc(C4=CCCN(Cc5ccccc5)C4)ccc32)nc1C(F)(F)F] | 606 | 2.16 | 1 | |
| I-71 | 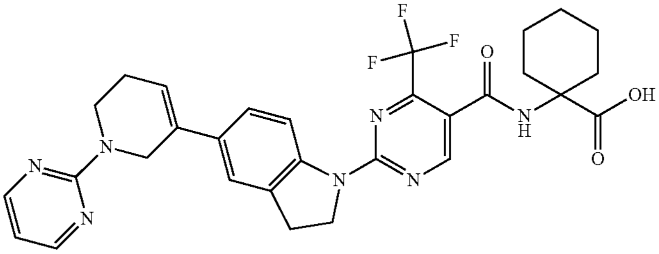 [SMILES: O=C(NC1(C(=O)O)CCCCC1)c1cnc(N2CCc3cc(C4=CCCN(c5ncccn5)C4)ccc32)nc1C(F)(F)F] | 594 | 2.76 | 1 | |
TABLE 11
| Compound No. | Chemical Structure | [M + H] | Retention Time (min) | LC/MS Condition | Stereo-Chemistry |
|---|---|---|---|---|---|
| I-72 | 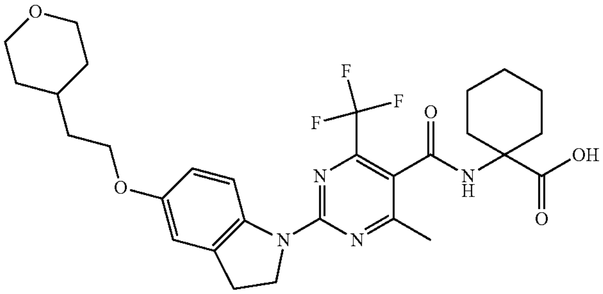 [SMILES: Cc1nc(N2CCc3cc(OCCC4CCOCC4)ccc32)nc(C(F)(F)F)c1C(=O)NC1(C(=O)O)CCCCC1] | 577 | 2.66 | 3 | |

TABLE 11-continued
| Compound No. | Chemical Structure | [M + H] | Retention Time (min) | LC/MS Condition | Stereo-Chemistry |
|---|---|---|---|---|---|
| I-73 | 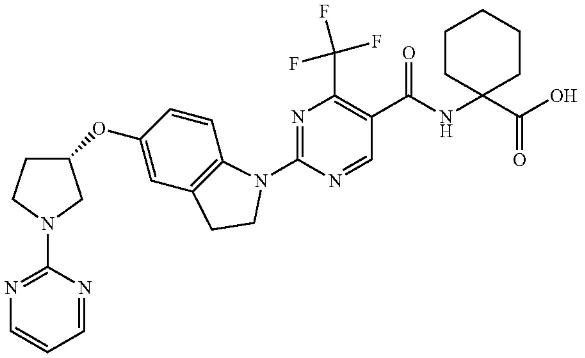 [SMILES: O=C(NC1(C(=O)O)CCCCC1)c1cnc(N2CCc3cc(O[C@H]4CCN(c5ncccn5)C4)ccc32)nc1C(F)(F)F] | 596 | 2.24 | 1 | |
| I-74 | 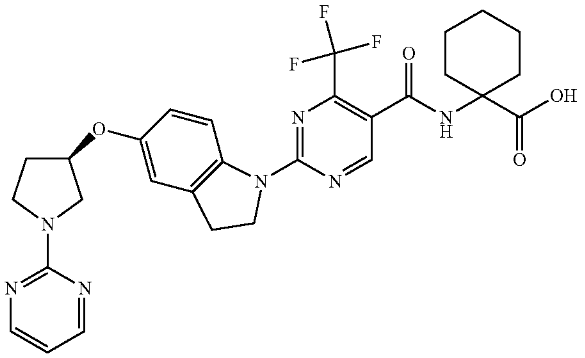 [SMILES: O=C(NC1(C(=O)O)CCCCC1)c1cnc(N2CCc3cc(O[C@@H]4CCN(c5ncccn5)C4)ccc32)nc1C(F)(F)F] | 598 | 2.24 | 1 | |
| I-75 | 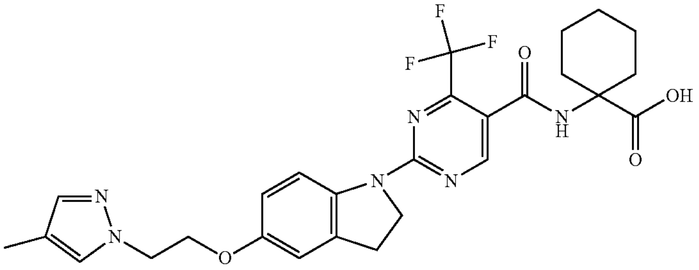 [SMILES: Cc1cnn(CCOc2ccc3c(c2)CCN3c2ncc(C(=O)NC3(C(=O)O)CCCCC3)c(C(F)(F)F)n2)c1] | 559 | 2.33 | 1 | |
| I-76 | 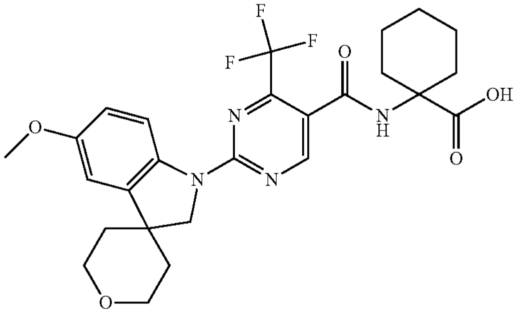 [SMILES: COc1ccc2c(c1)C1(CCOCC1)CN2c1ncc(C(=O)NC2(C(=O)O)CCCCC2)c(C(F)(F)F)n1] | 535 | 2.35 | 1 | |

TABLE 11-continued
| Compound No. | Chemical Structure | [M + H] | Retention Time (min) | LC/MS Condition | Stereo-Chemistry |
|---|---|---|---|---|---|
| I-77 | 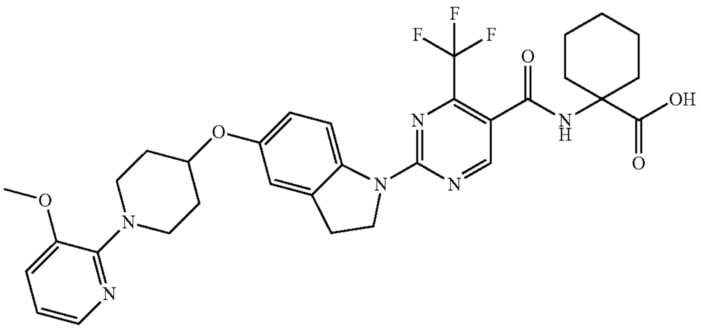 [SMILES: COc1cccnc1N1CCC(Oc2ccc3c(c2)CCN3c2ncc(C(=O)NC3(C(=O)O)CCCCC3)c(C(F)(F)F)n2)CC1] | 641 | 1.97 | 1 | |
TABLE 12
| Compound No. | Chemical Structure | [M + H] | Retention Time (min) | LC/MS Condition | Stereo-Chemistry |
|---|---|---|---|---|---|
| I-78 | 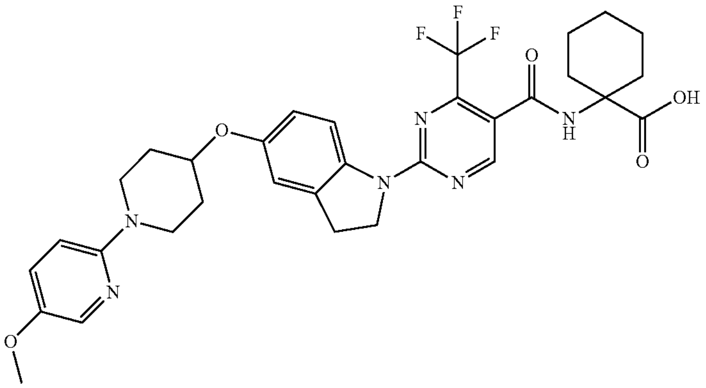 [SMILES: COc1ccc(N2CCC(Oc3ccc4c(c3)CCN4c3ncc(C(=O)NC4(C(=O)O)CCCCC4)c(C(F)(F)F)n3)CC2)nc1] | 641 | 1.94 | 1 | |
| I-79 | 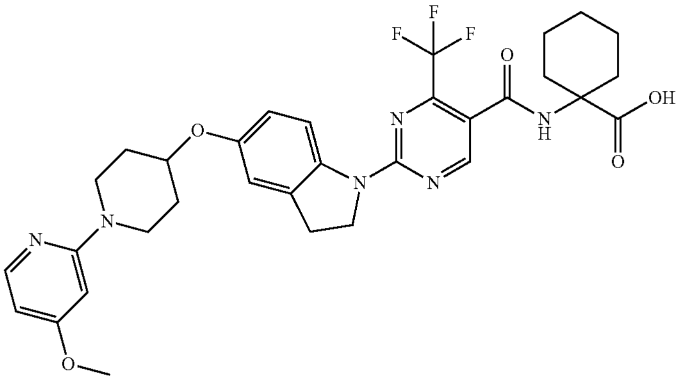 [SMILES: COc1ccnc(N2CCC(Oc3ccc4c(c3)CCN4c3ncc(C(=O)NC4(C(=O)O)CCCCC4)c(C(F)(F)F)n3)CC2)c1] | 641 | 1.84 | 1 | |

TABLE 12-continued
| Compound No. | Chemical Structure | [M + H] | Retention Time (min) | LC/MS Condition | Stereo-Chemistry |
|---|---|---|---|---|---|
| I-80 | 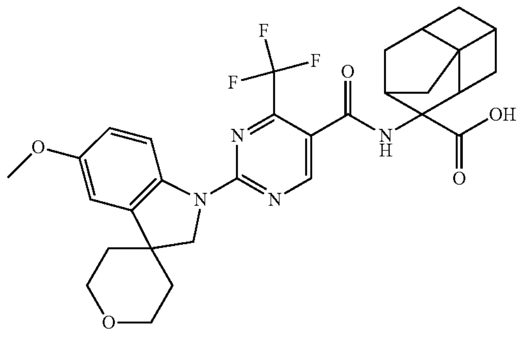 [SMILES: COc1ccc2c(c1)C1(CCOCC1)CN2c1ncc(C(=O)NC2(C(=O)O)C3CC4CC5CC2C45C3)c(C(F)(F)F)n1] | 587 | 2.63 | 1 | |
| I-81 | 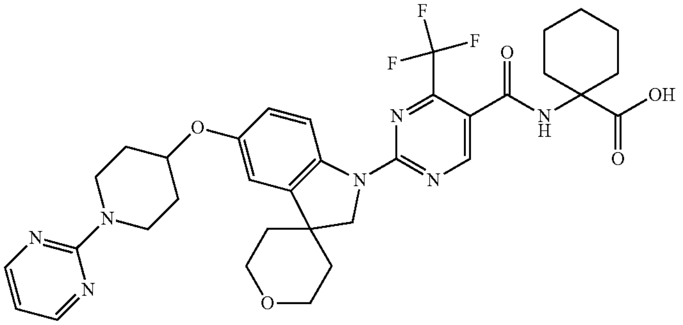 [SMILES: O=C(NC1(C(=O)O)CCCCC1)c1cnc(N2CC3(CCOCC3)c3cc(OC4CCN(c5ncccn5)CC4)ccc32)nc1C(F)(F)F] | 682 | 2.55 | 1 | |
| I-82 | 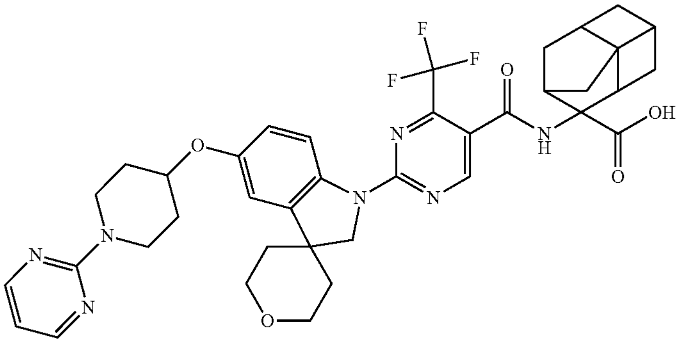 [SMILES: O=C(NC1(C(=O)O)C2CC3CC4CC1C34C2)c1cnc(N2CC3(CCOCC3)c3cc(OC4CCN(c5ncccn5)CC4)ccc32)nc1C(F)(F)F] | 734 | 2.85 | 1 | |
| I-83 | 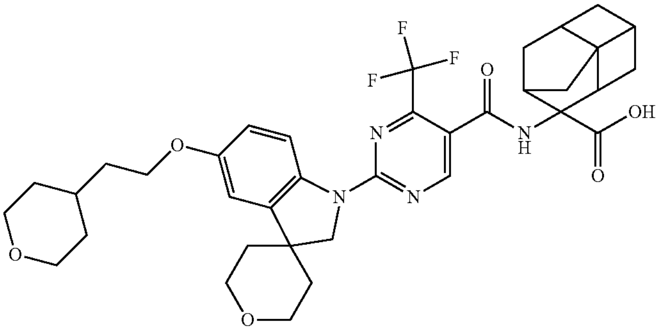 [SMILES: O=C(NC1(C(=O)O)C2CC3CC4CC1C34C2)c1cnc(N2CC3(CCOCC3)c3cc(OCCC4CCOCC4)ccc32)nc1C(F)(F)F] | 685 | 2.80 | 1 | |

TABLE 13
| Compound No. | Chemical Structure | [M + H] | Retention Time (min) | LC/MS Condition | Stereo-Chemistry |
|---|---|---|---|---|---|
| I-84 | 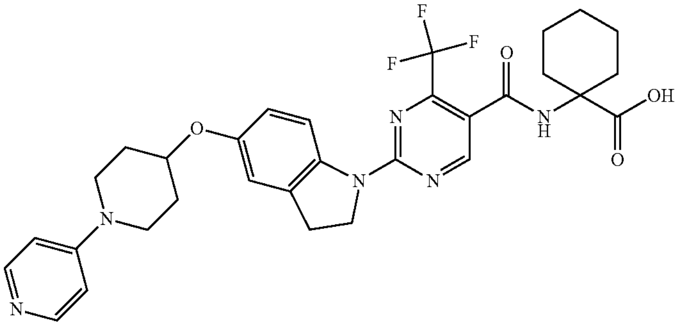 [SMILES: O=C(NC1(C(=O)O)CCCCC1)c1cnc(N2CCc3cc(OC4CCN(c5ccncc5)CC4)ccc32)nc1C(F)(F)F] | 611 | 2.02 | 1 | |
| I-85 | 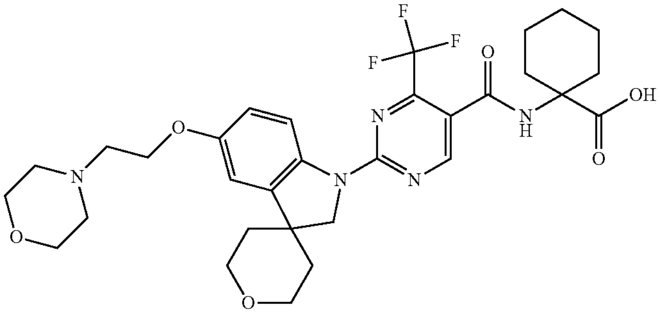 [SMILES: O=C(NC1(C(=O)O)CCCCC1)c1cnc(N2CC3(CCOCC3)c3cc(OCCN4CCOCC4)ccc32)nc1C(F)(F)F] | 634 | 1.85 | 3 | |
| I-86 | 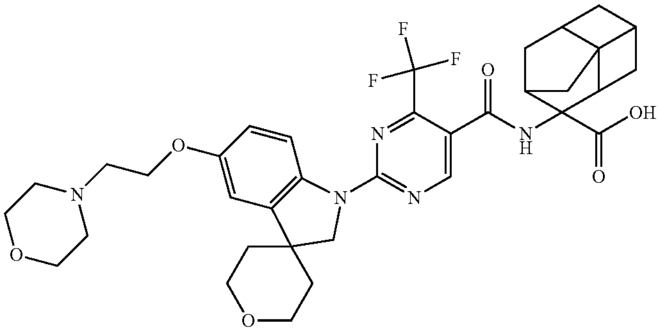 | 686 | 2.16 | 1 | |
| I-87 | 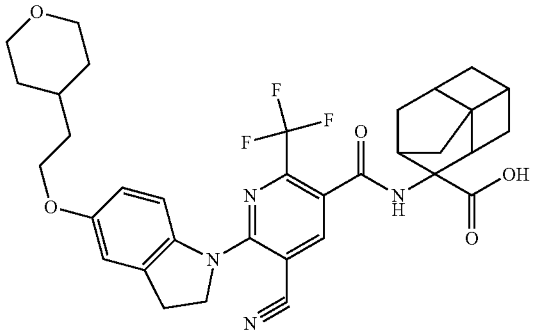 [SMILES: N#Cc1cc(C(=O)NC2(C(=O)O)C3CC4CC5CC2C45C3)c(C(F)(F)F)nc1N1CCc2cc(OCCC3CCOCC3)ccc21] | 639 | 2.85 | 3 | |

TABLE 13-continued
| Compound No. | Chemical Structure | [M + H] | Retention Time (min) | LC/MS Condition | Stereo-Chemistry |
|---|---|---|---|---|---|
| I-88 | 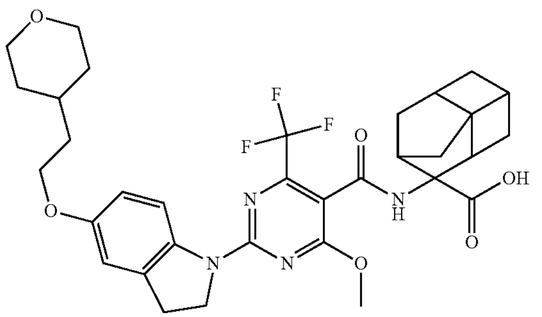 [SMILES: COc1nc(N2CCc3cc(OCCC4CCOCC4)ccc32)nc(C(F)(F)F)c1C(=O)NC1(C(=O)O)C2CC3CC4CC1C34C2] | 645 | 2.93 | 3 | |
| I-89 | 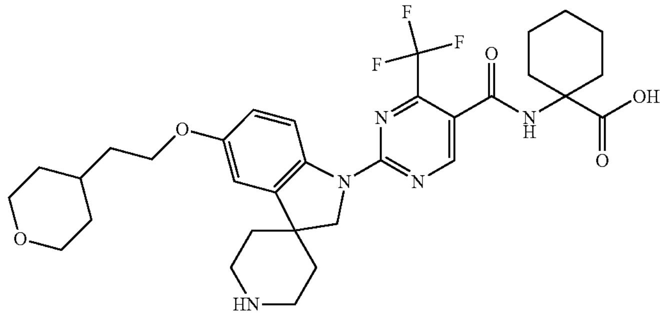 [SMILES: O=C(NC1(C(=O)O)CCCCC1)c1cnc(N2CC3(CCNCC3)c3cc(OCCC4CCOCC4)ccc32)nc1C(F)(F)F] | 632 | 2.13 | 1 | |
TABLE 14
| Compound No. | Chemical Structure | [M + H] | Retention Time (min) | LC/MS Condition | Stereo-Chemistry |
|---|---|---|---|---|---|
| I-90 | 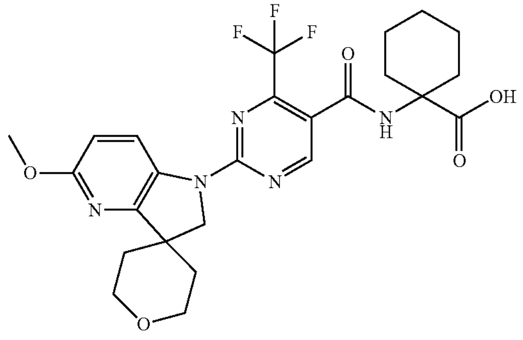 [SMILES: COc1ccc2c(n1)C1(CCOCC1)CN2c1ncc(C(=O)NC2(C(=O)O)CCCCC2)c(C(F)(F)F)n1] | 536 | 2.39 | 3 | |
| I-91 | 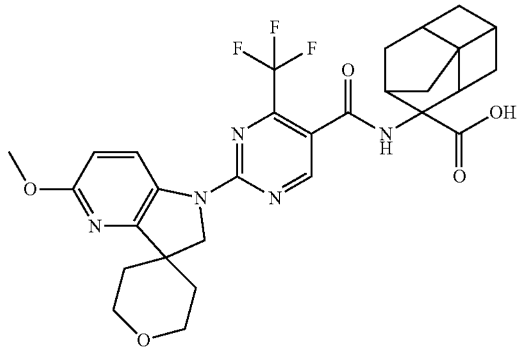 [SMILES: COc1ccc2c(n1)C1(CCOCC1)CN2c1ncc(C(=O)NC2(C(=O)O)C3CC4CC5CC2C45C3)c(C(F)(F)F)n1] | 588 | 2.70 | 3 | |

TABLE 14-continued
| Compound No. | Chemical Structure | [M + H] | Retention Time (min) | LC/MS Condition | Stereo-Chemistry |
|---|---|---|---|---|---|
| I-92 | 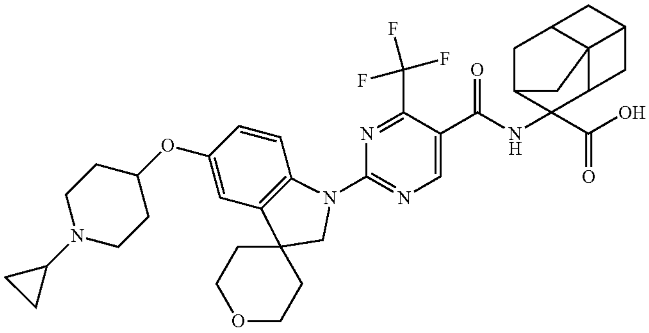 [SMILES: O=C(NC1(C(=O)O)C2CC3CC4CC1C34C2)c1cnc(N2CC3(CCOCC3)c3cc(OC4CCN(C5CC5)CC4)ccc32)nc1C(F)(F)F] | 696 | 2.39 | 1 | |
| I-93 | 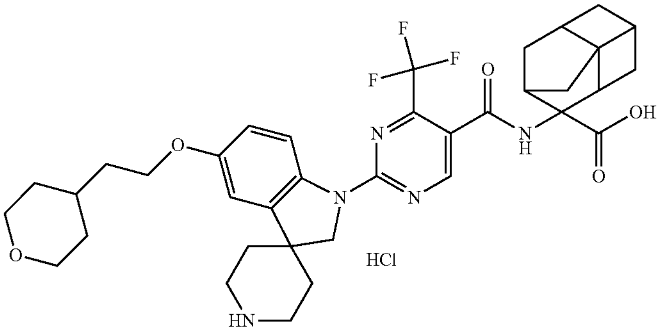 [SMILES: O=C(NC1(C(=O)O)C2CC3CC4CC1C34C2)c1cnc(N2CC3(CCNCC3)c3cc(OCCC4CCOCC4)ccc32)nc1C(F)(F)F ; Cl] HCl | 684 | 2.63 | 1 | |
| I-94 | 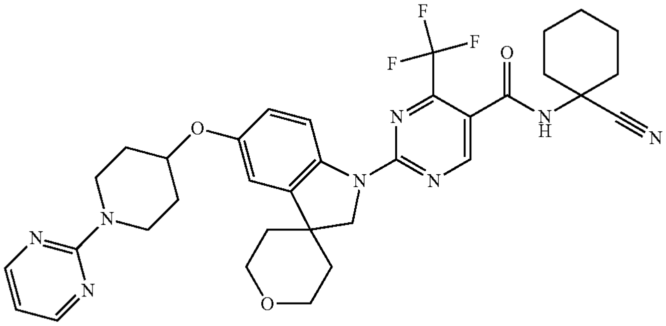 [SMILES: N#CC1(NC(=O)c2cnc(N3CC4(CCOCC4)c4cc(OC5CCN(c6ncccn6)CC5)ccc43)nc2C(F)(F)F)CCCCC1] | 663 | 2.76 | 1 | |
| I-95 | 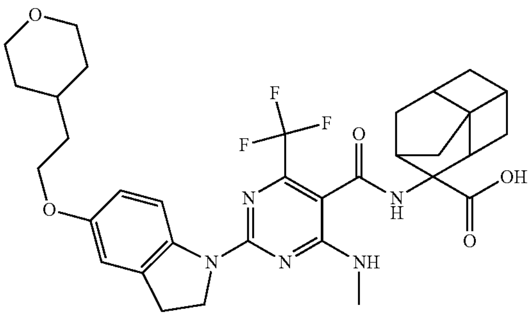 [SMILES: CNc1nc(N2CCc3cc(OCCC4CCOCC4)ccc32)nc(C(F)(F)F)c1C(=O)NC1(C(=O)O)C2CC3CC4CC1C34C2] | 644 | 3.05 | 3 | |

TABLE 15
| Compound No. | Chemical Structure | [M + H] | Retention Time (min) | LC/MS Condition | Stereo-Chemistry |
|---|---|---|---|---|---|
| I-96 | 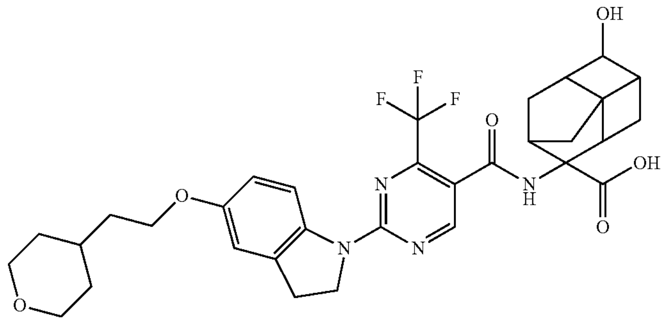 [SMILES: O=C(NC1(C(=O)O)C2CC3C(O)C4CC1C34C2)c1cnc(N2CCc3cc(OCCC4CCOCC4)ccc32)nc1C(F)(F)F] | 631 | 2.25 | 1 | b |
| I-97 | 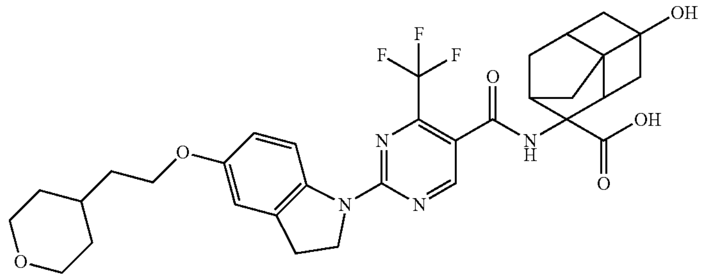 [SMILES: O=C(NC1(C(=O)O)C2CC3CC4(O)CC1C34C2)c1cnc(N2CCc3cc(OCCC4CCOCC4)ccc32)nc1C(F)(F)F] | 631 | 2.31 | 1 | b |
| I-98 | 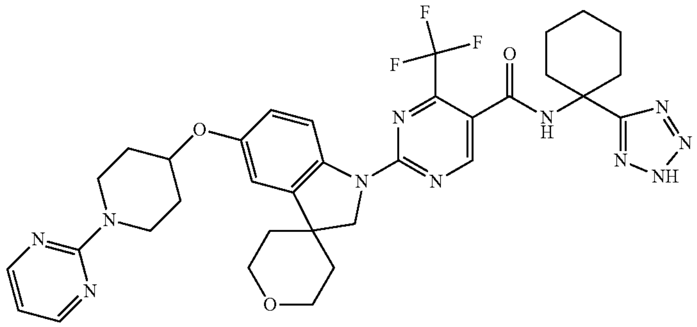 [SMILES: O=C(NC1(c2nn[nH]n2)CCCCC1)c1cnc(N2CC3(CCOCC3)c3cc(OC4CCN(c5ncccn5)CC4)ccc32)nc1C(F)(F)F] | 706 | 2.43 | 1 | |
| I-99 | 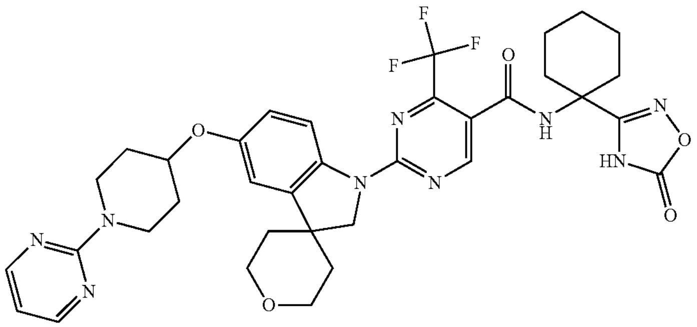 [SMILES: O=C(NC1(c2noc(=O)[nH]2)CCCCC1)c1cnc(N2CC3(CCOCC3)c3cc(OC4CCN(c5ncccn5)CC4)ccc32)nc1C(F)(F)F] | 722 | 2.59 | 1 | |

TABLE 15-continued
| Compound No. | Chemical Structure | [M + H] | Retention Time (min) | LC/MS Condition | Stereo-Chemistry |
|---|---|---|---|---|---|
| I-100 | 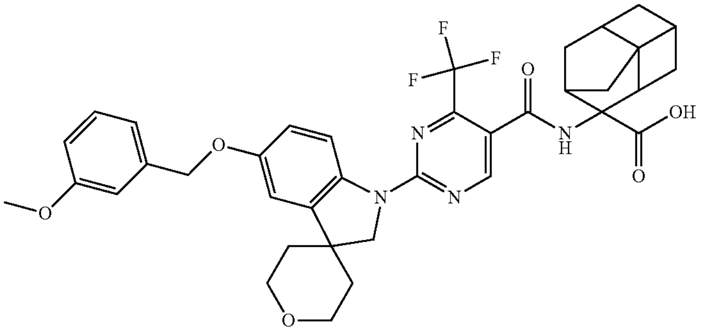 [SMILES: COc1cccc(COc2ccc3c(c2)C2(CCOCC2)CN3c2ncc(C(=O)NC3(C(=O)O)C4CC5CC6CC3C56C4)c(C(F)(F)F)n2)c1] | 698 | 2.98 | 1 | |
| I-101 | 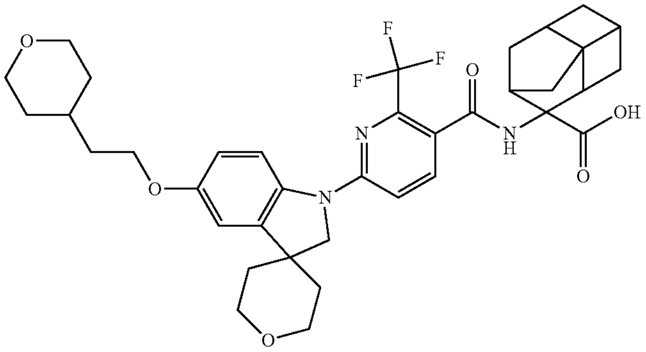 | 684 | 2.81 | 3 | |
TABLE 16
| Compound No. | Chemical Structure | [M + H] | Retention Time (min) | LC/MS Condition | Stereo-Chemistry |
|---|---|---|---|---|---|
| I-102 | 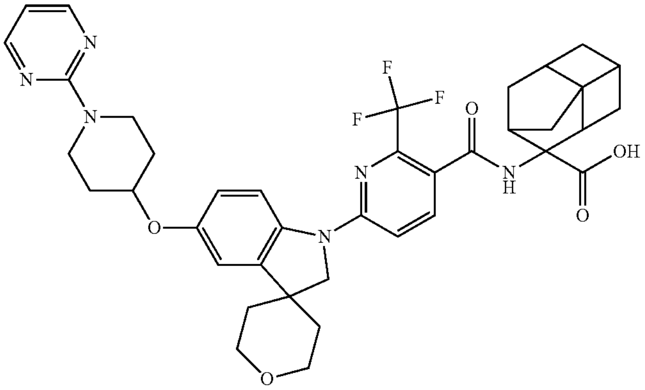 [SMILES: O=C(NC1(C(=O)O)C2CC3CC4CC1C34C2)c1ccc(N2CC3(CCOCC3)c3cc(OC4CCN(c5ncccn5)CC4)ccc32)nc1C(F)(F)F] | 733 | 2.83 | 3 | |

TABLE 16-continued
| Compound No. | Chemical Structure | [M + H] | Retention Time (min) | LC/MS Condition | Stereo-Chemistry |
|---|---|---|---|---|---|
| I-103 | 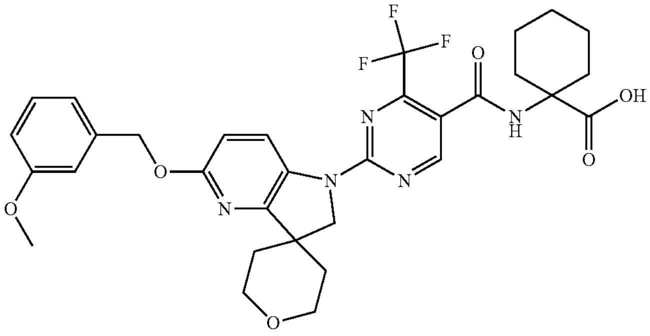 [SMILES: COc1cccc(COc2ccc3c(n2)C2(CCOCC2)CN3c2ncc(C(=O)NC3(C(=O)O)CCCCC3)c(C(F)(F)F)n2)c1] | 642 | 2.78 | 3 | |
| I-104 | 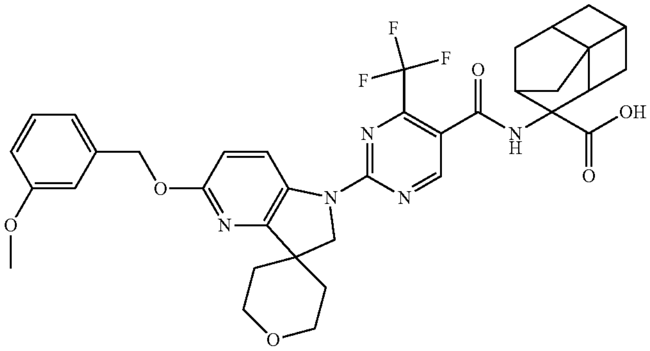 [SMILES: COc1cccc(COc2ccc3c(n2)C2(CCOCC2)CN3c2ncc(C(=O)NC3(C(=O)O)C4CC5CC6CC3C56C4)c(C(F)(F)F)n2)c1] | 694 | 3.05 | 3 | |
| I-105 | 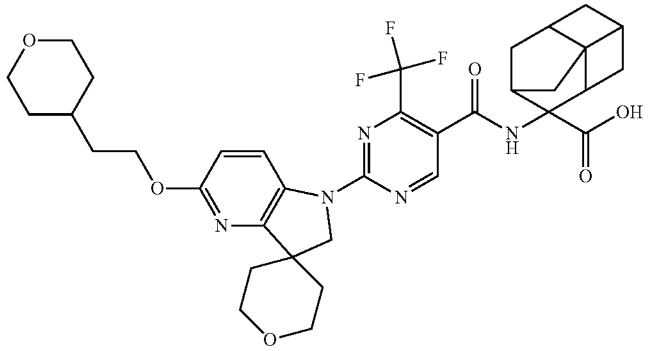 [SMILES: O=C(NC1(C(=O)O)C2CC3CC4CC1C34C2)c1cnc(N2CC3(CCOCC3)c3nc(OCCC4CCOCC4)ccc32)nc1C(F)(F)F] | 686 | 2.86 | 3 | |
| I-106 | 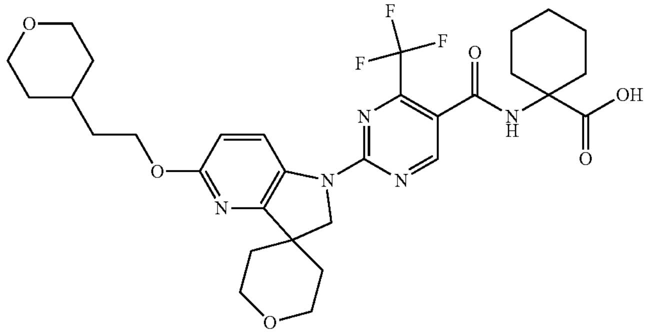 [SMILES: O=C(NC1(C(=O)O)CCCCC1)c1cnc(N2CC3(CCOCC3)c3nc(OCCC4CCOCC4)ccc32)nc1C(F)(F)F] | 634 | 2.58 | 3 | |

TABLE 16-continued
| Compound No. | Chemical Structure | [M + H] | Retention Time (min) | LC/MS Condition | Stereo-Chemistry |
|---|---|---|---|---|---|
| I-107 | 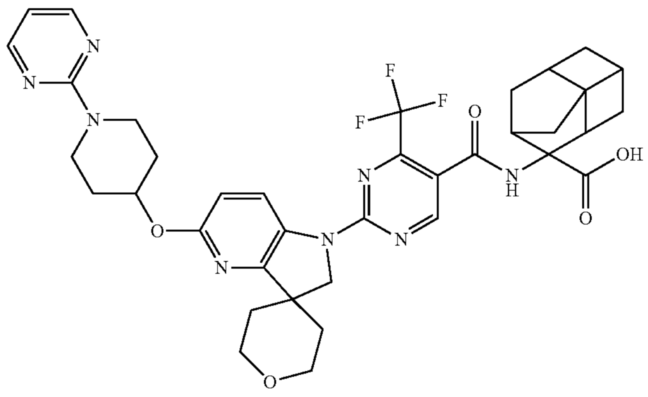 [SMILES: O=C(NC1(C(=O)O)C2CC3CC4CC1C34C2)c1cnc(N2CC3(CCOCC3)c3nc(OC4CCN(c5ncccn5)CC4)ccc32)nc1C(F)(F)F] | 735 | 2.94 | 3 | |
TABLE 17
| Compound No. | Chemical Structure | [M + H] | Retention Time (min) | LC/MS Condition | Stereo-Chemistry |
|---|---|---|---|---|---|
| I-108 | 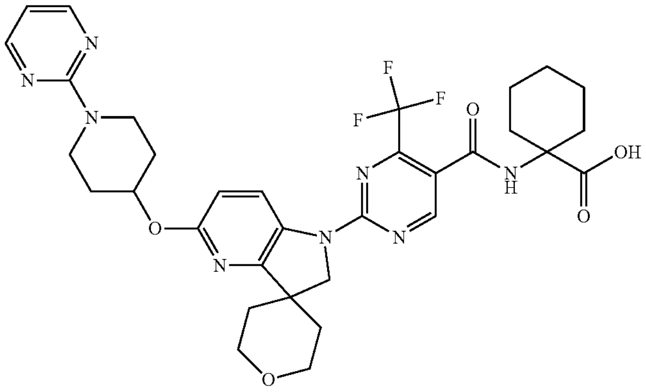 [SMILES: O=C(NC1(C(=O)O)CCCCC1)c1cnc(N2CC3(CCOCC3)c3nc(OC4CCN(c5ncccn5)CC4)ccc32)nc1C(F)(F)F] | 683 | 2.63 | 3 | |
| I-109 | 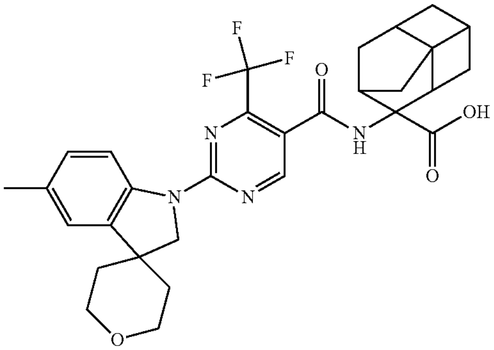 [SMILES: Cc1ccc2c(c1)C1(CCOCC1)CN2c1ncc(C(=O)NC2(C(=O)O)C3CC4CC5CC2C45C3)c(C(F)(F)F)n1] | 571 | 2.82 | 3 | |

TABLE 17-continued
| Compound No. | Chemical Structure | [M + H] | Retention Time (min) | LC/MS Condition | Stereo-Chemistry |
|---|---|---|---|---|---|
| I-110 | 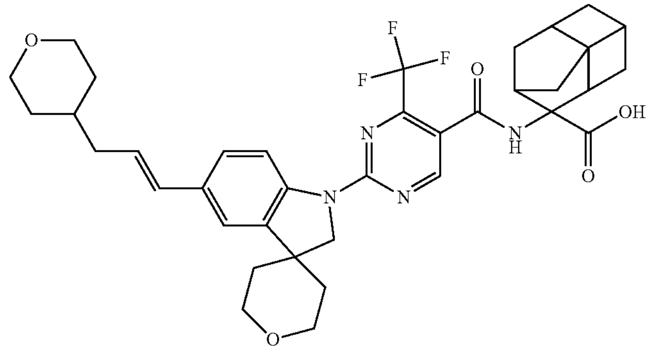 [SMILES: O=C(NC1(C(=O)O)C2CC3CC4CC1C34C2)c1cnc(N2CC3(CCOCC3)c3cc(/C=C/CC4CCOCC4)ccc32)nc1C(F)(F)F] | 681 | 2.99 | 3 | |
| I-111 | 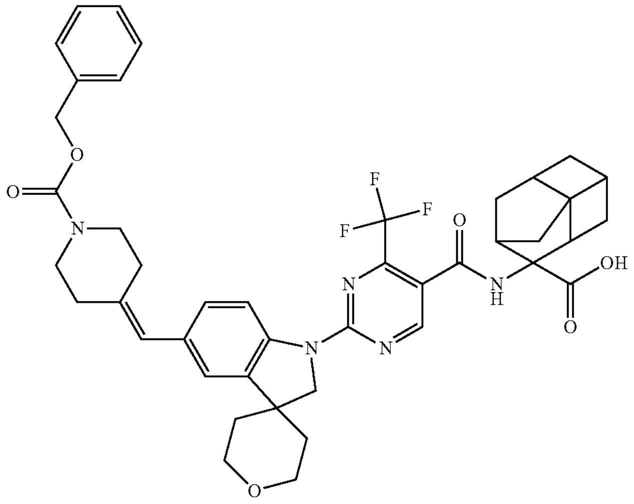 [SMILES: O=C(NC1(C(=O)O)C2CC3CC4CC1C34C2)c1cnc(N2CC3(CCOCC3)c3cc(C=C4CCN(C(=O)OCc5ccccc5)CC4)ccc32)nc1C(F)(F)F] | 786 | 3.18 | 3 | |
| I-112 | 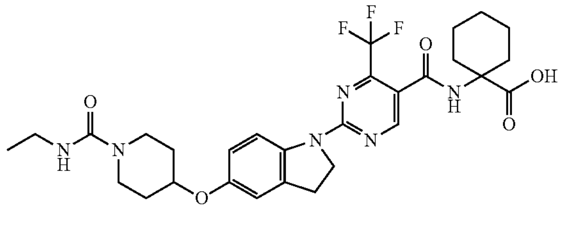 [SMILES: CCNC(=O)N1CCC(Oc2ccc3c(c2)CCN3c2ncc(C(=O)NC3(C(=O)O)CCCCC3)c(C(F)(F)F)n2)CC1] | 605 | 1.59 | 3 | |
| I-113 | 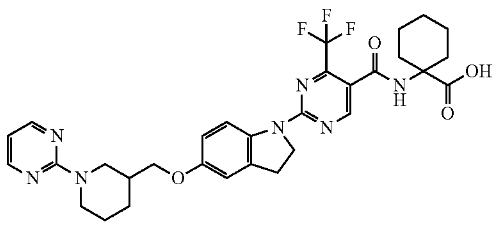 [SMILES: O=C(NC1(C(=O)O)CCCCC1)c1cnc(N2CCc3cc(OCC4CCCN(c5ncccn5)C4)ccc32)nc1C(F)(F)F] | 628 | 2.02 | 3 | a |

TABLE 18
| Compound No. | Chemical Structure | [M + H] | Retention Time (min) | LC/MS Condition | Stereo-Chemistry |
|---|---|---|---|---|---|
| I-114 | 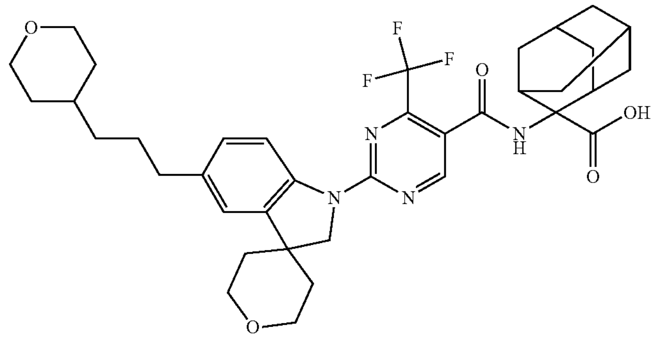 [SMILES: O=C(NC1(C(=O)O)C2CC3CC(C2)CC1C3)c1cnc(N2CC3(CCOCC3)c3cc(CCCC4CCOCC4)ccc32)nc1C(F)(F)F] | 683 | 3.09 | 3 | |
| I-115 | 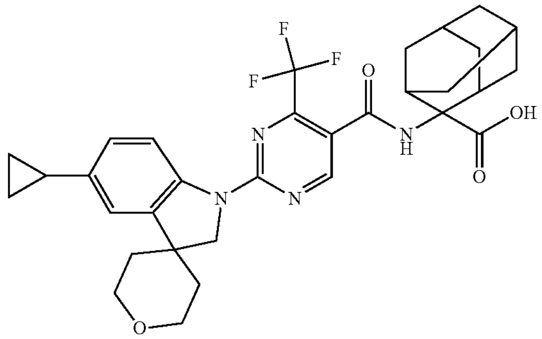 [SMILES: O=C(NC1(C(=O)O)C2CC3CC(C2)CC1C3)c1cnc(N2CC3(CCOCC3)c3cc(C4CC4)ccc32)nc1C(F)(F)F] | 597 | 2.93 | 3 | |
| I-116 | 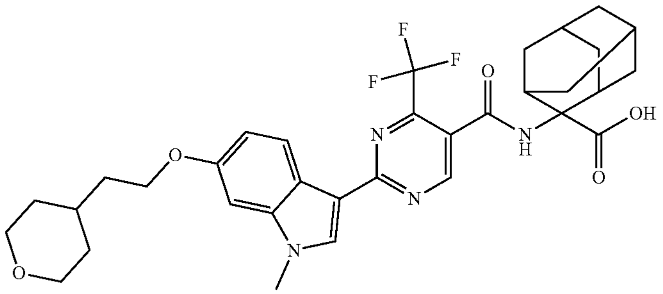 [SMILES: Cn1cc(-c2ncc(C(=O)NC3(C(=O)O)C4CC5CC(C4)CC3C5)c(C(F)(F)F)n2)c2ccc(OCCC3CCOCC3)cc21] | 627 | 2.82 | 1 | |
| I-117 | 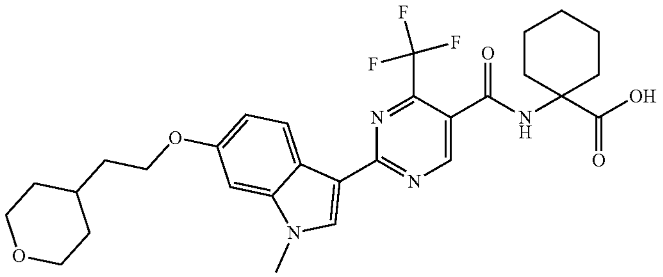 [SMILES: Cn1cc(-c2ncc(C(=O)NC3(C(=O)O)CCCCC3)c(C(F)(F)F)n2)c2ccc(OCCC3CCOCC3)cc21] | 575 | 2.54 | 1 | |

TABLE 18-continued
| Compound No. | Chemical Structure | [M + H] | Retention Time (min) | LC/MS Condition | Stereo-Chemistry |
|---|---|---|---|---|---|
| I-118 | 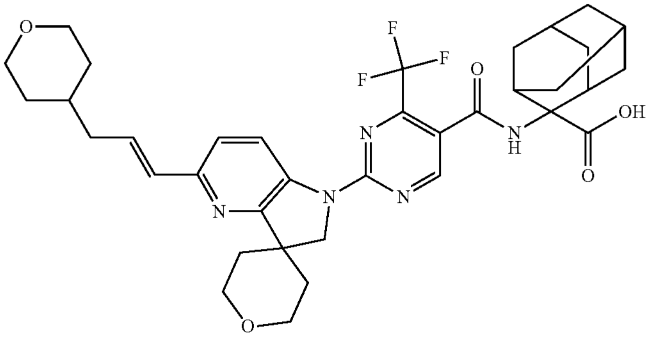 [SMILES: O=C(NC1(C(=O)O)C2CC3CC(C2)CC1C3)c1cnc(N2CC3(CCOCC3)c3nc(/C=C/CC4CCOCC4)ccc32)nc1C(F)(F)F] | 684 | 2.80 | 3 | |
| I-119 | 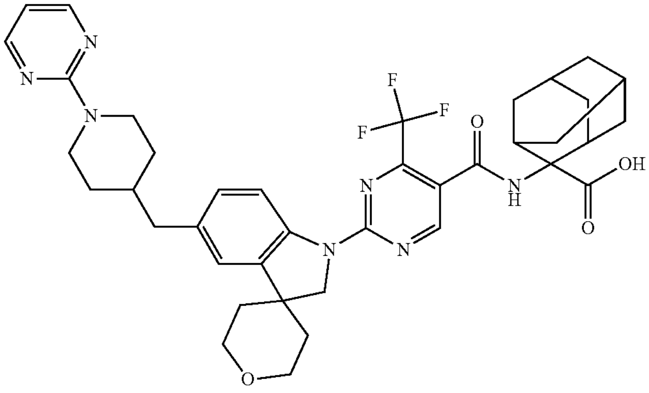 [SMILES: O=C(NC1(C(=O)O)C2CC3CC(C2)CC1C3)c1cnc(N2CC3(CCOCC3)c3cc(CC4CCN(c5ncccn5)CC4)ccc32)nc1C(F)(F)F] | 732 | 3.03 | 3 | |
TABLE 19
| Compound No. | Chemical Structure | [M + H] | Retention Time (min) | LC/MS Condition | Stereo-Chemistry |
|---|---|---|---|---|---|
| I-120 | 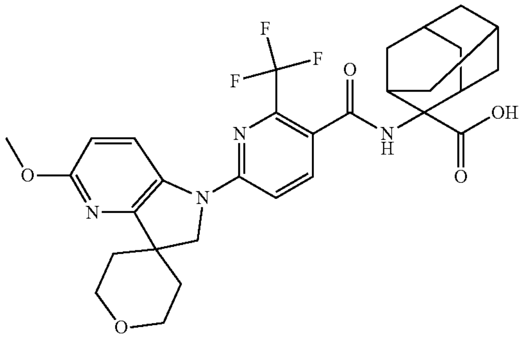 [SMILES: COc1ccc2c(n1)C1(CCOCC1)CN2c1ccc(C(=O)NC2(C(=O)O)C3CC4CC(C3)CC2C4)c(C(F)(F)F)n1] | 587 | 2.66 | 3 | |

TABLE 19-continued
| Compound No. | Chemical Structure | [M + H] | Retention Time (min) | LC/MS Condition | Stereo-Chemistry |
|---|---|---|---|---|---|
| I-121 | 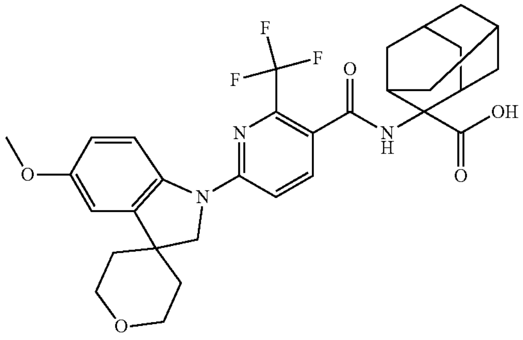 [SMILES: COc1ccc2c(c1)C1(CCOCC1)CN2c1ccc(C(=O)NC2(C(=O)O)C3CC4CC(C3)CC2C4)c(C(F)(F)F)n1] | 586 | 2.54 | 3 | |
| I-122 | 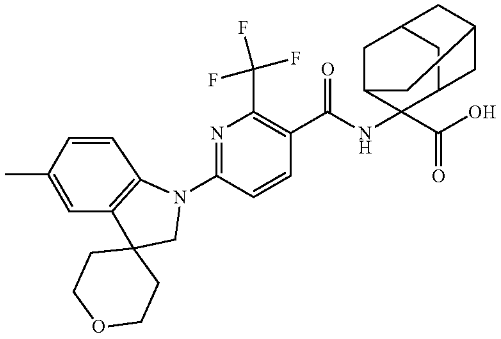 [SMILES: Cc1ccc2c(c1)C1(CCOCC1)CN2c1ccc(C(=O)NC2(C(=O)O)C3CC4CC(C3)CC2C4)c(C(F)(F)F)n1] | 570 | 2.81 | 3 | |
| I-123 | 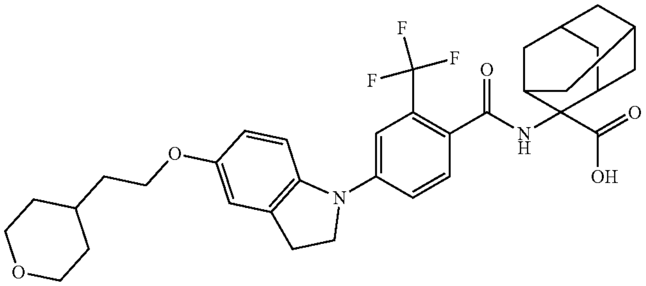 [SMILES: O=C(NC1(C(=O)O)C2CC3CC(C2)CC1C3)c1ccc(N2CCc3cc(OCCC4CCOCC4)ccc32)cc1C(F)(F)F] | 613 | 2.90 | 2 | |
| I-124 | 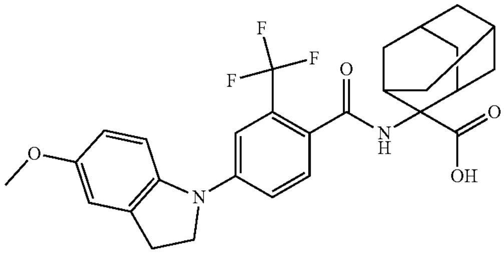 [SMILES: COc1ccc2c(c1)CCN2c1ccc(C(=O)NC2(C(=O)O)C3CC4CC(C3)CC2C4)c(C(F)(F)F)c1] | 515 | 2.71 | 2 | |
| I-125 | 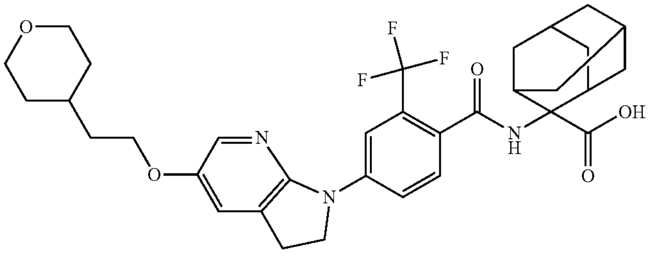 [SMILES: O=C(NC1(C(=O)O)C2CC3CC(C2)CC1C3)c1ccc(N2CCc3cc(OCCC4CCOCC4)cnc32)cc1C(F)(F)F] | 614 | 2.81 | 3 | |

TABLE 19-continued
| Compound No. | Chemical Structure | [M + H] | Retention Time (min) | LC/MS Condition | Stereo-Chemistry |
|---|---|---|---|---|---|
| I-126 | 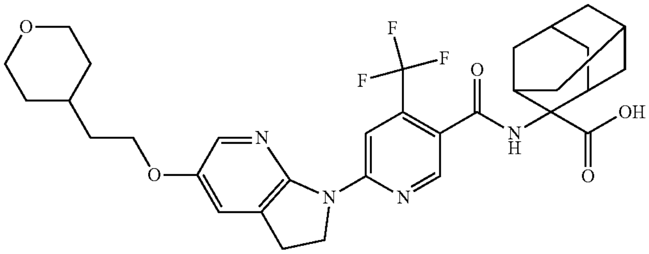 [SMILES: O=C(NC1(C(=O)O)C2CC3CC(C2)CC1C3)c1cnc(N2CCc3cc(OCCC4CCOCC4)cnc32)cc1C(F)(F)F] | 615 | 2.52 | 3 | |
TABLE 20
| Compound No. | Chemical Structure | [M + H] | Retention Time (min) | LC/MS Condition | Stereo-Chemistry |
|---|---|---|---|---|---|
| I-127 | 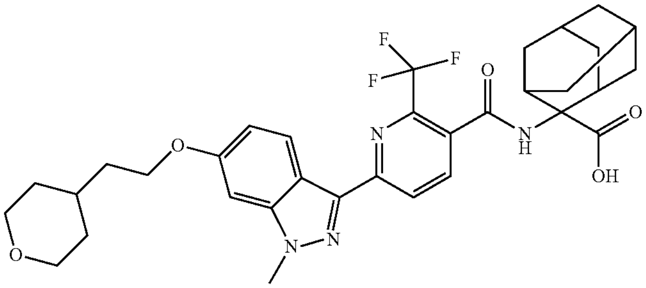 [SMILES: Cn1nc(-c2ccc(C(=O)NC3(C(=O)O)C4CC5CC(C4)CC3C5)c(C(F)(F)F)n2)c2ccc(OCCC3CCOCC3)cc21] | 627 | 2.89 | 2 | |
| I-128 | 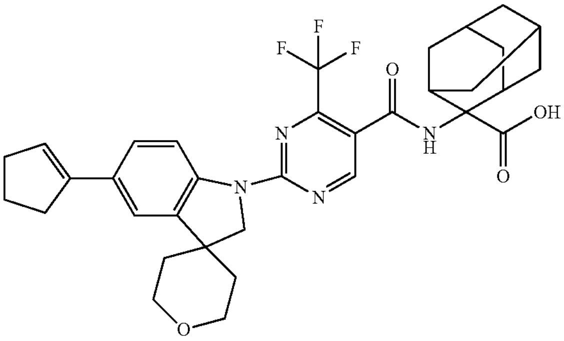 [SMILES: O=C(NC1(C(=O)O)C2CC3CC(C2)CC1C3)c1cnc(N2CC3(CCOCC3)c3cc(C4=CCCC4)ccc32)nc1C(F)(F)F] | 623 | 3.22 | 1 | |
| I-129 | 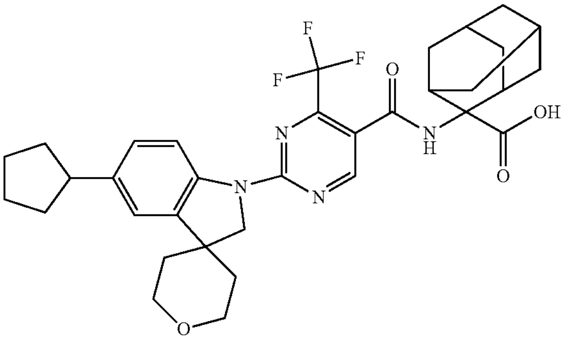 [SMILES: O=C(NC1(C(=O)O)C2CC3CC(C2)CC1C3)c1cnc(N2CC3(CCOCC3)c3cc(C4CCCC4)ccc32)nc1C(F)(F)F] | 625 | 3.26 | 1 | |

TABLE 20-continued
| Compound No. | Chemical Structure | [M + H] | Retention Time (min) | LC/MS Condition | Stereo-Chemistry |
|---|---|---|---|---|---|
| I-130 | 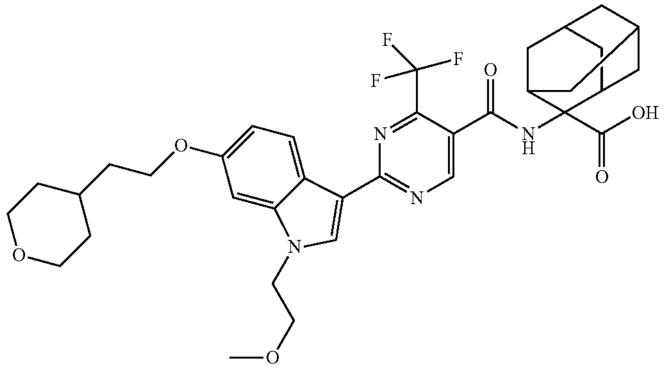 [SMILES: COCCn1cc(-c2ncc(C(=O)NC3(C(=O)O)C4CC5CC(C4)CC3C5)c(C(F)(F)F)n2)c2ccc(OCCC3CCOCC3)cc21] | 671 | 2.81 | 1 | |
| I-131 | 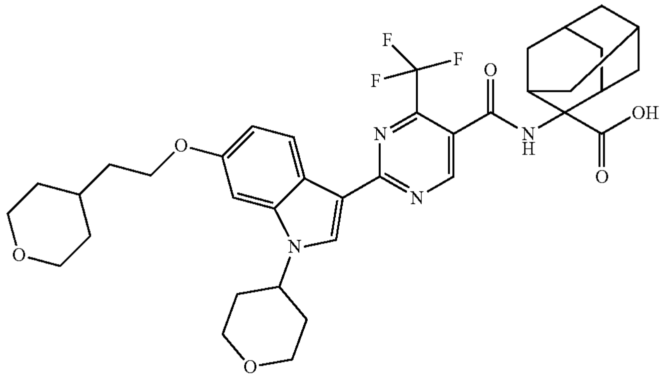 [SMILES: O=C(NC1(C(=O)O)C2CC3CC(C2)CC1C3)c1cnc(-c2cn(C3CCOCC3)c3cc(OCCC4CCOCC4)ccc23)nc1C(F)(F)F] | 697 | 2.82 | 1 | |
| I-132 | 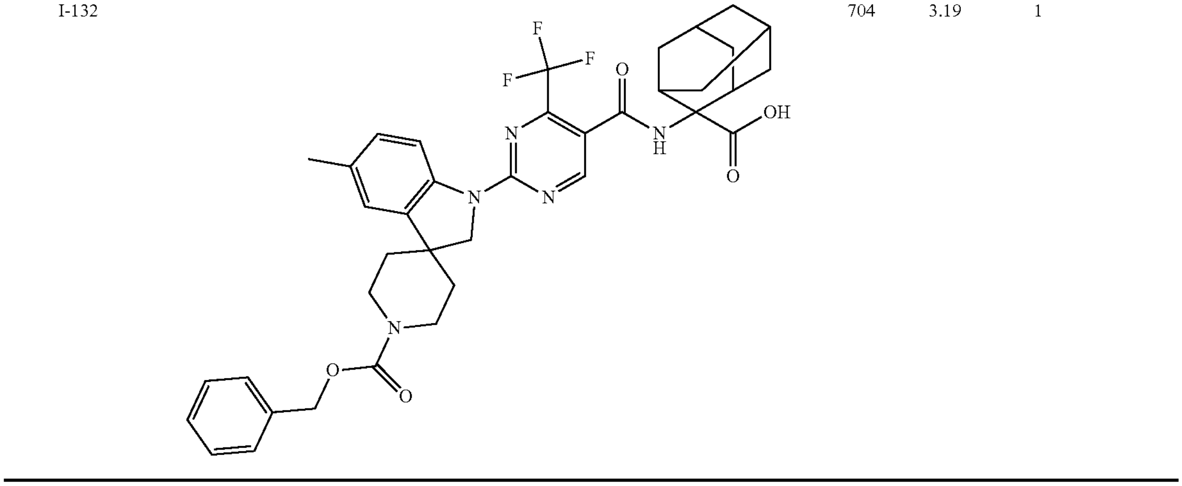 | 704 | 3.19 | 1 | |

TABLE 21
| Compound No. | Chemical Structure | [M + H] | Retention Time (min) | LC/MS Condition | Stereo-Chemistry |
|---|---|---|---|---|---|
| I-133 | 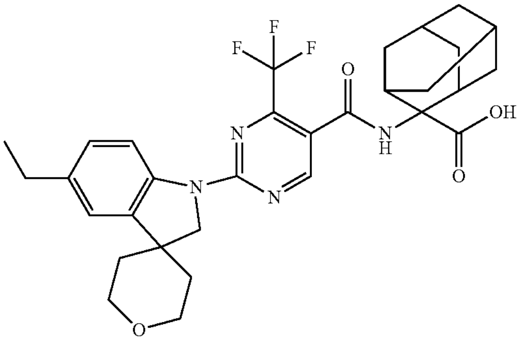 [SMILES: CCc1ccc2c(c1)C1(CCOCC1)CN2c1ncc(C(=O)NC2(C(=O)O)C3CC4CC(C3)CC2C4)c(C(F)(F)F)n1] | 585 | 2.94 | 1 | |
| I-134 | 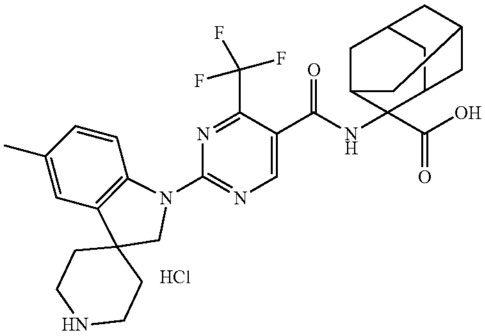 [SMILES: Cc1ccc2c(c1)C1(CCNCC1)CN2c1ncc(C(=O)NC2(C(=O)O)C3CC4CC(C3)CC2C4)c(C(F)(F)F)n1 ; Cl] HCl | 570 | 2.15 | 5 | |
| I-135 | 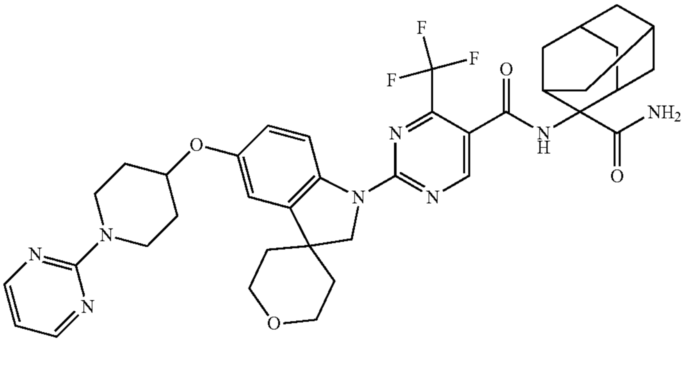 [SMILES: NC(=O)C1(NC(=O)c2cnc(N3CC4(CCOCC4)c4cc(OC5CCN(c6ncccn6)CC5)ccc43)nc2C(F)(F)F)C2CC3CC(C2)CC1C3] | 733 | 2.77 | 1 | |
| I-136 | 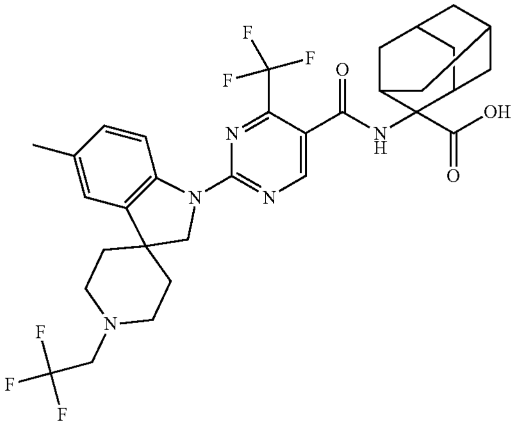 [SMILES: Cc1ccc2c(c1)C1(CCN(CC(F)(F)F)CC1)CN2c1ncc(C(=O)NC2(C(=O)O)C3CC4CC(C3)CC2C4)c(C(F)(F)F)n1] | 652 | 3.17 | 1 | |

TABLE 21-continued
| Compound No. | Chemical Structure | [M + H] | Retention Time (min) | LC/MS Condition | Stereo-Chemistry |
|---|---|---|---|---|---|
| I-137 | 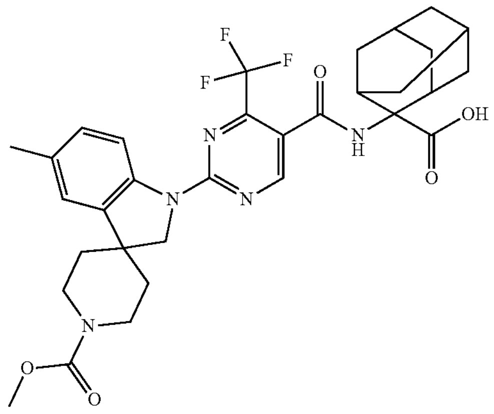 [SMILES: COC(=O)N1CCC2(CC1)CN(c1ncc(C(=O)NC3(C(=O)O)C4CC5CC(C4)CC3C5)c(C(F)(F)F)n1)c1ccc(C)cc12] | 626 | 2.86 | 1 | |
| I-138 | 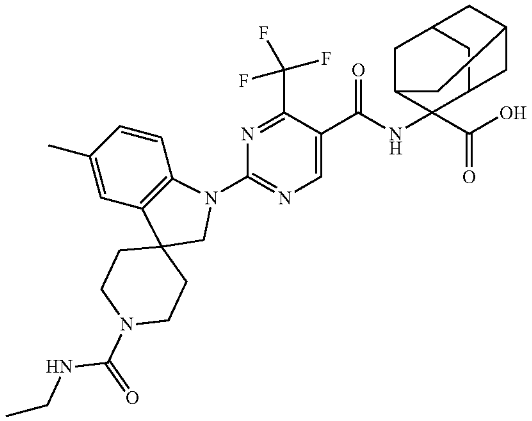 [SMILES: CCNC(=O)N1CCC2(CC1)CN(c1ncc(C(=O)NC3(C(=O)O)C4CC5CC(C4)CC3C5)c(C(F)(F)F)n1)c1ccc(C)cc12] | 641 | 2.60 | 1 | |
TABLE 22
| Compound No. | Chemical Structure | [M + H] | Retention Time (min) | LC/MS Condition | Stereo-Chemistry |
|---|---|---|---|---|---|
| I-139 | 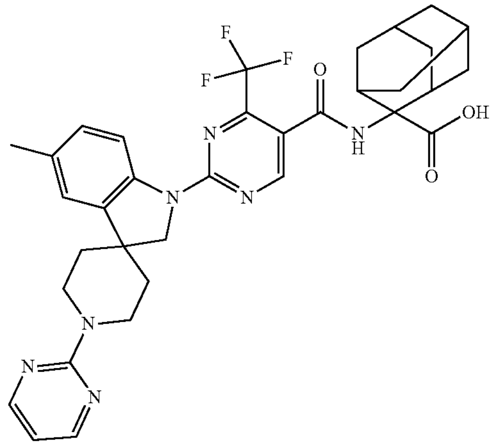 [SMILES: Cc1ccc2c(c1)C1(CCN(c3ncccn3)CC1)CN2c1ncc(C(=O)NC2(C(=O)O)C3CC4CC(C3)CC2C4)c(C(F)(F)F)n1] | 648 | 3.09 | 1 | |

TABLE 22-continued
| Compound No. | Chemical Structure | [M + H] | Retention Time (min) | LC/MS Condition | Stereo-Chemistry |
|---|---|---|---|---|---|
| I-140 | 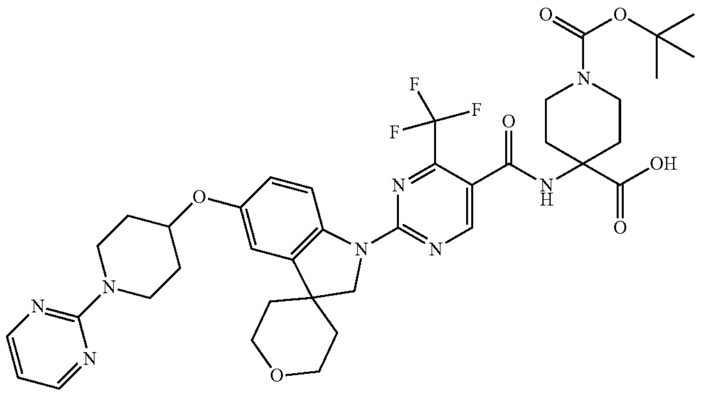 [SMILES: CC(C)(C)OC(=O)N1CCC(NC(=O)c2cnc(N3CC4(CCOCC4)c4cc(OC5CCN(c6ncccn6)CC5)ccc43)nc2C(F)(F)F)(C(=O)O)CC1] | 783 | 2.62 | 1 | |
| I-141 | 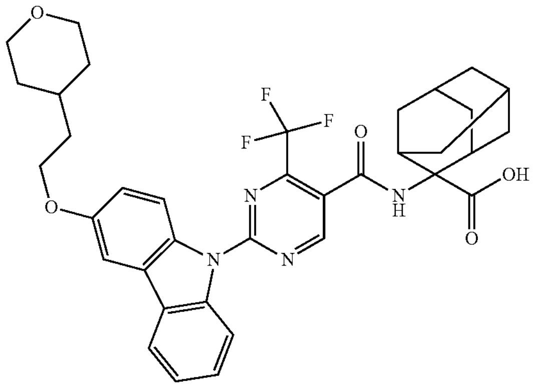 [SMILES: O=C(NC1(C(=O)O)C2CC3CC(C2)CC1C3)c1cnc(-n2c3ccccc3c3cc(OCCC4CCOCC4)ccc32)nc1C(F)(F)F] | 663 | 3.18 | 1 | |
| I-142 | 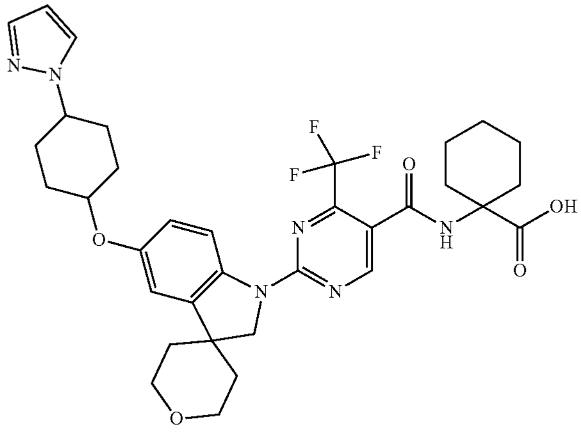 [SMILES: O=C(NC1(C(=O)O)CCCCC1)c1cnc(N2CC3(CCOCC3)c3cc(OC4CCC(n5cccn5)CC4)ccc32)nc1C(F)(F)F] | 569 | 2.47 | 1 | c |

TABLE 22-continued
| Compound No. | Chemical Structure | [M + H] | Retention Time (min) | LC/MS Condition | Stereo-Chemistry |
|---|---|---|---|---|---|
| I-143 | 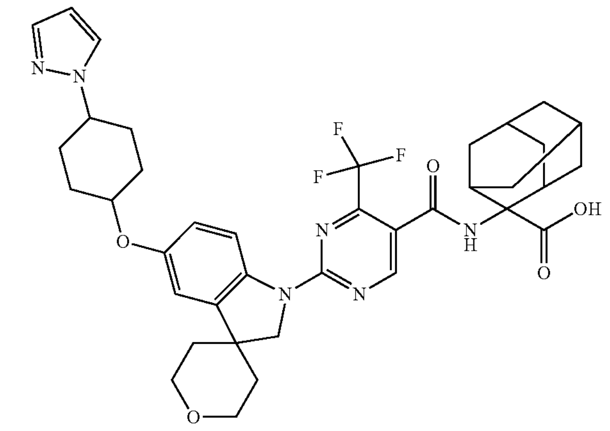 [SMILES: O=C(NC1(C(=O)O)C2CC3CC(C2)CC1C3)c1cnc(N2CC3(CCOCC3)c3cc(OC4CCC(n5cccn5)CC4)ccc32)nc1C(F)(F)F] | 721 | 2.75 | 1 | c |
TABLE 23
| Compound No. | Chemical Structure | [M + H] | Retention Time (min) | LC/MS Condition | Stereo-Chemistry |
|---|---|---|---|---|---|
| I-144 | HCl 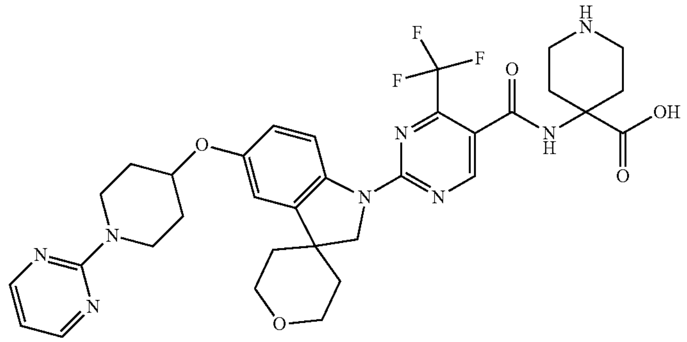 | 683 | 1.51 | 3 | |
| I-145 | 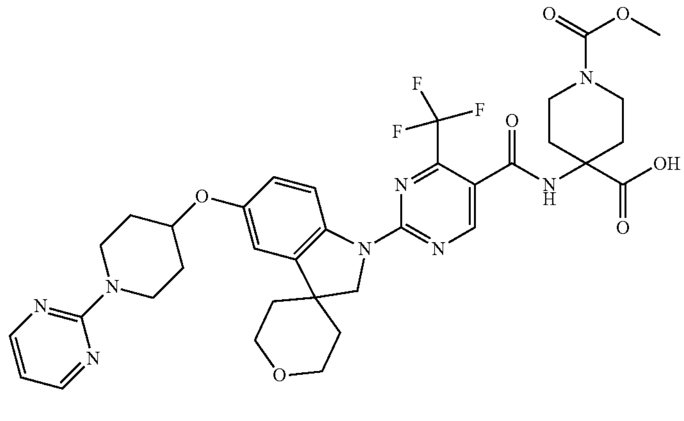 [SMILES: COC(=O)N1CCC(NC(=O)c2cnc(N3CC4(CCOCC4)c4cc(OC5CCN(c6ncccn6)CC5)ccc43)nc2C(F)(F)F)(C(=O)O)CC1] | 741 | 2.11 | 3 | |

TABLE 23-continued
| Compound No. | Chemical Structure | [M + H] | Retention Time (min) | LC/MS Condition | Stereo-Chemistry |
|---|---|---|---|---|---|
| I-146 | 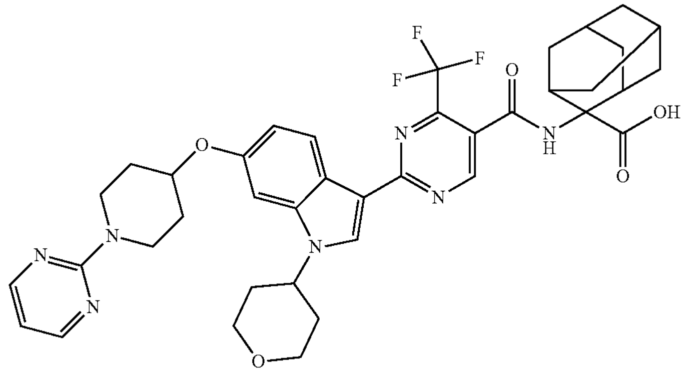 [SMILES: O=C(NC1(C(=O)O)C2CC3CC(C2)CC1C3)c1cnc(-c2cn(C3CCOCC3)c3cc(OC4CCN(c5ncccn5)CC4)ccc23)nc1C(F)(F)F] | 746 | 2.57 | 3 | |
| I-147 | 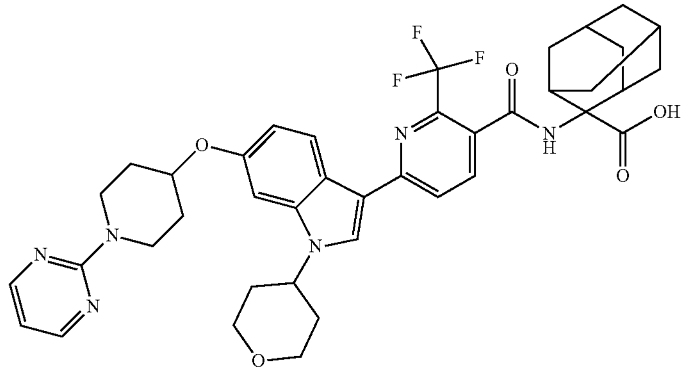 [SMILES: O=C(NC1(C(=O)O)C2CC3CC(C2)CC1C3)c1ccc(-c2cn(C3CCOCC3)c3cc(OC4CCN(c5ncccn5)CC4)ccc23)nc1C(F)(F)F] | 745 | 2.61 | 3 | |
| I-148 | 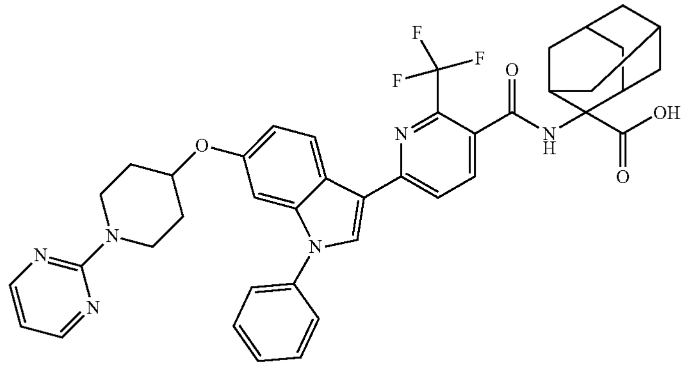 [SMILES: O=C(NC1(C(=O)O)C2CC3CC(C2)CC1C3)c1ccc(-c2cn(-c3ccccc3)c3cc(OC4CCN(c5ncccn5)CC4)ccc23)nc1C(F)(F)F] | 737 | 2.86 | 3 | |

TABLE 24
| Compound No. | Chemical Structure | [M + H] | Retention Time (min) | LC/MS Condition | Stereo-Chemistry |
|---|---|---|---|---|---|
| I-149 | 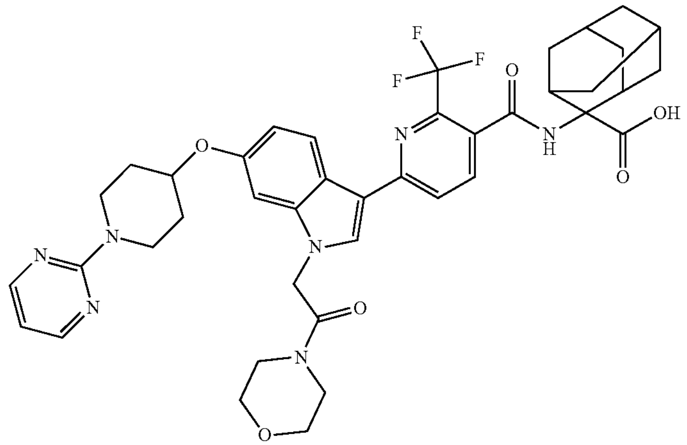 [SMILES: O=C(NC1(C(=O)O)C2CC3CC(C2)CC1C3)c1ccc(-c2cn(CC(=O)N3CCOCC3)c3cc(OC4CCN(c5ncccn5)CC4)ccc23)nc1C(F)(F)F] | 788 | 2.60 | 1 | |
| I-150 | 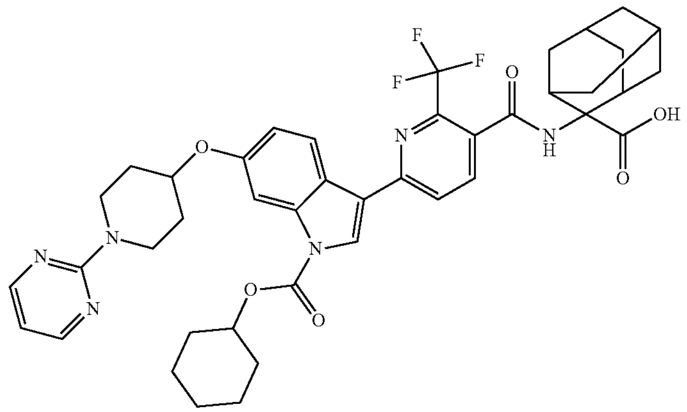 [SMILES: O=C(NC1(C(=O)O)C2CC3CC(C2)CC1C3)c1ccc(-c2cn(C(=O)OC3CCCCC3)c3cc(OC4CCN(c5ncccn5)CC4)ccc23)nc1C(F)(F)F] | 787 | 3.43 | 1 | |
| I-151 | 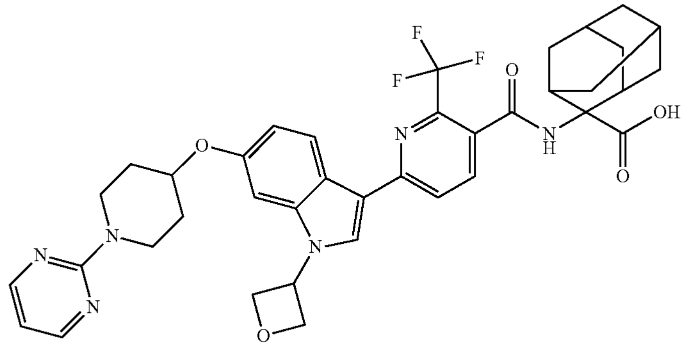 [SMILES: O=C(NC1(C(=O)O)C2CC3CC(C2)CC1C3)c1ccc(-c2cn(C3COC3)c3cc(OC4CCN(c5ncccn5)CC4)ccc23)nc1C(F)(F)F] | 717 | 2.76 | 1 | |

TABLE 24-continued
| Compound No. | Chemical Structure | [M + H] | Retention Time (min) | LC/MS Condition | Stereo-Chemistry |
|---|---|---|---|---|---|
| I-152 | 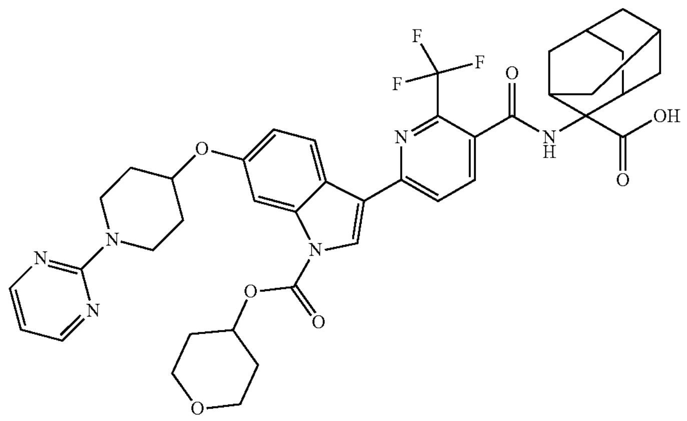 [SMILES: O=C(NC1(C(=O)O)C2CC3CC(C2)CC1C3)c1ccc(-c2cn(C(=O)OC3CCOCC3)c3cc(OC4CCN(c5ncccn5)CC4)ccc23)nc1C(F)(F)F] | 789 | 2.98 | 1 | |
| I-153 | 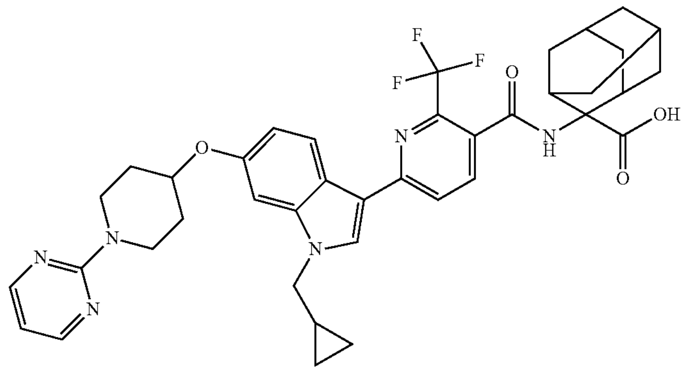 [SMILES: O=C(NC1(C(=O)O)C2CC3CC(C2)CC1C3)c1ccc(-c2cn(CC3CC3)c3cc(OC4CCN(c5ncccn5)CC4)ccc23)nc1C(F)(F)F] | 715 | 3.03 | 1 | |
TABLE 25
| Compound No. | Chemical Structure | [M + H] | Retention Time (min) | LC/MS Condition | Stereo-Chemistry |
|---|---|---|---|---|---|
| I-154 | 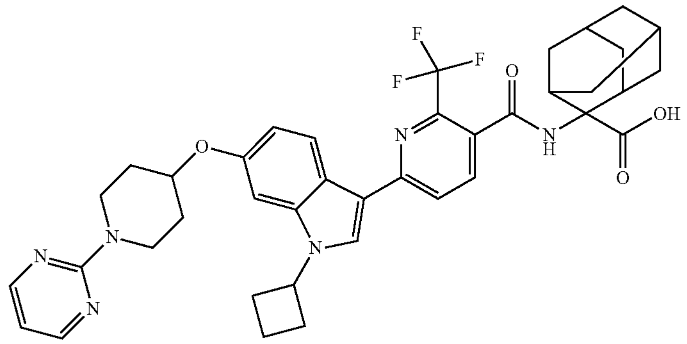 [SMILES: O=C(NC1(C(=O)O)C2CC3CC(C2)CC1C3)c1ccc(-c2cn(C3CCC3)c3cc(OC4CCN(c5ncccn5)CC4)ccc23)nc1C(F)(F)F] | 715 | 3.10 | 1 | |

TABLE 25-continued
| Compound No. | Chemical Structure | [M + H] | Retention Time (min) | LC/MS Condition | Stereo-Chemistry |
|---|---|---|---|---|---|
| I-155 | 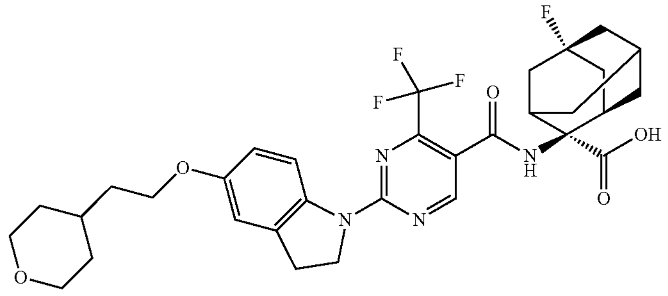 [SMILES: O=C(N[C@@]1(C(=O)O)C2CC3C[C@@H]1C[C@](F)(C3)C2)c1cnc(N2CCc3cc(OCCC4CCOCC4)ccc32)nc1C(F)(F)F] | 633 | 2.25 | 3 | |
| I-156 | 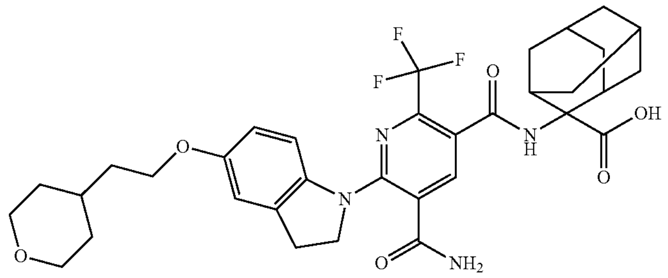 [SMILES: NC(=O)c1cc(C(=O)NC2(C(=O)O)C3CC4CC(C3)CC2C4)c(C(F)(F)F)nc1N1CCc2cc(OCCC3CCOCC3)ccc21] | 657 | 2.23 | 3 | |
| I-157 | 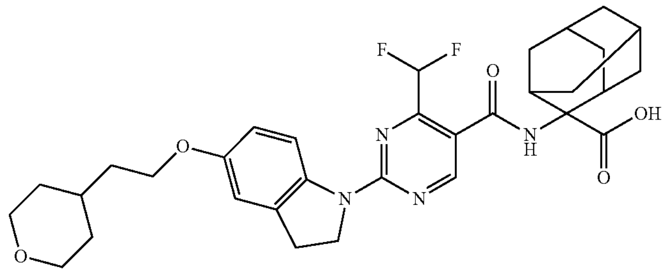 [SMILES: O=C(NC1(C(=O)O)C2CC3CC(C2)CC1C3)c1cnc(N2CCc3cc(OCCC4CCOCC4)ccc32)nc1C(F)F] | 597 | 2.58 | 3 | |
| I-158 | 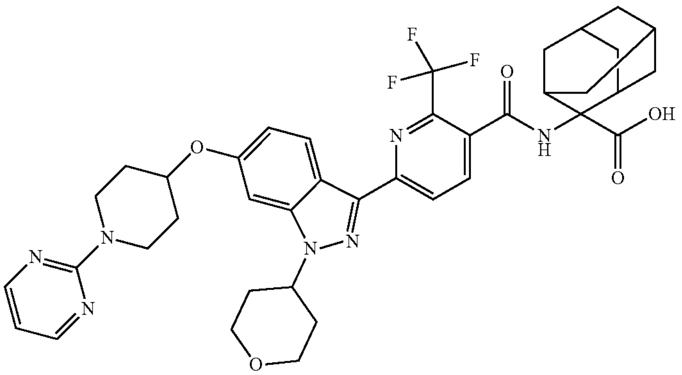 [SMILES: O=C(NC1(C(=O)O)C2CC3CC(C2)CC1C3)c1ccc(-c2nn(C3CCOCC3)c3cc(OC4CCN(c5ncccn5)CC4)ccc23)nc1C(F)(F)F] | 746 | 2.95 | 1 | |

TABLE 25-continued
| Compound No. | Chemical Structure | [M + H] | Retention Time (min) | LC/MS Condition | Stereo-Chemistry |
|---|---|---|---|---|---|
| I-159 | 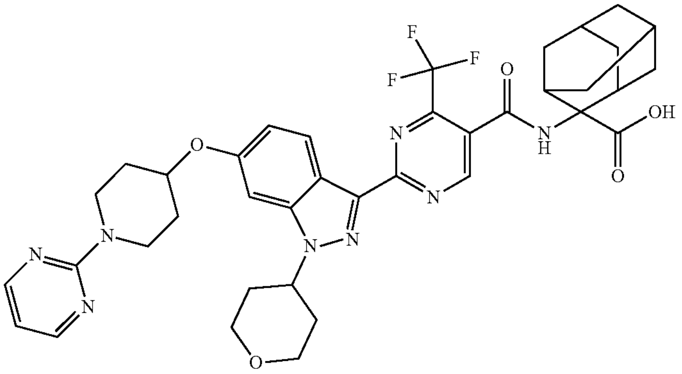 [SMILES: O=C(NC1(C(=O)O)C2CC3CC(C2)CC1C3)c1cnc(-c2nn(C3CCOCC3)c3cc(OC4CCN(c5ncccn5)CC4)ccc23)nc1C(F)(F)F] | 747 | 2.77 | 1 | |
TABLE 26
| Compound No. | Chemical Structure | [M + H] | Retention Time (min) | LC/MS Condition | Stereo-Chemistry |
|---|---|---|---|---|---|
| I-160 | 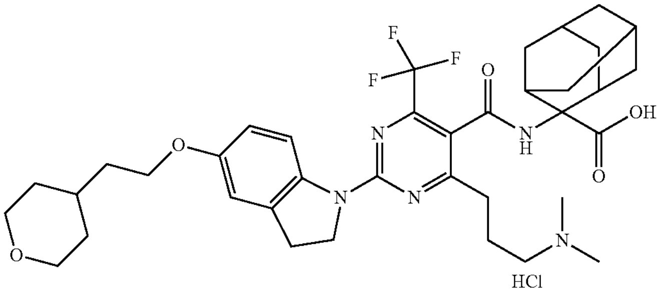 [SMILES: CN(C)CCCc1nc(N2CCc3cc(OCCC4CCOCC4)ccc32)nc(C(F)(F)F)c1C(=O)NC1(C(=O)O)C2CC3CC(C2)CC1C3 ; Cl] | 700 | 1.98 | 3 | |
| I-161 | 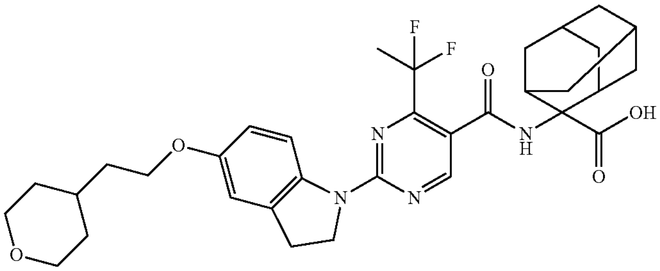 | 611 | 2.64 | 3 | |
| I-162 | 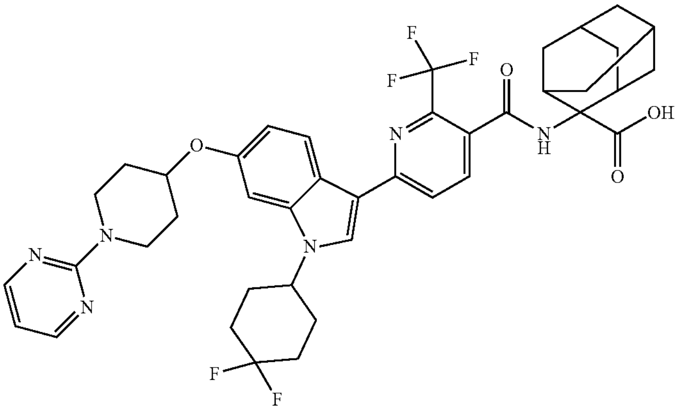 [SMILES: O=C(NC1(C(=O)O)C2CC3CC(C2)CC1C3)c1ccc(-c2cn(C3CCC(F)(F)CC3)c3cc(OC4CCN(c5ncccn5)CC4)ccc23)nc1C(F)(F)F] | 779 | 3.06 | 1 | |

TABLE 26-continued
| Compound No. | Chemical Structure | [M + H] | Retention Time (min) | LC/MS Condition | Stereo-Chemistry |
|---|---|---|---|---|---|
| I-163 | 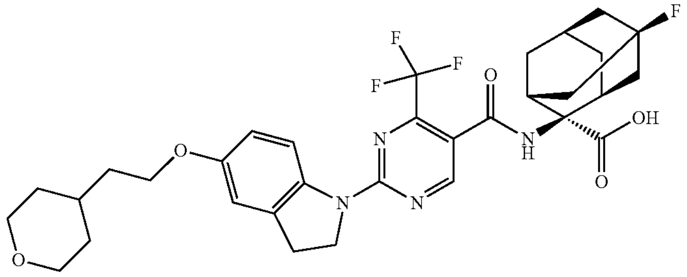 [SMILES: O=C(N[C@@]1(C(=O)O)[C@@H]2C[C@@H]3C[C@H]1C[C@@](F)(C3)C2)c1cnc(N2CCc3cc(OCCC4CCOCC4)ccc32)nc1C(F)(F)F] | 633 | 2.53 | 3 | |
| I-164 | 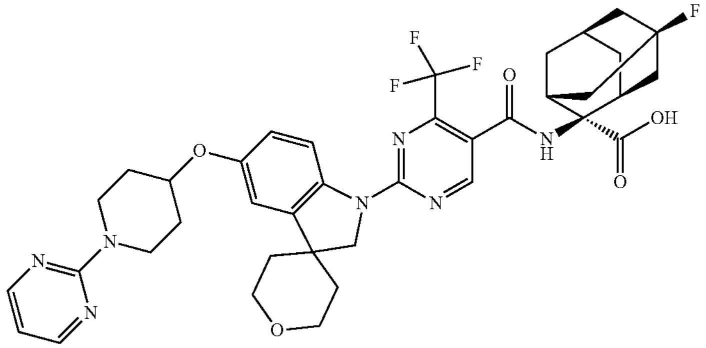 [SMILES: O=C(N[C@@]1(C(=O)O)[C@@H]2C[C@@H]3C[C@H]1C[C@@](F)(C3)C2)c1cnc(N2CC3(CCOCC3)c3cc(OC4CCN(c5ncccn5)CC4)ccc32)nc1C(F)(F)F] | 752 | 2.56 | 3 | |
| I-165 | 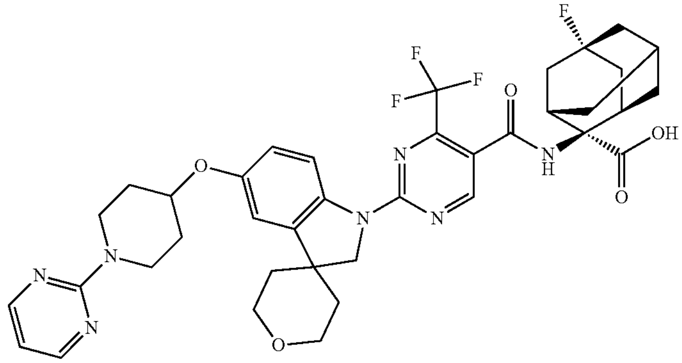 [SMILES: O=C(N[C@]1(C(=O)O)[C@@H]2CC3C[C@H]1C[C@@](F)(C3)C2)c1cnc(N2CC3(CCOCC3)c3cc(OC4CCN(c5ncccn5)CC4)ccc32)nc1C(F)(F)F] | 752 | 2.43 | 3 | |
TABLE 27
| Compound No. | Chemical Structure | [M + H] | Retention Time (min) | LC/MS Condition | Stereo-Chemistry |
|---|---|---|---|---|---|
| I-166 | 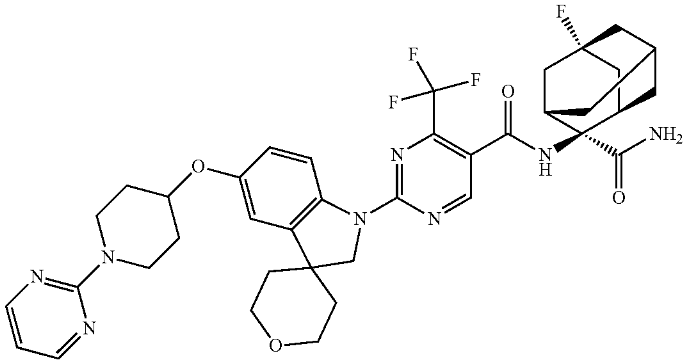 [SMILES: NC(=O)[C@@]1(NC(=O)c2cnc(N3CC4(CCOCC4)c4cc(OC5CCN(c6ncccn6)CC5)ccc43)nc2C(F)(F)F)[C@@H]2CC3C[C@H]1C[C@@](F)(C3)C2] | 751 | 2.41 | 3 | |

TABLE 27-continued
| Compound No. | Chemical Structure | [M + H] | Retention Time (min) | LC/MS Condition | Stereo-Chemistry |
|---|---|---|---|---|---|
| I-167 | 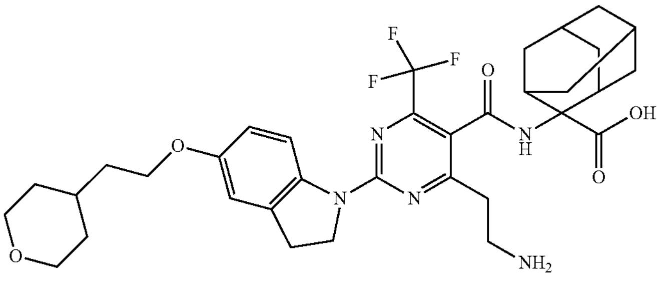 HCl | 658 | 1.98 | 3 | |
| I-168 | 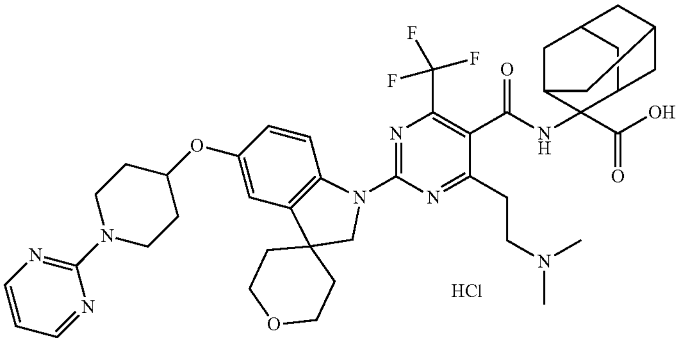 [SMILES: CN(C)CCc1nc(N2CC3(CCOCC3)c3cc(OC4CCN(c5ncccn5)CC4)ccc32)nc(C(F)(F)F)c1C(=O)NC1(C(=O)O)C2CC3CC(C2)CC1C3 ; Cl] HCl | 805 | 2.05 | 3 | |
| I-169 | 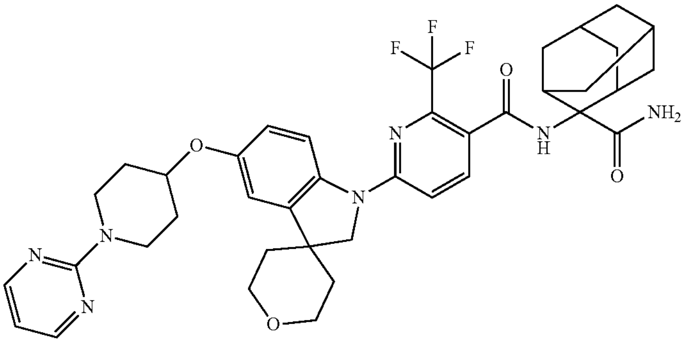 [SMILES: NC(=O)C1(NC(=O)c2ccc(N3CC4(CCOCC4)c4cc(OC5CCN(c6ncccn6)CC5)ccc43)nc2C(F)(F)F)C2CC3CC(C2)CC1C3] | 732 | 2.52 | 3 | |
| I-170 | 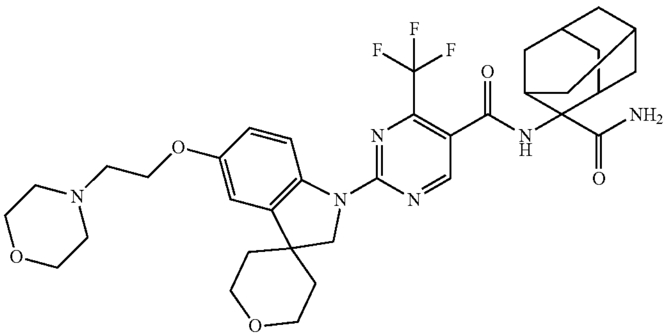 [SMILES: NC(=O)C1(NC(=O)c2cnc(N3CC4(CCOCC4)c4cc(OCCN5CCOCC5)ccc43)nc2C(F)(F)F)C2CC3CC(C2)CC1C3] | 685 | 1.57 | 3 | |

TABLE 27-continued
| Compound No. | Chemical Structure | [M + H] | Retention Time (min) | LC/MS Condition | Stereo-Chemistry |
|---|---|---|---|---|---|
| I-171 | 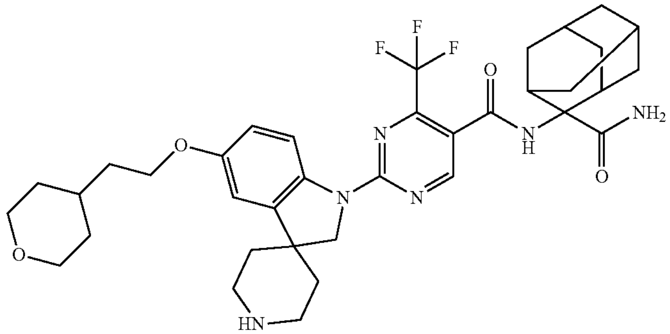 [SMILES: NC(=O)C1(NC(=O)c2cnc(N3CC4(CCNCC4)c4cc(OCCC5CCOCC5)ccc43)nc2C(F)(F)F)C2CC3CC(C2)CC1C3] | 683 | 1.56 | 3 | |
TABLE 28
| Compound No. | Chemical Structure | [M + H] | Retention Time (min) | LC/MS Condition | Stereo-Chemistry |
|---|---|---|---|---|---|
| I-172 | 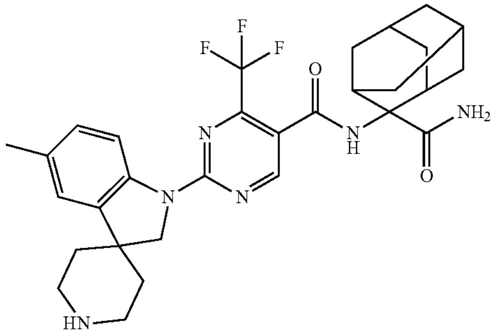 [SMILES: Cc1ccc2c(c1)C1(CCNCC1)CN2c1ncc(C(=O)NC2(C(N)=O)C3CC4CC(C3)CC2C4)c(C(F)(F)F)n1] | 569 | 1.60 | 3 | |
| I-173 | 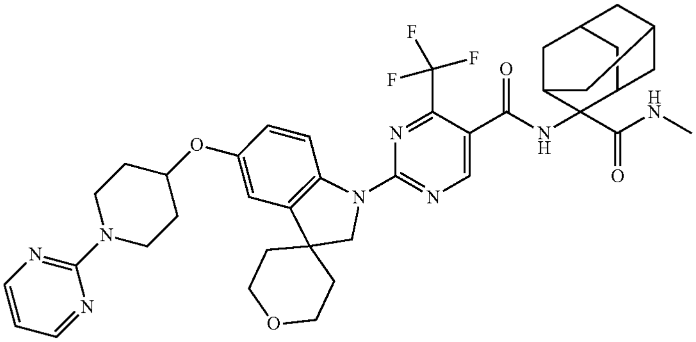 [SMILES: CNC(=O)C1(NC(=O)c2cnc(N3CC4(CCOCC4)c4cc(OC5CCN(c6ncccn6)CC5)ccc43)nc2C(F)(F)F)C2CC3CC(C2)CC1C3] | 747 | 2.70 | 3 | |
| I-174 | 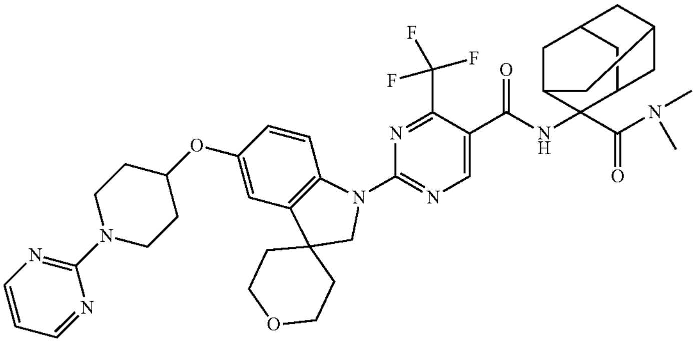 [SMILES: CN(C)C(=O)C1(NC(=O)c2cnc(N3CC4(CCOCC4)c4cc(OC5CCN(c6ncccn6)CC5)ccc43)nc2C(F)(F)F)C2CC3CC(C2)CC1C3] | 761 | 2.66 | 3 | |

TABLE 28-continued
| Compound No. | Chemical Structure | [M + H] | Retention Time (min) | LC/MS Condition | Stereo-Chemistry |
|---|---|---|---|---|---|
| I-175 | 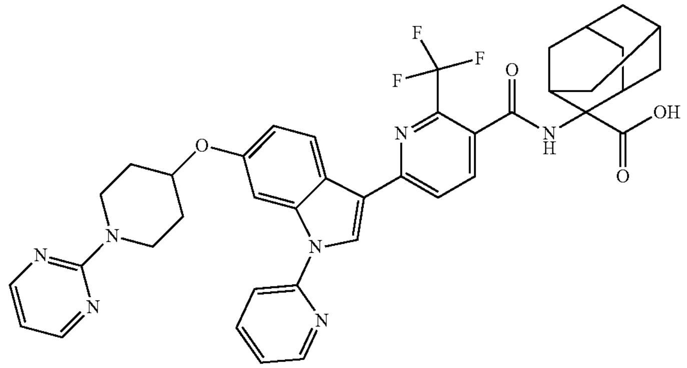 | 738 | 3.02 | 1 | |
| I-176 | 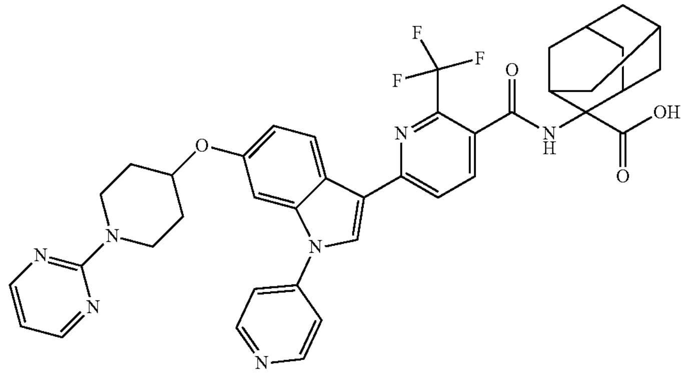 | 738 | 2.67 | 1 | |
| I-177 | 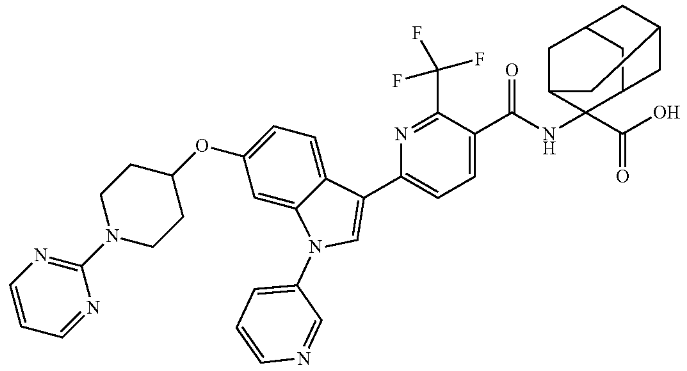 | 738 | 2.79 | 1 | |
TABLE 29
| Compound No. | Chemical Structure | [M + H] | Retention Time (min) | LC/MS Condition | Stereo-Chemistry |
|---|---|---|---|---|---|
| I-178 | 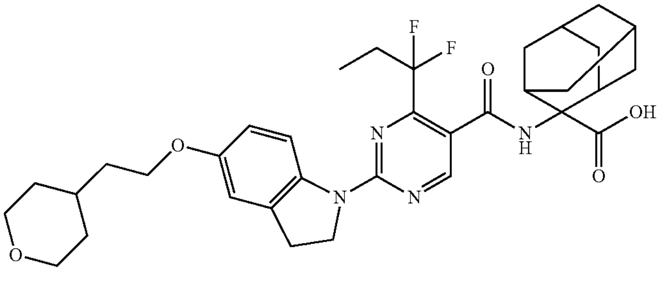 [SMILES: CCC(F)(F)c1nc(N2CCc3cc(OCCC4CCOCC4)ccc32)ncc1C(=O)NC1(C(=O)O)C2CC3CC(C2)CC1C3] | 625 | 2.70 | 3 | |

TABLE 29-continued
| Compound No. | Chemical Structure | [M + H] | Retention Time (min) | LC/MS Condition | Stereo-Chemistry |
|---|---|---|---|---|---|
| I-179 | 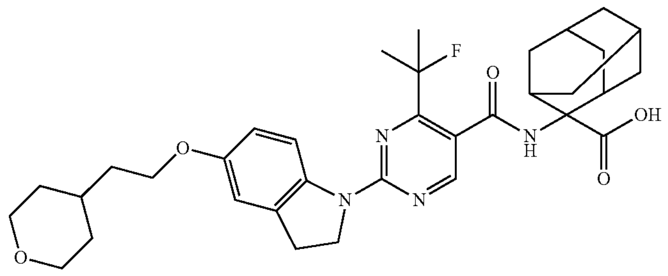 [SMILES: CC(C)(F)c1nc(N2CCc3cc(OCCC4CCOCC4)ccc32)ncc1C(=O)NC1(C(=O)O)C2CC3CC(C2)CC1C3] | 607 | 2.68 | 3 | |
| I-180 | 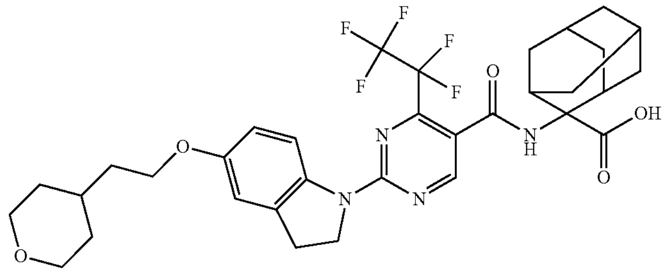 [SMILES: O=C(NC1(C(=O)O)C2CC3CC(C2)CC1C3)c1cnc(N2CCc3cc(OCCC4CCOCC4)ccc32)nc1C(F)(F)C(F)(F)F] | 665 | 2.81 | 3 | |
| I-181 | 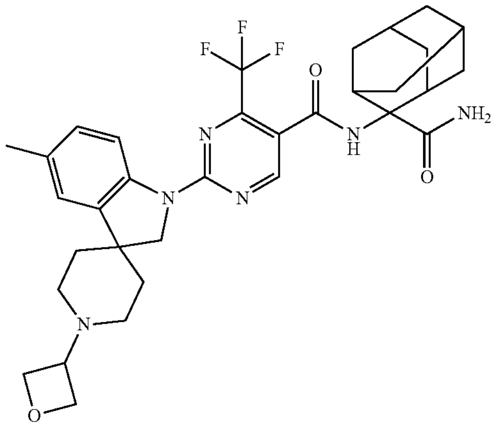 [SMILES: Cc1ccc2c(c1)C1(CCN(C3COC3)CC1)CN2c1ncc(C(=O)NC2(C(N)=O)C3CC4CC(C3)CC2C4)c(C(F)(F)F)n1] | 625 | 1.82 | 3 | |
| I-182 | 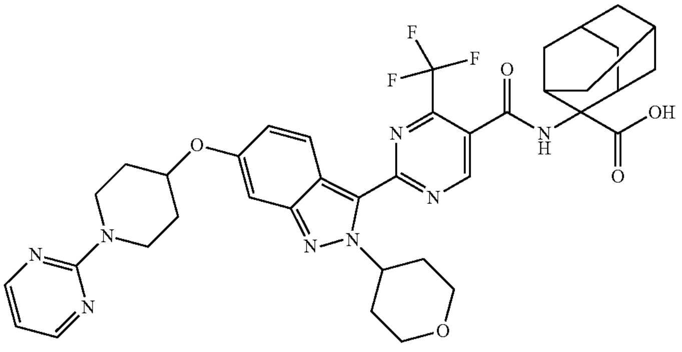 [SMILES: O=C(NC1(C(=O)O)C2CC3CC(C2)CC1C3)c1cnc(-c2c3ccc(OC4CCN(c5ncccn5)CC4)cc3nn2C2CCOCC2)nc1C(F)(F)F] | 747 | 2.83 | 1 | |

TABLE 29-continued
| Compound No. | Chemical Structure | [M + H] | Retention Time (min) | LC/MS Condition | Stereo-Chemistry |
|---|---|---|---|---|---|
| I-183 | 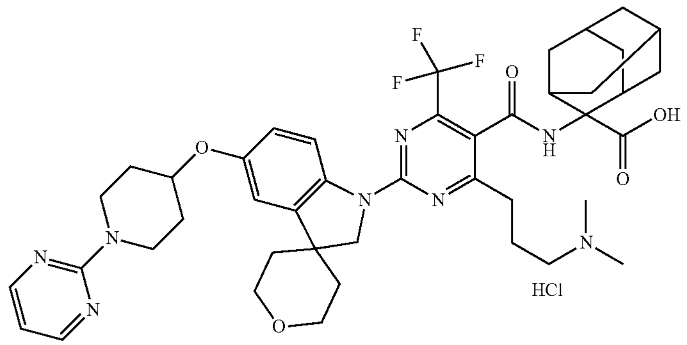 [SMILES: CN(C)CCCc1nc(N2CC3(CCOCC3)c3cc(OC4CCN(c5ncccn5)CC4)ccc32)nc(C(F)(F)F)c1C(=O)NC1(C(=O)O)C2CC3CC(C2)CC1C3 ; Cl] HCl | 819 | 2.43 | 5 | |
TABLE 30
| Compound No. | Chemical Structure | [M + H] | Retention Time (min) | LC/MS Condition | Stereo-Chemistry |
|---|---|---|---|---|---|
| I-184 | 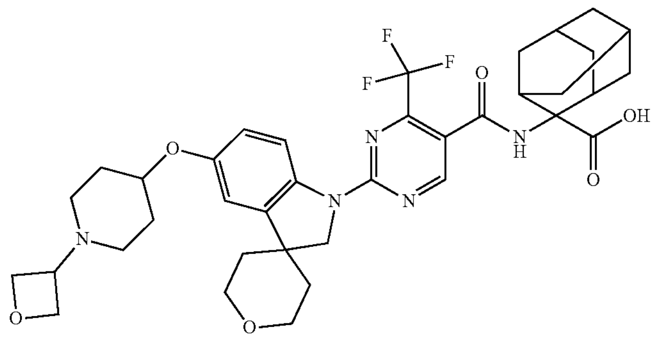 [SMILES: O=C(NC1(C(=O)O)C2CC3CC(C2)CC1C3)c1cnc(N2CC3(CCOCC3)c3cc(OC4CCN(C5COC5)CC4)ccc32)nc1C(F)(F)F] | 712 | 1.76 | 3 | |
| I-185 | 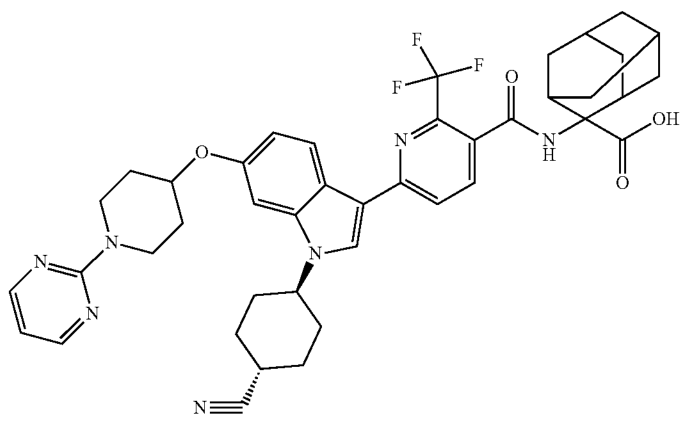 [SMILES: N#C[C@H]1CC[C@H](n2cc(-c3ccc(C(=O)NC4(C(=O)O)C5CC6CC(C5)CC4C6)c(C(F)(F)F)n3)c3ccc(OC4CCN(c5ncccn5)CC4)cc32)CC1] | 768 | 2.92 | 1 | |

TABLE 30-continued
| Compound No. | Chemical Structure | [M + H] | Retention Time (min) | LC/MS Condition | Stereo-Chemistry |
|---|---|---|---|---|---|
| I-186 | 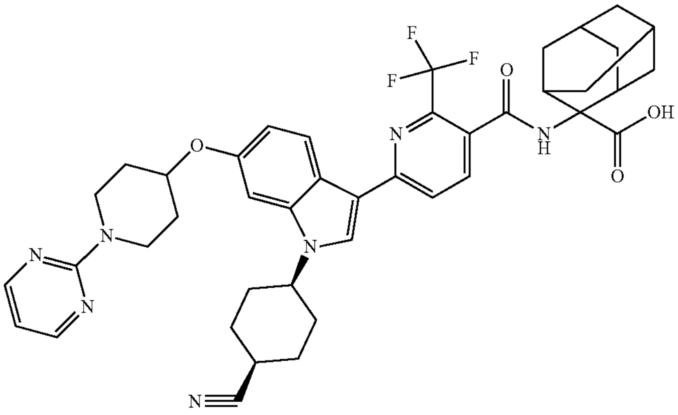 [SMILES: N#C[C@H]1CC[C@@H](n2cc(-c3ccc(C(=O)NC4(C(=O)O)C5CC6CC(C5)CC4C6)c(C(F)(F)F)n3)c3ccc(OC4CCN(c5ncccn5)CC4)cc32)CC1] | 768 | 2.94 | 1 | |
| I-187 | 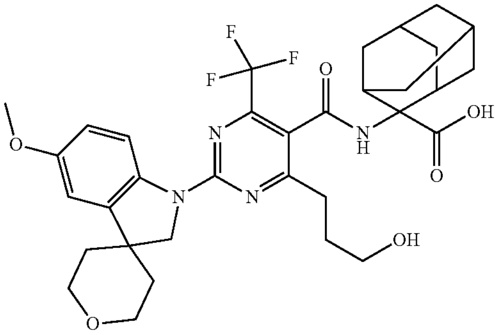 [SMILES: COc1ccc2c(c1)C1(CCOCC1)CN2c1nc(CCCO)c(C(=O)NC2(C(=O)O)C3CC4CC(C3)CC2C4)c(C(F)(F)F)n1] | 645 | 2.56 | 3 | |
| I-188 | 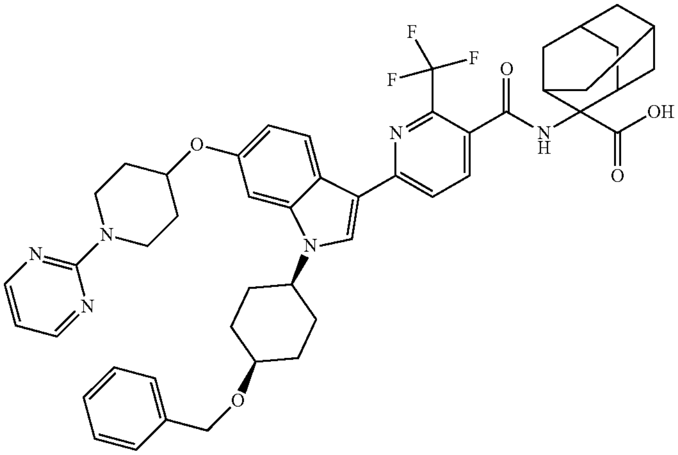 [SMILES: O=C(NC1(C(=O)O)C2CC3CC(C2)CC1C3)c1ccc(-c2cn([C@H]3CC[C@@H](OCc4ccccc4)CC3)c3cc(OC4CCN(c5ncccn5)CC4)ccc23)nc1C(F)(F)F] | 849 | 3.34 | 2 | |
| I-189 | 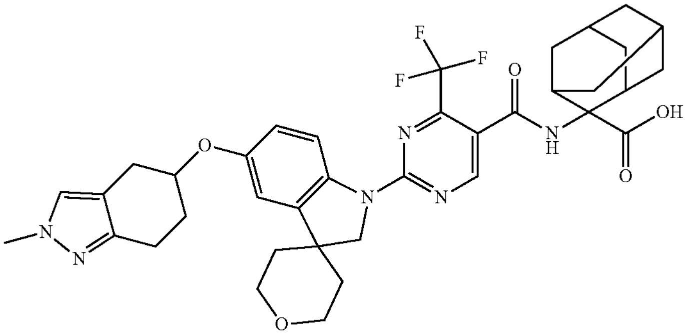 [SMILES: Cn1cc2c(n1)CCC(Oc1ccc3c(c1)C1(CCOCC1)CN3c1ncc(C(=O)NC3(C(=O)O)C4CC5CC(C4)CC3C5)c(C(F)(F)F)n1)C2] | 707 | 2.48 | 2 | a |

TABLE 31
| Compound No. | Chemical Structure | [M + H] | Retention Time (min) | LC/MS Condition | Stereo-Chemistry |
| --- | --- | --- | --- | --- | --- |
| I-190 | 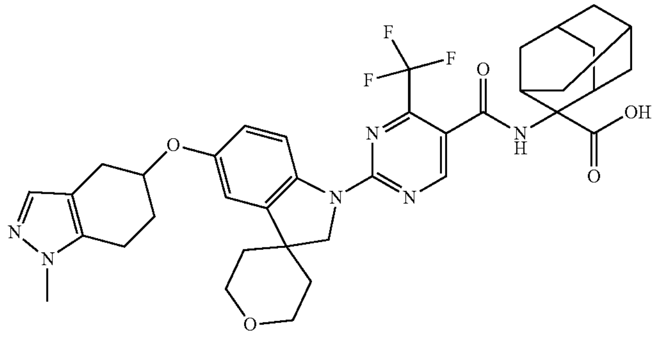 [SMILES: Cn1ncc2c1CCC(Oc1ccc3c(c1)C1(CCOCC1)CN3c1ncc(C(=O)NC3(C(=O)O)C4CC5CC(C4)CC3C5)c(C(F)(F)F)n1)C2] | 707 | 2.48 | 2 | b |
| I-191 | 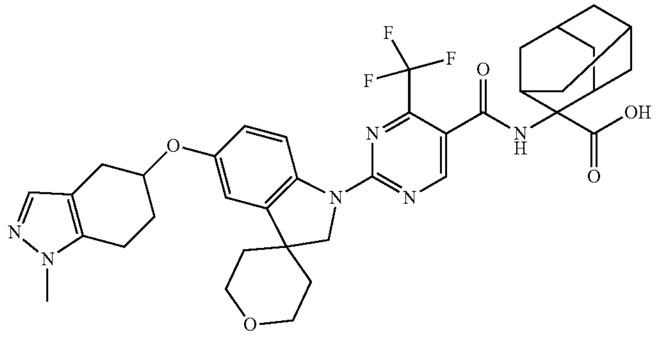 [SMILES: Cn1ncc2c1CCC(Oc1ccc3c(c1)C1(CCOCC1)CN3c1ncc(C(=O)NC3(C(=O)O)C4CC5CC(C4)CC3C5)c(C(F)(F)F)n1)C2] | 707 | 2.48 | 2 | b |
| I-192 | 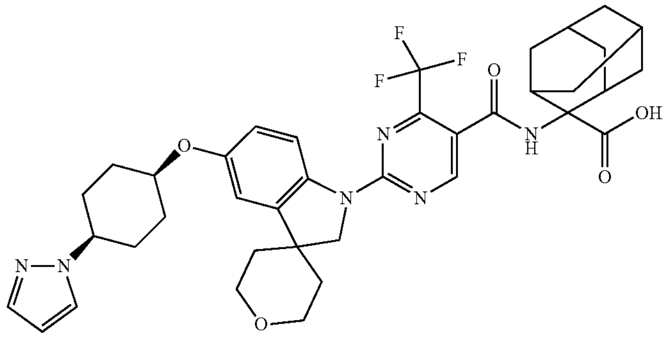 [SMILES: O=C(NC1(C(=O)O)C2CC3CC(C2)CC1C3)c1cnc(N2CC3(CCOCC3)c3cc(O[C@H]4CC[C@@H](n5cccn5)CC4)ccc32)nc1C(F)(F)F] | 721 | 2.69 | 3 | |
| I-193 | 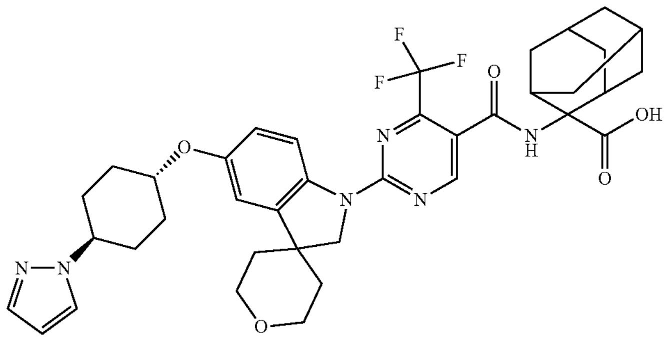 [SMILES: O=C(NC1(C(=O)O)C2CC3CC(C2)CC1C3)c1cnc(N2CC3(CCOCC3)c3cc(O[C@H]4CC[C@H](n5cccn5)CC4)ccc32)nc1C(F)(F)F] | 721 | 2.69 | 3 | |

TABLE 31-continued
| Compound No. | Chemical Structure | [M + H] | Retention Time (min) | LC/MS Condition | Stereo-Chemistry |
|---|---|---|---|---|---|
| I-194 | 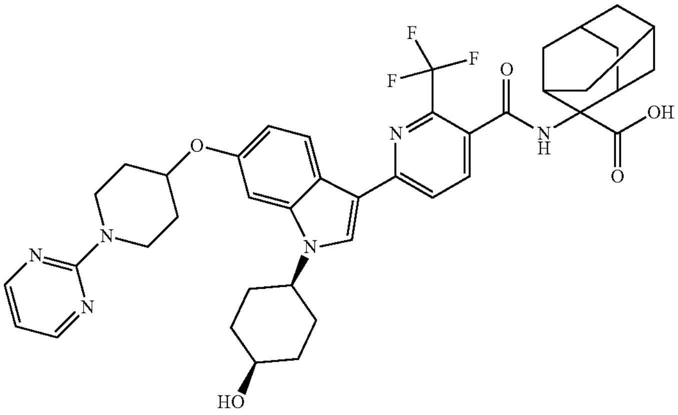 [SMILES: O=C(NC1(C(=O)O)C2CC3CC(C2)CC1C3)c1ccc(-c2cn([C@H]3CC[C@@H](O)CC3)c3cc(OC4CCN(c5ncccn5)CC4)ccc23)nc1C(F)(F)F] | 759 | 2.58 | 2 | |
| I-195 | 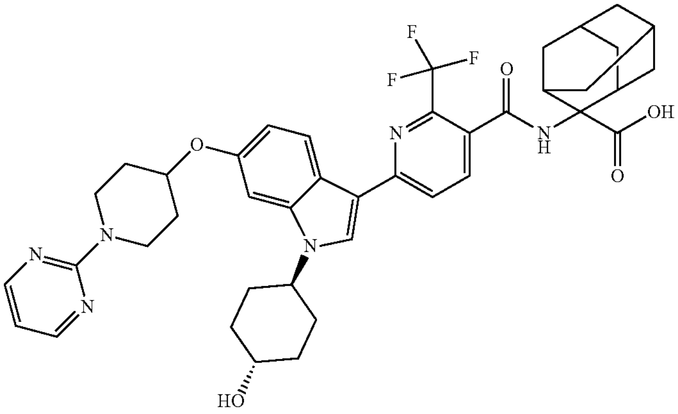 [SMILES: O=C(NC1(C(=O)O)C2CC3CC(C2)CC1C3)c1ccc(-c2cn([C@H]3CC[C@H](O)CC3)c3cc(OC4CCN(c5ncccn5)CC4)ccc23)nc1C(F)(F)F] | 759 | 2.52 | 2 | |
TABLE 32
| Compound No. | Chemical Structure | [M + H] | Retention Time (min) | LC/MS Condition | Stereo-Chemistry |
|---|---|---|---|---|---|
| I-196 | 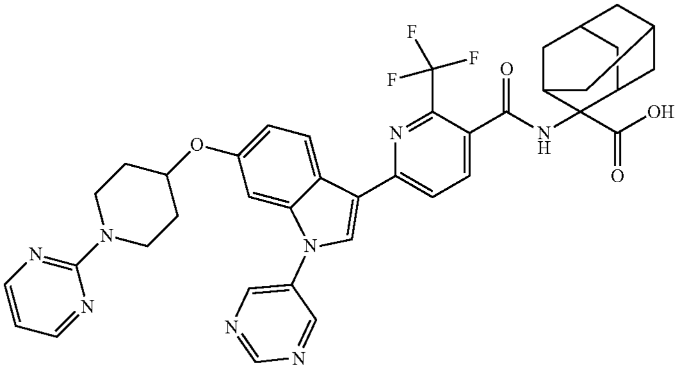 | 739 | 2.53 | 2 | |

TABLE 32-continued
| Compound No. | Chemical Structure | [M + H] | Retention Time (min) | LC/MS Condition | Stereo-Chemistry |
|---|---|---|---|---|---|
| I-197 | 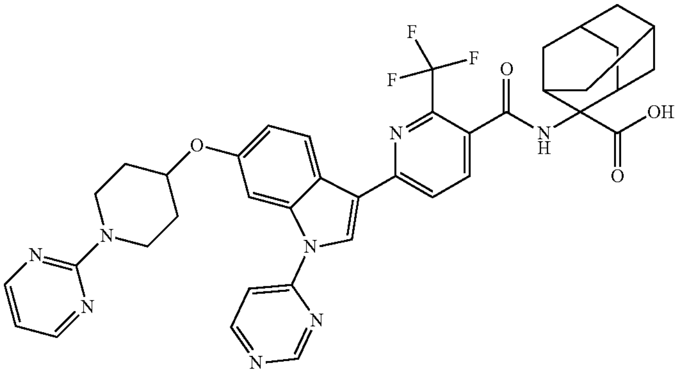 | 739 | 2.60 | 2 | |
| I-198 | 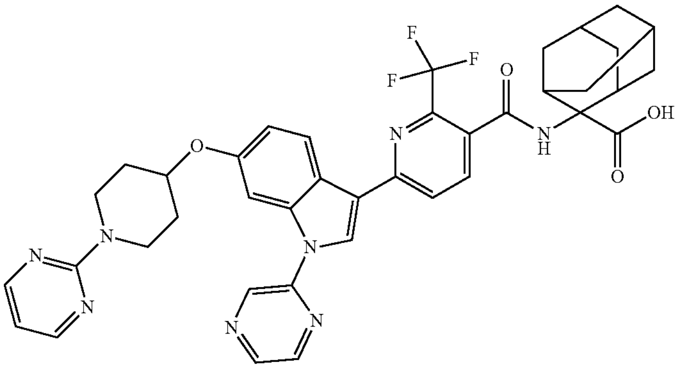 [SMILES: O=C(NC1(C(=O)O)C2CC3CC(C2)CC1C3)c1ccc(-c2cn(-c3cncnc3)c3cc(OC4CCN(c5ncccn5)CC4)ccc23)nc1C(F)(F)F] | 739 | 2.61 | 2 | |
| I-199 | 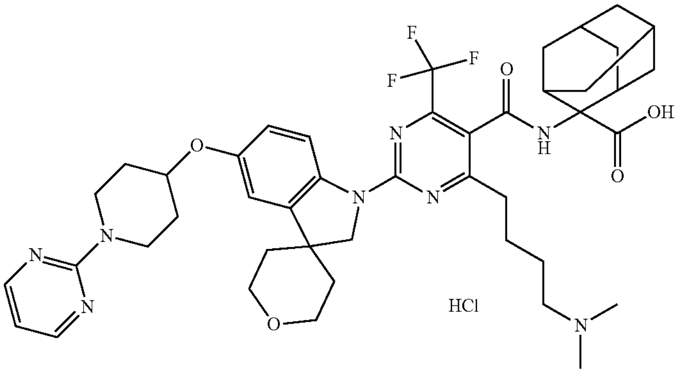 [SMILES: CN(C)CCCCc1nc(N2CC3(CCOCC3)c3cc(OC4CCN(c5ncccn5)CC4)ccc32)nc(C(F)(F)F)c1C(=O)NC1(C(=O)O)C2CC3CC(C2)CC1C3 ; Cl] HCl | 831 | 2.04 | 3 | |
| I-200 | 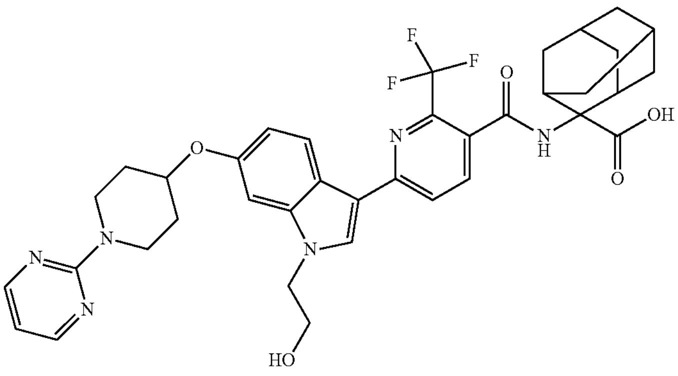 [SMILES: O=C(NC1(C(=O)O)C2CC3CC(C2)CC1C3)c1ccc(-c2cn(CCO)c3cc(OC4CCN(c5ncccn5)CC4)ccc23)nc1C(F)(F)F] | 705 | 2.44 | 1 | |

TABLE 32-continued
| Compound No. | Chemical Structure | [M + H] | Retention Time (min) | LC/MS Condition | Stereo-Chemistry |
|---|---|---|---|---|---|
| I-201 | 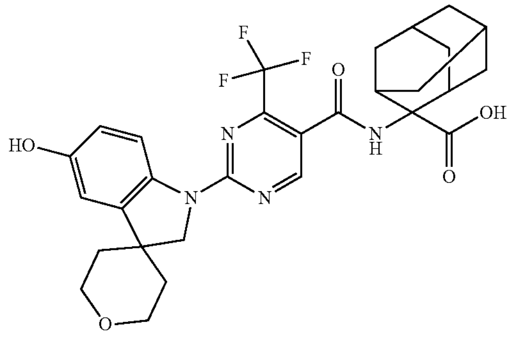 [SMILES: O=C(NC1(C(=O)O)C2CC3CC(C2)CC1C3)c1cnc(N2CC3(CCOCC3)c3cc(O)ccc32)nc1C(F)(F)F] | 573 | 2.21 | 3 | |
TABLE 33
| Compound No. | Chemical Structure | [M + H] | Retention Time (min) | LC/MS Condition | Stereo-Chemistry |
|---|---|---|---|---|---|
| I-202 | 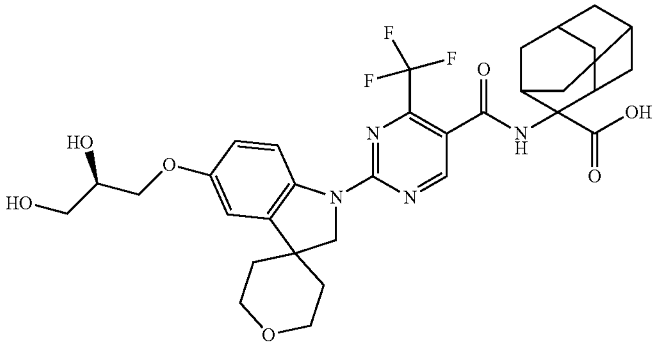 [SMILES: O=C(NC1(C(=O)O)C2CC3CC(C2)CC1C3)c1cnc(N2CC3(CCOCC3)c3cc(OC[C@H](O)CO)ccc32)nc1C(F)(F)F] | 847 | 2.05 | 3 | |
| I-203 | 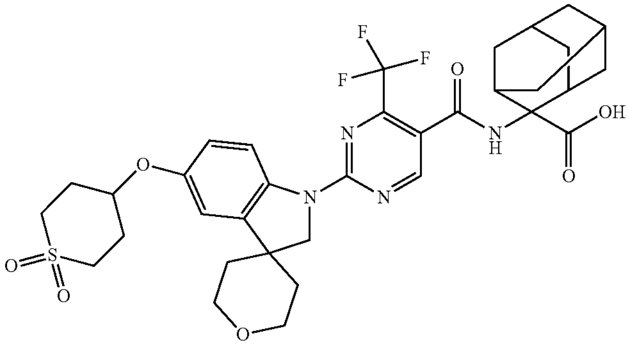 [SMILES: O=C(NC1(C(=O)O)C2CC3CC(C2)CC1C3)c1cnc(N2CC3(CCOCC3)c3cc(OC4CCS(=O)(=O)CC4)ccc32)nc1C(F)(F)F] | 705 | 2.33 | 3 | |
| I-204 | 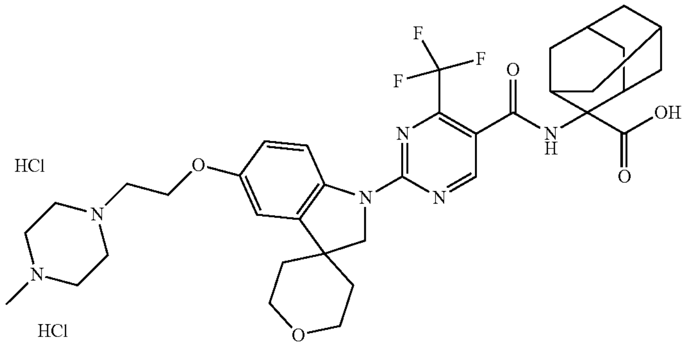 [SMILES: CN1CCN(CCOc2ccc3c(c2)C2(CCOCC2)CN3c2ncc(C(=O)NC3(C(=O)O)C4CC5CC(C4)CC3C5)c(C(F)(F)F)n2)CC1 ; Cl ; Cl] | 699 | 1.95 | 3 | |

TABLE 33-continued
| Compound No. | Chemical Structure | [M + H] | Retention Time (min) | LC/MS Condition | Stereo-Chemistry |
|---|---|---|---|---|---|
| I-205 | 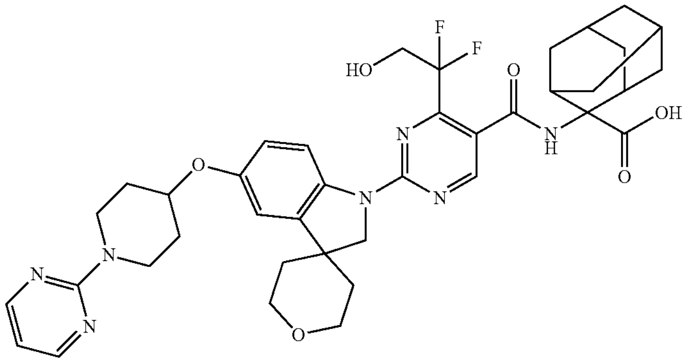 [SMILES: O=C(NC1(C(=O)O)C2CC3CC(C2)CC1C3)c1cnc(N2CC3(CCOCC3)c3cc(OC4CCN(c5ncccn5)CC4)ccc32)nc1C(F)(F)CO] | 746 | 2.47 | 2 | |
| I-206 | 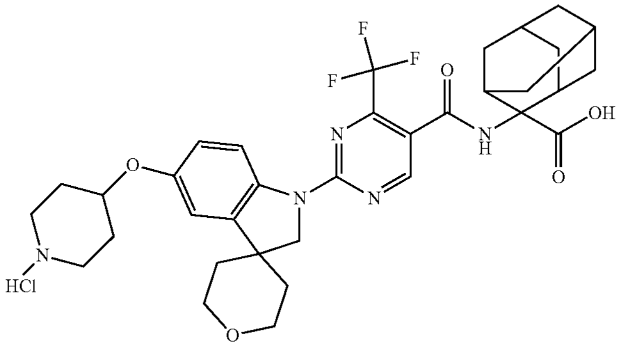 [SMILES: O=C(NC1(C(=O)O)C2CC3CC(C2)CC1C3)c1cnc(N2CC3(CCOCC3)c3cc(OC4CCN(Cl)CC4)ccc32)nc1C(F)(F)F] | 670 | 1.98 | 6 | |
| I-207 | 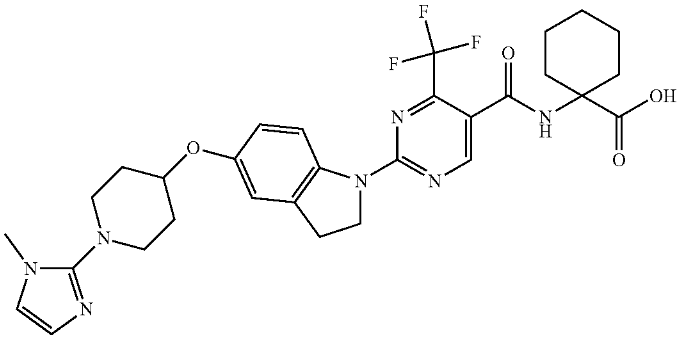 [SMILES: Cn1ccnc1N1CCC(Oc2ccc3c(c2)CCN3c2ncc(C(=O)NC3(C(=O)O)CCCCC3)c(C(F)(F)F)n2)CC1] | 614 | 1.74 | 1 | |
TABLE 34
| Compound No. | Chemical Structure | [M + H] | Retention Time (min) | LC/MS Condition | Stereo-Chemistry |
|---|---|---|---|---|---|
| I-208 | 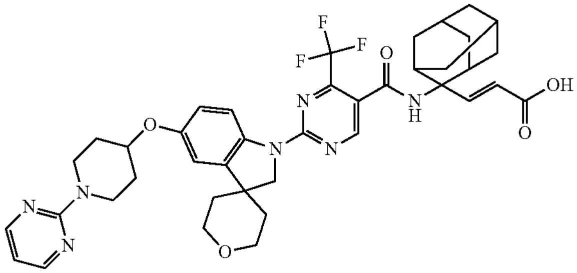 [SMILES: O=C(O)/C=C/C1(NC(=O)c2cnc(N3CC4(CCOCC4)c4cc(OC5CCN(c6ncccn6)CC5)ccc43)nc2C(F)(F)F)C2CC3CC(C2)CC1C3] | 760 | 2.86 | 3 | |

TABLE 34-continued
| Compound No. | Chemical Structure | [M + H] | Retention Time (min) | LC/MS Condition | Stereo-Chemistry |
|---|---|---|---|---|---|
| I-209 | 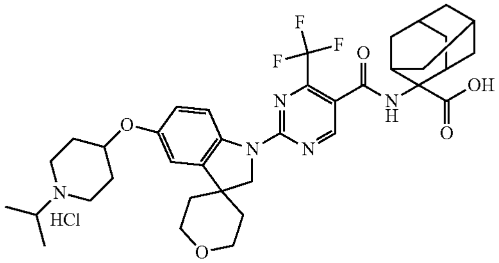 [SMILES: CC(C)N1CCC(Oc2ccc3c(c2)C2(CCOCC2)CN3c2ncc(C(=O)NC3(C(=O)O)C4CC5CC(C4)CC3C5)c(C(F)(F)F)n2)CC1 ; Cl] | 698 | 1.88 | 6 | |
| I-210 | 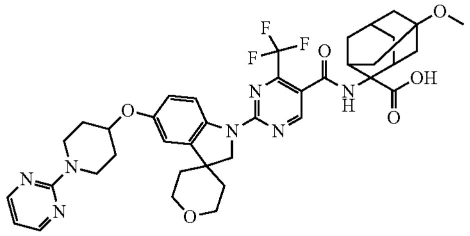 [SMILES: COC12CC3CC(C1)C(NC(=O)c1cnc(N4CC5(CCOCC5)c5cc(OC6CCN(c7ncccn7)CC6)ccc54)nc1C(F)(F)F)(C(=O)O)C(C3)C2] | 764 | 2.23 | 2 | b |
| I-211 | 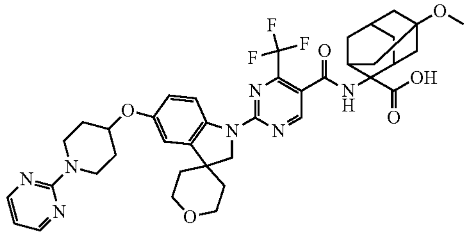 [SMILES: COC12CC3CC(C1)C(NC(=O)c1cnc(N4CC5(CCOCC5)c5cc(OC6CCN(c7ncccn7)CC6)ccc54)nc1C(F)(F)F)(C(=O)O)C(C3)C2] | 764 | 2.31 | 2 | b |
| I-212 | 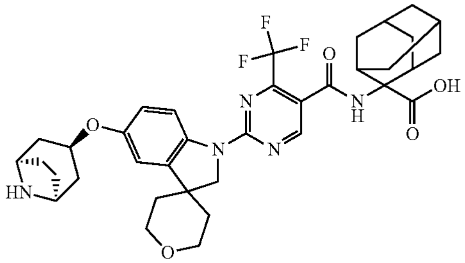 [SMILES: O=C(NC1(C(=O)O)C2CC3CC(C2)CC1C3)c1cnc(N2CC3(CCOCC3)c3cc(O[C@@H]4C[C@H]5CC[C@@H](C4)N5)ccc32)nc1C(F)(F)F] | 682 | 2.06 | 6 | |
| I-213 | 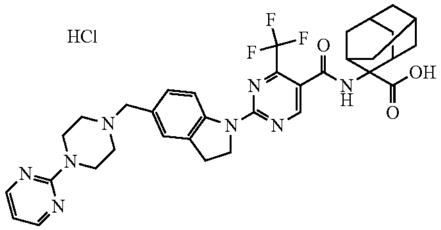 [SMILES: O=C(NC1(C(=O)O)C2CC3CC(C2)CC1C3)c1cnc(N2CCc3cc(CN4CCN(c5ncccn5)CC4)ccc32)nc1C(F)(F)F ; Cl] | 663 | 1.84 | 1 | |

TABLE 35
| Compound No. | Chemical Structure | [M + H] | Retention Time (min) | LC/MS Condition | Stereo-Chemistry |
|---|---|---|---|---|---|
| I-214 | 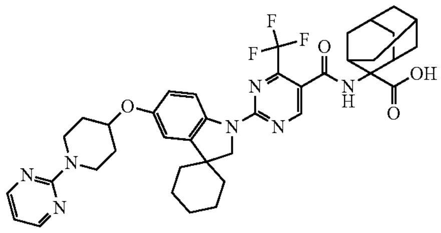 [SMILES: O=C(NC1(C(=O)O)C2CC3CC(C2)CC1C3)c1cnc(N2CC3(CCCCC3)c3cc(OC4CCN(c5ncccn5)CC4)ccc32)nc1C(F)(F)F] | 732 | 3.05 | 1 | |
| I-215 | 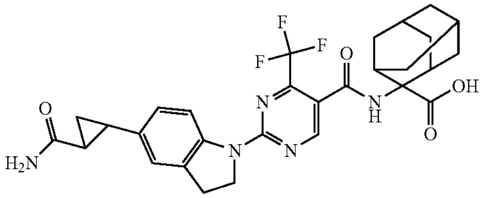 [SMILES: NC(=O)C1CC1c1ccc2c(c1)CCN2c1ncc(C(=O)NC2(C(=O)O)C3CC4CC(C3)CC2C4)c(C(F)(F)F)n1] | 570 | 2.25 | 1 | a |
| I-216 | 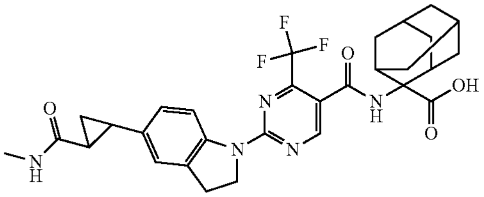 [SMILES: CNC(=O)C1CC1c1ccc2c(c1)CCN2c1ncc(C(=O)NC2(C(=O)O)C3CC4CC(C3)CC2C4)c(C(F)(F)F)n1] | 584 | 2.33 | 1 | a |
| I-217 | 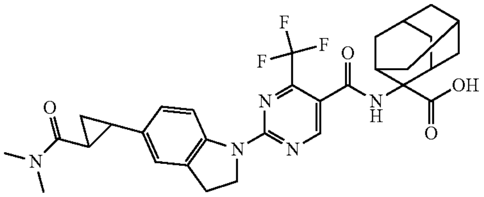 [SMILES: CN(C)C(=O)C1CC1c1ccc2c(c1)CCN2c1ncc(C(=O)NC2(C(=O)O)C3CC4CC(C3)CC2C4)c(C(F)(F)F)n1] | 596 | 2.45 | 1 | a |
| I-218 | 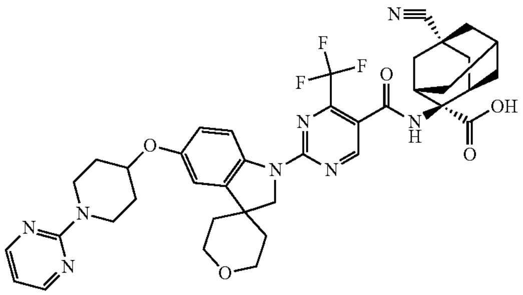 [SMILES: N#C[C@]12CC3C[C@H](C1)[C@](NC(=O)c1cnc(N4CC5(CCOCC5)c5cc(OC6CCN(c7ncccn7)CC6)ccc54)nc1C(F)(F)F)(C(=O)O)[C@@H](C3)C2] | 759 | 2.37 | 1 | |
| I-219 | 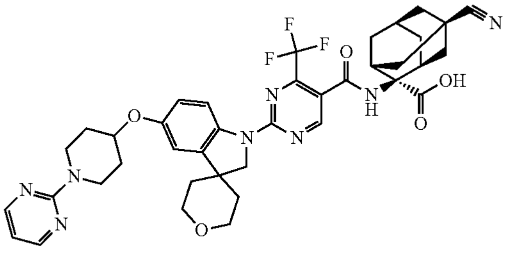 [SMILES: N#C[C@]12C[C@@H]3C[C@H](C1)[C@@](NC(=O)c1cnc(N4CC5(CCOCC5)c5cc(OC6CCN(c7ncccn7)CC6)ccc54)nc1C(F)(F)F)(C(=O)O)[C@@H](C3)C2] | 759 | 2.38 | 1 | |

TABLE 35-continued
| Compound No. | Chemical Structure | [M + H] | Retention Time (min) | LC/MS Condition | Stereo-Chemistry |
|---|---|---|---|---|---|
| I-220 | 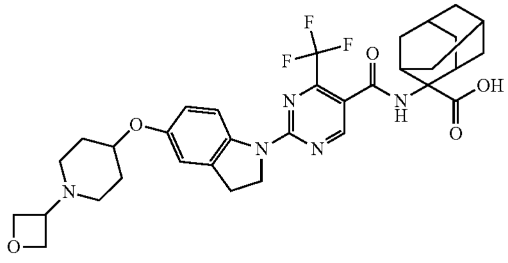 [SMILES: O=C(NC1(C(=O)O)C2CC3CC(C2)CC1C3)c1cnc(N2CCc3cc(OC4CCN(C5COC5)CC4)ccc32)nc1C(F)(F)F] | 642 | 1.78 | 1 | |
TABLE 36
| Compound No. | Chemical Structure | [M + H] | Retention Time (min) | LC/MS Condition | Stereo-Chemistry |
|---|---|---|---|---|---|
| I-221 | 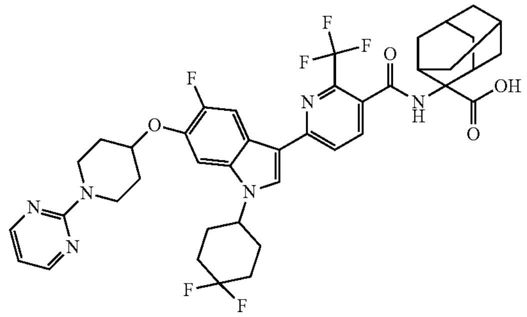 [SMILES: O=C(NC1(C(=O)O)C2CC3CC(C2)CC1C3)c1ccc(-c2cn(C3CCC(F)(F)CC3)c3cc(OC4CCN(c5ncccn5)CC4)c(F)cc23)nc1C(F)(F)F] | 797 | 2.89 | 1 | |
| I-222 | 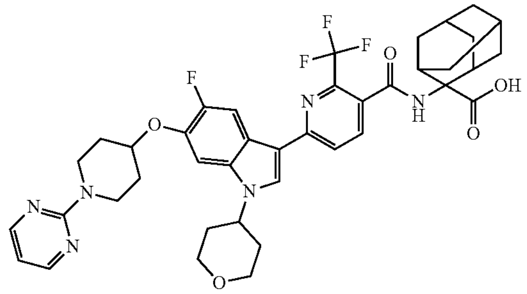 [SMILES: O=C(NC1(C(=O)O)C2CC3CC(C2)CC1C3)c1ccc(-c2cn(C3CCOCC3)c3cc(OC4CCN(c5ncccn5)CC4)c(F)cc23)nc1C(F)(F)F] | 763 | 2.66 | 1 | |
| I-223 | 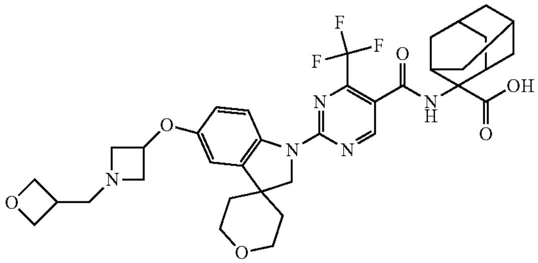 [SMILES: O=C(NC1(C(=O)O)C2CC3CC(C2)CC1C3)c1cnc(N2CC3(CCOCC3)c3cc(OC4CN(CC5COC5)C4)ccc32)nc1C(F)(F)F] | 696 | 1.69 | 5 | |

TABLE 36-continued
| Compound No. | Chemical Structure | [M + H] | Retention Time (min) | LC/MS Condition | Stereo-Chemistry |
|---|---|---|---|---|---|
| I-224 | 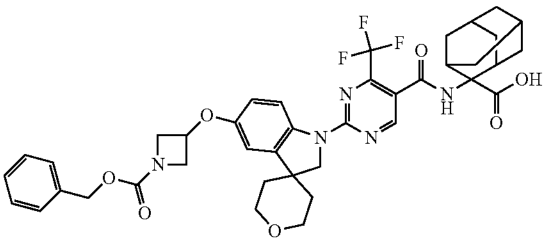 [SMILES: O=C(NC1(C(=O)O)C2CC3CC(C2)CC1C3)c1cnc(N2CC3(CCOCC3)c3cc(OC4CN(C(=O)OCc5ccccc5)C4)ccc32)nc1C(F)(F)F] | 762 | 2.75 | 5 | |
| I-225 | 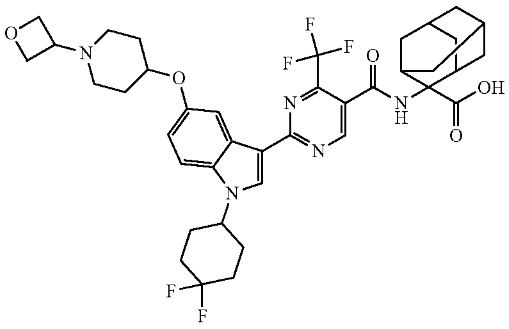 [SMILES: O=C(NC1(C(=O)O)C2CC3CC(C2)CC1C3)c1cnc(-c2cn(C3CCC(F)(F)CC3)c3ccc(OC4CCN(C5COC5)CC4)cc23)nc1C(F)(F)F] | 758 | 1.27 | 9 | |
| I-226 | 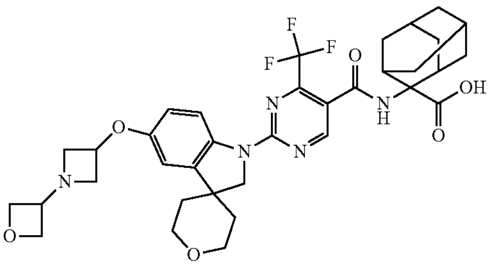 [SMILES: O=C(NC1(C(=O)O)C2CC3CC(C2)CC1C3)c1cnc(N2CC3(CCOCC3)c3cc(OC4CN(C5COC5)C4)ccc32)nc1C(F)(F)F] | 684 | 1.99 | 5 | |
TABLE 37
| Compound No. | Chemical Structure | [M + H] | Retention Time (min) | LC/MS Condition | Stereo-Chemistry |
|---|---|---|---|---|---|
| I-227 | 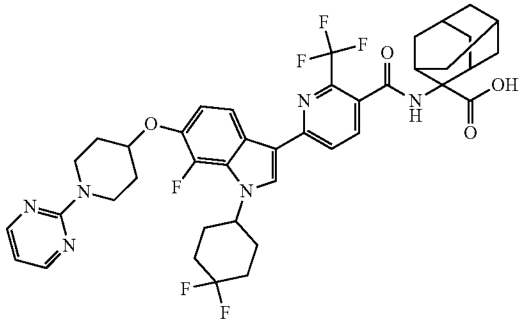 [SMILES: O=C(NC1(C(=O)O)C2CC3CC(C2)CC1C3)c1ccc(-c2cn(C3CCC(F)(F)CC3)c3c(F)c(OC4CCN(c5ncccn5)CC4)ccc23)nc1C(F)(F)F] | 797 | 3.07 | 2 | |

TABLE 37-continued
| Compound No. | Chemical Structure | [M + H] | Retention Time (min) | LC/MS Condition | Stereo-Chemistry |
|---|---|---|---|---|---|
| I-228 | 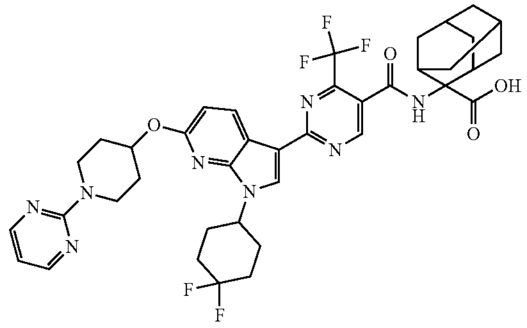 [SMILES: O=C(NC1(C(=O)O)C2CC3CC(C2)CC1C3)c1cnc(-c2cn(C3CCC(F)(F)CC3)c3nc(OC4CCN(c5ncccn5)CC4)ccc23)nc1C(F)(F)F] | 761 | 1.86 | 10 | |
| I-229 | 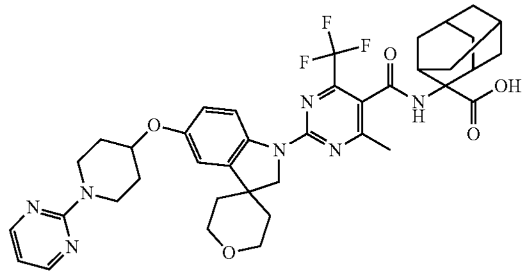 [SMILES: Cc1nc(N2CC3(CCOCC3)c3cc(OC4CCN(c5ncccn5)CC4)ccc32)nc(C(F)(F)F)c1C(=O)NC1(C(=O)O)C2CC3CC(C2)CC1C3] | 748 | 2.82 | 2 | |
| I-230 | 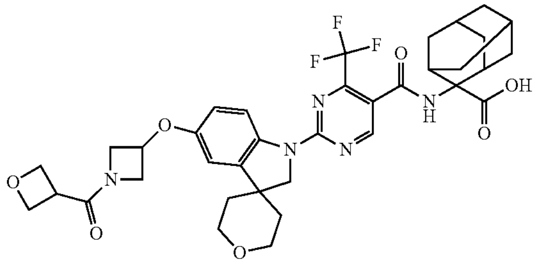 [SMILES: O=C(NC1(C(=O)O)C2CC3CC(C2)CC1C3)c1cnc(N2CC3(CCOCC3)c3cc(OC4CN(C(=O)C5COC5)C4)ccc32)nc1C(F)(F)F] | 712 | 2.14 | 2 | |
| I-231 | 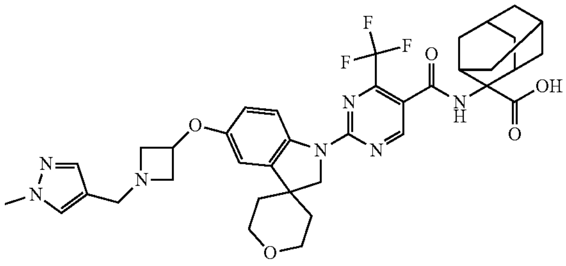 [SMILES: Cn1cc(CN2CC(Oc3ccc4c(c3)C3(CCOCC3)CN4c3ncc(C(=O)NC4(C(=O)O)C5CC6CC(C5)CC4C6)c(C(F)(F)F)n3)C2)cn1] | 722 | 2.04 | 2 | |
| I-232 | 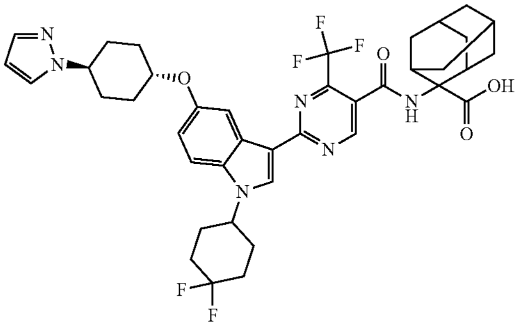 [SMILES: O=C(NC1(C(=O)O)C2CC3CC(C2)CC1C3)c1cnc(-c2cn(C3CCC(F)(F)CC3)c3ccc(O[C@H]4CC[C@H](n5cccn5)CC4)cc23)nc1C(F)(F)F] | 767 | 1.69 | 9 | |

TABLE 38
| Compound No. | Chemical Structure | [M + H] | Retention Time (min) | LC/MS Condition | Stereo-Chemistry |
|---|---|---|---|---|---|
| I-233 | 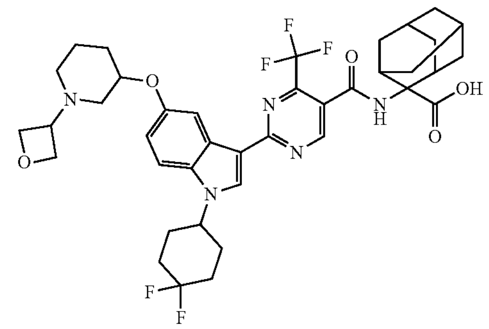 [SMILES: O=C(NC1(C(=O)O)C2CC3CC(C2)CC1C3)c1cnc(-c2cn(C3CCC(F)(F)CC3)c3ccc(OC4CCCN(C5COC5)C4)cc23)nc1C(F)(F)F] | 758 | 1.18 | 9 | a |
| I-234 | 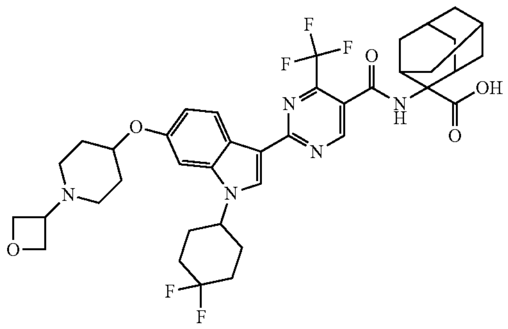 [SMILES: O=C(NC1(C(=O)O)C2CC3CC(C2)CC1C3)c1cnc(-c2cn(C3CCC(F)(F)CC3)c3cc(OC4CCN(C5COC5)CC4)ccc23)nc1C(F)(F)F] | 758 | 1.19 | 9 | |
| I-235 | 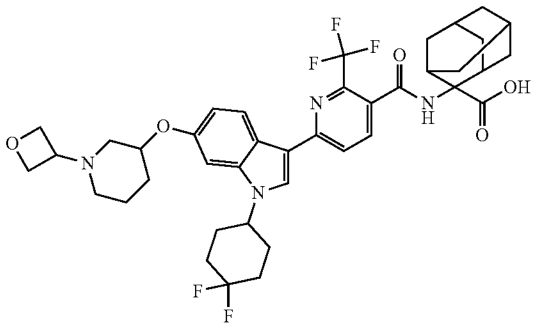 [SMILES: O=C(NC1(C(=O)O)C2CC3CC(C2)CC1C3)c1ccc(-c2cn(C3CCC(F)(F)CC3)c3cc(OC4CCCN(C5COC5)C4)ccc23)nc1C(F)(F)F] | 757 | 1.24 | 10 | a |
| I-236 | 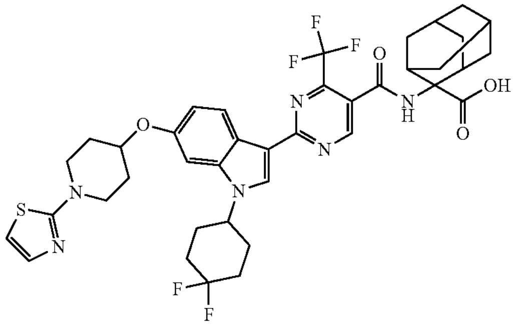 [SMILES: O=C(NC1(C(=O)O)C2CC3CC(C2)CC1C3)c1cnc(-c2cn(C3CCC(F)(F)CC3)c3cc(OC4CCN(c5nccs5)CC4)ccc23)nc1C(F)(F)F] | 785 | 1.61 | 9 | |

TABLE 38-continued
| Compound No. | Chemical Structure | [M + H] | Retention Time (min) | LC/MS Condition | Stereo-Chemistry |
|---|---|---|---|---|---|
| I-237 | 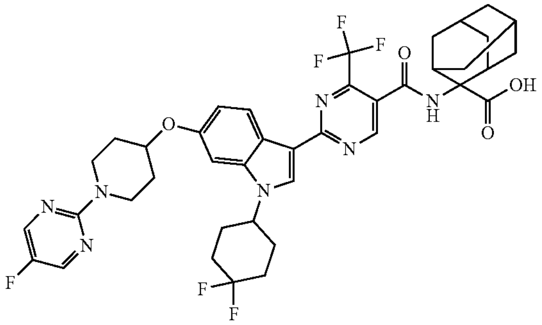 [SMILES: O=C(NC1(C(=O)O)C2CC3CC(C2)CC1C3)c1cnc(-c2cn(C3CCC(F)(F)CC3)c3cc(OC4CCN(c5ncc(F)cn5)CC4)ccc23)nc1C(F)(F)F] | 798 | 1.87 | 9 | |
TABLE 39
| Compound No. | Chemical Structure | [M + H] | Retention Time (min) | LC/MS Condition | Stereo-Chemistry |
|---|---|---|---|---|---|
| I-238 | 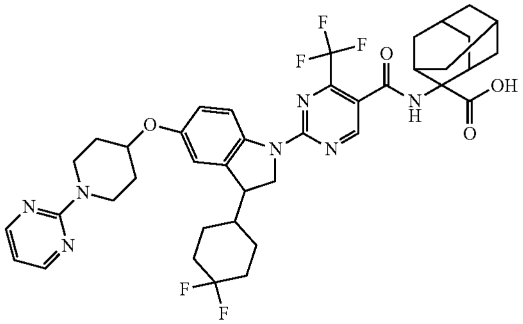 [SMILES: O=C(NC1(C(=O)O)C2CC3CC(C2)CC1C3)c1cnc(N2CC(C3CCC(F)(F)CC3)c3cc(OC4CCN(c5ncccn5)CC4)ccc32)nc1C(F)(F)F] | 768 | 2.88 | 2 | |
| I-239 | 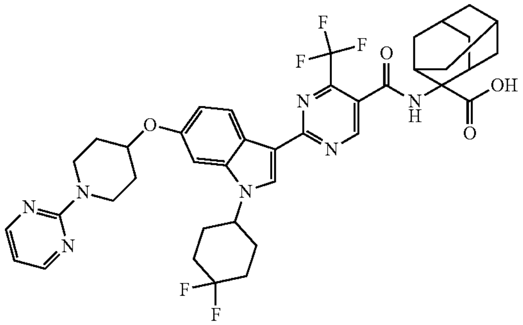 [SMILES: O=C(NC1(C(=O)O)C2CC3CC(C2)CC1C3)c1cnc(-c2cn(C3CCC(F)(F)CC3)c3cc(OC4CCN(c5ncccn5)CC4)ccc23)nc1C(F)(F)F] | 780 | 1.78 | 9 | |
| I-240 | 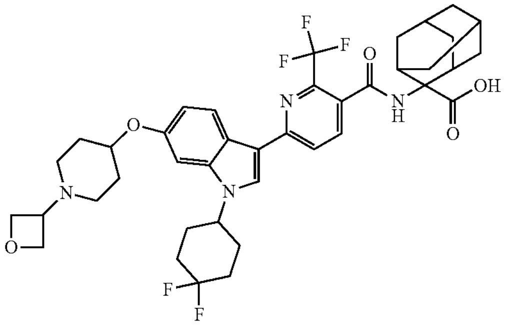 [SMILES: O=C(NC1(C(=O)O)C2CC3CC(C2)CC1C3)c1ccc(-c2cn(C3CCC(F)(F)CC3)c3cc(OC4CCN(C5COC5)CC4)ccc23)nc1C(F)(F)F] | 757 | 1.15 | 9 | |

TABLE 39-continued
| Compound No. | Chemical Structure | [M + H] | Retention Time (min) | LC/MS Condition | Stereo-Chemistry |
|---|---|---|---|---|---|
| I-241 | 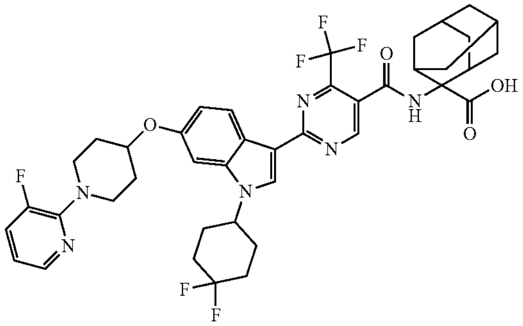 [SMILES: O=C(NC1(C(=O)O)C2CC3CC(C2)CC1C3)c1cnc(-c2cn(C3CCC(F)(F)CC3)c3cc(OC4CCN(c5ncccc5F)CC4)ccc23)nc1C(F)(F)F] | 797 | 1.87 | 9 | |
| I-242 | 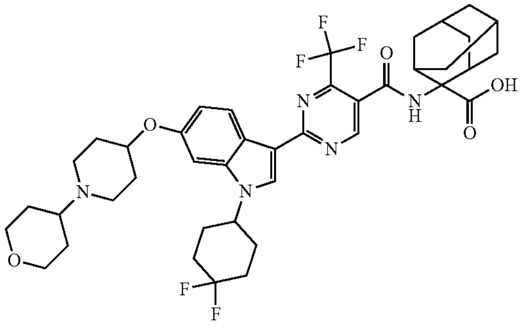 [SMILES: O=C(NC1(C(=O)O)C2CC3CC(C2)CC1C3)c1cnc(-c2cn(C3CCC(F)(F)CC3)c3cc(OC4CCN(C5CCOCC5)CC4)ccc23)nc1C(F)(F)F] | 786 | 1.22 | 9 | |
TABLE 40
| Compound No. | Chemical Structure | [M + H] | Retention Time (min) | LC/MS Condition | Stereo-Chemistry |
|---|---|---|---|---|---|
| I-243 | 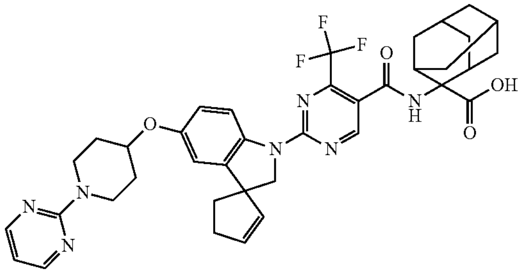 [SMILES: O=C(NC1(C(=O)O)C2CC3CC(C2)CC1C3)c1cnc(N2CC3(C=CCC3)c3cc(OC4CCN(c5ncccn5)CC4)ccc32)nc1C(F)(F)F] | 716 | 2.95 | 1 | a |
| I-244 | 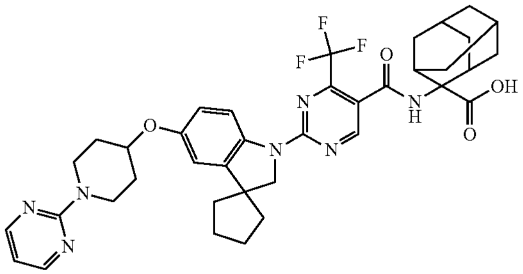 | 718 | 3.00 | 1 | |

TABLE 40-continued
| Compound No. | Chemical Structure | [M + H] | Retention Time (min) | LC/MS Condition | Stereo-Chemistry |
|---|---|---|---|---|---|
| I-245 | 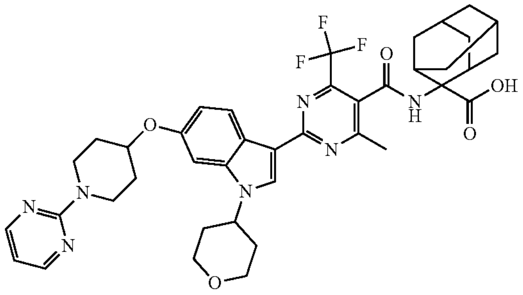 [SMILES: Cc1nc(-c2cn(C3CCOCC3)c3cc(OC4CCN(c5ncccn5)CC4)ccc23)nc(C(F)(F)F)c1C(=O)NC1(C(=O)O)C2CC3CC(C2)CC1C3] | 760 | 2.68 | 1 | |
| I-246 | 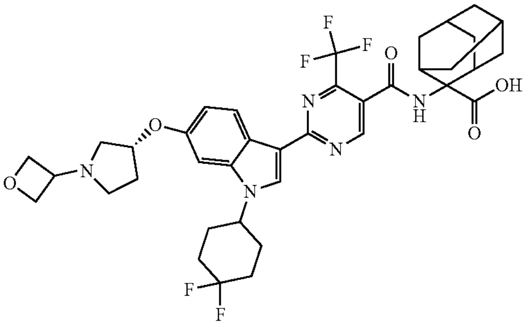 [SMILES: O=C(NC1(C(=O)O)C2CC3CC(C2)CC1C3)c1cnc(-c2cn(C3CCC(F)(F)CC3)c3cc(O[C@@H]4CCN(C5COC5)C4)ccc23)nc1C(F)(F)F] | 744 | 1.24 | 9 | |
| I-247 | 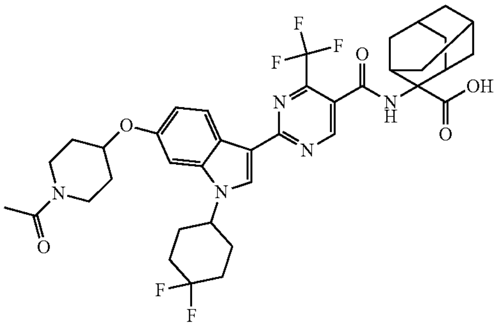 [SMILES: CC(=O)N1CCC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 744 | 1.49 | 10 | |
TABLE 41
| Compound No. | Chemical Structure | [M + H] | Retention Time (min) | LC/MS Condition | Stereo-Chemistry |
|---|---|---|---|---|---|
| I-248 | 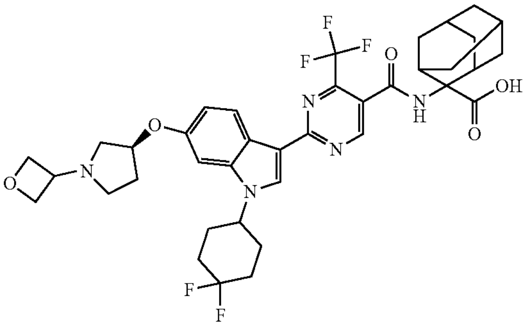 [SMILES: O=C(NC1(C(=O)O)C2CC3CC(C2)CC1C3)c1cnc(-c2cn(C3CCC(F)(F)CC3)c3cc(O[C@H]4CCN(C5COC5)C4)ccc23)nc1C(F)(F)F] | 744 | 1.25 | 9 | |

TABLE 41-continued
| Compound No. | Chemical Structure | [M + H] | Retention Time (min) | LC/MS Condition | Stereo-Chemistry |
|---|---|---|---|---|---|
| I-249 | 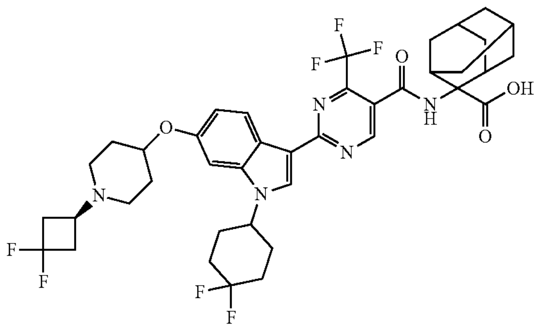 | 792 | 1.36 | 9 | |
| I-250 | 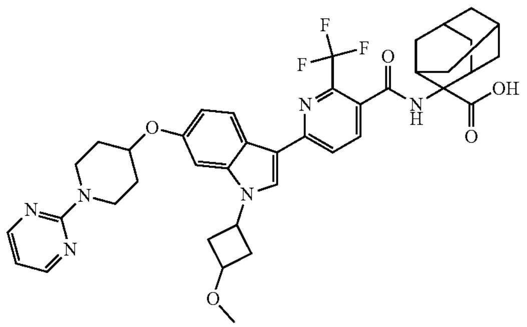 [SMILES: COC1CC(n2cc(-c3ccc(C(=O)NC4(C(=O)O)C5CC6CC(C5)CC4C6)c(C(F)(F)F)n3)c3ccc(OC4CCN(c5ncccn5)CC4)cc32)C1] | 745 | 1.71 | 9 | c |
| I-251 | 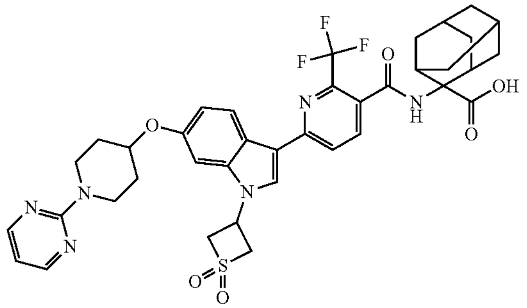 [SMILES: O=C(NC1(C(=O)O)C2CC3CC(C2)CC1C3)c1ccc(-c2cn(C3CS(=O)(=O)C3)c3cc(OC4CCN(c5ncccn5)CC4)ccc23)nc1C(F)(F)F] | 765 | 1.58 | 9 | |
| I-252 | 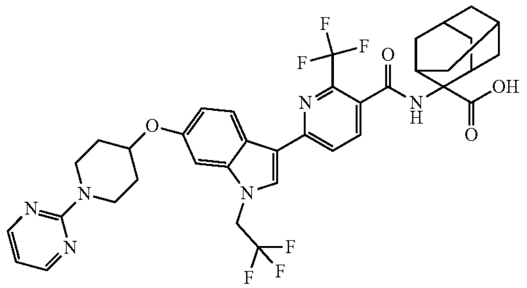 [SMILES: O=C(NC1(C(=O)O)C2CC3CC(C2)CC1C3)c1ccc(-c2cn(CC(F)(F)F)c3cc(OC4CCN(c5ncccn5)CC4)ccc23)nc1C(F)(F)F] | 743 | 1.70 | 9 | |

TABLE 42
| Compound No. | Chemical Structure | [M + H] | Retention Time (min) | LC/MS Condition | Stereo-Chemistry |
|---|---|---|---|---|---|
| I-253 | 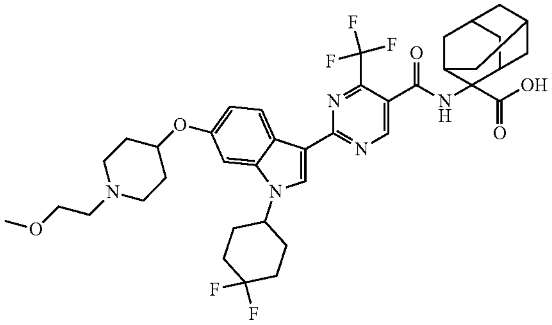 [SMILES: COCCN1CCC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 760 | 1.19 | 10 | |
| I-254 | 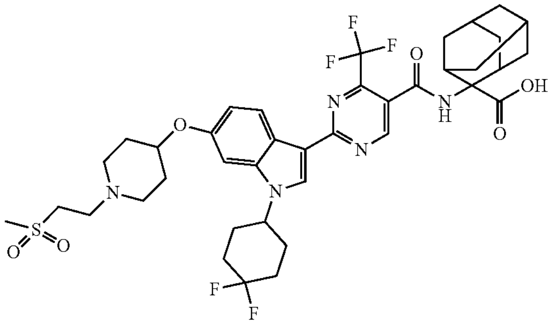 [SMILES: CS(=O)(=O)CCN1CCC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 808 | 1.18 | 10 | |
| I-255 | 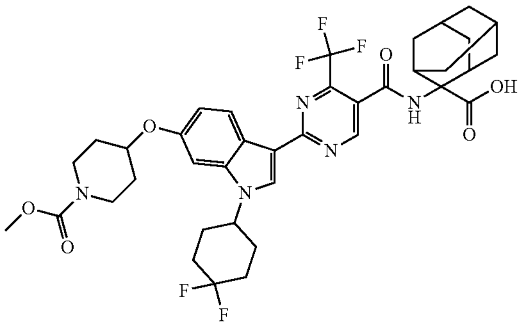 [SMILES: COC(=O)N1CCC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 760 | 1.64 | 10 | |
| I-256 | 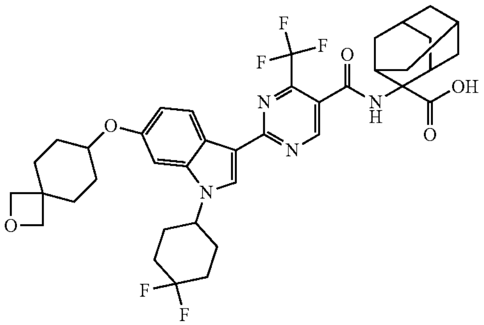 [SMILES: O=C(NC1(C(=O)O)C2CC3CC(C2)CC1C3)c1cnc(-c2cn(C3CCC(F)(F)CC3)c3cc(OC4CCC5(CC4)COC5)ccc23)nc1C(F)(F)F] | 743 | 1.67 | 10 | |

TABLE 42-continued
| Compound No. | Chemical Structure | [M + H] | Retention Time (min) | LC/MS Condition | Stereo-Chemistry |
|---|---|---|---|---|---|
| I-257 | 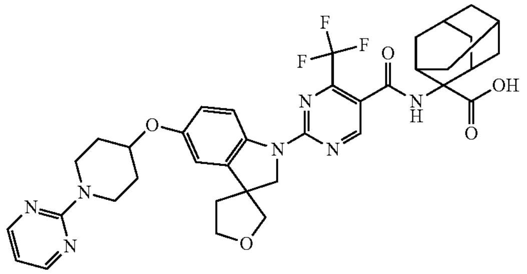 [SMILES: O=C(NC1(C(=O)O)C2CC3CC(C2)CC1C3)c1cnc(N2CC3(CCOC3)c3cc(OC4CCN(c5ncccn5)CC4)ccc32)nc1C(F)(F)F] | 720 | 2.63 | 1 | a |
TABLE 43
| Compound No. | Chemical Structure | [M + H] | Retention Time (min) | LC/MS Condition | Stereo-Chemistry |
|---|---|---|---|---|---|
| I-258 | 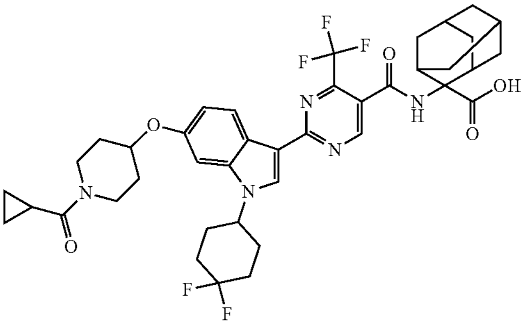 [SMILES: O=C(NC1(C(=O)O)C2CC3CC(C2)CC1C3)c1cnc(-c2cn(C3CCC(F)(F)CC3)c3cc(OC4CCN(C(=O)C5CC5)CC4)ccc23)nc1C(F)(F)F] | 770 | 1.67 | 11 | |
| I-259 | 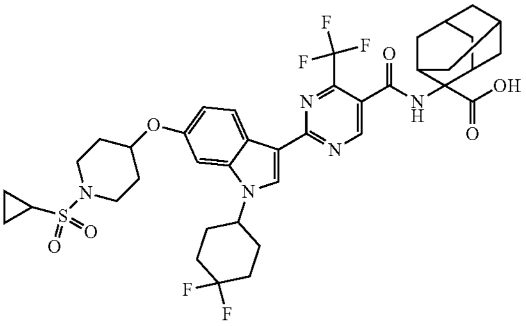 [SMILES: O=C(NC1(C(=O)O)C2CC3CC(C2)CC1C3)c1cnc(-c2cn(C3CCC(F)(F)CC3)c3cc(OC4CCN(S(=O)(=O)C5CC5)CC4)ccc23)nc1C(F)(F)F] | 806 | 1.63 | 10 | |
| I-260 | 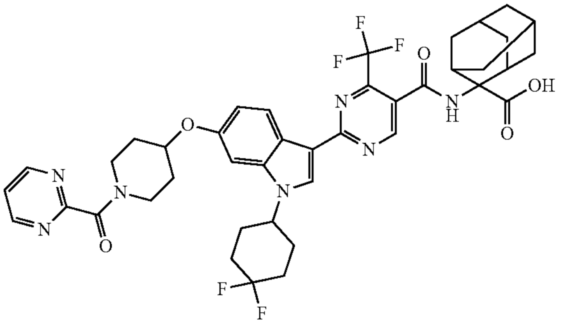 [SMILES: O=C(NC1(C(=O)O)C2CC3CC(C2)CC1C3)c1cnc(-c2cn(C3CCC(F)(F)CC3)c3cc(OC4CCN(C(=O)c5ncccn5)CC4)ccc23)nc1C(F)(F)F] | 808 | 1.47 | 10 | |

TABLE 43-continued
| Compound No. | Chemical Structure | [M + H] | Retention Time (min) | LC/MS Condition | Stereo-Chemistry |
|---|---|---|---|---|---|
| I-261 | 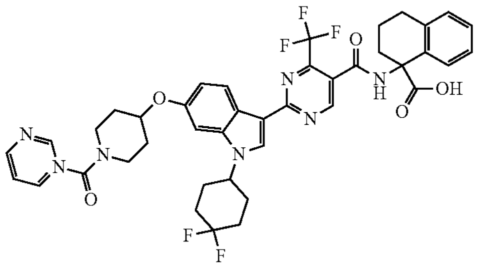 | 776 | 1.68 | 9 | a |
| I-262 | 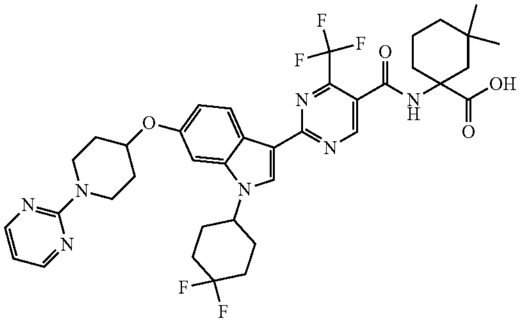 [SMILES: CC1(C)CCCC(NC(=O)c2cnc(-c3cn(C4CCC(F)(F)CC4)c4cc(OC5CCN(c6ncccn6)CC5)ccc34)nc2C(F)(F)F)(C(=O)O)C1] | 756 | 1.73 | 9 | a |
TABLE 44
| Compound No. | Chemical Structure | [M + H] | Retention Time (min) | LC/MS Condition | Stereo-Chemistry |
|---|---|---|---|---|---|
| I-263 | 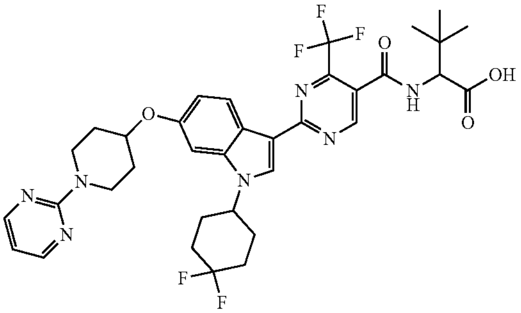 [SMILES: CC(C)(C)C(NC(=O)c1cnc(-c2cn(C3CCC(F)(F)CC3)c3cc(OC4CCN(c5ncccn5)CC4)ccc23)nc1C(F)(F)F)C(=O)O] | 716 | 1.62 | 9 | a |
| I-264 | 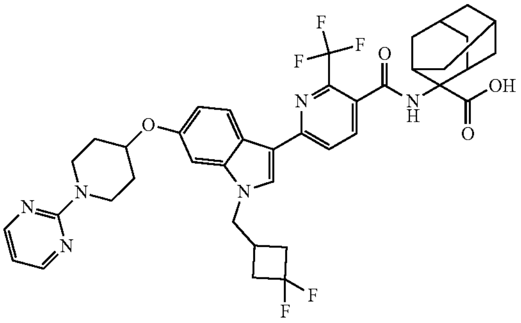 [SMILES: O=C(NC1(C(=O)O)C2CC3CC(C2)CC1C3)c1ccc(-c2cn(CC3CC(F)(F)C3)c3cc(OC4CCN(c5ncccn5)CC4)ccc23)nc1C(F)(F)F] | 765 | 1.72 | 10 | |

TABLE 44-continued
| Compound No. | Chemical Structure | [M + H] | Retention Time (min) | LC/MS Condition | Stereo-Chemistry |
|---|---|---|---|---|---|
| I-265 | 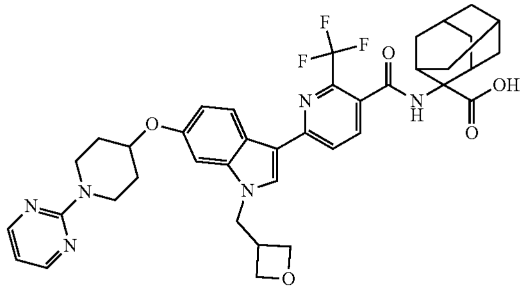 [SMILES: O=C(NC1(C(=O)O)C2CC3CC(C2)CC1C3)c1ccc(-c2cn(CC3COC3)c3cc(OC4CCN(c5ncccn5)CC4)ccc23)nc1C(F)(F)F] | 731 | 1.55 | 10 | |
| I-266 | 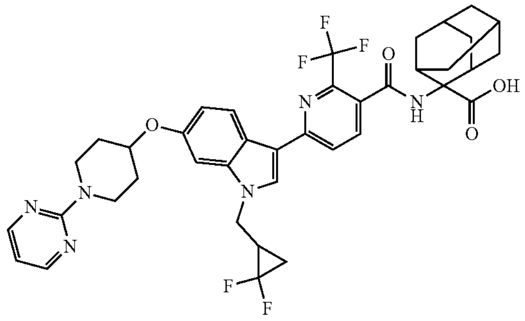 [SMILES: O=C(NC1(C(=O)O)C2CC3CC(C2)CC1C3)c1ccc(-c2cn(CC3CC3(F)F)c3cc(OC4CCN(c5ncccn5)CC4)ccc23)nc1C(F)(F)F] | 751 | 1.68 | 10 | a |
| I-267 | 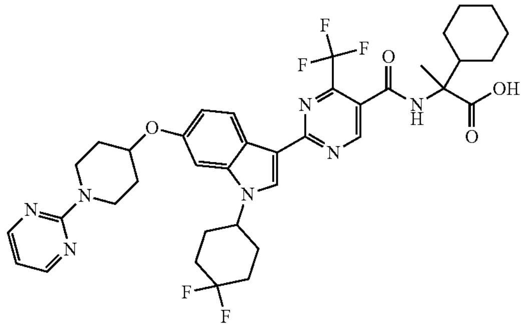 [SMILES: CC(NC(=O)c1cnc(-c2cn(C3CCC(F)(F)CC3)c3cc(OC4CCN(c5ncccn5)CC4)ccc23)nc1C(F)(F)F)(C(=O)O)C1CCCCC1] | 756 | 1.71 | 10 | a |
TABLE 45
| Compound No. | Chemical Structure | [M + H] | Retention Time (min) | LC/MS Condition | Stereo-Chemistry |
|---|---|---|---|---|---|
| I-268 | 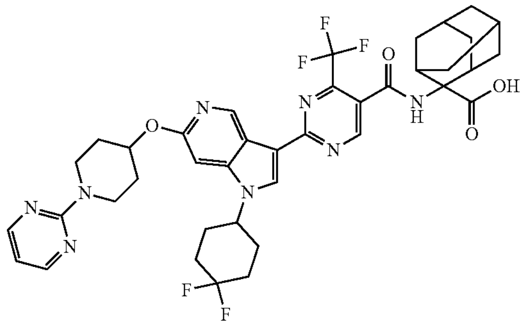 [SMILES: O=C(NC1(C(=O)O)C2CC3CC(C2)CC1C3)c1cnc(-c2cn(C3CCC(F)(F)CC3)c3cc(OC4CCN(c5ncccn5)CC4)ncc23)nc1C(F)(F)F] | 781 | 1.56 | 9 | |

TABLE 45-continued
| Compound No. | Chemical Structure | [M + H] | Retention Time (min) | LC/MS Condition | Stereo-Chemistry |
|---|---|---|---|---|---|
| I-269 | 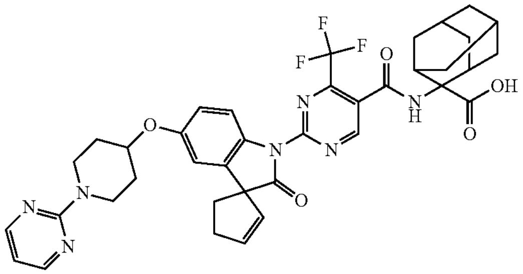 [SMILES: O=C(NC1(C(=O)O)C2CC3CC(C2)CC1C3)c1cnc(N2C(=O)C3(C=CCC3)c3cc(OC4CCN(c5ncccn5)CC4)ccc32)nc1C(F)(F)F] | 730 | 2.68 | 1 | a |
| I-270 | 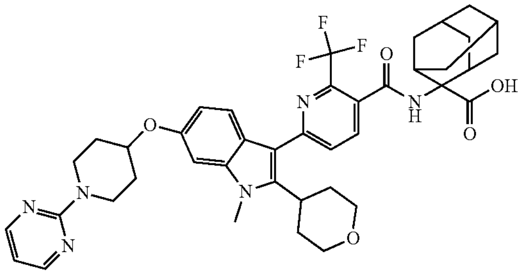 [SMILES: Cn1c(C2CCOCC2)c(-c2ccc(C(=O)NC3(C(=O)O)C4CC5CC(C4)CC3C5)c(C(F)(F)F)n2)c2ccc(OC3CCN(c4ncccn4)CC3)cc21] | 759 | 2.62 | 1 | |
| I-271 | 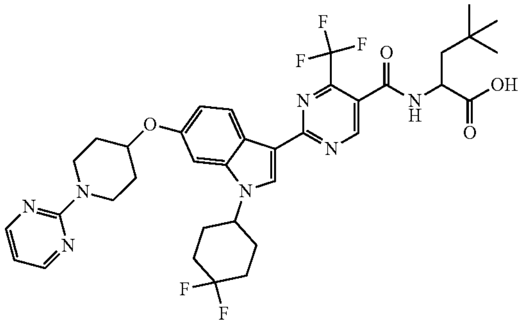 [SMILES: CC(C)(C)CC(NC(=O)c1cnc(-c2cn(C3CCC(F)(F)CC3)c3cc(OC4CCN(c5ncccn5)CC4)ccc23)nc1C(F)(F)F)C(=O)O] | 730 | 1.67 | 9 | a |
| I-272 | 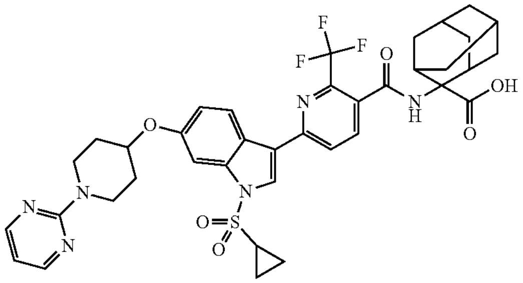 [SMILES: O=C(NC1(C(=O)O)C2CC3CC(C2)CC1C3)c1ccc(-c2cn(S(=O)(=O)C3CC3)c3cc(OC4CCN(c5ncccn5)CC4)ccc23)nc1C(F)(F)F] | 765 | 1.70 | 9 | |

TABLE 46
| Compound No. | Chemical Structure | [M + H] | Retention Time (min) | LC/MS Condition | Stereo-Chemistry |
|---|---|---|---|---|---|
| I-273 | 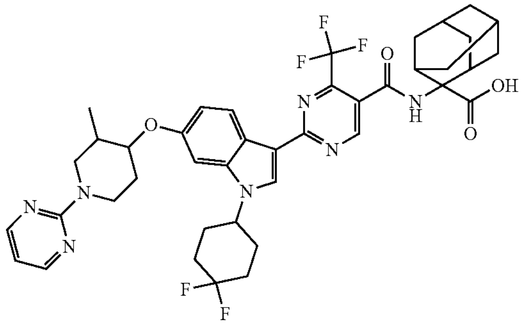 [SMILES: CC1CN(c2ncccn2)CCC1Oc1ccc2c(-c3ncc(C(=O)NC4(C(=O)O)C5CC6CC(C5)CC4C6)c(C(F)(F)F)n3)cn(C3CCC(F)(F)CC3)c2c1] | 794 | 1.82 | 10 | c |
| I-274 | 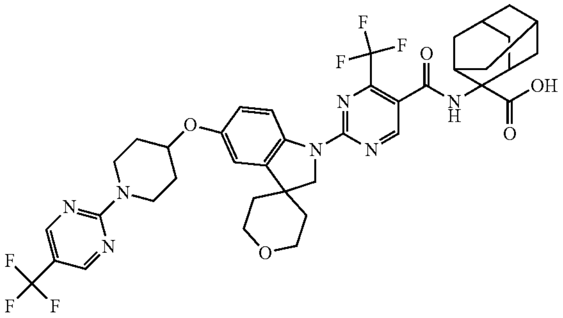 [SMILES: O=C(NC1(C(=O)O)C2CC3CC(C2)CC1C3)c1cnc(N2CC3(CCOCC3)c3cc(OC4CCN(c5ncc(C(F)(F)F)cn5)CC4)ccc32)nc1C(F)(F)F] | 802 | 3.31 | 1 | |
| I-275 | 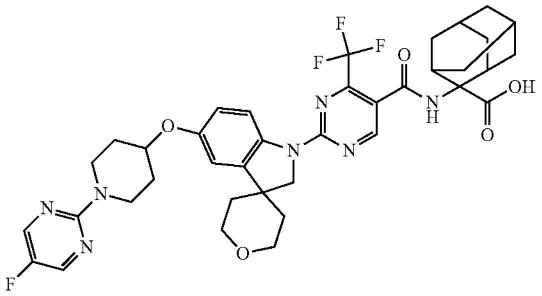 [SMILES: O=C(NC1(C(=O)O)C2CC3CC(C2)CC1C3)c1cnc(N2CC3(CCOCC3)c3cc(OC4CCN(c5ncc(F)cn5)CC4)ccc32)nc1C(F)(F)F] | 752 | 2.84 | 1 | |
| I-276 | 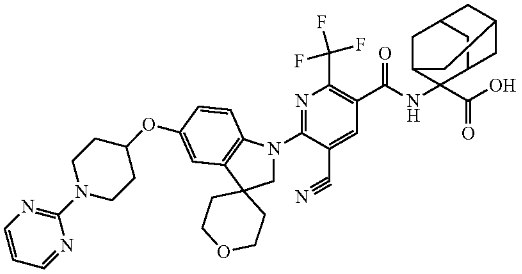 [SMILES: N#Cc1cc(C(=O)NC2(C(=O)O)C3CC4CC(C3)CC2C4)c(C(F)(F)F)nc1N1CC2(CCOCC2)c2cc(OC3CCN(c4ncccn4)CC3)ccc21] | 758 | 2.80 | 1 | |

TABLE 46-continued
| Compound No. | Chemical Structure | [M + H] | Retention Time (min) | LC/MS Condition | Stereo-Chemistry |
|---|---|---|---|---|---|
| I-277 | 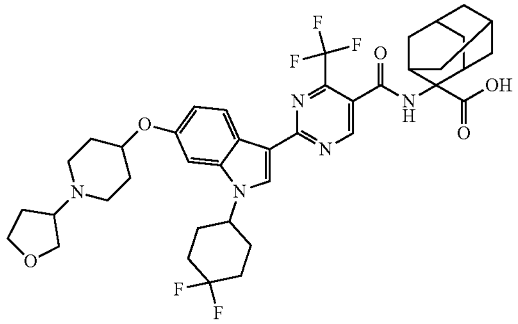 [SMILES: O=C(NC1(C(=O)O)C2CC3CC(C2)CC1C3)c1cnc(-c2cn(C3CCC(F)(F)CC3)c3cc(OC4CCN(C5CCOC5)CC4)ccc23)nc1C(F)(F)F] | 772 | 1.35 | 9 | a |
TABLE 47
| Compound No. | Chemical Structure | [M + H] | Retention Time (min) | LC/MS Condition | Stereo-Chemistry |
|---|---|---|---|---|---|
| I-278 | 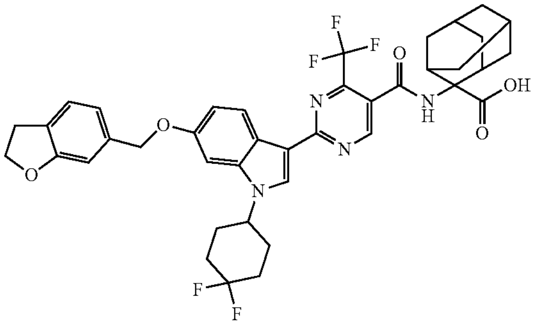 [SMILES: O=C(NC1(C(=O)O)C2CC3CC(C2)CC1C3)c1cnc(-c2cn(C3CCC(F)(F)CC3)c3cc(OCc4ccc5c(c4)OCC5)ccc23)nc1C(F)(F)F] | 751 | 1.80 | 9 | |
| I-279 | 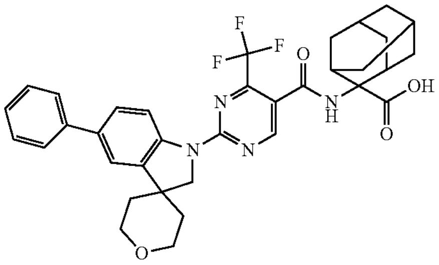 [SMILES: O=C(NC1(C(=O)O)C2CC3CC(C2)CC1C3)c1cnc(N2CC3(CCOCC3)c3cc(-c4ccccc4)ccc32)nc1C(F)(F)F] | 633 | 1.78 | 9 | |
| I-280 | 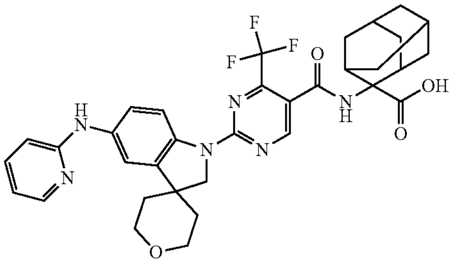 [SMILES: O=C(NC1(C(=O)O)C2CC3CC(C2)CC1C3)c1cnc(N2CC3(CCOCC3)c3cc(Nc4ccccn4)ccc32)nc1C(F)(F)F] | 649 | 1.03 | 10 | |

TABLE 47-continued
| Compound No. | Chemical Structure | [M + H] | Retention Time (min) | LC/MS Condition | Stereo-Chemistry |
|---|---|---|---|---|---|
| I-281 | 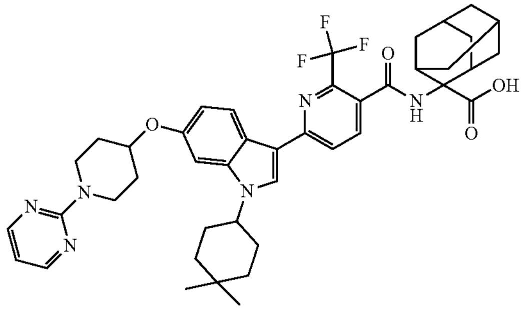 [SMILES: CC1(C)CCC(n2cc(-c3ccc(C(=O)NC4(C(=O)O)C5CC6CC(C5)CC4C6)c(C(F)(F)F)n3)c3ccc(OC4CCN(c5ncccn5)CC4)cc32)CC1] | 771 | 3.12 | 1 | |
| I-282 | 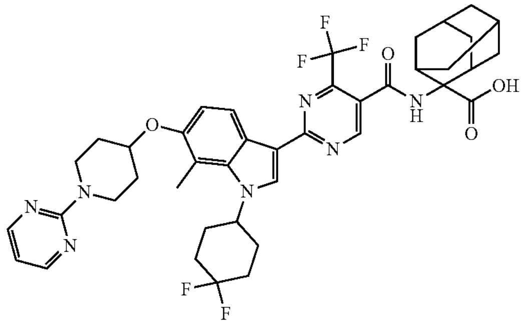 [SMILES: Cc1c(OC2CCN(c3ncccn3)CC2)ccc2c(-c3ncc(C(=O)NC4(C(=O)O)C5CC6CC(C5)CC4C6)c(C(F)(F)F)n3)cn(C3CCC(F)(F)CC3)c12] | 794 | 2.69 | 1 | |
| I-283 | 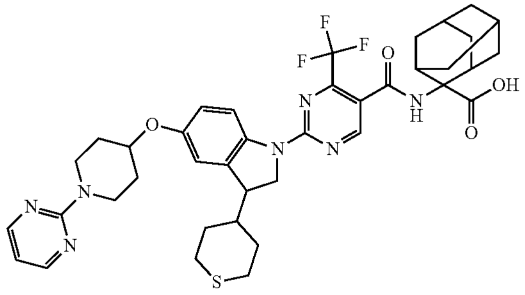 [SMILES: O=C(NC1(C(=O)O)C2CC3CC(C2)CC1C3)c1cnc(N2CC(C3CCSCC3)c3cc(OC4CCN(c5ncccn5)CC4)ccc32)nc1C(F)(F)F] | 750 | 2.85 | 1 | |
TABLE 48
| Compound No. | Chemical Structure | [M + H] | Retention Time (min) | LC/MS Condition | Stereo-Chemistry |
|---|---|---|---|---|---|
| I-284 | 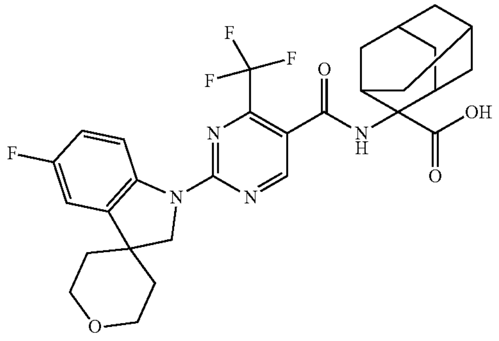 [SMILES: O=C(NC1(C(=O)O)C2CC3CC(C2)CC1C3)c1cnc(N2CC3(CCOCC3)c3cc(F)ccc32)nc1C(F)(F)F] | 575 | 2.66 | 1 | |

TABLE 48-continued
| Compound No. | Chemical Structure | [M + H] | Retention Time (min) | LC/MS Condition | Stereo-Chemistry |
|---|---|---|---|---|---|
| I-285 | 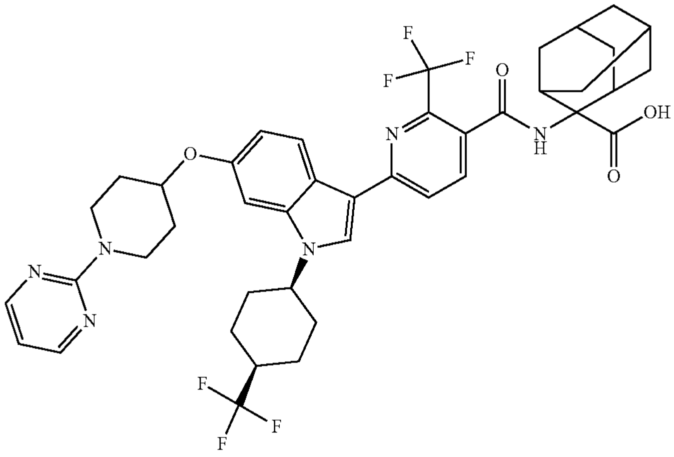 [SMILES: O=C(NC1(C(=O)O)C2CC3CC(C2)CC1C3)c1ccc(-c2cn([C@H]3CC[C@@H](C(F)(F)F)CC3)c3cc(OC4CCN(c5ncccn5)CC4)ccc23)nc1C(F)(F)F] | 811 | 3.19 | 1 | |
| I-286 | 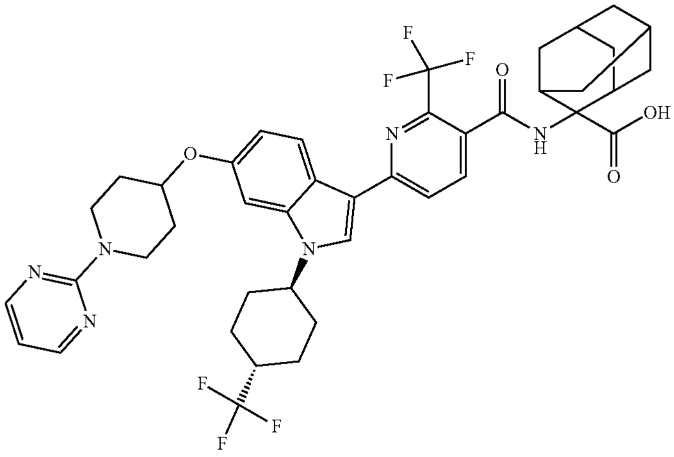 [SMILES: O=C(NC1(C(=O)O)C2CC3CC(C2)CC1C3)c1ccc(-c2cn([C@H]3CC[C@H](C(F)(F)F)CC3)c3cc(OC4CCN(c5ncccn5)CC4)ccc23)nc1C(F)(F)F] | 811 | 2.99 | 1 | |
| I-287 | 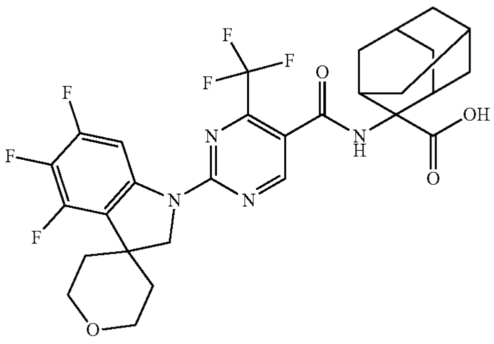 [SMILES: O=C(NC1(C(=O)O)C2CC3CC(C2)CC1C3)c1cnc(N2CC3(CCOCC3)c3c2cc(F)c(F)c3F)nc1C(F)(F)F] | 611 | 2.74 | 1 | |

TABLE 48-continued
| Compound No. | Chemical Structure | [M + H] | Retention Time (min) | LC/MS Condition | Stereo-Chemistry |
|---|---|---|---|---|---|
| I-288 | 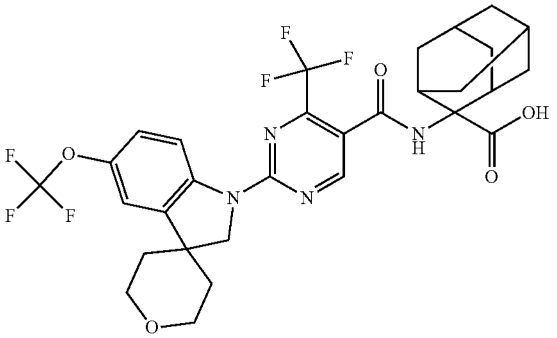 [SMILES: O=C(NC1(C(=O)O)C2CC3CC(C2)CC1C3)c1cnc(N2CC3(CCOCC3)c3cc(OC(F)(F)F)ccc32)nc1C(F)(F)F] | 841 | 2.80 | 1 | |
| I-289 | 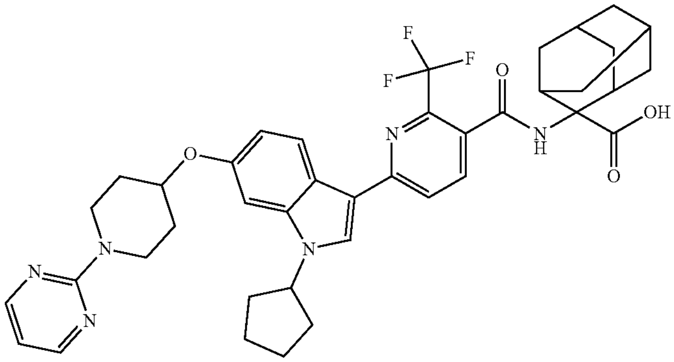 [SMILES: O=C(NC1(C(=O)O)C2CC3CC(C2)CC1C3)c1ccc(-c2cn(C3CCCC3)c3cc(OC4CCN(c5ncccn5)CC4)ccc23)nc1C(F)(F)F] | 729 | 1.82 | 10 | |
TABLE 49
| Compound No. | Chemical Structure | [M + H] | Retention Time (min) | LC/MS Condition | Stereo-Chemistry |
|---|---|---|---|---|---|
| I-290 | 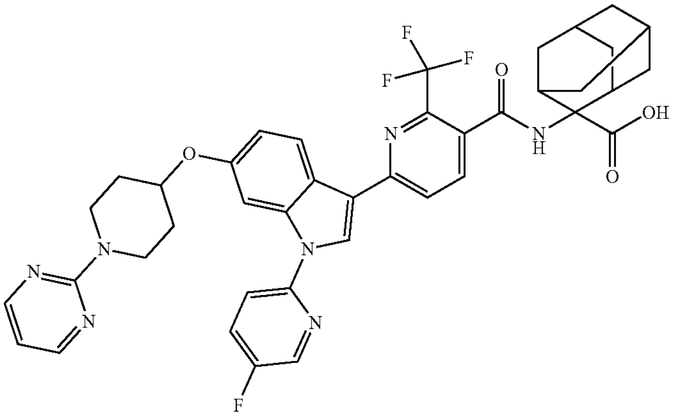 [SMILES: O=C(NC1(C(=O)O)C2CC3CC(C2)CC1C3)c1ccc(-c2cn(-c3ccc(F)cn3)c3cc(OC4CCN(c5ncccn5)CC4)ccc23)nc1C(F)(F)F] | 756 | 1.76 | 10 | |

TABLE 49-continued
| Compound No. | Chemical Structure | [M + H] | Retention Time (min) | LC/MS Condition | Stereo-Chemistry |
|---|---|---|---|---|---|
| I-291 | 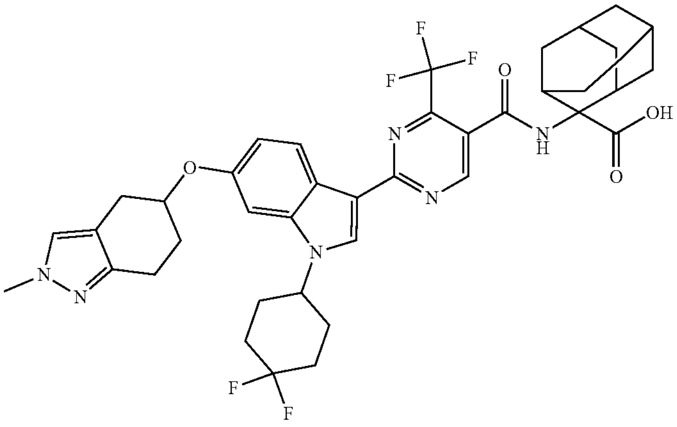 [SMILES: Cn1cc2c(n1)CCC(Oc1ccc3c(-c4ncc(C(=O)NC5(C(=O)O)C6CCC7CC(C6)CC5C7)c(C(F)(F)F)n4)cn(C4CCC(F)(F)CC4)c3c1)C2] | 753 | 1.61 | 9 | b |
| I-292 | 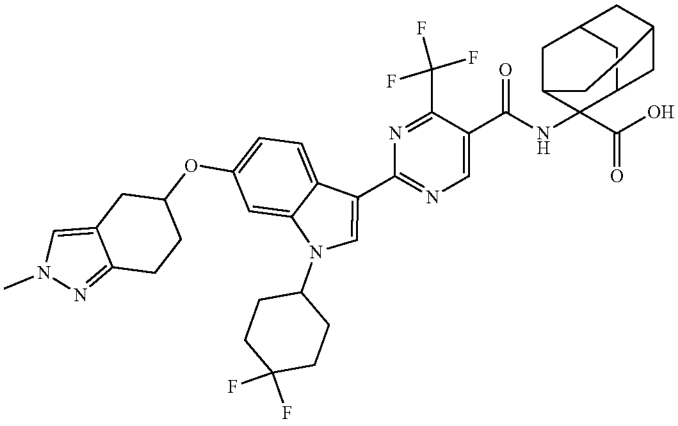 [SMILES: Cn1cc2c(n1)CCC(Oc1ccc3c(-c4ncc(C(=O)NC5(C(=O)O)C6CCC7CC(C6)CC5C7)c(C(F)(F)F)n4)cn(C4CCC(F)(F)CC4)c3c1)C2] | 753 | 1.61 | 9 | b |
| I-293 | 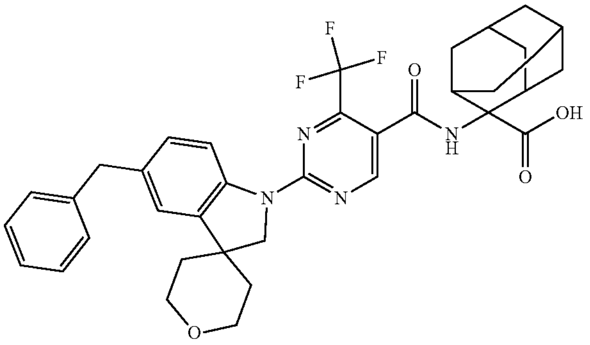 [SMILES: O=C(NC1(C(=O)O)C2CCC3CC(C2)CC1C3)c1cnc(N2CC3(CCOCC3)c3cc(Cc4ccccc4)ccc32)nc1C(F)(F)F] | 647 | 1.79 | 10 | |

TABLE 49-continued
| Compound No. | Chemical Structure | [M + H] | Retention Time (min) | LC/MS Condition | Stereo-Chemistry |
|---|---|---|---|---|---|
| I-294 | 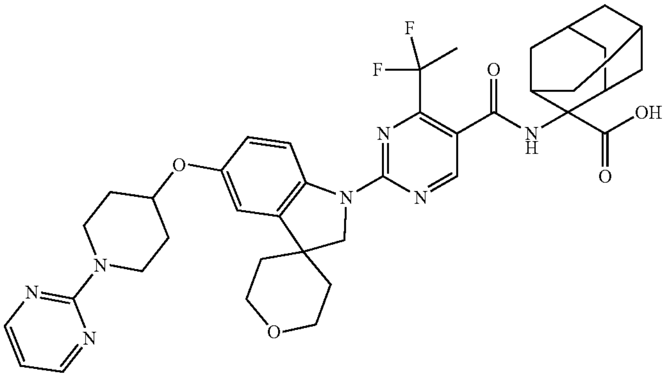 [SMILES: CC(F)(F)c1nc(N2CC3(CCOCC3)c3cc(OC4CCN(c5ncccn5)CC4)ccc32)ncc1C(=O)NC1(C(=O)O)C2CCC3CC(C2)CC1C3] | 730 | 2.57 | 1 | |
TABLE 50
| Compound No. | Chemical Structure | [M + H] | Retention Time (min) | LC/MS Condition | Stereo-Chemistry |
|---|---|---|---|---|---|
| I-295 | 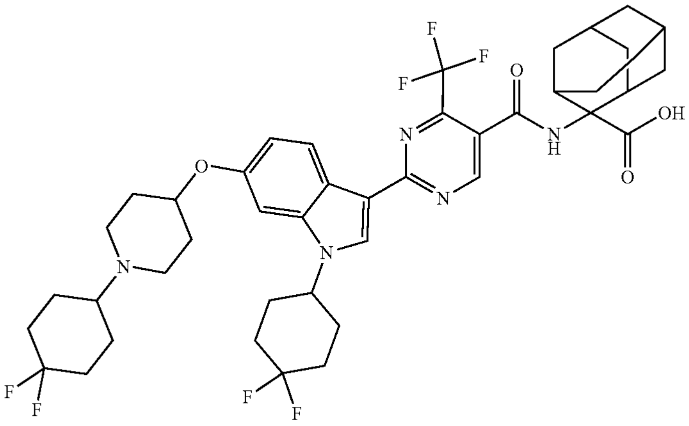 [SMILES: O=C(NC1(C(=O)O)C2CCC3CC(C2)CC1C3)c1cnc(-c2cn(C3CCC(F)(F)CC3)c3cc(OC4CCN(C5CCC(F)(F)CC5)CC4)ccc23)nc1C(F)(F)F] | 820 | 1.26 | 10 | |
| I-296 | 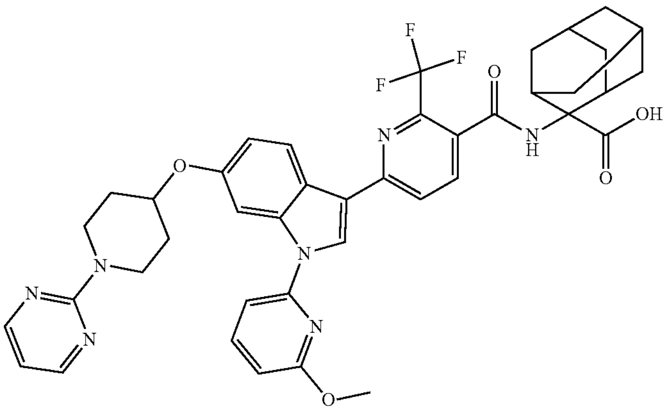 [SMILES: COc1cccc(-n2cc(-c3ccc(C(=O)NC4(C(=O)O)C5CCC6CC(C5)CC4C6)c(C(F)(F)F)n3)c3ccc(OC4CCN(c5ncccn5)CC4)cc32)n1] | 768 | 1.85 | 9 | |

TABLE 50-continued
| Compound No. | Chemical Structure | [M + H] | Retention Time (min) | LC/MS Condition | Stereo-Chemistry |
|---|---|---|---|---|---|
| I-297 | 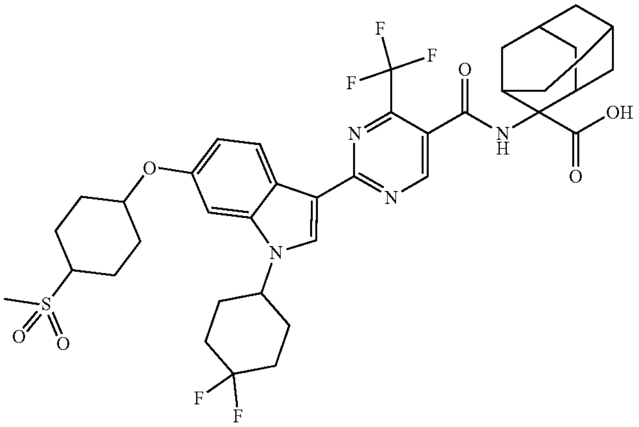 [SMILES: CS(=O)(=O)C1CCC(Oc2ccc3c(-c4ncc(C(=O)NC5(C(=O)O)C6CCC7CC(C6)CC5C7)c(C(F)(F)F)n4)cn(C4CCC(F)(F)CC4)c3c2)CC1] | 779 | 1.57 | 9 | c |
| I-298 | 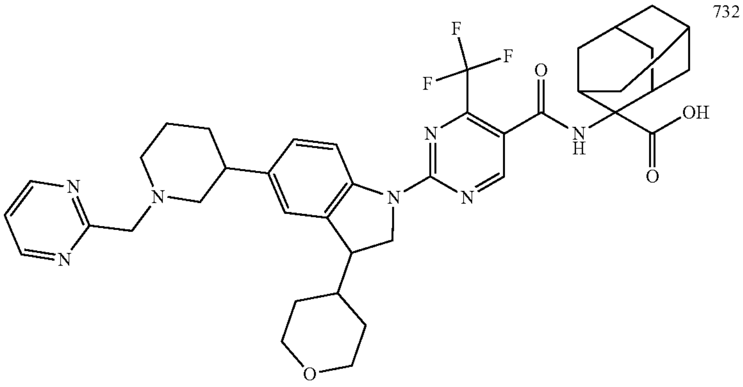 | 732 | 1.67 | 1 | a |
| I-299 | 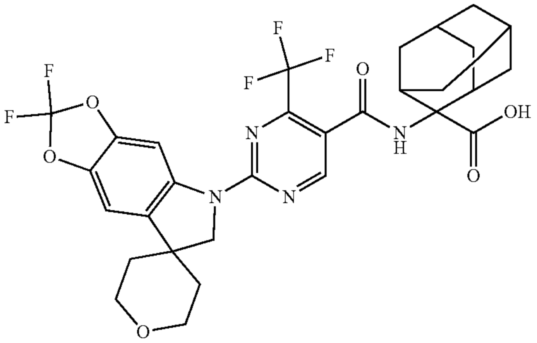 [SMILES: O=C(NC1(C(=O)O)C2CCC3CC(C2)CC1C3)c1cnc(N2CC3(CCOCC3)c3cc4c(cc32)OC(F)(F)O4)nc1C(F)(F)F] | 637 | 2.88 | 1 | |
| I-300 | 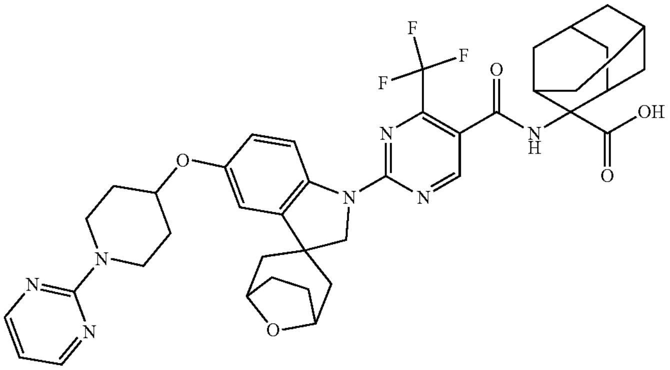 [SMILES: O=C(NC1(C(=O)O)C2CCC3CC(C2)CC1C3)c1cnc(N2CC3(CC4CCC(C3)O4)c3cc(OC4CCN(c5ncccn5)CC4)ccc32)nc1C(F)(F)F] | 760 | 2.63 | 1 | b |

TABLE 51
| Compound No. | Chemical Structure | [M + H] | Retention Time (min) | LC/MS Condition | Stereo-Chemistry |
|---|---|---|---|---|---|
| I-301 | 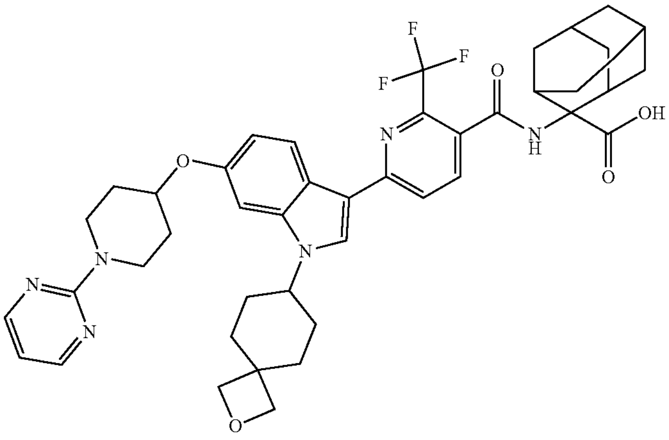 [SMILES: O=C(NC1(C(=O)O)C2CCC3CC(C2)CC1C3)c1ccc(-c2cn(C3CCC4(CC3)COC4)c3cc(OC4CCN(c5ncccn5)CC4)ccc23)nc1C(F)(F)F] | 785 | 2.69 | 1 | |
| I-302 | 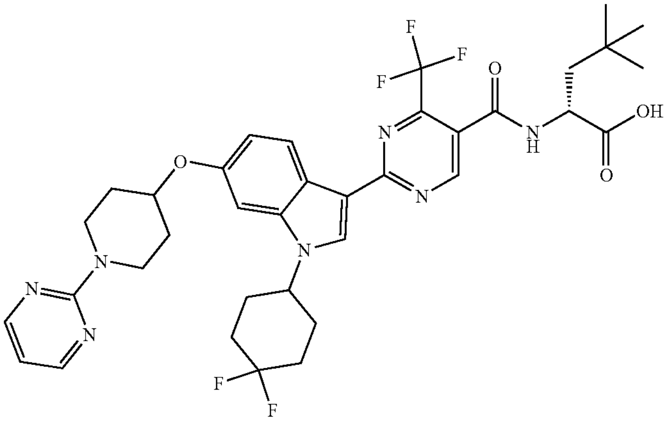 [SMILES: CC(C)(C)C[C@@H](NC(=O)c1cnc(-c2cn(C3CCC(F)(F)CC3)c3cc(OC4CCN(c5ncccn5)CC4)ccc23)nc1C(F)(F)F)C(=O)O] | 730 | 1.66 | 9 | |
| I-303 | 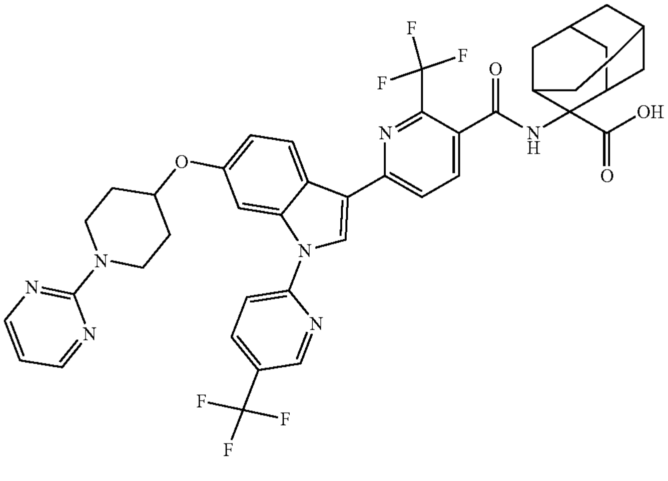 [SMILES: O=C(NC1(C(=O)O)C2CCC3CC(C2)CC1C3)c1ccc(-c2cn(-c3ccc(C(F)(F)F)cn3)c3cc(OC4CCN(c5ncccn5)CC4)ccc23)nc1C(F)(F)F] | 806 | 1.87 | 9 | |

TABLE 51-continued
| Compound No. | Chemical Structure | [M + H] | Retention Time (min) | LC/MS Condition | Stereo-Chemistry |
| --- | --- | --- | --- | --- | --- |
| I-304 | 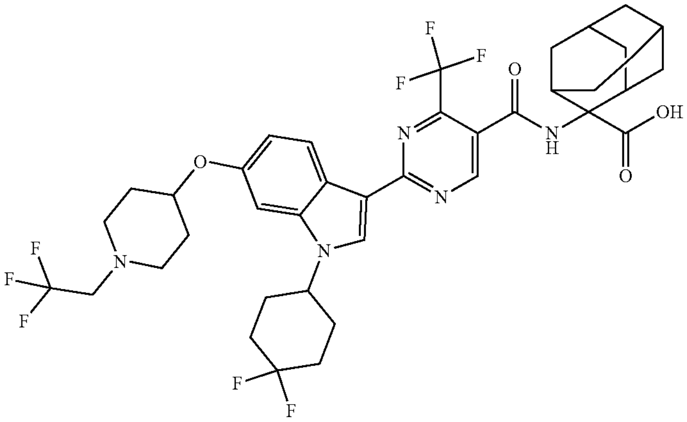 [SMILES: O=C(NC1(C(=O)O)C2CCC3CC(C2)CC1C3)c1cnc(-c2cn(C3CCC(F)(F)CC3)c3cc(OC4CCN(CC(F)(F)F)CC4)ccc23)nc1C(F)(F)F] | 784 | 1.78 | 10 | |
| I-305 | 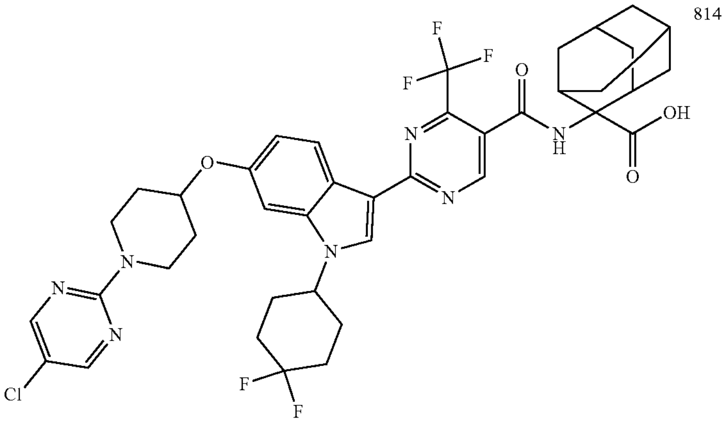 | 814 | 1.96 | 10 | |
TABLE 52
| Compound No. | Chemical Structure | [M + H] | Retention Time (min) | LC/MS Condition | Stereo-Chemistry |
| --- | --- | --- | --- | --- | --- |
| I-306 | 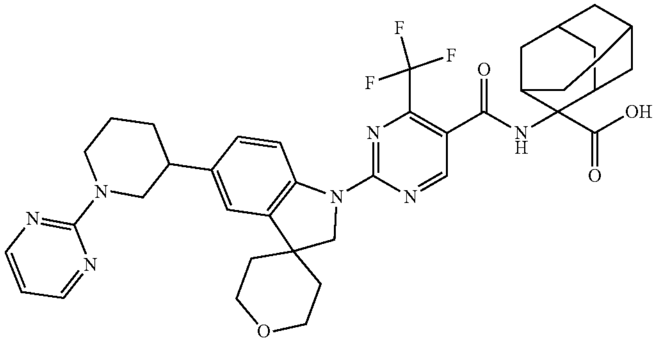 [SMILES: O=C(NC1(C(=O)O)C2CCC3CC(C2)CC1C3)c1cnc(N2CC3(CCOCC3)c3cc(C4CCCN(c5ncccn5)C4)ccc32)nc1C(F)(F)F] | 717 | 2.69 | 1 | a |

TABLE 52-continued
| Compound No. | Chemical Structure | [M + H] | Retention Time (min) | LC/MS Condition | Stereo-Chemistry |
|---|---|---|---|---|---|
| I-307 | 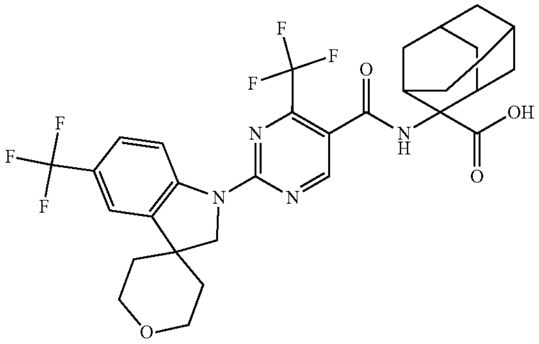 [SMILES: O=C(NC1(C(=O)O)C2CCC3CC(C2)CC1C3)c1cnc(N2CC3(CCOCC3)c3cc(C(F)(F)F)ccc32)nc1C(F)(F)F] | 625 | 2.82 | 1 | |
| I-308 | 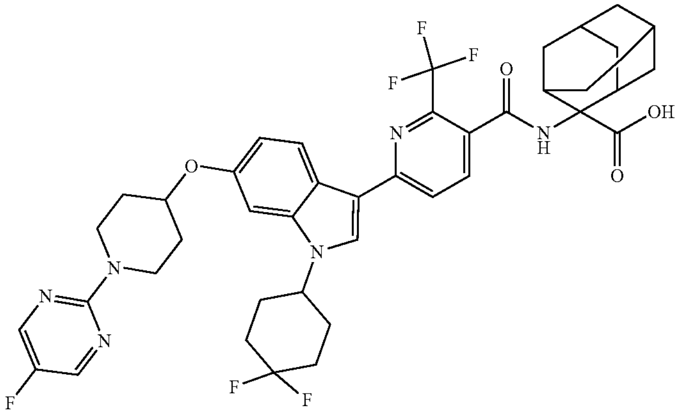 [SMILES: O=C(NC1(C(=O)O)C2CCC3CC(C2)CC1C3)c1ccc(-c2cn(C3CCC(F)(F)CC3)c3cc(OC4CCN(c5ncc(F)cn5)CC4)ccc23)nc1C(F)(F)F] | 797 | 3.01 | 1 | |
| I-309 | 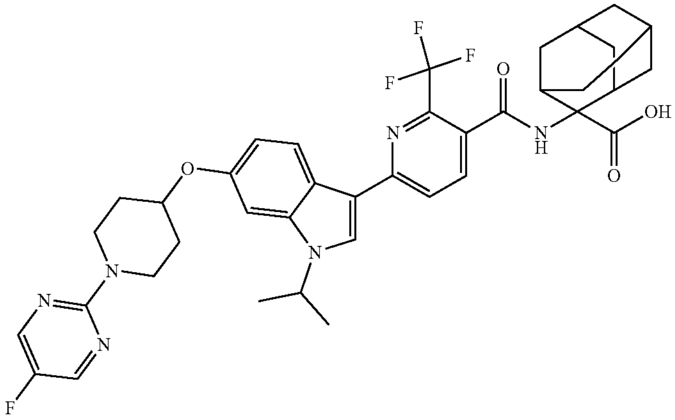 [SMILES: CC(C)n1cc(-c2ccc(C(=O)NC3(C(=O)O)C4CCC5CC(C4)CC3C5)c(C(F)(F)F)n2)c2ccc(OC3CCN(c4ncc(F)cn4)CC3)cc21] | 721 | 2.96 | 1 | |
| I-310 | 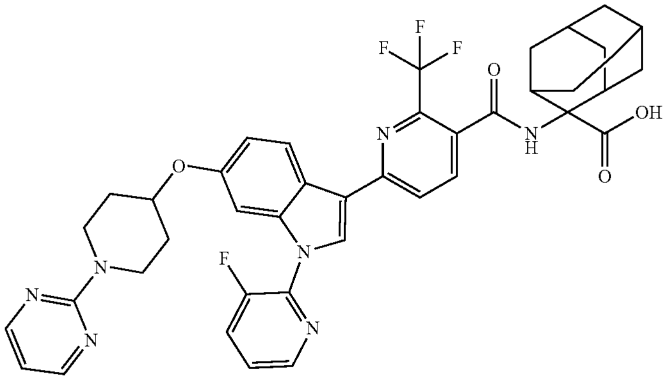 [SMILES: O=C(NC1(C(=O)O)C2CCC3CC(C2)CC1C3)c1ccc(-c2cn(-c3ncccc3F)c3cc(OC4CCN(c5ncccn5)CC4)ccc23)nc1C(F)(F)F] | 756 | 2.92 | 4 | |

TABLE 52-continued
| Compound No. | Chemical Structure | [M + H] | Retention Time (min) | LC/MS Condition | Stereo-Chemistry |
|---|---|---|---|---|---|
| I-311 | 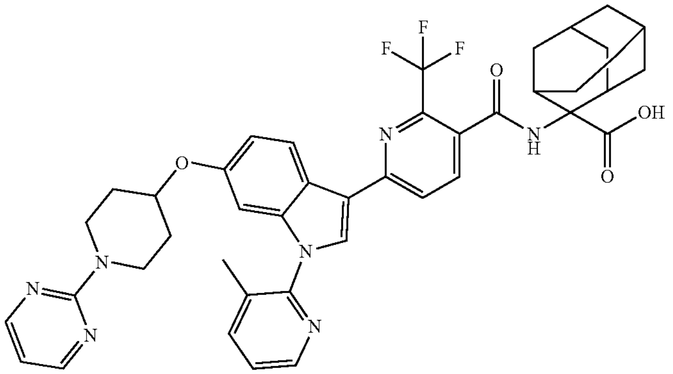 [SMILES: Cc1cccnc1-n1cc(-c2ccc(C(=O)NC3(C(=O)O)C4CCC5CC(C4)CC3C5)c(C(F)(F)F)n2)c2ccc(OC3CCN(c4ncccn4)CC3)cc21] | 752 | 2.88 | 4 | |
TABLE 53
| Compound No. | Chemical Structure | [M + H] | Retention Time (min) | LC/MS Condition | Stereo-Chemistry |
|---|---|---|---|---|---|
| I-312 | 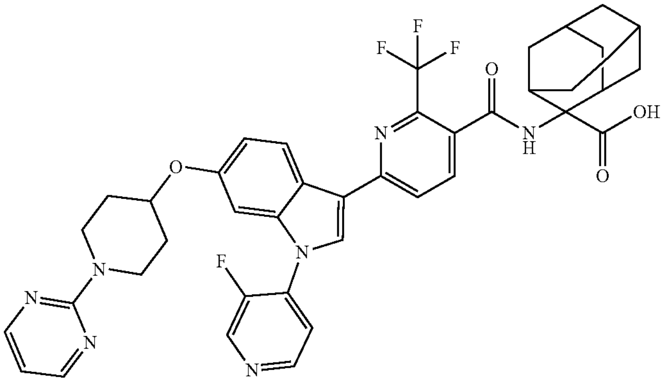 | 756 | 2.80 | 4 | |
| I-313 | 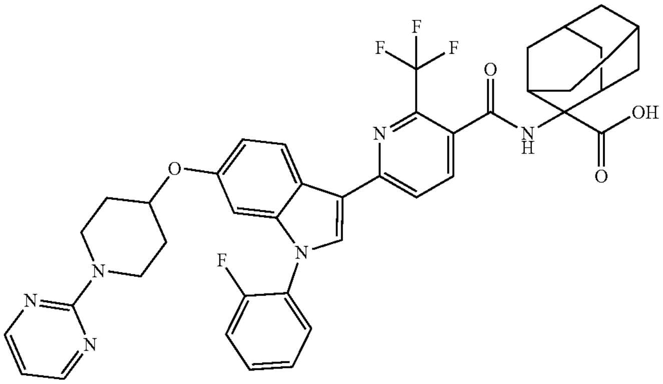 [SMILES: O=C(NC1(C(=O)O)C2CCC3CC(C2)CC1C3)c1ccc(-c2cn(-c3ccccc3F)c3cc(OC4CCN(c5ncccn5)CC4)ccc23)nc1C(F)(F)F] | 755 | 3.07 | 4 | |

TABLE 53-continued
| Compound No. | Chemical Structure | [M + H] | Retention Time (min) | LC/MS Condition | Stereo-Chemistry |
|---|---|---|---|---|---|
| I-314 | 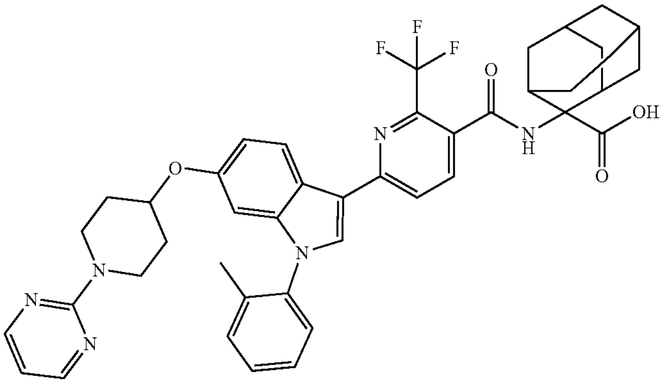 [SMILES: Cc1ccccc1-n1cc(-c2ccc(C(=O)NC3(C(=O)O)C4CCC5CC(C4)CC3C5)c(C(F)(F)F)n2)c2ccc(OC3CCN(c4ncccn4)CC3)cc21] | 751 | 3.19 | 4 | |
| I-315 | 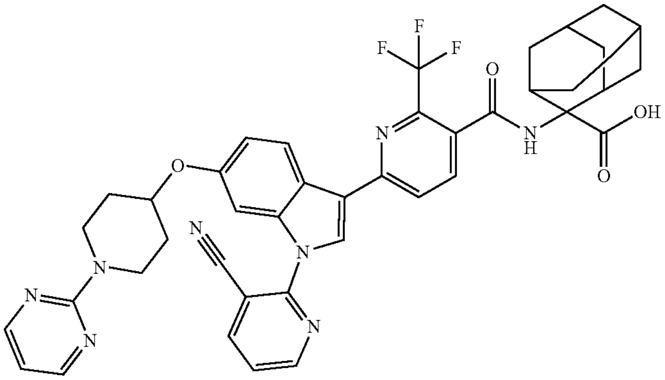 [SMILES: N#Cc1cccnc1-n1cc(-c2ccc(C(=O)NC3(C(=O)O)C4CCC5CC(C4)CC3C5)c(C(F)(F)F)n2)c2ccc(OC3CCN(c4ncccn4)CC3)cc21] | 762 | 2.92 | 4 | |
| I-316 | 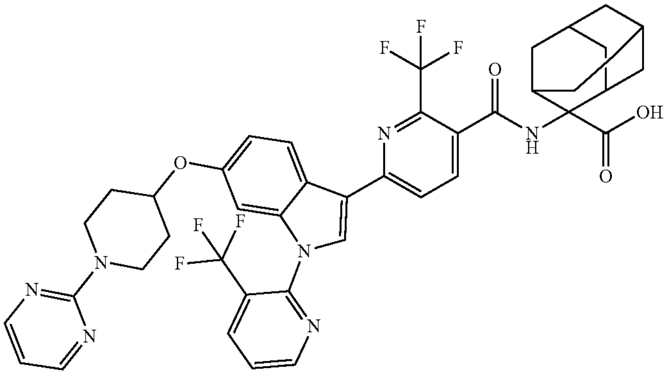 [SMILES: O=C(NC1(C(=O)O)C2CCC3CC(C2)CC1C3)c1ccc(-c2cn(-c3ncccc3C(F)(F)F)c3cc(OC4CCN(c5ncccn5)CC4)ccc23)nc1C(F)(F)F] | 806 | 2.92 | 4 | |
| I-317 | 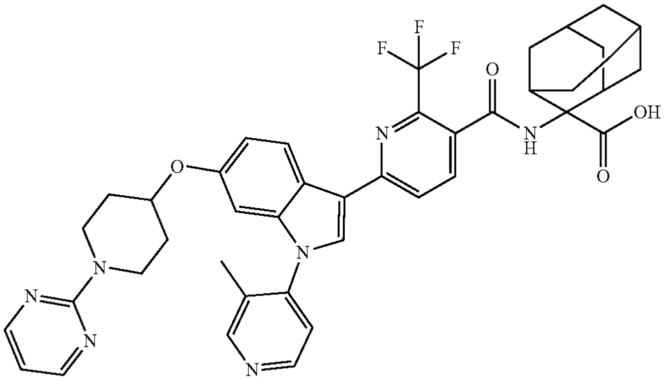 [SMILES: Cc1cnccc1-n1cc(-c2ccc(C(=O)NC3(C(=O)O)C4CCC5CC(C4)CC3C5)c(C(F)(F)F)n2)c2ccc(OC3CCN(c4ncccn4)CC3)cc21] | 752 | 2.60 | 4 | |

TABLE 54
| Compound No. | Chemical Structure | [M + H] | Retention Time (min) | LC/MS Condition | Stereo-Chemistry |
| --- | --- | --- | --- | --- | --- |
| I-318 | 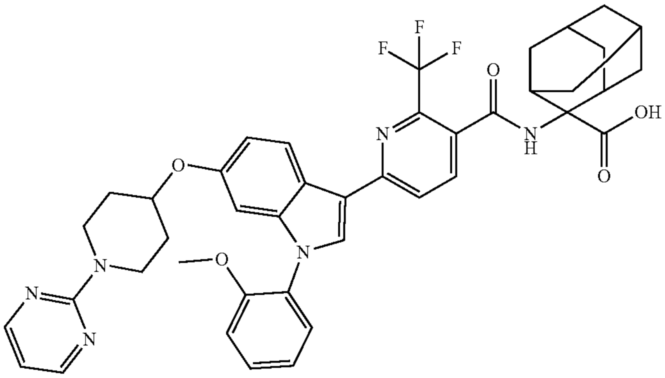 [SMILES: COc1ccccc1-n1cc(-c2ccc(C(=O)NC3(C(=O)O)C4CCC5CC(C4)CC3C5)c(C(F)(F)F)n2)c2ccc(OC3CCN(c4ncccn4)CC3)cc21] | 767 | 3.06 | 4 | |
| I-319 | 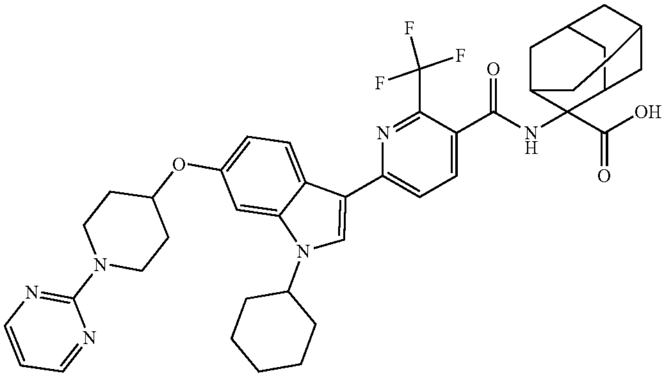 [SMILES: O=C(NC1(C(=O)O)C2CCC3CC(C2)CC1C3)c1ccc(-c2cn(C3CCCCC3)c3cc(OC4CCN(c5ncccn5)CC4)ccc23)nc1C(F)(F)F] | 743 | 1.87 | 9 | |
| I-320 | 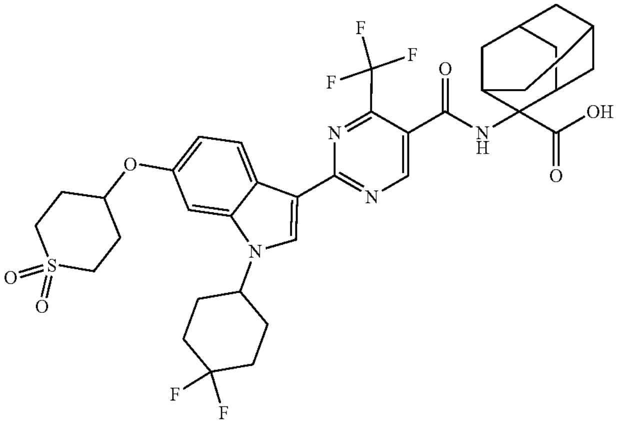 [SMILES: O=C(NC1(C(=O)O)C2CCC3CC(C2)CC1C3)c1cnc(-c2cn(C3CCC(F)(F)CC3)c3cc(OC4CCS(=O)(=O)CC4)ccc23)nc1C(F)(F)F] | 751 | 1.53 | 9 | |

TABLE 54-continued
| Compound No. | Chemical Structure | [M + H] | Retention Time (min) | LC/MS Condition | Stereo-Chemistry |
|---|---|---|---|---|---|
| I-321 | 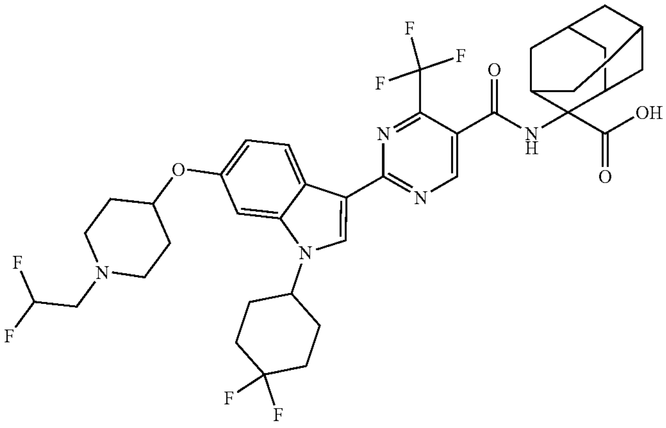 [SMILES: O=C(NC1(C(=O)O)C2CCC3CC(C2)CC1C3)c1cnc(-c2cn(C3CCC(F)(F)CC3)c3cc(OC4CCN(CC(F)F)CC4)ccc23)nc1C(F)(F)F] | 766 | 1.25 | 10 | |
| I-322 | 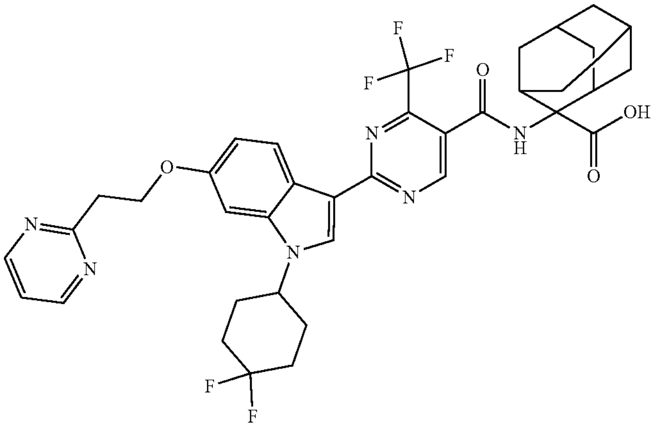 [SMILES: O=C(NC1(C(=O)O)C2CCC3CC(C2)CC1C3)c1cnc(-c2cn(C3CCC(F)(F)CC3)c3cc(OCCc4ncccn4)ccc23)nc1C(F)(F)F] | 725 | 1.57 | 10 | |
TABLE 55
| Compound No. | Chemical Structure | [M + H] | Retention Time (min) | LC/MS Condition | Stereo-Chemistry |
|---|---|---|---|---|---|
| I-323 | 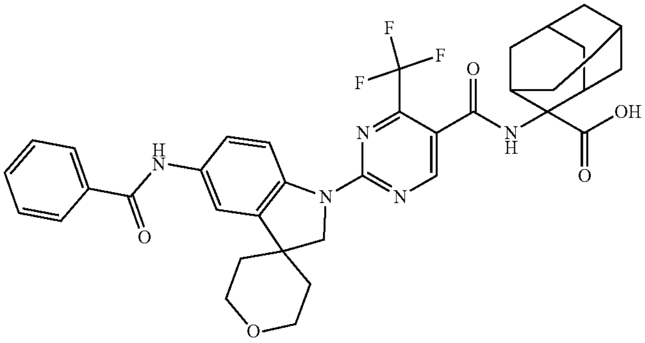 [SMILES: O=C(Nc1ccc2c(c1)C1(CCOCC1)CN2c1ncc(C(=O)NC2(C(=O)O)C3CCC4CC(C3)CC2C4)c(C(F)(F)F)n1)c1ccccc1] | 676 | 1.48 | 10 | |

TABLE 55-continued
| Compound No. | Chemical Structure | [M + H] | Retention Time (min) | LC/MS Condition | Stereo-Chemistry |
|---|---|---|---|---|---|
| I-324 | 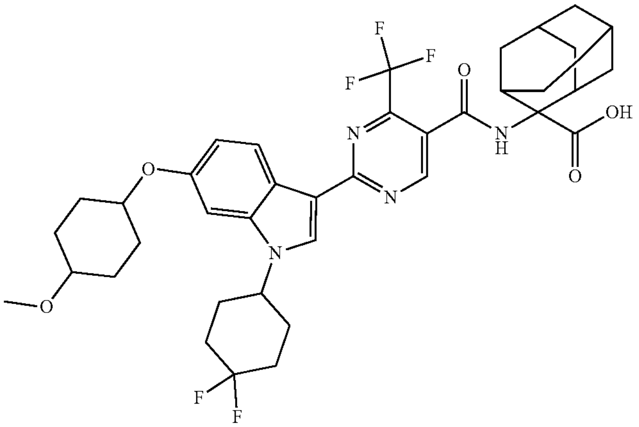 [SMILES: COC1CCC(Oc2ccc3c(-c4ncc(C(=O)NC5(C(=O)O)C6CCC7CC(C6)CC5C7)c(C(F)(F)F)n4)cn(C4CCC(F)(F)CC4)c3c2)CC1] | 731 | 1.77 | 9 | c |
| I-325 | 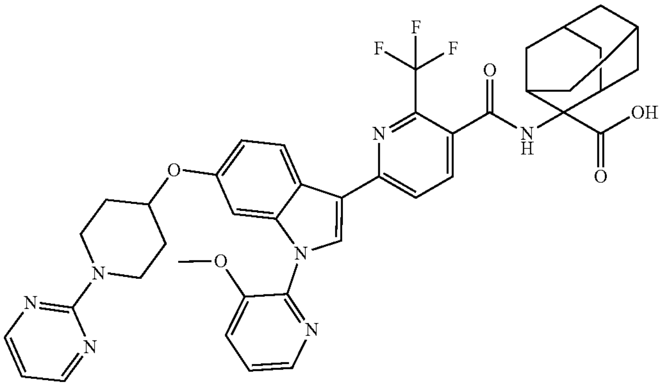 [SMILES: COc1cccnc1-n1cc(-c2ccc(C(=O)NC3(C(=O)O)C4CCC5CC(C4)CC3C5)c(C(F)(F)F)n2)c2ccc(OC3CCN(c4ncccn4)CC3)cc21] | 768 | 2.82 | 4 | |
| I-326 | 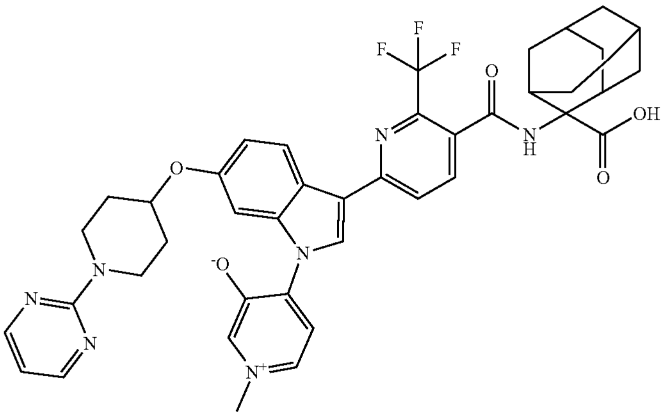 | 768 | 2.41 | 4 | |

TABLE 55-continued
| Compound No. | Chemical Structure | [M + H] | Retention Time (min) | LC/MS Condition | Stereo-Chemistry |
|---|---|---|---|---|---|
| I-327 | 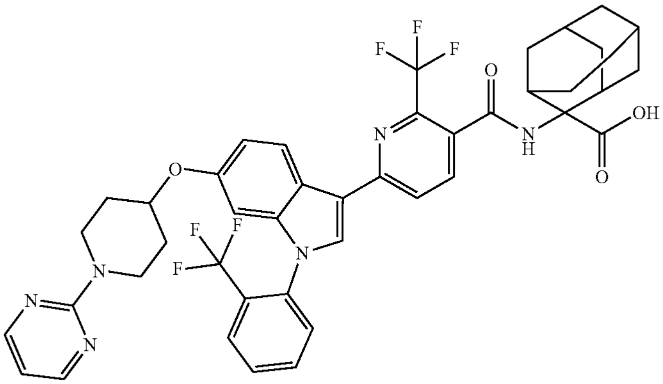 [SMILES: O=C(NC1(C(=O)O)C2CCC3CC(C2)CC1C3)c1ccc(-c2cn(-c3ccccc3C(F)(F)F)c3cc(OC4CCN(c5ncccn5)CC4)ccc23)nc1C(F)(F)F] | 805 | 3.08 | 4 | |
| I-328 | 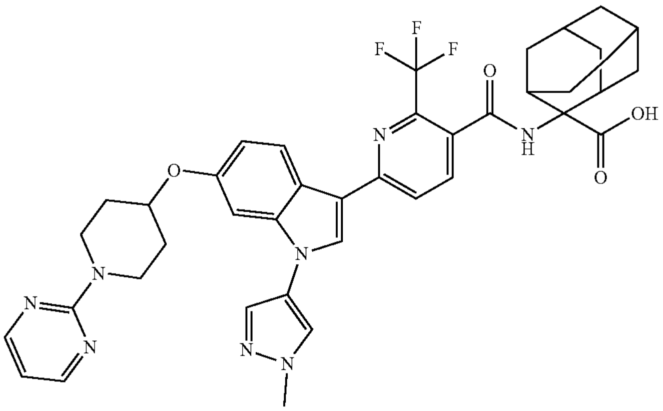 [SMILES: Cn1cc(-n2cc(-c3ccc(C(=O)NC4(C(=O)O)C5CCC6CC(C5)CC4C6)c(C(F)(F)F)n3)c3ccc(OC4CCN(c5ncccn5)CC4)cc32)cn1] | 741 | 2.72 | 4 | |
TABLE 56
| Compound No. | Chemical Structure | [M + H] | Retention Time (min) | LC/MS Condition | Stereo-Chemistry |
|---|---|---|---|---|---|
| I-329 | 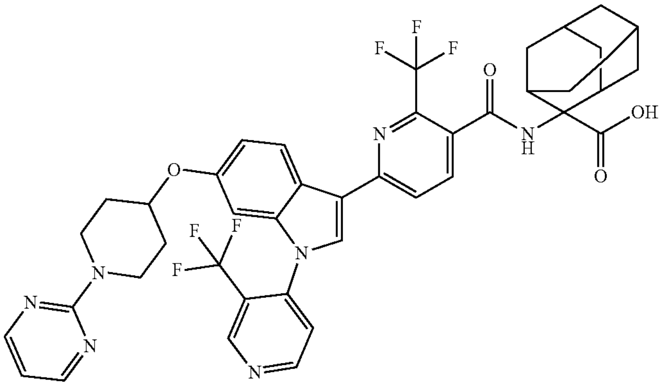 [SMILES: O=C(NC1(C(=O)O)C2CCC3CC(C2)CC1C3)c1ccc(-c2cn(-c3ccncc3C(F)(F)F)c3cc(OC4CCN(c5ncccn5)CC4)ccc23)nc1C(F)(F)F] | 806 | 2.88 | 4 | |

TABLE 56-continued
| Compound No. | Chemical Structure | [M + H] | Retention Time (min) | LC/MS Condition | Stereo-Chemistry |
| --- | --- | --- | --- | --- | --- |
| I-330 | 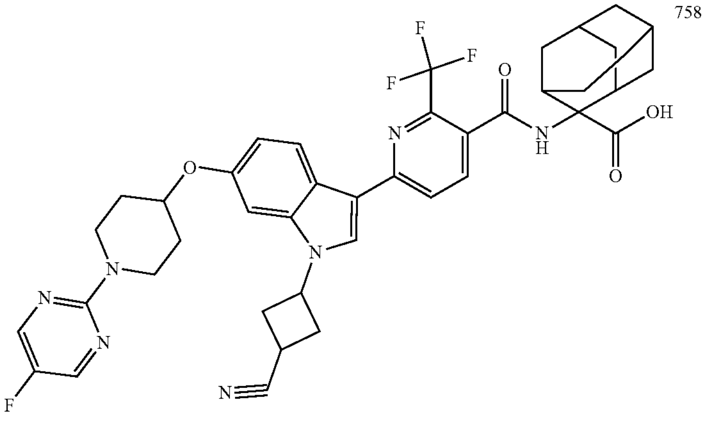 | 758 | 2.89 | 1 | b |
| I-331 | 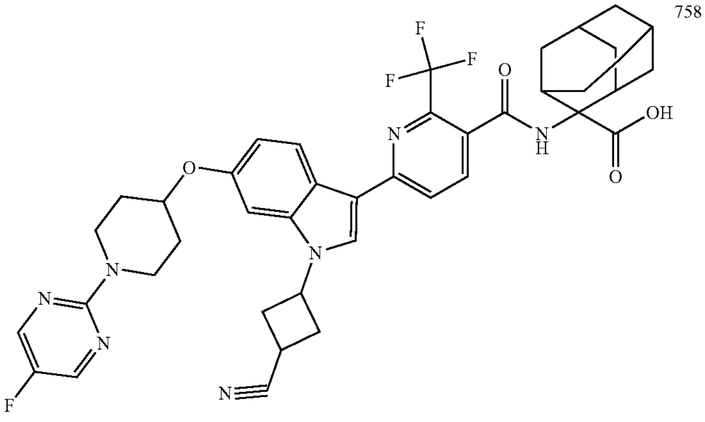 | 758 | 3.06 | 1 | b |
| I-332 | 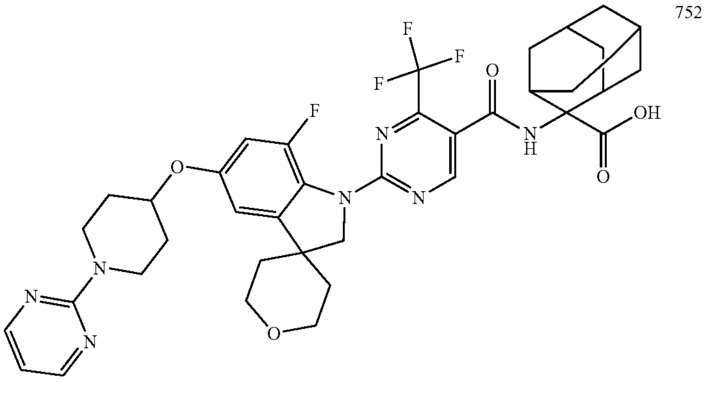 | 752 | 2.62 | 1 | |

TABLE 56-continued
| Compound No. | Chemical Structure | [M + H] | Retention Time (min) | LC/MS Condition | Stereo-Chemistry |
|---|---|---|---|---|---|
| I-333 | 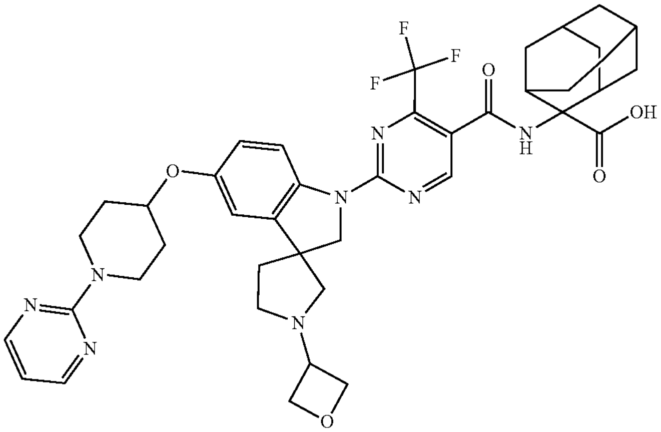 [SMILES: O=C(NC1(C(=O)O)C2CCC3CC(C2)CC1C3)c1cnc(N2CC3(CCN(C4COC4)C3)c3cc(OC4CCN(c5ncccn5)CC4)ccc32)nc1C(F)(F)F] | 775 | 2.08 | 1 | a |
TABLE 57
| Compound No. | Chemical Structure | [M + H] | Retention Time (min) | LC/MS Condition | Stereo-Chemistry |
|---|---|---|---|---|---|
| I-334 | 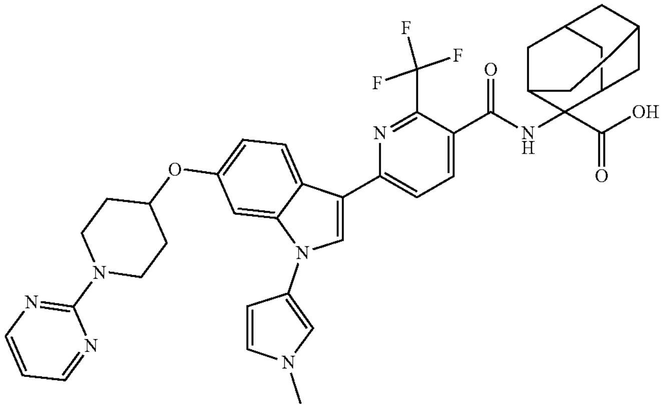 [SMILES: Cn1ccc(-n2cc(-c3ccc(C(=O)NC4(C(=O)O)C5CCC6CC(C5)CC4C6)c(C(F)(F)F)n3)c3ccc(OC4CCN(c5ncccn5)CC4)cc32)c1] | 740 | 2.81 | 1 | |
| I-335 | 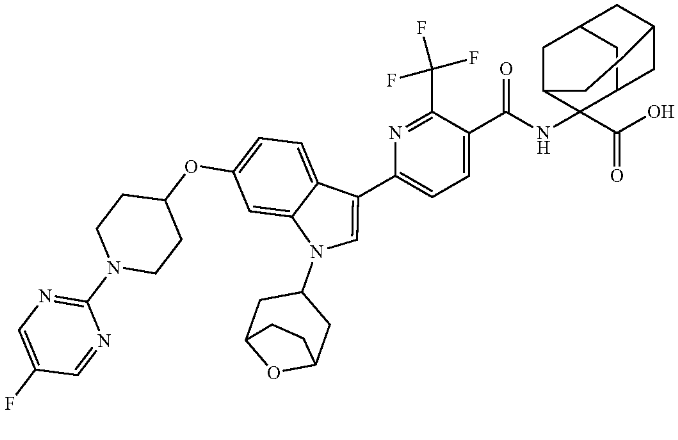 [SMILES: O=C(NC1(C(=O)O)C2CCC3CC(C2)CC1C3)c1ccc(-c2cn(C3CC4CCC(C3)O4)c3cc(OC4CCN(c5ncc(F)cn5)CC4)ccc23)nc1C(F)(F)F] | 789 | 3.10 | 1 | b |

TABLE 57-continued
| Compound No. | Chemical Structure | [M + H] | Retention Time (min) | LC/MS Condition | Stereo-Chemistry |
|---|---|---|---|---|---|
| I-336 | 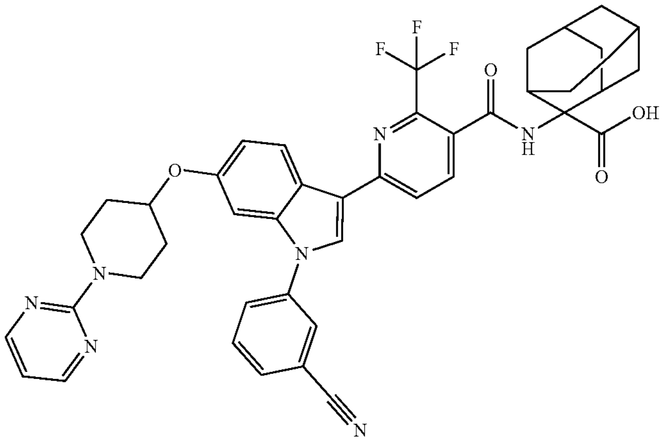 [SMILES: N#Cc1cccc(-n2cc(-c3ccc(C(=O)NC4(C(=O)O)C5CCC6CC(C5)CC4C6)c(C(F)(F)F)n3)c3ccc(OC4CCN(c5ncccn5)CC4)cc32)c1] | 762 | 2.99 | 4 | |
| I-337 | 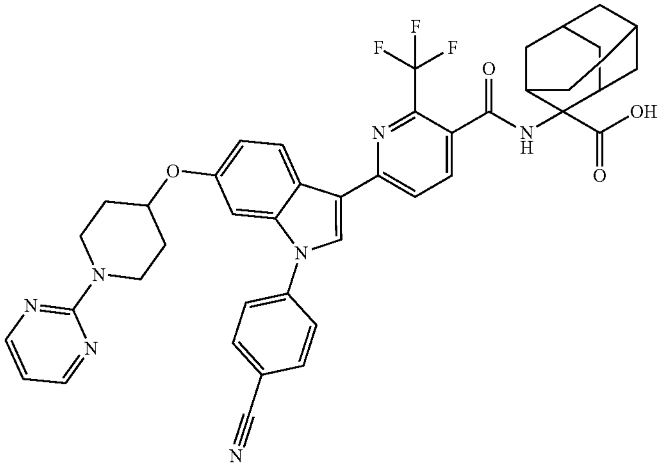 [SMILES: N#Cc1ccc(-n2cc(-c3ccc(C(=O)NC4(C(=O)O)C5CCC6CC(C5)CC4C6)c(C(F)(F)F)n3)c3ccc(OC4CCN(c5ncccn5)CC4)cc32)cc1] | 762 | 3.01 | 4 | |
| I-338 | 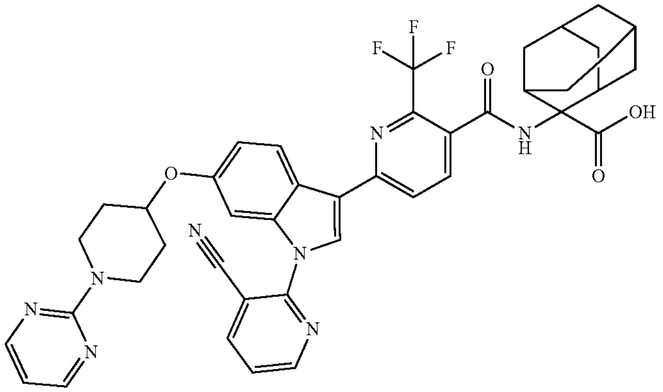 [SMILES: N#Cc1cccnc1-n1cc(-c2ccc(C(=O)NC3(C(=O)O)C4CCC5CC(C4)CC3C5)c(C(F)(F)F)n2)c2ccc(OC3CCN(c4ncccn4)CC3)cc21] | 763 | 2.82 | 4 | |

TABLE 58
| Compound No. | Chemical Structure | [M + H] | Retention Time (min) | LC/MS Condition | Stereo-Chemistry |
|---|---|---|---|---|---|
| I-339 | 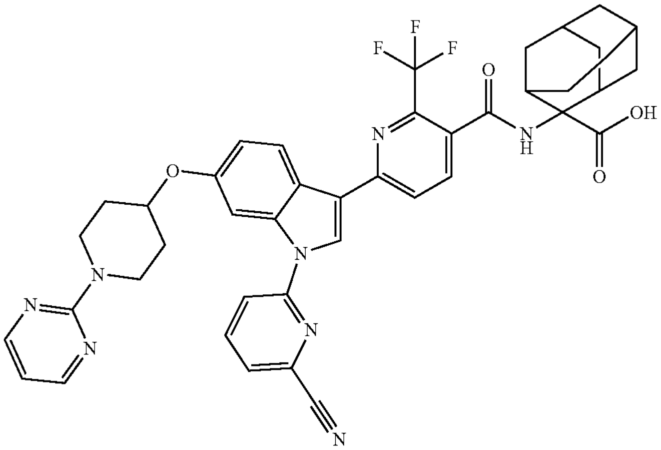 [SMILES: N#Cc1cccc(-n2cc(-c3ccc(C(=O)NC4(C(=O)O)C5CCC6CC(C5)CC4C6)c(C(F)(F)F)n3)c3ccc(OC4CCN(c5ncccn5)CC4)cc32)n1] | 763 | 3.00 | 4 | |
| I-340 | 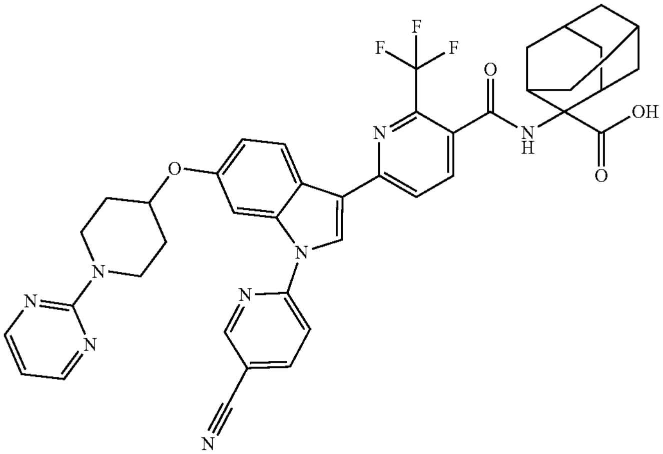 [SMILES: N#Cc1ccc(-n2cc(-c3ccc(C(=O)NC4(C(=O)O)C5CCC6CC(C5)CC4C6)c(C(F)(F)F)n3)c3ccc(OC4CCN(c5ncccn5)CC4)cc32)nc1] | 763 | 3.00 | 4 | |
| I-341 | 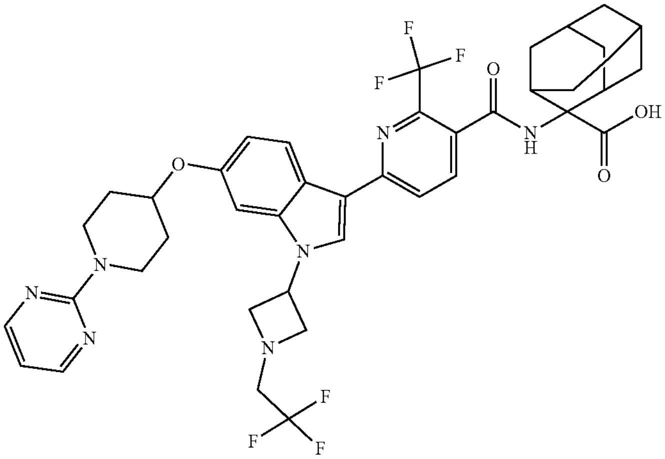 [SMILES: O=C(NC1(C(=O)O)C2CCC3CC(C2)CC1C3)c1ccc(-c2cn(C3CN(CC(F)(F)F)C3)c3cc(OC4CCN(c5ncccn5)CC4)ccc23)nc1C(F)(F)F] | 796 | 1.72 | 9 | |

TABLE 58-continued
| Compound No. | Chemical Structure | [M + H] | Retention Time (min) | LC/MS Condition | Stereo-Chemistry |
|---|---|---|---|---|---|
| I-342 | 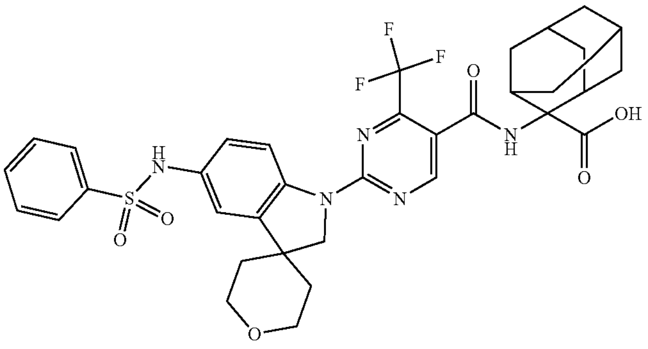 [SMILES: O=C(NC1(C(=O)O)C2CCC3CC(C2)CC1C3)c1cnc(N2CC3(CCOCC3)c3cc(NS(=O)(=O)c4ccccc4)ccc32)nc1C(F)(F)F] | 712 | 1.44 | 10 | |
| I-343 | 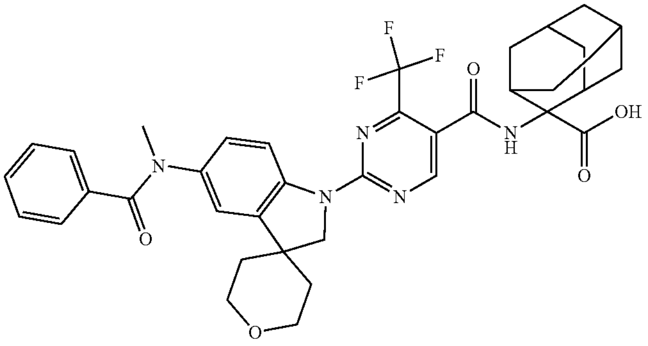 [SMILES: CN(C(=O)c1ccccc1)c1ccc2c(c1)C1(CCOCC1)CN2c1ncc(C(=O)NC2(C(=O)O)C3CCC4CC(C3)CC2C4)c(C(F)(F)F)n1] | 690 | 1.45 | 10 | |
TABLE 59
| Compound No. | Chemical Structure | [M + H] | Retention Time (min) | LC/MS Condition | Stereo-Chemistry |
|---|---|---|---|---|---|
| I-344 | 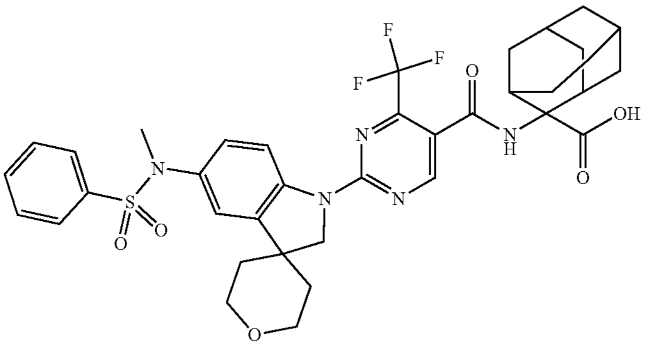 [SMILES: CN(c1ccc2c(c1)C1(CCOCC1)CN2c1ncc(C(=O)NC2(C(=O)O)C3CCC4CC(C3)CC2C4)c(C(F)(F)F)n1)S(=O)(=O)c1ccccc1] | 726 | 1.57 | 10 | |

TABLE 59-continued
| Compound No. | Chemical Structure | [M + H] | Retention Time (min) | LC/MS Condition | Stereo-Chemistry |
|---|---|---|---|---|---|
| I-345 | 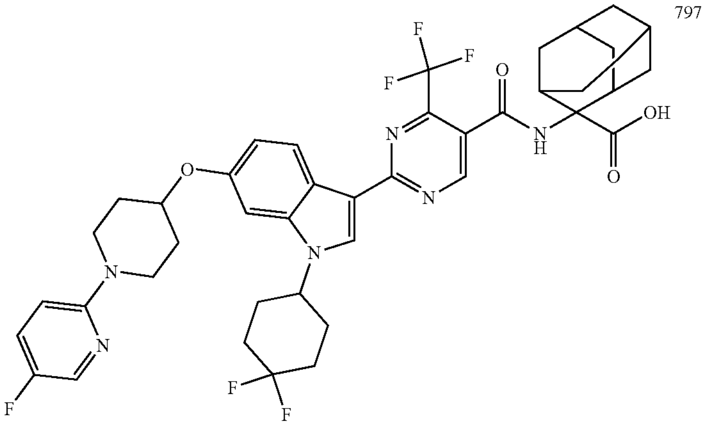 | 797 | 1.81 | 9 | |
| I-346 | 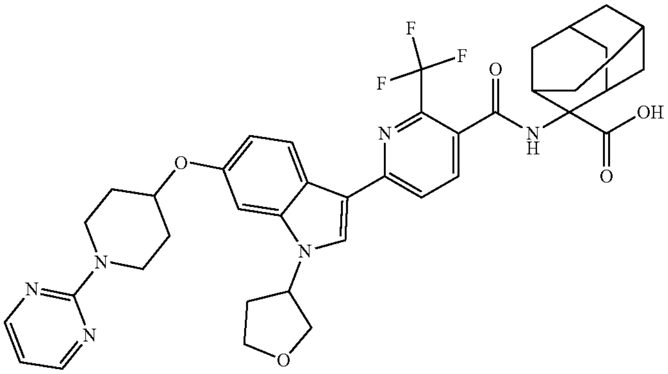 [SMILES: O=C(NC1(C(=O)O)C2CCC3CC(C2)CC1C3)c1ccc(-c2cn(C3CCOC3)c3cc(OC4CCN(c5ncccn5)CC4)ccc23)nc1C(F)(F)F] | 731 | 1.62 | 9 | a |
| I-347 | 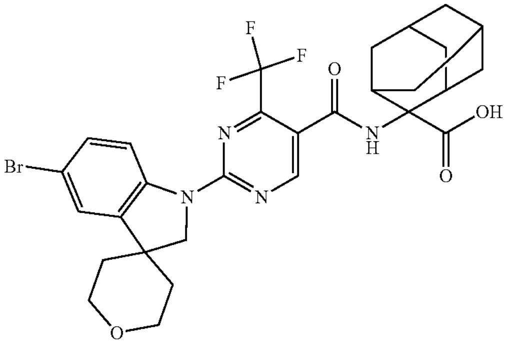 [SMILES: O=C(NC1(C(=O)O)C2CCC3CC(C2)CC1C3)c1cnc(N2CC3(CCOCC3)c3cc(Br)ccc32)nc1C(F)(F)F] | 637 | 1.69 | 9 | |
| I-348 | 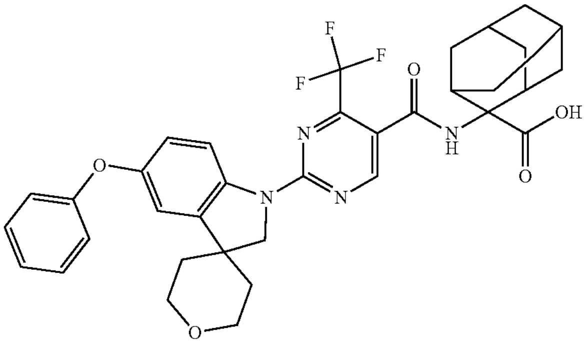 [SMILES: O=C(NC1(C(=O)O)C2CCC3CC(C2)CC1C3)c1cnc(N2CC3(CCOCC3)c3cc(Oc4ccccc4)ccc32)nc1C(F)(F)F] | 649 | 1.76 | 9 | |

TABLE 59-continued
| Compound No. | Chemical Structure | [M + H] | Retention Time (min) | LC/MS Condition | Stereo-Chemistry |
|---|---|---|---|---|---|
| I-349 | 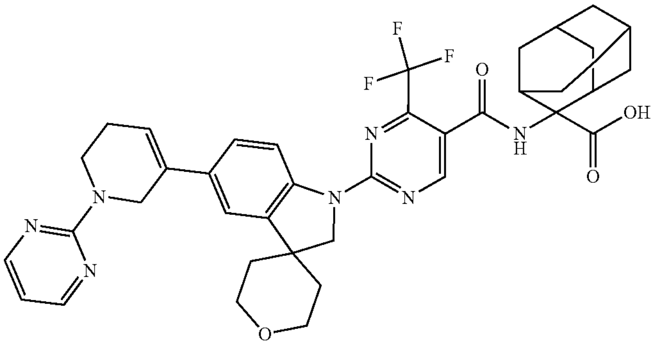 [SMILES: O=C(NC1(C(=O)O)C2CCC3CC(C2)CC1C3)c1cnc(N2CC3(CCOCC3)c3cc(C4=CCCN(c5ncccn5)C4)ccc32)nc1C(F)(F)F] | 716 | 2.68 | 10 | |
TABLE 60
| Compound No. | Chemical Structure | [M + H] | Retention Time (min) | LC/MS Condition | Stereo-Chemistry |
|---|---|---|---|---|---|
| I-350 | 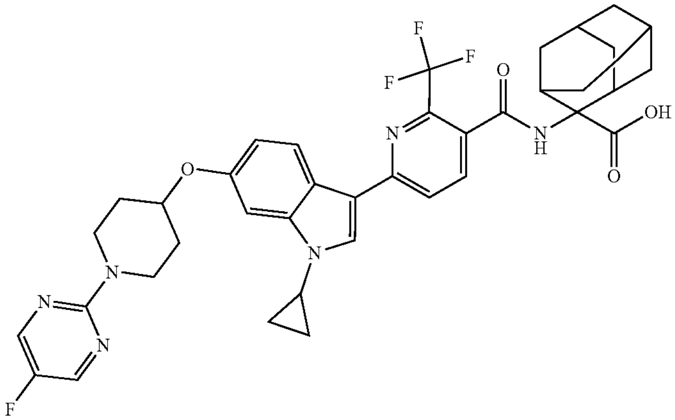 [SMILES: O=C(NC1(C(=O)O)C2CCC3CC(C2)CC1C3)c1ccc(-c2cn(C3CC3)c3cc(OC4CCN(c5ncc(F)cn5)CC4)ccc23)nc1C(F)(F)F] | 719 | 3.17 | 1 | |
| I-351 | 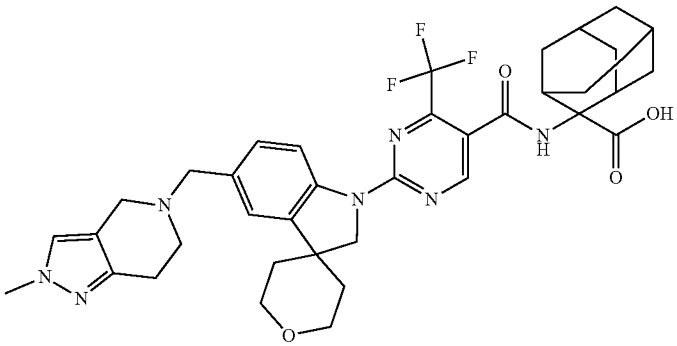 [SMILES: Cn1cc2c(n1)CCN(Cc1ccc3c(c1)C1(CCOCC1)CN3c1ncc(C(=O)NC3(C(=O)O)C4CCC5CC(C4)CC3C5)c(C(F)(F)F)n1)C2] | 706 | 1.87 | 1 | |

TABLE 60-continued
| Compound No. | Chemical Structure | [M + H] | Retention Time (min) | LC/MS Condition | Stereo-Chemistry |
|---|---|---|---|---|---|
| I-352 | 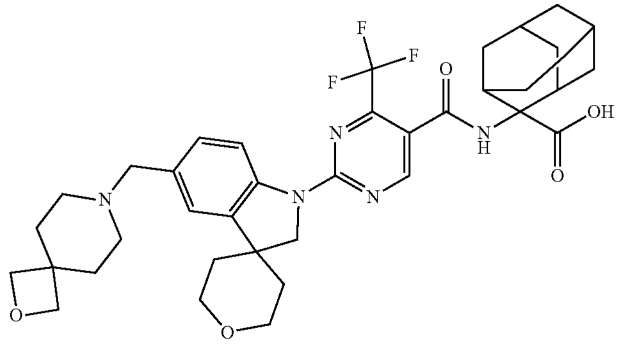 [SMILES: O=C(NC1(C(=O)O)C2CCC3CC(C2)CC1C3)c1cnc(N2CC3(CCOCC3)c3cc(CN4CCC5(CC4)COC5)ccc32)nc1C(F)(F)F] | 696 | 1.89 | 1 | |
| I-353 | 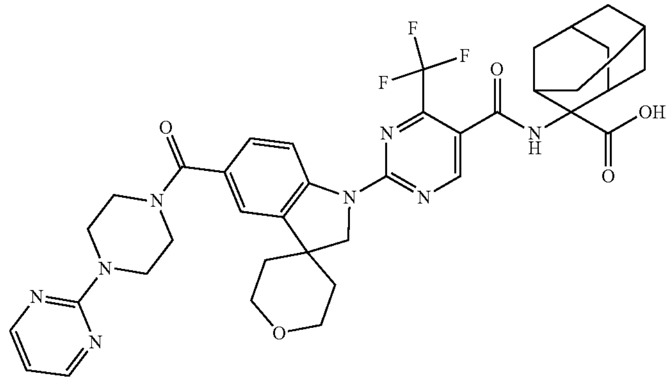 [SMILES: O=C(NC1(C(=O)O)C2CCC3CC(C2)CC1C3)c1cnc(N2CC3(CCOCC3)c3cc(C(=O)N4CCN(c5ncccn5)CC4)ccc32)nc1C(F)(F)F] | 747 | 1.38 | 9 | |
| I-354 | 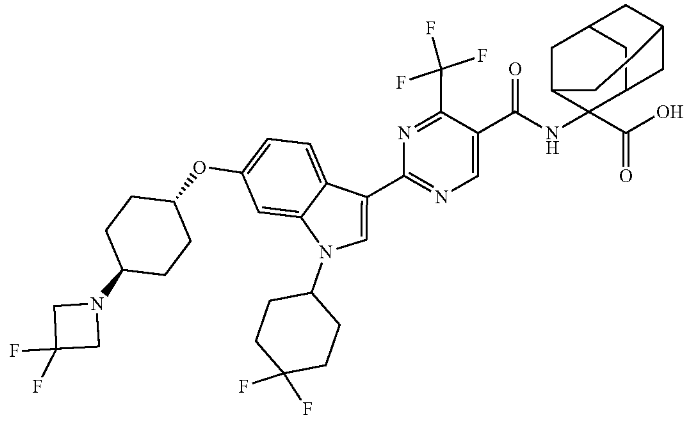 [SMILES: O=C(NC1(C(=O)O)C2CCC3CC(C2)CC1C3)c1cnc(-c2cn(C3CCC(F)(F)CC3)c3cc(O[C@H]4CC[C@H](N5CC(F)(F)C5)CC4)ccc23)nc1C(F)(F)F] | 792 | 1.39 | 9 | |
| I-355 | 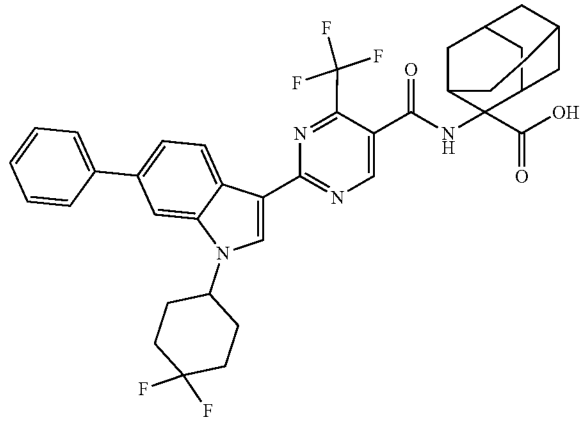 [SMILES: O=C(NC1(C(=O)O)C2CCC3CC(C2)CC1C3)c1cnc(-c2cn(C3CCC(F)(F)CC3)c3cc(-c4ccccc4)ccc23)nc1C(F)(F)F] | 679 | 1.85 | 10 | |

TABLE 61
| Compound No. | Chemical Structure | [M + H] | Retention Time (min) | LC/MS Condition | Stereo-Chemistry |
|---|---|---|---|---|---|
| I-356 | 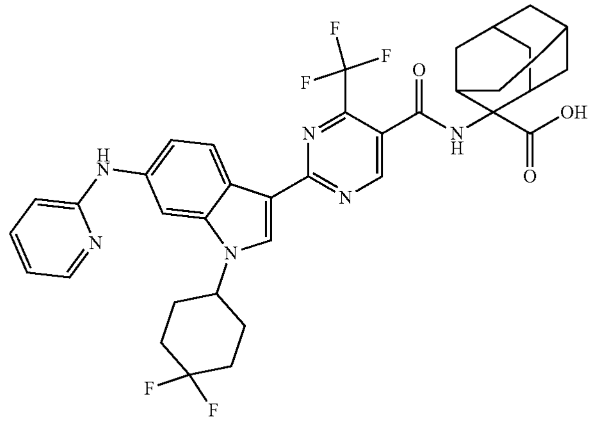 [SMILES: O=C(NC1(C(=O)O)C2CCC3CC(C2)CC1C3)c1cnc(-c2cn(C3CCC(F)(F)CC3)c3cc(Nc4ccccn4)ccc23)nc1C(F)(F)F] | 695 | 1.19 | 10 | |
| I-357 | 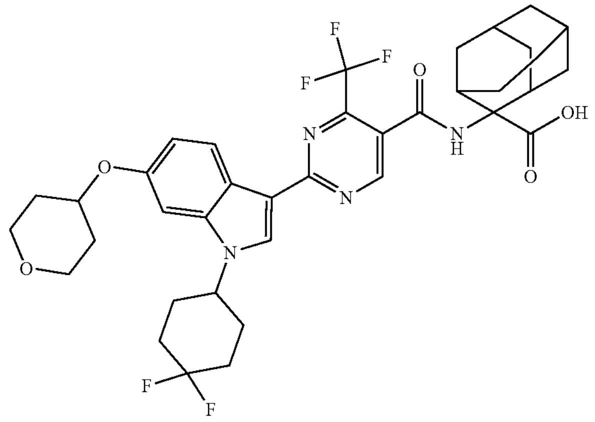 [SMILES: O=C(NC1(C(=O)O)C2CCC3CC(C2)CC1C3)c1cnc(-c2cn(C3CCC(F)(F)CC3)c3cc(OC4CCOCC4)ccc23)nc1C(F)(F)F] | 703 | 1.65 | 9 | |
| I-358 | 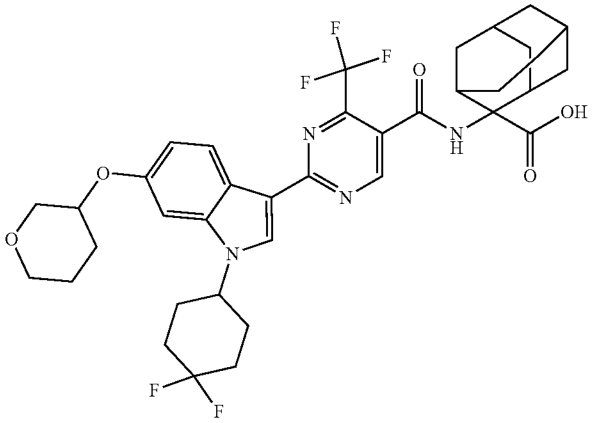 [SMILES: O=C(NC1(C(=O)O)C2CCC3CC(C2)CC1C3)c1cnc(-c2cn(C3CCC(F)(F)CC3)c3cc(OC4CCCOC4)ccc23)nc1C(F)(F)F] | 703 | 1.69 | 9 | a |

TABLE 61-continued
| Compound No. | Chemical Structure | [M + H] | Retention Time (min) | LC/MS Condition | Stereo-Chemistry |
|---|---|---|---|---|---|
| I-359 | 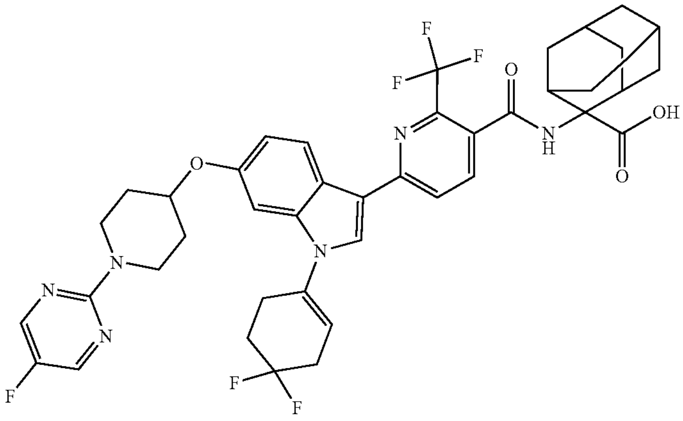 [SMILES: O=C(NC1(C(=O)O)C2CCC3CC(C2)CC1C3)c1ccc(-c2cn(C3=CCC(F)(F)CC3)c3cc(OC4CCN(c5ncc(F)cn5)CC4)ccc23)nc1C(F)(F)F] | 795 | 3.24 | 1 | |
| I-360 | 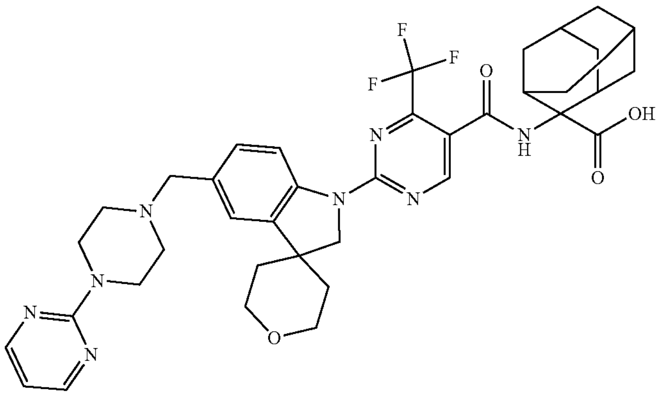 [SMILES: O=C(NC1(C(=O)O)C2CCC3CC(C2)CC1C3)c1cnc(N2CC3(CCOCC3)c3cc(CN4CCN(c5ncccn5)CC4)ccc32)nc1C(F)(F)F] | 733 | 1.97 | 1 | |
TABLE 62
| Compound No. | Chemical Structure | [M + H] | Retention Time (min) | LC/MS Condition | Stereo-Chemistry |
|---|---|---|---|---|---|
| I-361 | 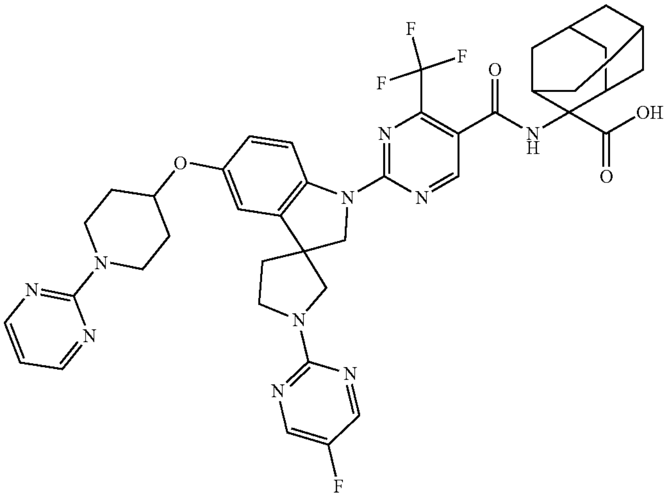 [SMILES: O=C(NC1(C(=O)O)C2CCC3CC(C2)CC1C3)c1cnc(N2CC3(CCN(c4ncc(F)cn4)C3)c3cc(OC4CCN(c5ncccn5)CC4)ccc32)nc1C(F)(F)F] | 815 | 2.96 | 1 | a |

TABLE 62-continued
| Compound No. | Chemical Structure | [M + H] | Retention Time (min) | LC/MS Condition | Stereo-Chemistry |
|---|---|---|---|---|---|
| I-362 | 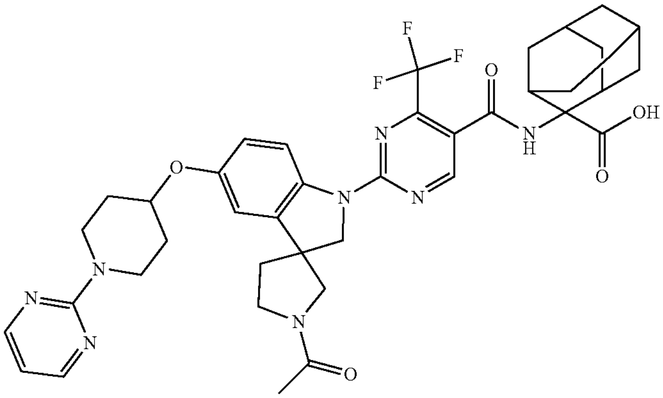 [SMILES: CC(=O)N1CCC2(C1)CN(c1ncc(C(=O)NC3(C(=O)O)C4CCC5CC(C4)CC3C5)c(C(F)(F)F)n1)c1ccc(OC3CCN(c4ncccn4)CC3)cc12] | 761 | 2.40 | 1 | a |
| I-363 | 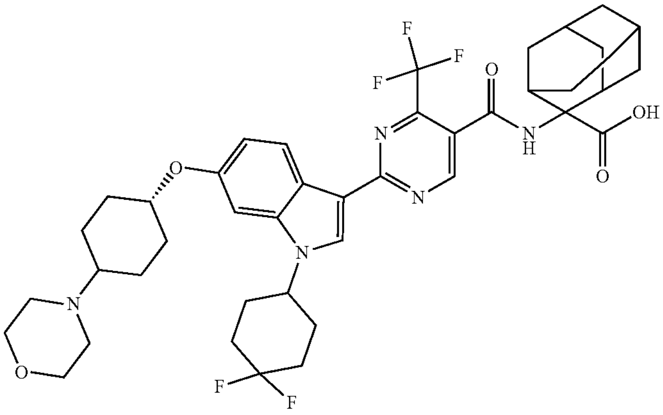 | 786 | 1.25 | 9 | |
| I-364 | 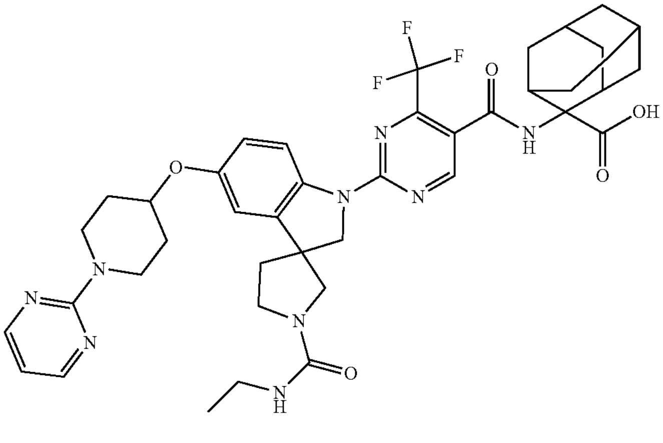 [SMILES: CCNC(=O)N1CCC2(C1)CN(c1ncc(C(=O)NC3(C(=O)O)C4CCC5CC(C4)CC3C5)c(C(F)(F)F)n1)c1ccc(OC3CCN(c4ncccn4)CC3)cc12] | 790 | 2.53 | 1 | a |

TABLE 62-continued
| Compound No. | Chemical Structure | [M + H] | Retention Time (min) | LC/MS Condition | Stereo-Chemistry |
|---|---|---|---|---|---|
| I-365 | 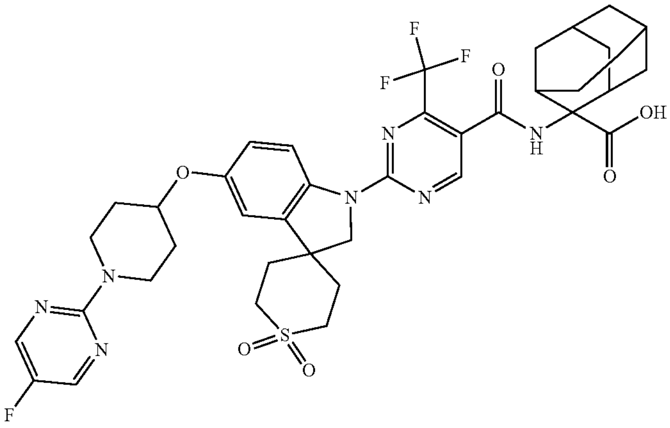 [SMILES: O=C(NC1(C(=O)O)C2CCC3CC(C2)CC1C3)c1cnc(N2CC3(CCS(=O)(=O)CC3)c3cc(OC4CCN(c5ncc(F)cn5)CC4)ccc32)nc1C(F)(F)F] | 800 | 2.86 | 1 | |
TABLE 63
| Compound No. | Chemical Structure | [M + H] | Retention Time (min) | LC/MS Condition | Stereo-Chemistry |
|---|---|---|---|---|---|
| I-366 | 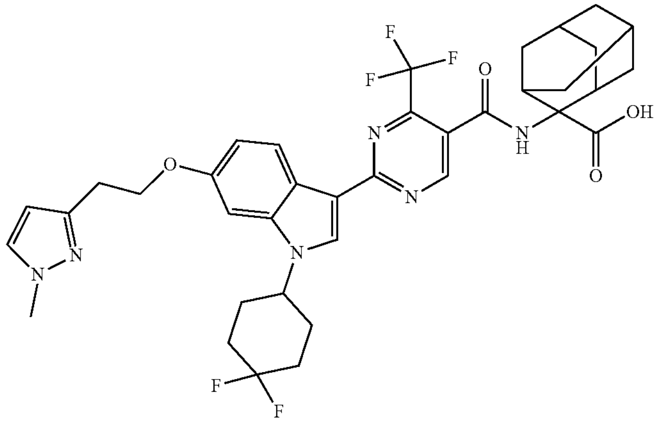 [SMILES: Cn1ccc(CCOc2ccc3c(-c4ncc(C(=O)NC5(C(=O)O)C6CC7CC(C6)CC5C7)c(C(F)(F)F)n4)cn(C4CCC(F)(F)CC4)c3c2)n1] | 727 | 1.60 | 10 | |
| I-367 | 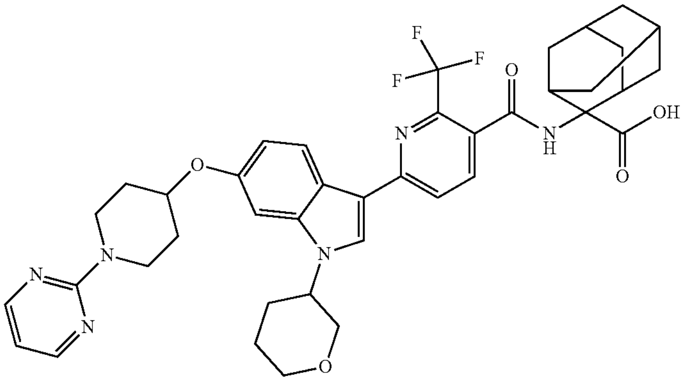 [SMILES: O=C(NC1(C(=O)O)C2CC3CC(C2)CC1C3)c1ccc(-c2cn(C3CCCOC3)c3cc(OC4CCN(c5ncccn5)CC4)ccc23)nc1C(F)(F)F] | 745 | 1.67 | 9 | a |

TABLE 63-continued
| Compound No. | Chemical Structure | [M + H] | Retention Time (min) | LC/MS Condition | Stereo-Chemistry |
|---|---|---|---|---|---|
| I-368 | 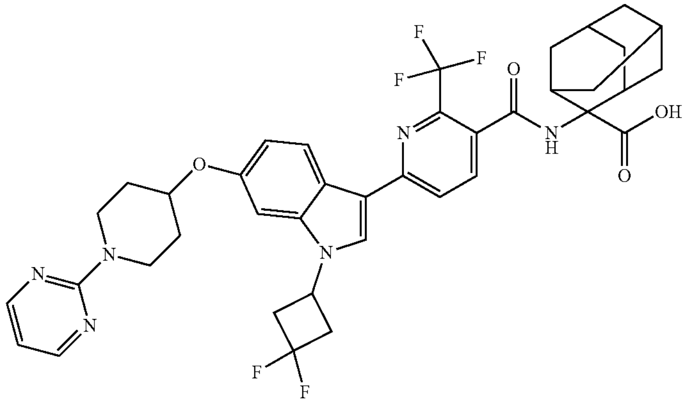 [SMILES: O=C(NC1(C(=O)O)C2CC3CC(C2)CC1C3)c1ccc(-c2cn(C3CC(F)(F)C3)c3cc(OC4CCN(c5ncccn5)CC4)ccc23)nc1C(F)(F)F] | 761 | 1.72 | 9 | |
| I-369 | 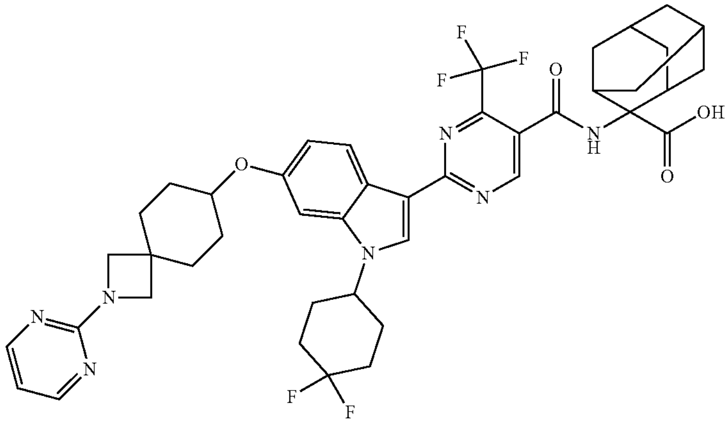 [SMILES: O=C(NC1(C(=O)O)C2CC3CC(C2)CC1C3)c1cnc(-c2cn(C3CCC(F)(F)CC3)c3cc(OC4CCC5(CC4)CN(c4ncccn4)C5)ccc23)nc1C(F)(F)F] | 820 | 1.67 | 10 | |
| I-370 | 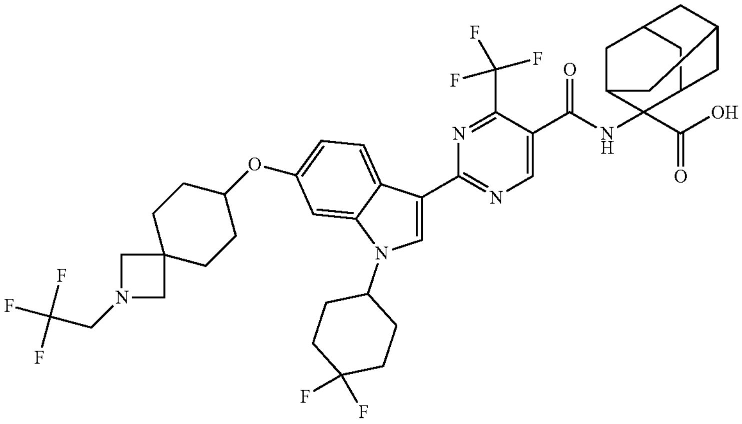 [SMILES: O=C(NC1(C(=O)O)C2CC3CC(C2)CC1C3)c1cnc(-c2cn(C3CCC(F)(F)CC3)c3cc(OC4CCC5(CC4)CN(CC(F)(F)F)C5)ccc23)nc1C(F)(F)F] | 824 | 1.57 | 10 | |

TABLE 64
| Compound No. | Chemical Structure | [M + H] | Retention Time (min) | LC/MS Condition | Stereo-Chemistry |
|---|---|---|---|---|---|
| I-371 | 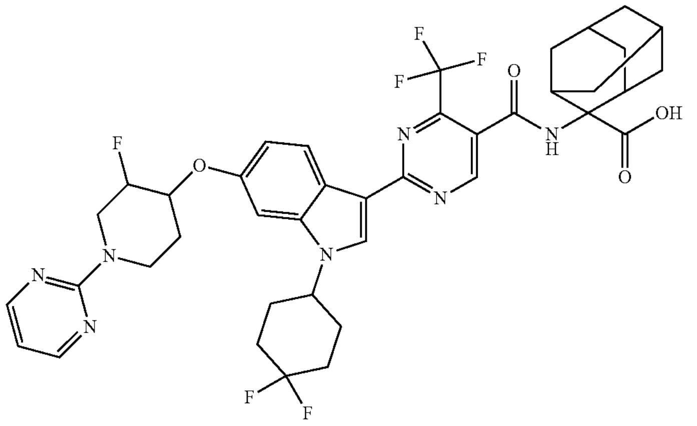 [SMILES: O=C(NC1(C(=O)O)C2CC3CC(C2)CC1C3)c1cnc(-c2cn(C3CCC(F)(F)CC3)c3cc(OC4CCN(c5ncccn5)CC4F)ccc23)nc1C(F)(F)F] | 798 | 1.76 | 10 | c |
| I-372 | 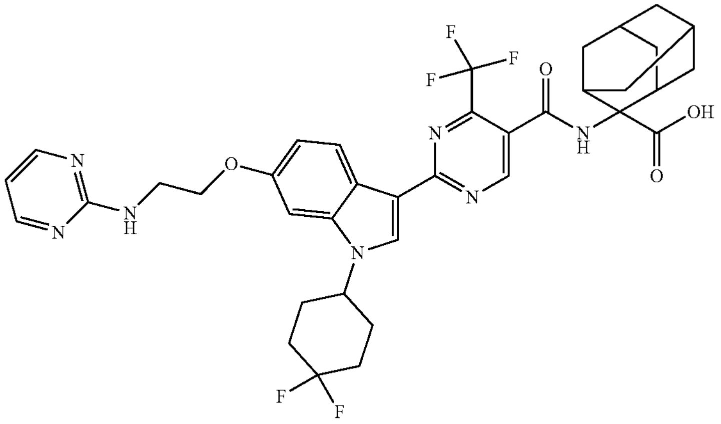 [SMILES: O=C(NC1(C(=O)O)C2CC3CC(C2)CC1C3)c1cnc(-c2cn(C3CCC(F)(F)CC3)c3cc(OCCNc4ncccn4)ccc23)nc1C(F)(F)F] | 740 | 1.58 | 10 | |
| I-373 | 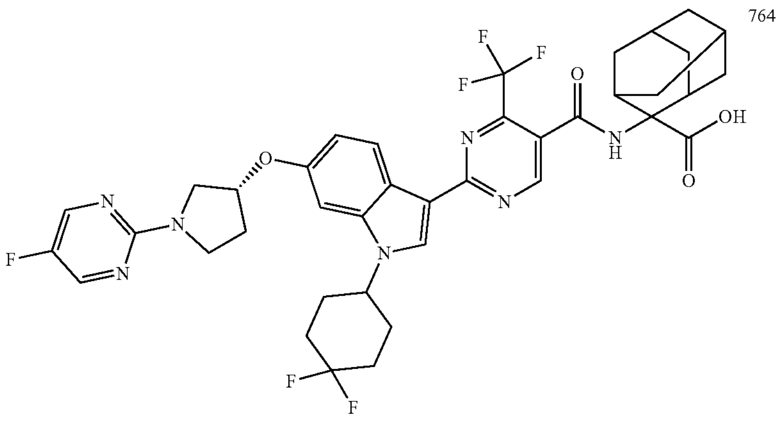 | 764 | 1.74 | 9 | |

TABLE 64-continued
| Compound No. | Chemical Structure | [M + H] | Retention Time (min) | LC/MS Condition | Stereo-Chemistry |
|---|---|---|---|---|---|
| I-374 | 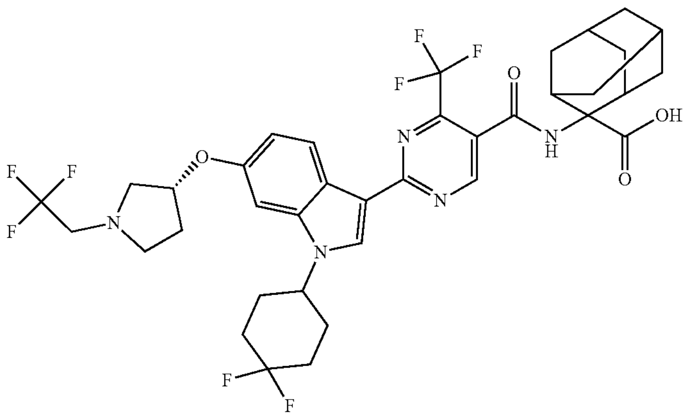 [SMILES: O=C(NC1(C(=O)O)C2CC3CC(C2)CC1C3)c1cnc(-c2cn(C3CCC(F)(F)CC3)c3cc(O[C@@H]4CCN(CC(F)(F)F)C4)ccc23)nc1C(F)(F)F] | 770 | 1.75 | 9 | |
| I-375 | 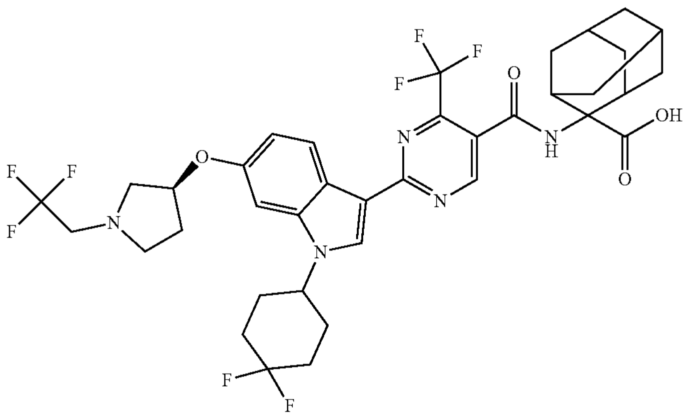 [SMILES: O=C(NC1(C(=O)O)C2CC3CC(C2)CC1C3)c1cnc(-c2cn(C3CCC(F)(F)CC3)c3cc(O[C@H]4CCN(CC(F)(F)F)C4)ccc23)nc1C(F)(F)F] | 770 | 1.75 | 9 | |
TABLE 65
| Compound No. | Chemical Structure | [M + H] | Retention Time (min) | LC/MS Condition | Stereo-Chemistry |
|---|---|---|---|---|---|
| I-376 | 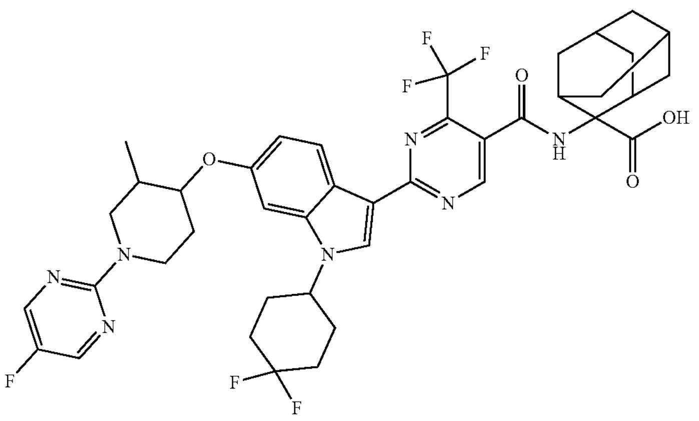 [SMILES: CC1CN(c2ncc(F)cn2)CCC1Oc1ccc2c(-c3ncc(C(=O)NC4(C(=O)O)C5CC6CC(C5)CC4C6)c(C(F)(F)F)n3)cn(C3CCC(F)(F)CC3)c2c1] | 812 | 1.95 | 10 | c |

TABLE 65-continued
| Compound No. | Chemical Structure | [M + H] | Retention Time (min) | LC/MS Condition | Stereo-Chemistry |
|---|---|---|---|---|---|
| I-377 | 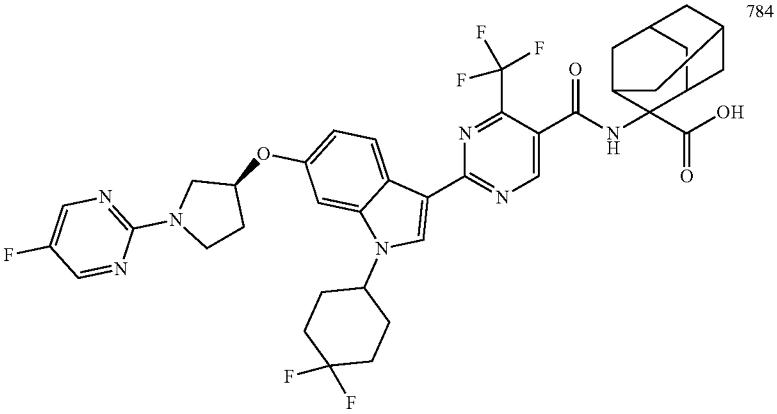 | 784 | 1.74 | 9 | |
| I-378 | 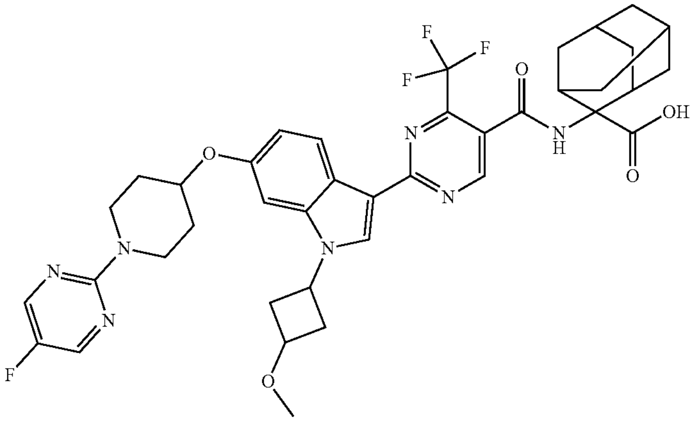 [SMILES: COC1CC(n2cc(-c3ncc(C(=O)NC4(C(=O)O)C5CC6CC(C5)CC4C6)c(C(F)(F)F)n3)c3ccc(OC4CCN(c5ncc(F)cn5)CC4)cc32)C1] | 764 | 1.82 | 9 | c |
| I-379 | 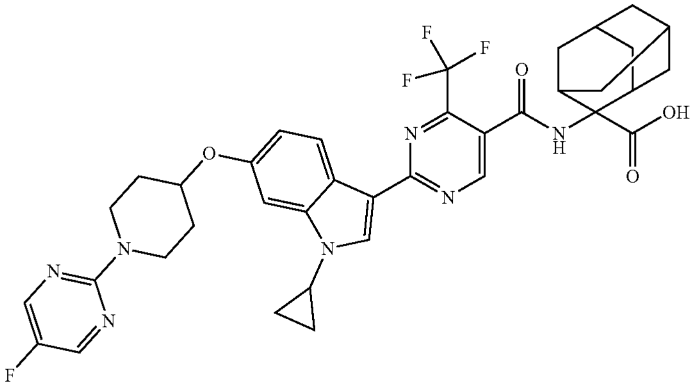 [SMILES: O=C(NC1(C(=O)O)C2CC3CC(C2)CC1C3)c1cnc(-c2cn(C3CC3)c3cc(OC4CCN(c5ncc(F)cn5)CC4)ccc23)nc1C(F)(F)F] | 720 | 1.65 | 9 | |

TABLE 65-continued
| Compound No. | Chemical Structure | [M + H] | Retention Time (min) | LC/MS Condition | Stereo-Chemistry |
| --- | --- | --- | --- | --- | --- |
| I-380 | 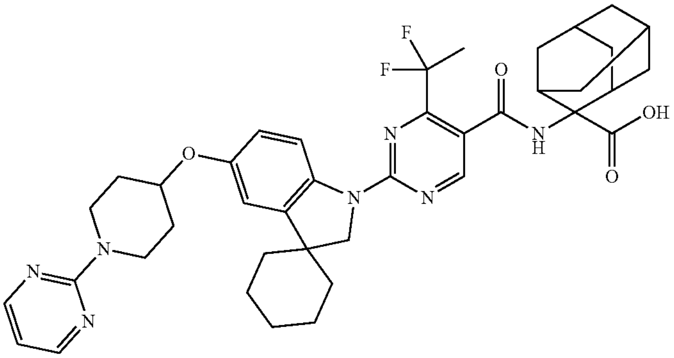 [SMILES: CC(F)(F)c1nc(N2CC3(CCCCC3)c3cc(OC4CCN(c5ncccn5)CC4)ccc32)ncc1C(=O)NC1(C(=O)O)C2CC3CC(C2)CC1C3] | 728 | 3.34 | 1 | |
| I-381 | 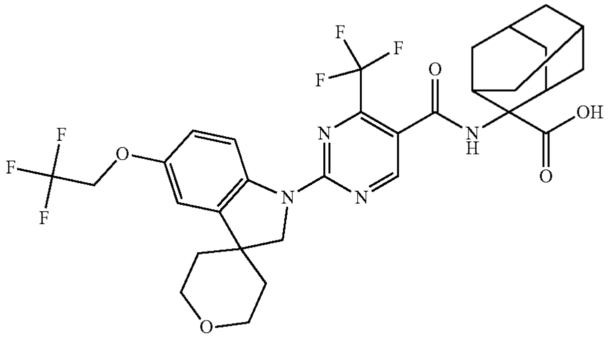 [SMILES: O=C(NC1(C(=O)O)C2CC3CC(C2)CC1C3)c1cnc(N2CC3(CCOCC3)c3cc(OCC(F)(F)F)ccc32)nc1C(F)(F)F] | 655 | 2.81 | 1 | |
TABLE 66
| Compound No. | Chemical Structure | [M + H] | Retention Time (min) | LC/MS Condition | Stereo-Chemistry |
| --- | --- | --- | --- | --- | --- |
| I-382 | 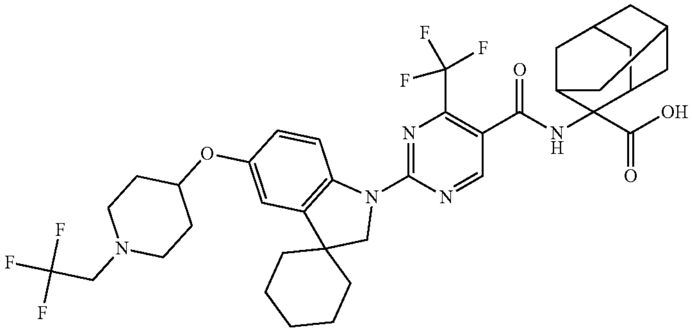 [SMILES: O=C(NC1(C(=O)O)C2CC3CC(C2)CC1C3)c1cnc(N2CC3(CCCCC3)c3cc(OC4CCN(CC(F)(F)F)CC4)ccc32)nc1C(F)(F)F] | 736 | 3.32 | 1 | |

TABLE 66-continued
| Compound No. | Chemical Structure | [M + H] | Retention Time (min) | LC/MS Condition | Stereo-Chemistry |
|---|---|---|---|---|---|
| I-383 | 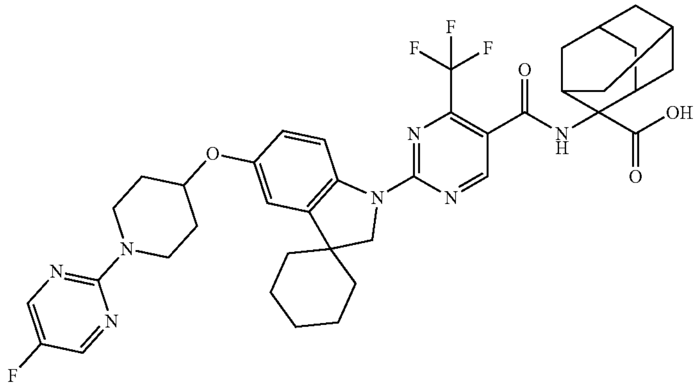 [SMILES: O=C(NC1(C(=O)O)C2CC3CC(C2)CC1C3)c1cnc(N2CC3(CCCCC3)c3cc(OC4CCN(c5ncc(F)cn5)CC4)ccc32)nc1C(F)(F)F] | 750 | 3.53 | 1 | |
| I-384 | 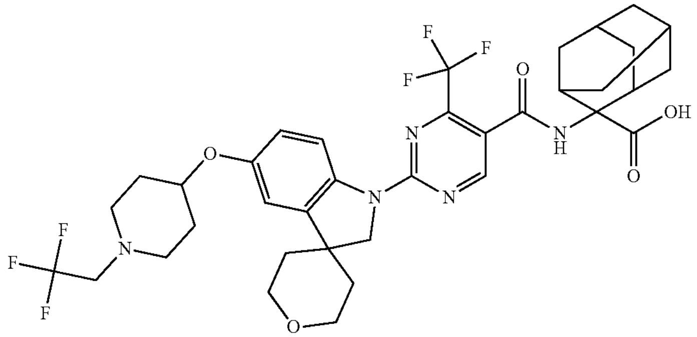 [SMILES: O=C(NC1(C(=O)O)C2CC3CC(C2)CC1C3)c1cnc(N2CC3(CCOCC3)c3cc(OC4CCN(CC(F)(F)F)CC4)ccc32)nc1C(F)(F)F] | 738 | 2.80 | 1 | |
| I-385 | 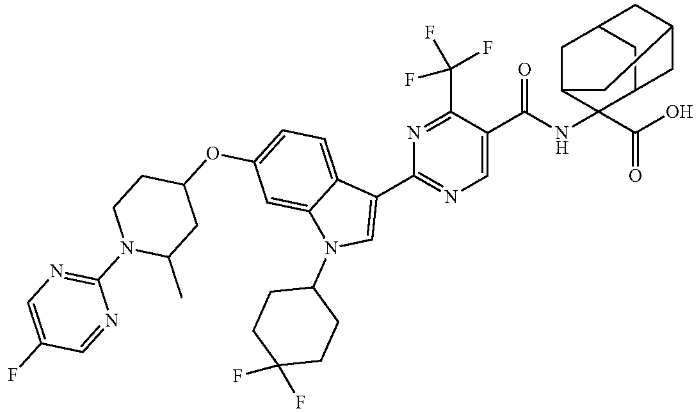 [SMILES: CC1CC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CCN1c1ncc(F)cn1] | 812 | 1.91 | 10 | f |
| I-386 | 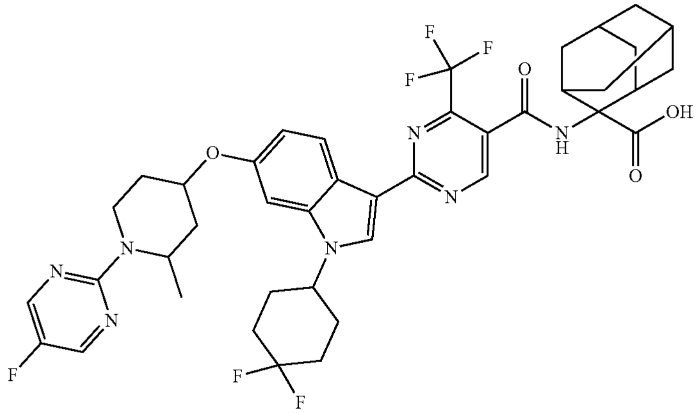 [SMILES: CC1CC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CCN1c1ncc(F)cn1] | 812 | 1.92 | 10 | f |

TABLE 66-continued
| Compound No. | Chemical Structure | [M + H] | Retention Time (min) | LC/MS Condition | Stereo-Chemistry |
|---|---|---|---|---|---|
| I-387 | 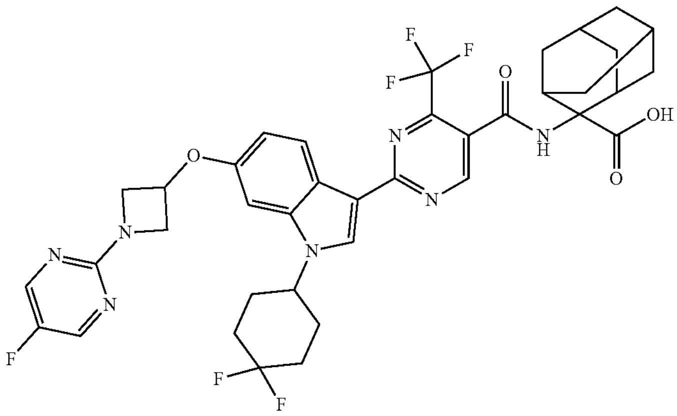 [SMILES: O=C(NC1(C(=O)O)C2CC3CC(C2)CC1C3)c1cnc(-c2cn(C3CCC(F)(F)CC3)c3cc(OC4CN(c5ncc(F)cn5)C4)ccc23)nc1C(F)(F)F] | 770 | 1.71 | 10 | |
TABLE 67
| Compound No. | Chemical Structure | [M + H] | Retention Time (min) | LC/MS Condition | Stereo-Chemistry |
|---|---|---|---|---|---|
| I-388 | 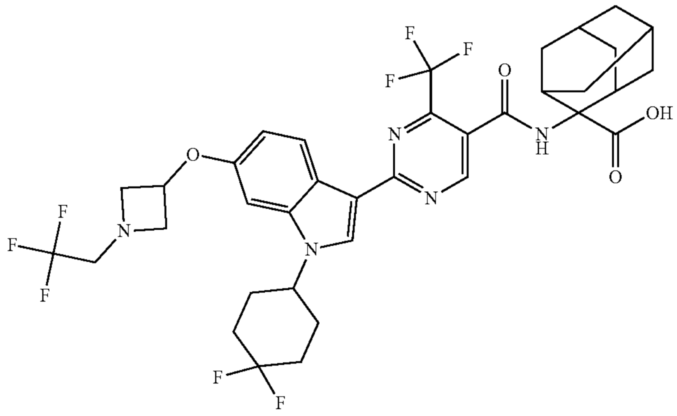 [SMILES: O=C(NC1(C(=O)O)C2CC3CC(C2)CC1C3)c1cnc(-c2cn(C3CCC(F)(F)CC3)c3cc(OC4CN(CC(F)(F)F)C4)ccc23)nc1C(F)(F)F] | 756 | 1.72 | 10 | |
| I-389 | 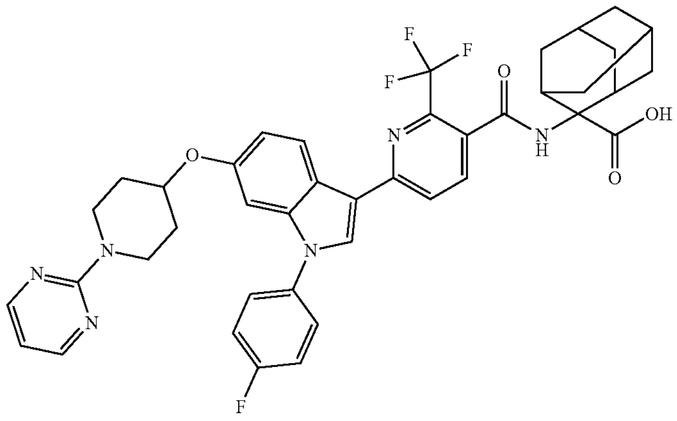 [SMILES: O=C(NC1(C(=O)O)C2CC3CC(C2)CC1C3)c1ccc(-c2cn(-c3ccc(F)cc3)c3cc(OC4CCN(c5ncccn5)CC4)ccc23)nc1C(F)(F)F] | 755 | 1.80 | 9 | |

TABLE 67-continued
| Compound No. | Chemical Structure | [M + H] | Retention Time (min) | LC/MS Condition | Stereo-Chemistry |
|---|---|---|---|---|---|
| I-390 | 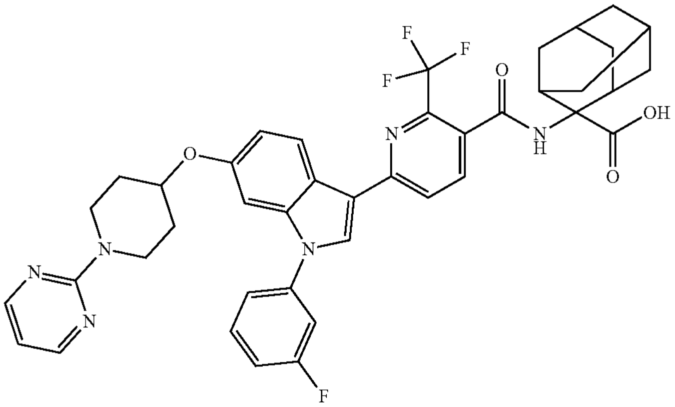 [SMILES: O=C(NC1(C(=O)O)C2CC3CC(C2)CC1C3)c1ccc(-c2cn(-c3cccc(F)c3)c3cc(OC4CCN(c5ncccn5)CC4)ccc23)nc1C(F)(F)F] | 755 | 1.82 | 9 | |
| I-391 | 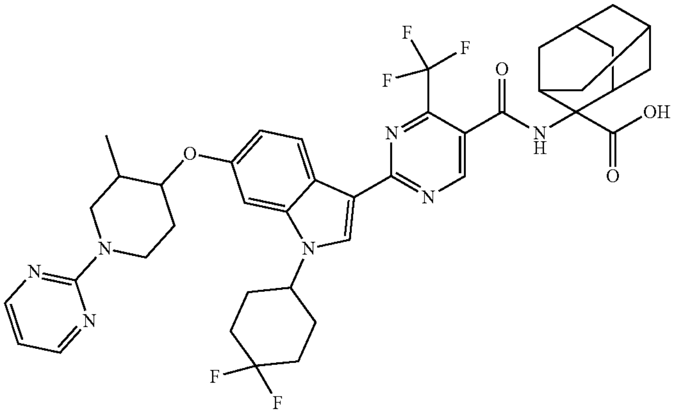 [SMILES: CC1CN(c2ncccn2)CCC1Oc1ccc2c(-c3ncc(C(=O)NC4(C(=O)O)C5CC6CC(C5)CC4C6)c(C(F)(F)F)n3)cn(C3CCC(F)(F)CC3)c2c1] | 794 | 1.83 | 9 | b |
| I-392 | 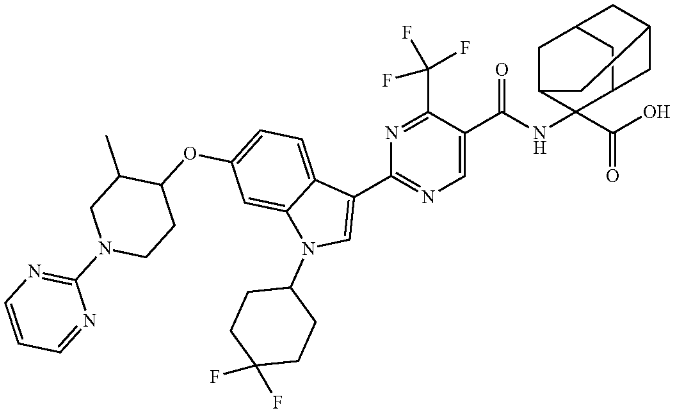 [SMILES: CC1CN(c2ncccn2)CCC1Oc1ccc2c(-c3ncc(C(=O)NC4(C(=O)O)C5CC6CC(C5)CC4C6)c(C(F)(F)F)n3)cn(C3CCC(F)(F)CC3)c2c1] | 794 | 1.82 | 9 | b |

TABLE 68
| Compound No. | Chemical Structure | [M + H] | Retention Time (min) | LC/MS Condition | Stereo-Chemistry |
|---|---|---|---|---|---|
| I-393 | 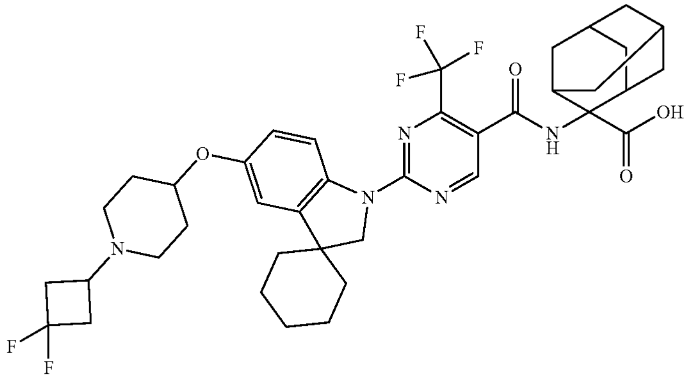 [SMILES: O=C(NC1(C(=O)O)C2CC3CC(C2)CC1C3)c1cnc(N2CC3(CCCCC3)c3cc(OC4CCN(C5CC(F)(F)C5)CC4)ccc32)nc1C(F)(F)F] | 744 | 2.33 | 1 | |
| I-394 | 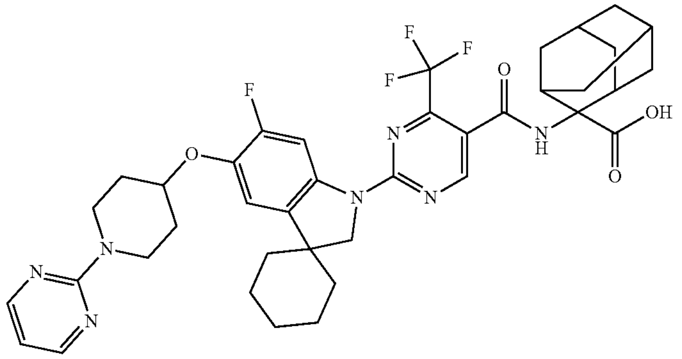 [SMILES: O=C(NC1(C(=O)O)C2CC3CC(C2)CC1C3)c1cnc(N2CC3(CCCCC3)c3cc(OC4CCN(c5ncccn5)CC4)c(F)cc32)nc1C(F)(F)F] | 750 | 3.35 | 1 | |
| I-395 | 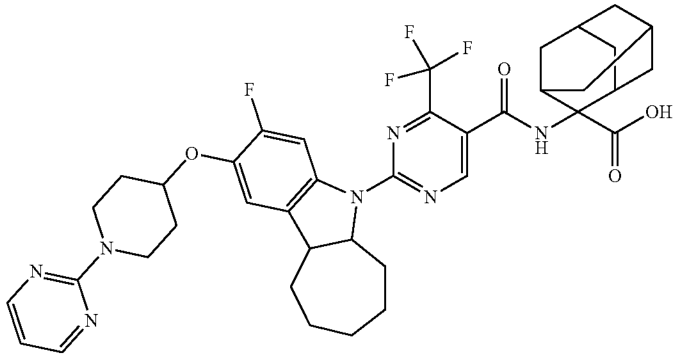 [SMILES: O=C(NC1(C(=O)O)C2CC3CC(C2)CC1C3)c1cnc(N2c3cc(F)c(OC4CCN(c5ncccn5)CC4)cc3C3CCCCCC32)nc1C(F)(F)F] | 750 | 3.42 | 1 | f |
| I-396 | 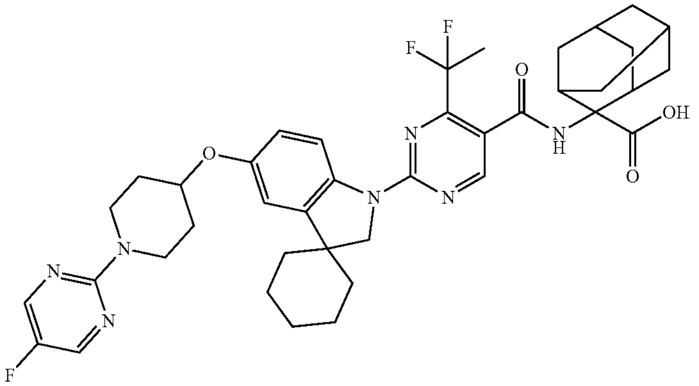 [SMILES: CC(F)(F)c1nc(N2CC3(CCCCC3)c3cc(OC4CCN(c5ncc(F)cn5)CC4)ccc32)ncc1C(=O)NC1(C(=O)O)C2CC3CC(C2)CC1C3] | 746 | 3.55 | 1 | |

TABLE 68-continued
| Compound No. | Chemical Structure | [M + H] | Retention Time (min) | LC/MS Condition | Stereo-Chemistry |
|---|---|---|---|---|---|
| I-397 | 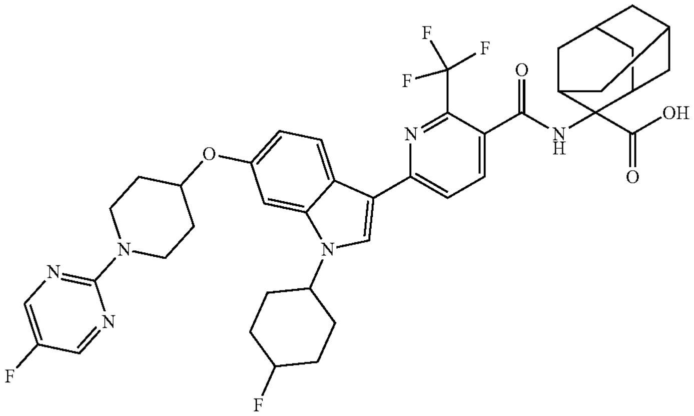 [SMILES: O=C(NC1(C(=O)O)C2CC3CC(C2)CC1C3)c1ccc(-c2cn(C3CCC(F)CC3)c3cc(OC4CCN(c5ncc(F)cn5)CC4)ccc23)nc1C(F)(F)F] | 779 | 3.20 | 1 | b |
| I-398 | 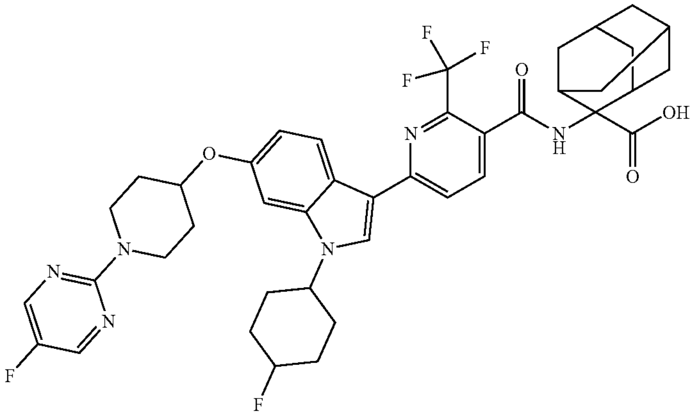 [SMILES: O=C(NC1(C(=O)O)C2CC3CC(C2)CC1C3)c1ccc(-c2cn(C3CCC(F)CC3)c3cc(OC4CCN(c5ncc(F)cn5)CC4)ccc23)nc1C(F)(F)F] | 779 | 2.98 | 1 | b |
TABLE 69
| Compound No. | Chemical Structure | [M + H] | Retention Time (min) | LC/MS Condition | Stereo-Chemistry |
|---|---|---|---|---|---|
| I-399 | 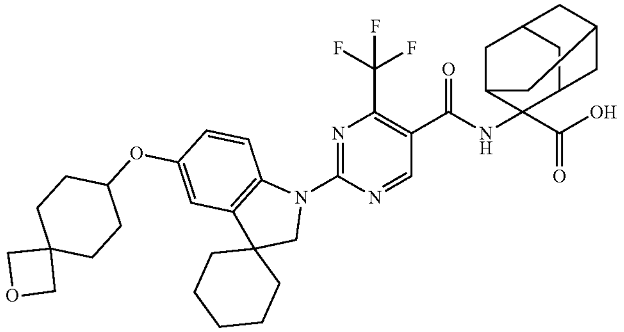 [SMILES: O=C(NC1(C(=O)O)C2CC3CC(C2)CC1C3)c1cnc(N2CC3(CCCCC3)c3cc(OC4CCC5(CC4)COC5)ccc32)nc1C(F)(F)F] | 695 | 3.24 | 1 | |

TABLE 69-continued
| Compound No. | Chemical Structure | [M + H] | Retention Time (min) | LC/MS Condition | Stereo-Chemistry |
|---|---|---|---|---|---|
| I-400 | 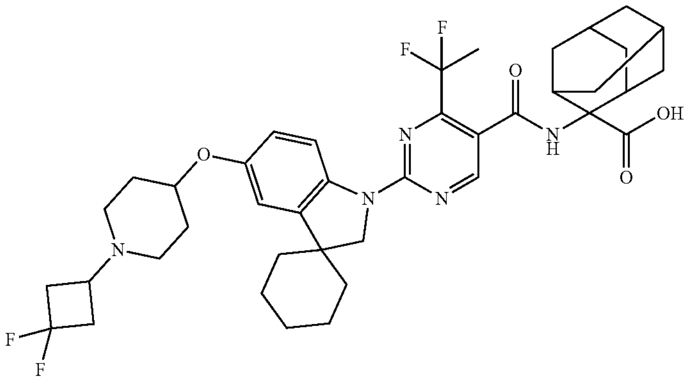 [SMILES: CC(F)(F)c1nc(N2CC3(CCCCC3)c3cc(OC4CCN(C5CC(F)(F)C5)CC4)ccc32)ncc1C(=O)NC1(C(=O)O)C2CC3CC(C2)CC1C3] | 740 | 2.19 | 1 | |
| I-401 | 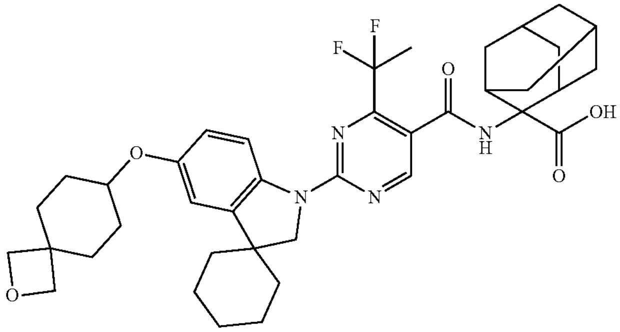 [SMILES: CC(F)(F)c1nc(N2CC3(CCCCC3)c3cc(OC4CCC5(CC4)COC5)ccc32)ncc1C(=O)NC1(C(=O)O)C2CC3CC(C2)CC1C3] | 691 | 3.19 | 1 | |
| I-402 | 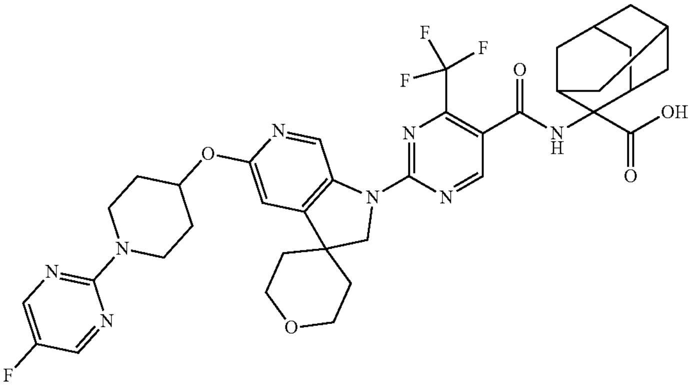 [SMILES: O=C(NC1(C(=O)O)C2CC3CC(C2)CC1C3)c1cnc(N2CC3(CCOCC3)c3cc(OC4CCN(c5ncc(F)cn5)CC4)ncc32)nc1C(F)(F)F] | 753 | 3.60 | 1 | |
| I-403 | 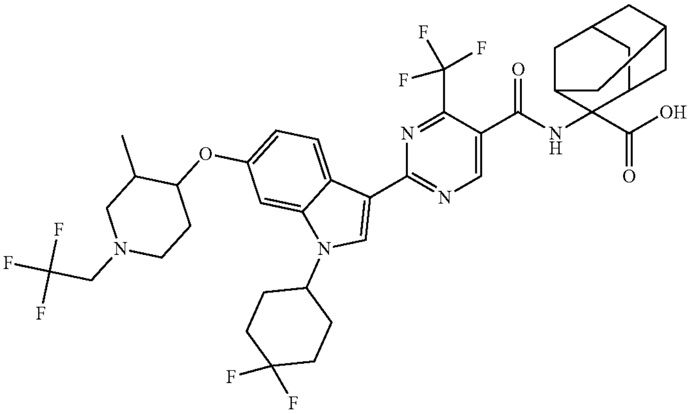 [SMILES: CC1CN(CC(F)(F)F)CCC1Oc1ccc2c(-c3ncc(C(=O)NC4(C(=O)O)C5CC6CC(C5)CC4C6)c(C(F)(F)F)n3)cn(C3CCC(F)(F)CC3)c2c1] | 798 | 1.85 | 9 | c |

TABLE 69-continued
| Compound No. | Chemical Structure | [M + H] | Retention Time (min) | LC/MS Condition | Stereo-Chemistry |
|---|---|---|---|---|---|
| I-404 | 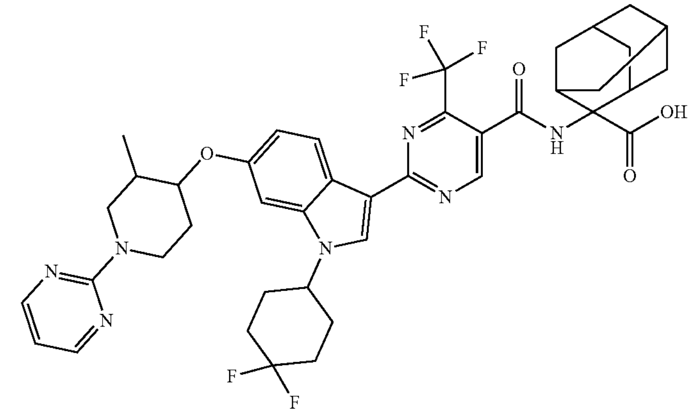 [SMILES: CC1CN(c2ncccn2)CCC1Oc1ccc2c(-c3ncc(C(=O)NC4(C(=O)O)C5CC6CC(C5)CC4C6)c(C(F)(F)F)n3)cn(C3CCC(F)(F)CC3)c2c1] | 794 | 1.84 | 9 | b |
TABLE 70
| Compound No. | Chemical Structure | [M + H] | Retention Time (min) | LC/MS Condition | Stereo-Chemistry |
|---|---|---|---|---|---|
| I-405 | 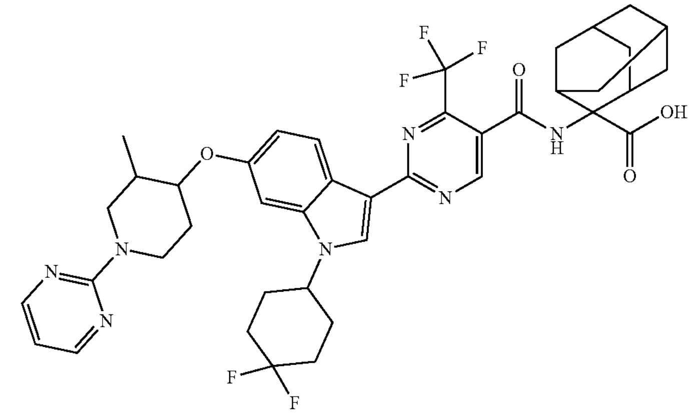 [SMILES: CC1CN(c2ncccn2)CCC1Oc1ccc2c(-c3ncc(C(=O)NC4(C(=O)O)C5CC6CC(C5)CC4C6)c(C(F)(F)F)n3)cn(C3CCC(F)(F)CC3)c2c1] | 794 | 1.83 | 9 | b |
| I-406 | 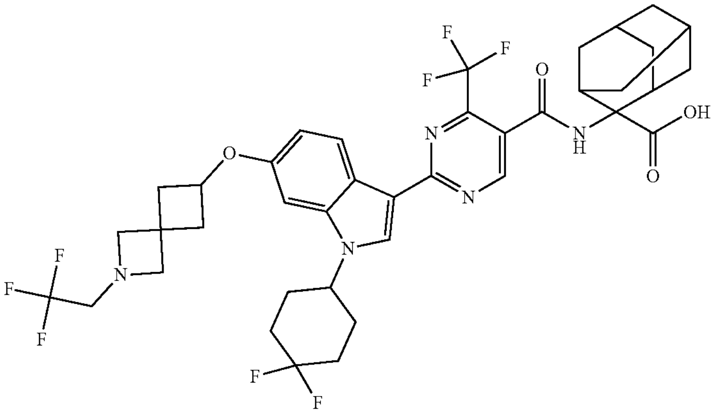 [SMILES: O=C(NC1(C(=O)O)C2CC3CC(C2)CC1C3)c1cnc(-c2cn(C3CCC(F)(F)CC3)c3cc(OC4CC5(C4)CN(CC(F)(F)F)C5)ccc23)nc1C(F)(F)F] | 796 | 1.55 | 9 | |

TABLE 70-continued
| Compound No. | Chemical Structure | [M + H] | Retention Time (min) | LC/MS Condition | Stereo-Chemistry |
|---|---|---|---|---|---|
| I-407 | 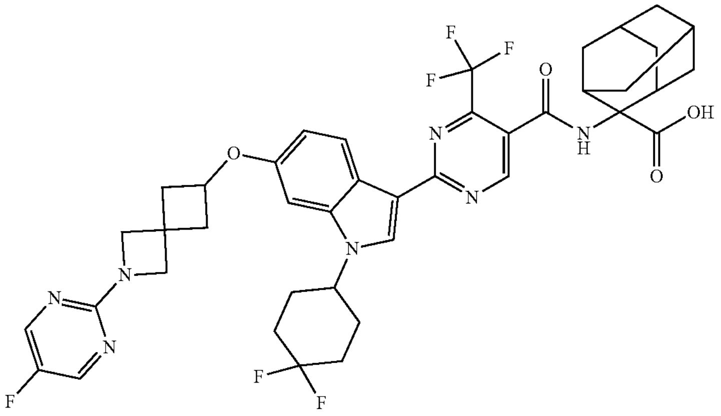 [SMILES: O=C(NC1(C(=O)O)C2CC3CC(C2)CC1C3)c1cnc(-c2cn(C3CCC(F)(F)CC3)c3cc(OC4CC5(C4)CN(c4ncc(F)cn4)C5)ccc23)nc1C(F)(F)F] | 810 | 1.75 | 9 | |
| I-408 | 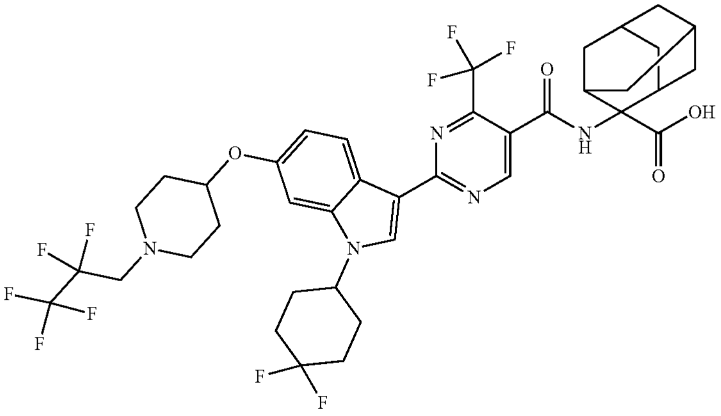 [SMILES: O=C(NC1(C(=O)O)C2CC3CC(C2)CC1C3)c1cnc(-c2cn(C3CCC(F)(F)CC3)c3cc(OC4CCN(CC(F)(F)C(F)(F)F)CC4)ccc23)nc1C(F)(F)F] | 834 | 1.90 | 9 | |
| I-409 | 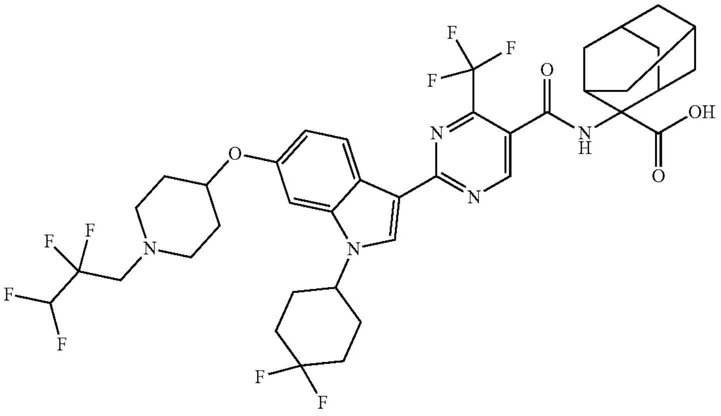 [SMILES: O=C(NC1(C(=O)O)C2CC3CC(C2)CC1C3)c1cnc(-c2cn(C3CCC(F)(F)CC3)c3cc(OC4CCN(CC(F)(F)C(F)F)CC4)ccc23)nc1C(F)(F)F] | 816 | 1.76 | 9 | |

TABLE 71
| Compound No. | Chemical Structure | [M + H] | Retention Time (min) | LC/MS Condition | Stereo-Chemistry |
|---|---|---|---|---|---|
| I-410 | 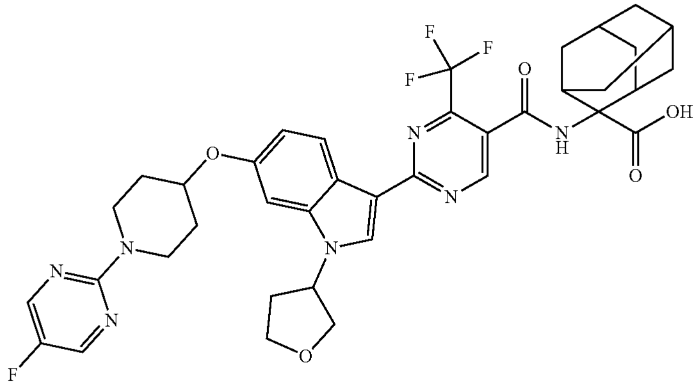 [SMILES: O=C(NC1(C(=O)O)C2CC3CC(C2)CC1C3)c1cnc(-c2cn(C3CCOC3)c3cc(OC4CCN(c5ncc(F)cn5)CC4)ccc23)nc1C(F)(F)F] | 750 | 1.76 | 9 | a |
| I-411 | 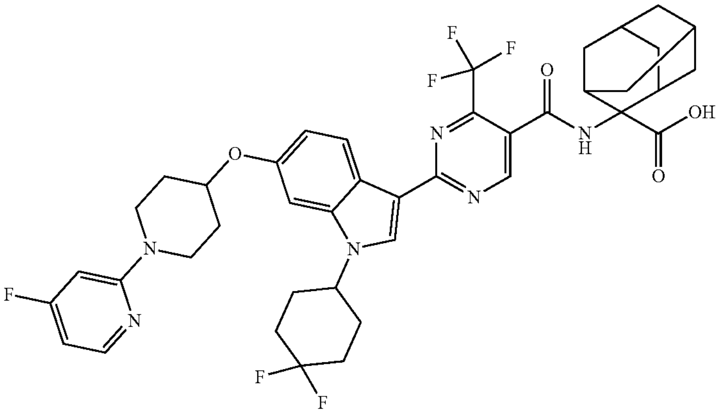 [SMILES: O=C(NC1(C(=O)O)C2CC3CC(C2)CC1C3)c1cnc(-c2cn(C3CCC(F)(F)CC3)c3cc(OC4CCN(c5cc(F)ccn5)CC4)ccc23)nc1C(F)(F)F] | 797 | 1.69 | 9 | |
| I-412 | 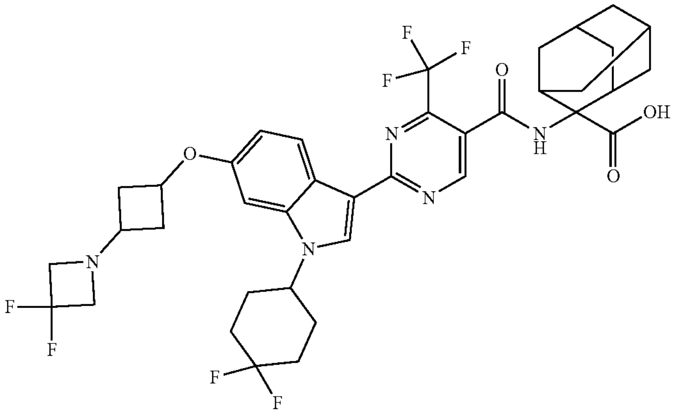 [SMILES: O=C(NC1(C(=O)O)C2CC3CC(C2)CC1C3)c1cnc(-c2cn(C3CCC(F)(F)CC3)c3cc(OC4CC(N5CC(F)(F)C5)C4)ccc23)nc1C(F)(F)F] | 764 | 1.45 | 10 | b |

TABLE 71-continued
| Compound No. | Chemical Structure | [M + H] | Retention Time (min) | LC/MS Condition | Stereo-Chemistry |
|---|---|---|---|---|---|
| I-413 | 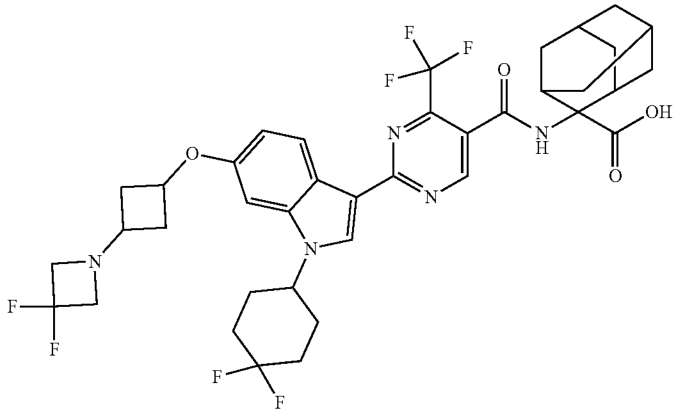 [SMILES: O=C(NC1(C(=O)O)C2CC3CC(C2)CC1C3)c1cnc(-c2cn(C3CCC(F)(F)CC3)c3cc(OC4CC(N5CC(F)(F)C5)C4)ccc23)nc1C(F)(F)F] | 764 | 1.56 | 10 | b |
| I-414 | 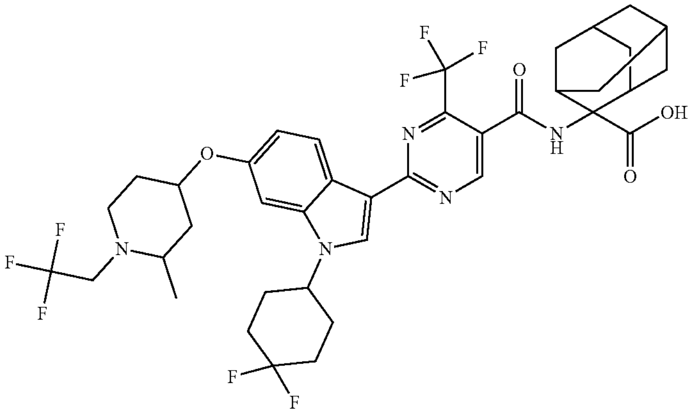 [SMILES: CC1CC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CCN1CC(F)(F)F] | 798 | 1.83, 1.84 | 10 | c |
TABLE 72
| Compound No. | Chemical Structure | [M + H] | Retention Time (min) | LC/MS Condition | Stereo-Chemistry |
|---|---|---|---|---|---|
| I-415 | 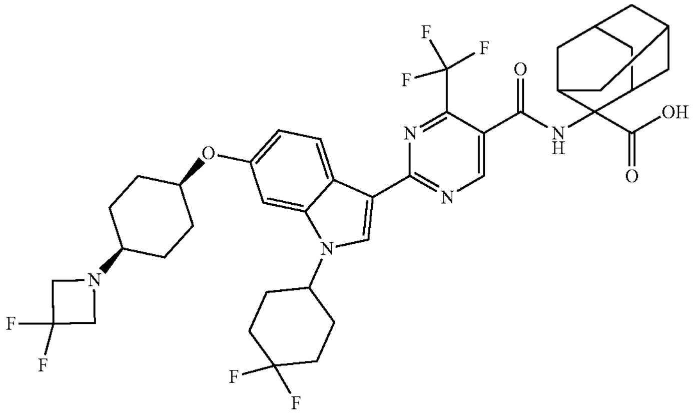 [SMILES: O=C(NC1(C(=O)O)C2CC3CC(C2)CC1C3)c1cnc(-c2cn(C3CCC(F)(F)CC3)c3cc(O[C@H]4CC[C@@H](N5CC(F)(F)C5)CC4)ccc23)nc1C(F)(F)F] | 792 | 1.36 | 9 | |

TABLE 72-continued
| Compound No. | Chemical Structure | [M + H] | Retention Time (min) | LC/MS Condition | Stereo-Chemistry |
|---|---|---|---|---|---|
| I-416 | 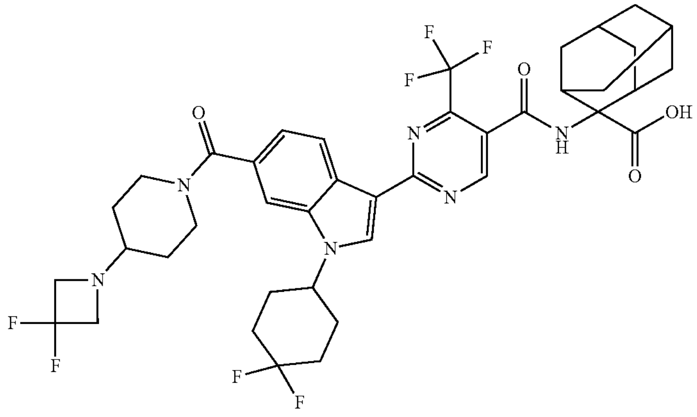 [SMILES: O=C(NC1(C(=O)O)C2CC3CC(C2)CC1C3)c1cnc(-c2cn(C3CCC(F)(F)CC3)c3cc(C(=O)N4CCC(N5CC(F)(F)C5)CC4)ccc23)nc1C(F)(F)F] | 805 | 1.31 | 10 | |
| I-417 | 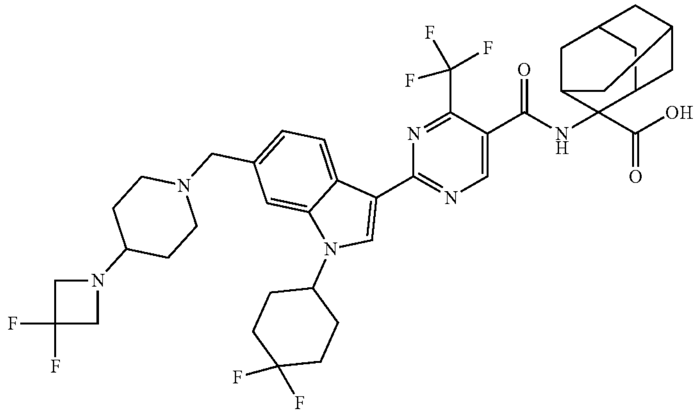 [SMILES: O=C(NC1(C(=O)O)C2CC3CC(C2)CC1C3)c1cnc(-c2cn(C3CCC(F)(F)CC3)c3cc(CN4CCC(N5CC(F)(F)C5)CC4)ccc23)nc1C(F)(F)F] | 791 | 1.18 | 10 | |
| I-418 | 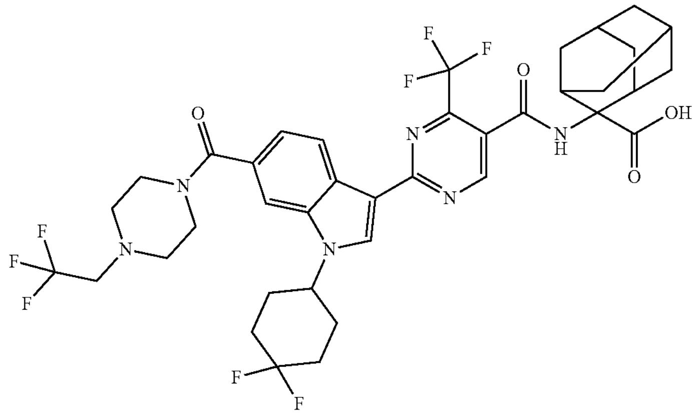 [SMILES: O=C(NC1(C(=O)O)C2CC3CC(C2)CC1C3)c1cnc(-c2cn(C3CCC(F)(F)CC3)c3cc(C(=O)N4CCN(CC(F)(F)F)CC4)ccc23)nc1C(F)(F)F] | 797 | 1.62 | 10 | |

TABLE 72-continued
| Compound No. | Chemical Structure | [M + H] | Retention Time (min) | LC/MS Condition | Stereo-Chemistry |
|---|---|---|---|---|---|
| I-419 | 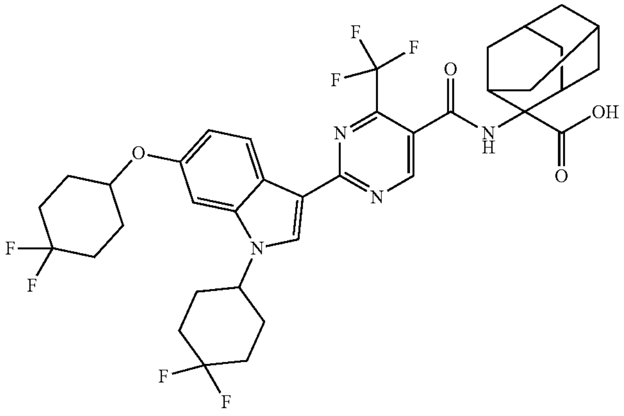 [SMILES: O=C(NC1(C(=O)O)C2CC3CC(C2)CC1C3)c1cnc(-c2cn(C3CCC(F)(F)CC3)c3cc(OC4CCC(F)(F)CC4)ccc23)nc1C(F)(F)F] | 737 | 1.82 | 10 | |
TABLE 73
| Compound No. | Chemical Structure | [M + H] | Retention Time (min) | LC/MS Condition | Stereo-Chemistry |
|---|---|---|---|---|---|
| I-420 | 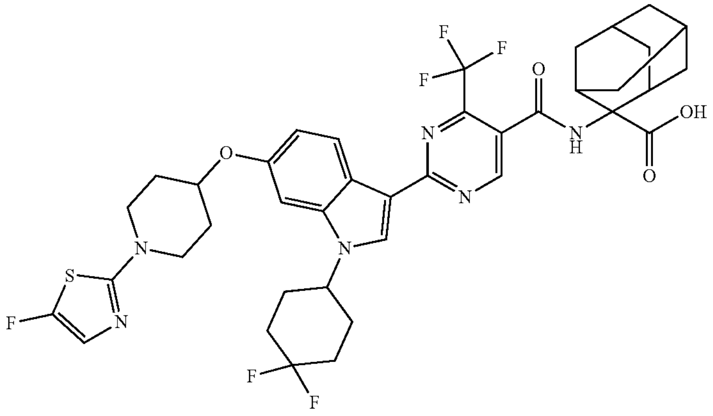 [SMILES: O=C(NC1(C(=O)O)C2CC3CC(C2)CC1C3)c1cnc(-c2cn(C3CCC(F)(F)CC3)c3cc(OC4CCN(c5ncc(F)s5)CC4)ccc23)nc1C(F)(F)F] | 803 | 1.85 | 9 | |
| I-421 | 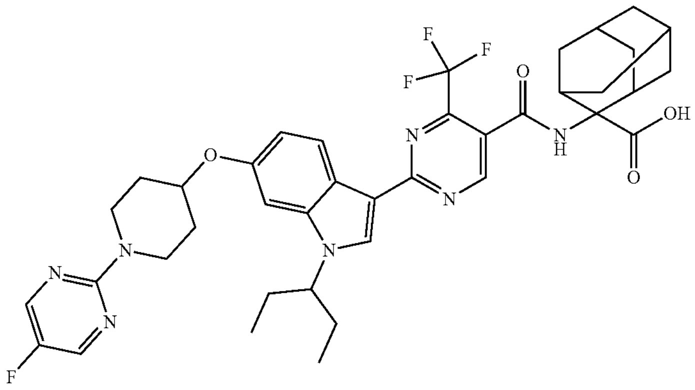 [SMILES: CCC(CC)n1cc(-c2ncc(C(=O)NC3(C(=O)O)C4CC5CC(C4)CC3C5)c(C(F)(F)F)n2)c2ccc(OC3CCN(c4ncc(F)cn4)CC3)cc21] | 750 | 1.94 | 9 | |

TABLE 73-continued
| Compound No. | Chemical Structure | [M + H] | Retention Time (min) | LC/MS Condition | Stereo-Chemistry |
| --- | --- | --- | --- | --- | --- |
| I-422 | 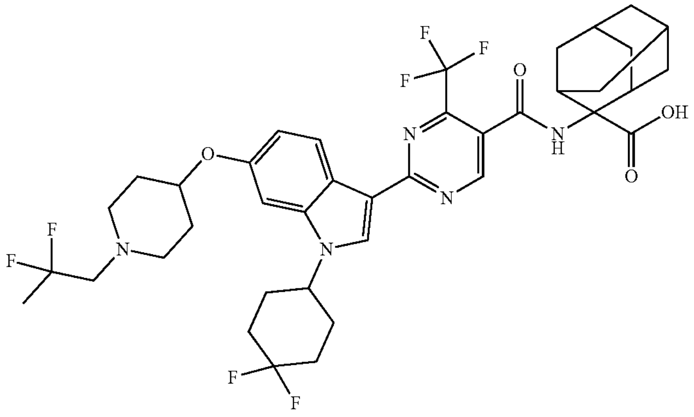 [SMILES: CC(F)(F)CN1CCC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 780 | 1.31 | 9 | |
| I-423 | 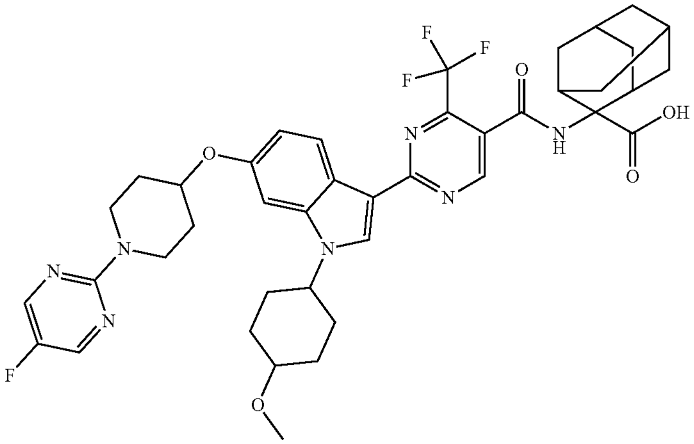 [SMILES: COC1CCC(n2cc(-c3ncc(C(=O)NC4(C(=O)O)C5CC6CC(C5)CC4C6)c(C(F)(F)F)n3)c3ccc(OC4CCN(c5ncc(F)cn5)CC4)cc32)CC1] | 792 | 1.89 | 9 | b |
| I-424 | 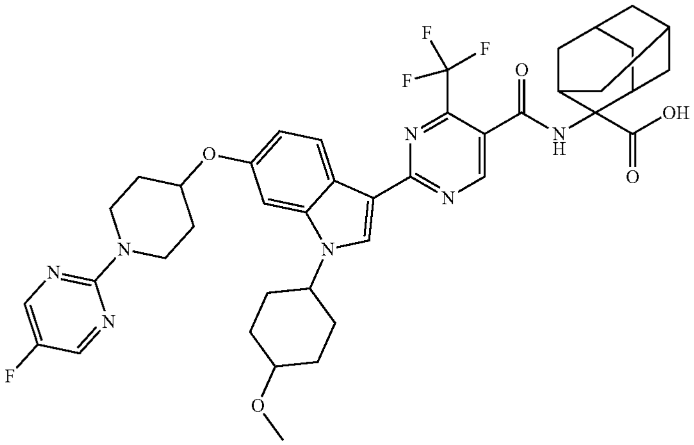 [SMILES: COC1CCC(n2cc(-c3ncc(C(=O)NC4(C(=O)O)C5CC6CC(C5)CC4C6)c(C(F)(F)F)n3)c3ccc(OC4CCN(c5ncc(F)cn5)CC4)cc32)CC1] | 792 | 1.85 | 9 | b |

TABLE 74
| Compound No. | Chemical Structure | [M + H] | Retention Time (min) | LC/MS Condition | Stereo-Chemistry |
|---|---|---|---|---|---|
| I-425 | 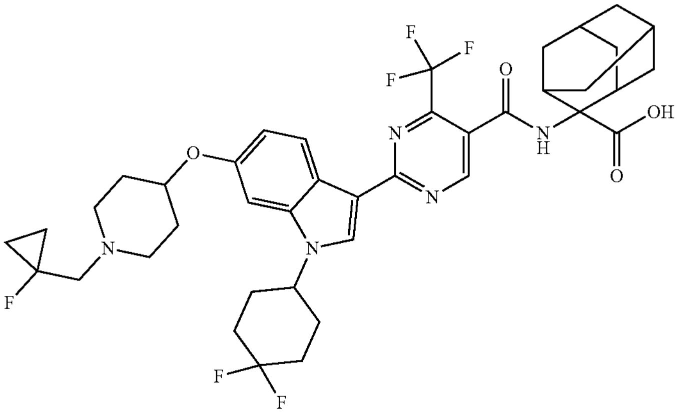 [SMILES: O=C(NC1(C(=O)O)C2CC3CC(C2)CC1C3)c1cnc(-c2cn(C3CCC(F)(F)CC3)c3cc(OC4CCN(CC5(F)CC5)CC4)ccc23)nc1C(F)(F)F] | 774 | 1.20 | 9 | |
| I-426 | 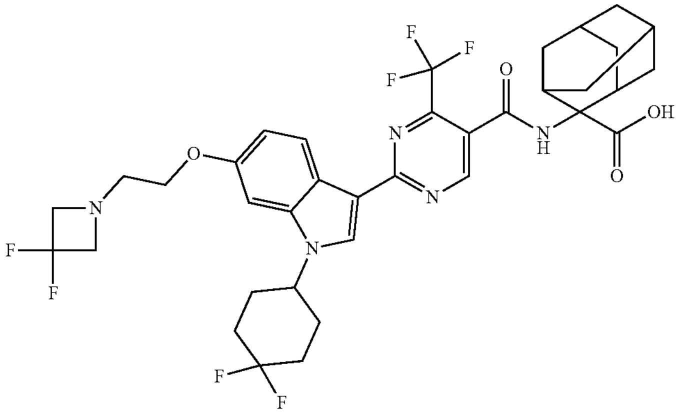 [SMILES: O=C(NC1(C(=O)O)C2CC3CC(C2)CC1C3)c1cnc(-c2cn(C3CCC(F)(F)CC3)c3cc(OCCN4CC(F)(F)C4)ccc23)nc1C(F)(F)F] | 738 | 1.35 | 9 | |
| I-427 | 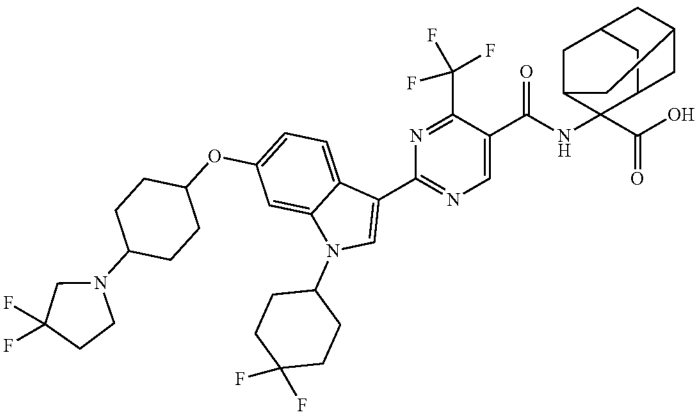 [SMILES: O=C(NC1(C(=O)O)C2CC3CC(C2)CC1C3)c1cnc(-c2cn(C3CCC(F)(F)CC3)c3cc(OC4CCC(N5CCC(F)(F)C5)CC4)ccc23)nc1C(F)(F)F] | 806 | 1.29 | 10 | b |

TABLE 74-continued
| Compound No. | Chemical Structure | [M + H] | Retention Time (min) | LC/MS Condition | Stereo-Chemistry |
|---|---|---|---|---|---|
| I-428 | 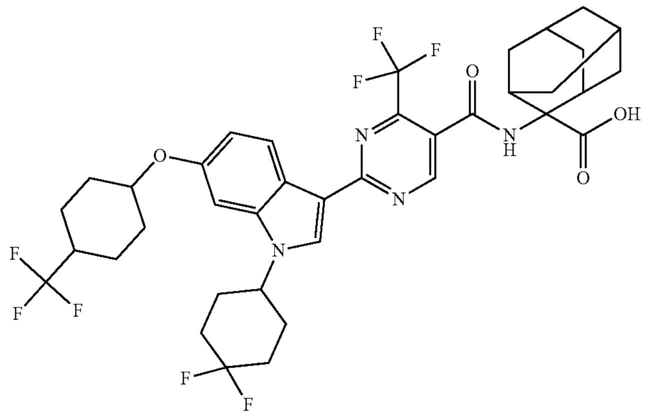 [SMILES: O=C(NC1(C(=O)O)C2CC3CC(C2)CC1C3)c1cnc(-c2cn(C3CCC(F)(F)CC3)c3cc(OC4CCC(C(F)(F)F)CC4)ccc23)nc1C(F)(F)F] | 769 | 1.90 | 10 | c |
| I-429 | 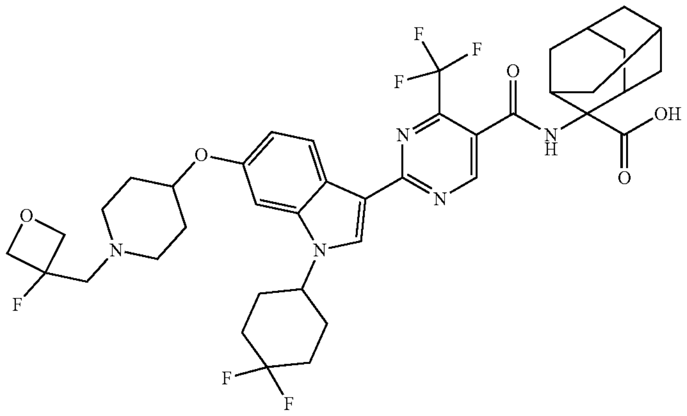 [SMILES: O=C(NC1(C(=O)O)C2CC3CC(C2)CC1C3)c1cnc(-c2cn(C3CCC(F)(F)CC3)c3cc(OC4CCN(CC5(F)COC5)CC4)ccc23)nc1C(F)(F)F] | 790 | 1.24 | 9 | |
TABLE 75
| Compound No. | Chemical Structure | [M + H] | Retention Time (min) | LC/MS Condition | Stereo-Chemistry |
|---|---|---|---|---|---|
| I-430 | 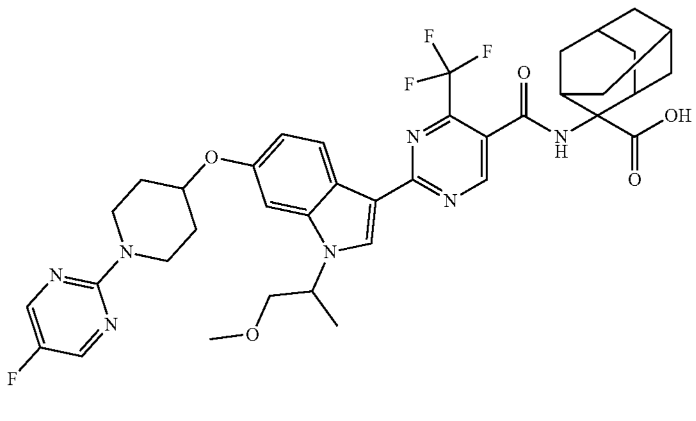 [SMILES: COCC(C)n1cc(-c2ncc(C(=O)NC3(C(=O)O)C4CC5CC(C4)CC3C5)c(C(F)(F)F)n2)c2ccc(OC3CCN(c4ncc(F)cn4)CC3)cc21] | 752 | 1.81 | 10 | a |

TABLE 75-continued
| Compound No. | Chemical Structure | [M + H] | Retention Time (min) | LC/MS Condition | Stereo-Chemistry |
|---|---|---|---|---|---|
| I-431 | 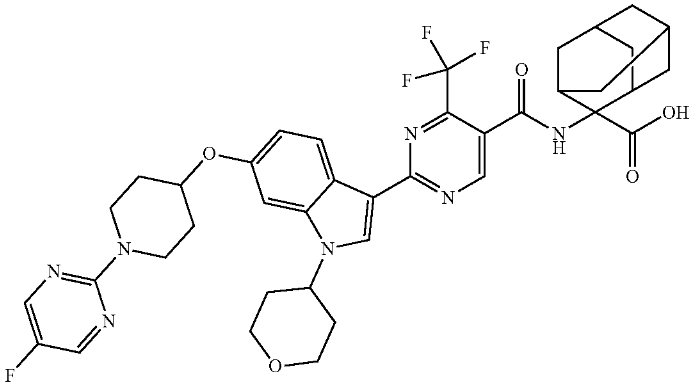 [SMILES: O=C(NC1(C(=O)O)C2CC3CC(C2)CC1C3)c1cnc(-c2cn(C3CCOCC3)c3cc(OC4CCN(c5ncc(F)cn5)CC4)ccc23)nc1C(F)(F)F] | 764 | 1.76 | 9 | |
| I-432 | 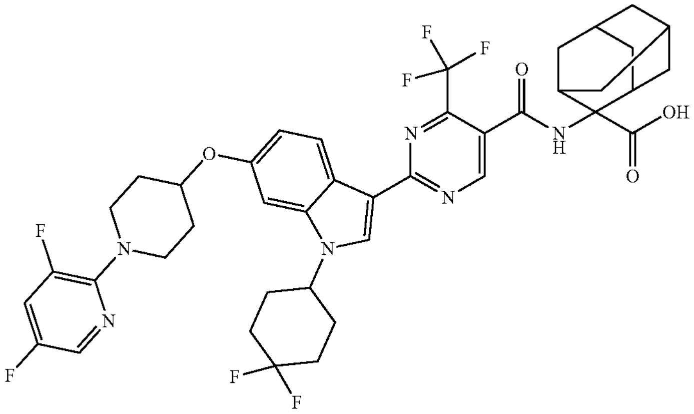 [SMILES: O=C(NC1(C(=O)O)C2CC3CC(C2)CC1C3)c1cnc(-c2cn(C3CCC(F)(F)CC3)c3cc(OC4CCN(c5ncc(F)cc5F)CC4)ccc23)nc1C(F)(F)F] | 815 | 1.90 | 9 | |
| I-433 | 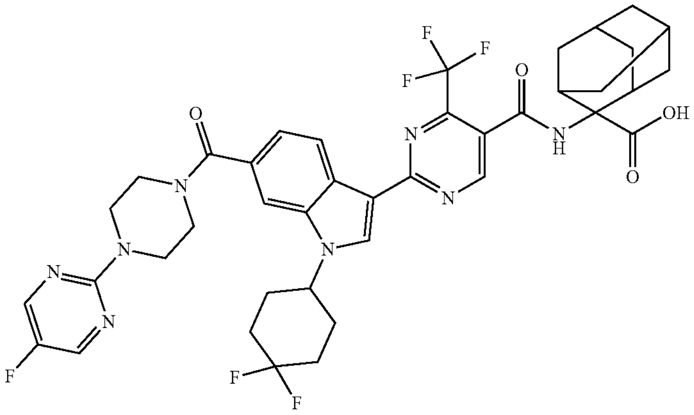 [SMILES: O=C(NC1(C(=O)O)C2CC3CC(C2)CC1C3)c1cnc(-c2cn(C3CCC(F)(F)CC3)c3cc(C(=O)N4CCN(c5ncc(F)cn5)CC4)ccc23)nc1C(F)(F)F] | 811 | 1.63 | 10 | |

TABLE 75-continued
| Compound No. | Chemical Structure | [M + H] | Retention Time (min) | LC/MS Condition | Stereo-Chemistry |
|---|---|---|---|---|---|
| I-434 | 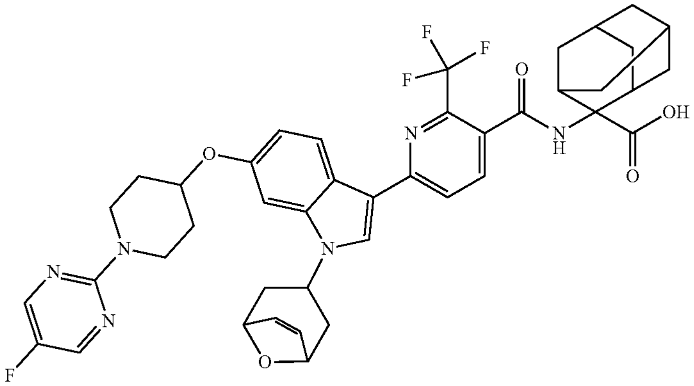 [SMILES: O=C(NC1(C(=O)O)C2CC3CC(C2)CC1C3)c1ccc(-c2cn(C3CC4C=CC(C3)O4)c3cc(OC4CCN(c5ncc(F)cn5)CC4)ccc23)nc1C(F)(F)F] | 787 | 3.07 | 1 | b |
| I-435 | 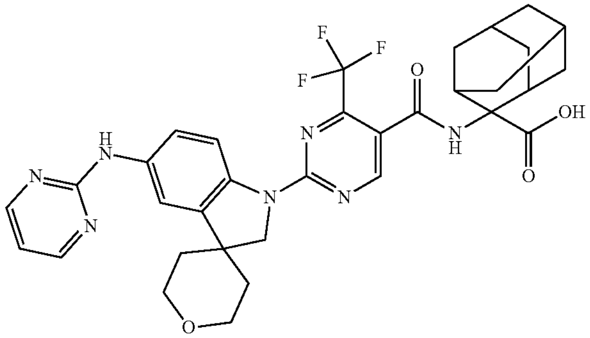 [SMILES: O=C(NC1(C(=O)O)C2CC3CC(C2)CC1C3)c1cnc(N2CC3(CCOCC3)c3cc(Nc4ncccn4)ccc32)nc1C(F)(F)F] | 650 | 1.41 | 9 | |
TABLE 76
| Compound No. | Chemical Structure | [M + H] | Retention Time (min) | LC/MS Condition | Stereo-Chemistry |
|---|---|---|---|---|---|
| I-436 | 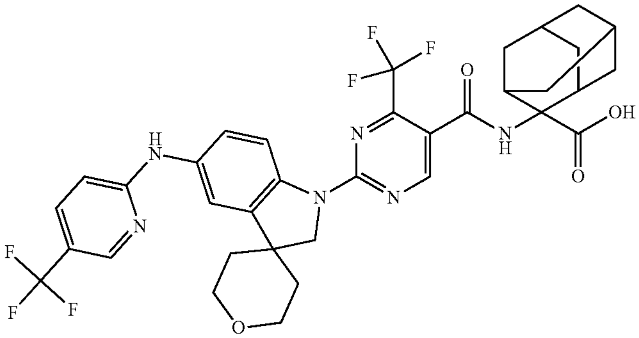 [SMILES: O=C(NC1(C(=O)O)C2CC3CC(C2)CC1C3)c1cnc(N2CC3(CCOCC3)c3cc(Nc4ccc(C(F)(F)F)cn4)ccc32)nc1C(F)(F)F] | 717 | 1.67 | 9 | |

TABLE 76-continued
| Compound No. | Chemical Structure | [M + H] | Retention Time (min) | LC/MS Condition | Stereo-Chemistry |
|---|---|---|---|---|---|
| I-437 | 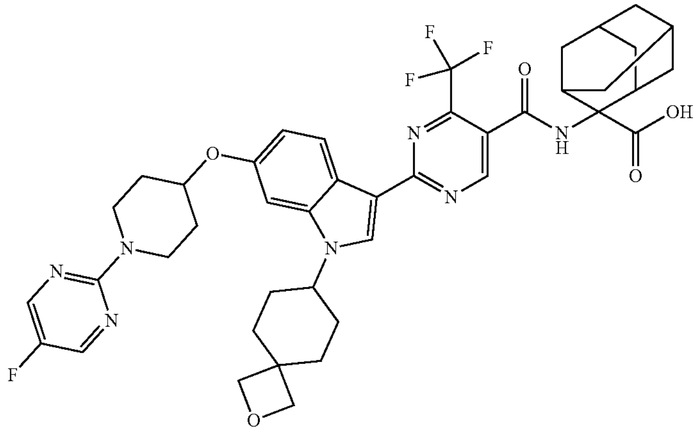 [SMILES: O=C(NC1(C(=O)O)C2CC3CC(C2)CC1C3)c1cnc(-c2cn(C3CCC4(CC3)COC4)c3cc(OC4CCN(c5ncc(F)cn5)CC4)ccc23)nc1C(F)(F)F] | 804 | 1.80 | 9 | |
| I-438 | 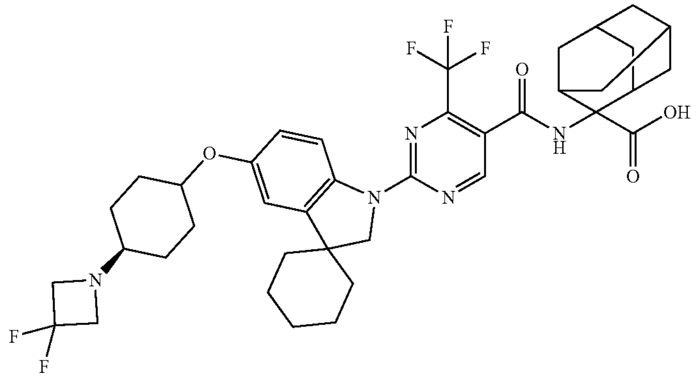 | 744 | 2.40 | 2 | |
| I-439 | 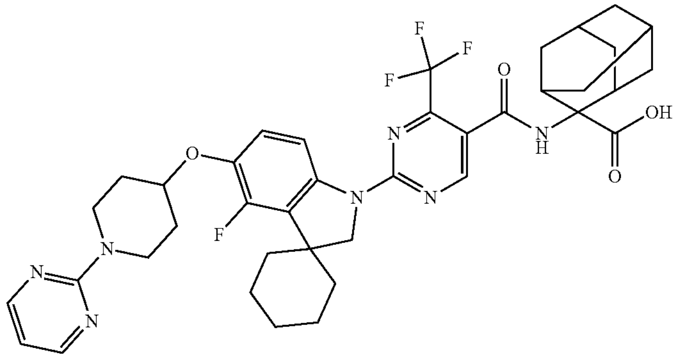 [SMILES: O=C(NC1(C(=O)O)C2CC3CC(C2)CC1C3)c1cnc(N2CC3(CCCCC3)c3c2ccc(OC2CCN(c4ncccn4)CC2)c3F)nc1C(F)(F)F] | 750 | 3.44 | 1 | |
| I-440 | 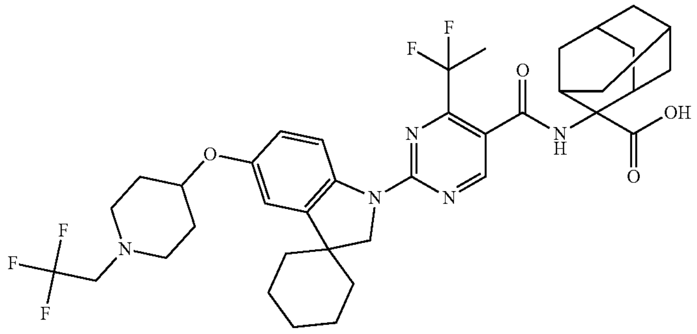 [SMILES: CC(F)(F)c1nc(N2CC3(CCCCC3)c3cc(OC4CCN(CC(F)(F)F)CC4)ccc32)ncc1C(=O)NC1(C(=O)O)C2CC3CC(C2)CC1C3] | 732 | 3.29 | 2 | |

TABLE 76-continued
| Compound No. | Chemical Structure | [M + H] | Retention Time (min) | LC/MS Condition | Stereo-Chemistry |
| --- | --- | --- | --- | --- | --- |
| I-441 | 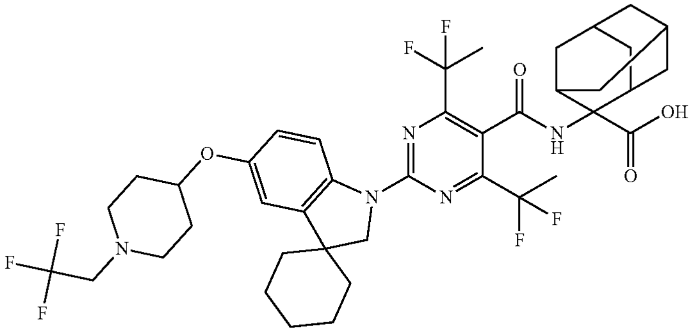 [SMILES: CC(F)(F)c1nc(N2CC3(CCCCC3)c3cc(OC4CCN(CC(F)(F)F)CC4)ccc32)nc(C(C)(F)F)c1C(=O)NC1(C(=O)O)C2CC3CC(C2)CC1C3] | 796 | 3.34 | 2 | |
TABLE 77
| Compound No. | Chemical Structure | [M + H] | Retention Time (min) | LC/MS Condition | Stereo-Chemistry |
| --- | --- | --- | --- | --- | --- |
| I-442 | 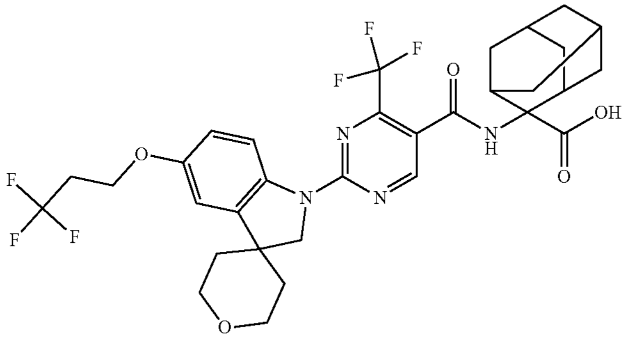 [SMILES: O=C(NC1(C(=O)O)C2CC3CC(C2)CC1C3)c1cnc(N2CC3(CCOCC3)c3cc(OCCC(F)(F)F)ccc32)nc1C(F)(F)F] | 669 | 2.86 | 1 | |
| I-443 | 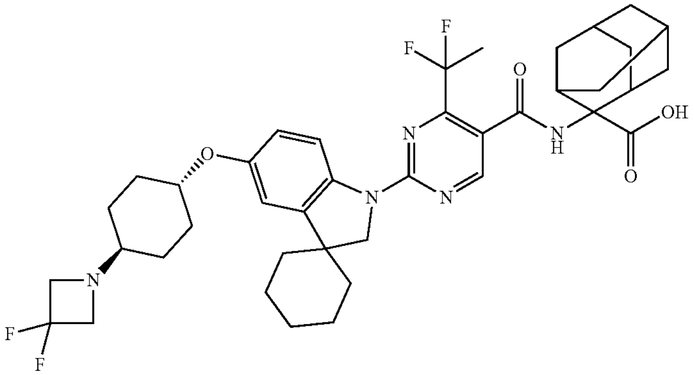 [SMILES: CC(F)(F)c1nc(N2CC3(CCCCC3)c3cc(O[C@H]4CC[C@H](N5CC(F)(F)C5)CC4)ccc32)ncc1C(=O)NC1(C(=O)O)C2CC3CC(C2)CC1C3] | 740 | 2.40 | 2 | |

TABLE 77-continued
| Compound No. | Chemical Structure | [M + H] | Retention Time (min) | LC/MS Condition | Stereo-Chemistry |
|---|---|---|---|---|---|
| I-444 | 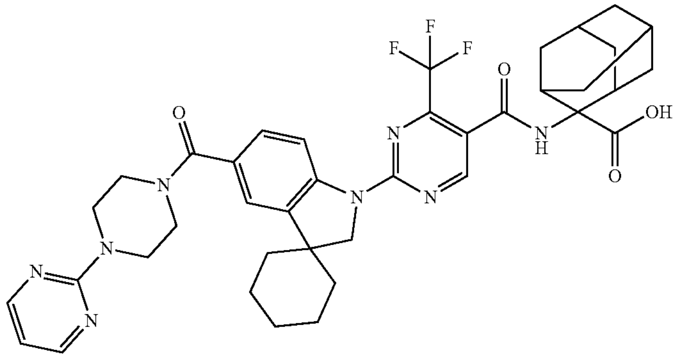 [SMILES: O=C(NC1(C(=O)O)C2CC3CC(C2)CC1C3)c1cnc(N2CC3(CCCCC3)c3cc(C(=O)N4CCN(c5ncccn5)CC4)ccc32)nc1C(F)(F)F] | 745 | 2.89 | 2 | |
| I-445 | 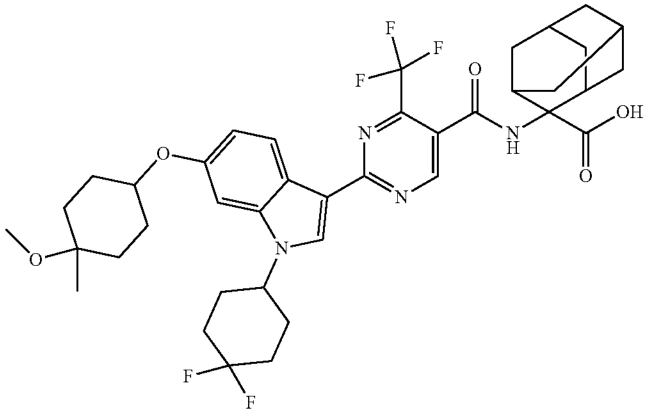 [SMILES: COC1(C)CCC(Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 745 | 1.84, 1.86 | 10 | c |
| I-446 | 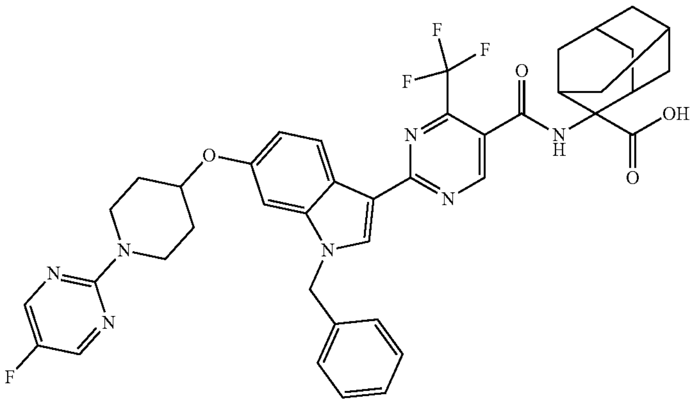 [SMILES: O=C(NC1(C(=O)O)C2CC3CC(C2)CC1C3)c1cnc(-c2cn(Cc3ccccc3)c3cc(OC4CCN(c5ncc(F)cn5)CC4)ccc23)nc1C(F)(F)F] | 770 | 1.78 | 10 | |

TABLE 77-continued
| Compound No. | Chemical Structure | [M + H] | Retention Time (min) | LC/MS Condition | Stereo-Chemistry |
| --- | --- | --- | --- | --- | --- |
| I-447 | 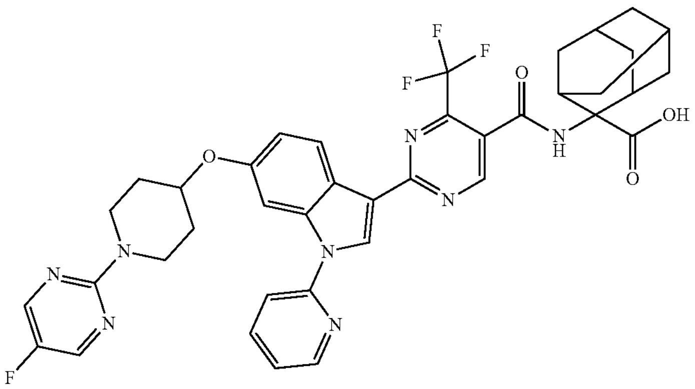 [SMILES: O=C(NC1(C(=O)O)C2CC3CC(C2)CC1C3)c1cnc(-c2cn(-c3ccccn3)c3cc(OC4CCN(c5ncc(F)cn5)CC4)ccc23)nc1C(F)(F)F] | 757 | 1.88 | 10 | |
TABLE 78
| Compound No. | Chemical Strcture | [M + H] | Retention Time (min) | LC/MS Condition | Stereo-Chemistry |
| --- | --- | --- | --- | --- | --- |
| I-448 | 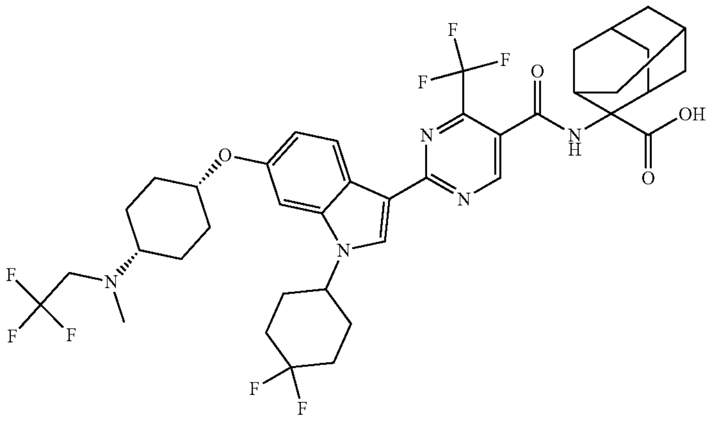 [SMILES: CN(CC(F)(F)F)[C@H]1CC[C@@H](Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 812 | 1.83 | 9 | |
| I-449 | 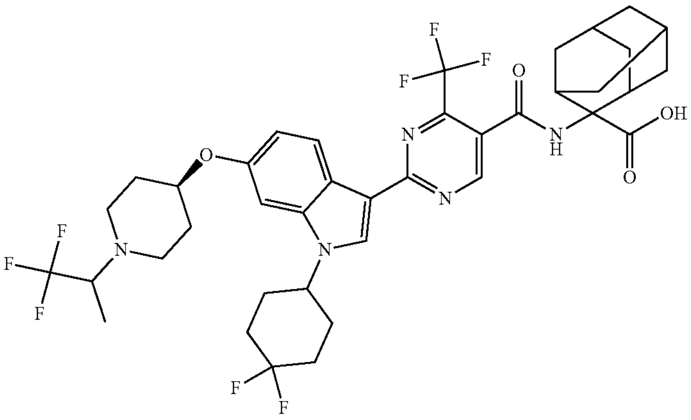 | 798 | 1.85 | 9 | a |

TABLE 78-continued
| Compound No. | Chemical Strcture | [M + H] | Retention Time (min) | LC/MS Condition | Stereo-Chemistry |
|---|---|---|---|---|---|
| I-450 | 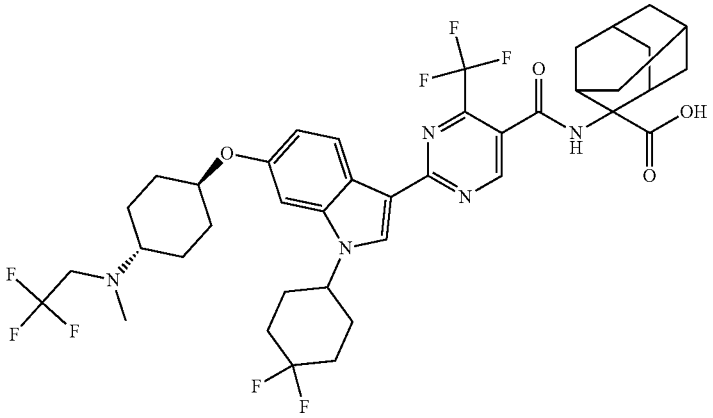 [SMILES: CN(CC(F)(F)F)[C@H]1CC[C@H](Oc2ccc3c(-c4ncc(C(=O)NC5(C(=O)O)C6CC7CC(C6)CC5C7)c(C(F)(F)F)n4)cn(C4CCC(F)(F)CC4)c3c2)CC1] | 812 | 1.85 | 9 | |
| I-451 | 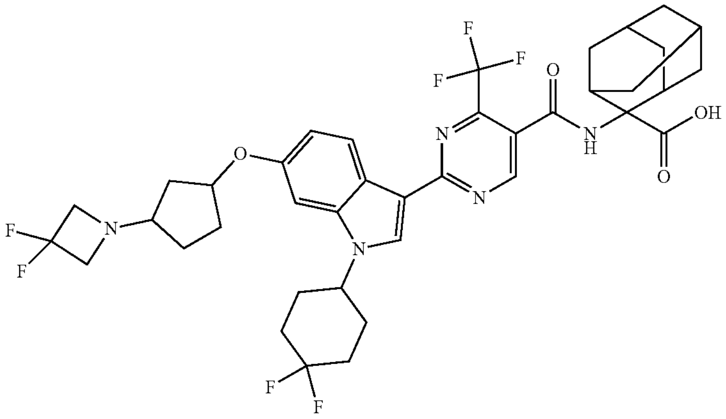 [SMILES: O=C(NC1(C(=O)O)C2CC3CC(C2)CC1C3)c1cnc(-c2cn(C3CCC(F)(F)CC3)c3cc(OC4CCC(N5CC(F)(F)C5)C4)ccc23)nc1C(F)(F)F] | 778 | 1.41 | 9 | c |
| I-452 | 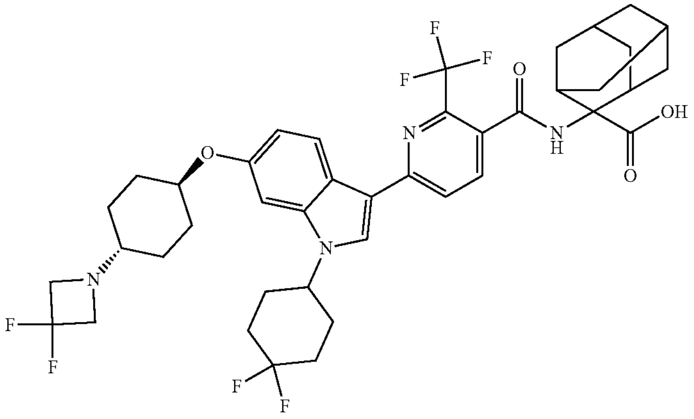 [SMILES: O=C(NC1(C(=O)O)C2CC3CC(C2)CC1C3)c1ccc(-c2cn(C3CCC(F)(F)CC3)c3cc(O[C@H]4CC[C@H](N5CC(F)(F)C5)CC4)ccc23)nc1C(F)(F)F] | 791 | 1.38 | 9 | |

TABLE 79
| Compound No. | Chemical Structure | [M + H] | Retention Time (min) | LC/MS Condition | Stereo-Chemistry |
|---|---|---|---|---|---|
| I-453 | 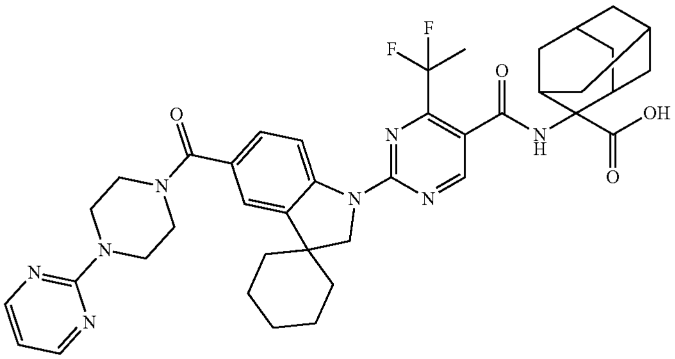 [SMILES: CC(F)(F)c1nc(N2CC3(CCCCC3)c3cc(C(=O)N4CCN(c5ncccn5)CC4)ccc32)ncc1C(=O)NC1(C(=O)O)C2CC3CC(C2)CC1C3] | 741 | 2.85 | 2 | |
| I-454 | 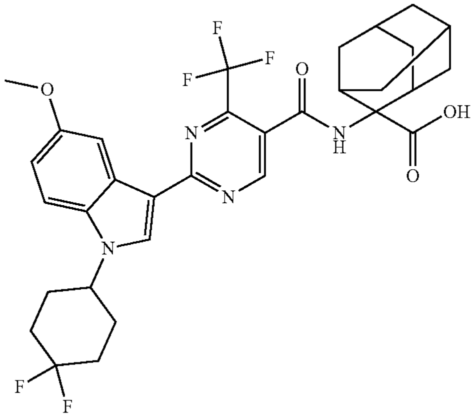 [SMILES: COc1ccc2c(c1)c(-c1ncc(C(=O)NC3(C(=O)O)C4CC5CC(C4)CC3C5)c(C(F)(F)F)n1)cn2C1CCC(F)(F)CC1] | 633 | 2.89 | 1 | |
| I-455 | 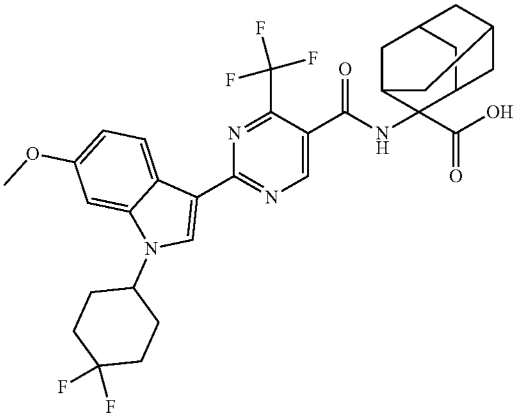 [SMILES: COc1ccc2c(-c3ncc(C(=O)NC4(C(=O)O)C5CC6CC(C5)CC4C6)c(C(F)(F)F)n3)cn(C3CCC(F)(F)CC3)c2c1] | 633 | 2.90 | 1 | |

TABLE 79-continued
| Compound No. | Chemical Structure | [M + H] | Retention Time (min) | LC/MS Condition | Stereo-Chemistry |
|---|---|---|---|---|---|
| I-456 | 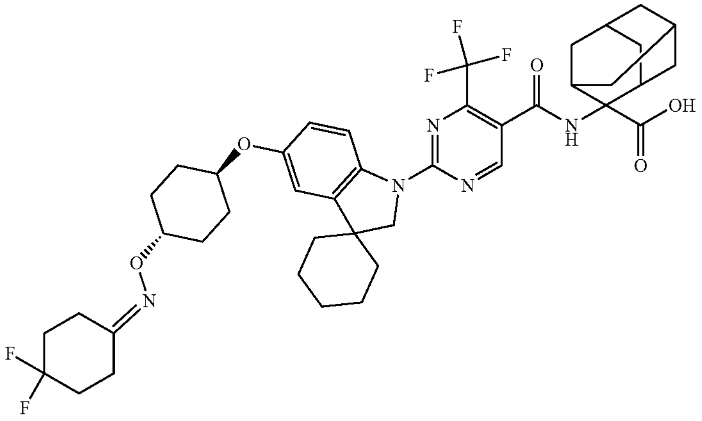 [SMILES: O=C(NC1(C(=O)O)C2CC3CC(C2)CC1C3)c1cnc(N2CC3(CCCCC3)c3cc(O[C@H]4CC[C@H](ON=C5CCC(F)(F)CC5)CC4)ccc32)nc1C(F)(F)F] | 800 | 3.61 | 1 | |
| I-457 | 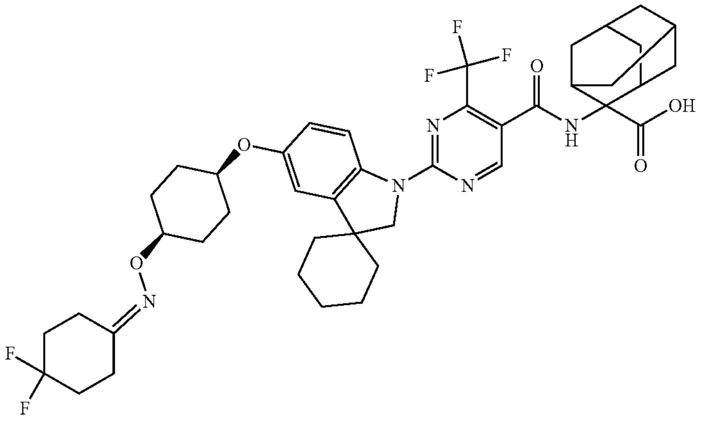 [SMILES: O=C(NC1(C(=O)O)C2CC3CC(C2)CC1C3)c1cnc(N2CC3(CCCCC3)c3cc(O[C@H]4CC[C@@H](ON=C5CCC(F)(F)CC5)CC4)ccc32)nc1C(F)(F)F] | 800 | 3.57 | 1 | |
TABLE 80
| Compound No. | Chemical Structure | [M + H] | Retention Time (min) | LC/MS Condition | Stereo-Chemistry |
|---|---|---|---|---|---|
| I-458 | 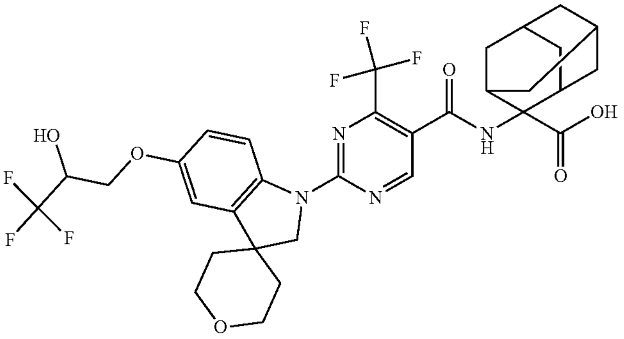 [SMILES: O=C(NC1(C(=O)O)C2CC3CC(C2)CC1C3)c1cnc(N2CC3(CCOCC3)c3cc(OCC(O)C(F)(F)F)ccc32)nc1C(F)(F)F] | 685 | 2.59 | 1 | a |

TABLE 80-continued
| Compound No. | Chemical Structure | [M + H] | Retention Time (min) | LC/MS Condition | Stereo-Chemistry |
|---|---|---|---|---|---|
| I-459 | 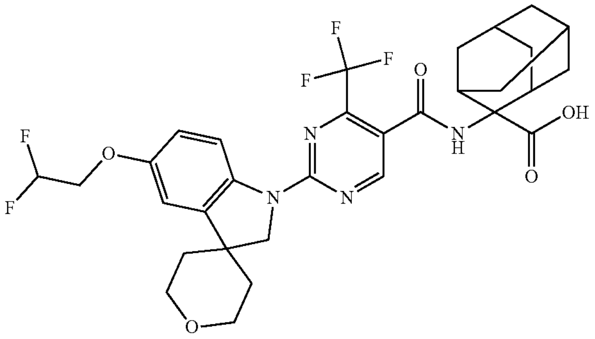 [SMILES: O=C(NC1(C(=O)O)C2CC3CC(C2)CC1C3)c1cnc(N2CC3(CCOCC3)c3cc(OCC(F)F)ccc32)nc1C(F)(F)F] | 637 | 2.71 | 1 | |
| I-460 | 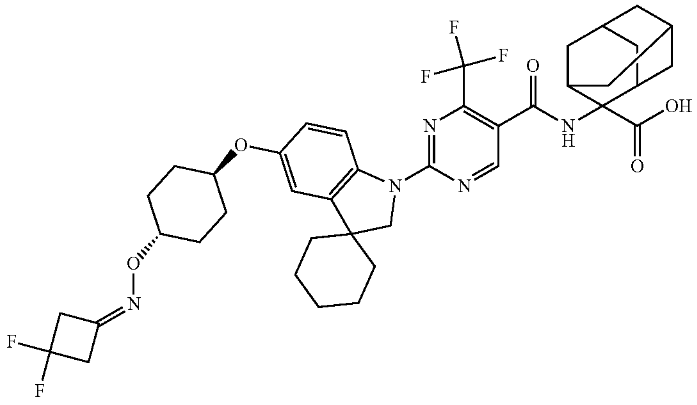 [SMILES: O=C(NC1(C(=O)O)C2CC3CC(C2)CC1C3)c1cnc(N2CC3(CCCCC3)c3cc(O[C@H]4CC[C@H](ON=C5CC(F)(F)C5)CC4)ccc32)nc1C(F)(F)F] | 772 | 3.57 | 1 | |
| I-461 | 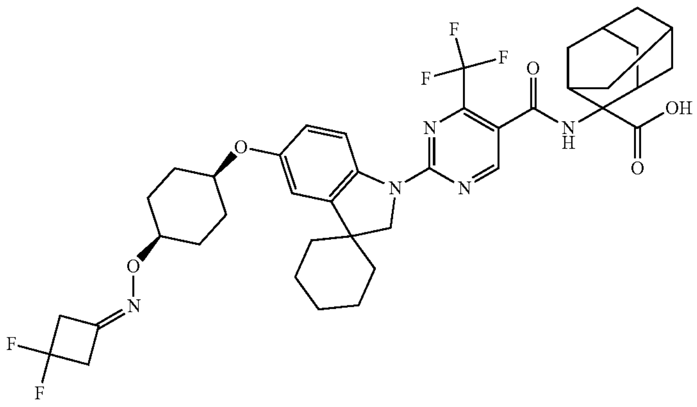 [SMILES: O=C(NC1(C(=O)O)C2CC3CC(C2)CC1C3)c1cnc(N2CC3(CCCCC3)c3cc(O[C@H]4CC[C@@H](ON=C5CC(F)(F)C5)CC4)ccc32)nc1C(F)(F)F] | 772 | 3.64 | 1 | |
| I-462 | 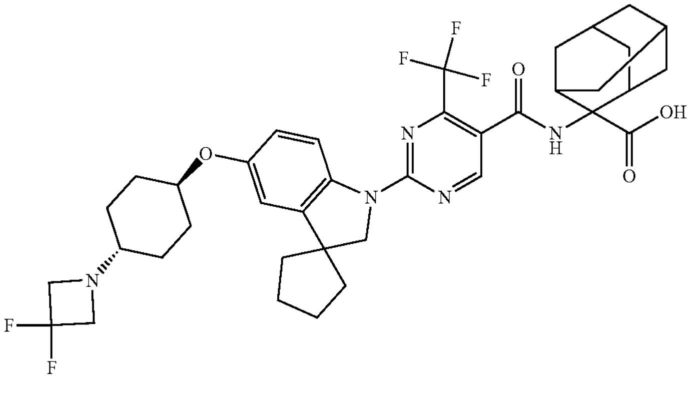 [SMILES: O=C(NC1(C(=O)O)C2CC3CC(C2)CC1C3)c1cnc(N2CC3(CCCC3)c3cc(O[C@H]4CC[C@H](N5CC(F)(F)C5)CC4)ccc32)nc1C(F)(F)F] | 730 | 2.36 | 1 | |

TABLE 80-continued
| Compound No. | Chemical Structure | [M + H] | Retention Time (min) | LC/MS Condition | Stereo-Chemistry |
|---|---|---|---|---|---|
| I-463 | 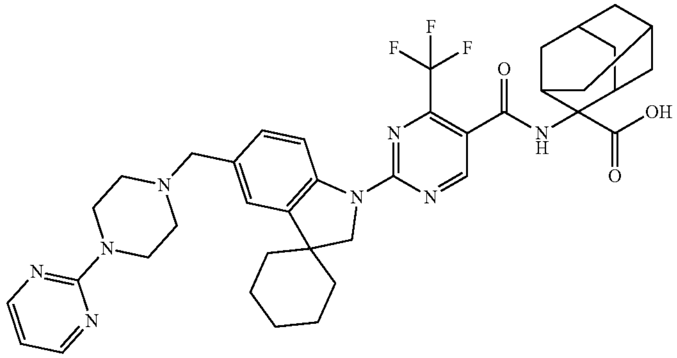 [SMILES: O=C(NC1(C(=O)O)C2CC3CC(C2)CC1C3)c1cnc(N2CC3(CCCCC3)c3cc(CN4CCN(c5ncccn5)CC4)ccc32)nc1C(F)(F)F] | 731 | 2.14 | 2 | |
TABLE 81
| Compound No. | Chemical Structure | [M + H] | Retention Time (min) | LC/MS Condition | Stereo-Chemistry |
|---|---|---|---|---|---|
| I-464 | 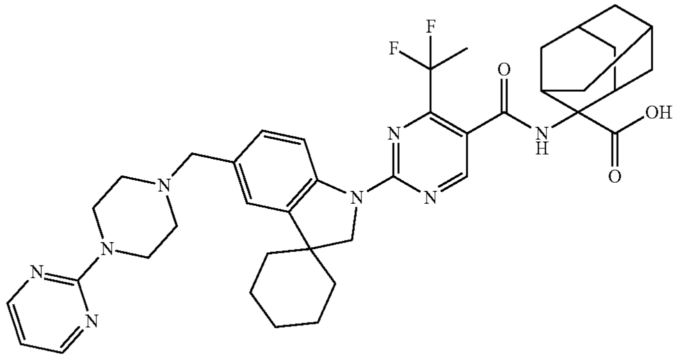 [SMILES: CC(F)(F)c1nc(N2CC3(CCCCC3)c3cc(CN4CCN(c5ncccn5)CC4)ccc32)ncc1C(=O)NC1(C(=O)O)C2CC3CC(C2)CC1C3] | 727 | 2.21 | 2 | |
| I-465 | 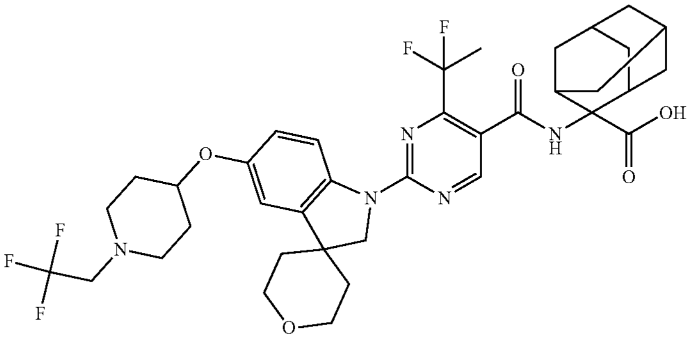 [SMILES: CC(F)(F)c1nc(N2CC3(CCOCC3)c3cc(OC4CCN(CC(F)(F)F)CC4)ccc32)ncc1C(=O)NC1(C(=O)O)C2CC3CC(C2)CC1C3] | 734 | 2.74 | 2 | |
| I-466 | 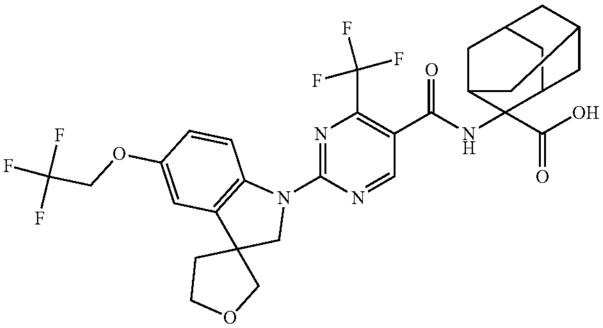 [SMILES: O=C(NC1(C(=O)O)C2CC3CC(C2)CC1C3)c1cnc(N2CC3(CCOC3)c3cc(OCC(F)(F)F)ccc32)nc1C(F)(F)F] | 641 | 2.80 | 1 | a |

TABLE 81-continued
| Compound No. | Chemical Structure | [M + H] | Retention Time (min) | LC/MS Condition | Stereo-Chemistry |
|---|---|---|---|---|---|
| I-467 | 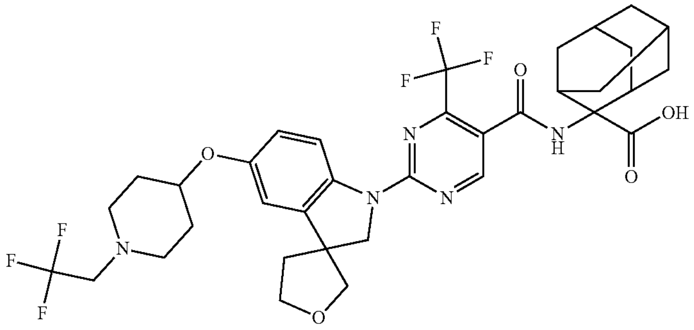 [SMILES: O=C(NC1(C(=O)O)C2CC3CC(C2)CC1C3)c1cnc(N2CC3(CCOC3)c3cc(OC4CCN(CC(F)(F)F)CC4)ccc32)nc1C(F)(F)F] | 724 | 2.77 | 1 | a |
| I-468 | 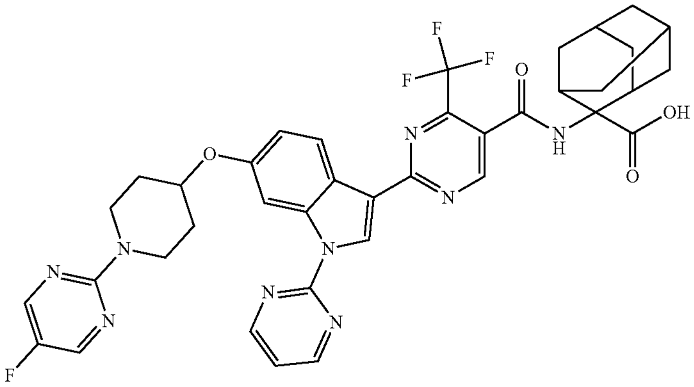 [SMILES: O=C(NC1(C(=O)O)C2CC3CC(C2)CC1C3)c1cnc(-c2cn(-c3ncccn3)c3cc(OC4CCN(c5ncc(F)cn5)CC4)ccc23)nc1C(F)(F)F] | 758 | 1.90 | 10 | |
| I-469 | 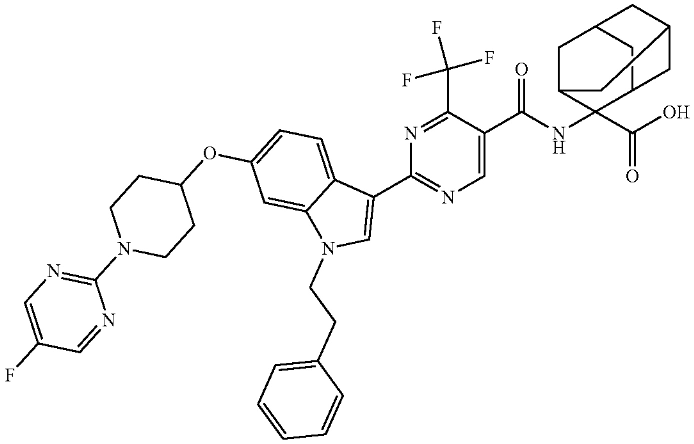 [SMILES: O=C(NC1(C(=O)O)C2CC3CC(C2)CC1C3)c1cnc(-c2cn(CCc3ccccc3)c3cc(OC4CCN(c5ncc(F)cn5)CC4)ccc23)nc1C(F)(F)F] | 784 | 1.92 | 10 | |

TABLE 82
| Compound No. | Chemical Structure | [M + H] | Retention Time (min) | LC/MS Condition | Stereo-Chemistry |
|---|---|---|---|---|---|
| I-470 | 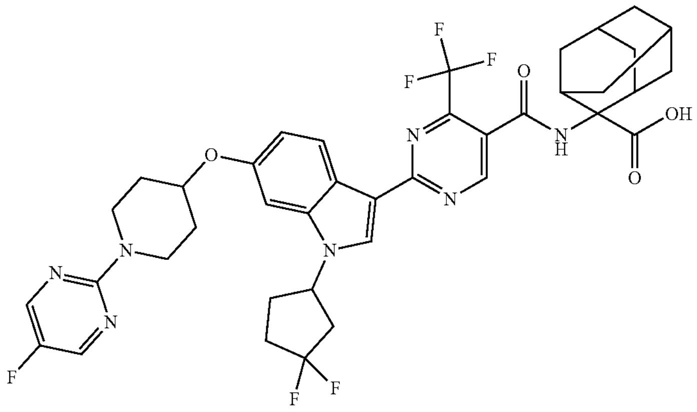 [SMILES: O=C(NC1(C(=O)O)C2CC3CC(C2)CC1C3)c1cnc(-c2cn(C3CCC(F)(F)C3)c3cc(OC4CCN(c5ncc(F)cn5)CC4)ccc23)nc1C(F)(F)F] | 784 | 1.85 | 9 | a |
| I-471 | 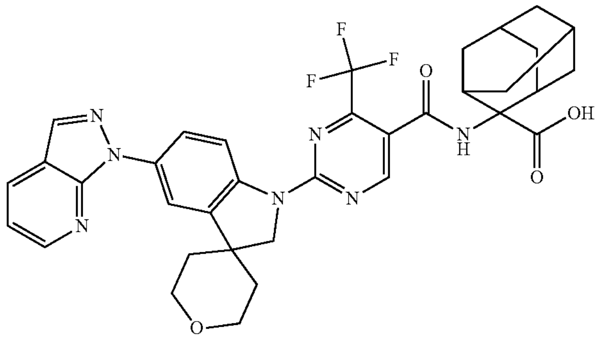 [SMILES: O=C(NC1(C(=O)O)C2CC3CC(C2)CC1C3)c1cnc(N2CC3(CCOCC3)c3cc(-n4ncc5cccnc54)ccc32)nc1C(F)(F)F] | 674 | 1.62 | 10 | |
| I-472 | 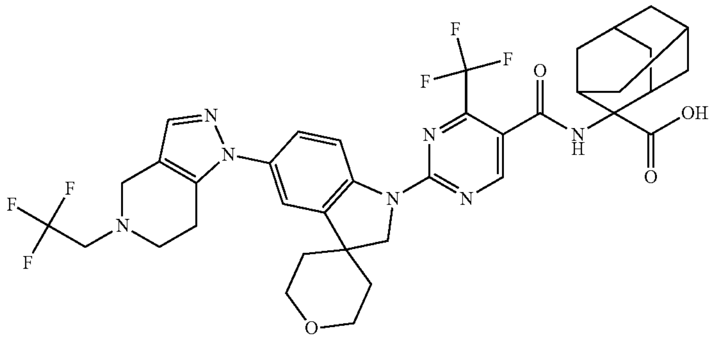 [SMILES: O=C(NC1(C(=O)O)C2CC3CC(C2)CC1C3)c1cnc(N2CC3(CCOCC3)c3cc(-n4ncc5c4CCN(CC(F)(F)F)C5)ccc32)nc1C(F)(F)F] | 760 | 1.63 | 10 | |
| I-473 | 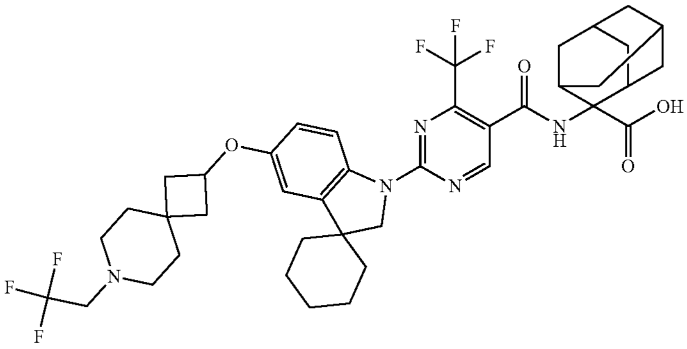 [SMILES: O=C(NC1(C(=O)O)C2CC3CC(C2)CC1C3)c1cnc(N2CC3(CCCCC3)c3cc(OC4CC5(CCN(CC(F)(F)F)CC5)C4)ccc32)nc1C(F)(F)F] | 776 | 3.38 | 2 | |

TABLE 82-continued
| Compound No. | Chemical Structure | [M + H] | Retention Time (min) | LC/MS Condition | Stereo-Chemistry |
|---|---|---|---|---|---|
| I-474 | 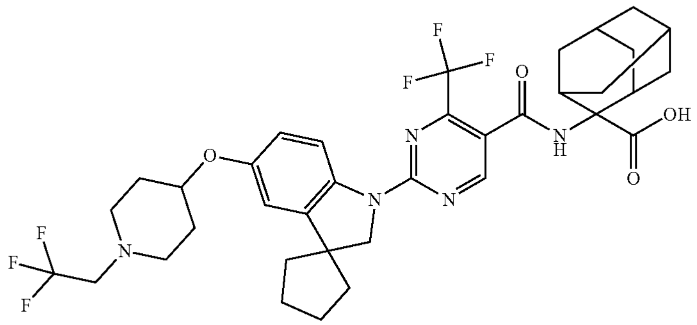 [SMILES: O=C(NC1(C(=O)O)C2CC3CC(C2)CC1C3)c1cnc(N2CC3(CCCC3)c3cc(OC4CCN(CC(F)(F)F)CC4)ccc32)nc1C(F)(F)F] | 722 | 3.22 | 1 | |
| I-475 | 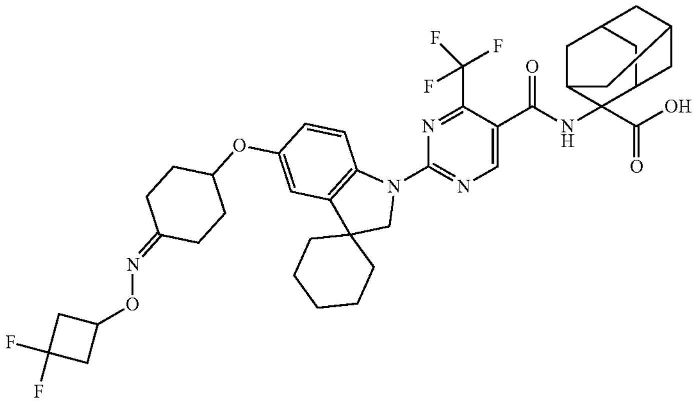 [SMILES: O=C(NC1(C(=O)O)C2CC3CC(C2)CC1C3)c1cnc(N2CC3(CCCCC3)c3cc(OC4CCC(=NOC5CC(F)(F)C5)CC4)ccc32)nc1C(F)(F)F] | 772 | 3.49 | 1 | a |
TABLE 83
| Compound No. | Chemical Structure | [M + H] | Retention Time (min) | LC/MS Condition | Stereo-Chemistry |
|---|---|---|---|---|---|
| I-476 | 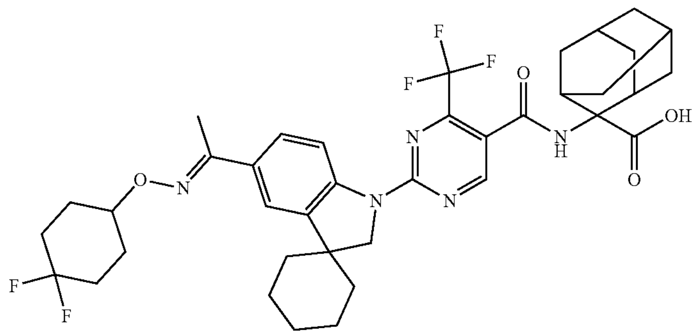 [SMILES: C/C(=N\OC1CCC(F)(F)CC1)c1ccc2c(c1)C1(CCCCC1)CN2c1ncc(C(=O)NC2(C(=O)O)C3CC4CC(C3)CC2C4)c(C(F)(F)F)n1] | 730 | 3.59 | 1 | b |
| I-477 | 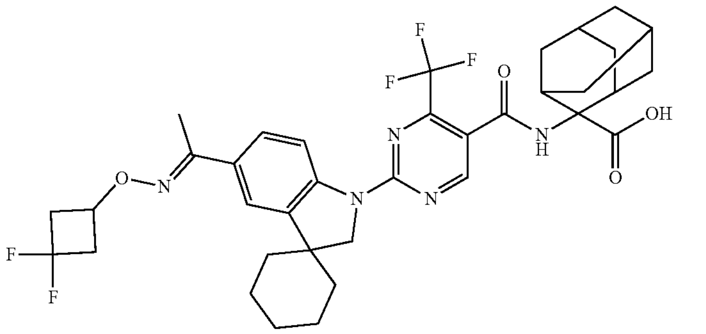 [SMILES: C/C(=N\OC1CC(F)(F)C1)c1ccc2c(c1)C1(CCCCC1)CN2c1ncc(C(=O)NC2(C(=O)O)C3CC4CC(C3)CC2C4)c(C(F)(F)F)n1] | 702 | 3.46 | 1 | b |

TABLE 83-continued
| Compound No. | Chemical Structure | [M + H] | Retention Time (min) | LC/MS Condition | Stereo-Chemistry |
|---|---|---|---|---|---|
| I-478 | 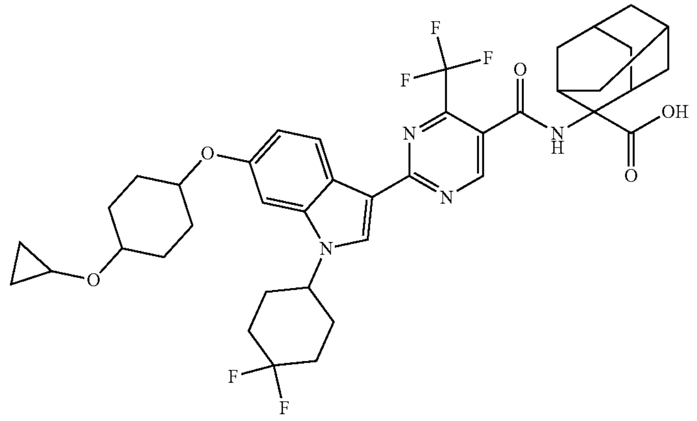 [SMILES: O=C(NC1(C(=O)O)C2CC3CC(C2)CC1C3)c1cnc(-c2cn(C3CCC(F)(F)CC3)c3cc(OC4CCC(OC5CC5)CC4)ccc23)nc1C(F)(F)F] | 757 | 1.88 | 9 | b |
| I-479 | 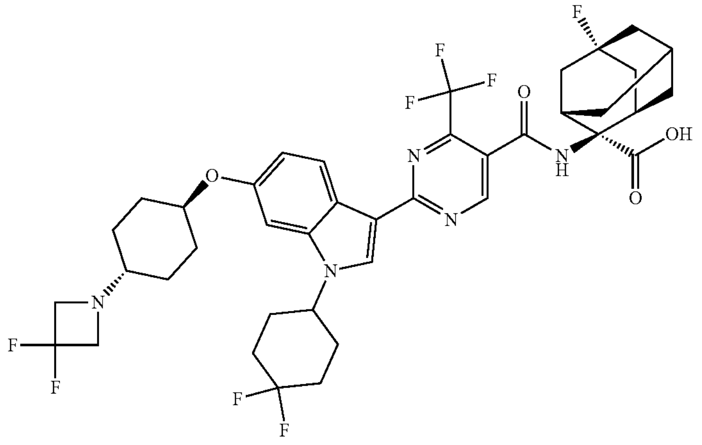 [SMILES: O=C(N[C@]1(C(=O)O)[C@@H]2CC3C[C@H]1C[C@@](F)(C3)C2)c1cnc(-c2cn(C3CCC(F)(F)CC3)c3cc(O[C@H]4CC[C@H](N5CC(F)(F)C5)CC4)ccc23)nc1C(F)(F)F] | 810 | 1.27 | 9 | |
| I-480 | 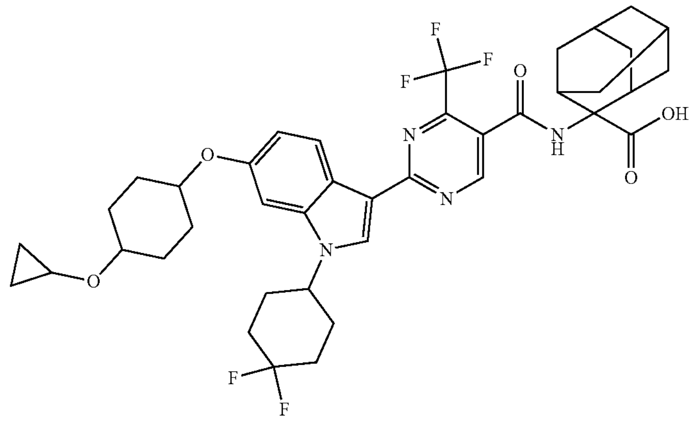 [SMILES: O=C(NC1(C(=O)O)C2CC3CC(C2)CC1C3)c1cnc(-c2cn(C3CCC(F)(F)CC3)c3cc(OC4CCC(OC5CC5)CC4)ccc23)nc1C(F)(F)F] | 757 | 1.88 | 9 | b |

TABLE 84
| Compound No. | Chemical Structure | [M + H] | Retention Time (min) | LC/MS Condition | Stereo-Chemistry |
|---|---|---|---|---|---|
| I-481 | 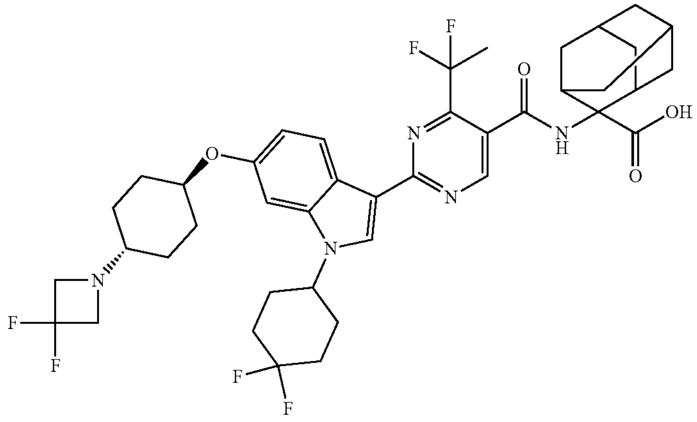 [SMILES: CC(F)(F)c1nc(-c2cn(C3CCC(F)(F)CC3)c3cc(O[C@H]4CC[C@H](N5CC(F)(F)C5)CC4)ccc23)ncc1C(=O)NC1(C(=O)O)C2CC3CC(C2)CC1C3] | 788 | 1.34 | 10 | |
| I-482 | 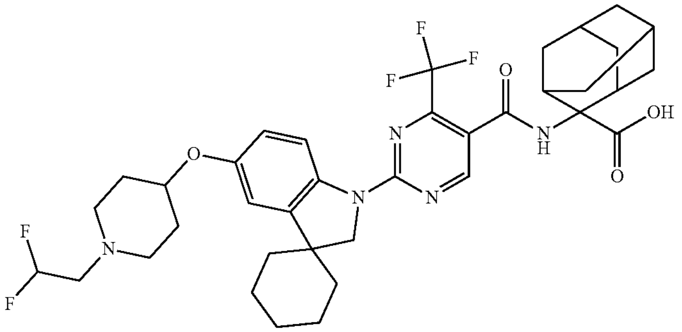 [SMILES: O=C(NC1(C(=O)O)C2CC3CC(C2)CC1C3)c1cnc(N2CC3(CCCCC3)c3cc(OC4CCN(CC(F)F)CC4)ccc32)nc1C(F)(F)F] | 718 | 2.28 | 1 | |
| I-483 | 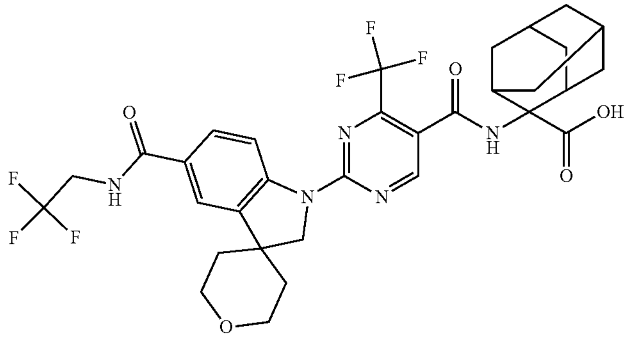 [SMILES: O=C(NCC(F)(F)F)c1ccc2c(c1)C1(CCOCC1)CN2c1ncc(C(=O)NC2(C(=O)O)C3CC4CC(C3)CC2C4)c(C(F)(F)F)n1] | 682 | 2.48 | 1 | |
| I-484 | 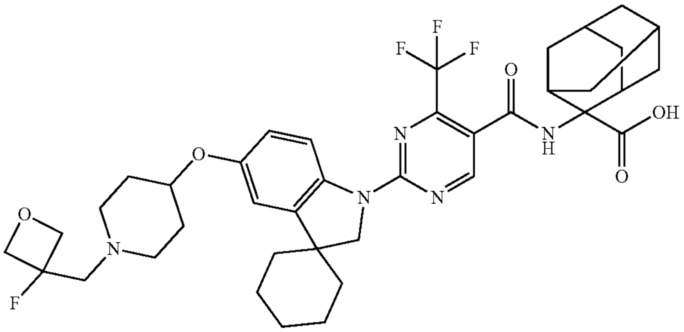 [SMILES: O=C(NC1(C(=O)O)C2CC3CC(C2)CC1C3)c1cnc(N2CC3(CCCCC3)c3cc(OC4CCN(CC5(F)COC5)CC4)ccc32)nc1C(F)(F)F] | 742 | 2.23 | 1 | |

TABLE 84-continued
| Compound No. | Chemical Structure | [M + H] | Retention Time (min) | LC/MS Condition | Stereo-Chemistry |
|---|---|---|---|---|---|
| I-485 | 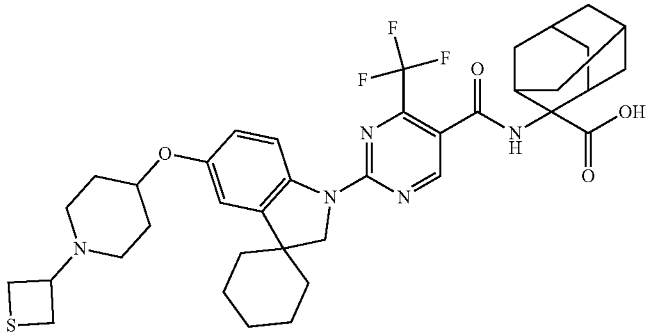 [SMILES: O=C(NC1(C(=O)O)C2CC3CC(C2)CC1C3)c1cnc(N2CC3(CCCCC3)c3cc(OC4CCN(C5CSC5)CC4)ccc32)nc1C(F)(F)F] | 726 | 2.37 | 1 | |
| I-486 | 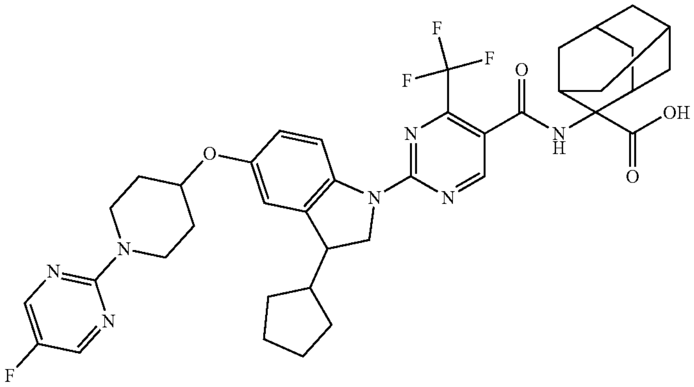 [SMILES: O=C(NC1(C(=O)O)C2CC3CC(C2)CC1C3)c1cnc(N2CC(C3CCCC3)c3cc(OC4CCN(c5ncc(F)cn5)CC4)ccc32)nc1C(F)(F)F] | 750 | 3.56 | 1 | a |
TABLE 85
| Compound No. | Chemical Structure | [M + H] | Retention Time (min) | LC/MS Condition | Stereo-Chemistry |
|---|---|---|---|---|---|
| I-487 | 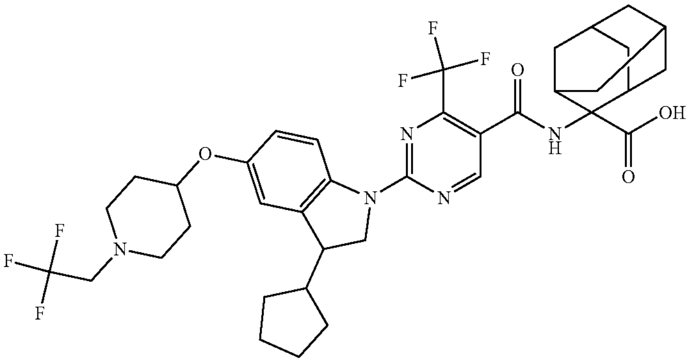 [SMILES: O=C(NC1(C(=O)O)C2CC3CC(C2)CC1C3)c1cnc(N2CC(C3CCCC3)c3cc(OC4CCN(CC(F)(F)F)CC4)ccc32)nc1C(F)(F)F] | 736 | 3.36 | 1 | a |

TABLE 85-continued
| Compound No. | Chemical Structure | [M + H] | Retention Time (min) | LC/MS Condition | Stereo-Chemistry |
|---|---|---|---|---|---|
| I-488 | 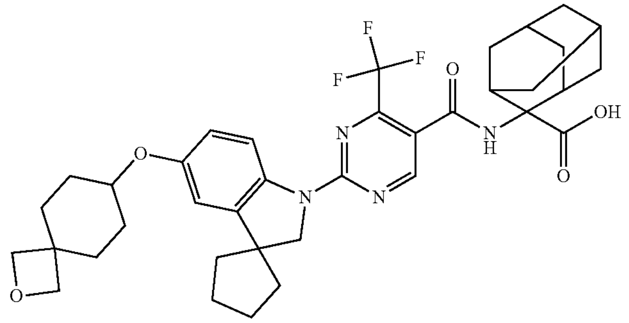 [SMILES: O=C(NC1(C(=O)O)C2CC3CC(C2)CC1C3)c1cnc(N2CC3(CCCC3)c3cc(OC4CCC5(CC4)COC5)ccc32)nc1C(F)(F)F] | 681 | 3.17 | 1 | |
| I-489 | 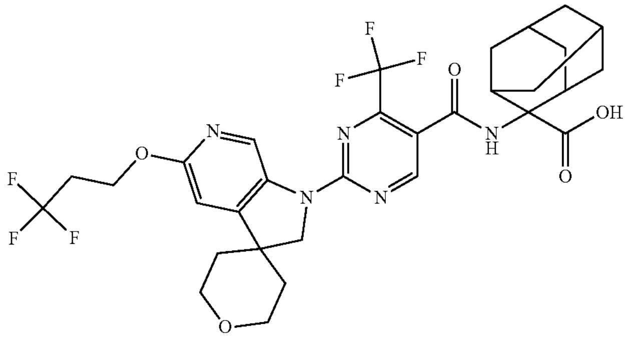 [SMILES: O=C(NC1(C(=O)O)C2CC3CC(C2)CC1C3)c1cnc(N2CC3(CCOCC3)c3cc(OCCC(F)(F)F)ncc32)nc1C(F)(F)F] | 670 | 2.80 | 1 | |
| I-490 | 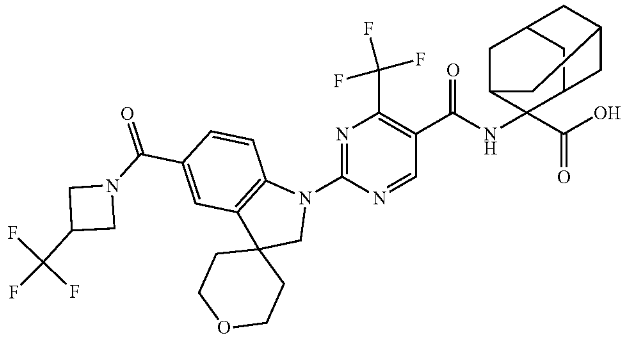 [SMILES: O=C(NC1(C(=O)O)C2CC3CC(C2)CC1C3)c1cnc(N2CC3(CCOCC3)c3cc(C(=O)N4CC(C(F)(F)F)C4)ccc32)nc1C(F)(F)F] | 708 | 2.52 | 1 | |
| I-491 | 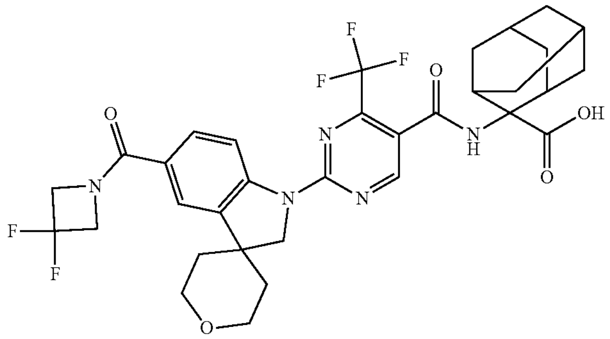 [SMILES: O=C(NC1(C(=O)O)C2CC3CC(C2)CC1C3)c1cnc(N2CC3(CCOCC3)c3cc(C(=O)N4CC(F)(F)C4)ccc32)nc1C(F)(F)F] | 676 | 2.47 | 1 | |

TABLE 85-continued
| Compound No. | Chemical Structure | [M + H] | Retention Time (min) | LC/MS Condition | Stereo-Chemistry |
|---|---|---|---|---|---|
| I-492 | 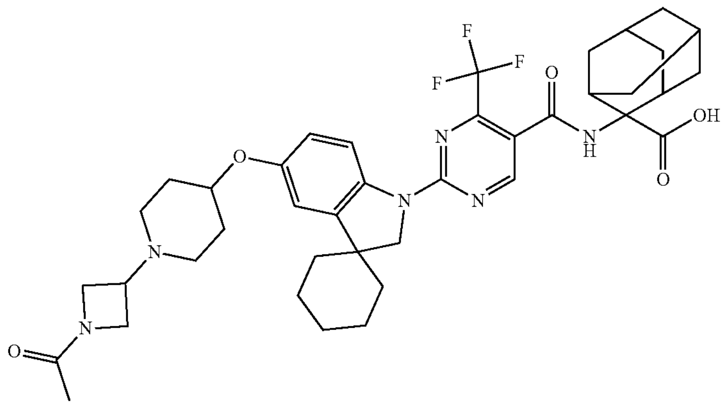 [SMILES: CC(=O)N1CC(N2CCC(Oc3ccc4c(c3)C3(CCCCC3)CN4c3ncc(C(=O)NC4(C(=O)O)C5CC6CC(C5)CC4C6)c(C(F)(F)F)n3)CC2)C1] | 751 | 2.52 | 1 | |
TABLE 86
| Compound No. | Chemical Structure | [M + H] | Retention Time (min) | LC/MS Condition | Stereo-Chemistry |
|---|---|---|---|---|---|
| I-493 | 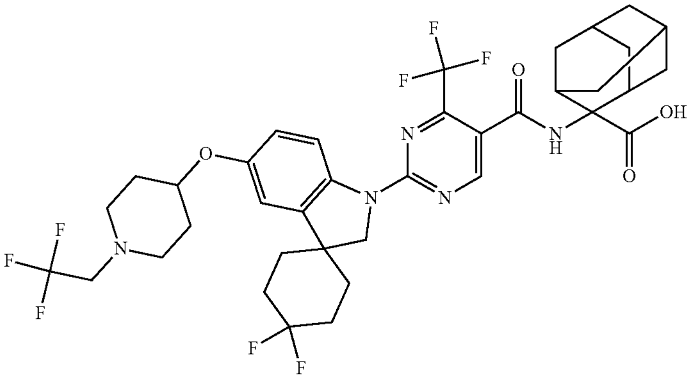 [SMILES: O=C(NC1(C(=O)O)C2CC3CC(C2)CC1C3)c1cnc(N2CC3(CCC(F)(F)CC3)c3cc(OC4CCN(CC(F)(F)F)CC4)ccc32)nc1C(F)(F)F] | 772 | 3.09 | 1 | |
| I-494 | 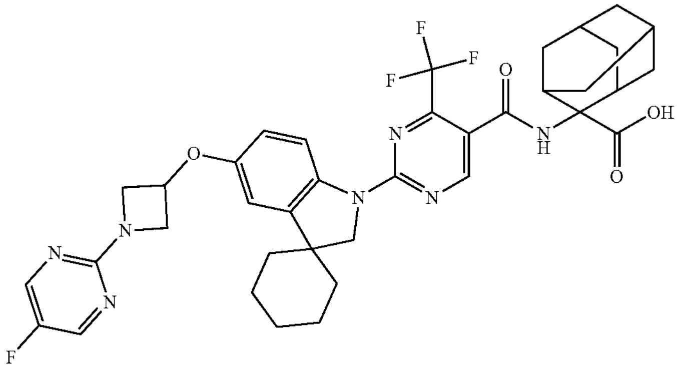 [SMILES: O=C(NC1(C(=O)O)C2CC3CC(C2)CC1C3)c1cnc(N2CC3(CCCCC3)c3cc(OC4CN(c5ncc(F)cn5)C4)ccc32)nc1C(F)(F)F] | 722 | 3.23 | 1 | |

TABLE 86-continued
| Compound No. | Chemical Structure | [M + H] | Retention Time (min) | LC/MS Condition | Stereo-Chemistry |
|---|---|---|---|---|---|
| I-495 | 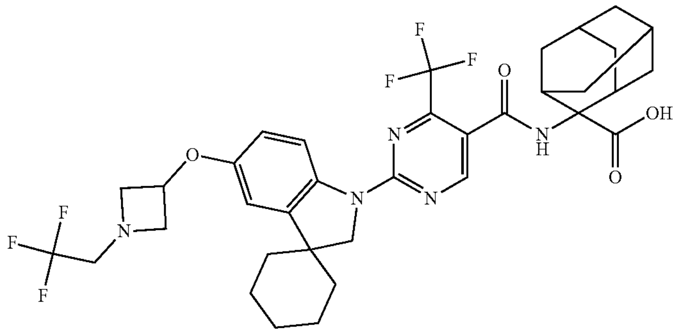 [SMILES: O=C(NC1(C(=O)O)C2CC3CC(C2)CC1C3)c1cnc(N2CC3(CCCCC3)c3cc(OC4CN(CC(F)(F)F)C4)ccc32)nc1C(F)(F)F] | 708 | 3.22 | 1 | |
| I-496 | 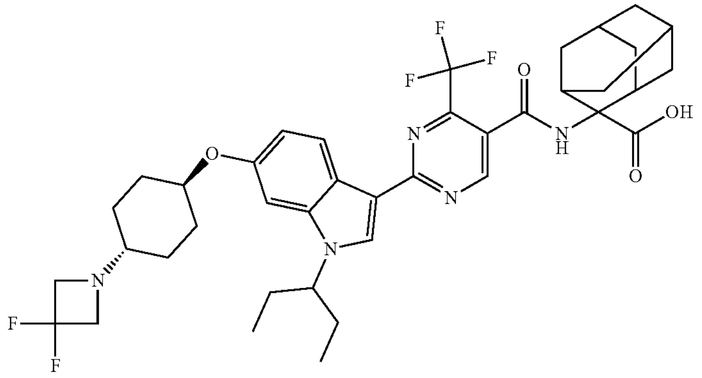 [SMILES: CCC(CC)n1cc(-c2ncc(C(=O)NC3(C(=O)O)C4CC5CC(C4)CC3C5)c(C(F)(F)F)n2)c2ccc(O[C@H]3CC[C@H](N4CC(F)(F)C4)CC3)cc21] | 744 | 1.40 | 9 | |
| I-497 | 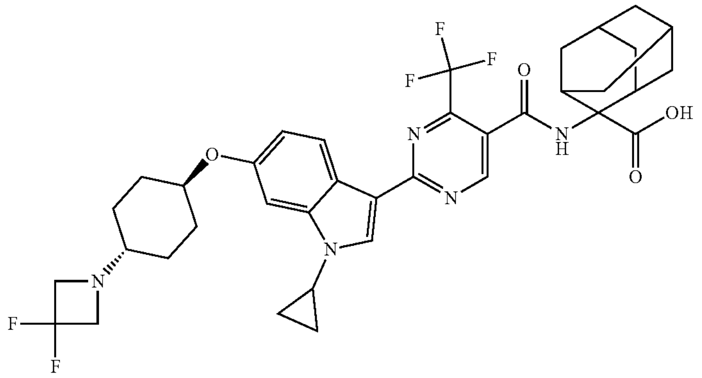 [SMILES: O=C(NC1(C(=O)O)C2CC3CC(C2)CC1C3)c1cnc(-c2cn(C3CC3)c3cc(O[C@H]4CC[C@H](N5CC(F)(F)C5)CC4)ccc23)nc1C(F)(F)F] | 714 | 1.26 | 9 | |
| I-498 | 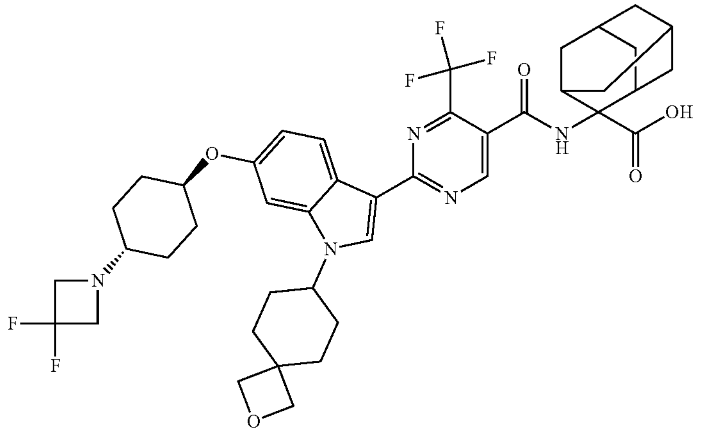 [SMILES: O=C(NC1(C(=O)O)C2CC3CC(C2)CC1C3)c1cnc(-c2cn(C3CCC4(CC3)COC4)c3cc(O[C@H]4CC[C@H](N5CC(F)(F)C5)CC4)ccc23)nc1C(F)(F)F] | 798 | 1.24 | 9 | |

TABLE 87
| Compound No. | Chemical Structure | [M + H] | Retention Time (min) | LC/MS Condition | Stereo-Chemistry |
|---|---|---|---|---|---|
| I-499 | 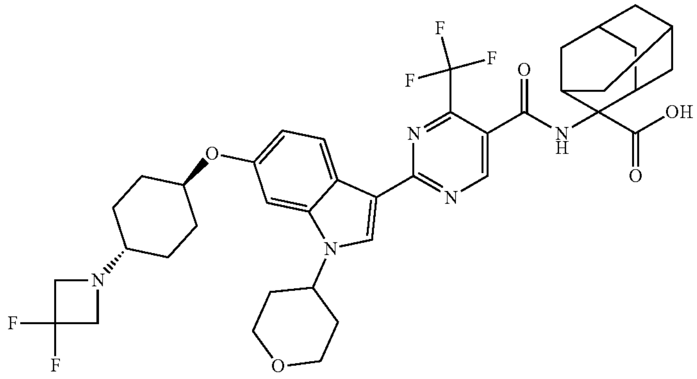 [SMILES: O=C(NC1(C(=O)O)C2CC3CC(C2)CC1C3)c1cnc(-c2cn(C3CCOCC3)c3cc(O[C@H]4CC[C@H](N5CC(F)(F)C5)CC4)ccc23)nc1C(F)(F)F] | 758 | 1.22 | 9 | |
| I-500 | 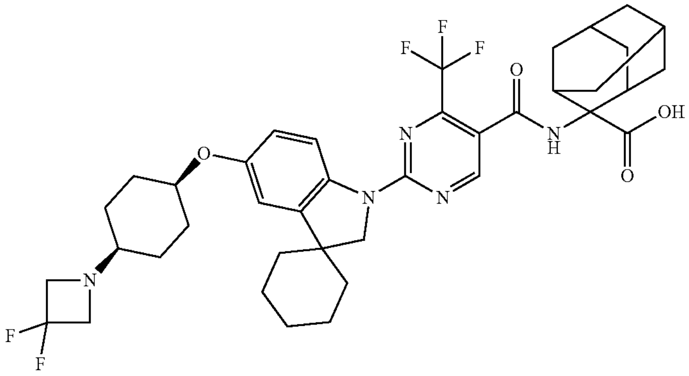 [SMILES: O=C(NC1(C(=O)O)C2CC3CC(C2)CC1C3)c1cnc(N2CC3(CCCCC3)c3cc(O[C@H]4CC[C@@H](N5CC(F)(F)C5)CC4)ccc32)nc1C(F)(F)F] | 744 | 2.49 | 1 | |
| I-501 | 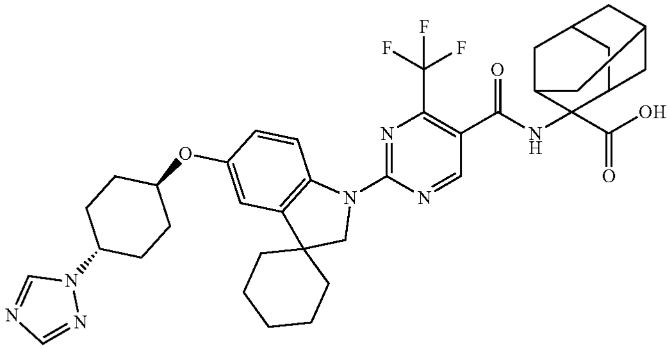 [SMILES: O=C(NC1(C(=O)O)C2CC3CC(C2)CC1C3)c1cnc(N2CC3(CCCCC3)c3cc(O[C@H]4CC[C@H](n5cncn5)CC4)ccc32)nc1C(F)(F)F] | 720 | 2.98 | 1 | |
| I-502 | 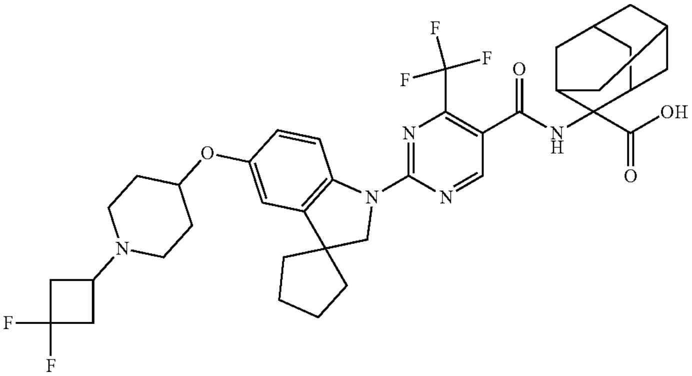 [SMILES: O=C(NC1(C(=O)O)C2CC3CC(C2)CC1C3)c1cnc(N2CC3(CCCC3)c3cc(OC4CCN(C5CC(F)(F)C5)CC4)ccc32)nc1C(F)(F)F] | 730 | 2.29 | 1 | |

TABLE 87-continued
| Compound No. | Chemical Structure | [M + H] | Retention Time (min) | LC/MS Condition | Stereo-Chemistry |
|---|---|---|---|---|---|
| I-503 | 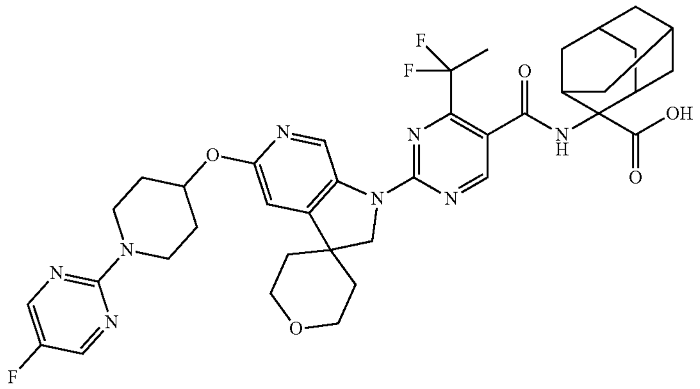 [SMILES: CC(F)(F)c1nc(N2CC3(CCOCC3)c3cc(OC4CCN(c5ncc(F)cn5)CC4)ncc32)ncc1C(=O)NC1(C(=O)O)C2CC3CC(C2)CC1C3] | 749 | 2.94 | 1 | |
| I-504 | 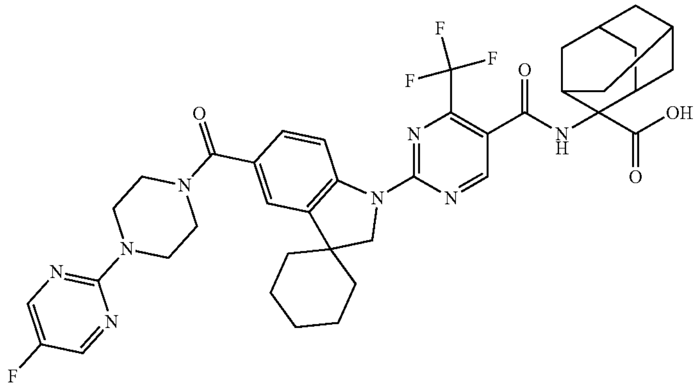 [SMILES: O=C(NC1(C(=O)O)C2CC3CC(C2)CC1C3)c1cnc(N2CC3(CCCCC3)c3cc(C(=O)N4CCN(c5ncc(F)cn5)CC4)ccc32)nc1C(F)(F)F] | 763 | 3.07 | 1 | |
TABLE 88
| Compound No. | Chemical Structure | [M + H] | Retention Time (min) | LC/MS Condition | Stereo-Chemistry |
|---|---|---|---|---|---|
| I-505 | 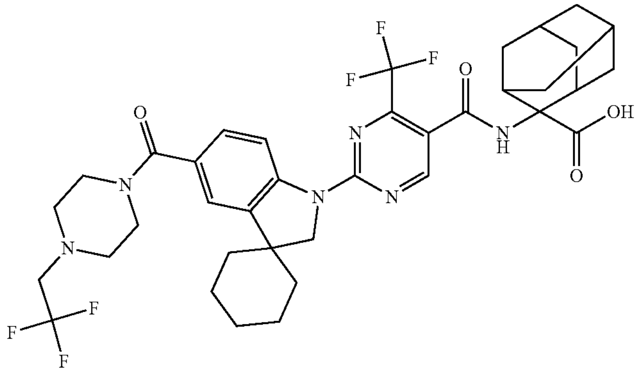 [SMILES: O=C(NC1(C(=O)O)C2CC3CC(C2)CC1C3)c1cnc(N2CC3(CCCCC3)c3cc(C(=O)N4CCN(CC(F)(F)F)CC4)ccc32)nc1C(F)(F)F] | 749 | 300 | 1 | |

TABLE 88-continued
| Compound No. | Chemical Structure | [M + H] | Retention Time (min) | LC/MS Condition | Stereo-Chemistry |
| --- | --- | --- | --- | --- | --- |
| I-506 | 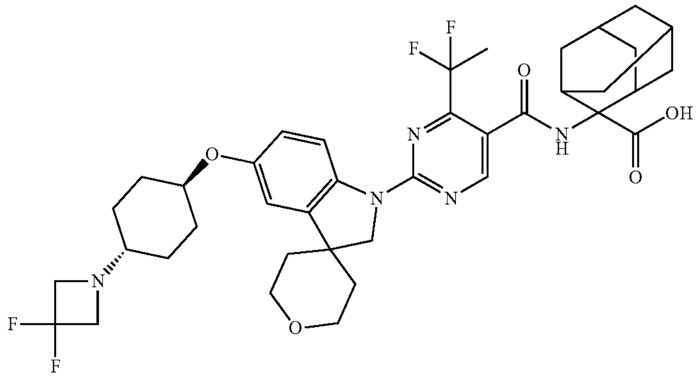 [SMILES: CC(F)(F)c1nc(N2CC3(CCOCC3)c3cc(O[C@H]4CC[C@H](N5CC(F)(F)C5)CC4)ccc32)ncc1C(=O)NC1(C(=O)O)C2CC3CC(C2)CC1C3] | 742 | 2.13 | 1 | |
| I-507 | 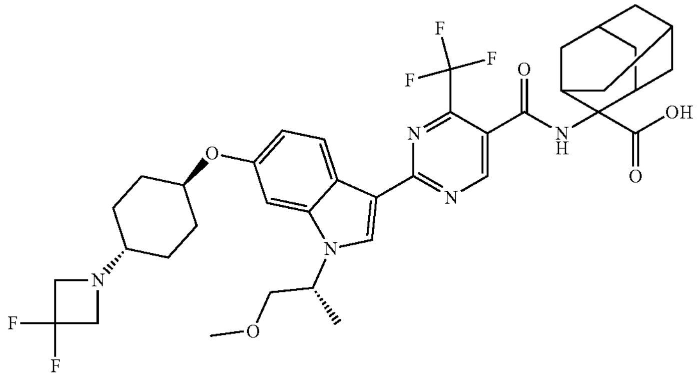 [SMILES: COC[C@@H](C)n1cc(-c2ncc(C(=O)NC3(C(=O)O)C4CC5CC(C4)CC3C5)c(C(F)(F)F)n2)c2ccc(O[C@H]3CC[C@H](N4CC(F)(F)C4)CC3)cc21] | 746 | 1.25 | 10 | |
| I-508 | 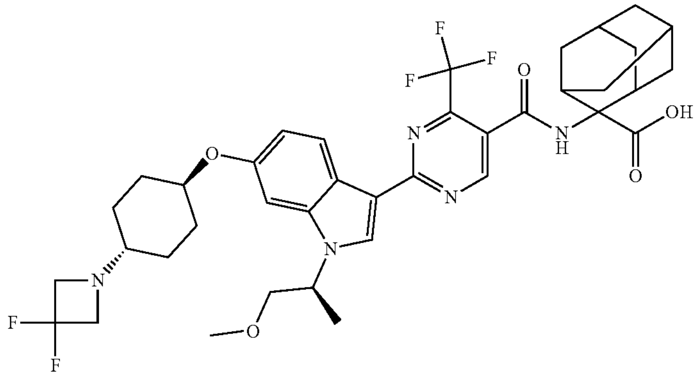 [SMILES: COC[C@H](C)n1cc(-c2ncc(C(=O)NC3(C(=O)O)C4CC5CC(C4)CC3C5)c(C(F)(F)F)n2)c2ccc(O[C@H]3CC[C@H](N4CC(F)(F)C4)CC3)cc21] | 746 | 1.25 | 10 | |
| I-509 | 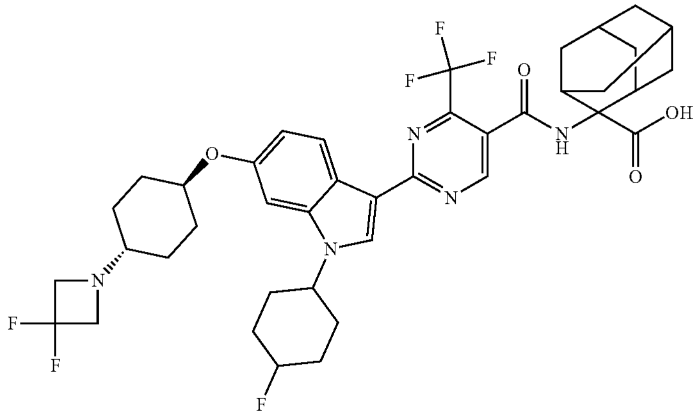 [SMILES: O=C(NC1(C(=O)O)C2CC3CC(C2)CC1C3)c1cnc(-c2cn(C3CCC(F)CC3)c3cc(O[C@H]4CC[C@H](N5CC(F)(F)C5)CC4)ccc23)nc1C(F)(F)F] | 774 | 1.34 | 10 | e |

TABLE 88-continued
| Compound No. | Chemical Structure | [M + H] | Retention Time (min) | LC/MS Condition | Stereo-Chemistry |
|---|---|---|---|---|---|
| I-510 | 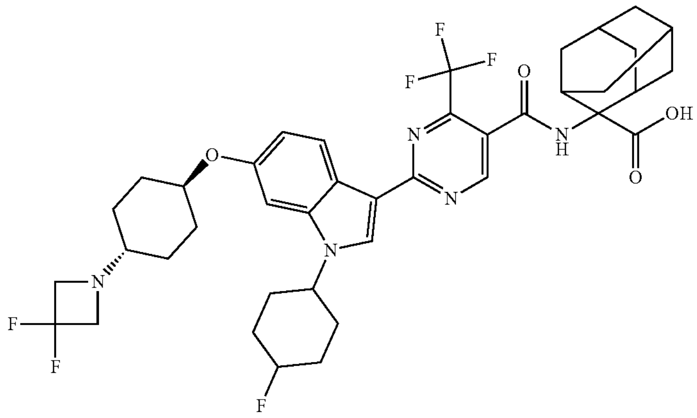 [SMILES: O=C(NC1(C(=O)O)C2CC3CC(C2)CC1C3)c1cnc(-c2cn(C3CCC(F)CC3)c3cc(O[C@H]4CC[C@H](N5CC(F)(F)C5)CC4)ccc23)nc1C(F)(F)F] | 774 | 1.33 | 9 | e |
TABLE 89
| Compound No. | Chemical Structure | [M + H] | Retention Time (min) | LC/MS Condition | Stereo-Chemistry |
|---|---|---|---|---|---|
| I-511 | 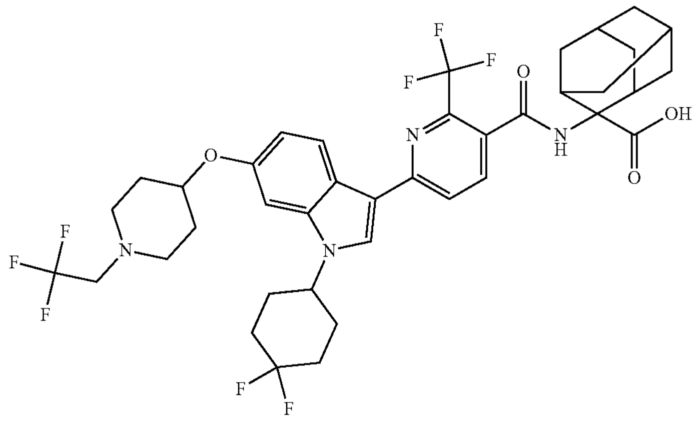 [SMILES: O=C(NC1(C(=O)O)C2CC3CC(C2)CC1C3)c1ccc(-c2cn(C3CCC(F)(F)CC3)c3cc(OC4CCN(CC(F)(F)F)CC4)ccc23)nc1C(F)(F)F] | 783 | 1.77 | 10 | |
| I-512 | 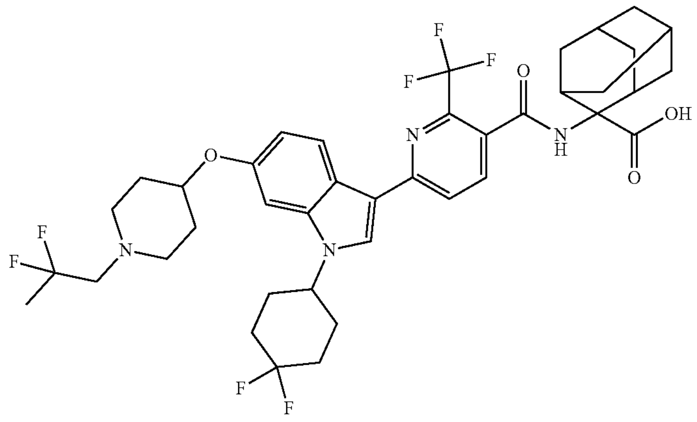 [SMILES: CC(F)(F)CN1CCC(Oc2ccc3c(-c4ccc(C(=O)NC5(C(=O)O)C6CC7CC(C6)CC5C7)c(C(F)(F)F)n4)cn(C4CCC(F)(F)CC4)c3c2)CC1] | 779 | 1.26 | 10 | |

TABLE 89-continued
| Compound No. | Chemical Structure | [M + H] | Retention Time (min) | LC/MS Condition | Stereo-Chemistry |
|---|---|---|---|---|---|
| I-513 | 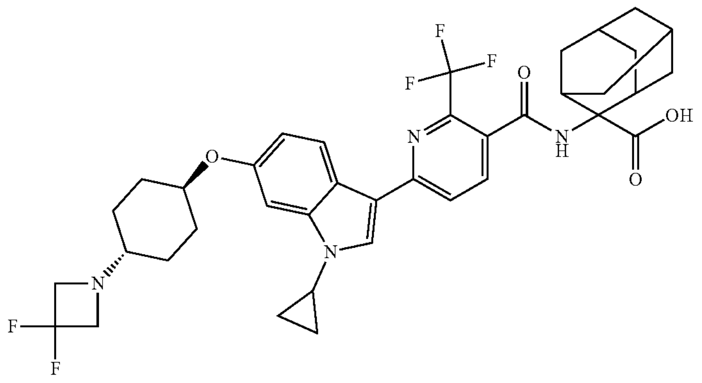 [SMILES: O=C(NC1(C(=O)O)C2CC3CC(C2)CC1C3)c1ccc(-c2cn(C3CC3)c3cc(O[C@H]4CC[C@H](N5CC(F)(F)C5)CC4)ccc23)nc1C(F)(F)F] | 713 | 1.27 | 10 | |
| I-514 | 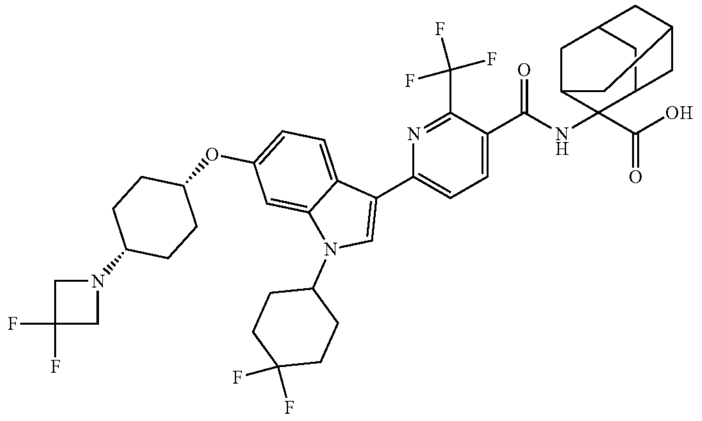 [SMILES: O=C(NC1(C(=O)O)C2CC3CC(C2)CC1C3)c1ccc(-c2cn(C3CCC(F)(F)CC3)c3cc(O[C@H]4CC[C@@H](N5CC(F)(F)C5)CC4)ccc23)nc1C(F)(F)F] | 791 | 1.30 | 9 | |
| I-515 | 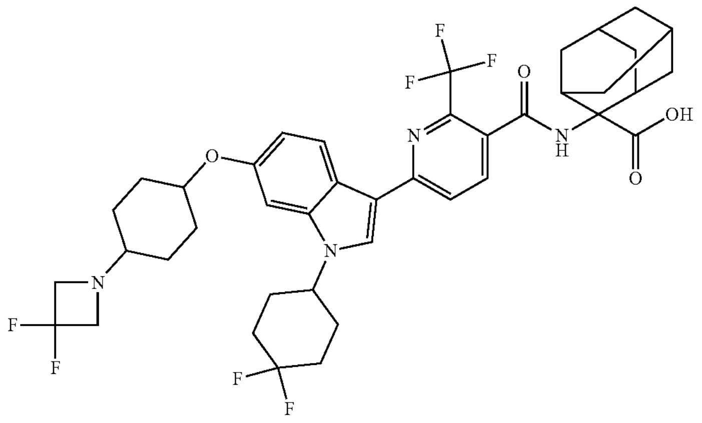 [SMILES: O=C(NC1(C(=O)O)C2CC3CC(C2)CC1C3)c1ccc(-c2cn(C3CCC(F)(F)CC3)c3cc(OC4CCC(N5CC(F)(F)C5)CC4)ccc23)nc1C(F)(F)F] | 763 | 1.42 | 9 | b |

TABLE 90
| Compound No. | Chemical Structure | [M + H] | Retention Time (min) | LC/MS Condition | Stereo-Chemistry |
|---|---|---|---|---|---|
| I-516 | 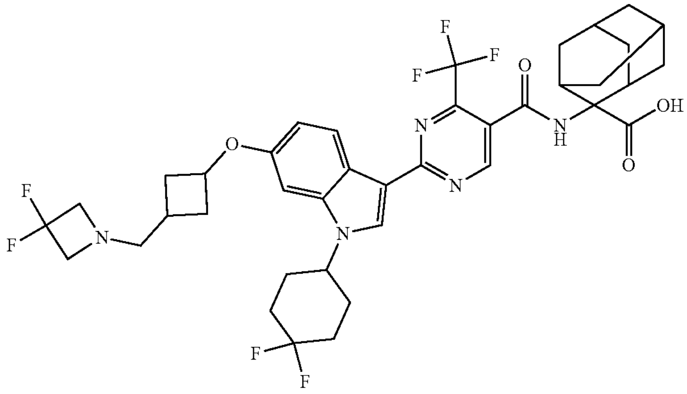 [SMILES: O=C(NC1(C(=O)O)C2CC3CC(C2)CC1C3)c1cnc(-c2cn(C3CCC(F)(F)CC3)c3cc(OC4CC(CN5CC(F)(F)C5)C4)ccc23)nc1C(F)(F)F] | 778 | 1.31 | 9 | b |
| I-517 | 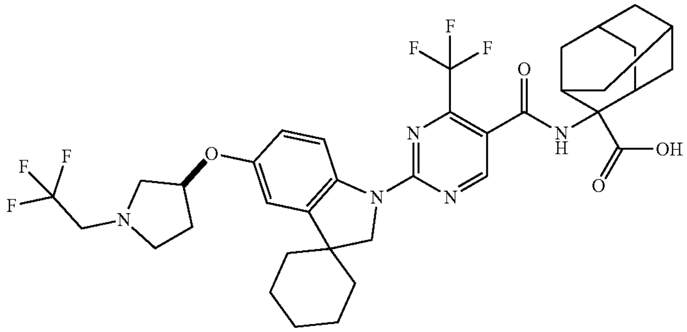 | 722 | 2.36 | 1 | |
| I-518 | 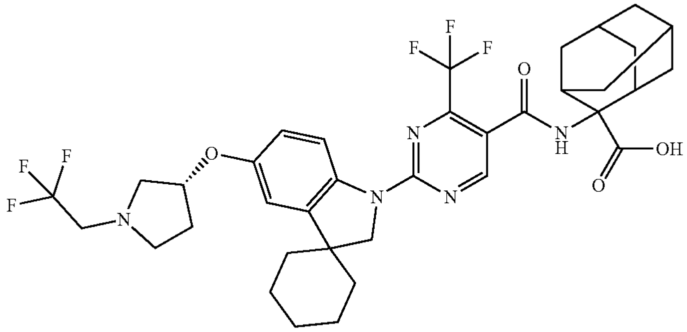 [SMILES: O=C(NC1(C(=O)O)C2CC3CC(C2)CC1C3)c1cnc(N2CC3(CCCCC3)c3cc(O[C@@H]4CCN(CC(F)(F)F)C4)ccc32)nc1C(F)(F)F] | 722 | 2.36 | 1 | |
| I-519 | 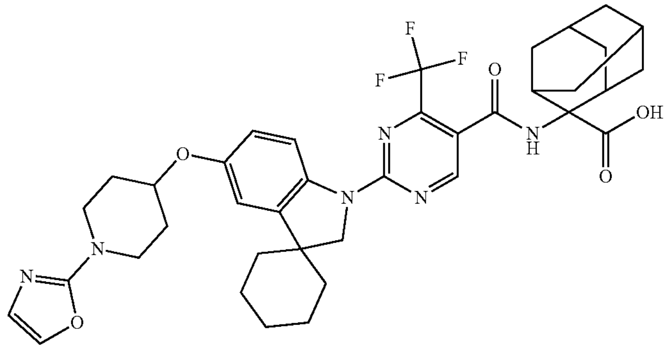 [SMILES: O=C(NC1(C(=O)O)C2CC3CC(C2)CC1C3)c1cnc(N2CC3(CCCCC3)c3cc(OC4CCN(c5ncco5)CC4)ccc32)nc1C(F)(F)F] | 721 | 2.99 | 1 | |

TABLE 90-continued
| Compound No. | Chemical Structure | [M + H] | Retention Time (min) | LC/MS Condition | Stereo-Chemistry |
|---|---|---|---|---|---|
| I-520 | 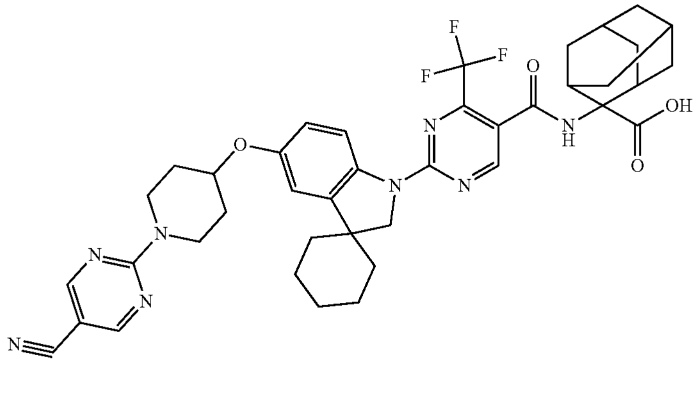 [SMILES: N#Cc1cnc(N2CCC(Oc3ccc4c(c3)C3(CCCCC3)CN4c3ncc(C(=O)NC4(C(=O)O)C5CC6CC(C5)CC4C6)c(C(F)(F)F)n3)CC2)nc1] | 757 | 3.39 | 1 | |
| I-521 | 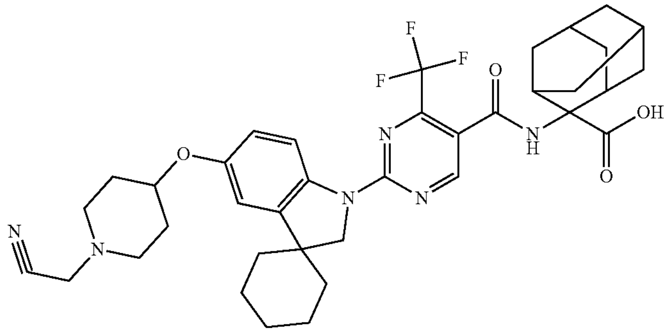 [SMILES: N#CCN1CCC(Oc2ccc3c(c2)C2(CCCCC2)CN3c2ncc(C(=O)NC3(C(=O)O)C4CC5CC(C4)CC3C5)c(C(F)(F)F)n2)CC1] | 693 | 3.03 | 1 | |
TABLE 91
| Compound No. | Chemical Structure | [M + H] | Retention Time (min) | LC/MS Condition | Stereo-Chemistry |
|---|---|---|---|---|---|
| I-522 | 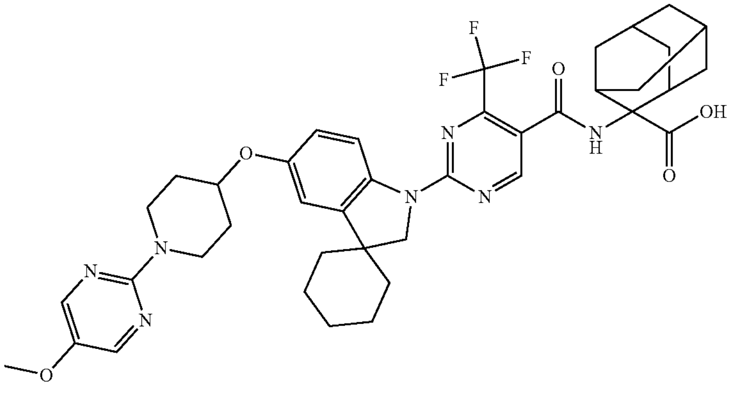 [SMILES: COc1cnc(N2CCC(Oc3ccc4c(c3)C3(CCCCC3)CN4c3ncc(C(=O)NC4(C(=O)O)C5CC6CC(C5)CC4C6)c(C(F)(F)F)n3)CC2)nc1] | 762 | 3.45 | 1 | |

TABLE 91-continued
| Compound No. | Chemical Structure | [M + H] | Retention Time (min) | LC/MS Condition | Stereo-Chemistry |
|---|---|---|---|---|---|
| I-523 | 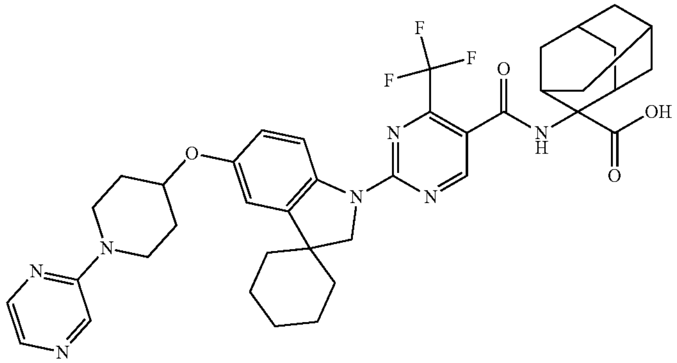 [SMILES: O=C(NC1(C(=O)O)C2CC3CC(C2)CC1C3)c1cnc(N2CC3(CCCCC3)c3cc(OC4CCN(c5cnccn5)CC4)ccc32)nc1C(F)(F)F] | 732 | 3.26 | 1 | |
| I-524 | 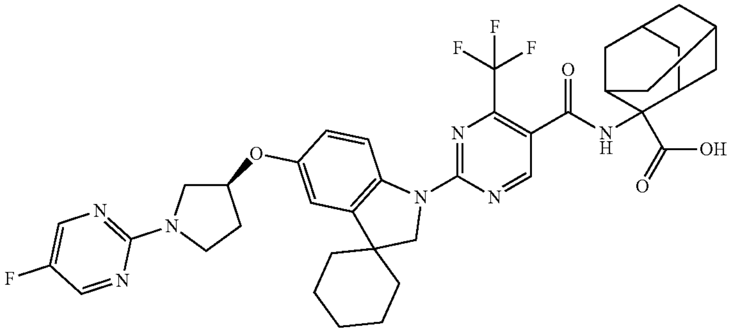 [SMILES: O=C(NC1(C(=O)O)C2CC3CC(C2)CC1C3)c1cnc(N2CC3(CCCCC3)c3cc(O[C@H]4CCN(c5ncc(F)cn5)C4)ccc32)nc1C(F)(F)F] | 736 | 2.42 | 1 | |
| I-525 | 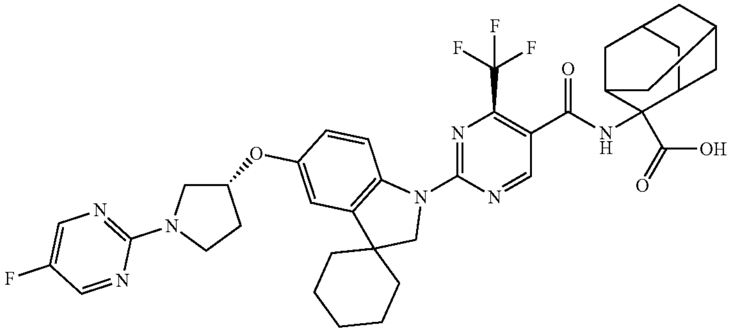 | 736 | 2.42 | 1 | |
| I-526 | 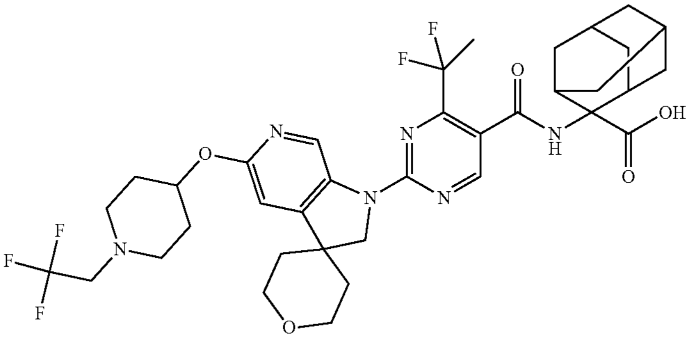 [SMILES: CC(F)(F)c1nc(N2CC3(CCOCC3)c3cc(OC4CCN(CC(F)(F)F)CC4)ncc32)ncc1C(=O)NC1(C(=O)O)C2CC3CC(C2)CC1C3] | 735 | 2.62 | 1 | |

TABLE 91-continued
| Compound No. | Chemical Structure | [M + H] | Retention Time (min) | LC/MS Condition | Stereo-Chemistry |
|---|---|---|---|---|---|
| I-527 | 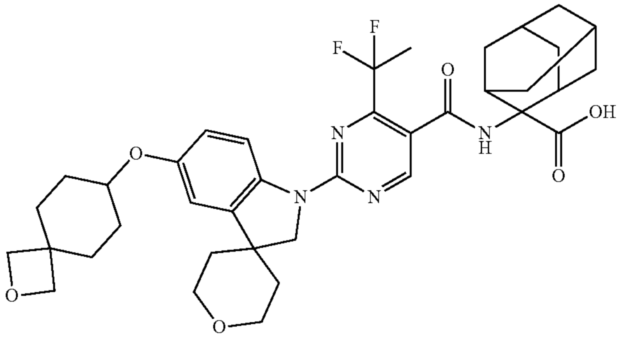 [SMILES: CC(F)(F)c1nc(N2CC3(CCOCC3)c3cc(OC4CCC5(CC4)COC5)ccc32)ncc1C(=O)NC1(C(=O)O)C2CC3CC(C2)CC1C3] | 693 | 2.70 | 1 | |
TABLE 92
| Compound No. | Chemical Structure | [M + H] | Retention Time (min) | LC/MS Condition | Stereo-Chemistry |
|---|---|---|---|---|---|
| I-528 | 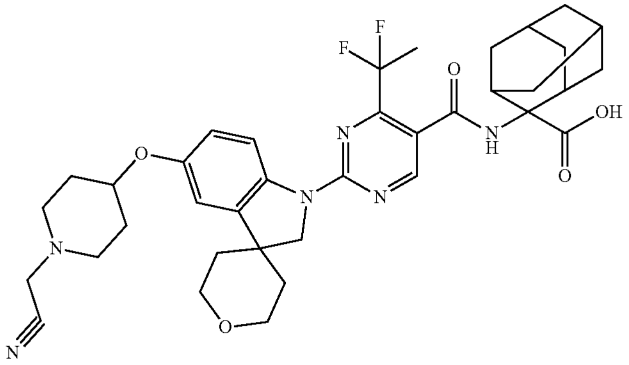 [SMILES: CC(F)(F)c1nc(N2CC3(CCOCC3)c3cc(OC4CCN(CC#N)CC4)ccc32)ncc1C(=O)NC1(C(=O)O)C2CC3CC(C2)CC1C3] | 691 | 2.44 | 1 | |
| I-529 | 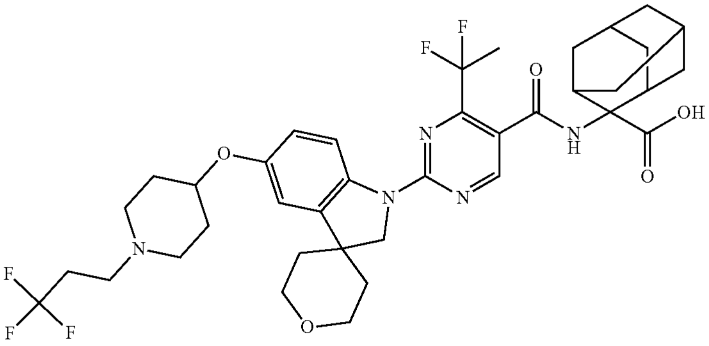 [SMILES: CC(F)(F)c1nc(N2CC3(CCOCC3)c3cc(OC4CCN(CCC(F)(F)F)CC4)ccc32)ncc1C(=O)NC1(C(=O)O)C2CC3CC(C2)CC1C3] | 748 | 2.22 | 1 | |

TABLE 92-continued
| Compound No. | Chemical Structure | [M + H] | Retention Time (min) | LC/MS Condition | Stereo-Chemistry |
|---|---|---|---|---|---|
| I-530 | 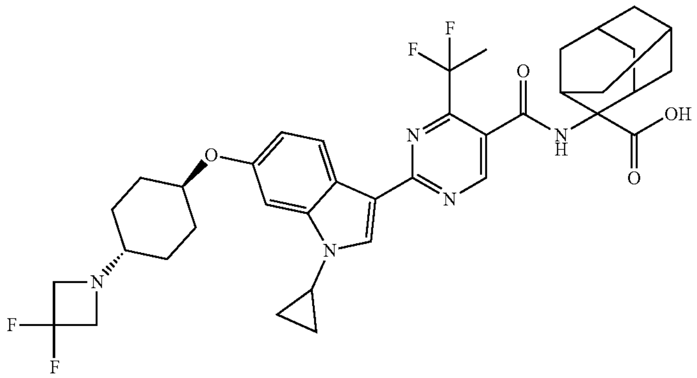 [SMILES: CC(F)(F)c1nc(-c2cn(C3CC3)c3cc(O[C@H]4CC[C@H](N5CC(F)(F)C5)CC4)ccc23)ncc1C(=O)NC1(C(=O)O)C2CC3CC(C2)CC1C3] | 710 | 1.26 | 10 | |
| I-531 | 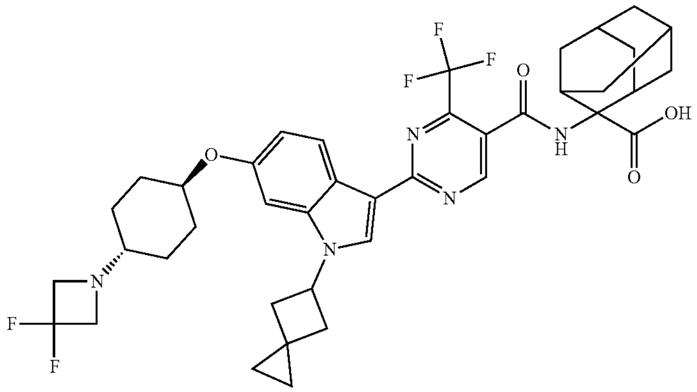 [SMILES: O=C(NC1(C(=O)O)C2CC3CC(C2)CC1C3)c1cnc(-c2cn(C3CC4(CC4)C3)c3cc(O[C@H]4CC[C@H](N5CC(F)(F)C5)CC4)ccc23)nc1C(F)(F)F] | 754 | 1.46 | 10 | |
| I-532 | 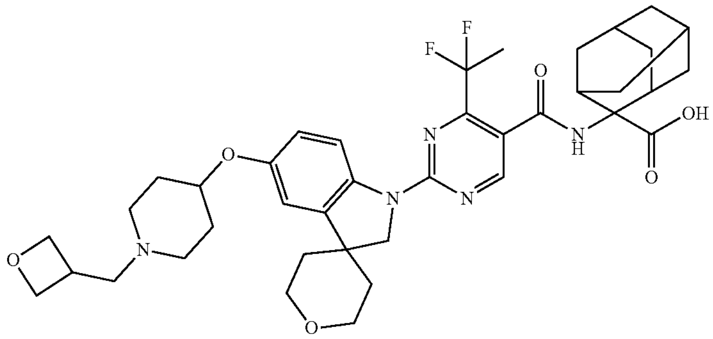 [SMILES: CC(F)(F)c1nc(N2CC3(CCOCC3)c3cc(OC4CCN(CC5COC5)CC4)ccc32)ncc1C(=O)NC1(C(=O)O)C2CC3CC(C2)CC1C3] | 722 | 1.95 | 1 | |
| I-533 | 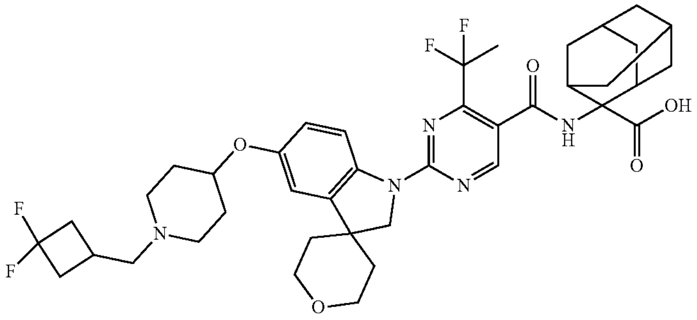 [SMILES: CC(F)(F)c1nc(N2CC3(CCOCC3)c3cc(OC4CCN(CC5CC(F)(F)C5)CC4)ccc32)ncc1C(=O)NC1(C(=O)O)C2CC3CC(C2)CC1C3] | 756 | 2.14 | 1 | |

TABLE 93
| Compound No. | Chemical Structure | [M + H] | Retention Time (min) | LC/MS Condition | Stereo-Chemistry |
| --- | --- | --- | --- | --- | --- |
| I-534 | 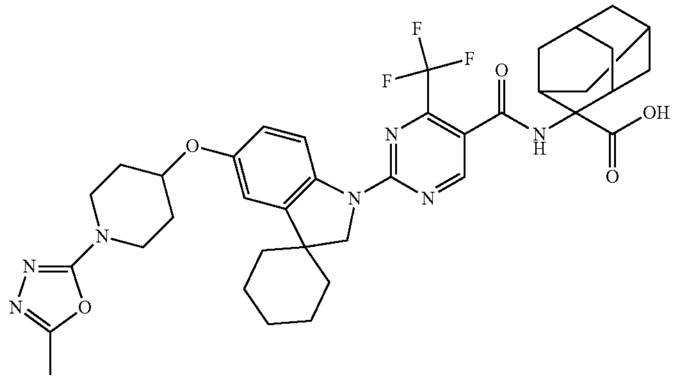 [SMILES: Cc1nnc(N2CCC(Oc3ccc4c(c3)C3(CCCCC3)CN4c3ncc(C(=O)NC4(C(=O)O)C5CC6CC(C5)CC4C6)c(C(F)(F)F)n3)CC2)o1] | 736 | 3.15 | 1 | |
| I-535 | 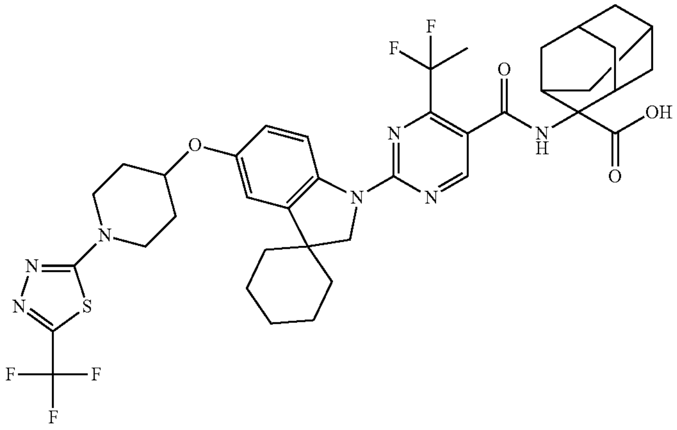 [SMILES: CC(F)(F)c1nc(N2CC3(CCCCC3)c3cc(OC4CCN(c5nnc(C(F)(F)F)s5)CC4)ccc32)ncc1C(=O)NC1(C(=O)O)C2CC3CC(C2)CC1C3] | 802 | 3.43 | 1 | |
| I-536 | 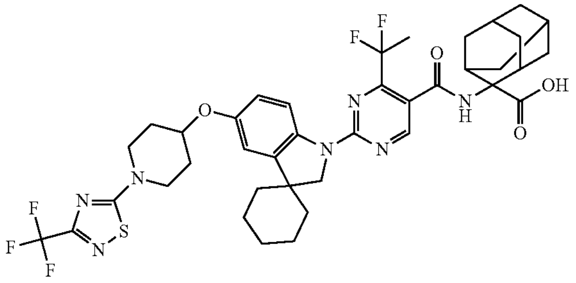 [SMILES: CC(F)(F)c1nc(N2CC3(CCCCC3)c3cc(OC4CCN(c5nc(C(F)(F)F)ns5)CC4)ccc32)ncc1C(=O)NC1(C(=O)O)C2CC3CC(C2)CC1C3] | 802 | 3.53 | 1 | |
| I-537 | 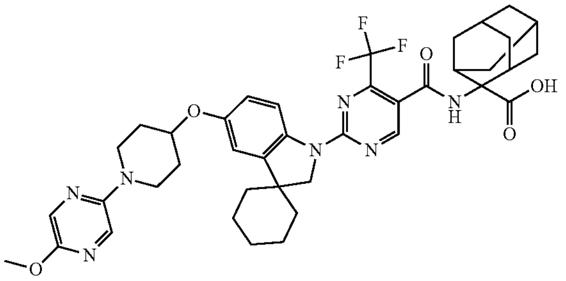 [SMILES: COc1cnc(N2CCC(Oc3ccc4c(c3)C3(CCCCC3)CN4c3ncc(C(=O)NC4(C(=O)O)C5CC6CC(C5)CC4C6)c(C(F)(F)F)n3)CC2)cn1] | 762 | 3.50 | 1 | |

TABLE 93-continued
| Compound No. | Chemical Structure | [M + H] | Retention Time (min) | LC/MS Condition | Stereo-Chemistry |
|---|---|---|---|---|---|
| I-538 | 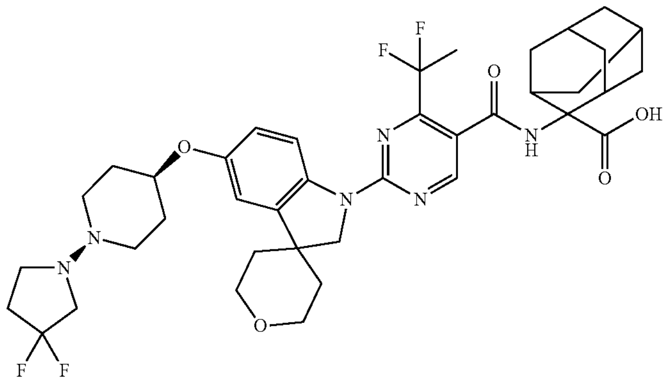 | 756 | 2.24 | 1 | |
TABLE 94
| Compound No. | Chemical Structure | [M + H] | Retention Time (min) | LC/MS Condition | Stereo-Chemistry |
|---|---|---|---|---|---|
| I-539 | 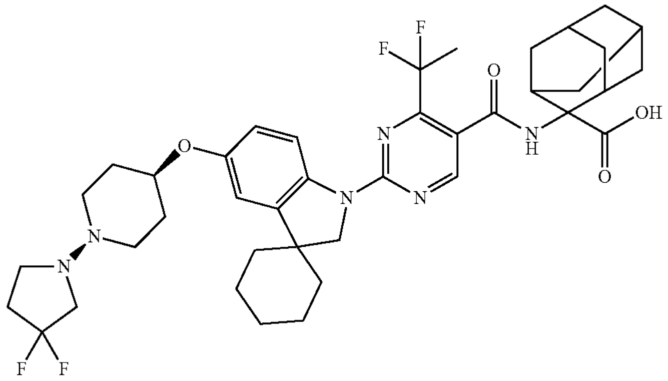 | 754 | 2.61 | 1 | |
| I-540 | 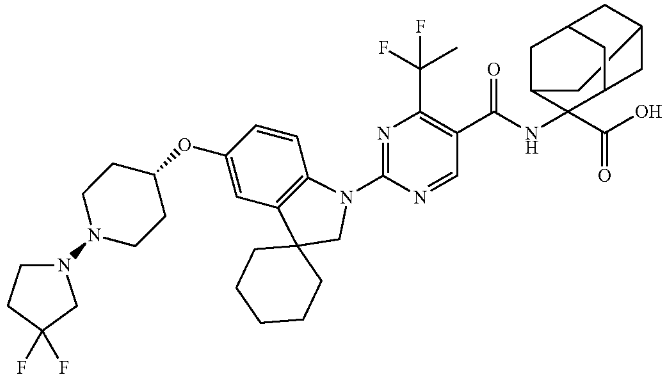 | 754 | 2.77 | 1 | |

TABLE 94-continued
| Compound No. | Chemical Structure | [M + H] | Retention Time (min) | LC/MS Condition | Stereo-Chemistry |
|---|---|---|---|---|---|
| I-541 | 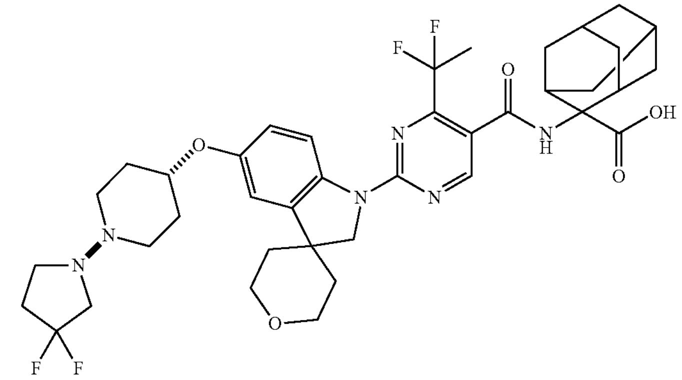 | 756 | 2.24 | 1 | |
| I-542 | 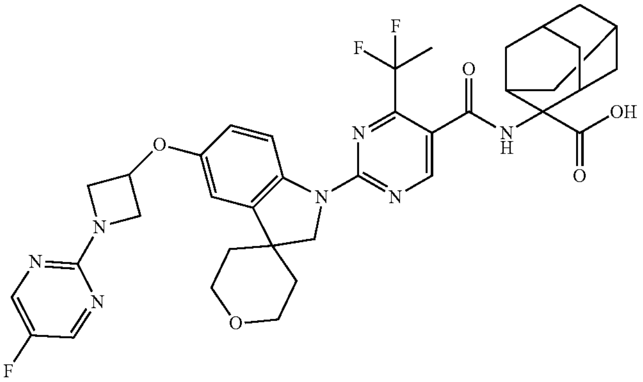 [SMILES: CC(F)(F)c1nc(N2CC3(CCOCC3)c3cc(OC4CN(c5ncc(F)cn5)C4)ccc32)ncc1C(=O)NC1(C(=O)O)C2CC3CC(C2)CC1C3] | 720 | 2.71 | 1 | |
| I-543 | 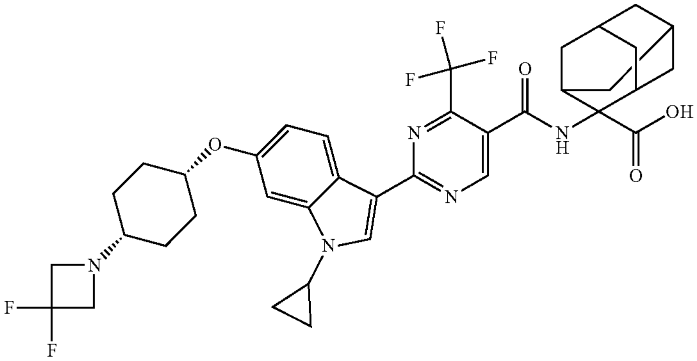 [SMILES: O=C(NC1(C(=O)O)C2CC3CC(C2)CC1C3)c1cnc(-c2cn(C3CC3)c3cc(O[C@H]4CC[C@@H](N5CC(F)(F)C5)CC4)ccc23)nc1C(F)(F)F] | 714 | 1.25 | 9 | |
| I-544 | 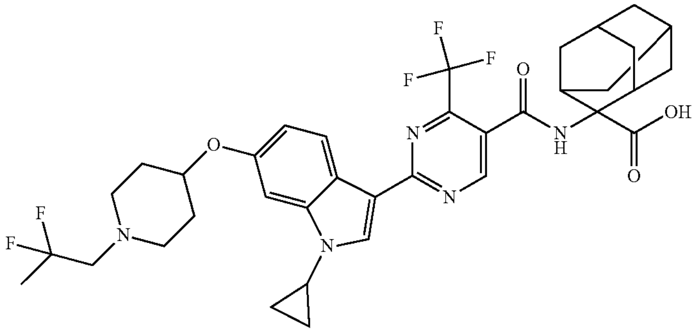 [SMILES: CC(F)(F)CN1CCC(Oc2ccc3c(-c4ncc(C(=O)NC5(C(=O)O)C6CC7CC(C6)CC5C7)c(C(F)(F)F)n4)cn(C4CC4)c3c2)CC1] | 702 | 1.21 | 9 | |

TABLE 95
| Compound No. | Chemical Structure | [M + H] | Retention Time (min) | LC/MS Condition | Stereo-Chemistry |
|---|---|---|---|---|---|
| I-545 | 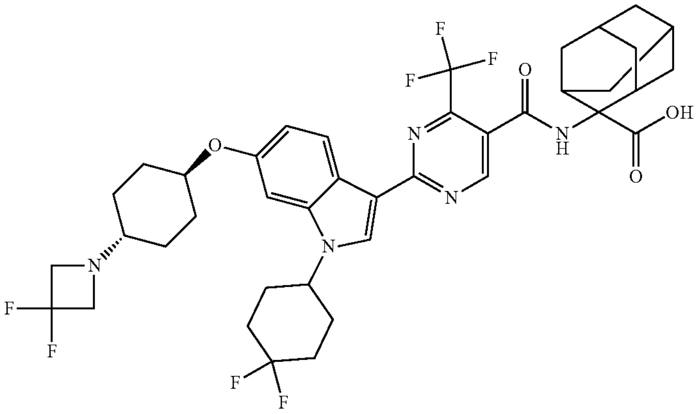 [SMILES: O=C(NC1(C(=O)O)C2CC3CC(C2)CC1C3)c1cnc(-c2cn(C3CCC(F)(F)CC3)c3cc(O[C@H]4CC[C@H](N5CC(F)(F)C5)CC4)ccc23)nc1C(F)(F)F] | 793 | 1.34 | 9 | |
| I-546 | 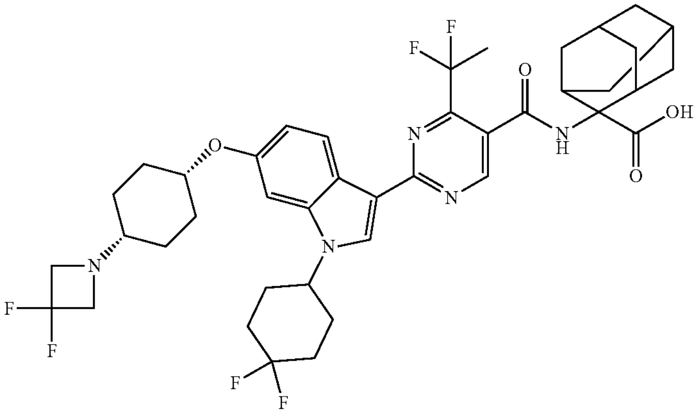 [SMILES: CC(F)(F)c1nc(-c2cn(C3CCC(F)(F)CC3)c3cc(O[C@H]4CC[C@@H](N5CC(F)(F)C5)CC4)ccc23)ncc1C(=O)NC1(C(=O)O)C2CC3CC(C2)CC1C3] | 788 | 1.28 | 9 | |
| I-547 | 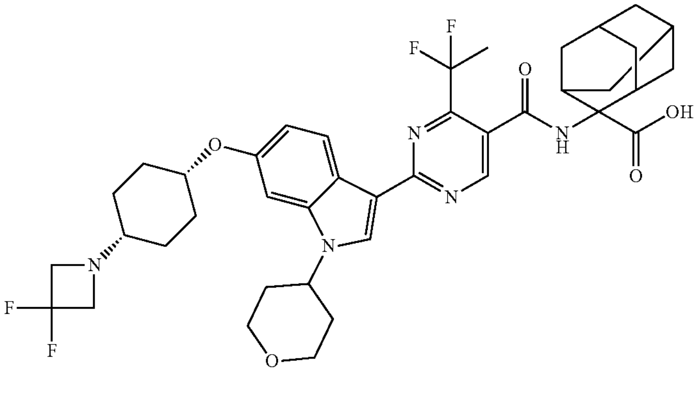 [SMILES: CC(F)(F)c1nc(-c2cn(C3CCOCC3)c3cc(O[C@H]4CC[C@@H](N5CC(F)(F)C5)CC4)ccc23)ncc1C(=O)NC1(C(=O)O)C2CC3CC(C2)CC1C3] | 754 | 1.14 | 9 | |
| I-548 | 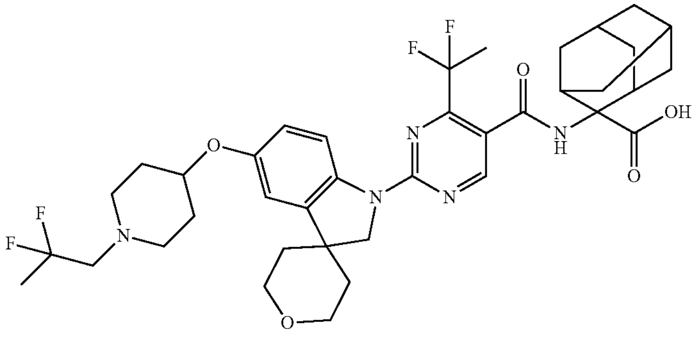 [SMILES: CC(F)(F)CN1CCC(Oc2ccc3c(c2)C2(CCOCC2)CN3c2ncc(C(=O)NC3(C(=O)O)C4CC5CC(C4)CC3C5)c(C(C)(F)F)n2)CC1] | 730 | 2.15 | 1 | |

TABLE 95-continued
| Compound No. | Chemical Structure | [M + H] | Retention Time (min) | LC/MS Condition | Stereo-Chemistry |
|---|---|---|---|---|---|
| I-549 | 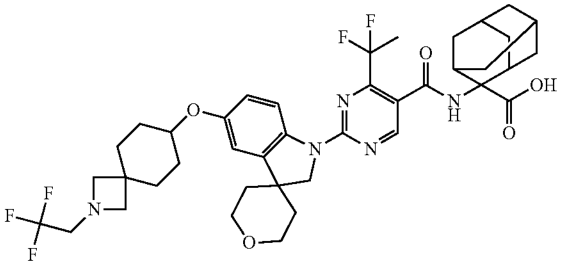 | 774 | 2.39 | 1 | |
| I-550 | 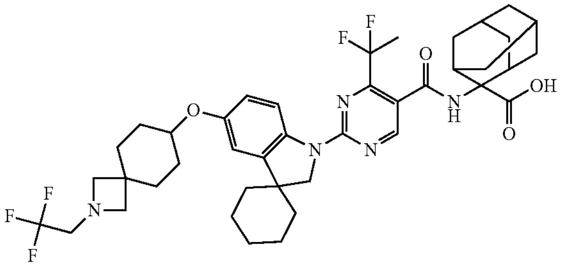 [SMILES: CC(F)(F)c1nc(N2CC3(CCCCC3)c3cc(OC4CCC5(CC4)CN(CC(F)(F)F)C5)ccc32)ncc1C(=O)NC1(C(=O)O)C2CC3CC(C2)CC1C3] | 772 | 2.96 | 1 | |
TABLE 96
| Compound No. | Chemical Structure | [M + H] | Retention Time (min) | LC/MS Condition | Stereo-Chemistry |
|---|---|---|---|---|---|
| I-551 | 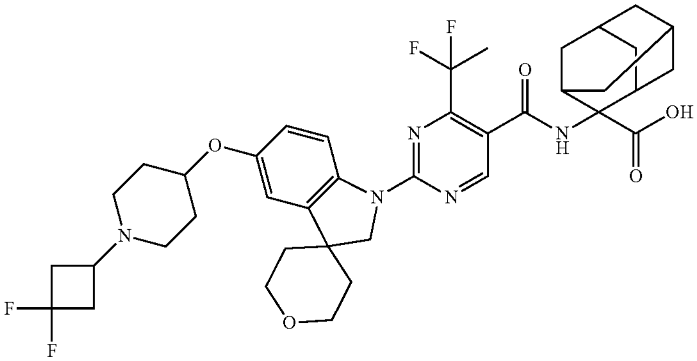 [SMILES: CC(F)(F)c1nc(N2CC3(CCOCC3)c3cc(OC4CCN(C5CC(F)(F)C5)CC4)ccc32)ncc1C(=O)NC1(C(=O)O)C2CC3CC(C2)CC1C3] | 742 | 2.24 | 1 | |
| I-552 | 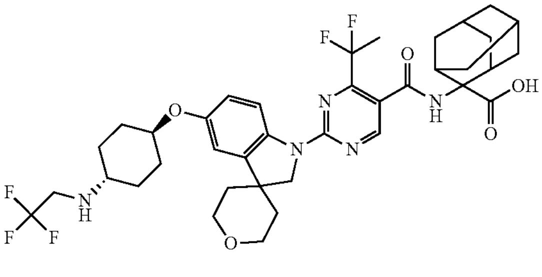 [SMILES: CC(F)(F)c1nc(N2CC3(CCOCC3)c3cc(O[C@H]4CC[C@H](NCC(F)(F)F)CC4)ccc32)ncc1C(=O)NC1(C(=O)O)C2CC3CC(C2)CC1C3] | 748 | 2.21 | 1 | |

TABLE 96-continued
| Compound No. | Chemical Structure | [M + H] | Retention Time (min) | LC/MS Condition | Stereo-Chemistry |
|---|---|---|---|---|---|
| I-553 | 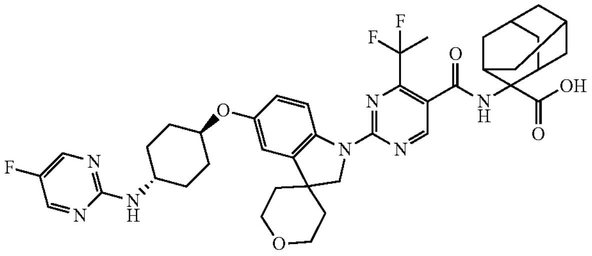 [SMILES: CC(F)(F)c1nc(N2CC3(CCOCC3)c3cc(O[C@H]4CC[C@H](Nc5ncc(F)cn5)CC4)ccc32)ncc1C(=O)NC1(C(=O)O)C2CC3CC(C2)CC1C3] | 762 | 2.88 | 1 | |
| I-554 | 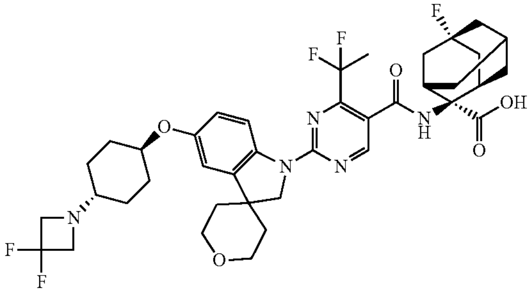 [SMILES: CC(F)(F)c1nc(N2CC3(CCOCC3)c3cc(O[C@H]4CC[C@H](N5CC(F)(F)C5)CC4)ccc32)ncc1C(=O)N[C@]1(C(=O)O)[C@@H]2CC3C[C@H]1C[C@@](F)(C3)C2] | 760 | 2.00 | 1 | |
| I-555 | 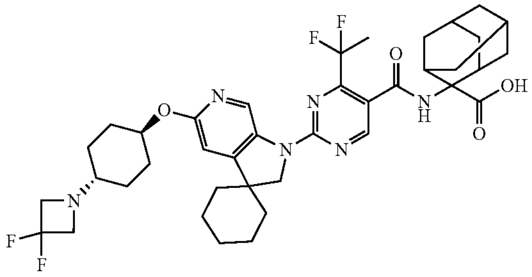 [SMILES: CC(F)(F)c1nc(N2CC3(CCCCC3)c3cc(O[C@H]4CC[C@H](N5CC(F)(F)C5)CC4)ncc32)ncc1C(=O)NC1(C(=O)O)C2CC3CC(C2)CC1C3] | 741 | 2.46 | 1 | |
| I-556 | 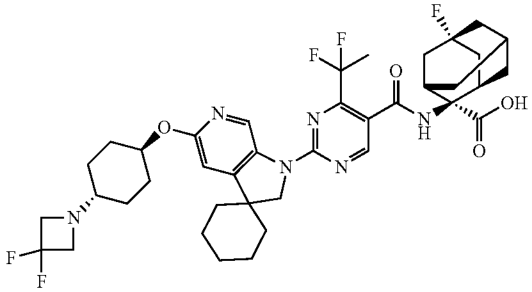 [SMILES: CC(F)(F)c1nc(N2CC3(CCCCC3)c3cc(O[C@H]4CC[C@H](N5CC(F)(F)C5)CC4)ncc32)ncc1C(=O)N[C@]1(C(=O)O)[C@@H]2CC3C[C@H]1C[C@@](F)(C3)C2] | 759 | 2.29 | 1 | |

TABLE 97
| Compound No. | Chemical Structure | [M + H] | Retention Time (min) | LC/MS Condition | Stereo-Chemistry |
|---|---|---|---|---|---|
| I-557 | 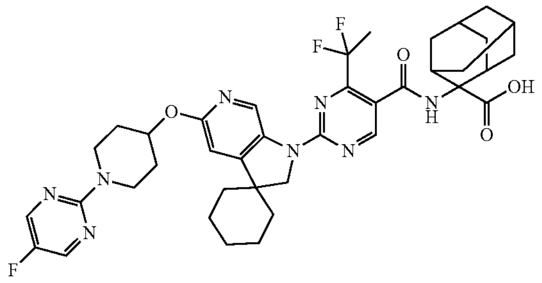 [SMILES: CC(F)(F)c1nc(N2CC3(CCCCC3)c3cc(OC4CCN(c5ncc(F)cn5)CC4)ncc32)ncc1C(=O)NC1(C(=O)O)C2CC3CC(C2)CC1C3] | 747 | 3.51 | 1 | |
| I-558 | 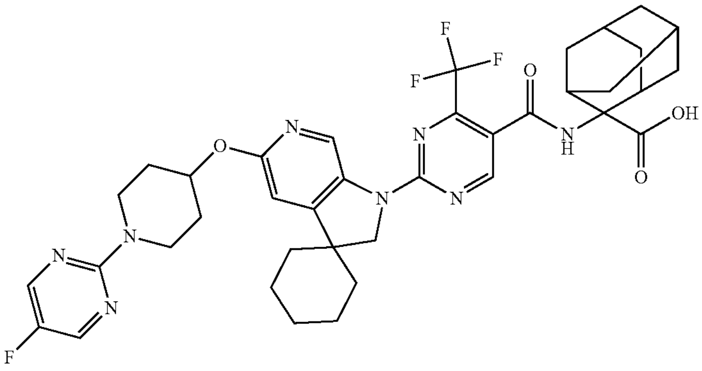 [SMILES: O=C(NC1(C(=O)O)C2CC3CC(C2)CC1C3)c1cnc(N2CC3(CCCCC3)c3cc(OC4CCN(c5ncc(F)cn5)CC4)ncc32)nc1C(F)(F)F] | 751 | 3.54 | 1 | |
| I-559 | 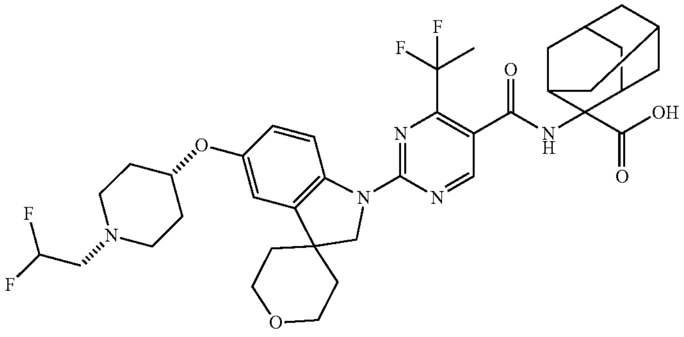 | 716 | 2.08 | 1 | |
| I-560 | 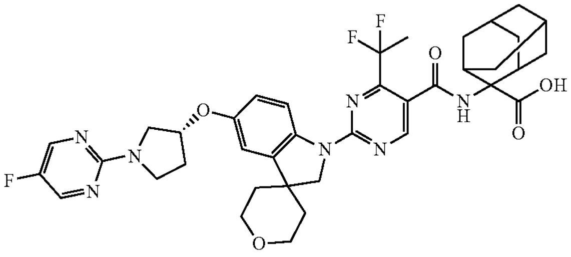 [SMILES: CC(F)(F)c1nc(N2CC3(CCOCC3)c3cc(O[C@@H]4CCN(c5ncc(F)cn5)C4)ccc32)ncc1C(=O)NC1(C(=O)O)C2CC3CC(C2)CC1C3] | 734 | 2.81 | 1 | |

TABLE 97-continued
| Compound No. | Chemical Structure | [M + H] | Retention Time (min) | LC/MS Condition | Stereo-Chemistry |
|---|---|---|---|---|---|
| I-561 | 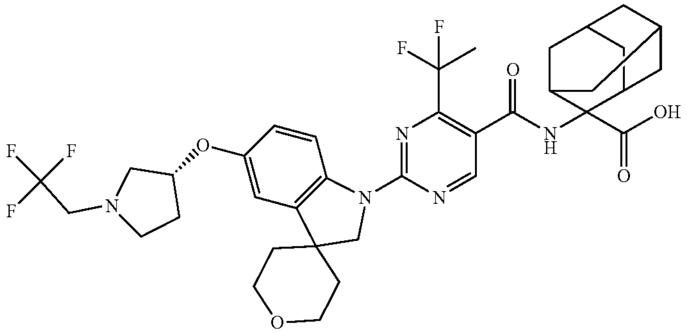 [SMILES: CC(F)(F)c1nc(N2CC3(CCOCC3)c3cc(O[C@@H]4CCN(CC(F)(F)F)C4)ccc32)ncc1C(=O)NC1(C(=O)O)C2CC3CC(C2)CC1C3] | 720 | 2.74 | 1 | |
| I-562 | 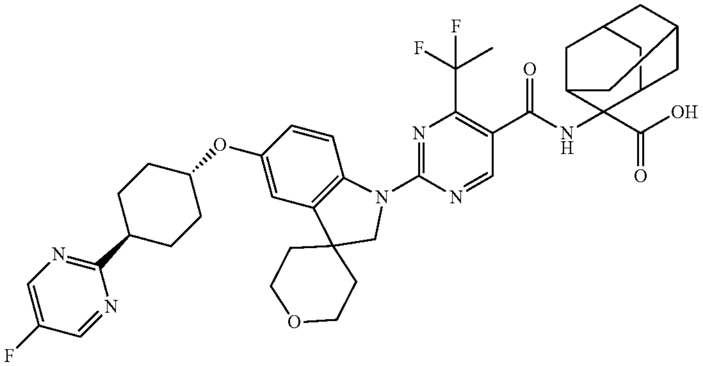 [SMILES: CC(F)(F)c1nc(N2CC3(CCOCC3)c3cc(O[C@H]4CC[C@H](c5ncc(F)cn5)CC4)ccc32)ncc1C(=O)NC1(C(=O)O)C2CC3CC(C2)CC1C3] | 747 | 2.94 | 1 | |
TABLE 98
| Compound No. | Chemical Structure | [M + H] | Retention Time (min) | LC/MS Condition | Stereo-Chemistry |
|---|---|---|---|---|---|
| I-563 | 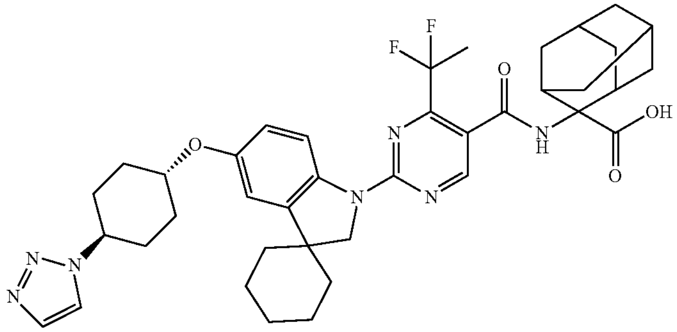 [SMILES: CC(F)(F)c1nc(N2CC3(CCCCC3)c3cc(O[C@H]4CC[C@H](n5ccnn5)CC4)ccc32)ncc1C(=O)NC1(C(=O)O)C2CC3CC(C2)CC1C3] | 716 | 2.99 | 1 | |
| I-564 | 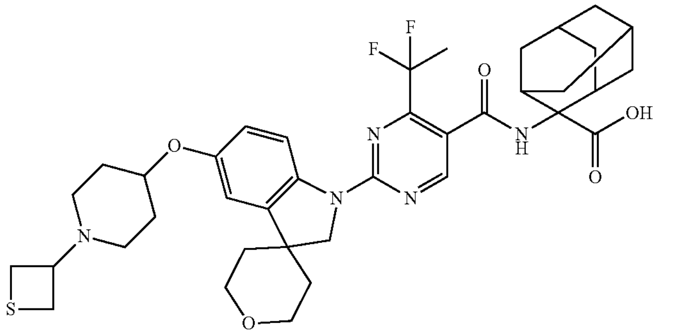 [SMILES: CC(F)(F)c1nc(N2CC3(CCOCC3)c3cc(OC4CCN(C5CSC5)CC4)ccc32)ncc1C(=O)NC1(C(=O)O)C2CC3CC(C2)CC1C3] | 724 | 2.14 | 1 | |

TABLE 98-continued
| Compound No. | Chemical Structure | [M + H] | Retention Time (min) | LC/MS Condition | Stereo-Chemistry |
|---|---|---|---|---|---|
| I-565 | 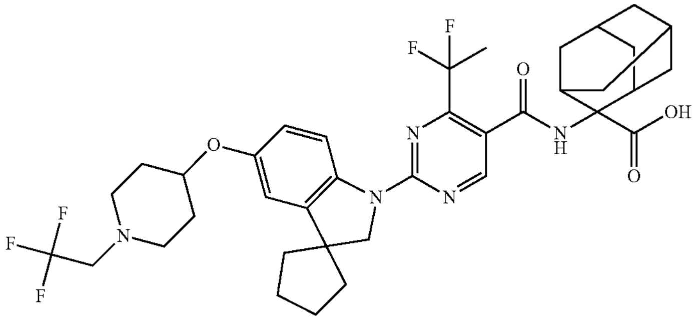 [SMILES: CC(F)(F)c1nc(N2CC3(CCCC3)c3cc(OC4CCN(CC(F)(F)F)CC4)ccc32)ncc1C(=O)NC1(C(=O)O)C2CC3CC(C2)CC1C3] | 718 | 3.25 | 1 | |
| I-566 | 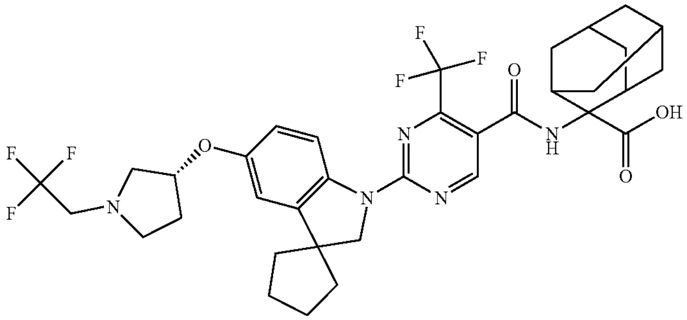 [SMILES: O=C(NC1(C(=O)O)C2CC3CC(C2)CC1C3)c1cnc(N2CC3(CCCC3)c3cc(O[C@@H]4CCN(CC(F)(F)F)C4)ccc32)nc1C(F)(F)F] | 708 | 3.22 | 1 | |
| I-567 | 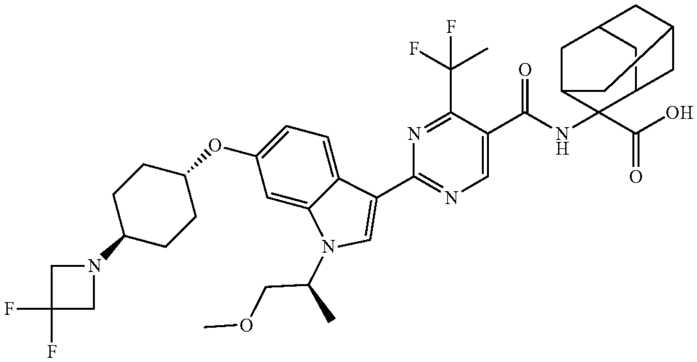 [SMILES: COC[C@H](C)n1cc(-c2ncc(C(=O)NC3(C(=O)O)C4CC5CC(C4)CC3C5)c(C(C)(F)F)n2)c2ccc(O[C@H]3CC[C@H](N4CC(F)(F)C4)CC3)cc21] | 742 | 1.23 | 10 | |
| I-568 | 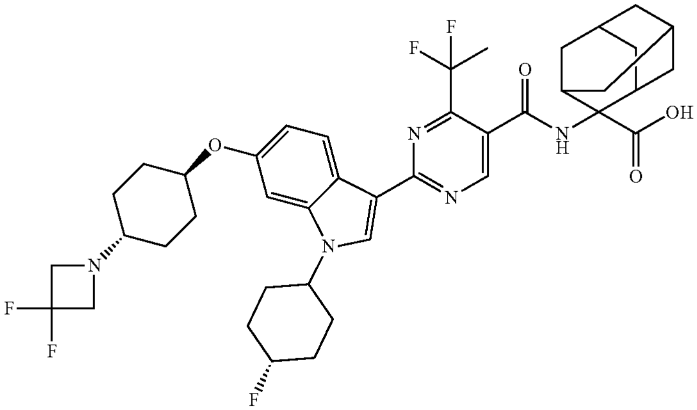 | 770 | 1.32 | 10 | e |

TABLE 99
| Compound No. | Chemical Structure | [M + H] | Retention Time (min) | LC/MS Condition | Stereo-Chemistry |
| --- | --- | --- | --- | --- | --- |
| I-569 | 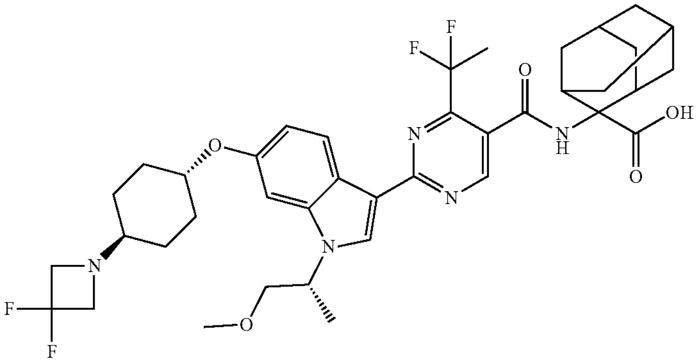 [SMILES: COC[C@@H](C)n1cc(-c2ncc(C(=O)NC3(C(=O)O)C4CC5CC(C4)CC3C5)c(C(C)(F)F)n2)c2ccc(O[C@H]3CC[C@H](N4CC(F)(F)C4)CC3)cc21] | 742 | 1.22 | 9 | |
| I-570 | 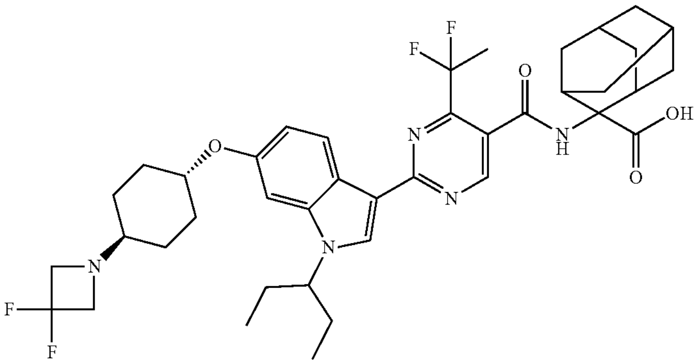 [SMILES: CCC(CC)n1cc(-c2ncc(C(=O)NC3(C(=O)O)C4CC5CC(C4)CC3C5)c(C(C)(F)F)n2)c2ccc(O[C@H]3CC[C@H](N4CC(F)(F)C4)CC3)cc21] | 740 | 1.36 | 9 | |
| I-571 | 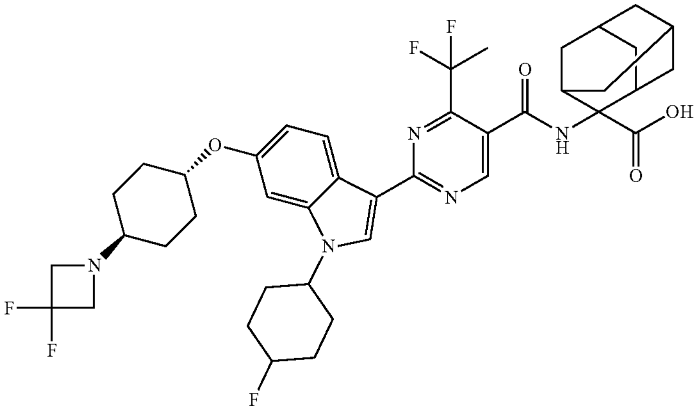 [SMILES: CC(F)(F)c1nc(-c2cn(C3CCC(F)CC3)c3cc(O[C@H]4CC[C@H](N5CC(F)(F)C5)CC4)ccc23)ncc1C(=O)NC1(C(=O)O)C2CC3CC(C2)CC1C3] | 770 | 1.30 | 9 | e |
| I-572 | 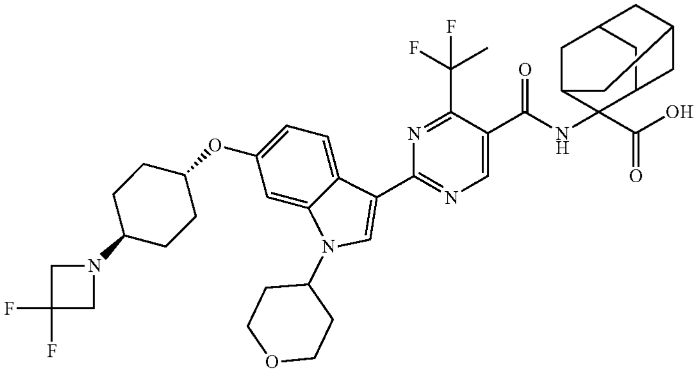 [SMILES: CC(F)(F)c1nc(-c2cn(C3CCOCC3)c3cc(O[C@H]4CC[C@H](N5CC(F)(F)C5)CC4)ccc23)ncc1C(=O)NC1(C(=O)O)C2CC3CC(C2)CC1C3] | 754 | 1.18 | 9 | |

TABLE 99-continued
| Compound No. | Chemical Structure | [M + H] | Retention Time (min) | LC/MS Condition | Stereo-Chemistry |
|---|---|---|---|---|---|
| I-573 | 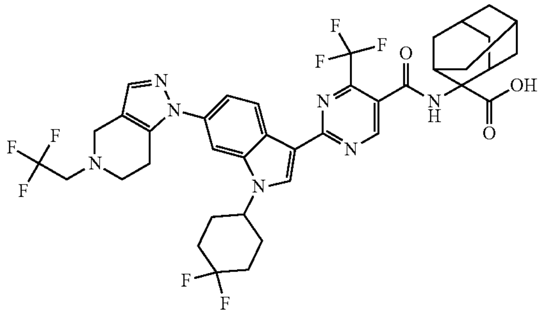 [SMILES: O=C(NC1(C(=O)O)C2CC3CC(C2)CC1C3)c1cnc(-c2cn(C3CCC(F)(F)CC3)c3cc(-n4ncc5c4CCN(CC(F)(F)F)C5)ccc23)nc1C(F)(F)F] | 806 | 1.75 | 10 | |
| I-574 | 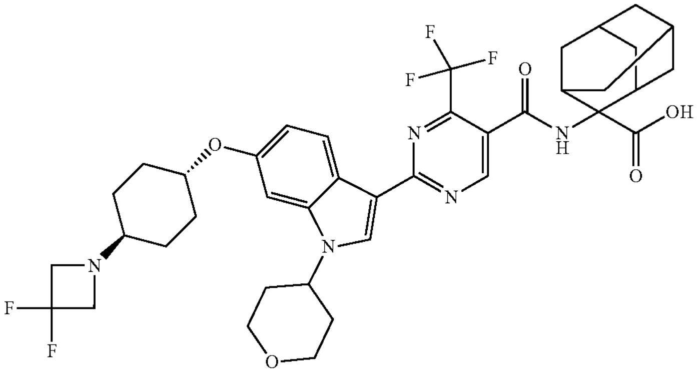 [SMILES: O=C(NC1(C(=O)O)C2CC3CC(C2)CC1C3)c1cnc(-c2cn(C3CCOCC3)c3cc(O[C@H]4CC[C@H](N5CC(F)(F)C5)CC4)ccc23)nc1C(F)(F)F] | 757 | 1.23 | 10 | |
TABLE 100
| Compound No. | Chemical Structure | [M + H] | Retention Time (min) | LC/MS Condition | Stereo-Chemistry |
|---|---|---|---|---|---|
| I-575 | 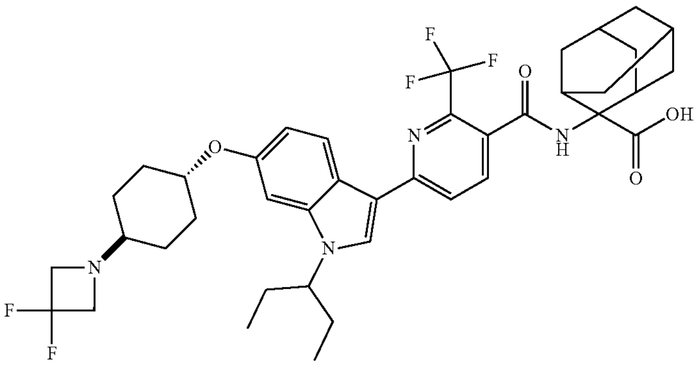 [SMILES: CCC(CC)n1cc(-c2ccc(C(=O)NC3(C(=O)O)C4CC5CC(C4)CC3C5)c(C(F)(F)F)n2)c2ccc(O[C@H]3CC[C@H](N4CC(F)(F)C4)CC3)cc21] | 743 | 1.39 | 10 | |
| I-576 | 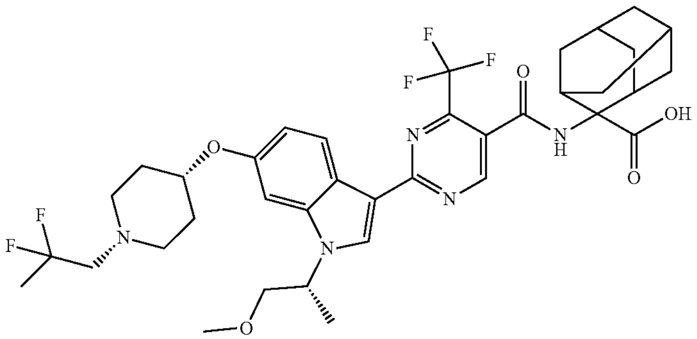 | 734 | 1.16 | 10 | |

TABLE 100-continued
| Compound No. | Chemical Structure | [M + H] | Retention Time (min) | LC/MS Condition | Stereo-Chemistry |
|---|---|---|---|---|---|
| I-577 | 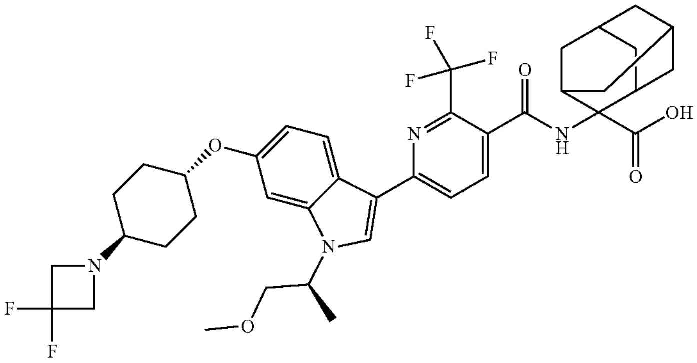 [SMILES: COC[C@H](C)n1cc(-c2ccc(C(=O)NC3(C(=O)O)C4CC5CC(C4)CC3C5)c(C(F)(F)F)n2)c2ccc(O[C@H]3CC[C@H](N4CC(F)(F)C4)CC3)cc21] | 745 | 1.25 | 10 | |
| I-578 | 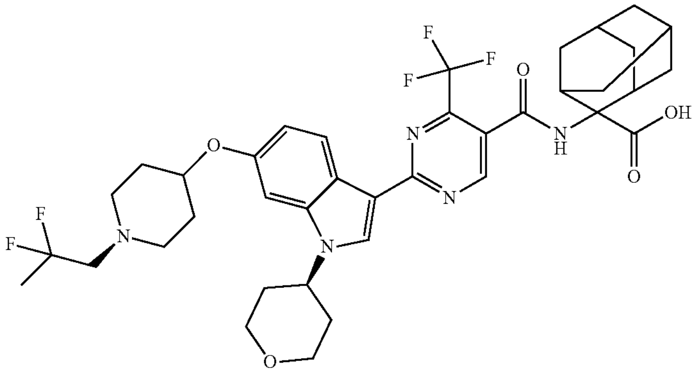 | 746 | 1.15 | 10 | |
| I-579 | 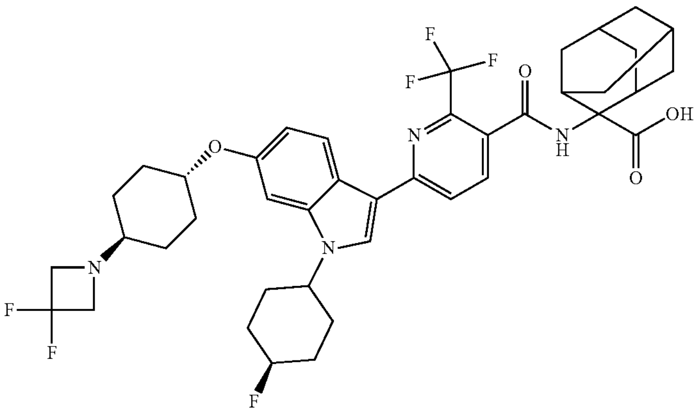 | 773 | 1.33 | 10 | e |

TABLE 100-continued
| Compound No. | Chemical Structure | [M + H] | Retention Time (min) | LC/MS Condition | Stereo-Chemistry |
| --- | --- | --- | --- | --- | --- |
| I-580 | 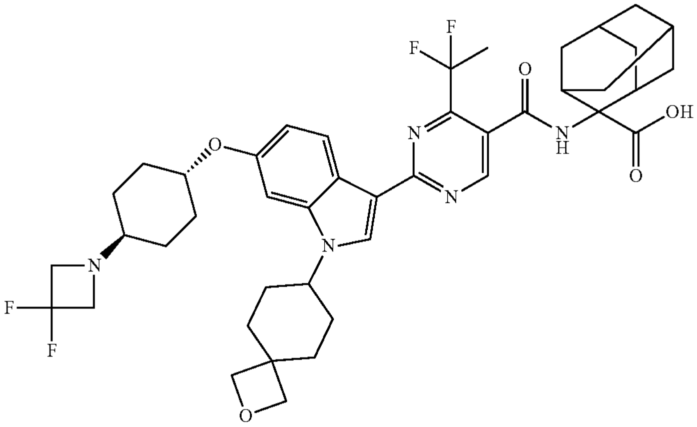 [SMILES: CC(F)(F)c1nc(-c2cn(C3CCC4(CC3)COC4)c3cc(O[C@H]4CC[C@H](N5CC(F)(F)C5)CC4)ccc23)ncc1C(=O)NC1(C(=O)O)C2CC3CC(C2)CC1C3] | 794 | 1.24 | 10 | |
TABLE 101
| Compound No. | Chemical Structure | [M + H] | Retention Time (min) | LC/MS Condition | Stereo-Chemistry |
| --- | --- | --- | --- | --- | --- |
| I-581 | 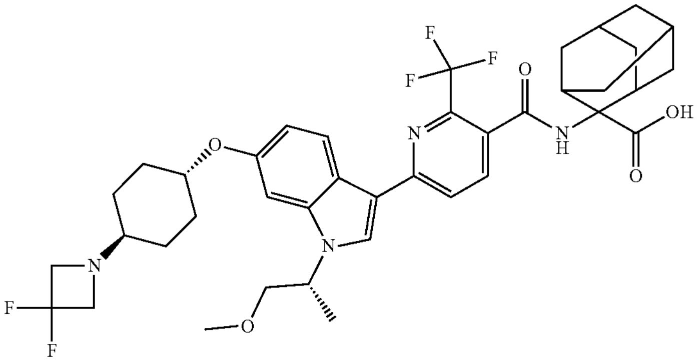 [SMILES: COC[C@@H](C)n1cc(-c2ccc(C(=O)NC3(C(=O)O)C4CC5CC(C4)CC3C5)c(C(F)(F)F)n2)c2ccc(O[C@H]3CC[C@H](N4CC(F)(F)C4)CC3)cc21] | 745 | 1.24 | 10 | |
| I-582 | 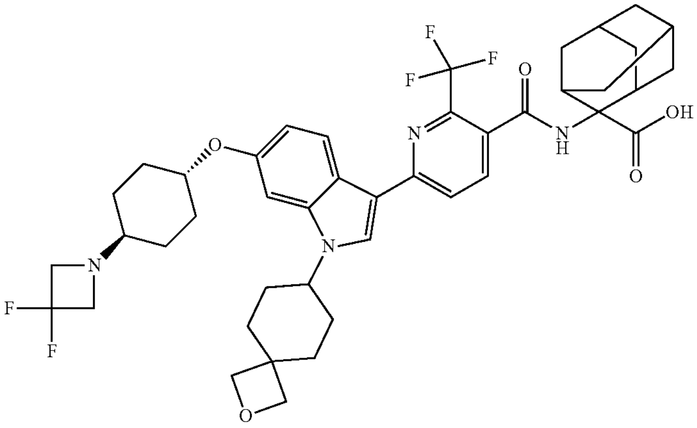 [SMILES: O=C(NC1(C(=O)O)C2CC3CC(C2)CC1C3)c1ccc(-c2cn(C3CCC4(CC3)COC4)c3cc(O[C@H]4CC[C@H](N5CC(F)(F)C5)CC4)ccc23)nc1C(F)(F)F] | 797 | 1.25 | 10 | |

TABLE 101-continued
| Compound No. | Chemical Structure | [M + H] | Retention Time (min) | LC/MS Condition | Stereo-Chemistry |
|---|---|---|---|---|---|
| I-583 | 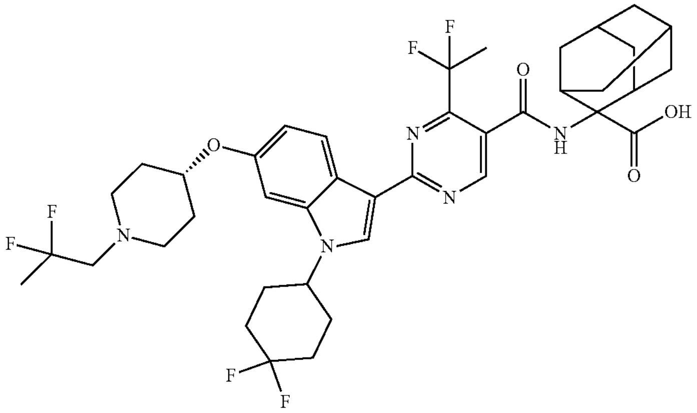 | 776 | 1.26 | 9 | |
| I-584 | 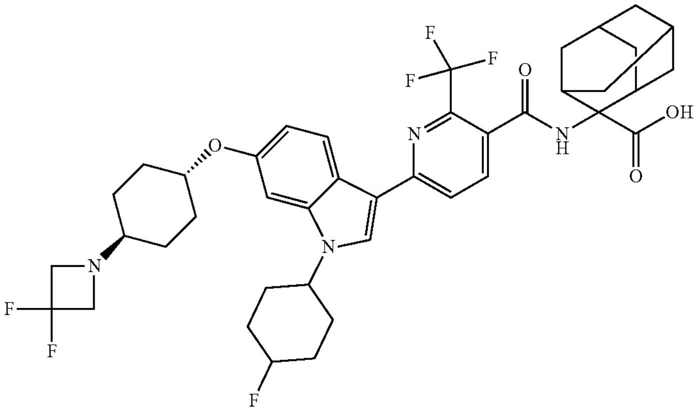 [SMILES: O=C(NC1(C(=O)O)C2CC3CC(C2)CC1C3)c1ccc(-c2cn(C3CCC(F)CC3)c3cc(O[C@H]4CC[C@H](N5CC(F)(F)C5)CC4)ccc23)nc1C(F)(F)F] | 773 | 1.33 | 9 | e |
| I-585 | 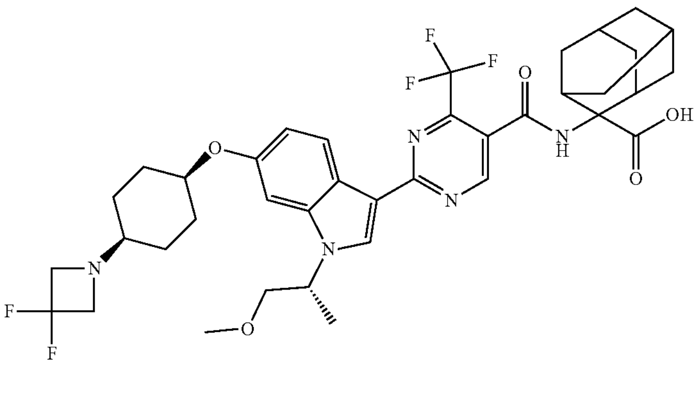 [SMILES: COC[C@@H](C)n1cc(-c2ncc(C(=O)NC3(C(=O)O)C4CC5CC(C4)CC3C5)c(C(F)(F)F)n2)c2ccc(O[C@H]3CC[C@@H](N4CC(F)(F)C4)CC3)cc21] | 746 | 1.21 | 9 | |

TABLE 101-continued
| Compound No. | Chemical Structure | [M + H] | Retention Time (min) | LC/MS Condition | Stereo-Chemistry |
|---|---|---|---|---|---|
| I-586 | 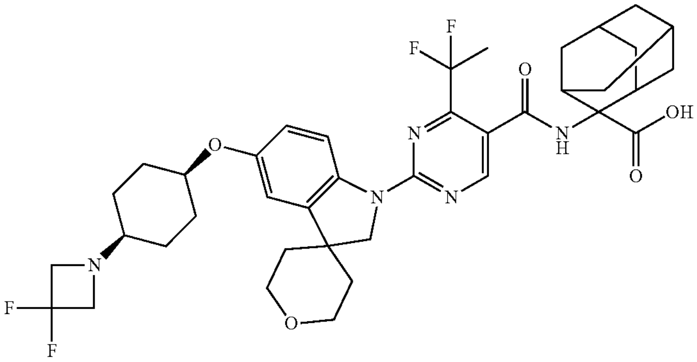 [SMILES: CC(F)(F)c1nc(N2CC3(CCOCC3)c3cc(O[C@H]4CC[C@@H](N5CC(F)(F)C5)CC4)ccc32)ncc1C(=O)NC1(C(=O)O)C2CC3CC(C2)CC1C3] | 742 | 2.07 | 1 | |
TABLE 102
| Compound No. | Chemical Structure | [M + H] | Retention Time (min) | LC/MS Condition | Stereo-Chemistry |
|---|---|---|---|---|---|
| I-587 | 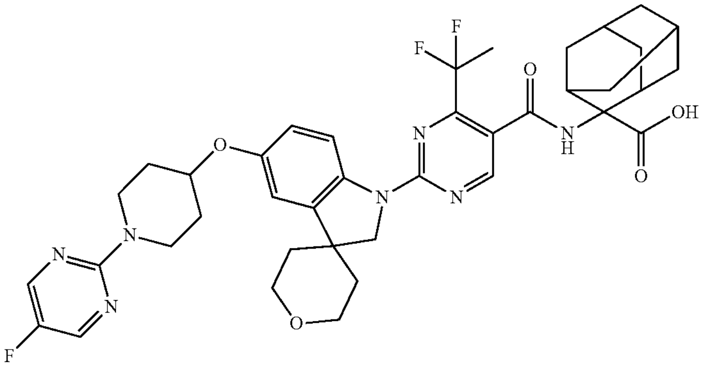 [SMILES: CC(F)(F)c1nc(N2CC3(CCOCC3)c3cc(OC4CCN(c5ncc(F)cn5)CC4)ccc32)ncc1C(=O)NC1(C(=O)O)C2CC3CC(C2)CC1C3] | 746 | 3.06 | 1 | |
| I-588 | 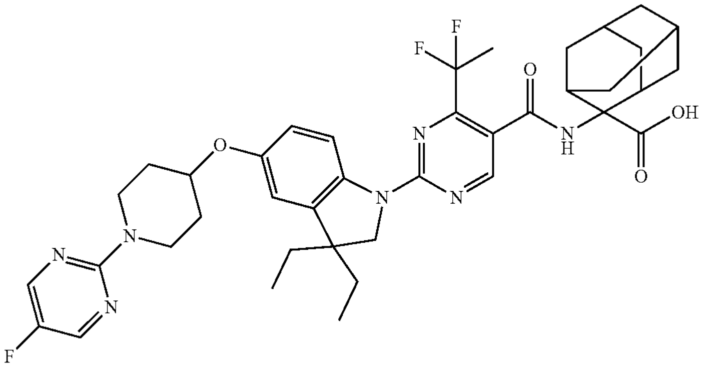 [SMILES: CCC1(CC)CN(c2ncc(C(=O)NC3(C(=O)O)C4CC5CC(C4)CC3C5)c(C(C)(F)F)n2)c2ccc(OC3CCN(c4ncc(F)cn4)CC3)cc21] | 734 | 3.50 | 1 | |

TABLE 102-continued
| Compound No. | Chemical Structure | [M + H] | Retention Time (min) | LC/MS Condition | Stereo-Chemistry |
|---|---|---|---|---|---|
| I-589 | 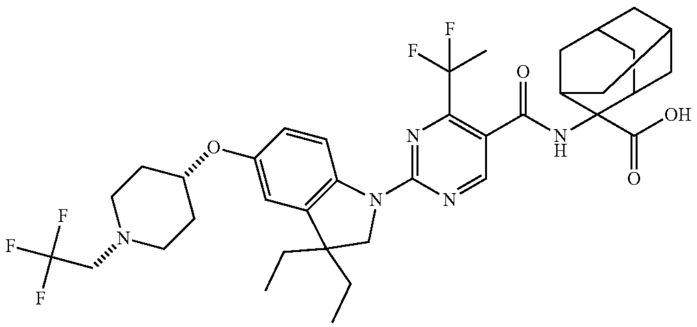 | 720 | 3.28 | 1 | |
| I-590 | 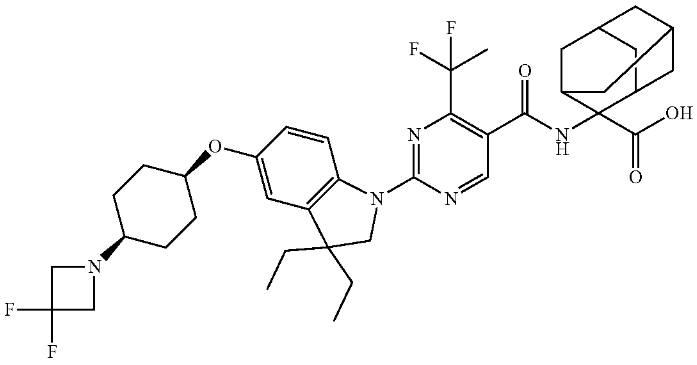 [SMILES: CCC1(CC)CN(c2ncc(C(=O)NC3(C(=O)O)C4CC5CC(C4)CC3C5)c(C(C)(F)F)n2)c2ccc(O[C@H]3CC[C@@H](N4CC(F)(F)C4)CC3)cc21] | 726 | 2.53 | 1 | |
| I-591 | 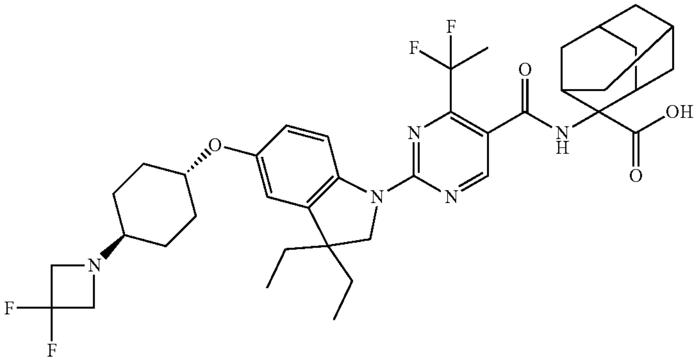 [SMILES: CCC1(CC)CN(c2ncc(C(=O)NC3(C(=O)O)C4CC5CC(C4)CC3C5)c(C(C)(F)F)n2)c2ccc(O[C@H]3CC[C@H](N4CC(F)(F)C4)CC3)cc21] | 726 | 2.54 | 1 | |
| I-592 | 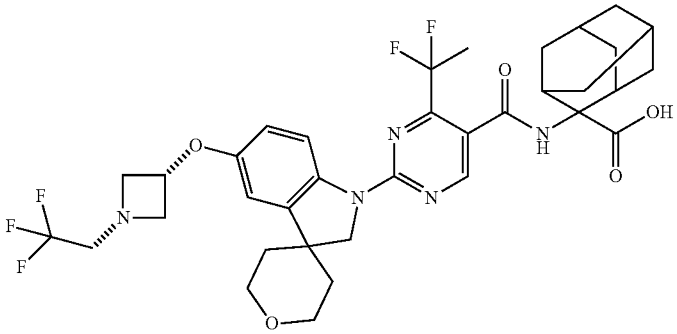 | 706 | 2.72 | 1 | |

TABLE 103
| Compound No. | Chemical Structure | [M + H] | Retention Time (min) | LC/MS Condition | Stereo-Chemistry |
|---|---|---|---|---|---|
| I-593 | 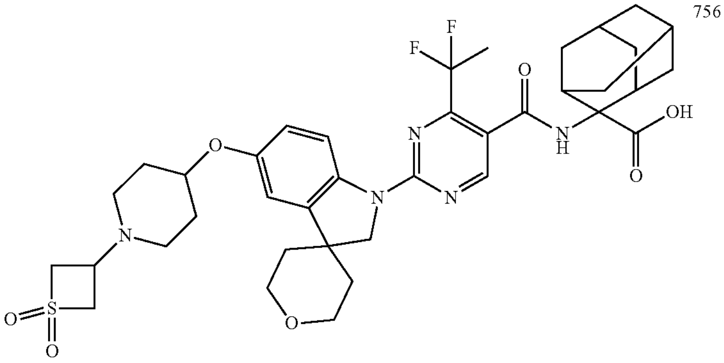 | 756 | 2.12 | 1 | |
| I-594 | 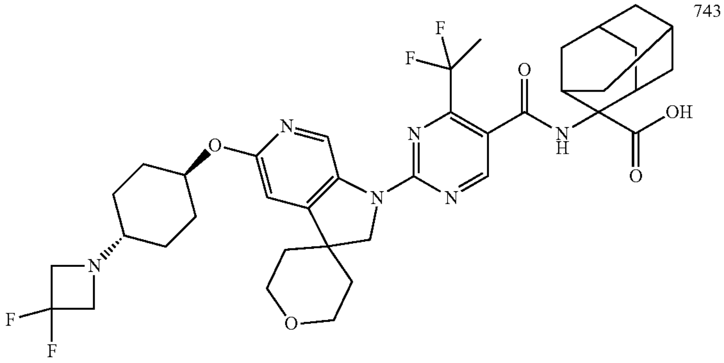 | 743 | 2.00 | 1 | |
| I-595 | 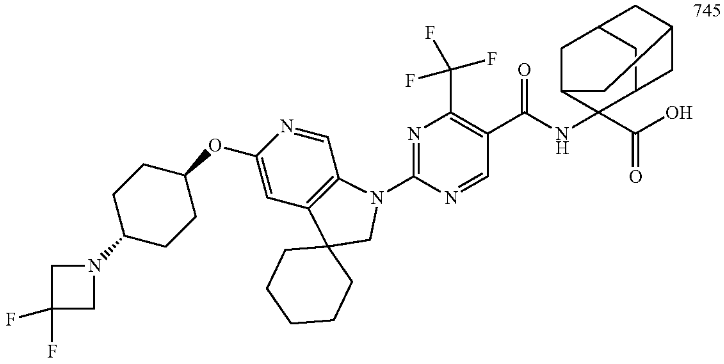 | 745 | 2.10 | 1 | |
| I-596 | 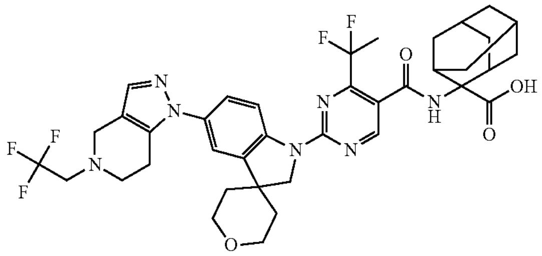 [SMILES: CC(F)(F)c1nc(N2CC3(CCOCC3)c3cc(-n4ncc5c4CCN(CC(F)(F)F)C5)ccc32)ncc1C(=O)NC1(C(=O)O)C2CC3CC(C2)CC1C3] | 756 | 2.79 | 1 | |

TABLE 103-continued
| Compound No. | Chemical Structure | [M + H] | Retention Time (min) | LC/MS Condition | Stereo-Chemistry |
|---|---|---|---|---|---|
| I-597 | 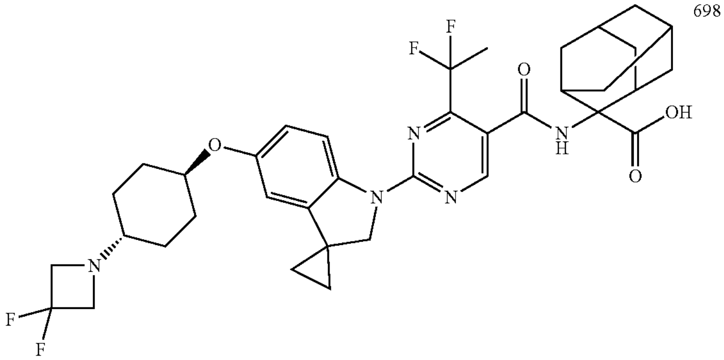 | 698 | 2.42 | 1 | |
| I-598 | 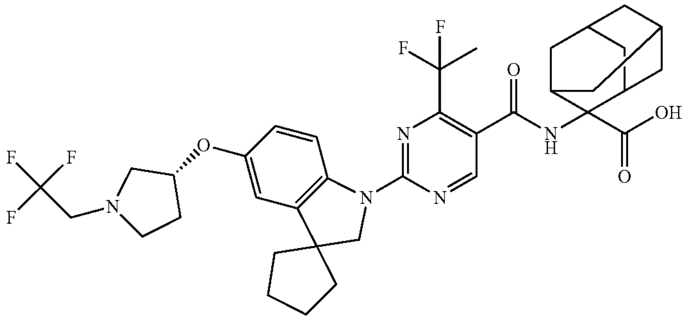 [SMILES: CC(F)(F)c1nc(N2CC3(CCCC3)c3cc(O[C@@H]4CCN(CC(F)(F)F)C4)ccc32)ncc1C(=O)NC1(C(=O)O)C2CC3CC(C2)CC1C3] | 704 | 3.18 | 1 | |
TABLE 104
| Compound No. | Chemical Structure | [M + H] | Retention Time (min) | LC/MS Condition | Stereo-Chemistry |
|---|---|---|---|---|---|
| I-599 | 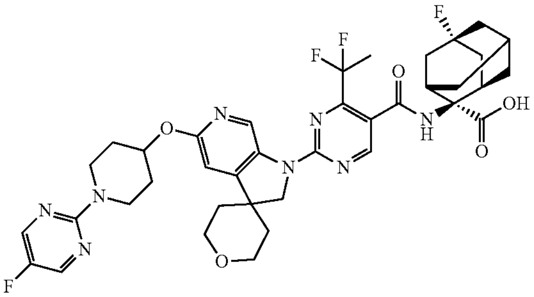 [SMILES: CC(F)(F)c1nc(N2CC3(CCOCC3)c3cc(OC4CCN(c5ncc(F)cn5)CC4)ncc32)ncc1C(=O)N[C@]1(C(=O)O)[C@@H]2CC3C[C@H]1C[C@@](F)(C3)C2] | 767 | 2.77 | 1 | |
| I-600 | 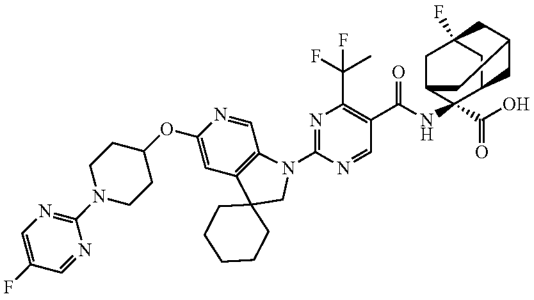 [SMILES: CC(F)(F)c1nc(N2CC3(CCCCC3)c3cc(OC4CCN(c5ncc(F)cn5)CC4)ncc32)ncc1C(=O)N[C@]1(C(=O)O)[C@@H]2CC3C[C@H]1C[C@@](F)(C3)C2] | 765 | 3.33 | 1 | |

TABLE 104-continued
| Compound No. | Chemical Structure | [M + H] | Retention Time (min) | LC/MS Condition | Stereo-Chemistry |
|---|---|---|---|---|---|
| I-601 | 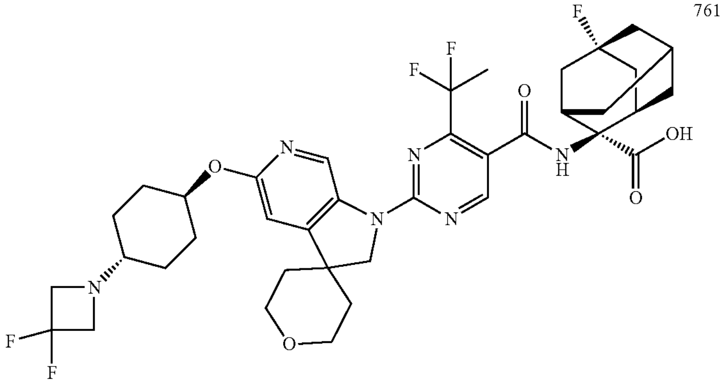 | 761 | 1.86 | 1 | |
| I-602 | 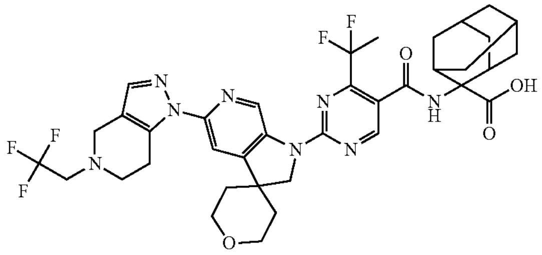 [SMILES: CC(F)(F)c1nc(N2CC3(CCOCC3)c3cc(-n4ncc5c4CCN(CC(F)(F)F)C5)ncc32)ncc1C(=O)NC1(C(=O)O)C2CC3CC(C2)CC1C3] | 757 | 2.79 | 1 | |
| I-603 | 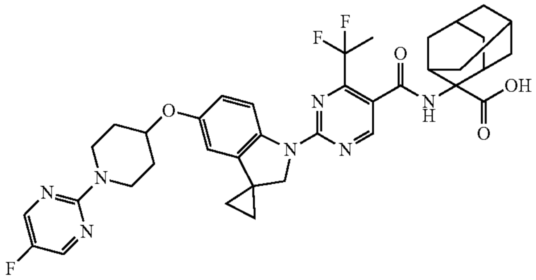 [SMILES: CC(F)(F)c1nc(N2CC3(CC3)c3cc(OC4CCN(c5ncc(F)cn5)CC4)ccc32)ncc1C(=O)NC1(C(=O)O)C2CC3CC(C2)CC1C3] | 704 | 3.25 | 1 | |
| I-604 | 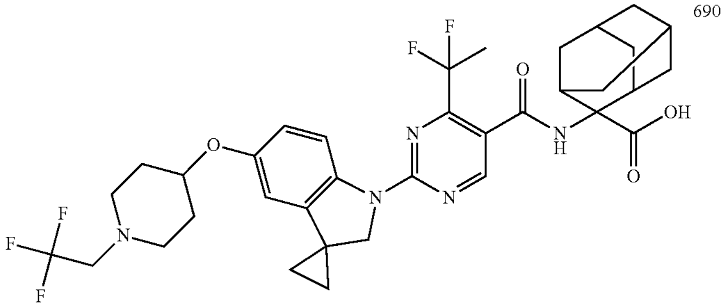 | 690 | 3.01 | 1 | |

TABLE 105
| Compound No. | Chemical Structure | [M + H] | Retention Time (min) | LC/MS Condition | Stereo-Chemistry |
|---|---|---|---|---|---|
| I-605 | 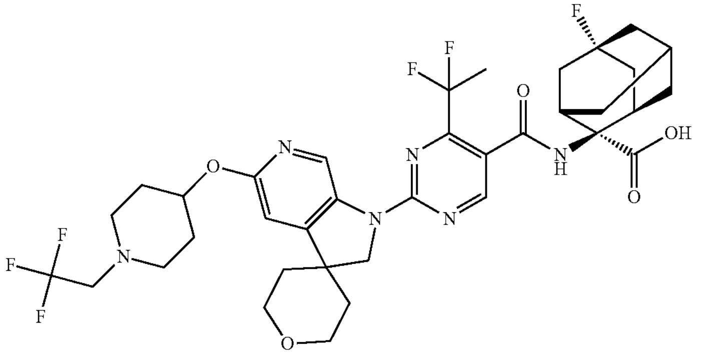 [SMILES: CC(F)(F)c1nc(N2CC3(CCOCC3)c3cc(OC4CCN(CC(F)(F)F)CC4)ncc32)ncc1C(=O)N[C@]1(C(=O)O)[C@@H]2CC3C[C@H]1C[C@@](F)(C3)C2] | 753 | 2.43 | 1 | |
| I-606 | 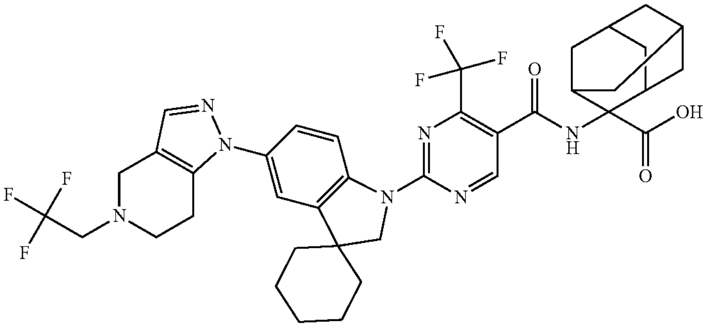 [SMILES: O=C(NC1(C(=O)O)C2CC3CC(C2)CC1C3)c1cnc(N2CC3(CCCCC3)c3cc(-n4ncc5c4CCN(CC(F)(F)F)C5)ccc32)nc1C(F)(F)F] | 758 | 3.30 | 1 | |
| I-607 | 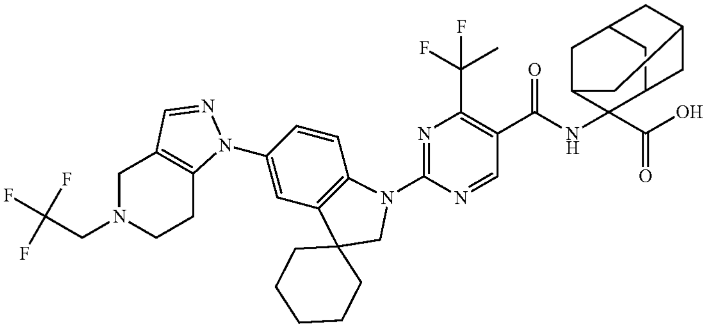 [SMILES: CC(F)(F)c1nc(N2CC3(CCCCC3)c3cc(-n4ncc5c4CCN(CC(F)(F)F)C5)ccc32)ncc1C(=O)NC1(C(=O)O)C2CC3CC(C2)CC1C3] | 754 | 3.28 | 1 | |
| I-608 | 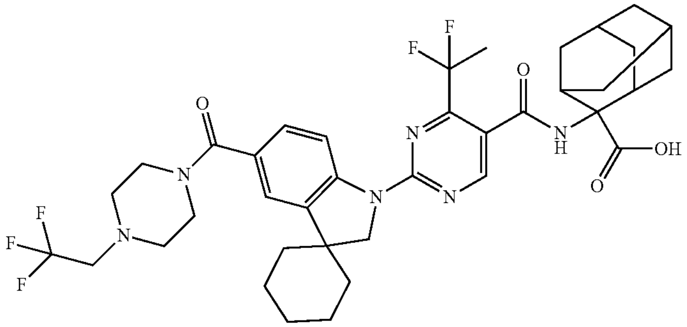 [SMILES: CC(F)(F)c1nc(N2CC3(CCCCC3)c3cc(C(=O)N4CCN(CC(F)(F)F)CC4)ccc32)ncc1C(=O)NC1(C(=O)O)C2CC3CC(C2)CC1C3] | 745 | 2.98 | 1 | |

TABLE 105-continued
| Compound No. | Chemical Structure | [M + H] | Retention Time (min) | LC/MS Condition | Stereo-Chemistry |
|---|---|---|---|---|---|
| I-609 | 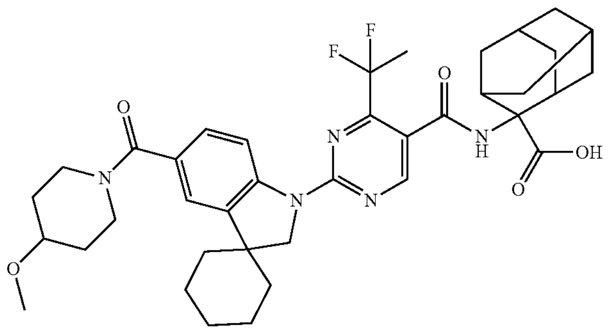 [SMILES: COC1CCN(C(=O)c2ccc3c(c2)C2(CCCCC2)CN3c2ncc(C(=O)NC3(C(=O)O)C4CC5CC(C4)CC3C5)c(C(C)(F)F)n2)CC1] | 692 | 2.82 | 1 | |
| I-610 | 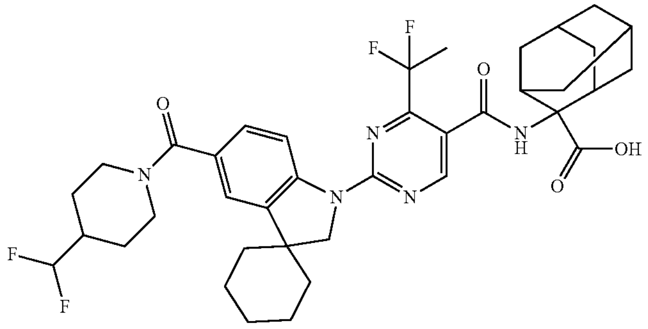 [SMILES: CC(F)(F)c1nc(N2CC3(CCCCC3)c3cc(C(=O)N4CCC(C(F)F)CC4)ccc32)ncc1C(=O)NC1(C(=O)O)C2CC3CC(C2)CC1C3] | 712 | 2.95 | 1 | |
TABLE 106
| Compound No. | Chemical Structure | [M + H] | Retention Time (min) | LC/MS Condition | Stereo-Chemistry |
|---|---|---|---|---|---|
| I-611 | 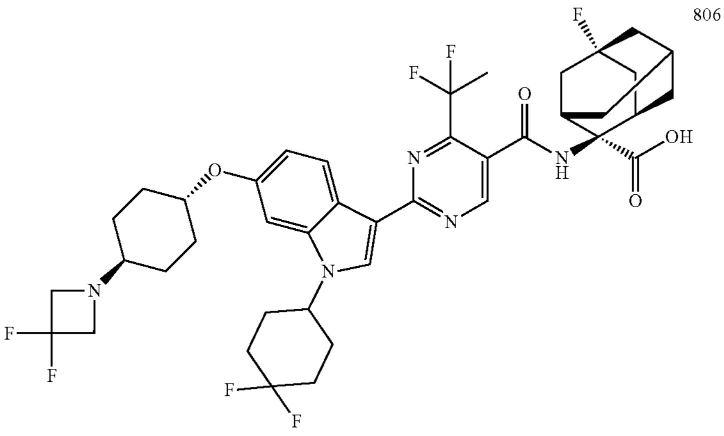 | 806 | 1.26 | 10 | |

TABLE 106-continued
| Compound No. | Chemical Structure | [M + H] | Retention Time (min) | LC/MS Condition | Stereo-Chemistry |
|---|---|---|---|---|---|
| I-612 | 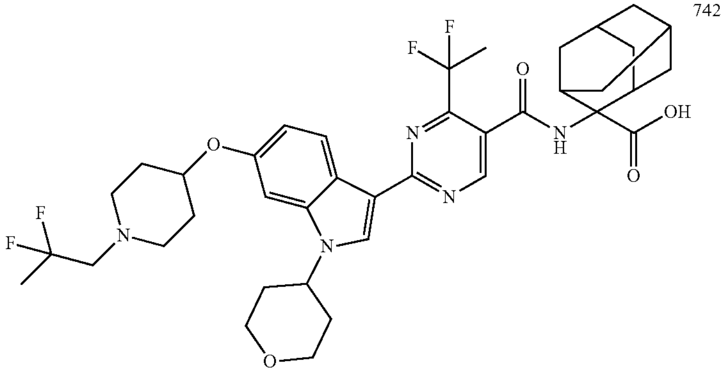 | 742 | 1.14 | 10 | |
| I-613 | 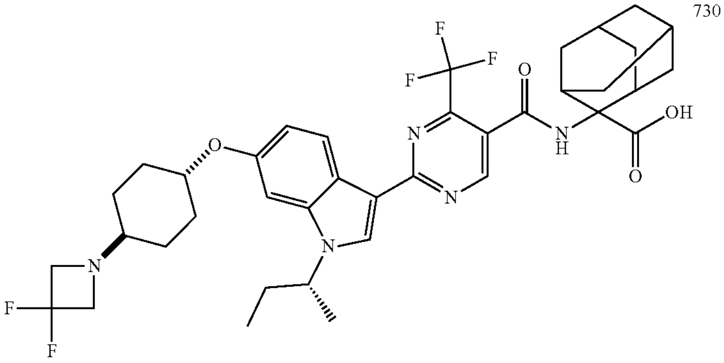 | 730 | 1.36 | 10 | |
| I-614 | 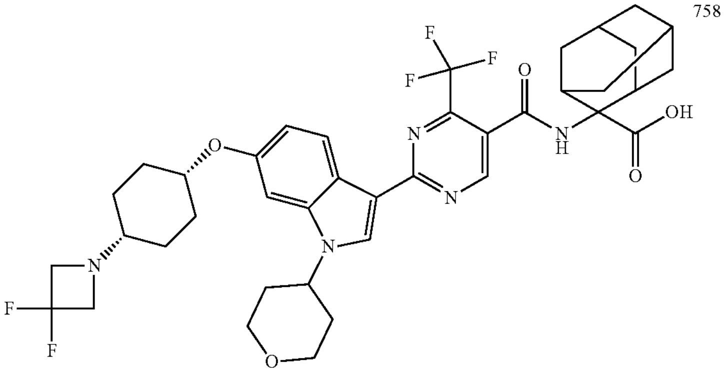 | 758 | 1.20 | 10 | |
| I-615 | 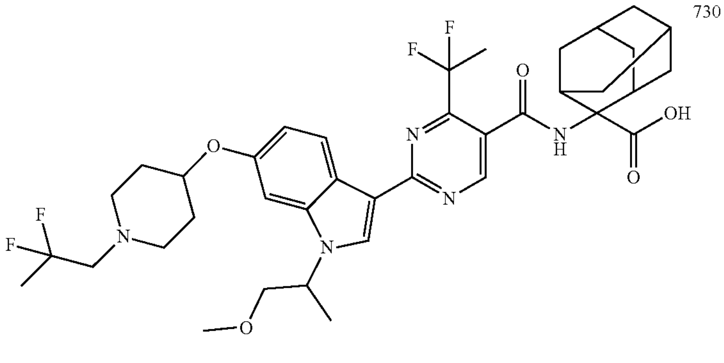 | 730 | 1.17 | 10 | |

TABLE 106-continued
| Compound No. | Chemical Structure | [M + H] | Retention Time (min) | LC/MS Condition | Stereo-Chemistry |
|---|---|---|---|---|---|
| I-616 | 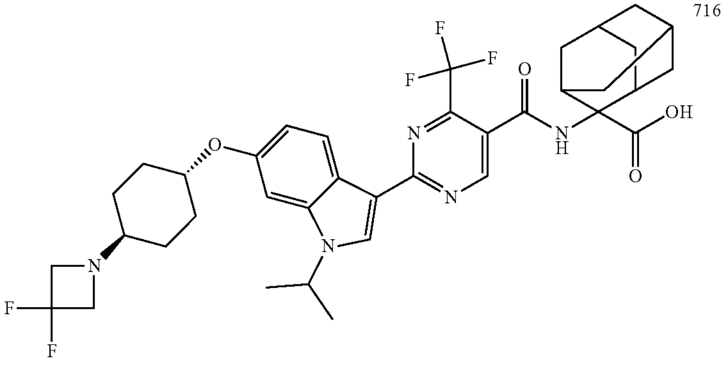 | 716 | 1.28 | 9 | |
TABLE 107
| Compound No. | Chemical Structure | [M + H] | Retention Time (min) | LC/MS Condition | Stereo-Chemistry |
|---|---|---|---|---|---|
| I-617 | 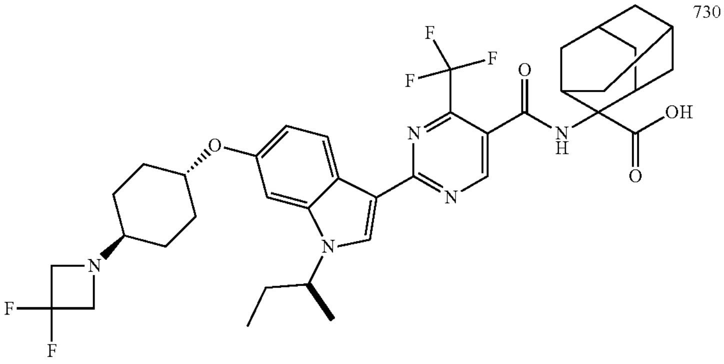 | 730 | 1.33 | 9 | |
| I-618 | 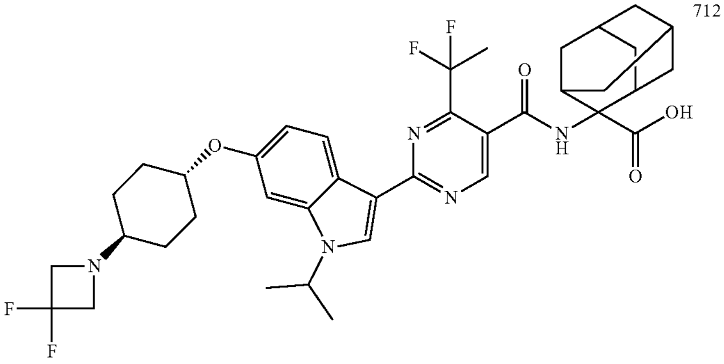 | 712 | 1.24 | 9 | |

TABLE 107-continued
| Compound No. | Chemical Structure | [M + H] | Retention Time (min) | LC/MS Condition | Stereo-Chemistry |
|---|---|---|---|---|---|
| I-619 | 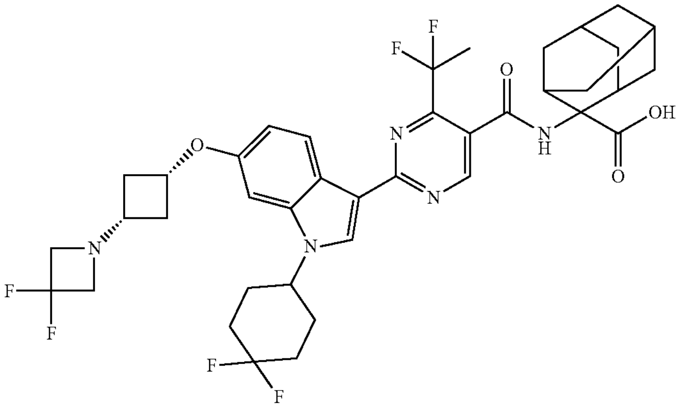 [SMILES: CC(F)(F)c1nc(-c2cn(C3CCC(F)(F)CC3)c3cc(O[C@H]4C[C@@H](N5CC(F)(F)C5)C4)ccc23)ncc1C(=O)NC1(C(=O)O)C2CC3CC(C2)CC1C3] | 760 | 1.40 | 9 | b |
| I-620 | 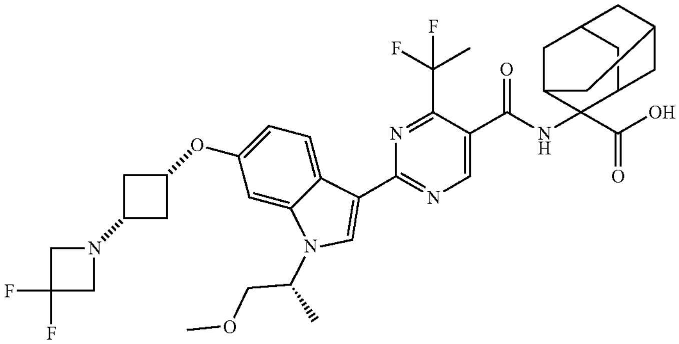 | 714 | 1.29 | 10 | d |
| I-621 | 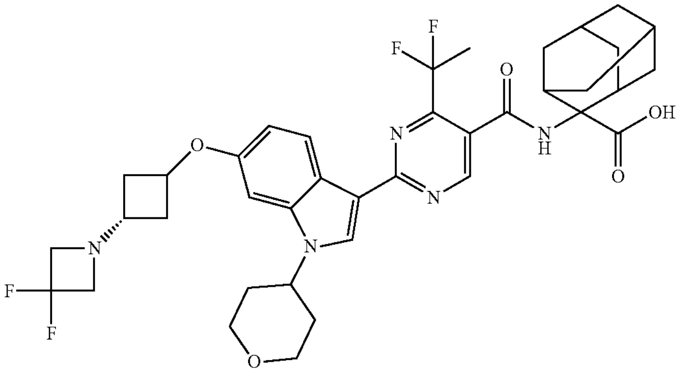 | 726 | 1.22 | 9 | b |
| I-622 | 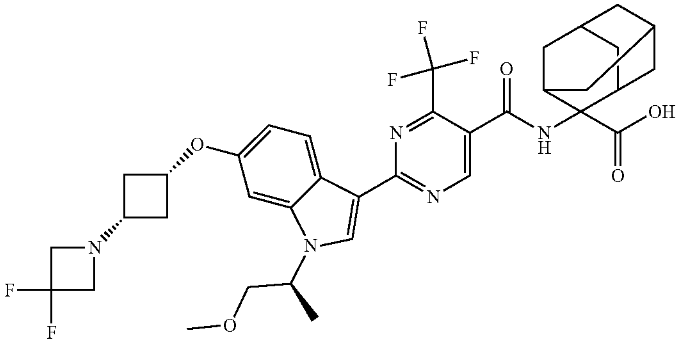 [SMILES: COC[C@H](C)n1cc(-c2ncc(C(=O)NC3(C(=O)O)C4CC5CC(C4)CC3C5)c(C(F)(F)F)n2)c2ccc(O[C@H]3C[C@@H](N4CC(F)(F)C4)C3)cc21] | 746 | 1.24 | 10 | |

Biological Test Examples for the compounds of the invention are described below.

A compound of the formula (I) of the present invention has an inhibitory effect on cytopathic effect caused by RS virus and inhibits cytopathic effect in humans.

Specifically, in the evaluation method described below, the IC50 value is preferably 5000 nM or less, more preferably 1000 nM or less, and even more preferably 100 nM or less.

Test Example 1: In Vitro CPE (CytoPathic Effect) Inhibition Effect Evaluation Test The test sample is diluted in advance to an appropriate concentration with DMSO, and 3-fold series of serial dilutions were prepared on a 384-well plate (0.32 μL/well). HEp-2 cells (CCL-23; ATCC) adjusted at appropriate number ($2.4\times10^5$ cells/mL) in 2% FBS E-MEM (prepared by adding kanamycin and FBS to Eagle's Minimum Essential Medium; Invitrogen) were added at 12.5 μL/well to the 384-well plate previously aliquoted with the test samples. The RSV A2 strain was diluted to an appropriate concentration in a culture medium and added to the 384-well plate containing the test sample at 12.5 μL/well. The culture medium was added additionally to the 384-well plate, and the test was started with 50 μL/well. Control wells were prepared with only virus-free culture medium. The plate was incubated in a 5% $CO_2$ incubator at 37° C. for 4 days, and the plate was then placed at room temperature for 30 minutes. CellTiter-Glo (registered trademark) 2.0 assay (Promega) was added at 15 μL/well, mixed for 30 seconds, and the plate was placed for approximately 1 hour. The luminescent signal was then measured by EnVision (PerkinElmer). The inhibitory effect of the test agents on RSV-induced CPE was calculated as 0% and 100% inhibition rate for each sample concentration based on the level of remaining viable cells by CellTiter-Glo (registered trademark) 2.0, with the EC50 value for each compound calculated by nonlinear regression as the concentration that inhibits RSV-induced CPE by 50%. In the case of evaluation against RSV type B, RSV B (Wash/18537 strain) was infected in the same manner as the type A, cultured for 5 days, and quantitated in the same manner as for the A2 strain.

Result

The compounds of the invention were tested essentially as described above. The inhibitory effect of the compounds against RSV type A is shown below. EC50 values less than 10 nM, 10 nM or more and less than 100 nM, and 100 nM or more and 5000 nM or less are indicated as "A", "B" and "C", respectively.

Compound No. I-23: 0.96 nM
Compound No. I-33: 7.5 nM
Compound No. I-82: 0.27 nM
Compound No. I-148: 1.5 nM
Compound No. I-159: 0.88 nM
Compound No. I-162: 0.88 nM
Compound No. I-165: 0.37 nM
Compound No. I-182: 0.39 nM
Compound No. I-228: 1.3 nM
Compound No. I-268: 1.4 nM
Compound No. I-269: 1.3 nM
Compound No. I-270: 37 nM
Compound No. I-486: 3 nM
Compound No. I-570: 0.70 nM
Compound No. I-591: 0.61 nM
Compound No. I-594: 0.38 nM

TABLE 108

| Compound No. | EC50 (nM) |
|---|---|
| I-1 | B |
| I-2 | B |
| I-3 | B |
| I-4 | B |
| I-5 | B |
| I-6 | B |
| I-7 | B |
| I-8 | B |
| I-9 | B |
| I-10 | C |
| I-11 | A |
| I-12 | A |
| I-13 | A |
| I-14 | C |
| I-15 | B |
| I-16 | A |
| I-17 | A |
| I-18 | A |
| I-19 | A |
| I-20 | B |
| I-21 | A |
| I-22 | A |
| I-24 | B |
| I-25 | B |
| I-26 | B |
| I-27 | B |
| I-28 | B |
| I-29 | A |
| I-30 | B |
| I-31 | A |
| I-32 | B |
| I-34 | A |
| I-35 | B |
| I-36 | A |
| I-37 | A |
| I-38 | B |
| I-39 | B |
| I-40 | A |
| I-41 | A |
| I-42 | A |
| I-43 | B |
| I-44 | B |
| I-45 | A |
| I-46 | B |
| I-47 | B |
| I-48 | A |
| I-49 | B |
| I-50 | B |
| I-51 | B |
| I-52 | B |
| I-53 | B |
| I-54 | A |
| I-55 | A |
| I-56 | A |
| I-57 | A |
| I-58 | B |
| I-59 | B |
| I-60 | B |
| I-61 | A |
| I-62 | A |
| I-63 | A |
| I-64 | C |
| I-65 | B |
| I-66 | B |
| I-67 | B |
| I-68 | B |
| I-69 | C |
| I-70 | B |
| I-71 | A |
| I-72 | A |
| I-73 | B |
| I-74 | A |
| I-75 | B |
| I-76 | B |
| I-77 | A |
| I-78 | A |
| I-79 | B |
| I-80 | A |

TABLE 108-continued

| Compound No. | EC50 (nM) |
|---|---|
| I-81 | A |
| I-83 | A |
| I-84 | B |
| I-85 | B |
| I-86 | A |
| I-87 | A |
| I-88 | A |
| I-89 | C |
| I-90 | C |
| I-91 | A |
| I-92 | A |
| I-93 | A |
| I-94 | A |
| I-95 | A |
| I-96 | A |
| I-97 | B |
| I-98 | A |
| I-99 | A |
| I-100 | A |
| I-101 | A |
| I-102 | A |
| I-103 | A |
| I-104 | A |
| I-105 | A |
| I-106 | A |
| I-107 | A |
| I-108 | A |
| I-109 | A |
| I-110 | A |
| I-111 | A |
| I-112 | B |
| I-113 | A |
| I-114 | A |
| I-115 | A |
| I-116 | A |
| I-117 | B |
| I-118 | A |
| I-119 | A |
| I-120 | A |
| I-121 | A |
| I-122 | A |
| I-123 | A |
| I-124 | B |
| I-125 | B |
| I-126 | A |
| I-127 | A |
| I-128 | A |
| I-129 | A |
| I-130 | A |
| I-131 | A |
| I-132 | B |
| I-133 | A |
| I-134 | A |
| I-135 | A |
| I-136 | A |
| I-137 | A |
| I-138 | A |
| I-139 | A |
| I-140 | B |
| I-141 | A |
| I-142 | A |
| I-143 | A |
| I-144 | C |
| I-145 | B |
| I-146 | A |
| I-147 | A |
| I-149 | A |
| I-150 | A |
| I-151 | A |
| I-152 | A |
| I-153 | A |
| I-154 | A |
| I-155 | A |
| I-156 | C |
| I-157 | A |
| I-158 | A |
| I-160 | B |
| I-161 | A |

TABLE 108-continued

| Compound No. | EC50 (nM) |
|---|---|
| I-163 | A |
| I-164 | A |
| I-166 | A |
| I-167 | C |
| I-168 | A |
| I-169 | A |
| I-170 | A |
| I-171 | B |
| I-172 | C |
| I-173 | B |
| I-174 | A |
| I-175 | A |
| I-176 | A |
| I-177 | A |
| I-178 | B |
| I-179 | A |
| I-180 | A |
| I-181 | B |
| I-183 | A |
| I-184 | A |
| I-185 | A |
| I-186 | A |
| I-187 | B |
| I-188 | A |
| I-189 | A |
| I-190 | A |
| I-191 | A |
| I-192 | A |
| I-193 | A |
| I-194 | A |
| I-195 | A |
| I-196 | A |
| I-197 | A |
| I-198 | A |
| I-199 | A |
| I-200 | A |
| I-201 | B |
| I-202 | B |
| I-203 | A |
| I-204 | A |
| I-205 | A |
| I-206 | A |
| I-207 | B |
| I-208 | A |
| I-209 | A |
| I-210 | A |
| I-211 | A |
| I-212 | C |

TABLE 109

| Compound No. | EC50 (nM) |
|---|---|
| I-213 | A |
| I-214 | A |
| I-215 | B |
| I-216 | B |
| I-217 | A |
| I-218 | A |
| I-219 | A |
| I-220 | A |
| I-221 | A |
| I-222 | A |
| I-223 | A |
| I-224 | A |
| I-225 | B |
| I-226 | A |
| I-227 | A |
| I-229 | A |
| I-230 | A |
| I-231 | A |
| I-232 | A |
| I-233 | B |
| I-234 | A |
| I-235 | A |

TABLE 109-continued

| Compound No. | EC50 (nM) |
|---|---|
| I-236 | A |
| I-237 | A |
| I-238 | A |
| I-239 | A |
| I-240 | A |
| I-241 | A |
| I-242 | A |
| I-243 | A |
| I-244 | A |
| I-245 | A |
| I-246 | A |
| I-247 | A |
| I-248 | A |
| I-249 | A |
| I-250 | A |
| I-251 | A |
| I-252 | A |
| I-253 | A |
| I-254 | B |
| I-255 | A |
| I-256 | A |
| I-257 | A |
| I-258 | A |
| I-259 | A |
| I-260 | B |
| I-261 | B |
| I-262 | A |
| I-263 | A |
| I-264 | A |
| I-265 | A |
| I-266 | A |
| I-267 | A |
| I-271 | A |
| I-272 | A |
| I-273 | A |
| I-274 | A |
| I-275 | A |
| I-276 | A |
| I-277 | A |
| I-278 | A |
| I-279 | A |
| I-280 | A |
| I-281 | A |
| I-282 | A |
| I-283 | A |
| I-284 | A |
| I-285 | A |
| I-286 | B |
| I-287 | A |
| I-288 | B |
| I-289 | A |
| I-290 | A |
| I-291 | A |
| I-292 | A |
| I-293 | B |
| I-294 | A |
| I-295 | B |
| I-296 | A |
| I-297 | A |
| I-298 | A |
| I-299 | B |
| I-300 | A |
| I-301 | A |
| I-302 | A |
| I-303 | A |
| I-304 | A |
| I-305 | A |
| I-306 | A |
| I-307 | A |
| I-308 | A |
| I-309 | A |
| I-310 | A |
| I-311 | A |
| I-312 | A |
| I-313 | A |
| I-314 | A |
| I-315 | A |
| I-316 | A |

TABLE 109-continued

| Compound No. | EC50 (nM) |
|---|---|
| I-317 | A |
| I-318 | A |
| I-319 | A |
| I-320 | A |
| I-321 | A |
| I-322 | A |
| I-323 | A |
| I-324 | A |
| I-325 | A |
| I-326 | A |
| I-327 | A |
| I-328 | A |
| I-329 | A |
| I-330 | A |
| I-331 | A |
| I-332 | A |
| I-333 | A |
| I-334 | A |
| I-335 | A |
| I-336 | A |
| I-337 | A |
| I-338 | A |
| I-339 | A |
| I-340 | A |
| I-341 | A |
| I-342 | C |
| I-343 | B |
| I-344 | B |
| I-345 | A |
| I-346 | A |
| I-347 | A |
| I-348 | A |
| I-349 | A |
| I-350 | A |
| I-351 | B |
| I-352 | B |
| I-353 | A |
| I-354 | A |
| I-355 | A |
| I-356 | A |
| I-357 | A |
| I-358 | A |
| I-359 | A |
| I-360 | A |
| I-361 | A |
| I-362 | A |
| I-363 | A |
| I-364 | A |
| I-365 | A |
| I-366 | A |
| I-367 | A |
| I-368 | A |
| I-369 | A |
| I-370 | A |
| I-371 | A |
| I-372 | A |
| I-373 | A |
| I-374 | A |
| I-375 | A |
| I-376 | A |
| I-377 | A |
| I-378 | A |
| I-379 | A |
| I-380 | A |
| I-381 | A |
| I-382 | A |
| I-383 | A |
| I-384 | A |
| I-385 | A |
| I-386 | A |
| I-387 | A |
| I-388 | A |
| I-389 | A |
| I-390 | A |
| I-391 | A |
| I-392 | A |
| I-393 | A |
| I-394 | A |

TABLE 109-continued

| Compound No. | EC50 (nM) |
|---|---|
| I-395 | A |
| I-396 | A |
| I-397 | A |
| I-398 | A |
| I-399 | A |
| I-400 | A |
| I-401 | A |
| I-402 | A |
| I-403 | A |
| I-404 | A |
| I-405 | A |
| I-406 | A |
| I-407 | A |
| I-408 | A |
| I-409 | A |
| I-410 | A |
| I-411 | A |
| I-412 | A |
| I-413 | A |
| I-414 | A |
| I-415 | A |
| I-416 | A |
| I-417 | A |
| I-418 | A |
| I-419 | A |
| I-420 | A |

TABLE 110

| Compound No. | EC50 (nM) |
|---|---|
| I-421 | A |
| I-422 | A |
| I-423 | A |
| I-424 | A |
| I-425 | A |
| I-426 | A |
| I-427 | A |
| I-428 | A |
| I-429 | A |
| I-430 | A |
| I-431 | A |
| I-432 | A |
| I-433 | A |
| I-434 | A |
| I-435 | A |
| I-436 | A |
| I-437 | A |
| I-438 | A |
| I-439 | A |
| I-440 | A |
| I-441 | B |
| I-442 | A |
| I-443 | A |
| I-444 | A |
| I-445 | A |
| I-446 | A |
| I-447 | A |
| I-448 | A |
| I-449 | A |
| I-450 | A |
| I-451 | A |
| I-452 | A |
| I-453 | A |
| I-454 | B |
| I-455 | B |
| I-456 | B |
| I-457 | B |
| I-458 | A |
| I-459 | A |
| I-460 | A |
| I-461 | B |
| I-462 | A |
| I-463 | A |
| I-464 | A |

TABLE 110-continued

| Compound No. | EC50 (nM) |
|---|---|
| I-465 | A |
| I-466 | A |
| I-467 | A |
| I-468 | A |
| I-469 | A |
| I-470 | A |
| I-471 | A |
| I-472 | A |
| I-473 | A |
| I-474 | A |
| I-475 | A |
| I-476 | B |
| I-477 | B |
| I-478 | A |
| I-479 | A |
| I-480 | A |
| I-481 | A |
| I-482 | A |
| I-483 | A |
| I-484 | A |
| I-485 | A |
| I-487 | A |
| I-488 | A |
| I-489 | A |
| I-490 | A |
| I-491 | A |
| I-492 | A |
| I-493 | A |
| I-494 | A |
| I-495 | A |
| I-496 | A |
| I-497 | A |
| I-498 | A |
| I-499 | A |
| I-500 | A |
| I-501 | A |
| I-502 | A |
| I-503 | A |
| I-504 | A |
| I-505 | A |
| I-506 | A |
| I-507 | A |
| I-508 | A |
| I-509 | A |
| I-510 | A |
| I-511 | A |
| I-512 | A |
| I-513 | A |
| I-514 | A |
| I-515 | A |
| I-516 | A |
| I-517 | A |
| I-518 | A |
| I-519 | A |
| I-520 | A |
| I-521 | A |
| I-522 | A |
| I-523 | A |
| I-524 | A |
| I-525 | A |
| I-526 | A |
| I-527 | A |
| I-528 | A |
| I-529 | A |
| I-530 | A |
| I-531 | A |
| I-532 | A |
| I-533 | A |
| I-534 | A |
| I-535 | A |
| I-536 | A |
| I-537 | A |
| I-538 | A |
| I-539 | A |
| I-540 | A |
| I-541 | A |
| I-542 | A |
| I-543 | A |

TABLE 110-continued

| Compound No. | EC50 (nM) |
|---|---|
| I-544 | A |
| I-545 | A |
| I-546 | A |
| I-547 | A |
| I-548 | A |
| I-549 | A |
| I-550 | A |
| I-551 | A |
| I-552 | A |
| I-553 | A |
| I-554 | A |
| I-555 | A |
| I-556 | A |
| I-557 | A |
| I-558 | A |
| I-559 | A |
| I-560 | A |
| I-561 | A |
| I-562 | A |
| I-563 | A |
| I-564 | A |
| I-565 | A |
| I-566 | A |
| I-567 | A |
| I-568 | A |
| I-569 | A |
| I-571 | A |
| I-572 | A |
| I-573 | A |
| I-574 | A |
| I-575 | A |
| I-576 | A |
| I-577 | A |
| I-578 | A |
| I-579 | A |
| I-580 | A |
| I-581 | A |
| I-582 | A |
| I-583 | A |
| I-584 | A |
| I-585 | A |
| I-586 | A |
| I-587 | A |
| I-588 | A |
| I-589 | A |
| I-590 | A |
| I-592 | A |
| I-593 | A |
| I-595 | A |
| I-596 | A |
| I-597 | A |
| I-598 | A |
| I-599 | A |
| I-600 | A |
| I-601 | A |
| I-602 | A |
| I-603 | A |
| I-604 | A |
| I-605 | A |
| I-606 | A |
| I-607 | A |
| I-608 | A |
| I-609 | A |
| I-610 | A |
| I-611 | A |
| I-612 | A |
| I-613 | A |
| I-614 | A |
| I-615 | A |
| I-616 | A |
| I-617 | A |
| I-618 | A |
| I-619 | A |
| I-620 | A |
| I-621 | A |
| I-622 | A |

The compounds of the invention were tested essentially as described above. The inhibitory effect of the compounds against RSV type B is shown below. EC50 values less than 10 nM, 10 nM or more and less than 100 nM, and 100 nM or more and 5000 nM or less are indicated as “A”, “B” and “C”, respectively.

Compound No. I-23: 16 nM
Compound No. I-33: 110 nM
Compound No. I-82: 0.34 nM
Compound No. I-148: 2.8 nM
Compound No. I-159: 3 nM
Compound No. I-162: 3.3 nM
Compound No. I-165: 0.62 nM
Compound No. I-182: 2.1 nM
Compound No. I-228: 36 nM
Compound No. I-268: 4.3 nM
Compound No. I-486: 28 nM
Compound No. I-570: 2.1 nM
Compound No. I-591: 2.2 nM
Compound No. I-594: 4.2 nM

TABLE 111

| Compound No. | EC50 (nM) |
|---|---|
| I-1 | C |
| I-2 | C |
| I-3 | B |
| I-4 | C |
| I-5 | C |
| I-7 | C |
| I-8 | B |
| I-9 | C |
| I-16 | B |
| I-21 | B |
| I-31 | B |
| I-36 | B |
| I-45 | A |
| I-56 | B |
| I-72 | C |
| I-80 | A |
| I-81 | A |
| I-83 | A |
| I-86 | A |
| I-87 | B |
| I-88 | B |
| I-91 | B |
| I-92 | A |
| I-93 | B |
| I-109 | B |
| I-135 | B |
| I-146 | A |
| I-147 | A |
| I-151 | A |
| I-152 | A |
| I-155 | B |
| I-158 | A |
| I-160 | C |
| I-175 | A |
| I-176 | A |
| I-177 | A |
| I-183 | B |
| I-184 | A |
| I-189 | A |
| I-190 | A |
| I-191 | A |
| I-193 | A |
| I-199 | B |
| I-203 | A |
| I-204 | B |
| I-214 | A |
| I-218 | A |
| I-221 | C |
| I-227 | A |
| I-234 | B |
| I-237 | A |
| I-239 | A |

TABLE 111-continued

| Compound No. | EC50 (nM) |
|---|---|
| I-245 | A |
| I-249 | B |
| I-250 | A |
| I-256 | A |
| I-257 | A |
| I-272 | B |
| I-275 | A |
| I-276 | A |
| I-301 | A |
| I-353 | A |
| I-354 | A |
| I-370 | B |
| I-379 | A |
| I-380 | A |
| I-382 | B |
| I-384 | A |
| I-393 | B |
| I-396 | A |
| I-397 | A |
| I-399 | B |
| I-400 | B |
| I-401 | B |
| I-402 | A |
| I-406 | B |
| I-407 | C |
| I-412 | B |
| I-413 | B |
| I-415 | A |
| I-418 | A |
| I-421 | A |
| I-422 | A |
| I-423 | A |
| I-429 | B |
| I-430 | A |
| I-431 | A |
| I-434 | A |
| I-437 | A |
| I-438 | A |
| I-440 | B |
| I-443 | A |
| I-444 | A |
| I-445 | A |
| I-447 | A |
| I-451 | B |
| I-452 | A |
| I-453 | A |
| I-463 | C |
| I-464 | C |
| I-465 | A |
| I-466 | B |
| I-467 | A |
| I-472 | A |
| I-473 | C |
| I-474 | B |
| I-475 | B |
| I-476 | C |
| I-477 | C |
| I-478 | A |
| I-479 | A |
| I-480 | B |
| I-481 | A |
| I-482 | B |
| I-483 | C |
| I-484 | B |
| I-485 | B |
| I-487 | B |
| I-488 | A |
| I-489 | A |
| I-490 | A |
| I-491 | B |
| I-492 | B |
| I-493 | A |
| I-494 | A |
| I-495 | A |
| I-496 | A |
| I-497 | A |
| I-498 | A |
| I-499 | A |

TABLE 111-continued

| Compound No. | EC50 (nM) |
|---|---|
| I-500 | A |
| I-501 | A |
| I-502 | B |
| I-503 | A |
| I-504 | A |
| I-505 | A |
| I-506 | A |
| I-507 | A |
| I-508 | A |
| I-509 | A |
| I-510 | A |
| I-511 | B |
| I-512 | B |
| I-513 | A |
| I-514 | B |
| I-515 | B |
| I-516 | B |
| I-517 | B |
| I-518 | A |
| I-519 | A |
| I-520 | A |
| I-521 | B |
| I-522 | A |
| I-523 | A |
| I-524 | C |
| I-525 | A |
| I-526 | A |
| I-527 | A |
| I-528 | C |
| I-529 | A |
| I-530 | A |
| I-531 | A |
| I-532 | B |
| I-533 | A |
| I-534 | A |
| I-535 | B |
| I-536 | B |
| I-537 | B |
| I-538 | A |
| I-539 | B |
| I-540 | B |
| I-541 | A |
| I-542 | A |
| I-543 | A |
| I-544 | B |
| I-545 | A |
| I-546 | A |
| I-547 | A |
| I-548 | A |
| I-549 | A |
| I-550 | B |
| I-551 | A |
| I-552 | A |
| I-553 | B |
| I-554 | A |
| I-555 | B |
| I-556 | B |
| I-557 | A |
| I-558 | A |
| I-559 | A |
| I-560 | A |
| I-561 | A |
| I-562 | A |
| I-563 | A |
| I-564 | A |
| I-565 | A |
| I-566 | A |
| I-567 | A |
| I-568 | A |
| I-569 | A |
| I-571 | A |
| I-572 | A |
| I-573 | A |
| I-574 | A |
| I-575 | A |
| I-576 | A |
| I-577 | A |
| I-578 | A |

TABLE 111-continued

| Compound No. | EC50 (nM) |
|---|---|
| I-579 | A |
| I-580 | A |
| I-581 | A |
| I-582 | A |
| I-583 | A |
| I-584 | A |
| I-585 | A |
| I-586 | A |
| I-587 | A |
| I-588 | A |
| I-589 | A |
| I-590 | A |
| I-592 | A |
| I-593 | A |
| I-595 | A |
| I-596 | A |
| I-597 | A |
| I-598 | A |
| I-599 | A |
| I-600 | A |
| I-601 | A |
| I-602 | A |
| I-603 | A |
| I-604 | A |
| I-605 | A |
| I-606 | A |
| I-607 | A |
| I-608 | A |
| I-609 | A |
| I-610 | A |
| I-611 | A |
| I-612 | A |
| I-613 | A |
| I-614 | A |
| I-615 | A |
| I-616 | A |
| I-617 | A |
| I-618 | A |
| I-619 | A |
| I-620 | A |
| I-621 | A |
| I-622 | A |

Test Example 2: In Vivo Mouse Drug Efficacy Test

Although mice are semipermissive for human RSV replication, they are frequently used as a model in preclinical screening tests for RSV therapeutics. In vivo drug efficacy is evaluated using Balb/c mice, which is good for RSV A2 strain propagation. BALB/c mice (female, 6 week old) are inoculated intranasally with RSV A2 strain at $5\times10^6$ PFU/mouse. After infection, test sample is administered at a fixed dose twice daily (8 h/16 h interval), and a lung is removed on day 4 or 5. The lung is homogenized in PBS, rapidly frozen and stored at −80° C. Viral titers in supernatants of lung homogenates are quantified by tissue culture infectious dose 50 (TCID50) method using immunoblotting.

Test Example 3: CYP Inhibition Test

Using commercially available pooled human liver microsomes, and as marker reactions of human main five CYP enzyme isoforms (CYP1A2, 2C9, 2C19, 2D6, 3A4), 7-ethoxyresorufin O-deethylation (CYP1A2), tolbutamide methyl-hydroxylation (CYP2C9), mephenytoin 4'-hydroxylation (CYP2C19), dextromethorphan O-demethylation (CYP2D6), and terfenadine hydroxylation (CYP3A4), an inhibitory degree of each metabolite production amount by the compound of the present invention is assessed.

The reaction conditions are as follows: substrate, 0.5 μmol/L ethoxyresorufin (CYP1A2), 100 μmol/L tolbutamide (CYP2C9), 50 μmol/L S-mephenytoin (CYP2C19), 5 μmol/L dextromethorphan (CYP2D6), 1 μmol/L terfenadine (CYP3A4); reaction time, 15 minutes; reaction temperature, 37° C.; enzyme, pooled human liver microsomes 0.2 mg protein/mL; concentrations of the compound of the present invention, 1, 5, 10, 20 μmol/L (four points).

Each five kinds of substrates, human liver microsomes, or the compound of the present invention in 50 mmol/L Hepes buffer are added to a 96-well plate at the composition as described above as a reaction solution, NADPH, as a cofactor is added to initiate metabolism reactions. After the incubation at 37° C. for 15 minutes, methanol/acetonitrile=1/1 (V/V) solution is added to stop the reaction. After the centrifugation at 3000 rpm for 15 minutes, resorufin (CYP1A2 metabolite) in the supernatant is quantified by a fluorescent multilabel counter or LC/MS/MS, and hydroxy tolbutamide (CYP2C9 metabolite), 4'-hydroxy mephenytoin (CYP2C19 metabolite), dextrorphan (CYP2D6 metabolite), and terfenadine alcohol metabolite (CYP3A4 metabolite) are quantified by LC/MS/MS.

The dilution concentration and dilution solvent are changed as necessary.

Addition of only DMSO being a solvent dissolving a compound of the present invention to a reaction system is adopted as a control (100%), remaining activity (%) is calculated at each concentration of a compound of the present invention added as the solution and $IC_{50}$ is calculated by reverse presumption by a logistic model using a concentration and an inhibition rate.

Test Example 4: CYP3A4 (MDZ) MBI Test

CYP3A4 (MDZ) MBI test is a test of investigating mechanism based inhibition (MBI) potential on CYP3A4 inhibition of a compound. CYP3A4 inhibition is evaluated using 1-hydroxylation reaction of midazolam (MDZ) by pooled human liver microsomes as a marker reaction.

The reaction conditions are as follows: substrate, 10 μmol/L MDZ; pre-reaction time, 0 or 30 minutes; substrate reaction time, 2 minutes; reaction temperature, 37° C.; protein content of pooled human liver microsomes, at pre-reaction time 0.5 mg/mL, at reaction time 0.05 mg/mL (at 10-fold dilution); concentrations of the compound of the present invention, at pre-reaction time 1, 5, 10, 20 μmol/L or 0.83, 5, 10, 20 μmol/L (four points).

Pooled human liver microsomes and a compound of the present invention solution in a K-Pi buffer (pH 7.4) as a pre-reaction solution are added to a 96-well plate at the composition of the pre-reaction. A part of pre-reaction solution is transferred to another 96-well plate, and diluted 10-fold by K-Pi buffer containing a substrate. NADPH as a co-factor is added to initiate the marker reaction (preincubation 0 min). After a predetermined time of the reaction, methanol/acetonitrile=1/1 (v/v) solution is added to stop the reaction. On the other hand, NADPH is also added to a remaining pre-reaction solution to initiate a pre-reaction (preincubation 30 min). After a predetermined time of the pre-reaction, a part is transferred to another 96-well plate, and diluted 10-fold by a substrate in a K-Pi buffer containing a substrate to initiate the marker reaction. After a predetermined time of the reaction, methanol/acetonitrile=1/1 (v/v) solution is added to stop the reaction. After centrifuged at 3000 rpm for 15 minutes, 1-hydroxymidazolam in the supernatant is quantified by LC/MS/MS.

The concentration and solvent for dilution is changed as necessary.

The sample adding DMSO to a reaction system instead of compound of the present invention solution is adopted as a control (100%), because DMSO is used as a solvent to dissolve a compound of the present invention. Remaining activity (%) is calculated at each concentration of the compound of the present invention compared to a control, and IC value is calculated by reverse-presumption by a logistic model using a concentration and an inhibition rate. IC at Preincubation 0 min/IC at Preincubation 30 min is defined as a value of Shifted IC, and a case that Shifted IC is 1.5 or more is regarded as Positive, and a case that Shifted IC is 1.0 or less is regarded as Negative.

Test Example 5: BA Test

Materials and methods for experiments to evaluate oral absorption (1) Animal: mice or rats are used.

(2) Breeding conditions: mice or rats are allowed to freely take solid food and sterilized tap water.

(3) Dose and grouping setting: oral administration and intravenous administration are performed with a predetermined dosage. Grouping is set as belows (dosage changed per compound):

Oral administration: 2 to 60 μmol/kg or 1 to 30 mg/kg (n=2 to 3) Intravenous administration: 1 to 30 μmol/kg or 0.5 to 10 mg/kg (n=2 or 3)

(4) Preparation of dosing formulation: oral administration is performed in the form of a suspension or a solution. Intravenous administration is performed after solubilization.

(5) Routes of administration: oral administration into the stomach is performed using feeding tube. Intravenous administration into tail vein is performed using a syringe equipped with injection needle.

(6) Evaluation items: blood is collected over time, and the concentration of the compound of the invention in plasma is measured by LC/MS/MS.

(7) Statistical analysis: regarding the plasma concentration profile of the compound of the invention, the area under the concentration time curve (AUC) is calculated by the moment analysis method, and the bioavailability (BA) of the compound of the invention is calculated from the dose ratio and the AUC ratio of the oral administration group and the intravenous administration group.

The dilution concentration and dilution solvent should be changed as necessary.

Test Example 6: Clearance Evaluation Test

Material and Method (1) Animal: SD rats are used.

(2) Breeding conditions: rats are allowed to freely take solid food and sterilized tap water.

(3) Dose and grouping setting: intravenous administration is performed with a predetermined dosage. Grouping is set as follows: Intravenous administration: 1 μmol/kg (n=2)

(4) Preparation of dosing formulation: The test sample is solubilized using a solvent of dimethyl sulfoxide/propylene glycol 1/1, and administered.

(5) Route of administration: Administration into tail vein is performed using a syringe equipped with injection needle.

(6) Evaluation Items: Blood is collected over time, and the concentration of the compound of the invention in plasma is measured by LC/MS/MS.

(7) Statistical analysis: regarding plasma concentration profile of the compound, total body clearance (CLtot) is calculated by the moment analysis method. The dilution concentration and dilution solvent should be changed as necessary.

Test Example 7: Metabolic Stability Test

Using pooled human liver microsomes and pooled rat liver microsomes, a compound of the invention is reacted for a constant time, and the remaining rate is calculated by comparing the reacted sample and the unreacted sample, thereby, a degree of metabolism in liver is assessed.

A reaction is performed (oxidative reaction) at 37° C. for 0 or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human or rat liver microsomes. After the reaction, 50 μL of the reaction solution is added to 100 μL of a methanol/acetonitrile=1/1 (v/v) solution, mixed and centrifuged at 3000 rpm for 15 minutes. The compound of the invention in the centrifuged supernatant is quantified by LC/MS/MS or solid-phase extraction (SPE)/MS. The amount of the compound of the invention remaining after the reaction is calculated with the amount of the compound at 0 minutes of the reaction defined as 100%. Hydrolysis reaction is performed in the absence of NADPH, and glucuronidation reaction is performed in the presence of 5 mmol/L UDP-glucuronic acid in place of NADPH, followed by similar procedures. Dilution concentrations and dilution solvents are changed if necessary.

Test Example 8: Metabolic Stability Test (Hepatocytes)

Using human, rat, dog or monkey hepatocytes, a compound of the invention is reacted for a constant time, and the remaining rate is calculated by comparing the reacted sample and the unreacted sample, thereby, a degree of metabolism in liver is assessed. In order to take into account the effect of serum protein binding on metabolism, up to 10% of serum of the species corresponding to each hepatocyte may be added to the medium.

Human, rat, dog or monkey hepatocytes are suspended in William's medium E at $1\times10^6$ cells/mL and reacted with the compound of the invention at 37° C. for 0, 1 or 2 hours. If the serum is added, up to 10% of the serum is added to William's medium E in advance, and then the hepatocytes are suspended. After the reaction, 120 μL of methanol/acetonitrile=1/1 (v/v) solution to 30 μL of the reaction solution, mixed and centrifuged at 3000 rpm for 15 minutes. The compound of the invention in the centrifuged supernatant is quantified by LC/MS/MS or solid-phase extraction (SPE)/MS. The amount of the compound of the invention remaining after the reaction is calculated with the amount of the compound at 0 minutes of the reaction defined as 100%. Dilution concentrations and dilution solvents are changed if necessary.

INDUSTRIAL APPLICABILITY

The compound of the invention has an inhibitory effect on RSV and is useful for the treatment and/or prevention of RSV infection and related diseases caused by the infection.

The invention claimed is:

1. A compound of the formula (I):

(I)

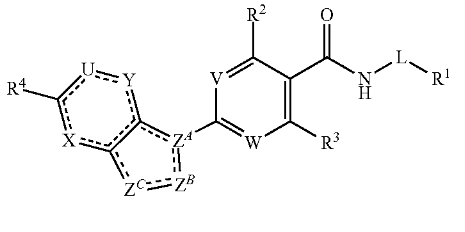

wherein:

the dashed line indicates the presence or absence of a bond;

$R^1$ is carboxy, cyano, substituted or unsubstituted aromatic heterocyclyl, —C(═O)—$NR^{1B}R^{1C}$ or —CH═CHC(═O)—OH;

$R^{1B}$ and $R^{1C}$ are each independently a hydrogen atom, substituted or unsubstituted alkyl, substituted or unsubstituted aminosulfonyl or substituted or unsubstituted non-aromatic heterocyclylsulfonyl;

L is substituted or unsubstituted non-aromatic carbocyclyldiyl, substituted or unsubstituted non-aromatic heterocyclyldiyl or substituted or unsubstituted alkylene;

$R^2$ is substituted or unsubstituted alkyl;

$R^3$ is a hydrogen atom, substituted or unsubstituted alkyl, substituted or unsubstituted alkyloxy, substituted or unsubstituted amino or substituted or unsubstituted carbamoyl;

X is ═$CR^X$— or ═N—;

Y is ═$CR^Y$— or ═N—;

U is —$CR^U$═ or —N═;

V is —$CR^V$═ or —N═;

W is ═$CR^W$— or ═N—;

$Z^A$ is —C═ or —N—;

$Z^B$ is —$CR^5R^6$—, —$CR^5$═, —$NR^5$— or —N═;

$Z^C$ is —$CR^7R^8$—, —$CR^7$═, —$NR^7$— or ═N—;

$R^X$, $R^Y$, $R^V$ and $R^W$ are each independently a hydrogen atom, cyano, halogen, substituted or unsubstituted alkyl or substituted or unsubstituted carbamoyl;

$R^U$ is a hydrogen atom, substituted or unsubstituted alkyloxy, substituted or unsubstituted non-aromatic heterocyclyloxy, substituted or unsubstituted non-aromatic carbocyclyloxy, substituted or unsubstituted alkyl, substituted or unsubstituted alkenyl, substituted or unsubstituted amino, hydroxy, halogen, substituted or unsubstituted aromatic carbocyclyl, substituted or unsubstituted aromatic heterocyclyl, substituted or unsubstituted non-aromatic heterocyclyl or substituted or unsubstituted non-aromatic carbocyclyl;

$R^5$ and $R^6$ are each independently a hydrogen atom, substituted or unsubstituted non-aromatic heterocyclyl, hydroxy or substituted or unsubstituted alkyl, or $R^5$ and $R^6$ are taken together to form oxo;

$R^7$ and $R^8$ are each independently a hydrogen atom, substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl, substituted or unsubstituted non-aromatic carbocyclylsulfonyl, substituted or unsubstituted alkylsulfonyl, or $R^7$ and $R^8$ are taken together with the carbon atom to which they are attached to form a substituted or unsubstituted non-aromatic carbon ring or a substituted or unsubstituted non-aromatic heterocyclic ring; or $R^5$ and $R^7$ are taken together with the carbon atoms to which they are attached to form a substituted or unsubstituted non-aromatic carbon ring or a substituted or unsubstituted aromatic carbon ring; or $R^4$ is a hydrogen atom, substituted or unsubstituted alkyloxy, substituted or unsubstituted non-aromatic heterocyclyloxy, substituted or unsubstituted non-aromatic carbocyclyloxy, substituted or unsubstituted aromatic carbocyclyloxy, substituted or unsubstituted aromatic heterocyclyloxy, substituted or unsubstituted alkyl, substituted or unsubstituted alkenyl, substituted or unsubstituted amino, substituted or unsubstituted carbamoyl, hydroxy, halogen, substituted or unsubstituted aromatic carbocyclyl, substituted or unsubstituted aromatic heterocyclyl, substituted or unsubstituted non-aromatic heterocyclyl, substituted or unsubstituted non-aromatic carbocyclyl or substituted or unsubstituted non-aromatic heterocyclylcarbonyl, or $R^4$ and $R^U$ are taken together with the carbon atom to which they are attached to form a substituted or unsubstituted non-aromatic heterocyclic ring, or a pharmaceutically acceptable salt thereof.

2. The compound according to claim 1, wherein $R^1$ is carboxy, or a pharmaceutically acceptable salt thereof.

3. The compound according to claim 1, wherein L is substituted or unsubstituted non-aromatic carbocyclyldiyl, or a pharmaceutically acceptable salt thereof.

4. The compound according to claim 1, wherein $R^3$ is a hydrogen atom, or a pharmaceutically acceptable salt thereof.

5. The compound according to claim 1, wherein V is —N═ and W is ═N—, or a pharmaceutically acceptable salt thereof.

6. The compound according to claim 1, wherein the group of the formula:

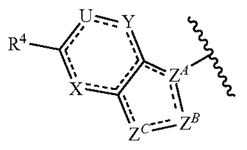

is

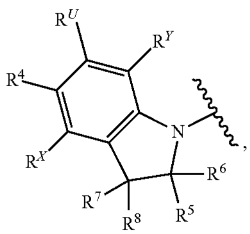

,

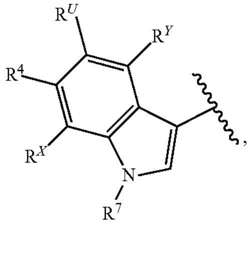

,

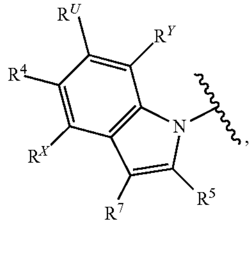

,

-continued

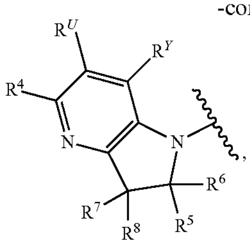,

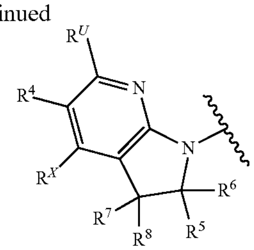,

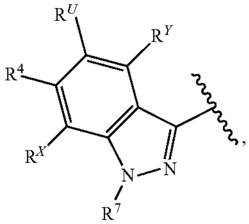,

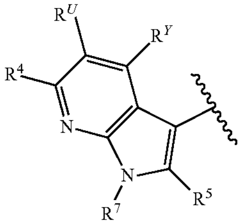,

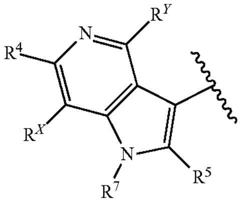

or

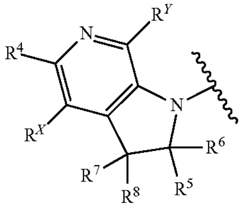

wherein each symbol is as defined in claim 1, or a pharmaceutically acceptable salt thereof.

7. The compound according to claim 1, wherein the group of the formula:

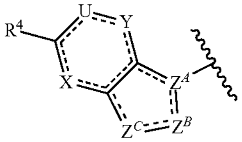

is

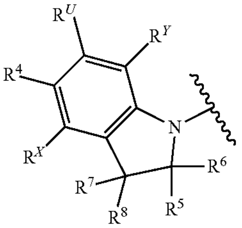

or

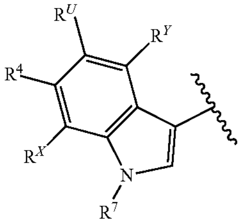

wherein each symbol is as define in claim 1, or a pharmaceutically acceptable salt thereof.

8. The compound according to claim 1, wherein the group of the formula:

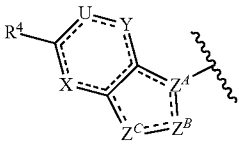

is

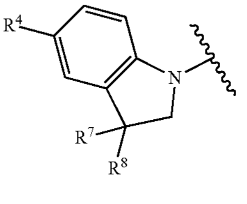

or

-continued

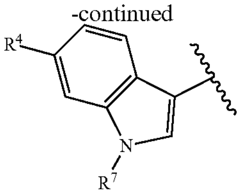

wherein each symbol is as defined in claim 1, or a pharmaceutically acceptable salt thereof.

9. The compound according to claim 1, wherein the group of the formula:

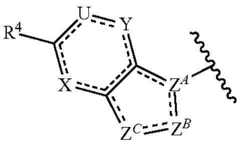

is

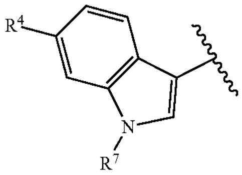

wherein $R^4$ is as defined in claim 1; and $R^7$ is substituted or unsubstituted alkyl, substituted or unsubstituted non-aromatic carbocyclyl, substituted or unsubstituted non-aromatic heterocyclyl, substituted or unsubstituted aromatic carbocyclyl, substituted or unsubstituted aromatic heterocyclyl, substituted or unsubstituted non-aromatic carbocyclyloxycarbonyl, substituted or unsubstituted non-aromatic heterocyclyloxycarbonyl or substituted or unsubstituted non-aromatic carbocyclylsulfonyl, or a pharmaceutically acceptable salt thereof.

10. The compound according to claim 1, wherein the group of the formula:

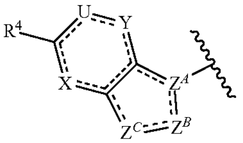

is

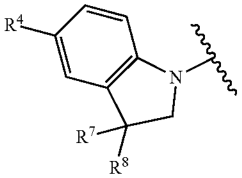

wherein $R^4$ is as defined in claim 1; and $R^7$ and $R^8$ are each independently a hydrogen atom or substituted or unsubstituted alkyl, or $R^7$ and $R^8$ are taken together with the carbon atom to which they are attached to form a substituted or unsubstituted non-aromatic carbon ring or a substituted or unsubstituted non-aromatic heterocyclic ring, or a pharmaceutically acceptable salt thereof.

11. The compound according to claim 1, wherein $R^4$ is substituted or unsubstituted alkyloxy, substituted or unsubstituted non-aromatic heterocyclyloxy, substituted or unsubstituted non-aromatic carbocyclyloxy, substituted or unsubstituted aromatic carbocyclyloxy, substituted or unsubstituted alkyl, substituted or unsubstituted alkenyl, substituted or unsubstituted amino, hydroxy, halogen, substituted or unsubstituted aromatic carbocyclyl, substituted or unsubstituted non-aromatic heterocyclyl or substituted or unsubstituted non-aromatic carbocyclyl, or a pharmaceutically acceptable salt thereof.

12. The compound according to claim 1, wherein $R^4$ is substituted or unsubstituted non-aromatic heterocyclyloxy or substituted or unsubstituted non-aromatic carbocyclyloxy,
or a pharmaceutically acceptable salt thereof.
13. The compound according to claim 1, which is selected from the group consisting of
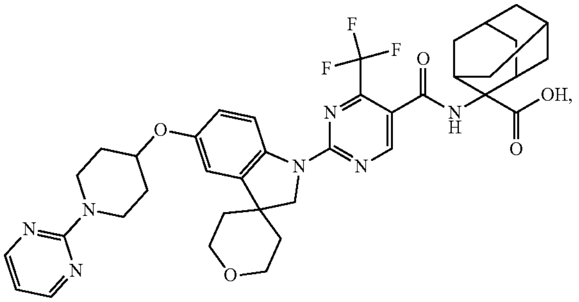 [SMILES: O=C(NC1(C(=O)O)C2CC3CC(C2)CC1C3)c1cnc(N2CC3(CCOCC3)c3cc(OC4CCN(c5ncccn5)CC4)ccc32)nc1C(F)(F)F]
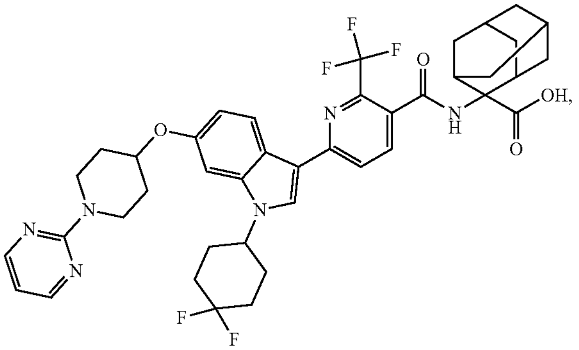 [SMILES: O=C(NC1(C(=O)O)C2CC3CC(C2)CC1C3)c1ccc(-c2cn(C3CCC(F)(F)CC3)c3cc(OC4CCN(c5ncccn5)CC4)ccc23)nc1C(F)(F)F]
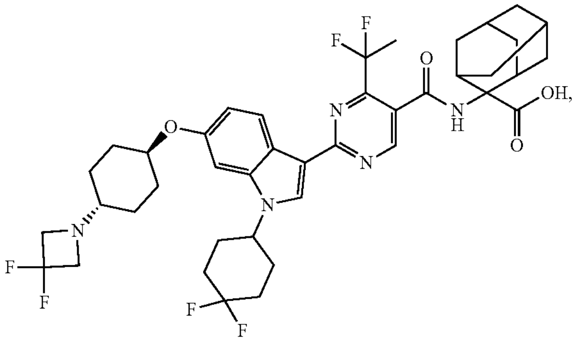
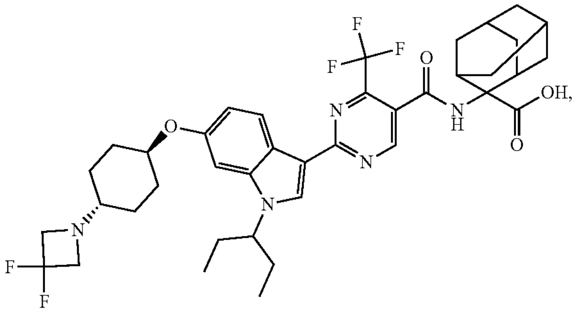
-continued
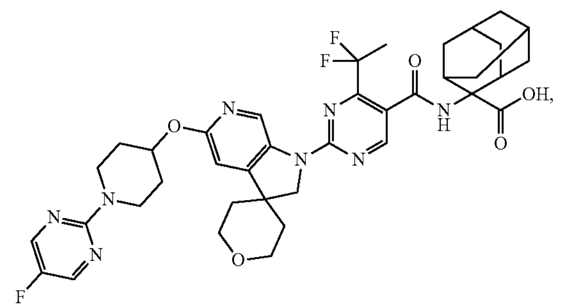
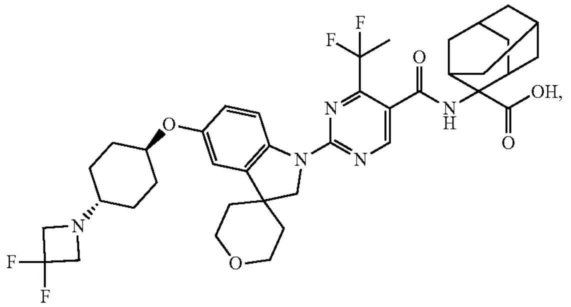 [SMILES: CC(F)(F)c1nc(N2CC3(CCOCC3)c3cc(O[C@H]4CC[C@H](N5CC(F)(F)C5)CC4)ccc32)ncc1C(=O)NC1(C(=O)O)C2CC3CC(C2)CC1C3]
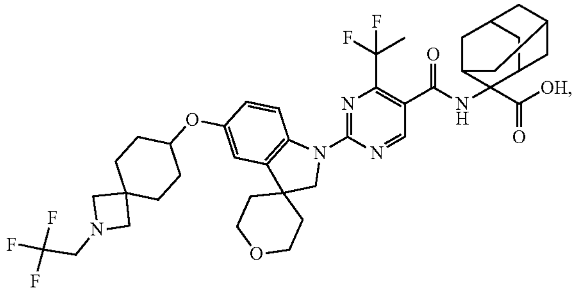
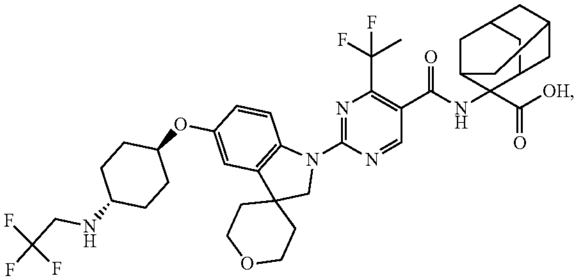
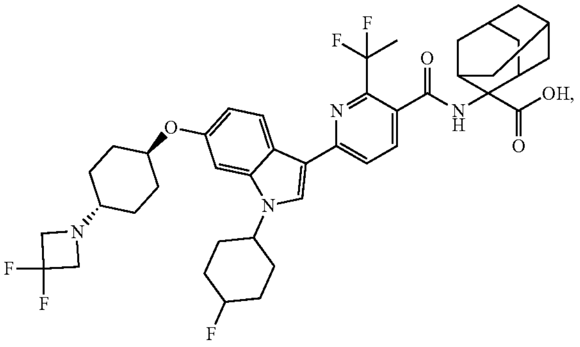

-continued

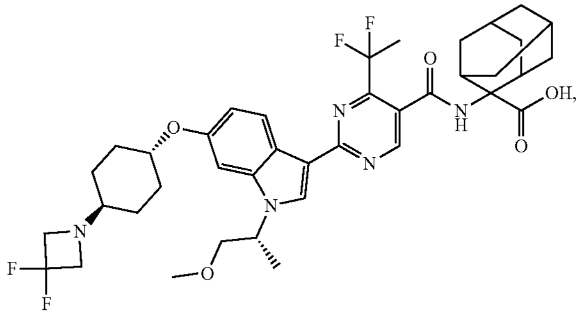 [SMILES: COC[C@@H](C)n1cc(-c2ncc(C(=O)NC3(C(=O)O)C4CC5CC(C4)CC3C5)c(C(C)(F)F)n2)c2ccc(O[C@H]3CC[C@H](N4CC(F)(F)C4)CC3)cc21]

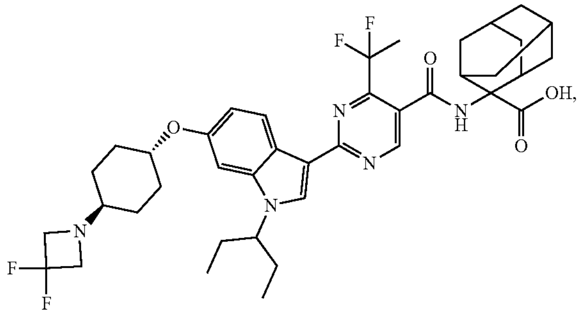

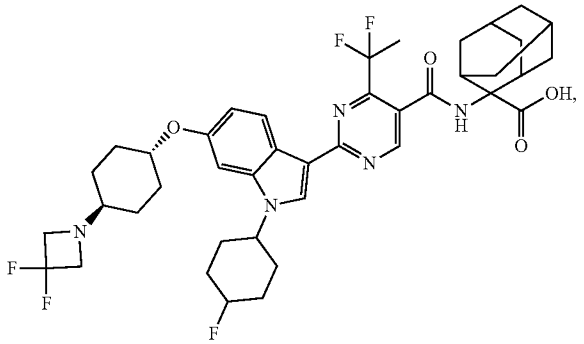

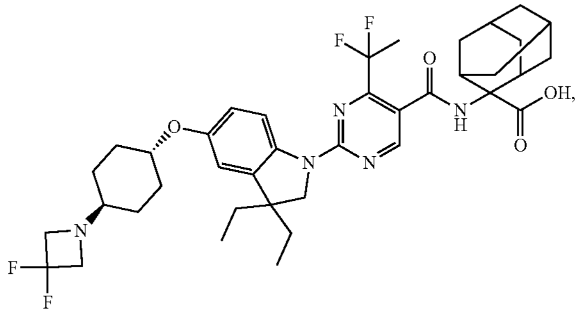

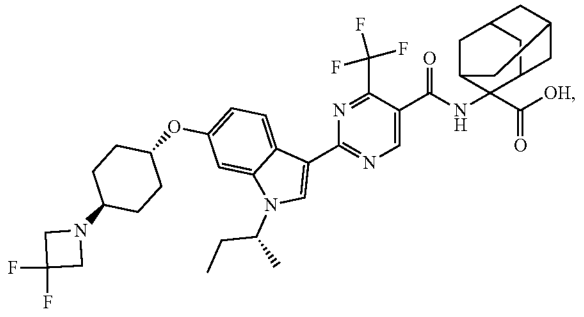

-continued

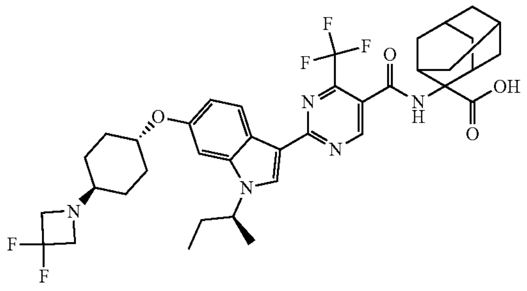

and

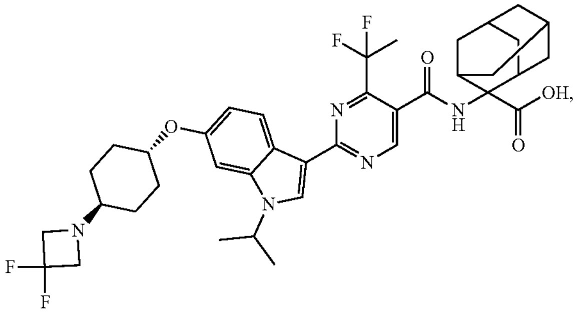 [SMILES: CCC(CC)n1cc(-c2ncc(C(=O)NC3(C(=O)O)C4CC5CC(C4)CC3C5)c(C(C)(F)F)n2)c2ccc(O[C@H]3CC[C@H](N4CC(F)(F)C4)CC3)cc21]

or a pharmaceutically acceptable salt thereof.

14. A pharmaceutical composition comprising the compound of claim 1, or a pharmaceutically acceptable salt thereof, and a pharmaceutically acceptable carrier or diluent.

15. The pharmaceutical composition according to claim 14 having an anti-RS virus activity.

16. A method for the treatment and/or prevention of RSV infection, comprising administering a compound of claim 1 or a pharmaceutically acceptable salt thereof to a patient in need thereof.

17. The compound according to claim 1 or a pharmaceutically acceptable salt thereof, for the treatment and/or prevention of RSV infection.

18. A method for the manufacture of a medicament for the treatment and/or prevention of RSV infection, comprising combining a compound of claim 1 or a pharmaceutically acceptable salt thereof with a pharmaceutically acceptable carrier or diluent.

19. The compound according to claim 1, which is:

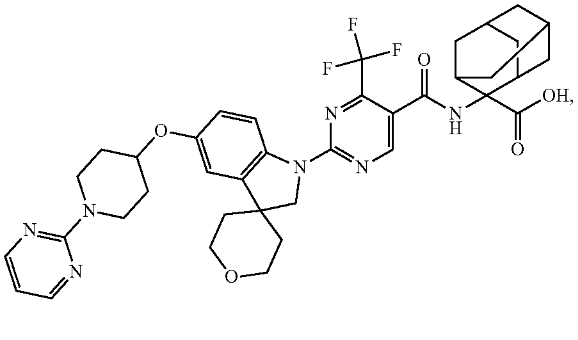

or a pharmaceutically acceptable salt thereof.

20. A pharmaceutical composition comprising the compound of claim 19, or a pharmaceutically acceptable salt thereof, and a pharmaceutically acceptable carrier or diluent.

21. The compound according to claim 1, which is:

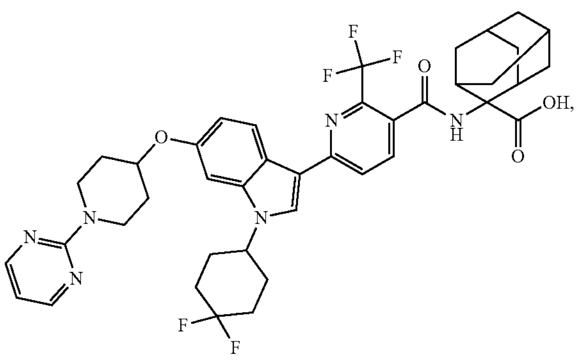

or a pharmaceutically acceptable salt thereof.

22. A pharmaceutical composition comprising the compound of claim 21, or a pharmaceutically acceptable salt thereof, and a pharmaceutically acceptable carrier or diluent.

23. The compound according to claim 1, which is:

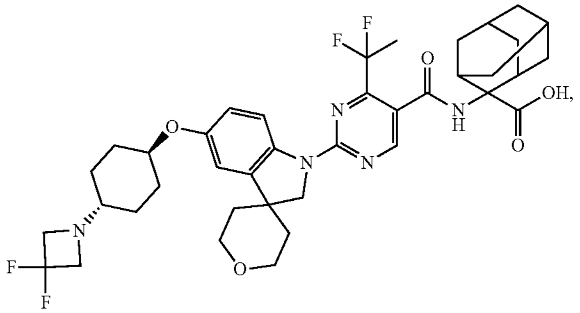

or a pharmaceutically acceptable salt thereof.

24. A pharmaceutical composition comprising the compound of claim 23, or a pharmaceutically acceptable salt thereof, and a pharmaceutically acceptable carrier or diluent.

25. The compound according to claim 1, which is:

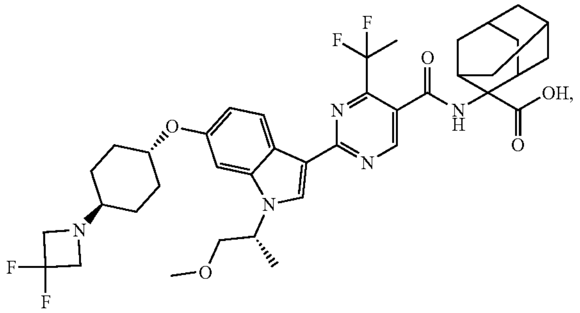

or a pharmaceutically acceptable salt thereof.

26. A pharmaceutical composition comprising the compound of claim 25, or a pharmaceutically acceptable salt thereof, and a pharmaceutically acceptable carrier or diluent.

27. The compound according to claim 1, which is:

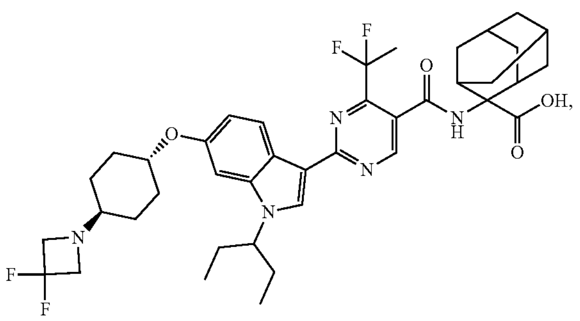

or a pharmaceutically acceptable salt thereof.

28. A pharmaceutical composition comprising the compound of claim 27, or a pharmaceutically acceptable salt thereof, and a pharmaceutically acceptable carrier or diluent.

29. The compound according to claim 1, which is:

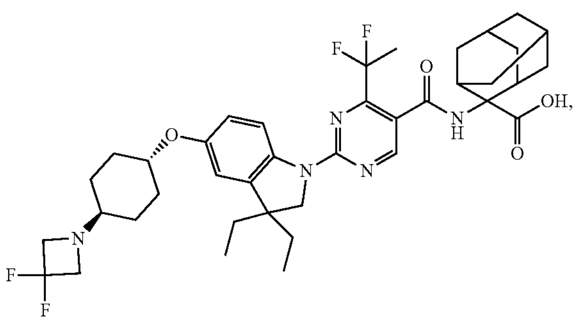 [SMILES: CCC1(CC)CN(c2ncc(C(=O)NC3(C(=O)O)C4CC5CC(C4)CC3C5)c(C(C)(F)F)n2)c2ccc(O[C@H]3CC[C@H](N4CC(F)(F)C4)CC3)cc21]

or a pharmaceutically acceptable salt thereof.

30. A pharmaceutical composition comprising the compound of claim 29, or a pharmaceutically acceptable salt thereof, and a pharmaceutically acceptable carrier or diluent.

31. The compound according to claim 1, which is:

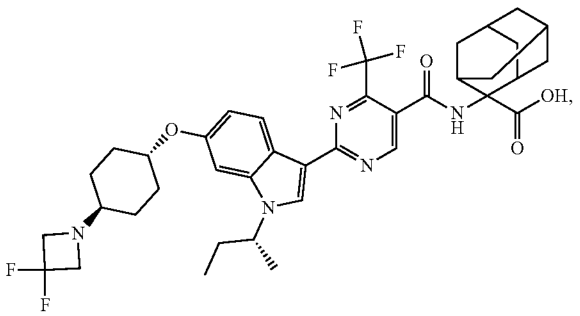 [SMILES: CC[C@@H](C)n1cc(-c2ncc(C(=O)NC3(C(=O)O)C4CC5CC(C4)CC3C5)c(C(F)(F)F)n2)c2ccc(O[C@H]3CC[C@H](N4CC(F)(F)C4)CC3)cc21]

or a pharmaceutically acceptable salt thereof.

32. A pharmaceutical composition comprising the compound of claim 31, or a pharmaceutically acceptable salt thereof, and a pharmaceutically acceptable carrier or diluent.

* * * * *